United States Patent
Guzi et al.

(10) Patent No.: US 6,362,188 B1
(45) Date of Patent: Mar. 26, 2002

(54) FARNESYL PROTEIN TRANSFERASE INHIBITORS

(75) Inventors: Timothy Guzi, Chatham; Dinanath F. Rane, Morganville; Alan K. Mallams, Hackettstown; Alan B. Cooper, West Caldwell; Ronald J. Doll, Maplewood; Viyyoor M. Girijavallabhan, Parsippany; Arthur G. Taveras, Denville; Corey Strickland, North Plainfield; Joseph M. Kelly, Parlin; Jianping Chao, Summit, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/465,523

(22) Filed: Dec. 16, 1999

Related U.S. Application Data

(60) Provisional application No. 60/112,943, filed on Dec. 18, 1998.

(51) Int. Cl.[7] .................... A61K 31/496; A61K 31/541; A61K 31/55; C07D 403/14; C07D 417/14; A61P 35/00
(52) U.S. Cl. ............... 514/253.02; 514/217.05; 514/228.2; 514/232.8; 514/218; 540/544; 540/598; 540/575; 544/60; 544/121; 544/361; 544/370; 544/360
(58) Field of Search .................. 544/361, 370, 544/60, 121; 514/254, 255, 252, 232.8, 253.03, 253.02, 228.2, 217.05; 540/598, 544

(56) References Cited

U.S. PATENT DOCUMENTS

| | | |
|---|---|---|
| 5,416,087 A | 5/1995 | Wong et al ............ 514/252 |
| 5,712,286 A | 1/1998 | Gill et al. |
| 5,719,148 A * | 2/1998 | Bishop ................ 514/228.2 |
| 5,801,175 A * | 9/1998 | Afonso ................ 514/254 |

FOREIGN PATENT DOCUMENTS

| | | | |
|---|---|---|---|
| EP | 0157399 | 9/1985 | ......... C07D/211/14 |
| WO | WO 95/10516 | 4/1995 | |
| WO | WO 96/31478 | 10/1996 | |
| WO | WO 98/57960 | 12/1998 | |

OTHER PUBLICATIONS

Khosravi–Far R. et al. Cells & Differentiation,. 3, 461–468, Jul. 1992.*

* cited by examiner

Primary Examiner—Evelyn Mei Huang
(74) Attorney, Agent, or Firm—Henry C. Jeanette

(57) ABSTRACT

Disclosed are compounds of the formula:

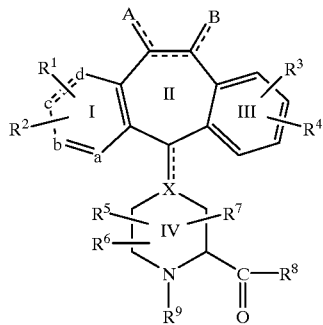

(1.0)

wherein $R^8$ represents a cyclic moiety to which is bound an imodazolylalkyl group; $R^9$ represents a carbamate, urea, amide or sulfonamide group; and the remaining substituents are as defined herein. Also disclosed is a method of treating cancer and a method of inhibiting farnesyl protein transferase using the disclosed compounds.

29 Claims, No Drawings

FARNESYL PROTEIN TRANSFERASE INHIBITORS

REFERENCE TO RELATED APPLICATIONS

This application claims the benefit of U.S. Provisional Application Ser. No. 60/112,943 filed Dec. 18, 1998.

BACKGROUND

WO 95/10516, published Apr. 20, 1995, WO96/31478, published Oct. 10, 1996, and copending application Ser. No. 09/094687 filed Jun. 15, 1998 discloses tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The compounds of this invention are represented by the formula:

A compound of the formula:

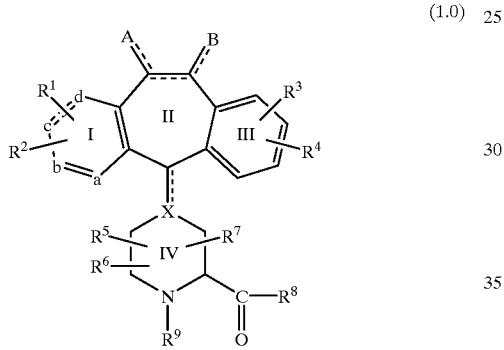

(1.0)

or a pharmaceutically acceptable salt or solvate thererof, wherein:

one of a, b, c and d represents N or $N^+O^-$, and the remaining a, b, c and d groups represent $CR^1$ or $CR^2$; or each of a, b, c, and d are independently selected from $CR^1$ or $CR^2$;

each $R^1$ and each $R^2$ is independently selected from H, halo, $-CF_3$, $-OR^{10}$ (e.g., $-OCH_3$), $-COR^{10}$, $-SR^{10}$ (e.g., $-SCH_3$ and $-SCH_2C_6H_5$), $-S(O)_tR^{11}$ (wherein t is 0, 1 or 2, e.g., $-SOCH_3$ and $-SO_2CH_3$), $-N(R^{10})_2$, $-NO_2$, $-OC(O)R^{10}$, $-CO_2R^{10}$, $-OCO_2R^{11}$, $-CN$, $-NR^{10}COOR^{11}$, $-SR^{11}C(O)$ $OR^{11}$, (e.g., $-SCH_2CO_2CH_3$), $-SR^{11}N(R^{75})_2$ (provided that $R^{11}$ in $-SR^{11}N(R^{75})_2$ is not $-CH_2-$) wherein each $R^{75}$ is independently selected from H or $-C(O)OR^{11}$ (e.g., $-S(CH_2)_2NHC(O)O$-t-butyl and $-S(CH_2)_2NH_2$), benzotriazol1-yloxy, tetrazol-5-ylthio, or substituted tetrazol-5-ylthio (e.g., alkyl substituted tetrazol5-ylthio such as 1-methyl-tetrazol-5-ylthio), alkynyl, alkenyl or alkyl, said alkyl or alkenyl group optionally being substituted with halo, $-OR^{10}$ or $-CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5-C_7$ fused ring to the benzene ring (Ring III);

$R^5$, $R^6$, and $R^7$ each independently represents H, $-CF_3$, $-COR^{10}$, alkyl or aryl, said alkyl or aryl optionally being substituted with $-OR^{10}$, $-SR^{10}$, $-S(O)_tR^{11}$, $-NR^{10}COOR^{11}$, $-N(R^{10})_2$, $-NO_2$, $-COR^{10}$, $-OCOR^{10}$, $-OCO_2R^{11}$, $-CO_2R^{10}$, $OPO_3R^{10}$, or $R^5$ is combined with $R^6$ to represent $=O$ or $=S$; provided that for the groups $-OR^{10}$, $-SR^{10}$, and $-N(R^{10})_2R^{10}$ is not H;

$R^{10}$ represents H, alkyl, aryl, or aralkyl (e.g., benzyl);

$R^{11}$ represents alkyl or aryl;

X represents N, CH or C, and when X is C the optional bond (represented by the dotted line) to carbon atom 11 is present, and when X is CH the optional bond (represented by the dotted line) to carbon atom 11 is absent:

the dotted line between carbon atoms 5 and 6 represents an optional bond, such that when a double bond is present, A and B independently represent $-R^{10}$, halo, $-OR^{11}$, $-OCO_2R^{11}$ or $-OC(O)R^{10}$, and when no double bond is present between carbon atoms 5 and 6, A and B each independently represent $H_2$, $-(OR^{11})_2$, H and halo, dihalo, alkyl and H, (alkyl)$_2$, $-H$ and $-OC(O)R^{10}$, H and $-OR^{10}$, $=O$, aryl and H, $=NOR^{10}$ or $-O-(CH_2)_p-O-$ wherein p is 2, 3 or 4;

$R^8$ represents a heterocyclic ring selected from:

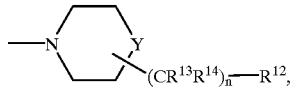

(2.0)

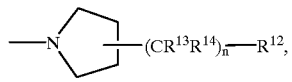

(3.0)

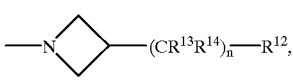

(4.0)

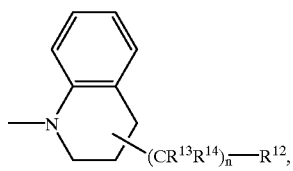

(5.0)

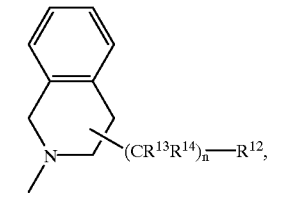

(6.0)

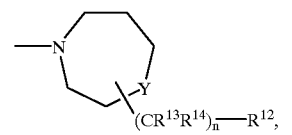

(7.0)

-continued

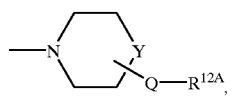
(2.1)

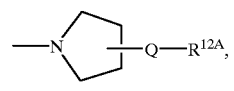
(3.1)

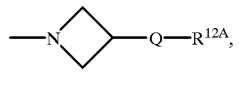
(4.1)

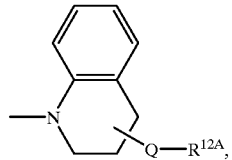
(5.1)

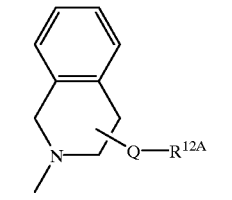
(6.1)

or

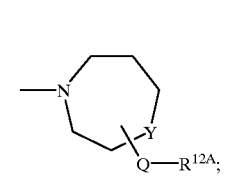
(7.1)

said heterocyclic rings (2.0 to 7.0 and 2.1 to 7.1) being optionally substituted with one or more substituents independently selected from:
(a) alkyl (e.g., methyl, ethyl, isopropyl, and the like),
(b) substituted alkyl wherein said substituents are selected from: halo, aryl, —$OR^{15}$ or —$N(R^{15})_2$, heteroaryl, heterocycloalkyl, cycloalkyl, wherein each $R^{15}$ group is the same or different, provided that said optional substituent is not bound to a carbon atom that is adjacent to an oxygen or nitrogen atom, and wherein $R^{15}$ is selected from: H, alkyl, aryl, arylalkyl, heteroaryl, heteroarylalkyl, cycloalkyl, or cycloalkylalkyl;
(c) hydroxyl, with the proviso that carbon atoms adjacent to the nitrogen, sulfur or oxygen atoms of the ring are not substituted with hydroxyl;
(d) alkyloxy or
(e) arylalkyloxy;
(i.e., each substitutable H atom on each substitutable carbon atom in said heterocyclic rings is optionally replaced with substituents selected from (a) to (e) defined above);
Y represents $CH_2$, $NR^{16}$, O, S, SO, or $SO_2$ wherein $R^{16}$ is selected from: H, alkyl, cycloalkyl, cycloalkylalkyl, aryl, arylalkyl, heteroaryl, heteroarylalkyl, acyl, aroyl, carbamoyl, carboxamido, alkylsulfonyl, arylsulfonyl, arylalkylsulfonyl, sulfonamido, alkylsulfonamido, arylsulfonamido and arylalkylsulfonamido;
n is 0 to 6 (preferably 1–3);

Q represents O or N, provided that Q is not adjacent to a heteroatom in the heterocycloalkyl rings of 2.1, 3.1, 4.1, 5.1, 6.1 and 7.1;
$R^{12}$ is selected from:

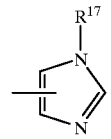
(8.0)

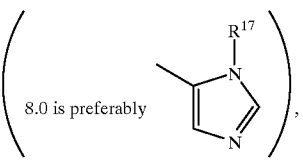
(8.1)

8.0 is preferably

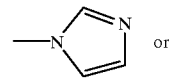
or
(9.0)

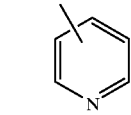
(9.1)

(e.g., $R^{12}$ is 9.0):
wherein $R^{17}$ is selected from; (1) H, (2) alkyl, (3) aryl, (4) arylalkyl, (5) substituted arylalkyl wherein the substituents are selected from halo (e.g., F and Cl) or CN, (6) —C(aryl)$_3$ (e.g., —C(phenyl)$_3$, i.e., trityl), (7) cycloalkyl, (8) substituted alkyl (as defined above in (b)), or (9) cycloalkylalkyl;
$R^{12A}$ is selected from rings 8.0, 8.1 or 9.1, defined above;
said imidazolyl ring 8.0 and 8.1 optionally being substituted with one or two substituents, said imidazole ring 9.0 optionally being substituted with 1–3 substituents, and said pyridyl ring 9.1 optionally being substituted with 1–4 substituents, wherein said optional substituents for rings 8.0, 8.1, 9.0 and 9.1 are bound to the carbon atoms of said rings and are independently selected from: —NHC(O)$R^{15}$, —C($R^{18}$)$_2$O$R^{19}$, —O$R^{15}$, —S$R^{15}$, F, Cl, Br, alkyl (e.g., methyl, such as 4-methyl in 9.0), substituted alkyl (as defined above in (b)), aryl, arylalkyl, cycloalkyl, or —N($R^{15}$)$_2$; $R^{15}$ is as defined above; each $R^{18}$ is independently selected from H or alkyl (preferably —$CH_3$), preferably H; $R^{19}$ is selected from H or —C(O)NH$R^{20}$, and $R^{20}$ is as defined below;
$R^{13}$ and $R^{14}$ for each n are independently selected from: H, F, alkyl, aryl, arylalkyl, heteroaryl, heteroarylalkyl, cycloalkyl, cycloalkylalkyl or —CON($R^{15}$)$_2$ (wherein $R^{15}$ is as defined above), —O$R^{15}$ or —N($R^{15}$)$_2$ provided that the —O$R^{15}$ and —N($R^{15}$)$_2$ groups are not bound to a carbon atom that is adjacent to a nitrogen atom, and provided that there can be only one —OH group on each carbon; and the substitutable $R^{13}$ and $R^{14}$ groups are optionally substituted with one or more (e.g., 1–3) substituents selected from: F, alkyl (e.g., methyl, ethyl, isopropyl, and the like), cycloalkyl, arylalkyl, or heteroarylalkyl (i.e., the $R^{13}$ and/or $R^{14}$ groups can be unsubtituted or can be substituted with 1–3 of the substituents described above, except when $R^{13}$ and/or $R^{14}$ is H); or $R^{13}$ and $R^{14}$, for each n, together with the carbon atom to which they are bound, form a $C_3$ to $C_6$ cycloalkyl ring;

$R^9$ is selected from:

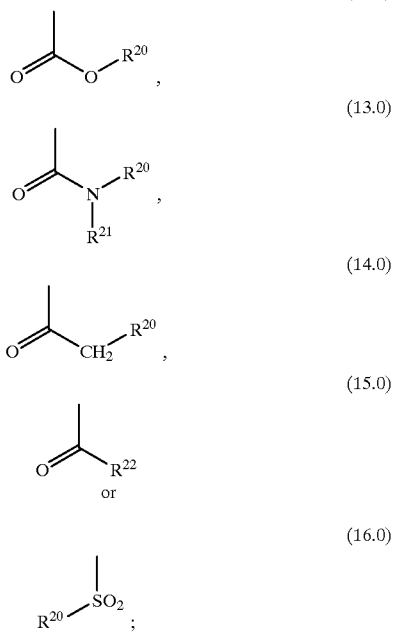

$R^{20}$ is selected from: H, alkyl, aryl, arylalkyl, cycloalkyl, cycloalkylalkyl, heteroaryl, heteroarylalkyl, heterocycloalkyl, or heterocyloalkylalkyl, provided that $R^{20}$ is not H when $R^9$ is group 12.0 or 16.0;

when $R^{20}$ is other than H, then said $R^{20}$ group is optionally substituted with one or more (e.g., 1–3) substituents selected from: halo, alkyl, aryl, —OC(O)$R^{15}$ (e.g., —OC(O)CH$_3$), —OR$^{15}$ or —N($R^{15}$)$_2$, wherein each $R^{15}$ group is the same or different, and wherein $R^{15}$ is as defined above, provided that said optional substituent is not bound to a carbon atom that is adjacent to an oxygen or nitrogen atom;

$R^{21}$ is selected from: H, alkyl, aryl, arylalkyl, cycloalkyl, cycloalkylalkyl, heteroaryl, heteroarylalkyl, heterocycloalkyl or heterocycloalkylalkyl;

when $R^{21}$ is other than H, then said $R^{21}$ group is optionally substituted with one or more (e.g., 1–3) substituents selected from: alkyl, aryl, wherein each $R^{15}$ group is the same or different, and wherein $R^{15}$ is as defined above; and $R^{22}$ is selected from cycloalkyl (e.g., cyclopropylmethyl, i.e.,

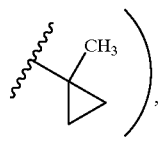

heterocycloalkyl, aryl (e.g., phenyl), substituted aryl (e.g., halo as a substituent, such as F or Cl), alkyl (e.g., t-butyl), or substituted alkyl or substituted cycloalkyl (substituents include —OH, —CO$_2$H, and —C(O)NH$_2$).

Thus, in one embodiment of this invention $R^9$ is 12.0. In another embodiment $R^9$ is 13.0. In another embodiment $R^9$ is 14.0. In another embodiment $R^9$ is 15.0. In another embodiment $R^9$ is 16.0.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the tricyclic compounds described above. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the tricylic compounds, described herein, to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, melanoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The tricyclic compounds useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

MH+—represents the molecular ion plus hydrogen of the molecule in the mass spectrum;

BOC—represents tert-butyloxycarbonyl;

BOC-ON—represents 1-(tert-butoxycarbonyl)-2-tert-butyl-3-methyl-4-imidazolidinone nitrile;

CBZ—represents —C(O)OCH$_2$C$_6$H$_5$ (i.e., benzyloxycarbonyl);

CBZ-OSUC—represents benzyloxycarbonyl-O-succinimide;

CH$_2$Cl$_2$—represents dichloromethane;

CIMS—represents chemical ionization mass spectrum;

DEAD—represents diethylazodicarboxylate;

DEC—represents EDC which represents 1-(3-dimethylaminopropyl)-3-ethylcarbodiimide hydrochloride;

DMF—represents N,N-dimethylformamide;

Et—represents ethyl;

EtOAc—represents ethyl acetate;

EtOH—represents ethanol;

HOBT—represents 1-hydroxybenzotriazole hydrate;

IPA—represents isopropanol;

iPrOH—represents isopropanol;

LAH—represents lithium aluminum hydride;

LDA—represents lithium diisopropylamide;

MCPBA—represents meta-chloroperbenzoic acid;

Me—represents methyl;

MeOH—represents methanol;

MS—represents mass spectroscopy;

NMM—represents N-methylmorpholine;

Ph—represents phenyl;

Pr—represents propyl;

TBDMS—represents tert-butyldimethylsilyl;

TEA—represents triethylamine;

TFA—represents trifluoroacetic acid;

THF—represents tetrahydrofuran;

Tr—represents trityl;

alkyl—represents straight and branched carbon chains and contains from one to twenty carbon atoms, preferably one to six carbon atoms said cycloalkyl ring being optionally substituted with one or more (e.g., 1, 2 or 3) alkyl groups (e.g., methyl or ethyl) and when there is more than one alkyl group each alkyl group can be the same or different;

acyl—represents a G—C(O)— group wherein G represents alkyl, aryl, heteroaryl, cycloalkyl, heterocycloalkyl, —O-alkyl, —O-aryl, or NR$^{25}$R$^{26}$ wherein R$^{25}$ and R$^{26}$ are independently selected from alkyl or aryl;

arylalkyl—represents an alkyl group, as defined above, substituted with an aryl group, as defined below, such that the bond from another substituent is to the alkyl moiety;

aryl-(including the aryl portion of arylalkyl)—represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, CF$_3$, —C(O)N(R$^{18}$)$_2$, —SO$_2$R$^{18}$, —SO$_2$N(R$^{18}$)$_2$, amino, alkylamino, dialkylamino, —COOR$^{23}$ or —NO$_2$, wherein R$^{23}$ represents alkyl or aryl;

aroyl—represents —C(O)aryl wherein aryl is as defined above (e.g., —C(O)phenyl);

cycloalkyl—represents saturated carbocyclic rings of from 3 to 20 carbon atoms, preferably 3 to 7 carbon atoms, said cycloalkyl ring optionally substituted with one or more (e.g., 1, 2 or 3) alkyl groups (e.g., methyl or ethyl) and when there is more than one alkyl group each alkyl group can be the same or different;

cycloalkylalkyl—represents a cycloalkyl group, as defined above, substituted with an alkyl group, as defined above, such that the bond from another substituent is to the alkyl moiety;

halo—represents fluoro, chloro, bromo and iodo;

heteroaralkyl—represents an alkyl group, as defined above, substituted with a heteroaryl group, as defined below, such that the bond from another substituent is to the alkyl moiety;

heteroaryl—represents cyclic groups, optionally substituted with R$^3$ and R$^4$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadizolyl], 2-, 3-, 4-, 5-, 6- or 7-benzofuranyl,2-, 3-, 4-, 5-, 6- or 7-indolyl, 3-, 4- or 5-pyrazolyl, 2-, 4- or 5-oxazolyl, triazolyl, 2-, 3- or 4-pyridyl or pyridyl N-oxide (optionally substituted with R$^3$ and R$^4$), wherein pyridyl N-oxide can be represented as:

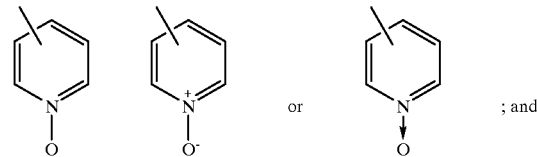

heterocycloalkyl—represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —NR$^{24}$, wherein R$^{24}$ represents alkyl, aryl, —C(O)N(R$^{18}$)$_2$, wherein R$^{18}$ is as above defined (e.g., —C(O)NH$_2$) or acyl-(suitable heterocycloalkyl groups include 2- or 3-tetrahydrofuranyl, 2- or 3- tetrahydrothienyl, tetrahydropyranyl, 2-, 3- or 4-piperidinyl, 2- or 3-pyrrolidinyl, 2- or 3-piperazinyl, 2- or 4-dioxanyl, morpholinyl, etc.).

The positions in the tricyclic ring system are:

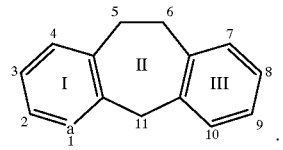

The compounds of formula 1.0 include the 2R and 2S isomers shown below (2R is preferred):

(1.0A)
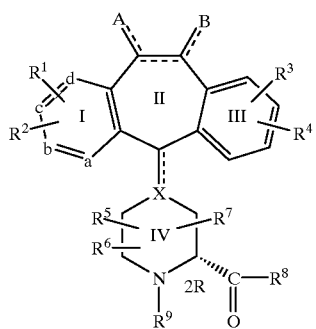

(1.0B)
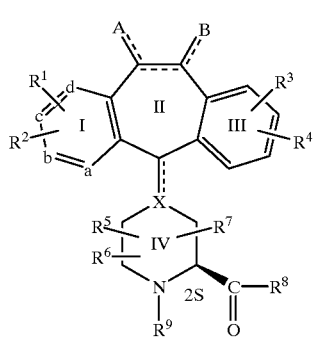

Examples of the optional substituents for the $R^{12}$ or $R^{12A}$ moiety include: —$CH_3$, —$CH_2OH$, —$CH_2OC(O)O$-cyclohexyl, —$CH_2OC(O)O$-cyclopenity, ethyl, isopropyl, $NH_2$, and —$NHC(O)CF_3$.

Examples of $R^{17}$ include: —$C(O)NH$-cyclohexyl, —$C(phenyl)_3$, H, methyl or ethyl.

Examples of $R^{20}$ include t-butyl, i-propyl, neopentyl, cyclohexyl, cyclopropylmethyl,

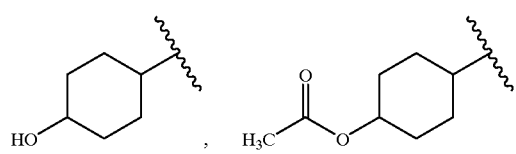

or 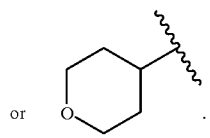.

Examples of $R^{20}$ for group 12.0 include: t-butyl, ethyl, benzyl, —$CH(CH_3)_2$, —$CH_2CH(CH_3)_2$, —$(CH_2)_2CH_3$, n-butyl, n-hexyl, n-octyl, p-chlorophenyl, cyclohexyl, cyclopentyl, neopentyl, cyclopropylmethyl or

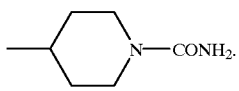

Examples of $R^{20}$ and $R^{21}$ for 13.0 include: cyclohexyl, t-butyl, H, —$CH(CH_3)_2$, ethyl, —$(CH_2)_2CH_3$, phenyl, benzyl, —$(CH_2)_2$phenyl, and —$CH_3$.

Examples of $R^{20}$ for 14.0 include: 4-pyridylNO, —$OCH_3$, —$CH(CH_3)_2$, -t-butyl, H, propyl, cyclohexyl and

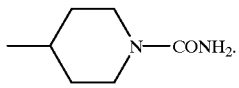

Examples for $R^{22}$ for 15.0 include: t-butyl, cyclohexyl, cyclopentyl, cyclobutyl, cyclopropyl, cyclopropylmethyl, phenyl, substitued phenyl (e.g., halo, Such as F or Cl),

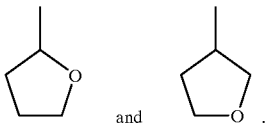

Examples for $R^{20}$ for 16.0 include: methyl, phenyl, iso-propyl and cyclohexylmethyl.

Examples of $R^{13}$ and $R^{14}$ include: H, F, phenyl, —$CH_3$, —$CH_2CH(CH_3)_2$, —$(CH_2)_3CH_3$, benzyl, ethyl, p-chlorophenyl, and —OH (provided that that there can only be one OH on each carbon).

Cyclopropyl is an Example of the $R^{13}$ and $R^{14}$ group being taken together with the carbon atom to which they are bound to form a cycloalkyl ring.

$R^1$, $R^2$, $R^3$, and $R^4$ are preferably selected from H and halo, and are more preferably selected from H, Br, F and Cl. Representative compounds of formula 1.0 include trihalo, dihalo and monohalo substituted compounds, such as, for example: (1) 3,8,10-trihalo; (2) 3,7,8-trihalo; (3) 3,8-dihalo; (4) 8-halo; (5) 10-halo; and (6) 3-halo (i.e., no substituent in Ring III) substituted compounds; wherein each halo is independently selected. Preferred compounds of formula 1.0 include: (1) 3-Br-8-Cl-10-Br-substituted compounds; (2) 3-Br-7-Br-8-Cl-substituted compounds; (3) 3-Br-8-Cl-substituted compounds; (4) 3-Cl-8-Cl-substituted compounds; (5) 3-F-8-Cl-substituted compounds; (6) 8-Cl-substituted compounds; (7) 10-Cl-substituted compounds; (8) 3-Cl-substituted compounds; (9) 3-Br-substituted compounds; and (10) 3-F-substituted compounds.

Substituent a is preferably N or $N^+O^-$ with N being preferred.

A and B are preferably $H_2$, i.e., the optional bond is absent and the C5–C6 bridge is unsubstituted.

$R^5$, $R^6$, and $R^7$ are preferably H.

X is preferably N or CH (i.e., the optional bond is absent), and more preferably X is N.

When one or more of the carbon atoms of the imidazole ring 8.0 or 9.0 are substituted, the substituents are generally selected from: —N($R^{15}$)$_2$, —NHC(O)$R^{15}$, —C($R^{18}$)$_2$O$R^{19}$, or alkyl, e.g., —CH$_3$, —CH$_2$OH, —CH$_2$OC(O)O-cyclolhexyl, —CH$_2$OC(O)O-cyclopentyl, ethyl, isopropyl, NH$_2$, or —NHC(O)CF$_3$.

$R^{17}$ is preferably H or alkyl, most preferably H, methyl or ethyl, and more preferably methyl.

$R^{20}$ in substituent 12.0 is preferably selected from: alkyl or cycloalkyl, most preferably t-butyl, isopropyl, neopentyl, cyclohexyl or cyclopropylmethyl.

$R^{20}$ in substituent 13.0 is preferably selected from: alkyl or cycloalkyl; most preferably t-butyl, isopropyl or cyclohexyl. $R^{21}$ is preferably selected from: H or alkyl; most preferably H, methyl or isopropyl; and more preferably H.

$R^{20}$ in substituent 14.0 is preferably selected from: cycloalkyl or alkyl.

$R^{22}$ in substituent 15.0 is preferably selected from: phenyl, cyclopropyl, cyclobutyl, cyclopentyl, cyclohexyl, t-butyl, cyclopropylmethyl,

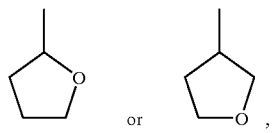

and most preferably selected from: t-butyl, cyclopropyl, cyclobutyl, cyclopentyl or cyclohexyl.

$R^{20}$ in substituent 16.0 is preferably selected from: alkyl or cycloalkylalkyl; most preferably methyl, isopropyl or cyclohexylmethyl; more preferably methyl or isopropyl; and even more preferably methyl.

$R^{13}$ and $R^{14}$ are preferably selected from: H, F, Cl to C$_4$ alkyl (e.g., methyl or isopropyl), —CON($R^{15}$)$_2$ (e.g., —CONH$_2$), —O$R^{15}$ (e.g., —OH), aryl (e.g., phenyl) or arylalkyl (e.g., benzyl): or when $R^{13}$ and $R^{14}$ are taken together to form a cycloalkyl ring, said ring is preferably cyclopropyl cyclopentyl or cyclohexyl. Most preferably $R^{13}$ and $R^{14}$ are H.

For compounds of the invention, n is preferably 1–3, most preferably 1–2.

For compounds wherein $R^8$ is ring 2.0 or 7.0, the —(C$R^{13}R^{14}$)$_n$—$R^{12}$ substituent can be in the 2-, 3- or 4-position relative to the ring nitrogen, provided that the —(C$R^{13}R^{14}$)$_n$—$R^{12}$ substituent is not in the 4-position when Y is O, S, SO or SO$_2$. Preferably, the —(C$R^{13}R^{14}$)$_n$—$R^{12}$ substituent is in the 2- or 3-position, and most preferably in the 3-position. More preferably, the —(C$R^{13}$ $^{R14}$)$_n$—$R^{12}$ substituent is in the 2-position when n is 2, and in the 3-position when n is 1.

Compounds of formula 1.0, wherein X is N or CH, include, with reference to the C-11 bond, the R- and S-isomers:

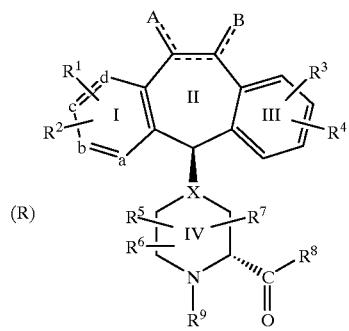

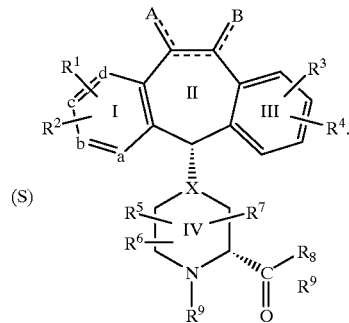

Compounds of this invention include the C-11 R- and S-isomers having the 2S stereochemistry.

Compounds of this invention include:

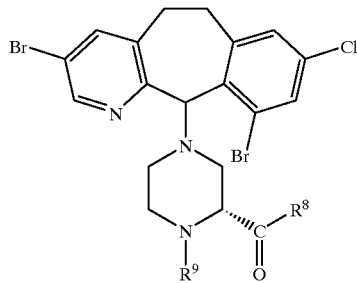

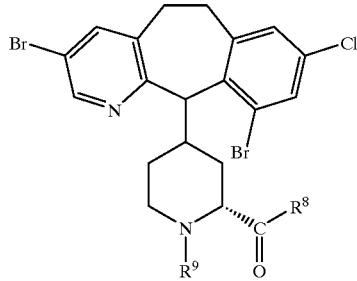

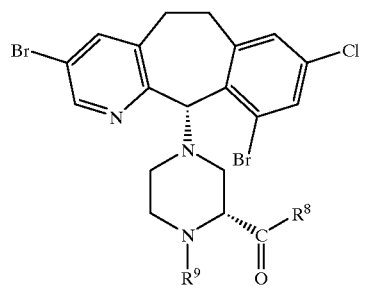
(21.0)
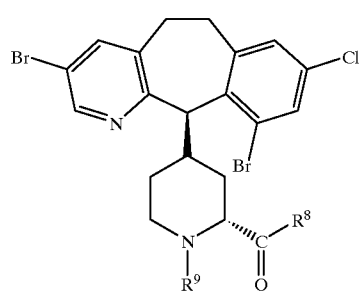
(22.0)
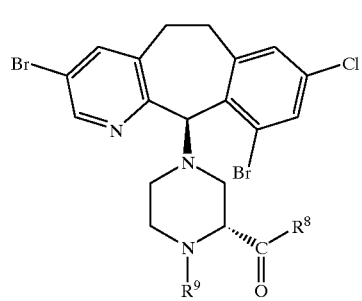
(23.0)
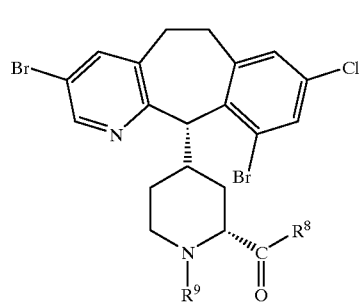
(24.0)
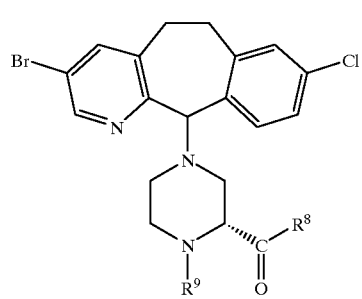
(25.0)
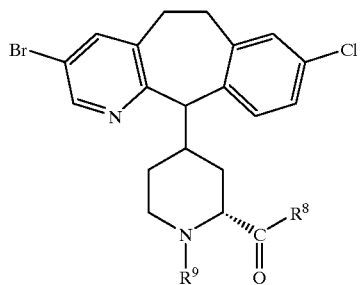
(26.0)

(27.0)
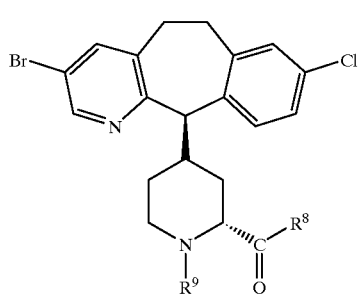
(28.0)
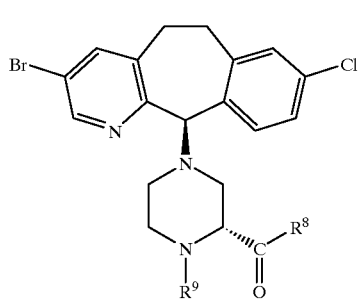
(29.0)
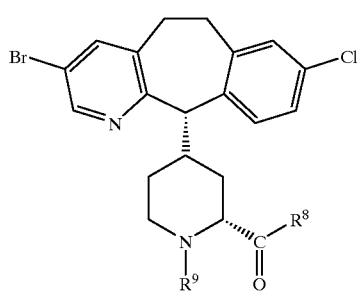
(30.0)

(31.0)
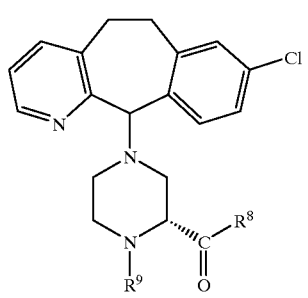
(32.0)
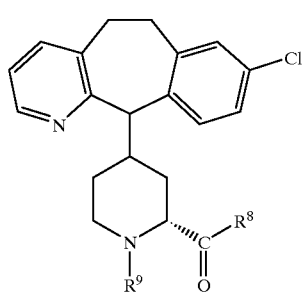
(33.0)

(34.0)
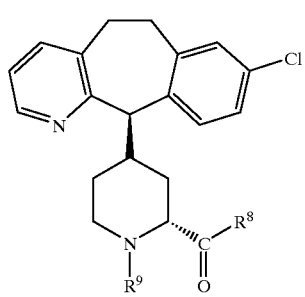
(39.0)
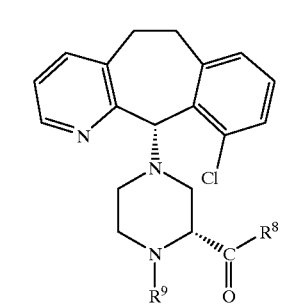
(40.0)
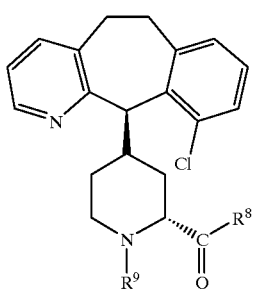
(41.0)
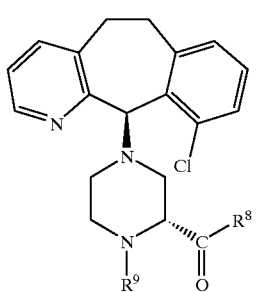
(42.0)
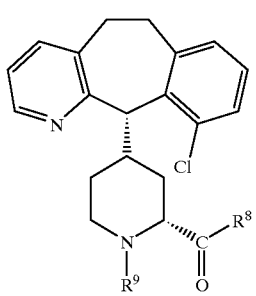
(42.0A)
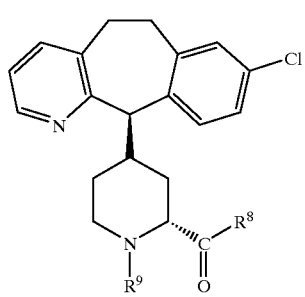
(42.0B)
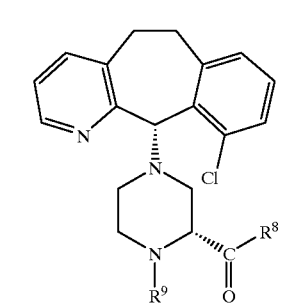

-continued
(42.0C)
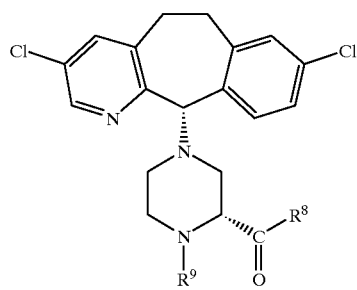
(42.0D)
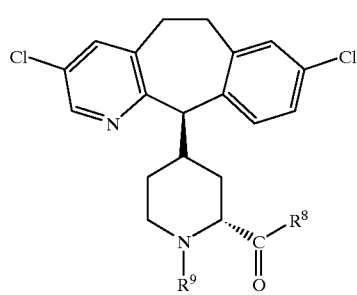
(42.0E)
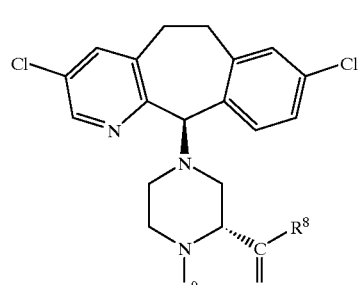
(42.0F)
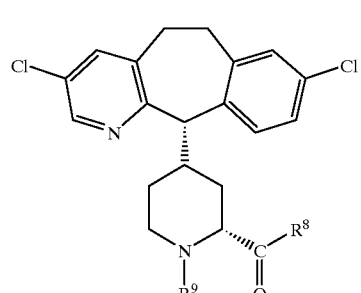
(42.0G)
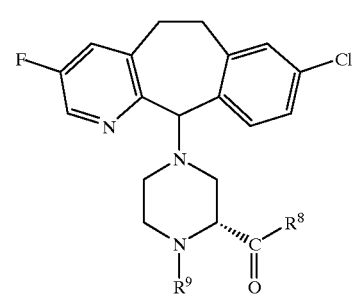
-continued
(42.0H)
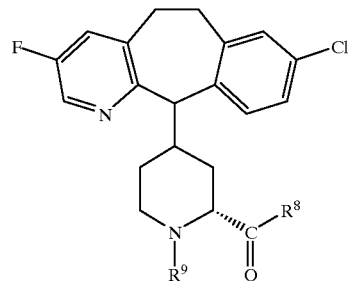
(42.0I)
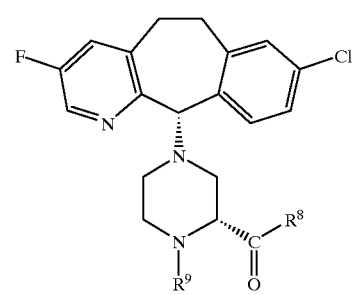
(42.0J)
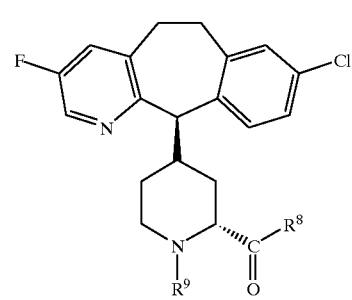
(42.0K)
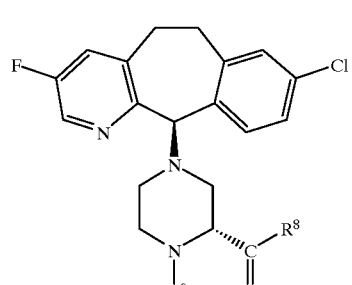
(42.0L)
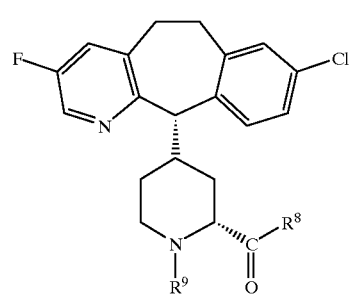

(42.0M)
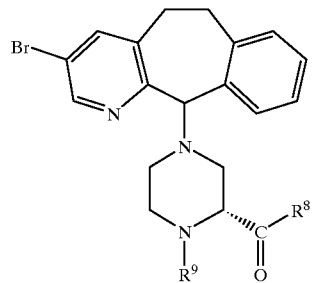
(42.0N)
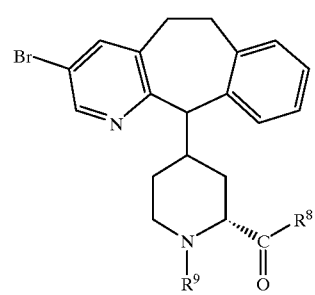
(42.0O)
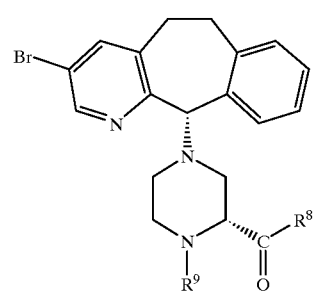
(42.0P)
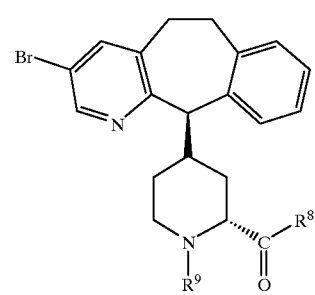
(42.0Q)
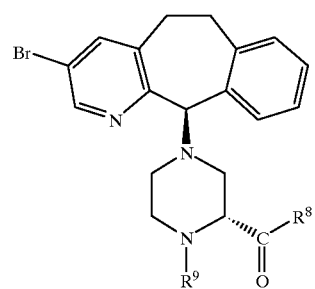
(42.0R)
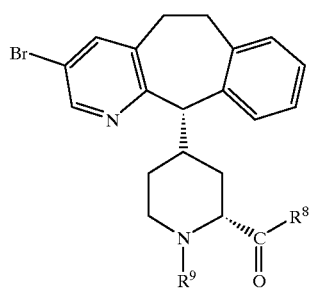
(42.0S)
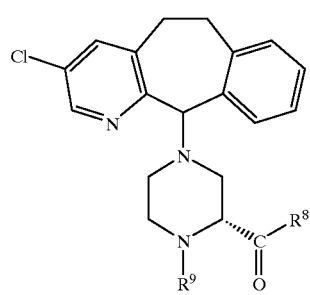
(42.0T)
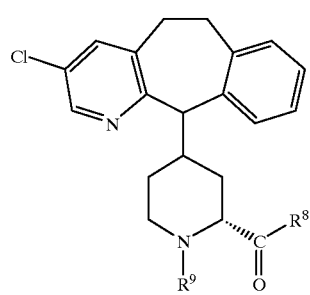
(42.0U)
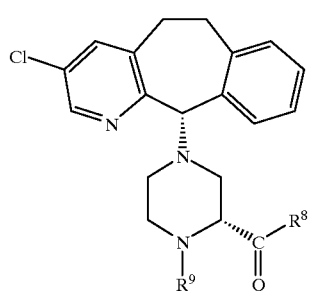
(42.0V)

(42.0W) 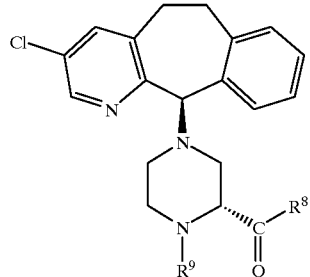

(42.0X) 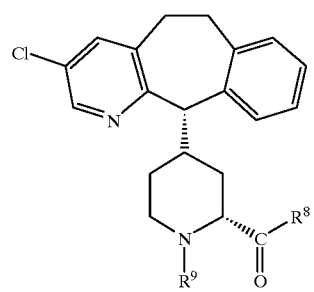

(42.0Y) 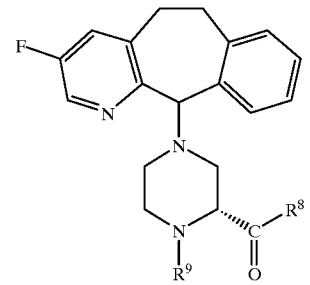

(42.0Z) 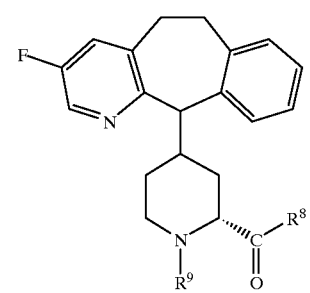

(42.0AA) 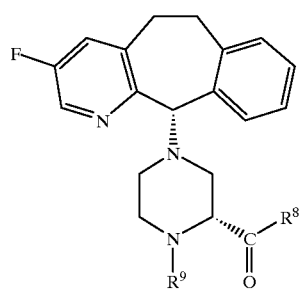

(42.0BB) 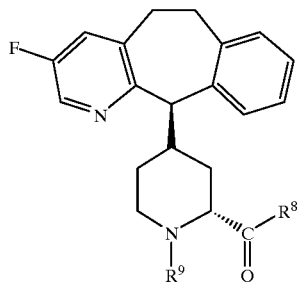

(42.0CC) 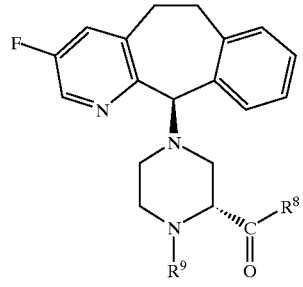

(42.0DD) 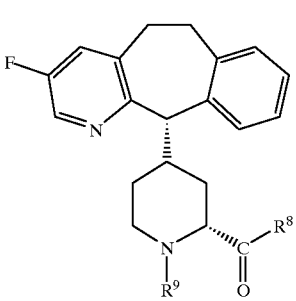

Compounds of the invention also include compounds corresponding to 19.0–42.0 DD, except that Ring I is phenyl instead of pyridyl.

Compounds of the invention also include compounds corresponding to 19.0–42.0 DD except that Ring I is phenyl instead of Pyridyl, and the compounds have the 2S stereochemistry.

Compounds of this invention also include compounds corresponding to 19.0–42.0 DD except that the compounds have the 2S stereochemistry.

Compounds of formula 1.0 include compounds of formula 1.0(C)

1.0(C)

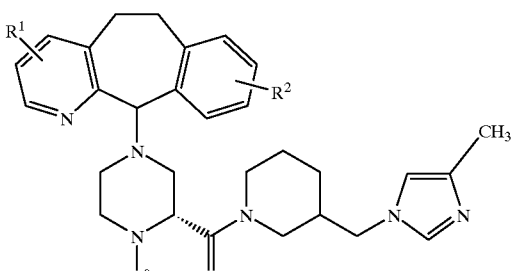

wherein $R^1$ is H or halo (preferably Br, Cl or F), and $R^2$ is H or halo (preferably Cl), and $R^9$ is as defined for formula 1.0. Preferably. $R^1$ is halo (most preferably Br, Cl or F), and $R^2$ is H or halo (preferably Cl). Those skilled in the art will appreciate that compounds of formula 1.0(C) include compounds of formulas 1.0(D) to 1.0(G):

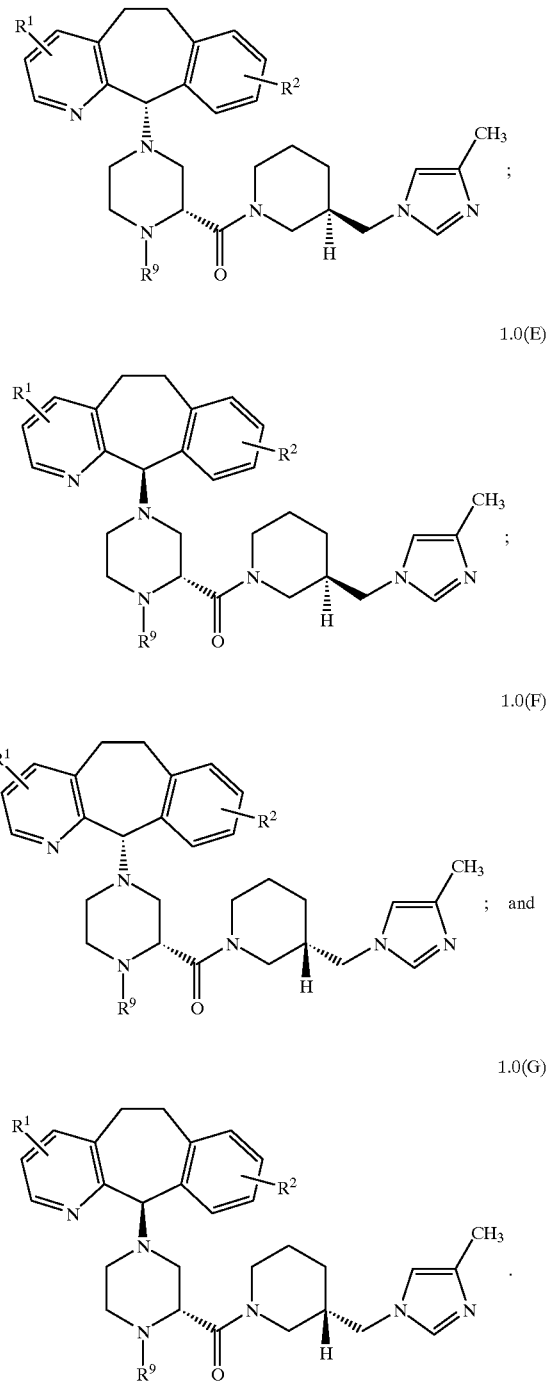

1.0(D)

1.0(E)

1.0(F) ; and 1.0(G)

Lines drawn into the ring systems indicate that the indicated bond may be attached to any of the substitutable ring carbon atoms of any ring when more than one ring is present (e.g., ring 5.0).

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The compounds of formula 1.0 can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Compounds of the invention may be prepared according to the procedures described in WO 95/10516 published Apr. 20, 1995, WO96/31478 published Oct. 10, 1996, WO 97/23478 published Jul. 3, 1997, U.S. Pat. No. 5,719,148 issued Feb. 17, 1998, and copending application Ser. No. 09/094687 filed Jun. 15, 1998 (see also WO98/57960 Published Dec. 23, 1998); the disclosures of each being incorporated herein by reference thereto; and according to the procedures described below.

Compounds of the invention can be prepared according to the reaction schemes described below.

Scheme 1

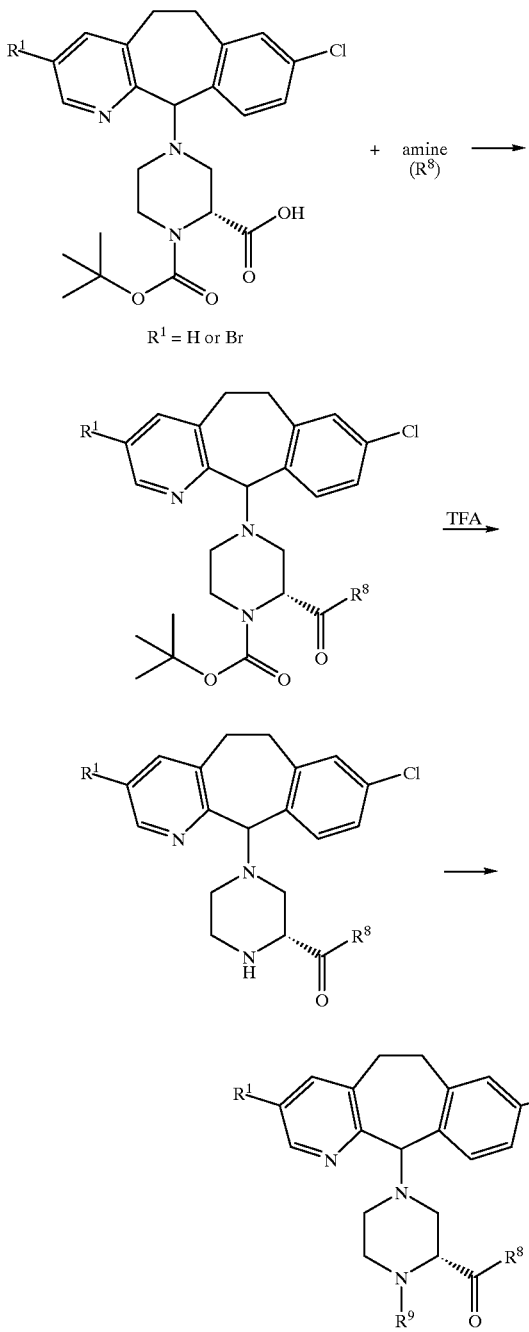

Scheme 2

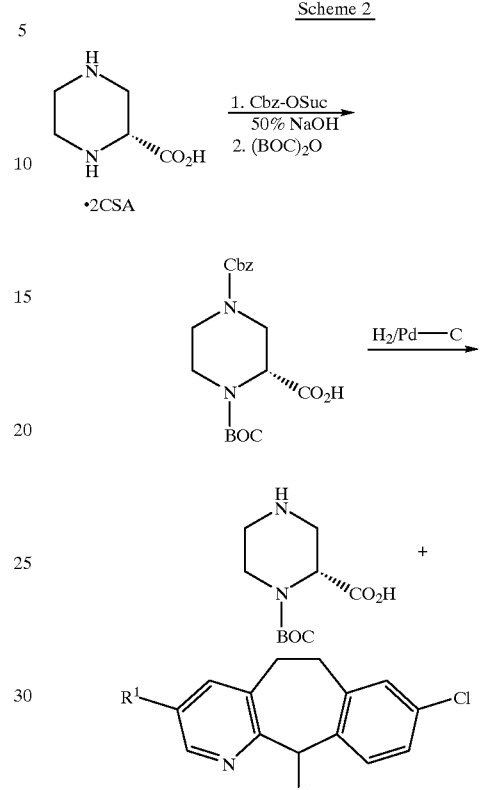

The synthesis of the carboxylic acid (Scheme 1) begins with the differential protection (*J. Med. Chem.* (1994) 37, 3443–3451) of the piperazine dicamphorsulfonic acid salt (*Helv. Chim. Acta*, (1960) 117, 888–896) as illustrated in Scheme 2. Reaction of the distal amine with CBZ-OSuc at pH 11 followed by acylation with (BOC)$_2$O gives the differentially protected acid. Hydrogenation over Pd—C selectively removes the CBZ group and the resulting amino acid was coupled with the desired tricyclic chloride. Compounds containing various functional groups can also be prepared by the different protection strategy shown in Scheme 3. except for the compounds wherein R$^{20}$ is tert-butyl.

Scheme 3

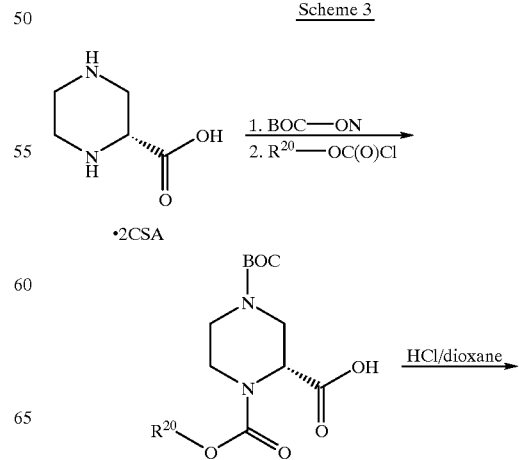

-continued

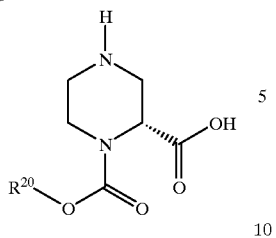

Alternatively, the amine can be coupled to the di-BOC-protected acid intermediate prior to incorporation of the tricycle (Scheme 4). This derivative can be prepared from the di-CSA salt (Scheme 1) upon treatment of the salt with two equivalents $(BOC)_2O$ under basic conditions. Coupling of the desired amine to this intermediate under standard conditions (DEC, HOBT, NMM) gives the amide, which upon TFA-mediated removal of the BOC-protecting groups can be selectively alkylated by the desired tricyclic chloride (TEA, DMF, rt, 48 hours). At this stage, the free amine can be acylated, alkylated, or amidated under conditions obvious to one skilled in the art. When R=Br, chiral HPLC separation can be employed to readily resolve the C-11 diastereomers.

Scheme 4

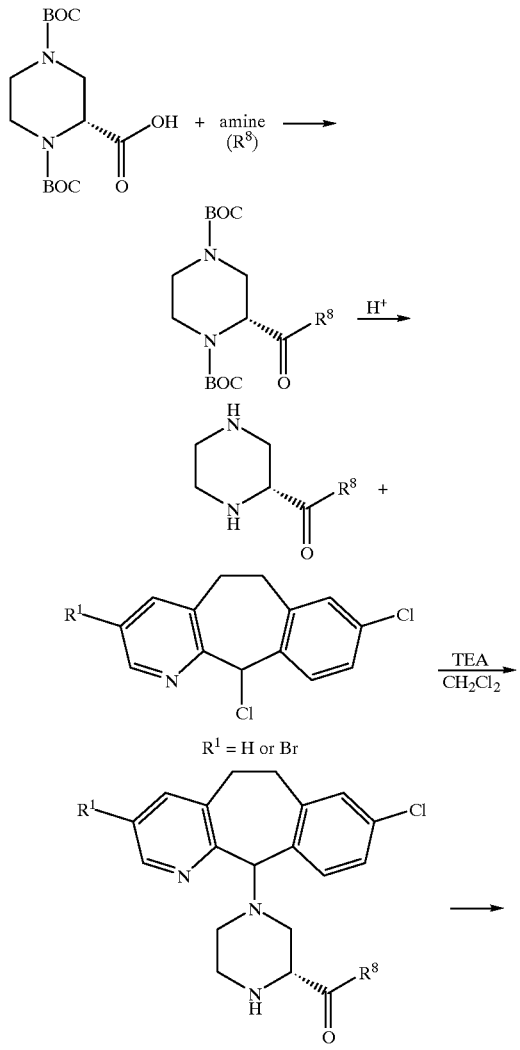

-continued

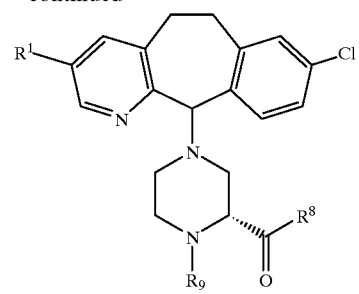

Finally, the anhydride derivative can be opened with the appropriate amine (rt, $CH_2Cl_2$), followed by acylation, alkylation, or amidation of the resulting free amine. From there, a similar sequence as illustrated in Scheme 4 (Scheme 5) may be employed for the synthesis of the desired derivatives.

Scheme 5

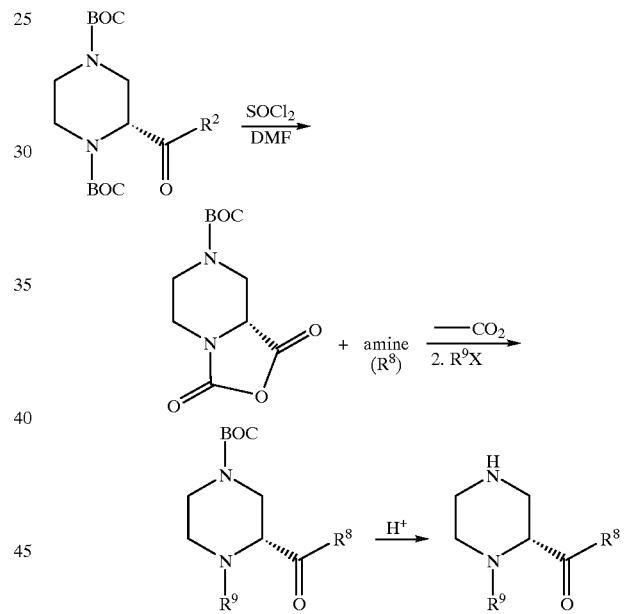

The synthesis of the requisite amines are described generally in the following schemes. In each, one skilled in the art can appreciate the areas where synthetic generalities can be applied for the synthesis of a wider variety of compounds than those specifically illustrated.

The majority of the 2- and 3-substituted piperidine and pyrrolidine derivatives can be prepared through similar methods as illustrated in Scheme 6 beginning with the appropriate amino alcohol. Likewise, various imidazole derivatives may be prepared by employing the sodium salt of the desired imidazole derivative. This general scheme is not applicable where indicated i.e. piperidines with a 2-hydroxymethyl substitutent cannot be prepared using an N-carbamoyl protecting group due to the formation of undesired oxazolones. In these cases the NH must be protected as the N-benzyl or N-allyl derivative.

Scheme 6

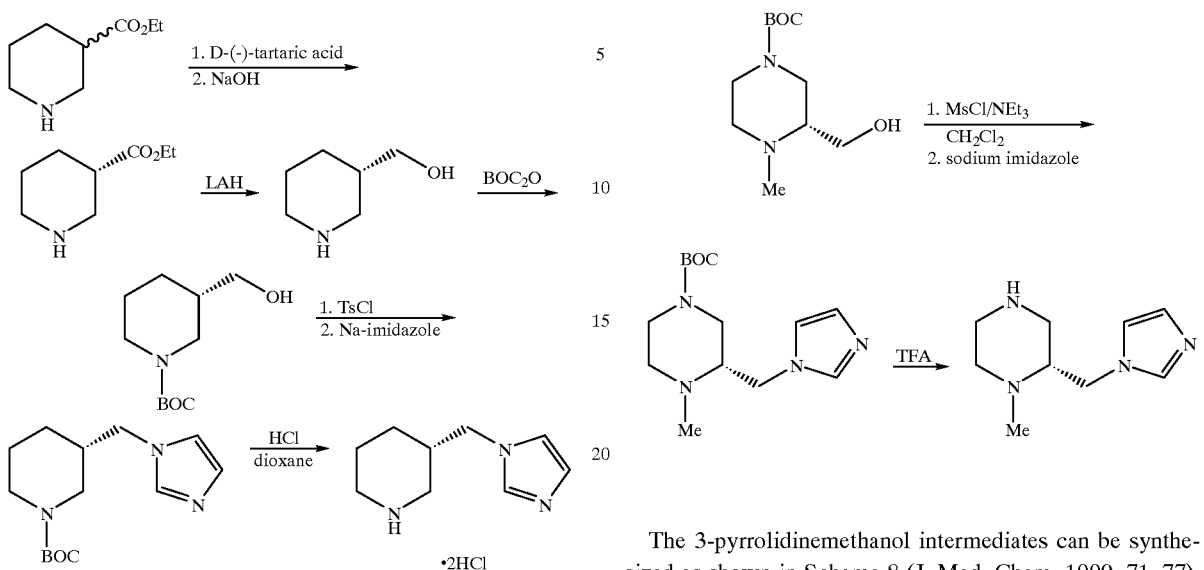

Resolution of ethyl nipecotate with D- or L-tartaric acid (*J. Org. Chem.* (1991) 56, 1166–1170: *Gazz. Chim. Ital.* (1972) 102, 189–195.) gives the desired enantiomer which is converted to the free base by treatment with NaOH. Reduction of the acid with LAH followed by protection of the amine as the BOC derivative gives the alcohol. Treatment of the alcohol with p-toluenesulfonyl chloride in pyridine at 0° C., followed by displacement with the sodium salt of the desired imidazole derivative and removal of the BOC-protecting group with Hcl/dioxane results in the desired amine as the hydrochloride salt.

The corresponding 2- and 3-substituted piperazine derivatives can generally be accessed through the anhydride (Scheme 5) as shown in Scheme 7. Ring opening of the anhydride with EtOH followed by reduction with NaBH$_4$ gives the amino alcohol which can be converted to the N-substituted derivative by reductive amination with paraformaldehyde or another relevant aldehyde. Conversion to the desired imidazole derivative can be accomplished by displacement of the mesylate or tosylate with the sodium salt of the imidazole which upon removal of the BOC-protecting group gives the desired amine.

Scheme 7

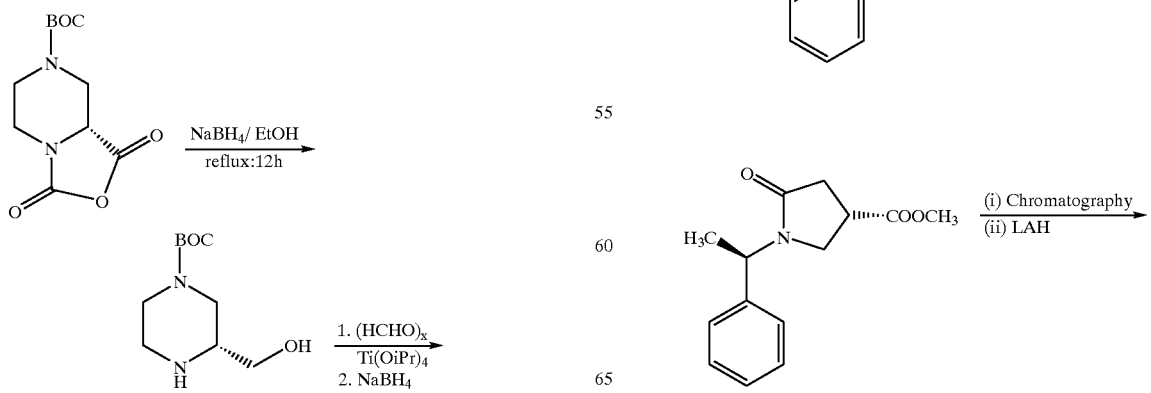

The 3-pyrrolidinemethanol intermediates can be synthesized as shown in Scheme 8 (*J. Med. Chem.* 1990, 71–77). Treatment of the amine with the enoate gives a mixture of diastereomers which are readily separated by silica gel chromatography. Reduction of the amide with LAH and conversion to the imidazole derivative can be carried out as previously described. Catalytic hydrogenation gives the free amine.

Scheme 8

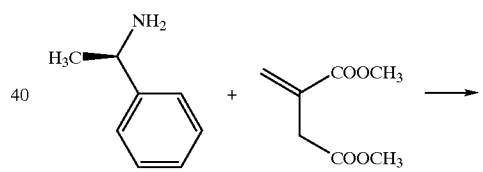

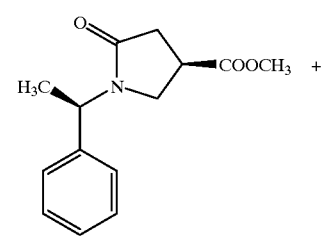

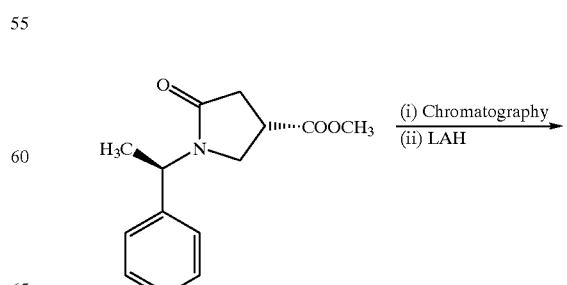

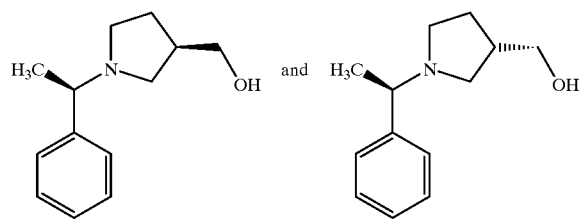

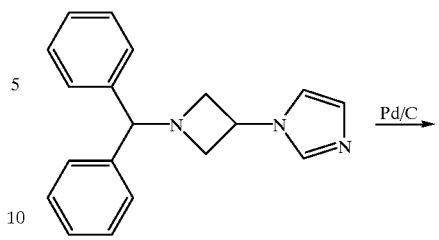

(i) MsCl  
   Et₃N  
(ii) Na-Imizadole (i) MsCl  (ii) Na-  
   Et₃N     Imidazole

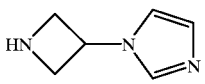

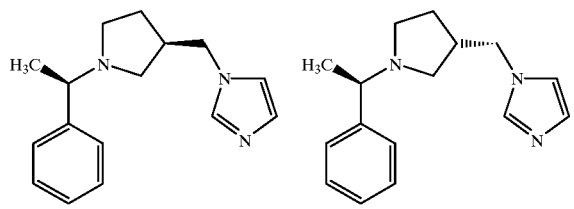

H₂C | Pd/C      H₂C | Pd/C

For 4-membered ring compounds with a methylene spacer between the imidazole and the ring, displacement of the mesylate with NaCN gives the nitrile which is readily hydrolyzed to the acid with NaOH and esterified under Fischer esterification conditions. The desired amine can be realized via transformations previously discussed.

Scheme 10

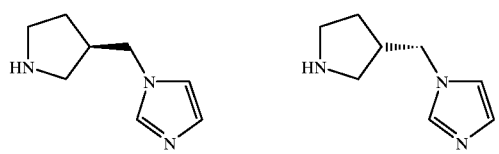

The 4-membered ring analogs can be synthesized as illustrated in Schemes 9 and 10. When the imidazole is directly attached to the ring, the sequence begins with mesylation of the alcohol followed by displacement with the sodium salt of the desired imidazole derivative. Removal of the benzhydryl protecting group is accomplished by catalytic hydrogenation.

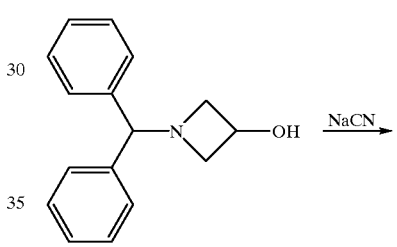

Scheme 9

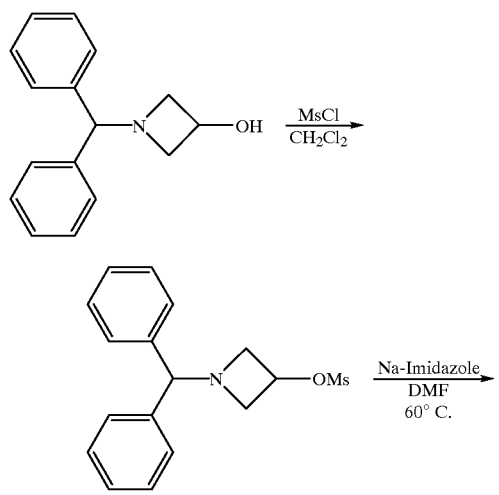

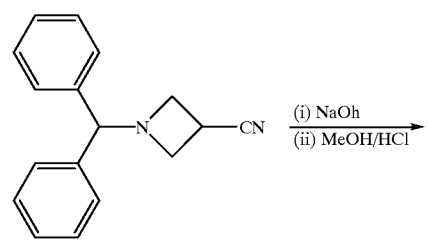

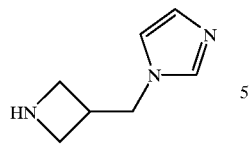

The morpholino side chains are prepared beginning with the epichlorohydrin as shown in Scheme 11 (Heterocycle, 38, 1033, 1994). Ring opening of the epoxide with benzyl amine followed by alkylation of the resulting amino alcohol gives the amide. Reduction of the amide with $BH_3$ gives the morpholine into which the imidazole is incorporated by previously discussed methodology. Removal of the N-benzyl protecting group gives the desired amine.

Following the above procedure, but using the epichlorohydrin

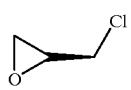

gives the amine

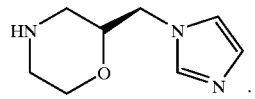

Scheme 11

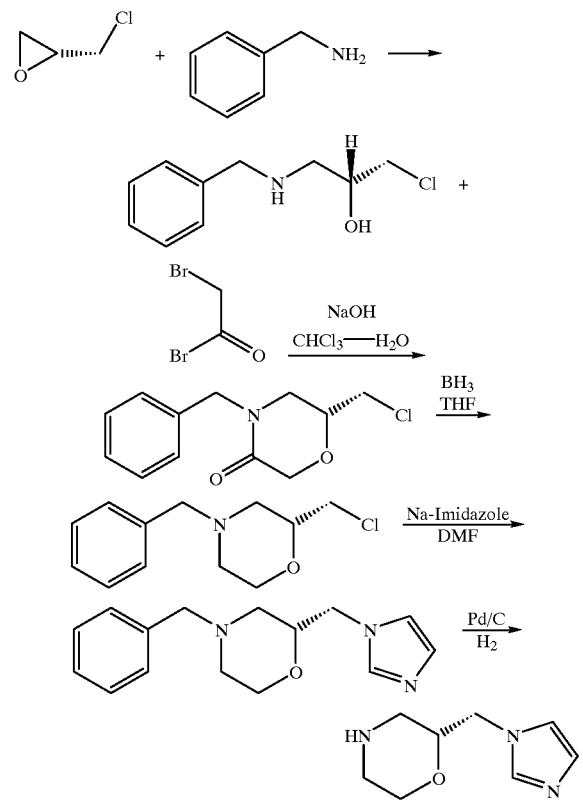

Compounds with a 7-membered ring in the side-chain may be prepared as shown in Scheme 12. α-Bromination of caprolactam followed by displacement with NaCN gives the nitrile. Methanolysis and subsequent reduction with LAH gives the amino alcohol which can easily be converted to the desired compound by previously described methodology.

Scheme 12

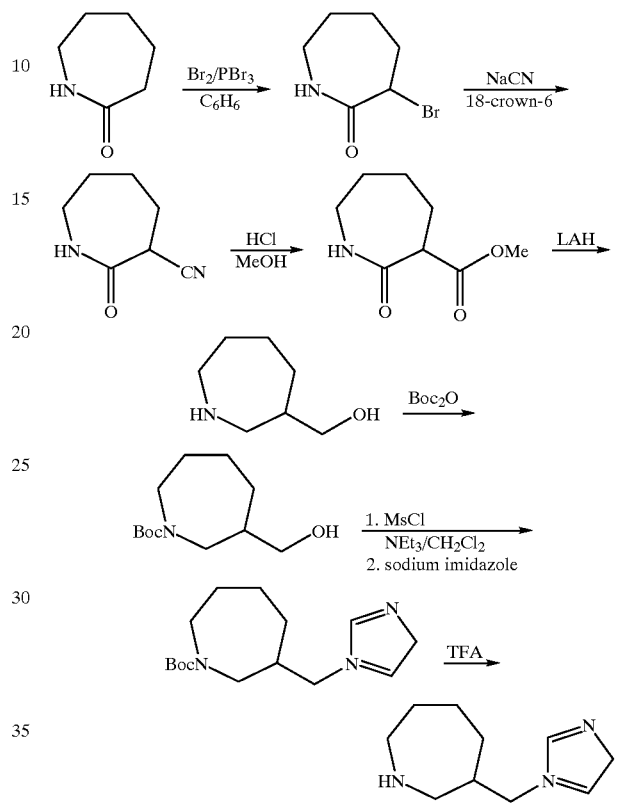

The 4-substituted piperidine-3-methanol derivatives can be synthesized as illustrated in Scheme 13. Protection of the carboxylic acid as the oxazoline also serves to activate the pyridine ring toward nucleoplhilic attack by MeLi. Rearomatization with sulfur, hydrolysis of the oxazoline, and esterification gives the ester which upon quaternization and reduction gives the enoate. Conjugate addition with MeI gives the 4,4-dimethyl derivative. This ester may be converted into the desired compound by previously described procedures.

Scheme 13

Ref. J. Pharm. Sci. (1992)81, 1015; U.S. Pat. (1949) 2546652.

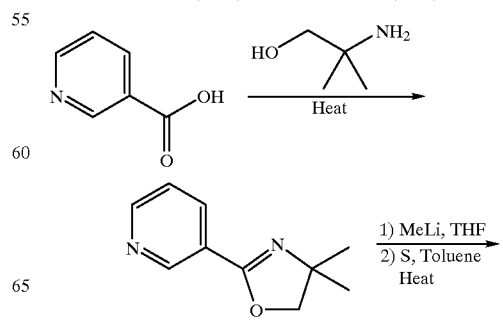

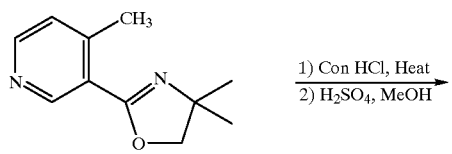
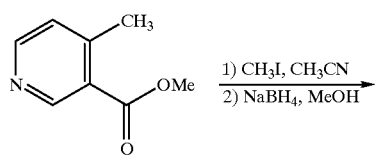
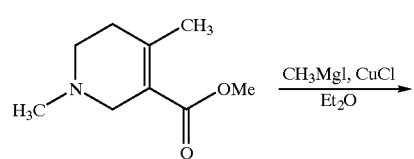
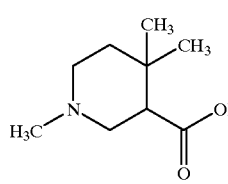
Scheme 14
THIOMORPHOLINE DERIVATIVES
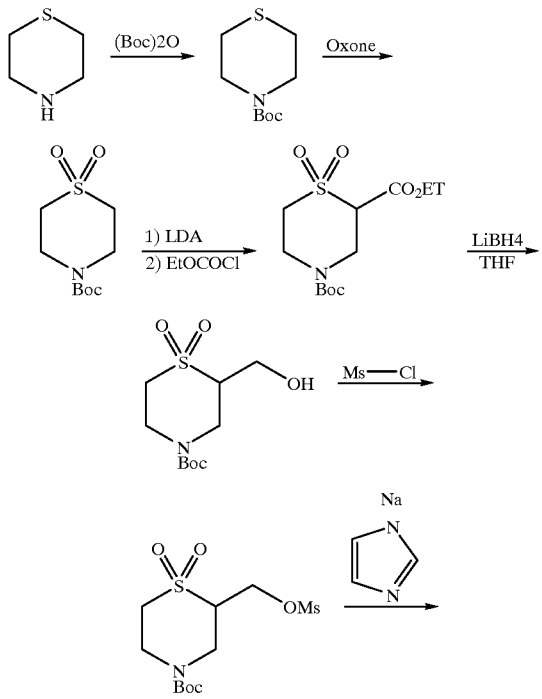
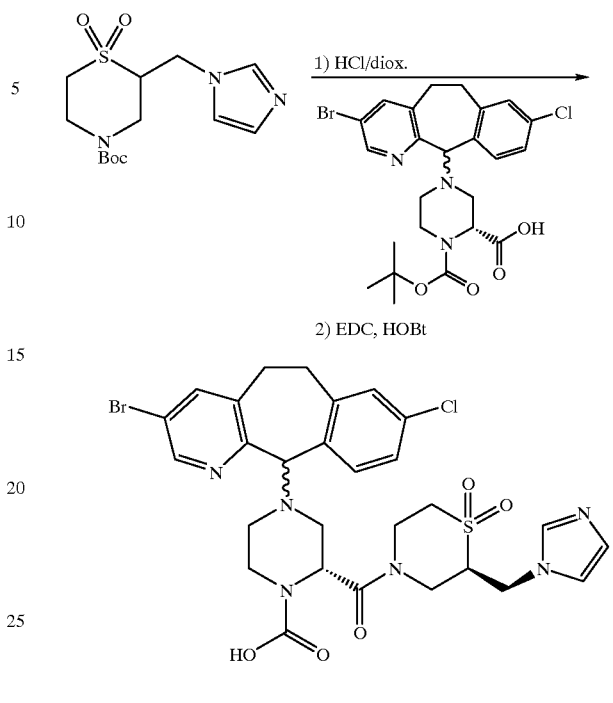
Scheme 15
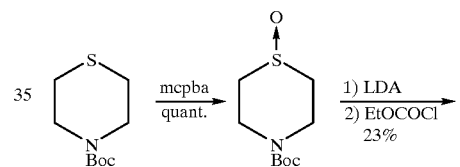
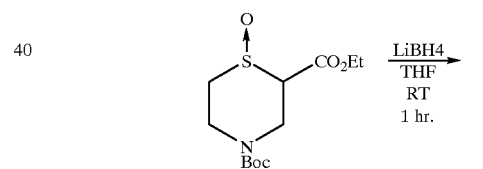
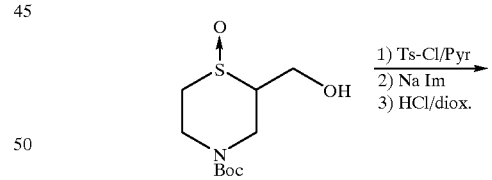
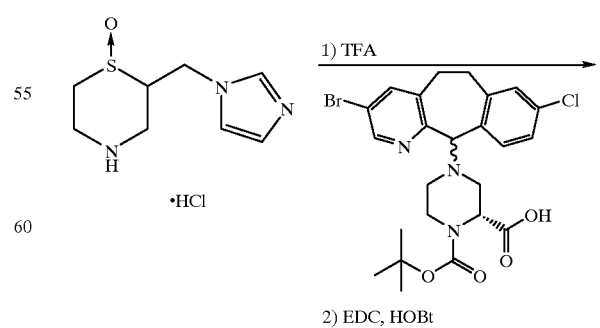

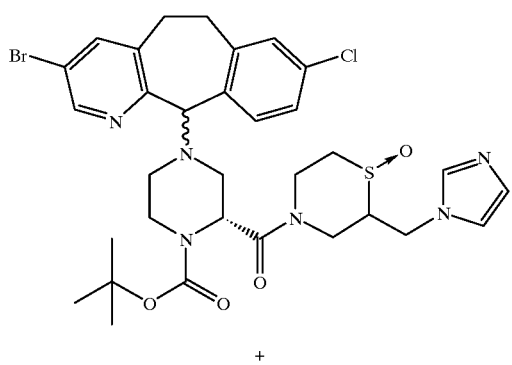
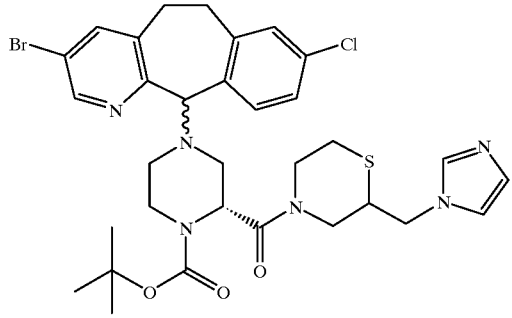
Scheme 16
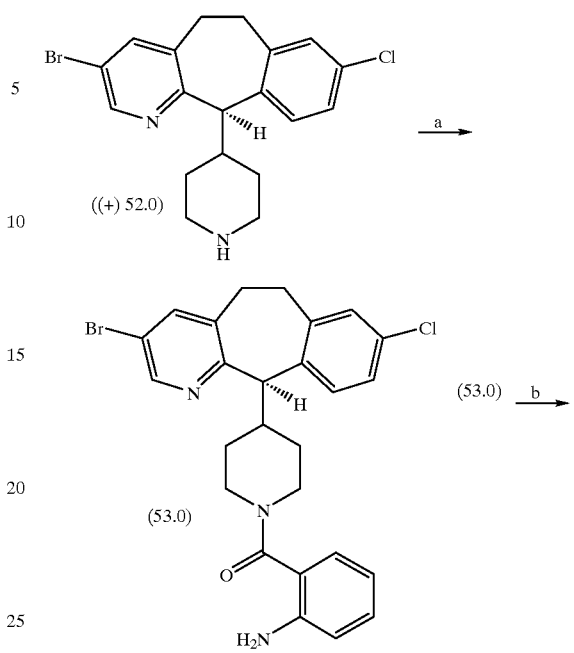
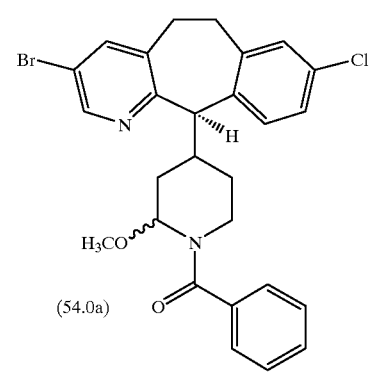
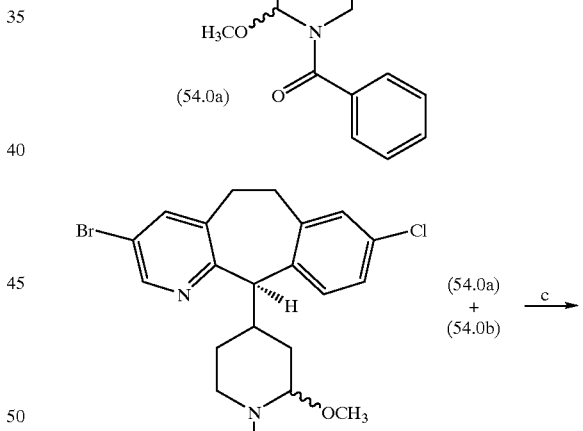
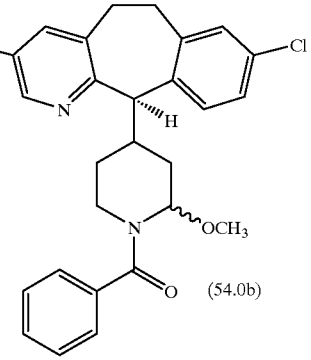
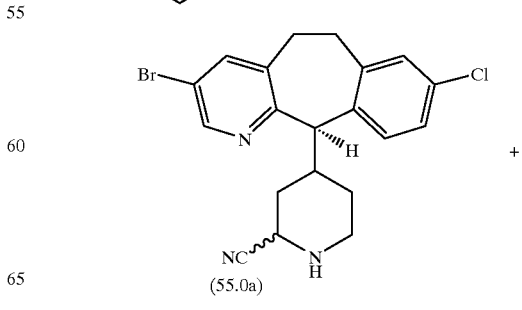

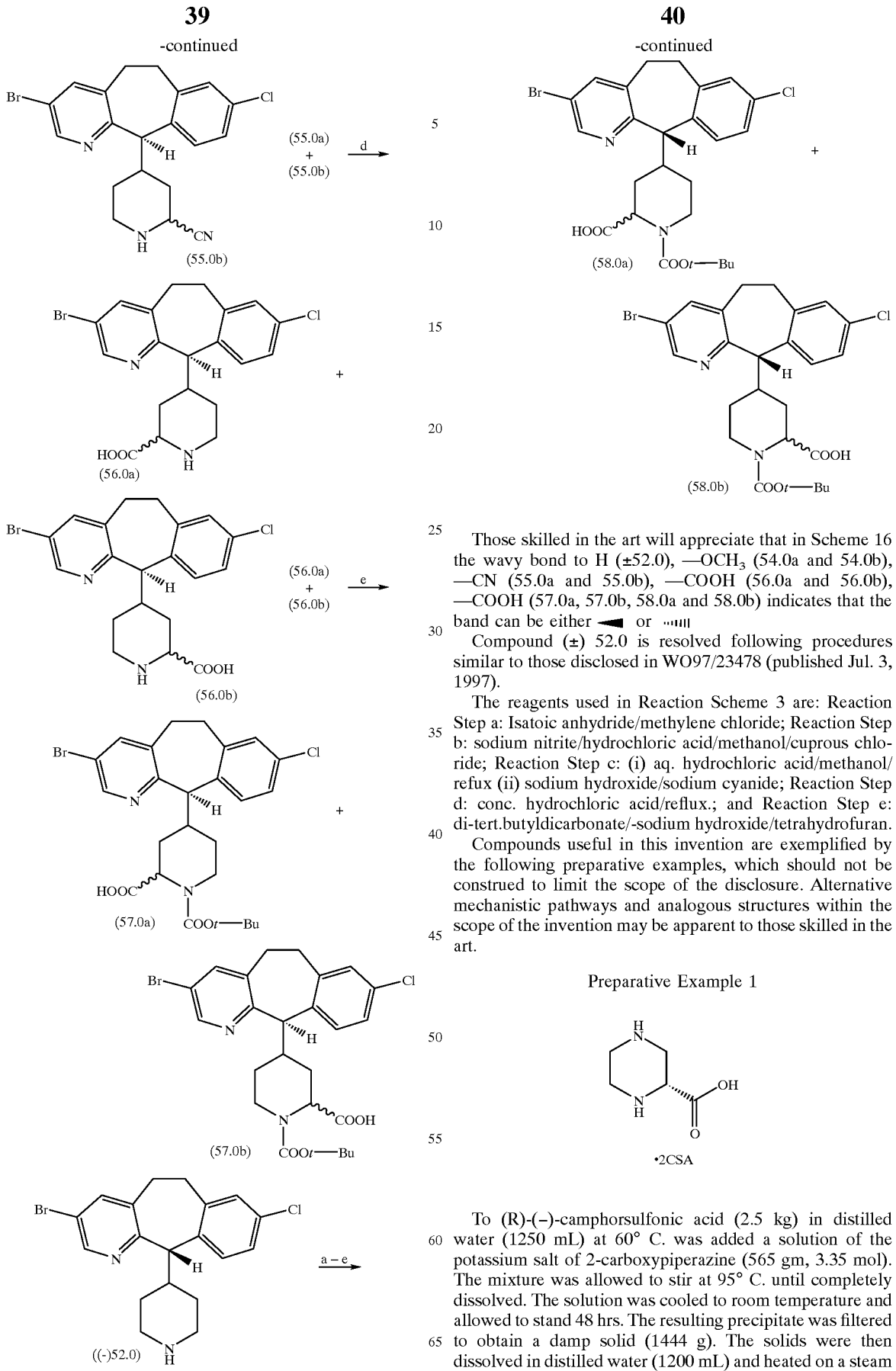

Those skilled in the art will appreciate that in Scheme 16 the wavy bond to H (±52.0), —OCH₃ (54.0a and 54.0b), —CN (55.0a and 55.0b), —COOH (56.0a and 56.0b), —COOH (57.0a, 57.0b, 58.0a and 58.0b) indicates that the band can be either ◄— or ·····|||

Compound (±) 52.0 is resolved following procedures similar to those disclosed in WO97/23478 (published Jul. 3, 1997).

The reagents used in Reaction Scheme 3 are: Reaction Step a: Isatoic anhydride/methylene chloride; Reaction Step b: sodium nitrite/hydrochloric acid/methanol/cuprous chloride; Reaction Step c: (i) aq. hydrochloric acid/methanol/reflux (ii) sodium hydroxide/sodium cyanide; Reaction Step d: conc. hydrochloric acid/reflux.; and Reaction Step e: di-tert.butyldicarbonate/-sodium hydroxide/tetrahydrofuran.

Compounds useful in this invention are exemplified by the following preparative examples, which should not be construed to limit the scope of the disclosure. Alternative mechanistic pathways and analogous structures within the scope of the invention may be apparent to those skilled in the art.

Preparative Example 1

To (R)-(−)-camphorsulfonic acid (2.5 kg) in distilled water (1250 mL) at 60° C. was added a solution of the potassium salt of 2-carboxypiperazine (565 gm, 3.35 mol). The mixture was allowed to stir at 95° C. until completely dissolved. The solution was cooled to room temperature and allowed to stand 48 hrs. The resulting precipitate was filtered to obtain a damp solid (1444 g). The solids were then dissolved in distilled water (1200 mL) and heated on a steam bath until all solids dissolved. The resulting solution was cooled slowly to room temperature and let stand 72 hrs. The crystalline solids were filtered to give a white crystalline solid (362 g), $[\alpha]_D = -14.9°$.

Preparative Example 2

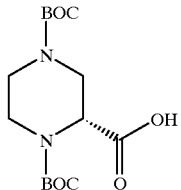

The title compound from Preparative Example 1 (362 gm, 0.608 mol) was dissolved in distilled water (1400 mL) and methanol (1400 mL). 50% NaOH was added to the stirred reaction mixture until the pH reached ~9.5. To this solution was added di-tert.butyldicarbonate (336 gm, 1.54 mol) portionwise. The pH of the reaction mixture was maintained at 9.5 with 50% NaOH (total of 175 ml), and the reaction mixture stirred for 2.5 hours to obtain a white precipitate. The reaction mixture was diluted with ice/water (9000 mL) and washed with $Et_2O$ (2000 mL). The $Et_2O$ was discarded and the pH of the aqueous layer adjusted to pH 3.0 by the portionwise addition of solid citric acid and extracted with $CH_2Cl_2$ (3×2000 mL). The organic layers were combined, dried over $Na_2SO_4$, filtered and evaporated to give the title compound as a white glassy solid (201.6 g). FABMS: $MH^+=331$.

Preparative Example 3

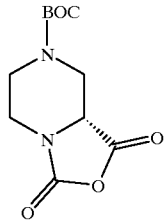

To an ice cold solution DMF (49.6 ml) under a nitrogen atmosphere was added, dropwise, $SOCl_2$ (46.7 ml) over a period of 5 minutes in a 5 L round bottom flask The reaction mixture was allowed to stir for 5 minutes, warmed to room temperature, and stirred 30 minutes. The resulting solution was cooled to 0° C. and the title compound from Preparative Example 2 (201.6 gm, 0.61 mmol) in pyridine (51.7 mL) and $CH_3CN$ (1900 mL) was added via canulae. The resulting solution was warmed to room temperature to obtain a yellowish turbid solution and stirred 18 hours. The reaction mixture was filtered and the filtrate poured into ice water (7L) and then extracted with EtOAc (4×2000 mL). The combined organics were dried over $Na_2SO_4$, filtered, and evaporated to dryness in vacuo to give the title product as a white solid (115.6 g 73% yield).

Preparative Example 4

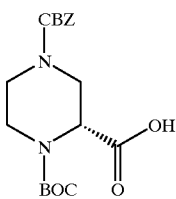

The title compound from Preparative Example 1 (17.85 gm, 30 mmol) was dissolved in distilled water (180 mL). Dioxane (180 mL) was added and the pH adjusted to ~11.0 with 50% NaOH. The reaction mixture was cooled to 0–5° C. in an ice-MeOH bath and a solution of benzylchloroformate (4.28 mL, 30 mmol) in dioxane (80 mL) was added over a period of 30–45 minutes while stirring at 0–5° C. and keeping the pH at 10.5 to 11.0 with 50% NaOH. After the addition was complete, stirring was continued for 1 hr. The reaction mixture was then concentrated under reduced pressure. The residue was dissolved in distilled water (180 mL), the pH adjusted slowly to 4.0 with 1N HCl, and extracted with EtOAc (3×180 mL). The combined organics were dried over $MgSO_4$, filtered, and evaporated to obtain the N,N-di-CBZ-2-carboxy-piperazine byproduct. The pH of the aqueous layer was adjusted to ~10.5 with 50% NaOH and solid $(Boc)_2O$ (7.86 gm, 36 mmol) was added and the mixture was stirred while keeping the pH at ~10.5 with 50% NaOH. After 1 hr. the pH stablized. The reaction was checked by tlc (30% $MeOH/NH_3/CH_2Cl_2$) and if not complete, more $(Boc)_2O$ was added keeping the pH at ~10.5. When reaction was shown to be complete by TLC, the reaction mixture was washed with $Et_2O$ (2×180 mL) (check that the product is not in the $Et_2O$ layer and dispose of the $Et_2O$ layer). The aqueous layer was cooled in an ice bath and pH to adjusted to 2.0 with 1N HCl (slowly) (get bubbling initially). The aqueous layer was extracted with EtOAc (3×200 mL) and the combined organics dried over $MgSO_4$, filtered and evaporated in vacuo to obtain a white solid (9.68 g, 88% yield).

Preparative Example 5

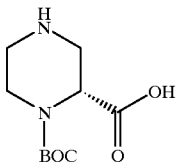

The title compound from Preparative Example 4 (9.6 gm, 26.3 mmol) was dissolved in absoluteEtOH (100 mL) in a hydrogenation vessel. The vessel was flushed with $N_2$ and 10% Pd/C (3.0 g, 50% by weight with water) was added. The mixture was hydrogenated at 55 psi of $H_2$ for 18 hours during which time a precipitate formed. When the reaction was complete (TLC, 30% $MeOH/NH_3/CH_2Cl_2$), the reaction mixture was filtered through a pad of celite, and the pad washed with EtOH followed by distilled $H_2O$. The filtrate was evaporated to ~⅓ the volume and distilled $H_2O$ (200 mL) was added. The resulting solution was extracted with EtOAc (contains pure N,N-Di-Boc-2-carboxy-piperazine which was saved). The water layer was evaporated to dryness with azeotropic removal of residual $H_2O$ with methanol (2×) to give pure product (3.98 g).

Preparative Example 6
4-(3-bromo-8-chloro-6, 11-dihydro-5H benzo[5,6]cyclohepta[1,2-b]pyridin-11-yl)-1-[(1,1-dimethylethoxy)carbonyl]-2(R)-piperazinecarboxylic acid

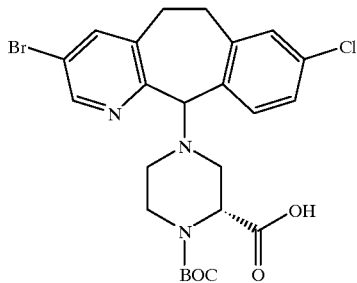

The tricyclic alcohol

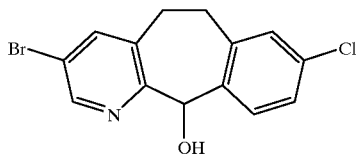

(5.6 gm, 17.33 mmol) was dissolved in $CH_2Cl_2$ (56 mL) and $SOCl_2$ (2.46 mL) was added while stirring under a dry $N_2$ atmosphere. After 5 hrs. the tlc was checked (by adding an aliquot of the reaction mixture to 1N NaOH and shaking with $CH_2Cl_2$) and checking the $CH_2Cl_2$ layer by tlc using 50% EtOAc/Hexanes as the eluent). The mixture was evaporated to give a gum which was evaporated from dry toluene twice and once from $CH_2Cl_2$ to give a foamy solid. The resulting chloro-tricyclic compound was dissolved in dry DMF (100 mL) and the title compound from Preparative Example 5 (3.98 gm) was added followed by triethylamine (12.11 mL) and the mixture stirred at ambient temperature under a nitrogen atmosphere. After 24 hours. the reaction mixture was concentrated and the residue dissolved in EtOAc (200 mL) and washed with brine. The brine layer was extracted with EtOAc (2x) and the combined organics were dried over $MgSO_4$, filtered, and evaporated to give a foamy solid. The solid was chromatographed on a 1½"×14" column of silica gel eluting with 2L of 0.4% 7N MeOH/$NH_3$:$CH_2Cl_2$, 6L of 0.5% 7N MeOH/$NH_3$:$CH_2Cl_2$, 2L of 0.65% 7N MeOH/$NH_3$:$CH_2Cl_2$, 2L of 0.8% 7N MeOH/$NH_3$:$CH_2Cl_2$, 4L of 1% 7N MeOH/$NH_3$:$CH_2Cl_2$, 2L of 3% 2N MeOH/$NH_3$:$CH_2Cl_2$, 2L of 5% 2N MeOH/$NH_3$:$CH_2Cl_2$, 2L of 10% 2N MeOH/$NH_3$:$CH_2Cl_2$, 2L of 15% 2N MeOH/$NH_3$:$CH_2Cl_2$, 4L of 20% 2N MeOH/$NH_3$:$CH_2Cl_2$ to obtain 4.63 gm of final product.

Preparative Example 7
Step A
Ref: *Gazz. Chim. Ital.* (1972) 102, 189–195; *J. Org. Chem.* (1991) 56, 1166–1170.

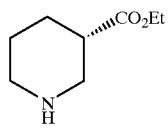

Ethyl nipecotate (70.16 g, 0.446 mmol) and D-tartaric acid (67 g, 1.0 eq) were dissolved in hot 95% EtOH (350 mL). The resulting solution was cooled to room temperature and filtered and the crystals washed with ice-cold 95% EtOH. The crystals were then recrystallized from 95% EtOH (550 mL) to give the tartrate salt (38.5 g, 56% yield). The salt (38.5 g) was dissolved in water (300 mL) and cooled to 0° C. before neutralizing with 3M NaOH. The solution was extracted with $CH_2Cl_2$ (5×100 mL) and the combined organics dried over $Na_2SO_4$ and concentrated under reduced pressure to give a clear oil (19.0 g, 89% yield). CIMS: $MH^+$=158.
Step B

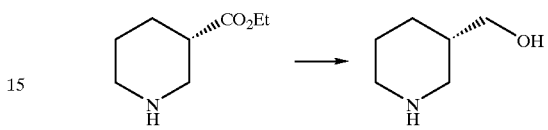

LAH (118 mL, 1.0 M in $Et_2O$, 1.0 eq.) was added to a solution of the title compound from Step A (18.5 g, 0.125 mmol) in THF (250 mL) at 0° C. over 20 minutes. The resulting solution was warmed slowly to room temperature and then heated at reflux 2 hours. The reaction was cooled to room temperature and quenched by the slow addition of saturated $Na_2SO_4$. The resulting slurry was dried by the addition of $Na_2SO_4$, filtered through Celite and concentrated to give a colorless oil (13.7 g, 98% crude yield). CIMS: $MH^+$=116; $[\alpha]^{20}_D$=-8.4° (5.0 mg in 2 mL MeOH).
Step C

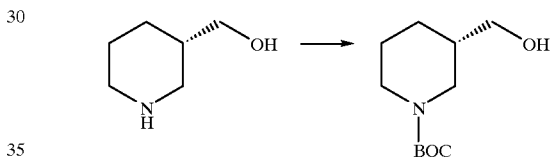

The title compound from Step B (13.6 g, 0.104 mmol) was dissolved in MeOH (100 mL) and $H_2O$ (100 mL) and di-tert-butyl dicarbonate (27.24, 1.2 eq.) was added portionwise keeping the pH >10.5 by the addition of 50% NaOH. The reaction mixture was stirred at room temperature an additional 2.5 hours and concentrated in vacuo. The residue was diluted with $H_2O$ (350 mL) and extracted with $CH_2Cl_2$ (3×150 mL). The combined organics were dried over $Na_2SO_4$, filtered, and concentrated under reduced pressure. The crude product was purified by Flash chromatography using a 50% EtOAc in hexanes solution as eluent to give a white solid (12.13 g, 48% yield). FABMS: $MH^+$=216; $[\alpha]^{20}_D$=+15.2 (5.0 mg in MeOH).
Step D

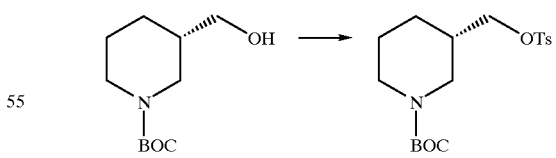

p-Toluenesulfonyl chloride (12.75 g, 1.2 eq.) was added portionwise to the title compound from Step C (12.00 g, 55.74 mmol) in pyridine (120 mL) at 0° C. The resulting solution was stirred 0° C. overnight. The reaction mixture was diluted with EtOAc (300 mL) and washed with cold 1N HCl (5×300 mL), saturated $NaHCO_3$ (2×150 mL), $H_2O$ (1×100 mL), brine (1×100 mL), and dried over $Na_2SO_4$ and concentrated in vacuo to give a pale yellow solid (21.0 g, 100% crude yield). FABMS: $MH^+$=370.

Step E

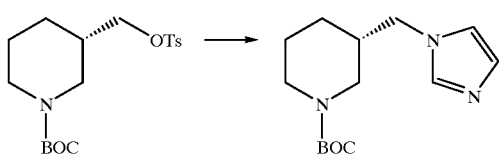

The title compound from Step D (21.0 g, 55.74 mmol) in DMF (300 mL) was treated with sodium imidazole (8.37 g, 1.5 eq.) and the resulting solution heated at 60° C. for 2 hours. The reaction mixture was cooled to room temperature and concentrated in vacuo. The residue was diluted with H$_2$O (300 mL) and extracted with CH$_2$Cl$_2$ (3×150 mL). The combined organics were dried over Na$_2$SO$_4$, filtered, and concentrated. The crude product was purified by flash chromatography using a 7% MeOH in CH$_2$Cl$_2$ solution as eluent to give a pale yellow solid (7.25 g, 49% yield). FABMS: MH$^+$=266; [α]$^{20}_D$=+8.0 (5.0 mg in MeOH).

Step F

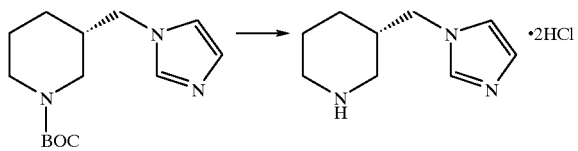

The title compound from Step E (5.50 g, 20.73 mmol) stirred at room temperature in 4M HCl in dioxane (50 mL) overnight. The resulting solution was concentrated and the residue triturated with Et$_2$O to give a yellow solid (4.90 g, 99% yield). CIMS: MH$^+$=166.

Preparative Example 8

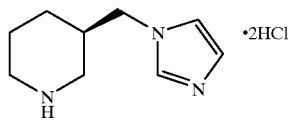

By essentially the same procedure set forth in Preparative Example 7 except using L-tartaric acid instead of D-tartaric acid in Step A, the title compound was prepared.

Preparative Example 9

Step A

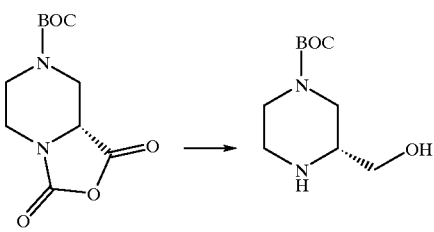

A mixture of the piperazine anhydride (2.56 g, 10.00 mmol, 1.0 eq.) and sodium borohydride (965 mg, 25.00 mmol, 2.5 eq.) in absolute ethanol (50 ml) was gently refluxed under a nitrogen atmosphere for 48 h. The reaction volume was decreased to approximately 10 ml under house vacuum and diluted with brine (50 ml). The mixture was extracted with ethyl acetate (8×25 ml). The combined organic extracts were washed with brine (50 ml), dried over Na$_2$SO$_4$, filtered, and concentrated under house vacuum at 30° C. The residue was flash chromatographed (CH$_2$Cl$_2$: 10% NH$_4$OH/MeOH=17:1 v/v) over silica gel to give the title compound (1.09 g, 50%) as a light-yellow, viscous oil. EIMS: m/z 217 ([M+H[$^+$, 46%), 161 (B$^+$). HR-MS (FAB): Calculated for C$_{10}$H$_{21}$N$_2$O$_3$ ([M+H]$^+$): 217.1552. Found: 217.1549.

Step B (Bhattacharyya, S. *Tetrahedron Lett.* 1994, 35, 2401.)

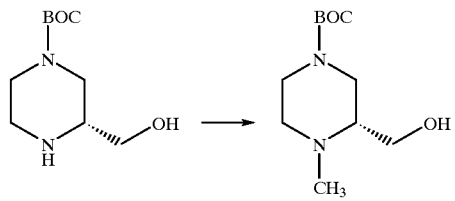

A mixture of the title compound from Step A (1.09 g, 5.04 mmol, 1.0 eq.), paraformaldehyde (300 mg, .10.08 mmol, 2.0 eq.), and titanium isopropoxide (1.5 ml, 5.04 mmol, 1.0 eq.) in absolute ethanol (5 ml) was stirred at 70° C. for 30 minutes and at room temperature for another 30 minutes. Sodium borohydride (195 mg, 5.04 mmol, 1.0 eq.) was added to the colorless solution. The solution was stirred at room temperature for 12 h and at 60° C. for another 3 h. The solution was cooled to 0° C. and treated with a 2.0 M aqueous ammonia solution (25 ml, 50.00 mmol, excess) to give a snow-white suspension. The suspension was filtered through a Celite 521 plugs and the filtrate was extracted with diethyl ether (4×25 ml). The ethereal extracts were combined and washed with brine (10 ml), dried over Na$_2$SO$_4$, filtered, and concentrated under house vacuum at 30° C. The residue was flash chromatographed (CH$_2$Cl$_2$: 10% NH$_4$OH/MeOH=9:1 v/v) over silica gel to give the title compound (1.10 g, 95%) as a light-yellow, viscous oil. MS (EI): m/z 231 ([M+H]$^+$, 59%), 175(B$^+$). HR-MS(FAB): Calculated for C$_{11}$H$_{22}$N$_2$O$_3$ ([M+H]$^+$): 231.1709. Found: 231.1716.

Step C

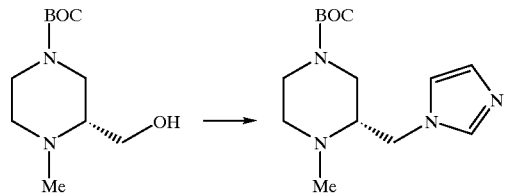

Methanesulfonyl chloride (296 μl, 3.80 mmol, 1.25 eq.) was added dropwise to a stirred solution of the title compound from Step B (700 mg, 3.04 mmol, 1.0 eq.) and triethylamine (640 μl, 4.56 mmol, 1.50 eq.) in anhydrous dichloromethane (5 ml) at 0° C. under a nitrogen atmosphere. The resulting yellow suspension was stirred at 0° C. for 1 h and at room temperature for another 3 h. The mixture was poured onto brine (25 ml) and extracted with dichloromethane (5×10 ml). The combined organic extracts were dried over Na$_2$SO$_4$, filtered, and concentrated under house vacuum at 25° C. to give a quantitative yield (940 mg) of crude mesylate, which was used directly in the next transformation (vide infra) without any attempts at characterization or purification.

A mixture of crude mesylate (940 mg, 3.05 mmol, 1.0 eq.) and sodium imidazole (608 mg, 6.08 mmol, 2.0 eq.) in anhydrous N,N-dimethylformamide (10 ml) was stirred at 60° C. for 12 h under a nitrogen atmosphere. The brownish mixture was cooled to room temperature and diluted with brine (25 ml). The layers were separated and the aqueous layer was extracted with dichloromethane (4×25 ml). The combined organic extracts were dried over $Na_2SO_4$, filtered, and concentrated under house vacuum at 50° C. The residue was flash chromatographed ($CH_2Cl_2$: 10% $NH_4OH/MeOH$= 19:1 v/v) over silica gel to give the title compound (432 mg, 1.54 mmol, 51%) as a thick, greenish oil. MS (EI): m/z 281 ([M+H]$^+$, B$^+$), 225 (79), 157 (91). HR-MS (FAB): Calculated for $C_{14}H_{25}N_4O_2$([M+H]$^+$): 281.1978. Found: 28 1 11976.

Step D

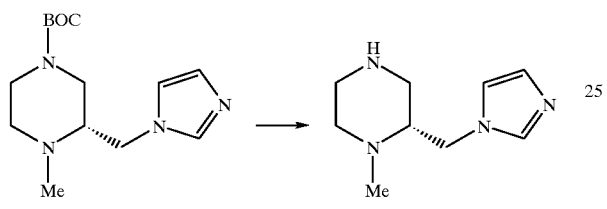

A solution of the title compound from Step C (400 mg, 1.43 mmol, 1.0 eq.) in anhydrous trifluoroacetic acid-dichloromethane (10 ml, 1:1 v/v) was stirred at room temperature under a nitrogen atmosphere for 12 h. The volatiles were removed under house vacuum at 40° C. and the residue was redissolved in 2.0 M aqueous NaOH solution (10 ml). The volatiles were again removed under house vacuum, but at a bath temperature of 60° C. The residue was flash chromatographed ($CH_2Cl_2$: 10% $NH_4OH/MeOH$=6:4 v/v) over silica gel to give the title compound (136 mg, 0.76 mmol, 53%) as a thick, yellow oil. MS (EI): m/z 181 ([M+H]$^+$, B$^+$), 161 (76). HR-MS (FAB): Calculated for $C_9H_{17}N_4$ ([M+H]$^+$): 181.1453. Found: 181.1458.

Preparative Example 10

Step A
N-Butoxycarbonyl-thiomorpholine

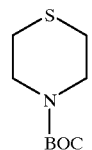

Thiomorpholine (6 gm, 58 mmol) was dissolved in $CH_2Cl_2$ (200 mL) under a dry nitrogen atmosphere and the reaction mixture cooled in an ice bath. A solution of di-tert.butyl-dicarbonate (15.3 gm, 70 mmol) in $CH_2Cl_2$ (50 mL) was added dropwise and the reaction mixture stirred for 4 hours. The reaction mixture was washed with brine, followed by saturated $NaHCO_3$, dried over $MgSO_4$, filtered, and evaporated to obtain 14.37 gm of title product as a crystalline solid. mp=72.9–78.9° C.

Step B
N-Butoxycarbonyl-thiomorpholinesulfone

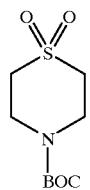

The title compound from Step A (16 gm, 78.7 mmol) was dissolved in 50% $CH_3OH$—$H_2O$ (500 mL) at 0° C. A slurry of Oxone® (72.6 gm, 118.05 mmol) was added portionwise while monitoring the pH at 10.5 with 25% NaOH. After 2 hours, the reaction mixture was filtered and the $CH_3OH$ was evaporated under reduced pressure. The residue was extracted with EtOAc 3 times to obtain 15.5 gm (84%) of title product as a crystalline solid. mp=157–159.2° C.

Step C
N-Butoxycarbonyl-2-carboxyethyl-thiomorpholinesulfone

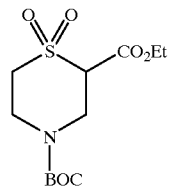

The title compound from Step B (3.0 gm, 12.7 mmol) was dissolved in THF (30 mL). The reaction mixture was cooled to −78° C. in a dryice acetone bath under a dry nitrogen atmosphere and 8.5 ml of a 1.5 Molar solution of lithium diisopropylamide in cyclohexane (LDA) was added dropwise and the solution stirred for ½ hour. Ethylchloroformate (1.83 mL, 19.05 mmol) was added dropwise and the solution stirred at −78° C. for 1 hour. The temperature was allowed to rise to ambient and the reaction mixture stirred an additional 2 hours. The reaction mixture was added to brine and the product extracted three times with EtOAc to obtain 2.87 gm of crude product which was used in the next step without purification.

Step D
N-Butoxycarbonyl-2-hydroxymethyl-thiomorpholinesulfone

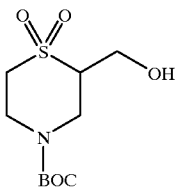

The crude tile compound from Step C was dissolved in 30 ml of THF, cooled in an ice bath, and stirred. A 2M THF solution of Lithium borohydride (9 mL, 18 mmol) was added dropwise and the reaction mixture stirred for 3 hours. 1N HCl (~10 mL) was added slowly and the mixture stirred for 5 min. 1N NaOH (~20 mL) was added and the crude product extracted with ethylacetate, dried over magnesium sulfate, filtered, and evaporated to obtain a crude oil. The crude oil was chromatographed on silica gel using 20% ethyl acetate/hexanes to 40% ethylacetate/hexanes to obtain 0.88 gm of title product as a solid. mp=126.9–131.9° C.

Step E
N-Butoxycarbonyl-2-imidazolylmethyl-thiomorpholinesulfone

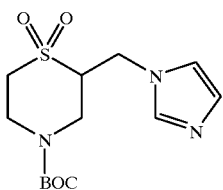

The title compound from Step D (0.56 gm, 2.14 mmol) and diisopropylethylamine(0.372 ml, 2.14 mmol) was dissolved in 5 mL of dichloromethane. Methanesulfonyl chloride (0.198 ml, 2.56 mmol) was added and the reaction mixture stirred under a dry nitrogen atmosphere for 30 min. The reaction mixture was added slowly to melted imidazole (2.9 gm, 20 eq.) at 120° C. After the dichloromethane evaporated the reaction mixture was cooled to ambient to obtain a brown solid. The solid was dissolved in water and the product extracted with ethylacetate three times to obtain 0.449 gm of title product. mp=149.7–151.3° C., FABMS (M+1)=316.2.

Step F
Preparation of 2-imidazolylmethyl-thiomorpholinesulfone

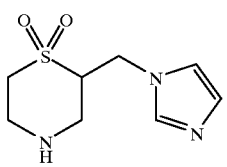

·2HCl

The title compound from Step E (0.44 gm, 1.4 mmol) was dissolved in 5 ml of 4NHCl/dioxane and stirred for 1 hr. The mixture was evaporated to obtain 0.45 gm of title product.

Preparative Example 11

Step A
N-Butoxycarbonyl-thiomorpholinesulfoxide

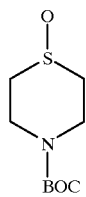

N-Butoxycarbonyl-thiomorpholine from Preparative Example 10 Step A (7.07 gm, 58 mmol) was dissolved in 200 ml of dichloromethane. 50–60% mCPBA (13.7 gm, 80 mmol) was added portionwise over a period of 15 min. After 2 hours at ambient temperature the reaction mixture was washed with sat. sodium bisulfite, followed by sat. sodium bicarbonate, and the dried over magnesium sulfate, filtered, and evaporated to obtain 13.08 gm of a white solid. FABMS (M+1)=220.

Step B

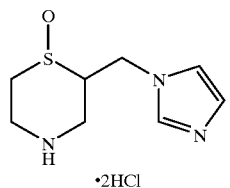

·2HCl

By essentially the same procedures set forth in Preparative Example 10 Step C–F, the title compound was prepared.

Preparative Example 12

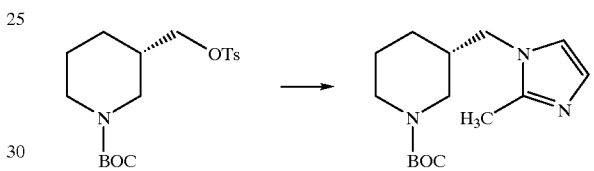

2-Methylimidazole (0.27 g, 1.3 eq.) was added to a solution of NaH (0.13 g, 1.3 eq., 60% in mineral oil) in DMF (5 mL) at room temperature and the resulting solution stirred 20 minutes before adding the title compound from Preparative Example 7 Step D (0.94 g, 2.54 mmol). The reaction mixture was heated to 60° C. for 2 hours, cooled to room temperature and concentrated. The crude product was diluted with $H_2O$ (50 mL) and extracted with $CH_2Cl_2$ (3×75 mL). The combined organics were dried over $Na_2SO_4$, filtered and concentrated in vacuo. The product was purified by flash chromatography using a 7% MeOH in $CH_2Cl_2$ solution as eluent to give a white solid (0.66 g, 93% yield). CIMS: $MH^+$=280; $[\alpha]^{20}_D$=+4.9 (6.5 mg in 2.0 mL MeOH).

By essentially the same procedure set forth in Preparative Example 7 Step E, the following title compounds in Column 4 were synthesized beginning with the tosylate in column 2, using the imidazole derivative in Column 3, Table 1:

TABLE 1

| Prep Ex. | Column 2 | Column 3 | Column 4 |
|---|---|---|---|
| 13 | ![structure with OTs, BOC] | ![4-methylimidazole] | ![product structure with BOC and CH3] |

TABLE 1-continued

| Prep Ex. | Column 2 | Column 3 | Column 4 |
|---|---|---|---|
| 14 | | | LCMS: MH⁺ = 280 |
| 15 | | | |
| 16 | | | |
| 16(A) | | | |
| 16(B) | | | |
| 16(C) | | | |

TABLE 1-continued

| Prep Ex. | Column 2 | Column 3 | Column 4 |
|---|---|---|---|
| 16(D) | ![structure] | ![structure] | ![structure] |
| 16(E) | ![structure] | ![structure] | ![structure] |

Preparative Example 17

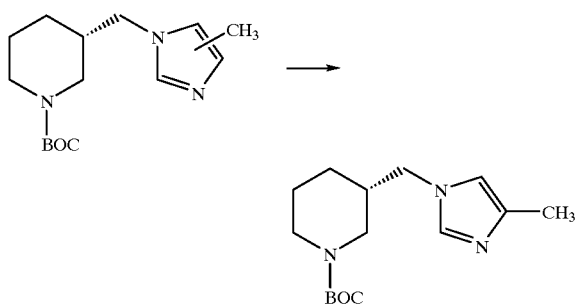

To the title compound from Preparative Example 13 (1.0 g, 3.58 mmol, 69:31 4-Me: 5-Me) in CH$_2$Cl$_2$ (10 mL) at 0° C. was added TrCl (0.32 g, 1.05 eq. based on 5-Me). The resulting solution was stirred at 0° C. for 2 hours and concentrated under reduced pressure. The crude mixture was purifed by flash chromatography using a 50% acetone in EtOAc solution as eluent to give the title compound as a clear oil (0.50 g, 72% yield). CIMS: MH$^+$=280.

Preparative Example 18

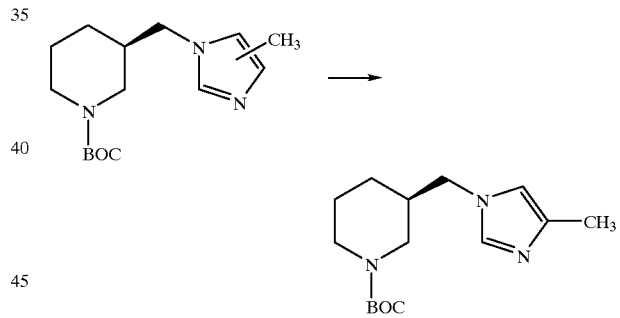

By essentially the same procedure set forth in Preparative Example 17, the title compound was prepared (0.49 g, 82% yield).

By essentially the same procedure set forth in Preparative Example 7 Step F except using the compounds prepared in Preparative Examples 12, 13, 14, 15, 16 (Column 2, Table 2), 16A, 16B, 16C, 16D, 17, 18, 71A (step D), 71A (step F) 16E, 72A, 74A, 75A and 76, the amine hydrochlorides in Column 3, Table 2 were prepared:

TABLE 2

| Prep Ex. | N-Boc Amine | Amine |
|---|---|---|
| 19 | ![structure] | ![structure] |

TABLE 2-continued

| Prep Ex. | N-Boc Amine | Amine |
|---|---|---|
| 20 | (3R)-N-Boc-3-((4-methyl-1H-imidazol-1-yl)methyl)piperidine | (3R)-3-((4-methyl-1H-imidazol-1-yl)methyl)piperidine · 2HCl  CIMS: MH$^+$ = 180 |
| 21 | (3S)-N-Boc-3-((4-methyl-1H-imidazol-1-yl)methyl)piperidine | (3S)-3-((4-methyl-1H-imidazol-1-yl)methyl)piperidine · 2HCl  CIMS: MH$^+$ = 180 |
| 22 | N-Boc-3-((2-methyl-1H-imidazol-1-yl)methyl)piperidine | 3-((2-methyl-1H-imidazol-1-yl)methyl)piperidine · 2HCl |
| 23 | N-Boc-3-((2-ethyl-1H-imidazol-1-yl)methyl)piperidine | 3-((2-ethyl-1H-imidazol-1-yl)methyl)piperidine · 2HCl |
| 23(A) | N-Boc-3-((1H-imidazol-4-yl)methyl)piperidine | 3-((1H-imidazol-4-yl)methyl)piperidine · 2HCl |
| 23(B) | N-Boc-3-((1-methyl-1H-imidazol-5-yl)methyl)piperidine | 3-((1-methyl-1H-imidazol-5-yl)methyl)piperidine · 2HCl |
| 23(C) | (3R)-N-Boc-3-((1H-imidazol-4-yl)methyl)piperidine | (3R)-3-((1H-imidazol-4-yl)methyl)piperidine · 2HCl |
| 23(D) | N-Boc-3-(pyridin-3-yloxy)piperidine | 3-(pyridin-3-yloxy)piperidine · 2HCl |

TABLE 2-continued
| Prep Ex. | N-Boc Amine | Amine |
|---|---|---|
| 23(E) | 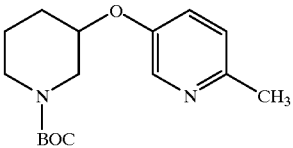 | 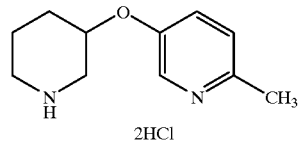 2HCl |
| 23(F) | 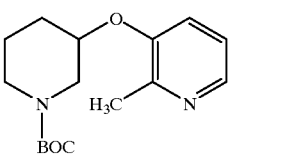 | 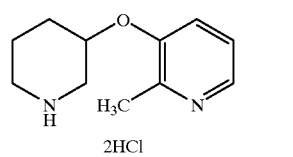 2HCl |
| 23(H) | 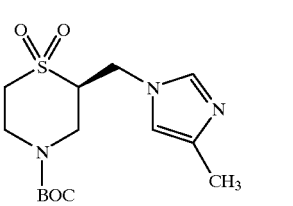 | 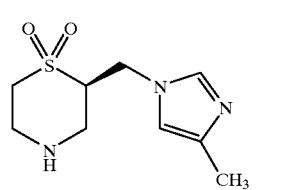 2HCl |
| 23(I) | 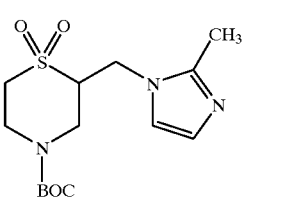 | 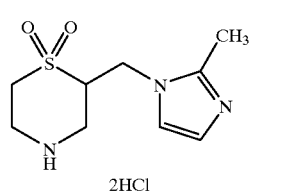 2HCl |
| 23(J) | 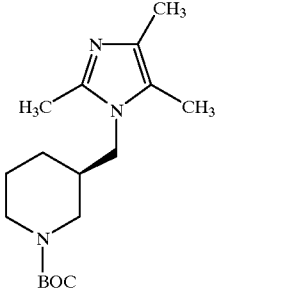 | 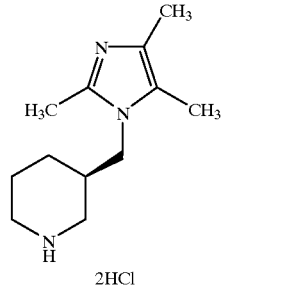 2HCl |
| 23(K) | 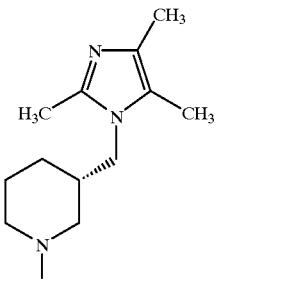 | 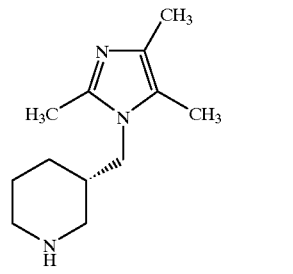 2HCl |

TABLE 2-continued

| Prep Ex. | N-Boc Amine | Amine |
|---|---|---|
| 23(L) | (structure: HO-CH2-imidazole-CH3, N-CH2-piperidine-N-BOC) | (structure: HO-CH2-imidazole-CH3, N-CH2-piperidine-NH, 2HCl) |

EXAMPLE 1

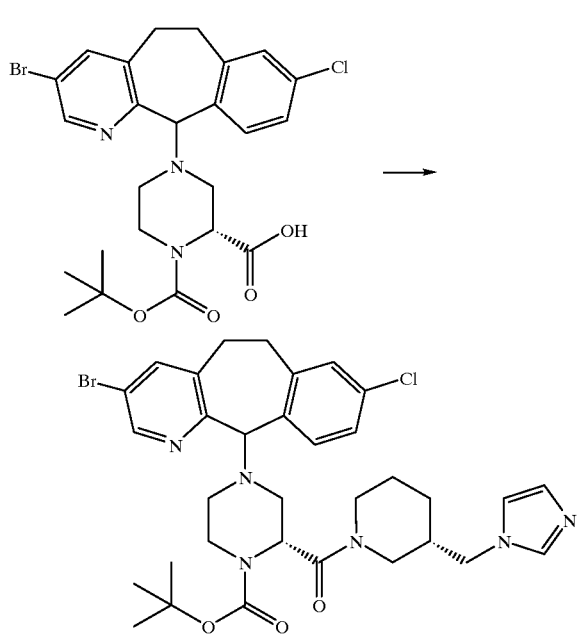

The title compound from Preparative Example 6 (1.0 g, 1.15 eq.) was added to a solution of the title compound from Preparative Example 1 (2.43 g, 3.81 mmol), DEC (0.95 g, 1.3 eq.). HOBT (2.57 g, 5 eq.) and NMM (2.51 mL, 6.0 eq.) in DMF (50 mL). The resulting solution was stirred at room temperature 24 hours. The reaction mixture was diluted with $H_2O$ until precipitation ceased and the slurry filtered. The precipitate was diluted with $CH_2Cl_2$ (200 mL), washed with $H_2O$ (2×100 mL), dried over $Na_2SO_4$ and concentrated. The crude product was purified by flash chromatography using a 5% (10%$NH_4OH$ in MeOH) solution in $CH_2Cl_2$ as eluent to give a pale yellow solid (1.8 g, 68% yield). LCMS: $MH^+$ = 683.

By essentially the same procedure set forth in Example 1 only substituting the appropriate amine, one can obtain compounds of the formula shown below with R as listed in Column 2 of Table 3.

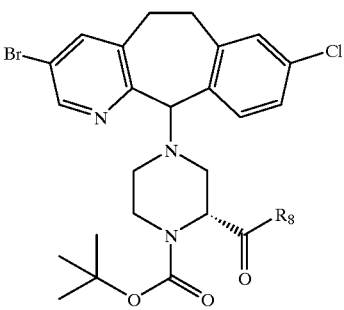

TABLE 3

| Ex. | $R^8$ = | MP (° C.) CMPD | |
|---|---|---|---|
| 2 | (structure with piperidine-CH2-imidazole) 11-(R,S) | — | LCMS: $MH^+$ = 683 |
| 3 | (structure with piperidine-CH2-imidazole-CH3) 11-(R,S) | 126–131 | LCMS: $MH^+$ = 697 |
| 4 | (structure with piperidine-CH2-imidazole-CH3) 11-(R,S) | 128–133 | LCMS: $MH^+$ = 697 |

TABLE 3-continued

| Ex. | R⁸ = | MP (° C.) | CMPD |
|---|---|---|---|
| 4.1 | ![structure] | 114–121 | LCMS: MH⁺ = 697 |
| 4.2 | ![structure] | 131–135 | LCMS: MH⁺ = 697 |
| 5 | ![structure] 11-(R,S) | 123–134 | FABMS: MH⁺ = 698 |
| 6 | ![structure] | — | FABMS: MH⁺ = 701 |
| 7 | ![structure] | — | FABMS: MH⁺ = 717 |
| 8 | ![structure] | 179–182 | FABMS: MH⁺ = 733 |
| 9 | ![structure] 11-(R,S) | 175–183 | FABMS: MH⁺ = 669 |

EXAMPLE 10 AND EXAMPLE 11

The title compound from Example 1 was separated into individual (R)- and (S)-isomers by Preparative HPLC with a CHIRALPAK AD column using a 15% iPrOH in hexanes solution with 0.2% DEA as eluent.

EXAMPLE 10

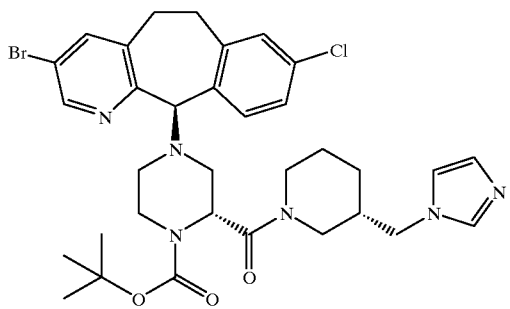

11-(R)-isomer: retention time (analytical)=8.845 minutes; $[\alpha]_D$=+14.0 (2.72 mg in 2.0 mL MeOH); mp=130–134° C. LCMS: MH⁺=683.

EXAMPLE 11

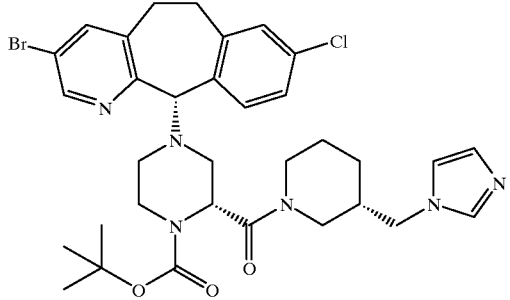

11-(S)-isomer: retention time (analytical)=15.416 minutes; $[\alpha]_D$=; mp=122–127 ° C.; LCMS: MH⁺=683.

EXAMPLE 12 AND EXAMPLE 13

By essentially the same procedure set forth in Example 10 and 11 except using the title compound from Example 2, the title compounds were prepared.

EXAMPLE 12

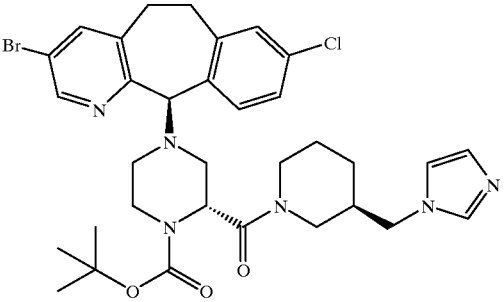

11-(R)-isomer: retention time (analytical-15% iPrOH: 0.2% DEA in hexanes)=18.84 minutes: $[\alpha]_D$=; mp=135–138° C.; MS: MH⁺=683.

EXAMPLE 13

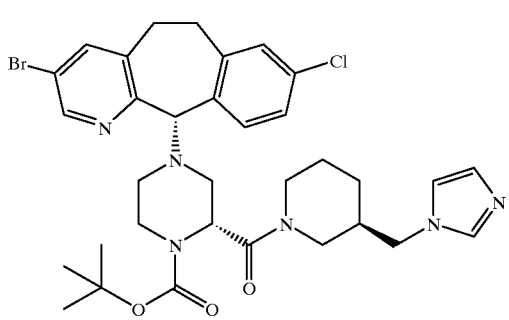

11-(S)-isomer: retention time (analytical-15% iPrOH: 0.2% DEA in hexanes)=23.758 minutes: $[\alpha]_D$=; mp=127–130° C; MS: MH$^+$=683.

Preparative Example 24

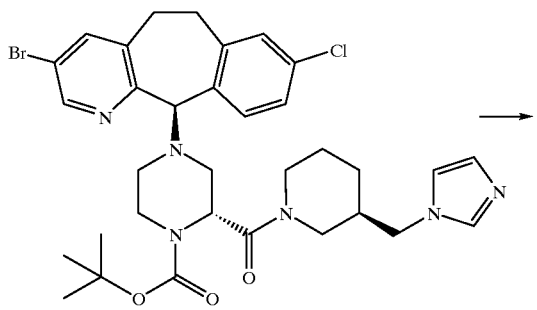

The title compound from Example 12 (0.87 g, 1.27 mmol) in CH$_2$Cl$_2$ (9.0 mL) was stirred with TFA (9.0 mL) at room temperature 1 hour. The reaction mixture was cooled to 0° C. and neutralized with 50% NaOH, separated, and the aqueous layer extracted with CH$_2$Cl$_2$ (3×200 mL). The combined organics were dried over Na$_2$SO$_4$, filtered, and concentrated in vacuo (0.56 g, 75% crude yield).

EXAMPLE 14

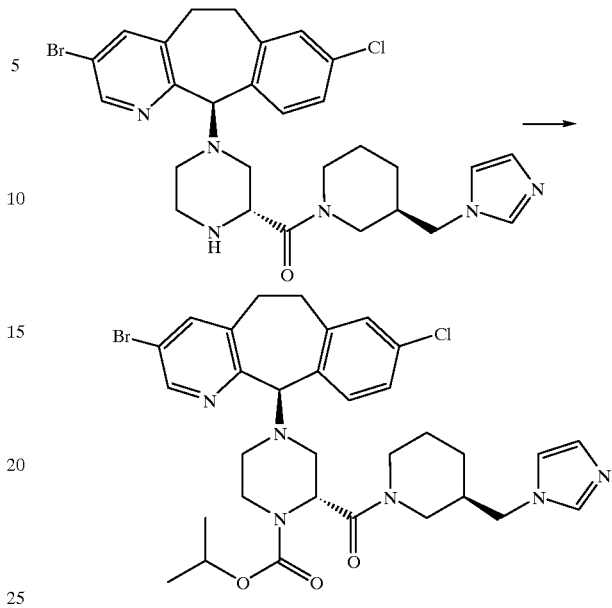

The title compound from Preparative Example 24 (0.12 g, 0.21 mmol) and TEA (0.15 mL, 5.0 eq.) were dissolved in CH$_2$Cl$_2$ (5.0 mL) and isopropyl chloroformate (1.05 mL 5.0 eq.) was added. The reaction mixture was stirred at room temperature overnight before adding H$_2$O (15.0 mL) and extracting with CH$_2$Cl$_2$ (2×100 mL). The combined organics were dried over Na$_2$SO$_4$, filtered, and concentrated in vacuo. The crude product was purified by flash chromatography using a 2.5% (10% NH$_4$OH in MeOH) solution in CH$_2$Cl$_2$ as eluent (0.096 g, 69% yield). FABMS: MH$^+$=669; mp=126–128° C.

EXAMPLE 15

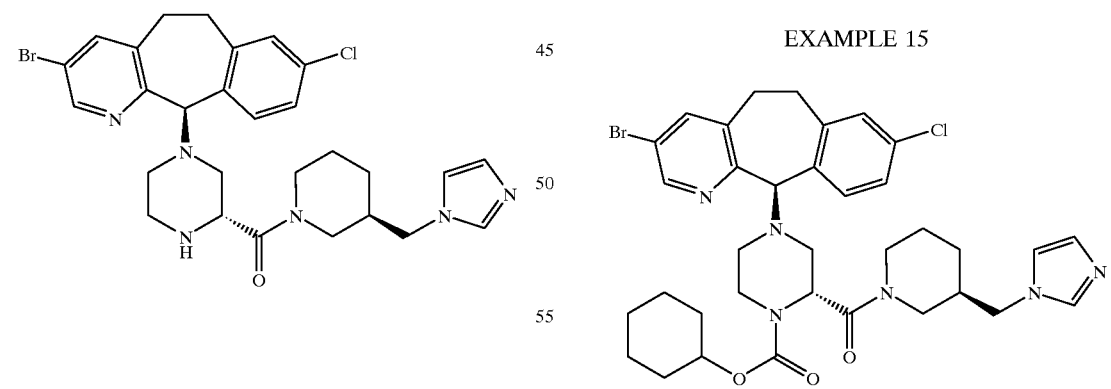

By essentially the same procedure set forth in Example 14 only substituting cyclohexyl chloroformate, the title compound was prepared (0.053 g, 44% yield). FABMS: MH$^+$=709; mp=140–144° C.

EXAMPLE 16

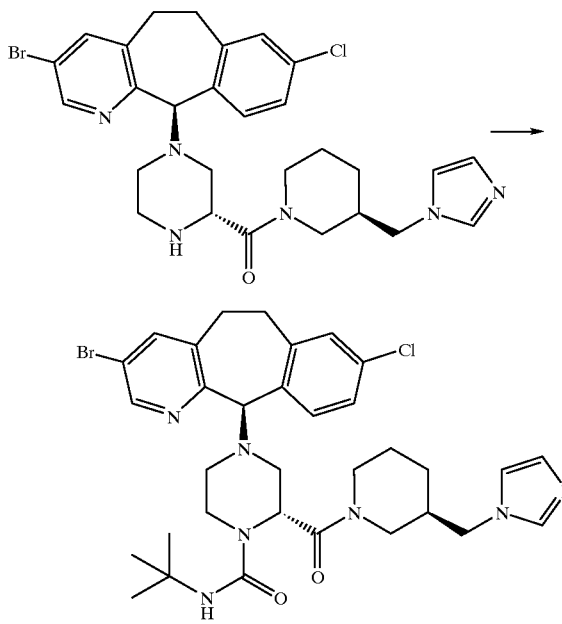

The title compound from Preparative Example 24 (0.13 g, 0.23 mmol) was dissolved in CH$_2$C$_2$ (4.0 mL) and t-butylisocyanate (0.13 mL, 5.0 eq.) was added. The resulting solution was stirred at room temperature 2 hours diluted with H$_2$O (15 mL) and extracted with CH$_2$Cl$_2$ (3×50 mL). The combined organics were dried over Na$_2$SO$_4$, filtered, and concentrated in vacuo. The crude product was purified by flash chromatography using gradient of 2.5% MeOH in CH$_2$Cl$_2$, 5%MeOH in CH$_2$Cl$_2$, and finally a 10% (10% NH$_4$OH in MeOH) in CH$_2$Cl$_2$ as eluent (0.069 g, 44% yield). LCMS: MH$^+$=682; mp=148–153° C.

EXAMPLE 17

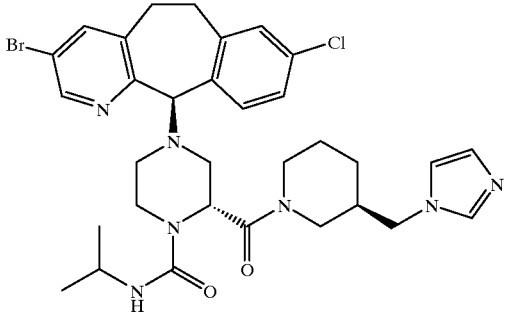

By essentially the same procedure set forth in Example 16 only substituting the isopropylisocyanate, the title compound was prepared (0.09 g, 64% yield). LCMS: MH$^+$=668; mp=132–136° C.

Preparative Example 25

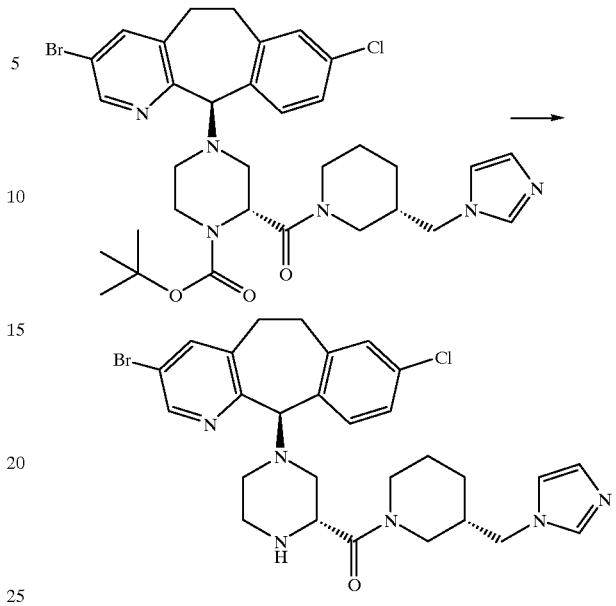

By essentially the same procedure set forth in Preparative Example 24 only using the title compound from Example 10, the title compound was prepared.

EXAMPLE 18

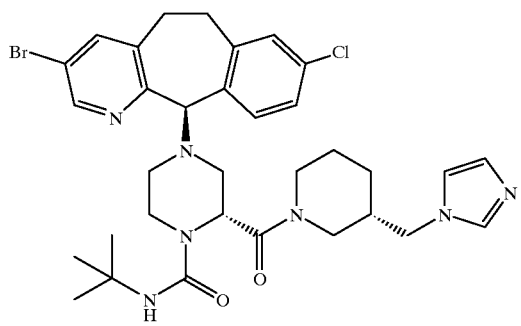

By essentially the same procedure set forth in Example 16 only substituting the title compound from Preparative Example 25, the title compound was prepared. FABMS: MH$^+$=682; mp=112–120° C.

EXAMPLE 19

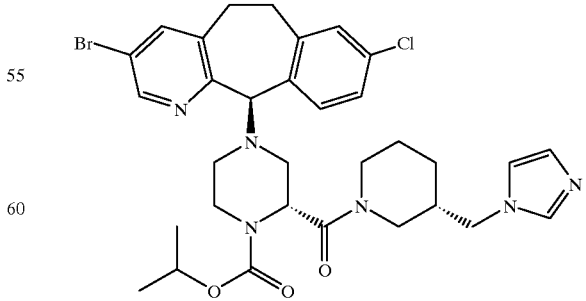

By essentially the same procedure set forth in Example 14 only substituting the title compound from Preparative Example 25, the title compound was prepared. FABMS: MH⁺=669; mp=123–132° C.; [α]²⁰_D=+16.4 (4.5 mg in 2.0 mL MeOH)

Preparative Example 26

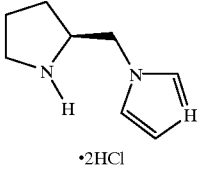

·2HCl

By essentially the same procedure set forth in Preparative Example 7 Steps C to F only beginning with L-prolinol, the title compound was prepared.

Preparative Example 27

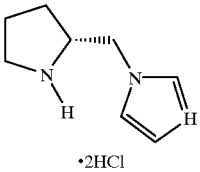

·2HCl

By essentially the same procedure set forth in Preparative Example 24. only beginning with D-prolinol, the title compound was prepared.

Preparative Example 28

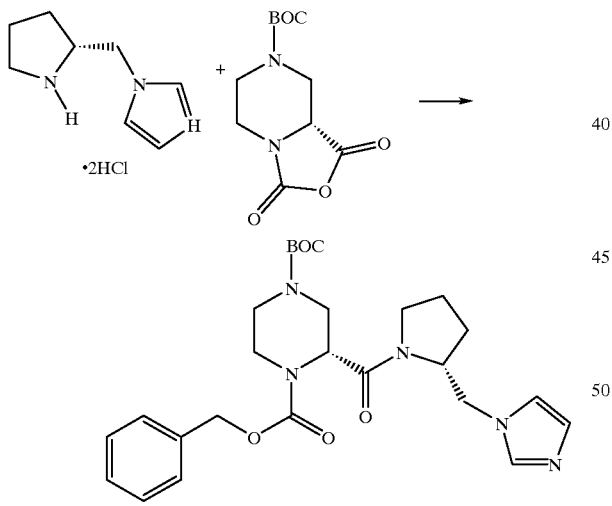

Piperazine anhydride (1.03 g, 1.2 eq.) was added portion-wise to a solution of the title compound from Preparative Example 27 (0.75 g, 3.35 mmol) in CH₂Cl₂ (5.0 mL) and TEA (2.33 mL, 5.0 eq.) and the resulting solution was stirred 10 minutes at room temperature before adding CBZ-OSuc (1.00 g, 1.0 eq.) The resulting mixture was stirred at room temperature overnight, and concentrated in vacuo. The crude product was purified by flash chromatography using a 5% MeOH in CH₂Cl₂ solution as eluent to yield a white solid (0.94 g, 56% yield). LCMS: MH⁺=498: [α]²⁰_D=+61.6° (3.8 mg in 2.0 mL CHCl₃).

EXAMPLE 20

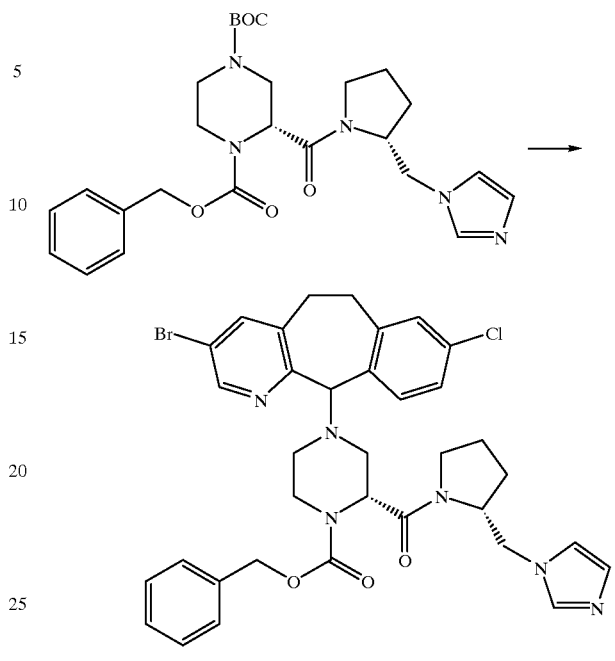

A solution of the title compound from Preparative Example 28 (0.85 g, 1.71 mmol) was stirred at room temperature in CH₂Cl₂ (10 mL) and TFA (3 mL) three hours. The reaction mixture was concentrated under reduced pressure and the compound was redissolved in CH₂Cl₂ (7 mL), treated with chloride {Scheme7 4} (0.29 g, 1.0 eq.) and TEA (1.75 mL, 15 eq.). The resulting solution was stirred at room temperature 96 hours. The reaction mixture was diluted with saturated NaHCO₃ (50 mL), water (50 mL), and CH₂Cl₂ (50 mL) and separated. The aqueous layer was extracted with CH₂Cl₂ (2×75 mL) and the combined organics dried over Na₂SO₄, filtered, and concentrated under reduced pressure. The crude product was purified by flash chromatography using a 6% (10% NH₄OH in MeOH) solution in CH₂Cl₂ as eluent to yield a tan solid (0.29 g, 48% yield). mp 80–84° C.; LCMS: MH⁺=703.

Preparative Example 29

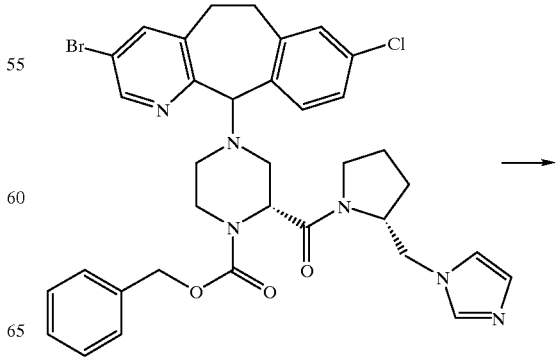

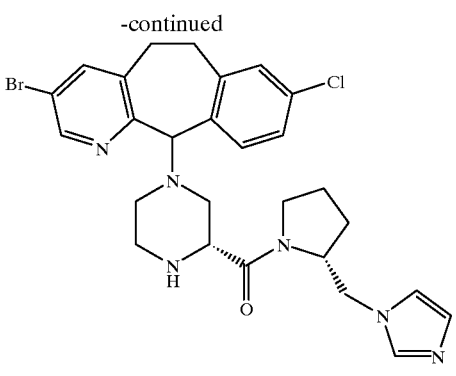

The title compound from Example 20 (0.24 g 0.341 mmol) was stirred at room temperature in HBr/AcOH (2.0 mL) 2 hours. The reaction mixture was triturated with Et$_2$O and any remaining AcOH removed by azeotroping with toluene to give the HBr salt which was neutralized with 1N NaOH and extracted into CH$_2$Cl$_2$ (3×50 mL). The combined organics were dried over Na$_2$SO$_4$, filtered, and concentrated in vacuo to give a tan solid (0.18 g, 95% yield) which was used without further purification. LCMS: MH$^+$=569.

EXAMPLE 21

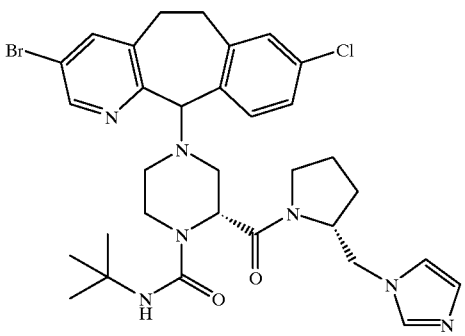

By essentially the same procedure set forth in Example 16, only using the title compound from Preparative Example 29, the title compound was prepared (0.029 g, 50% yield). LCMS: MH$^+$=668; mp=137–139° C.

EXAMPLE 22

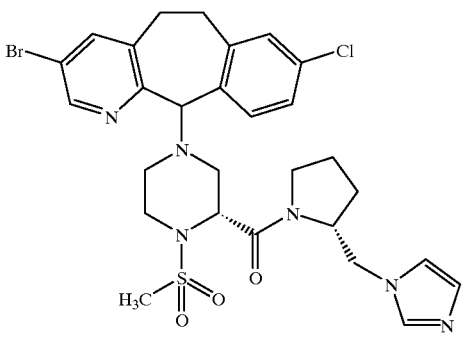

To the title compound from Preparative Example 29 (0.10 g, 0.175 mmol) and TEA (0.037 mL, 1.5 eq.) in CH$_2$Cl$_2$ (5.0 mL) was added MsCl (0.16 uL, 1.2 eq.) and the resulting solution was stirred at room temperature overnight. The resulting solution was quenched by the addition of saturated NaHCO$_3$ (10 mL), diluted with H$_2$O (25 mL) and extracted with CH$_2$Cl$_2$ (3×25 mL). The combined organics were dried over Na$_2$SO$_4$, filtered, and concentrated in vacuo. The crude product was purified by flash chromatography using a 10% (100% NH$_4$OH in MeOH) solution in CH$_2$Cl$_2$ as eluent to yield a tan solid (0.70 g, 64% yield). LCMS: MH$^+$=647; mp=135–141° C.

EXAMPLE 23

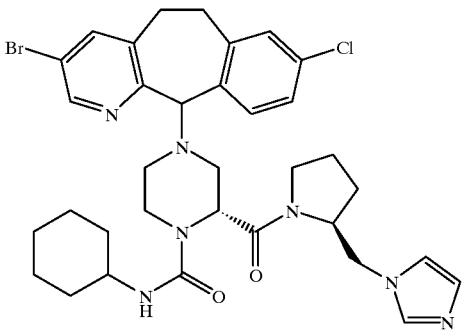

By essentially the same procedure set forth in Example 22 only substituting the amine hydrochloride from Preparative Example 26 and quenching with cyclohexyl isocyanate in place of CBC-OSuc, the title compound was prepared. LCMS: MH$^+$=669; mp=187.

Preparative Example 30

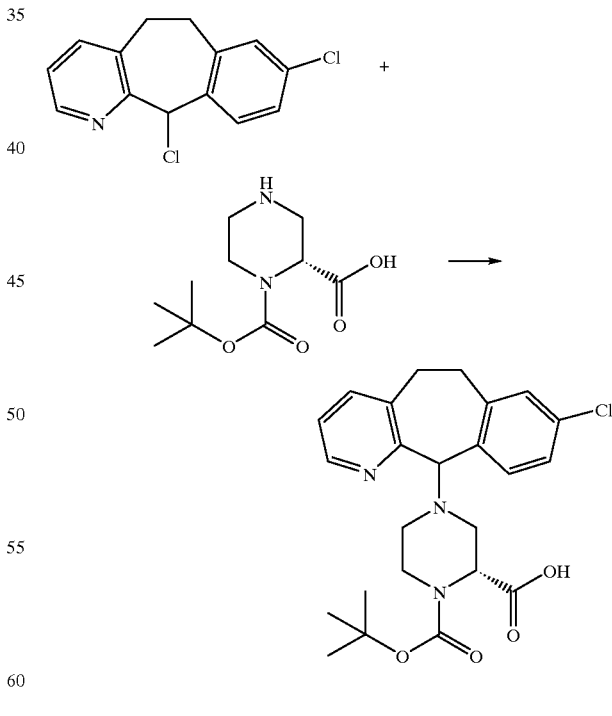

Tricyclic chloride (5.04 g, 1.1 eq.) was added to a solution of the title compound from Preparative Example 5 (4.0 g, 17.3 mmol) and TEA (12.05 mL, 5 eq.) in DMF (60 mL). The resulting solution was stirred at room temperature 72 hours at which time the reaction mixture was concentrated under reduced pressure. The residue was diluted with 3M NaOH and extracted with EtOAc. The aqueous layer was neutralized with 50% citric acid and extracted with EtOAc. The combine organics were dried over Na$_2$SO$_4$, filtered, and concentrated in vacuo. The crude product was purified by flash chromatography using a 12% (10% NH$_4$OH in MeOH) solution in CH$_2$Cl$_2$ as eluent to give the C-11 (S)-isomer (2.13 g, 54%) as the first eluting isomer and the C-11 (R)-isomer (2.4 g, 61%) as the second eluting isomer.

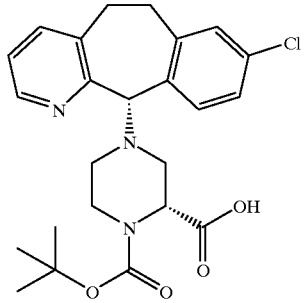

11-(S)-isomer (first eluting isomer): $[\alpha]^{20}_D=-13.4°$ (3.72 mg in 2.0 mL MeOH); LCMS: MH$^+$=458.

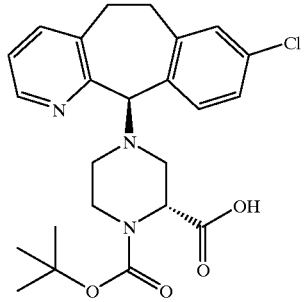

11-(R)-isomer (second eluting isomer): $[\alpha]^{20}_D=+84.90°$ (5.18 mg in 5.0 mL MeOH): FABMS: MH$^+$=458.

EXAMPLES 24–35G

By essentially the same procedure set forth in Example 1 only using the title compounds from Preparative Example 30 (individual C-11 (S)- and (R)-isomers) as listed in column 2 of Table 4 and substituting the appropriate amine, the title compounds of the formula shown below with R$^8$ as listed in column 3 of Table 4 are obtained.

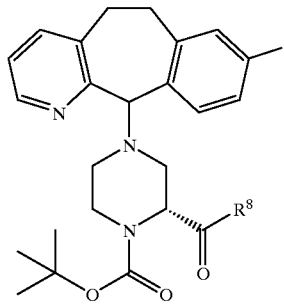

TABLE 4

| EX. | C-11 isomer | R$^8$ = | MP (° C.) | CMPD |
|---|---|---|---|---|
| 24 | S | (piperidine-CH$_2$-imidazole) | 115–126 | LCMS: MH$^+$ = 605 |
| 25 | R | (piperidine-CH$_2$-imidazole) | 124–143 | LCMS: MH$^+$ = 605 |
| 26 | S | (piperidine-CH$_2$-2-methylimidazole) | 120–132 | LCMS: MH$^+$ = 619 |
| 27 | R | (piperidine-CH$_2$-2-methylimidazole) | 110–119 | LCMS: MH$^+$ = 619 |
| 28 | S | (piperidine-CH$_2$-4-methylimidazole) | 115–132 | LCMS: MH$^+$ = 619 |
| 29 | R | (piperidine-CH$_2$-4-methylimidazole) | 109–124 | LCMS: MH$^+$ = 619 |
| 30 | S | (piperidine-CH$_2$-2-methylimidazole) | 105–119 | LCMS: MH$^+$ = 619 |
| 31 | R | (piperidine-CH$_2$-2-methylimidazole) | 121–142 | LCMS: MH$^+$ = 619 |
| 32 | S | (piperidine-CH$_2$-4-methylimidazole) | 80–85 | LCMS: MH$^+$ = 619 |

TABLE 4-continued

| EX. | C-11 isomer | R⁸ = | MP (°C.) | CMPD |
|---|---|---|---|---|
| 33 | R | (3-piperidinylmethyl-4-methylimidazole) | 117–120 | LCMS: MH⁺ = 619 |
| 34 | S | (3-piperidinylmethyl-2-ethylimidazole) | — | LCMS: MH⁺ = 634 |
| 35 | R | (3-piperidinylmethyl-2-ethylimidazole) | — | LCMS: MH⁺ = 634 |
| 35(A) | S | (3-piperidinylmethyl-4-ethylimidazole) | 110–112 | MS: MH⁺ = 633 |
| 35(B) | R | (3-piperidinylmethyl-4-ethylimidazole) | 89–92 | MS: MH⁺ = 633 |
| 35(C) | S | (3-piperidinylmethyl-5-ethylimidazole) | 104–106 | MS: MH⁺ = 633 |
| 35(D) | R | (3-piperidinylmethyl-5-ethylimidazole) | 79–81 | MS: MH⁺ = 633 |

TABLE 4-continued

| EX. | C-11 isomer | R⁸ = | MP (°C.) | CMPD |
|---|---|---|---|---|
| 35(E) | R | (thiomorpholine dioxide with 2-methylimidazole) | — | FABMS: MH⁺ = 670 |
| 35(F) | S | (pyrrolidinylmethyl-4-methylimidazole) | 115–120 | LCMS: MH⁺ = 606 |
| 35(G) | S | (3-piperidinylmethyl-imidazole) | 97–122 | LCMS: MH⁺ = 605 |

Preparative Example 31

Step A

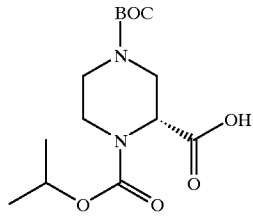

50% NaOH was added to a solution of the title compound from Preparative Example 1 (11.47 g, 19.28 mmol) in dioxane:H₂O (1:1, 64 mnL) until the pH was ~11.5 and BOC-ON (5.22 g, 1.1 eq.) was added in two portions. 50% NaOH was added to keep the pH at ~11.5. When the pH stabilized the resulting solution was stirred at room temperature overnight. The pH was adjusted to ~9.5 ny the addition of 1M HCl and isopropyl chloroformate (21.21 mL, 1.0 M in toluene, 1.1 eq.) was added. The resulting solution was kept at pH ~9.5 and stirred 3 days. The reaction mixture was concentrated and extracted with Et₂O, readjusting the pH to ~9.5 following each extraction. When the pH stabilized at ~9.5 for 3 consecutive extractions the aqueous layer was acidified to pH ~4.5 with 50% citric acid and to pH ~3 with 1M HCl and extracted with EtOAc (3×100 mL). The combined organics were dried over Na₂SO₄, filtered, and concentrated under reduced pressure to give a white solid (5.8 g, 90% yield).FABMS: MH⁺=317. Treatment of the product with TFA yielded the deprotected amine which was used without further purification.

Step B

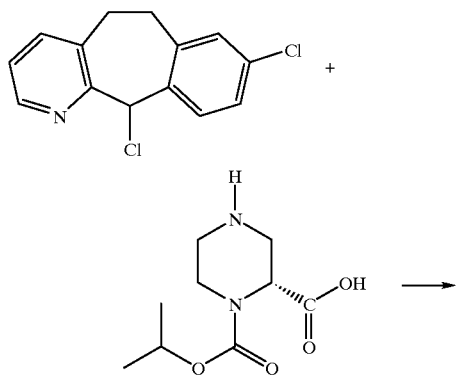

By essentially the same procedure set forth in Preparative Example 30 only substituting the compound from Preparative Example 31 Step A, the title compound was prepared and separated into C-11 isomers:

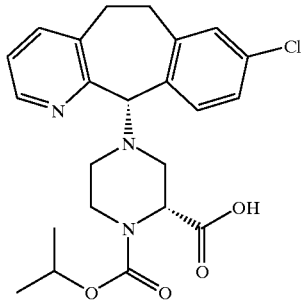

11-(S)-isomer (first eluting isomer): LCMS: MH⁺=444.

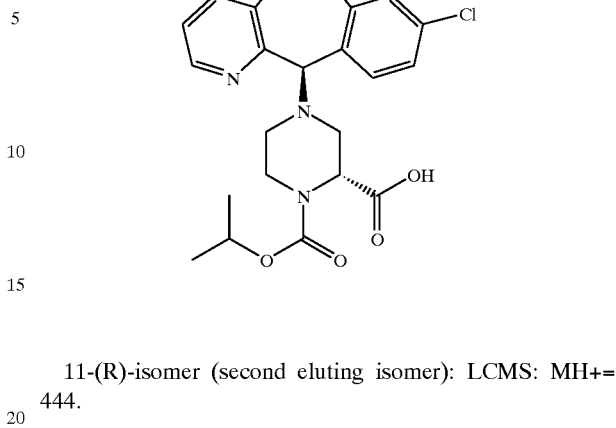

11-(R)-isomer (second eluting isomer): LCMS: MH+= 444.

EXAMPLES 36–41I

By essentially the same procedure set forth in Example 1 only substituting the title compounds from Preparative Example 31 (individual C-11 (S)- and (R)-isomers) and substituting the appropriate amine, the compounds of the formula shown below with $R^8$ listed in column 3 of Table 5 are obtained.

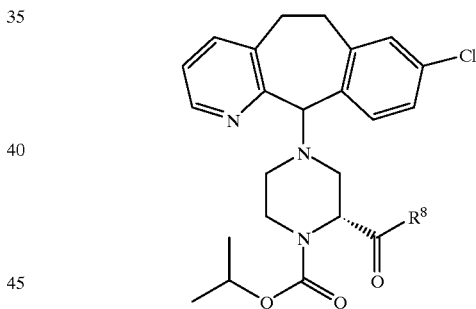

TABLE 5

| EX. | C-11 isomer | $R^8 =$ | MP (° C.) | CMPD |
|---|---|---|---|---|
| 36 | S | ![piperidine-imidazole-CH₃] | 123–132 | LCMS: MH⁺ = 605 |

TABLE 5-continued

| EX. | C-11 isomer | R⁸ = | MP (° C.) | CMPD |
|---|---|---|---|---|
| 37 | R | (piperidine-CH2-N-imidazole-4-CH3) | 95–111 | LCMS: MH⁺ = 605 |
| 38 | S | (piperidine-CH2-N-imidazole-2-CH3) | 92–101 | FABMS: MH⁺ = 605 |
| 39 | R | (piperidine-CH2-N-imidazole-2-CH3) | 111–125 | FABMS: MH⁺ = 605 |
| 40 | S | (piperidine-CH2-N-imidazole-2-CH3) | 107–112 | FABMS: MH⁺ = 605 |
| 41 | R | (piperidine-CH2-N-imidazole-2-CH3) | 95–100 | FABMS: MH⁺ = 605 |
| 41(A) | S | (piperidine-CH2-N-imidazole-4-CH3) | 117–120 | LCMS: MH⁺ = 605 |
| 41(B) | R | (piperidine-CH2-N-imidazole-4-CH3) | 101–120 | LCMS: MH⁺ = 605 |
| 41(C) | S | (piperidine-O-pyridine) Isomer 1,2 | 104–108 | LCMS: MH⁺ = 604 |
| 41(D) | S | (piperidine-O-pyridine) Isomer 1 | 98–100 | LCMS: MH⁺ = 604 |

TABLE 5-continued

| EX. | C-11 isomer | R⁸ = | MP (° C.) | CMPD |
|---|---|---|---|---|
| 41(E) | S | 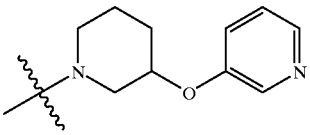 Isomer 2 | 100–103 | LCMS: MH⁺ = 604 |
| 41(F) | S | 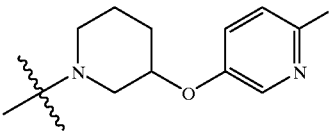 Isomer 1,2 | 90–105 | LCMS: MH⁺ = 618 |
| 41(G) | S | 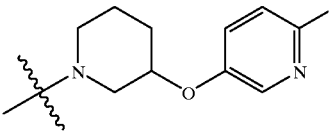 Isomer 1 | 90–105 | LCMS: MH⁺ = 618 |
| 41(H) | S | 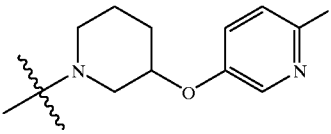 Isomer 2 | 95–105 | LCMS: MH⁺ = 618 |
| 41(I) | S | 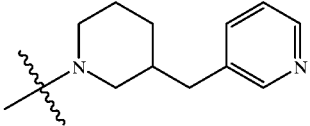 Isomer 1,2 | 95–104 | LCMS: MH⁺ = 602 |

Preparative Example 32

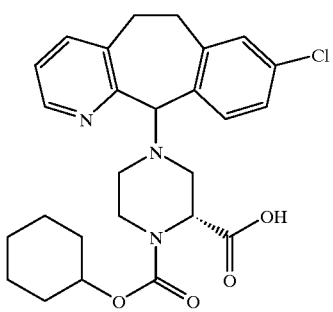

By essentially the same procedure set forth in Preparative Example 31 only substituting cyclohexyl chloroformate for isopropyl chloroformate in Step A, the title compounds (C-11 (S)- and (R)-isomers) were prepared and separated into individual diastereomers:

11-(S)-isomer (first eluting isomer): FABMS: MH⁺=484.

11-(R)-isomer (second eluting isomer): FABMS: MH⁺=484.

EXAMPLES 42–47CC

By essentially the same procedure set forth in Example 1 only substituting the title compounds from Preparative Example 32 (individual C-11 (S)- and (R)-isomers) and substituting the appropriate amine, the compounds of the formula shown below with R⁸ as listed in Column 3 of Table 6 can be obtained.

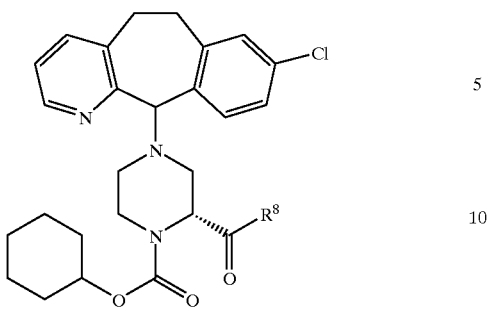
TABLE 6
| EX. | C-11 isomer | R⁸ = | MP (° C.) | CMPD |
|---|---|---|---|---|
| 42 | S | piperidine-CH₂-(4-methylimidazol-1-yl) | 99–113 | FABMS: MH⁺ = 645 |
| 43 | R | piperidine-CH₂-(4-methylimidazol-1-yl) | 108–118 | FABMS: MH⁺ = 645 |
| 44 | S | piperidine-CH₂-(2-methylimidazol-1-yl) | 112–135 | FABMS: MH⁺ = 645 |
| 45 | R | piperidine-CH₂-(2-methylimidazol-1-yl) | 108–123 | FABMS: MH⁺ = 645 |
| 46 | S | piperidine-CH₂-(2-methylimidazol-1-yl) | 91–94 | FABMS: MH⁺ = 645 |
| 47 | R | piperidine-CH₂-(2-methylimidazol-1-yl) | 100–106 | FABMS: MH⁺ = 645 |

TABLE 6-continued

| EX. | C-11 isomer | R⁸ = | MP (° C.) | CMPD |
|---|---|---|---|---|
| 47(A) | S | (piperidine-CH₂-N-imidazole with 4-CH₃) | 122–127 | FABMS: MH⁺ = 645 |
| 47(B) | R | (piperidine-CH₂-N-imidazole with 4-CH₃) | 133–139 | FABMS: MH⁺ = 645 |
| 47(C) | R | (piperidine-CH₂-N-imidazole with 4-ethyl) | 74–76 | MS: MH⁺ = 659 |
| 47(D) | S | (piperidine-CH₂-N-imidazole with 4-ethyl) | 66–68 | MS: MH⁺ = 659 |
| 47(E) | R | (piperidine-CH₂-N-imidazole with 4-ethyl) | 85–89 | MS: MH⁺ = 659 |
| 47(F) | S | (piperidine-CH₂-N-imidazole with 4-ethyl) | 48–52 | MS: MH⁺ = 659 |
| 47(G) | S | (piperidine-CH₂-N-imidazole with 4-CH₃, 5-CH₃) | 98–130 | LCMS: MH⁺ = 659 |

TABLE 6-continued

| EX. | C-11 isomer | R⁸ = | MP (° C.) | CMPD |
|---|---|---|---|---|
| 47(H) | S | (piperidine-CH₂-4,5-dimethylimidazole) | 106–125 | LCMS: MH⁺ = 659 |
| 47(I) | S | (piperidine-CH₂-1H-imidazol-4-yl) | 113–115 | LCMS: MH⁺ = 631 |
| 47(J) | S | (piperidine-CH₂-1H-imidazol-4-yl) | 106–132 | LCMS: MH⁺ = 631 |
| 47(K) | S | (piperidine-CH₂-1-methylimidazol-5-yl) | 101–123 | LCMS: MH⁺ = 645 |
| 47(L) | S | (thiomorpholine-S,S-dioxide-CH₂-4-methylimidazol-1-yl) | — | FABMS: MH⁺ = 696 |
| 47(M) | R | (thiomorpholine-S,S-dioxide-CH₂-4-methylimidazol-1-yl) | — | FABMS: MH⁺ = 696 |
| 47(N) | S | (thiomorpholine-S,S-dioxide-CH₂-4-methylimidazol-1-yl) | — | FABMS: MH⁺ = 696 |

TABLE 6-continued

| EX. | C-11 isomer | R⁸ = | MP (° C.) | CMPD |
|---|---|---|---|---|
| 47(O) | R | | — | FABMS: MH⁺ = 696 |
| 47(P) | S | | — | FABMS: MH⁺ = 674 |
| 47(Q) | R | | — | FABMS: MH⁺ = 674 |
| 47(R) | S | | — | FABMS: MH⁺ = 674 |
| 47(S) | S | | — | FABMS: MH⁺ = 646 |
| 47(T) | S | | — | FABMS: MH⁺ = 646 |
| 47(U) | S | Isomer 1 | 117–120 | FABMS: MH⁺ = 644 |

TABLE 6-continued

| EX. | C-11 isomer | R⁸ = | MP (° C.) | CMPD |
|---|---|---|---|---|
| 47(V) | S | (piperidine-N-linked, 3-O-pyridin-3-yl) Isomer 2 | 105–108 | FABMS: MH⁺ = 644 |
| 47(W) | S | (piperidine-N-linked, 3-O-(6-methylpyridin-3-yl)) (Isomer 1, 2) | 94–113 | LCMS: MH⁺ = 658 |
| 47(X) | S | (piperidine-N-linked, 3-O-(6-methylpyridin-3-yl)) Isomer 1 | 94–113 | FABMS: MH⁺ = 658 |
| 47(Y) | S | (piperidine-N-linked, 3-O-(6-methylpyridin-3-yl)) Isomer 2 | 100–118 | LCMS: MH⁺ = 658 |
| 47(Z) | S | (piperidine-N-linked, 3-O-(2-methylpyridin-3-yl)) Isomer 1, 2 | 100–108 | LCMS: MH⁺ = 658 |
| 47(AA) | S | (piperidine-N-linked, 3-O-(2-methylpyridin-3-yl)) Isomer 1 | 100–115 | LCMS: MH⁺ = 658 |
| 47(BB) | S | (piperidine-N-linked, 3-O-(2-methylpyridin-3-yl)) Isomer 2 | 108–120 | LCMS: MH⁺ = 658 |

TABLE 6-continued

| EX. | C-11 isomer | R⁸ = | MP (° C.) | CMPD |
|---|---|---|---|---|
| 47(CC) | S | 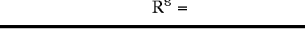 | 108–113 | FABMS: MH⁺ = 659 |

Isomer 1, 2

Preparative Example 33

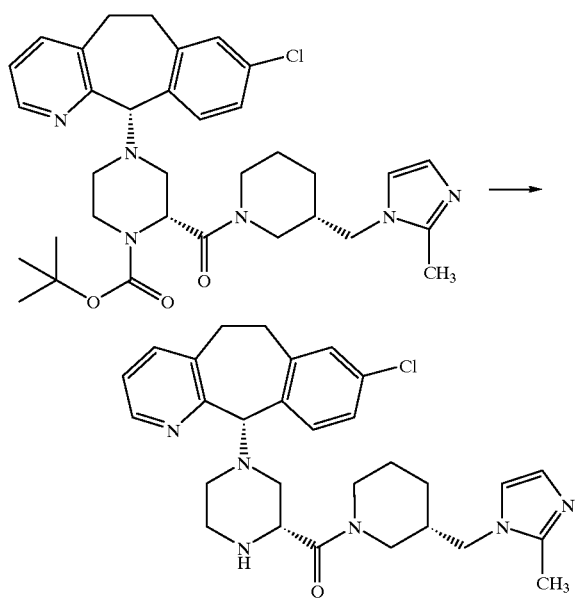

By essentially the same procedure set forth in Preparative Example 24, only using the title compounds from Example 26, the title compound was prepared.

By essentially the same procedure set forth in Preparative Example 33 only substituting the compound from the example listed in column 2 of Table 7, the title compounds of the formula shown below with R⁸ as in column 4 of Table 7 were prepared:

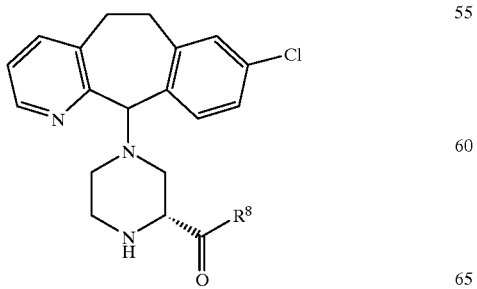

TABLE 7

| Prep. Ex. | Ex. | C-11 Isomer | R⁸ = |
|---|---|---|---|
| 34 | 27 | R | 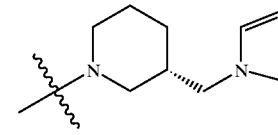 |
| 35 | 28 | S | 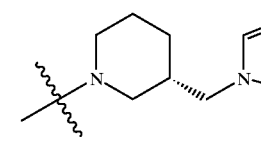 |
| 36 | 29 | R | 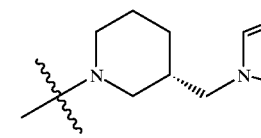 |
| 36(A) | 30 | S | 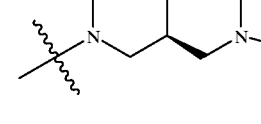 MP = 99–112° C. LCMS: MH⁺ 618 |
| 36(B) | 31 | R | 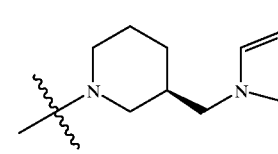 MP = 110–123° C. LCMS: MH⁺ = 618 |

TABLE 7-continued

| Prep. Ex. | Ex. | C-11 Isomer | R⁸ = |
|---|---|---|---|
| 36(C) | 32 | S | (structure) MP = 96–106° C. LCMS: MH⁺ = 618 |
| 36(D) | 33 | R | (structure) MP = 150–152° C. LCMS: MH⁺ = 618 |

EXAMPLE 48

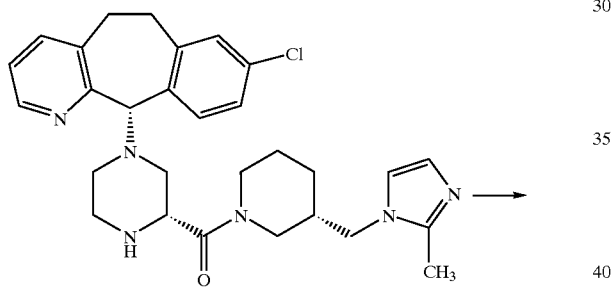

→

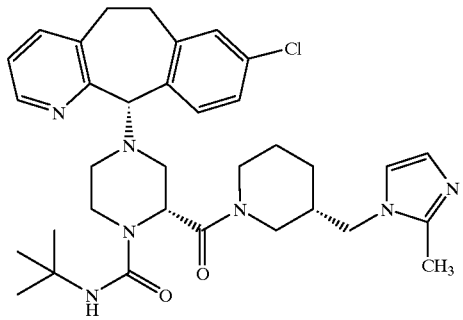

By essentially the same procedure set forth in Example 16 only substituting the title compound from Preparative Example 33, the title compound was prepared. FABMS: MH⁺=618; mp=111–140° C.

By essentially the same procedure set forth in Example 48 only substituting the title compounds from the Preparative Example listed in column 2 of Table 8, the title compounds of the formula shown below with R⁸ listed as in column 4 of Table 8 are obtained.

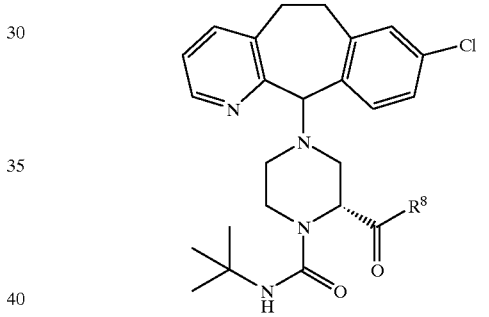

TABLE 8

| Prep. Ex. | Ex. | C-11 isomer | R⁸ = | MP (° C.) | CMPD |
|---|---|---|---|---|---|
| 49 | 34 | R | (structure) | 102–125 | FABMS: MH⁺ = 618 |
| 50 | 35 | S | (structure) | 123–135 | FABMS: MH⁺ = 618 |

TABLE 8-continued
| Ex. | Prep. Ex. | C-11 isomer | R⁸ = | MP (° C.) | CMPD |
|---|---|---|---|---|---|
| 51 | 36 | R | | 112–130 | FABMS: MH⁺ = 618 |
| 51A | 36A | S | | 99–112 | LCMS: MH⁺ = 618 |
| 51B | 36B | R | | 110–123 | LCMS: MH⁺ = 618 |
| 51C | 36C | S | | 96–106 | LCMS: MH⁺ = 618 |
| 51D | 36D | R | | 150–152 | LCMS: MH⁺ = 618 |
Preparative Example 48
(R) and (S)-[2-(1H-imidazol-1-yl)methyl]morpholines
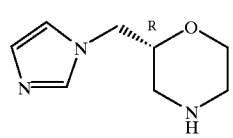
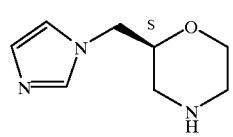
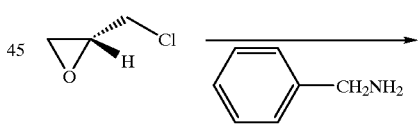
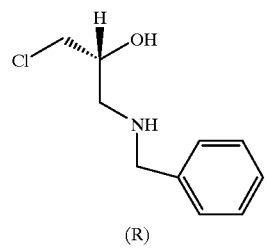
Step A
(R) and (S)-3-chloro-1(benzylamino)-2-propanols
(T.Mori et al Heterocycles 38,5 1033, 1994)

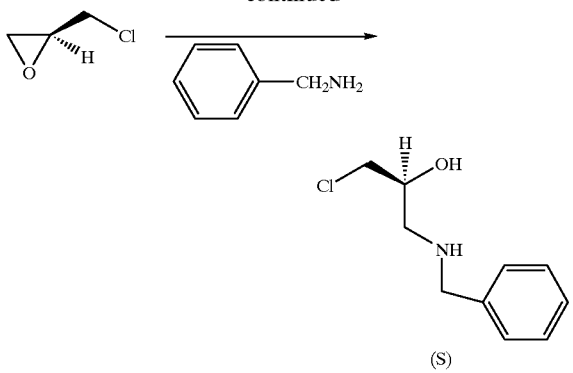

A mixture of (R)-epichlorohydrin (5 g, 54.03 mmoles) and benzylamine (5.8 g, 54.03 mmoles) in cyclohexane (50 mL) was stirred at room temperature for 16 h. The resulting precipitates were collected to give the title compound (5.4 g, 50.09%): $\delta_H$ (DMSO-d$_6$) 2.28 (bs, 1H), 2.43–2.67 (m, 2H), 3.45–3.85 (m, 5H), 5.13 (bs, 1H), 7.05–7.48 (m, 5H).

In a similar manner (S) isomer was prepared from (S)-epichlorohydrin in 67% yield.

Step B
(R) and (S)-2-chloromethyl-4-benzyl-5-oxomorpholines

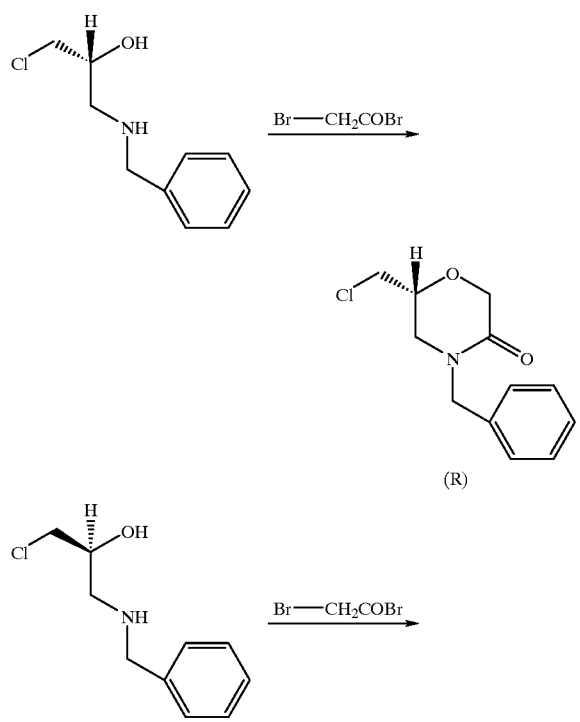

To a mixture of the title compound from step A above (5.3 g, 26.57 mmoles), NaOH (10.62 g, 265 mmoles) CHCl$_3$ (50 mL) and H$_2$O (20 mL) was added dropwise a solution of bromoacetyl bromide (14.98 g, 74.25 mmoles) in CHCl$_3$ (15 mL) over a period of 1 h at 0° C. and then at room temperature for 16 h. The organic layer was separated and washed successively with water, 1NHCl, and brine. The solvent evaporated to leave the title compound ((R) isomer) (5.43 g, 84.4%): FABMS (M+1)=240; $\delta_H$ (CDCl$_3$) 3.2–3.33 (m,2H). 3.50 (dd, 1H), 3.51 (dd, 1H), 4.0 (m,1H), 4.25 (d, 1H), 4.4 (d, 1H), 4.52 (d, 1H), 4.7 (d. 1H), 7.20–7.33 (m, 5H).

In a similar manner (S) isomer was prepared (67%). FABMS (M+1)=240; $\delta_H$ (CDCl$_3$) 3.2–3.33 (m,2H). 3.50 (dd, 1H), 3.51 (dd, 1H), 4.0 (m,1H), 4.25 (d, 1H), 4.4 (d, 1H), 4.52 (d, 1H), 4.7 (d, 1H), 7.20–7.33 (m, 5H).

Step C
(R)-2-chloromethyl-4-benzyl-moropholines

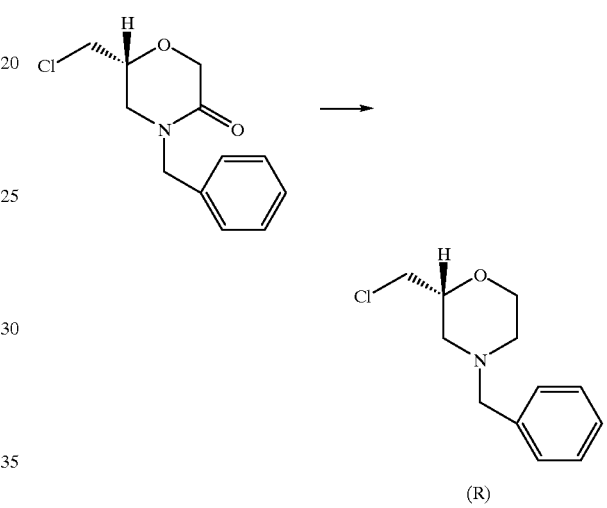

A solution of the title compound from Step B (5.09 g, 21.23 mmoles) in anhydrous THF (55 mL) was added to a stirred 1.0 M BH$_3$-THF complex (109 mL) over a period of 0.5 h at -15° C. under nitrogen atmosphere. The mixture was stirred at room temperature for 1 h, heated to reflux overnight and then cooled to 0° C. After concentrated HCl (75 mL) was added to the reaction mixture, THF was evaporated in vacuo. The resulting aqueous solution was basified with 10% NaOH and extracted with CH$_2$Cl$_2$. The extract was successively washed with water and brine, and the CH$_2$Cl$_2$ was evaporated to leave a crude product, which was chromatographed on silica gel with CH$_2$Cl$_2$-2% acetone to give the title compound (3.2 g, 80%). FABMS (M+1)= 226, $\delta_H$ (CDCl$_3$) 2.1 (dd, 1H), 2.3 (dd, 1H), 2.72 (m, 1H), 2.84 (m,1H), 3.5–3.6 (s, 2H), 3.62–3.98 (m, 31H), 7.2–7.4 (m, 5H).

Step D
(R)-4-benzyl-2-(1H-imidazol-yl)methyl-morpholines

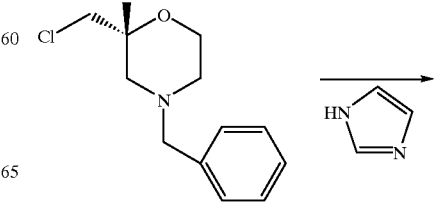

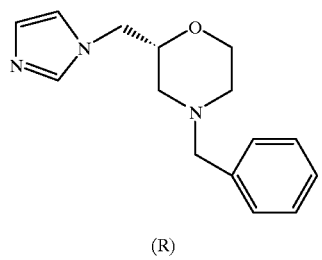

(R)

A solution of the title compound from Step C (3.1 g, 13.77 mmoles) in DMF (15 mL) was added to a stirred solution of NaH (1.29 g 53.75 mmoles) and imidazole (3.67 g, 53.97 mmoles) in DMF (50 mL) under nitrogen atmosphere. The mixture was stirred at 60° C. for 16 h. DMF was evaporated in vacuo. The resulting crude product was extracted with $CH_2Cl_2$ and the extract was successively washed with water and brine, and the $CH_2Cl_2$ was evaporated to leave a crude product, which was chromatographed on silica gel with $CH_2Cl_2$-5% (10% $NH_4OH$ in methanol) to give the title compound (1.65 g, 45%). FABMS (M+1)=258 (MH$^+$); $\delta_H$ (CDCl3) 1.8 (m, 1H), 2.15 (m, 1H), 2.8 (m, 2H), 3.4–3.8 (m, 7H), 6.9 (S,1H), 7.02 (S, 1H), 7.3 (m, 5H), 7.5 (S, 1H).

Step E (S)-4-benzyl-2-(1H-imidazol-yl)methyl-5-oxomorpholines

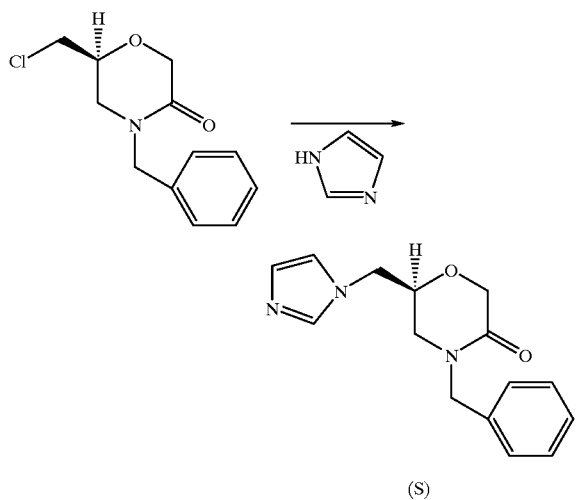

(S)

A solution of the title compound from Step B (2.73 g, 11.37 mmoles) in DMF (15 mL) was added to a stirred solution of NaH (1.55 g 22.79 mmoles) and imidazole 0.55 g, 22.75 mmoles) in DMF (25 mL) under nitrogen atmosphere. The mixture was stirred at 60° C. for 16 h. DMF was evaporated in vacuo. The resulting crude product was extracted with $CH_2Cl_2$ and the extract was successively washed with water and brine, and the $CH_2Cl_2$ was evaporated to leave a crude product, which was chromatographed on silica gel with $CH_2Cl_2$ 2–5% (10% NH4OH in methanol) to give the title compound (0.761 g, 24.7%). FABMS (M+1)=272 (MH$^+$); $\delta_H$ (CDCl3 3.12 (m, 2H), 3.98–4.71 (m, 7H), 6.98 (S,1H), 7.1 (S, 1H), 7.2–7.4 (m, 5H), 7.98 (S, 1H).

Step F
(S)-4-benzyl-2-(1H-imidazol-yl)methyl-morpholines

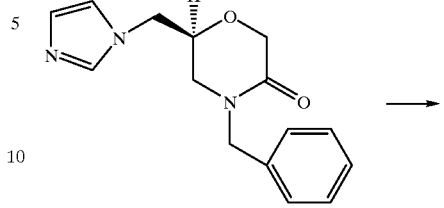

1 N LAH in ether (5.5 mL) was added to a stirred solution of the title compound (0.75 g, 2.75 mmole) from step E in anhydrous THF (25 mL) dropwise over a period of 0.5 h and the resulting mixture was refluxed for 4 h. The reaction mixture was slowly decomposed with ice-water and extracted with $CH_2Cl_2$. The extract was washed with with water and brine and dried (MgSO$_4$), filtered and evaporated to dryness to give the title compound (0.53 g, 75%). FABMS (M+1)=258 $\delta_H$ (CDCl3) 1.8 (m,1H), 2.15 (m, 1H), 2.8 (m, 2H), 3.4–3.8 (m, 7H), 6.9 (S,1H), 7.02 (S, 1H), 7.3 (m, 5H), 7.5 (S, 1H).

Step G
(R) AND (S)-[2-(1H-imidazol-1-yl)methyl]morpholines

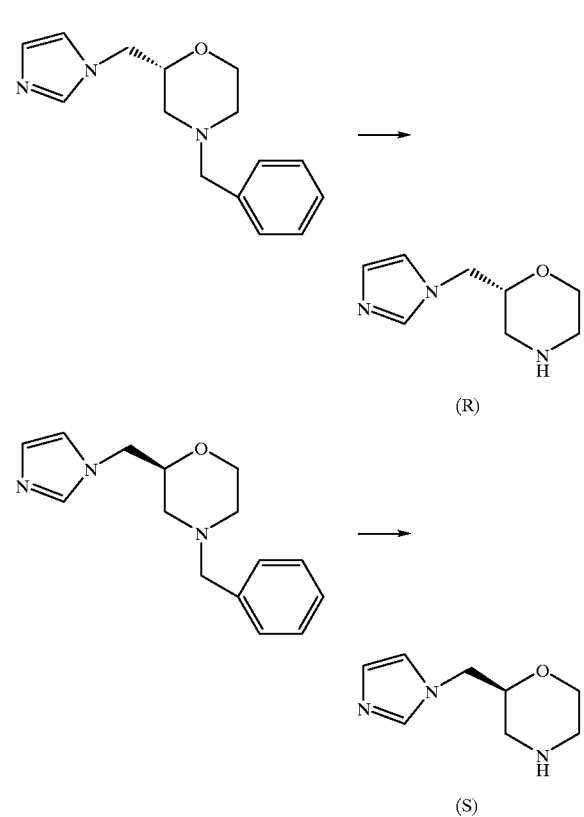

A mixture of the title compound(1.6 g) from Step D and Pd(OH)$_2$ on carbon (0.32 g) in EtOH (20 mL) was stirred at 50 psi under an atmosphere of hydrogen for 24 h. The catalyst was filtered to give the title compound (1.03 g, 99.9%). FABMS (M+1)=168; $\delta_H$ (CDCl$_3$) 2.4–2.5 (m, 1H), 2.8 (m, 3H), 3.5–3.9 (m, 5H), 6.9 (S,1H), 7.02 (S, 1H), 7.45 (S, 1H).

In a similar manner (S) isomer was prepared from (0.5 g) and Pd(OH)$_2$ on carbon (0.2 g) in 99% yield. FABMS (M+1)=168; $\delta_H$ (CDCl$_3$) 2.4–2.5 (m, 1H), 2.8 (m, 3H), 3.5–3.9 (m, 5H), 6.9 (S,1H), 7.02 (S, 1H), 7.45 (S, 1H).

Preparative Example 49
[4-(1H-imidazol-1-yl)methyl]piperidine

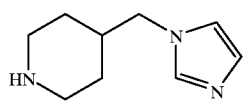

Step A
1N-tert-butoxycarbonyl-4-hydroxymethyl-piperidine

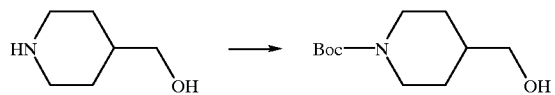

To a solution of 4-hydroxymethyl-piperidine (5 g, 43.41 mmoles) and triethylamine (8.78 g, 86.82 mmoles) in CH$_2$Cl$_2$ (100 mL), di-tert-butyldicarbonate (18.95 g, 86.82 mmoles) was added and stirred at room temperature for 16 h. The solution was diluted with CH$_2$Cl$_2$ and washed with water, dried(MgSO$_4$) filtered and evaporated to give the title compound (9.04 g, 99%). FABMS (M+1)=216.

Step B
1N-tert-butoxycarbonyl-4-methanesulfonyloxymethyl-piperidine

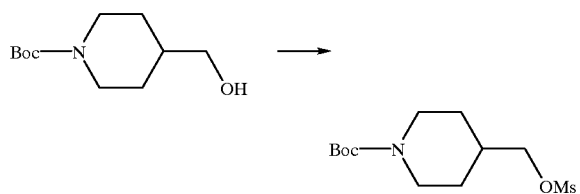

The title compound from Step A above (8.8 g, 40.87 mmoles) and triethylamine (8.55 mL, 61.31 mmoles) were dissolved in CH$_2$Cl$_2$ (100 mL) and the mixture was stirred under nitrogen at 0° C. Methanesulfonylchloride (3.8 mL mL, 49.05 mmoles) was added and the solution was stirred at room temperature for 2 h. The solution was diluted with CH$_2$Cl$_2$ and washed with saturated aqueous sodium bicarbonate, water and dried (MgSO$_4$), filtered and evaporated to dryness to give the title compound (12.8 g) FABMS (M+1)=294.3.

Step C
1N-tert-butoxycarbonyl-4-(1H-imidazol-1-yl)methyl-piperidine

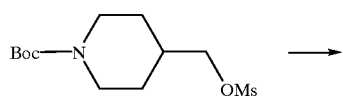

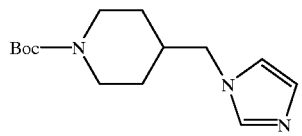

A solution of the title compound from Step B (1.0 g, 3.408 mmoles) in DMF (15 mL) was added to a stirred solution of NaH (0.27 g, 6.817 mmoles) and imidazole (0.464 g, 6.817 mmoles) in DMF (15 mL) under nitrogen atmosphere. The mixture was stirred at 60° C. for 16 h. DMF was evaporated in vacuo. The resulting crude product was extracted with CH$_2$Cl$_2$ and the extract was successively washed with water and brine, and the CH$_2$Cl$_2$ was evaporated to leave the title residue which was chromatographed on silica gel using 3% (10% conc NH$_4$OH in methanol)-CH$_2$Cl$_2$ as eluant to give the title compound (0.823 g). FABMS (M+1)=266.2, $\delta_H$ (CDCl$_3$) 0.8–1.0 (m, 2H), 1.2 (s, 9H), 1.2–1.4 (m, 1H), 1.65 (m, 1H), 2.4 (dt, 2H), 3.6 (d, 2H), 4.8 (d, 2H), 6.7 (s, 1H), 6.8 (s, 1H), 7.2 (s, 1H).

Step D
4-(1H-imidazol-1-yl)methyl-piperidine

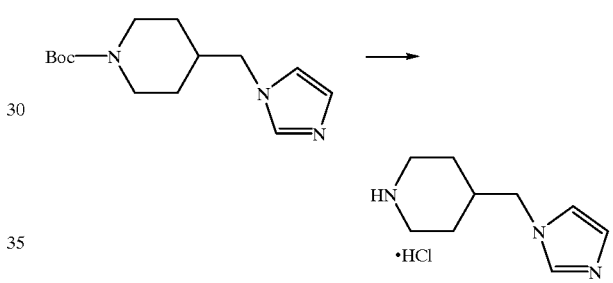

The title compound(0. 187 g, 0.705 mmoles) from Step C was stirred in 4N HCl in dioxane (20 mL) for 2 h and then evaporated to dryness to give the title compound which was used to couple with the tricyclic acid.

Preparative Example 50
3(R) and 3(S)-(1H-imidazol-1-yl)methyl]pyrrolidines

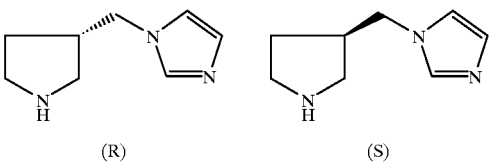

Step A
1N-tert-butoxycarbonyl-3(R) and 3(S)-(1H-imidazol-1-yl)methyl)pyrrolidines

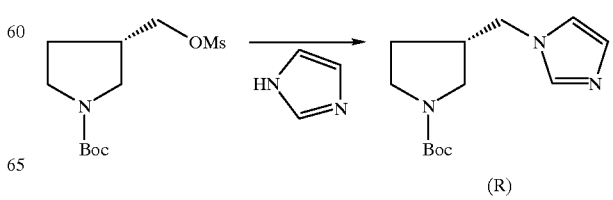

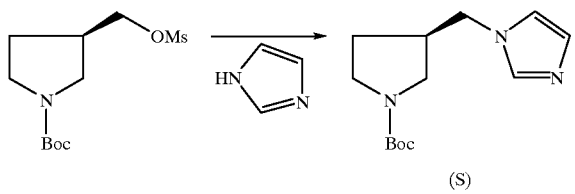

3(R)-(3-Methanesulfonyloxymethyl)pyrrolidine (J. Med. Chem. 1990, 33, 77—77) (0.993 g, 3.56 mmoles) was dissolved in anhydrous DMF (25 mL) and sodium imidazole (0.6 g, 10 mmoles) was added. The mixture was heated at 60° C. for 2 h and then evaporated to dryness. The product was extracted with $CH_2Cl_2$ and washed with brine. $CH_2Cl_2$ extract was evaporated to dryness to give the titled compound (1.1409 g, 100%), ESMS: FABMS (M+1)=252; $\delta_H$ ($CDCl_3$) 1.45 (s, 9H), 1.5–1.7 (m, 1H), 1.9–2.1 (m, 1H), 2.5–2.7 (m, 1H), 3.0–3.2 (m, 1H), 3.3–3.6 (m, 2H), 3.9 (dd, 2H), 6.9 (s, 1H), 7.1(s, 1H), 7.45 (s, 1H)

In a similar manner, (S) isomer was prepared from 3(S)-(3-Methanesulfonyloxymethyl) pyrrolidine (0.993 g, 3.56 mmoles to give the title compound (1.1409 g, 100%).

Step B

3(R) and 3(S)-(1H-imidazol-1-yl)methyl]pyrrolidines

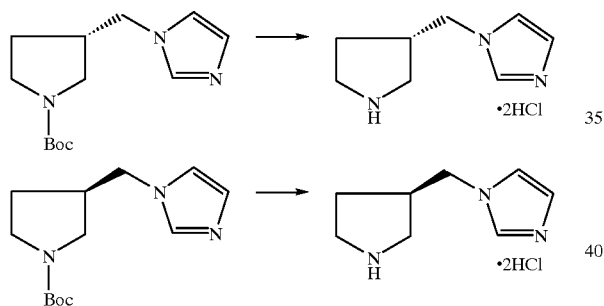

The title compound(0.48 g, 1.91 mmoles) from Step A was stirred in 4N HCl in dioxane (10 mL) for 2 h and then evaporated to dryness to give the title compound which was used to couple with the tricylic acid.

In a similar manner (S) isomer was prepared.

Preparative Example 51

3(S)-(1H-4(5)-methylimidazol-1-yl)methyl]pyrrolidine

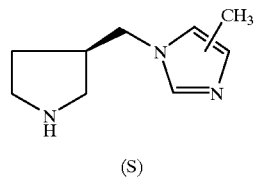

Step A
1N-tert-butoxycarbonyl-3(S)-(1H-4-(5)-methylimidazol-I-yl)methyl)pyrrolidine

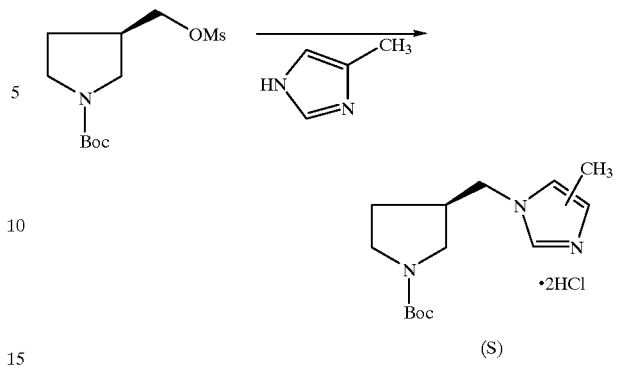

3(S)-(3-Methanesulfonyloxymethyl)pyrrolidine (1.05 g, 3.77 mmoles) was dissolved in anhydrous DMF (25 mL) and sodium 4-methylimidazole (0.74 g, 10 mmoles) was added. The mixture was heated at 60° C. for 2 h and then evaporated to dryness. The product was extracted with $CH_2Cl_2$ and washed with brine. $CH_2Cl_2$ was evaporated to dryness to give the titled compound (0.92 g, 100%), FABMS (M+1)= 266.

Step B
3(S)-(1H-4(5)-methylimidazol-1-yl)methyl]pyrrolidine

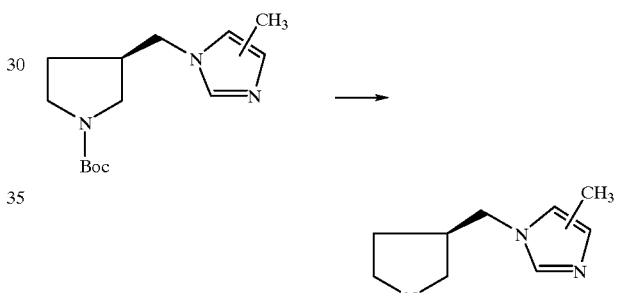

The title compound(0.31 g, 1.17 mmoles) from Step A was stirred in 4N HCl in dioxanie (10 mL) for 2 h and then evaporated to dryness to give the title compound which was used to couple with the tricylic acid.

Preparative Example 52
3-(1H-imidazol-1-yl)methyl-pyrrolidine

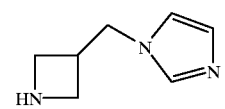

Step A
1N-diphenylmethyl-azetidine-4-methylcarboxylate

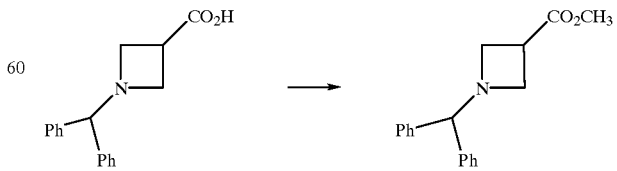

1N-Diphenylmethyl-azetidine-3-carboxylic acid (J. Chem. Res. 1996, 430) (5.38 g, 20.16 mmoles) was refluxed with conc, H₂SO₄ (2 mL) and MgSO₄ (5 g) in anhydrous methanol (25 mL) for 16 h. Evaporated to dryness and the residue was extracted with ethylacetate and washed the extract with 10% sodiumbicarbonate and water. Ethylacetate was evaporated to give a residue which was chromatographed on silica gel using hexane- 10% ethylacetate as the eluant afforded the title compound (2.2 g, 40.64%), FABMS (M+1)=282; $\delta_H$ (CDCl3) 3.2–3.6 (m, 5H), 3.7 (s, 3H), 4.45 (s, 1H), 7.2–7.4 (m, 10H).

Step B 1N-diphenylmethyl-3-hydroxymethyl-azetidine

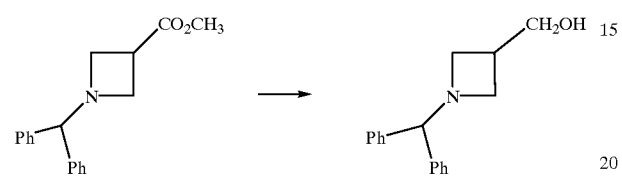

1 N LAH in ether (20 mL) was added to a stirred solution of the title compound (2 g, 7.11 mmole) from Step A in anhydrous ether (25 mL) dropwise over a period of 0.5 h and the resulting mixture was refluxed for 4 h. The reaction mixture was slowly decomposed with ice-water and extracted with ethylacetate. The extract was washed with with water and brine and dried (MgSO₄), filtered and evaporated to dryness to give title compound (1.72 g, 98%). FABMS (M+1)=254.

Step C 1N-diphenylmethyl-3-methanesulfonyloxymethyl-azetidine

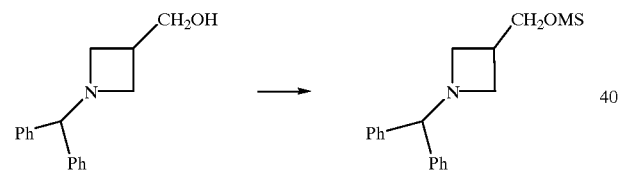

The title compound from Step B above (1.7 g, 6.72 mmoles) and triethylamine (1.1 g, 10.87 mmoles) were dissolved in CH₂Cl₂ (20 mL) and the mixture was stirred under nitrogen at 0° C. Methanesulfonylchloride (1.1 g, 9.6 mmoles) was added and the solution was stirred at room temperature for 2 h. The solution was diluted with CH₂Cl₂ and washed with saturated aqueous sodium bicarbonate, water and dried (MgSO₄), filtered and evaporated to dryness to give the title compound (2.32 g, 99%). FABMS (M+1)=332.

Step D 1N-diphenylmethyl-3-(1H-imidazol-1yl)methyl-azetidine

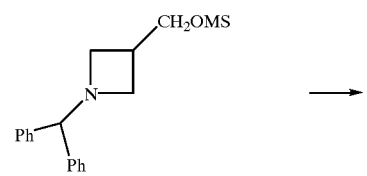

-continued

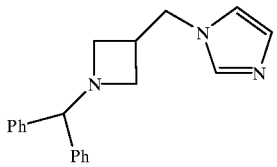

A solution of the title compound from Step C (2.3 g, 6.95 mmoles) in DMF (15 mL) was added to a stirred solution of NaH (0.25 g, 10.42 mmoles) and imidazole (0.71 g, 10.44 mmoles) in DMF (10 mL) under nitrogen atmosphere. The mixture was stirred at 60° C. for 16 h. DMF was evaporated in vacuo. The resulting crude product was extracted with CH₂Cl₂ and the extract was successively washed with water and brine, and the CH₂Cl₂ was evaporated to leave the title compound (2.1 g, 100%). FABMS (M+1)=304

Step E 3-(1H-imidazol-1-yl)methyl-pyrrolidine

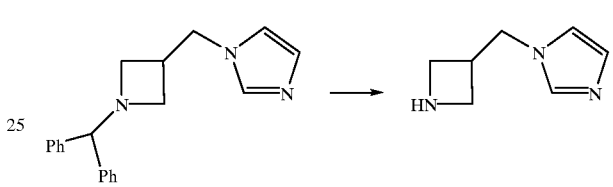

A mixture of the title compound(1.7 g) from Step D and Pd(OH)₂ on carbon (0.2 g) in EtOH (20 mL) was stirred at 50 psi under an atmosphere of hydrogen for 24 h. The catalyst was filtered to give the title compound (0.508 g, 66.8%). m/z=137 (MH⁺)

Preparative Example 53

4-(1H-imidazol-1-yl)-piperidine

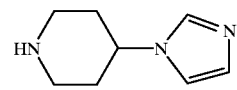

Step A 1N-tert-butoxycarbonyl-4-hydroxy-piperidine

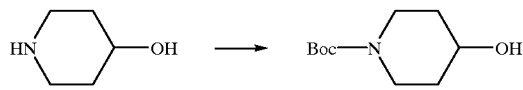

To a solution of 4-hydroxy-piperidine (2 g, 19.78 mmoles) and triethylamine (4.16 mL, 29.67 mmoles) in CH₂Cl₂ (20 mL), di-tert-butyldicarbonate (5.18 g, 23.72 mmoles) was added and stirred at room temperature for 16 h. The solution was diluted with CH₂Cl₂ and washed with water, dried (MgSO₄) filtered and evaporated to give the title compound (3.95 g, 99%). FABMS (M+1)=202.

Step B 1N-tert-butoxycarbonyl-4-methanesulfonyloxy-piperidine

The title compound from Step A above (3.5 g, 17.39 mmoles) and triethylamine (4.856 mL, 34.79 mmoles) were dissolved in CH₂Cl₂ (30 mL) and the mixture was stirred under nitrogen at 0° C. Methanesulfonylchloride (1.62 mL, 20.88 mmoles) was added and the solution was stirred at room temperature for 2 h. The solution was diluted with CH₂Cl₂ and washed with saturated aqueous sodium bicarbonate, water and dried (MgSO₄), filtered and evaporated to dryness to give the title compound (4.68 g, 96.4%). ESMS: m/z=280 (MH⁺)

Step C 1N-tert-butoxycarbonyl-4-(1H-imidazol-1-yl)-piperidine

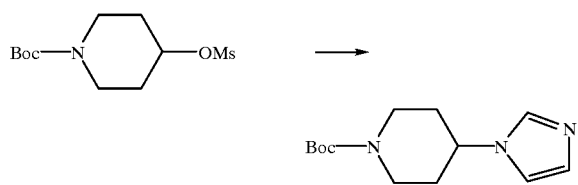

A solution of the title compound from Step B (4.0 g, 14.32 mmoles) in DMF (120 mL) was added to a stirred solution of NaH (0.52 g, 21.66 mmoles) and imidazole (1.46 g, 21.47 mmoles) in DMF (20 mL) under nitrogen atmosphere. The mixture was stirred at 60° C. for 16 h. DMF was evaporated in vacuo. The resulting crude product was extracted with CH₂Cl₂ and the extract was successively washed with water and brine, and the CH₂Cl₂ was evaporated to leave the title residue which was chromatographed on silica gel using 3% (10% conc NH₄OH in methanol)-CH₂Cl₂ as eluant to give the title compound (0.94 g, 26%). FABMS (M+1)=252; δ$_H$ (CDCl₃) 1.4 (s, 9H), 1.6–1.8 (m, 2H), 2.0 (dd, 2H), 2.8 (dt, 2H), 4.05 (m, 1H), 4.2 m, 2H), 6.9 (s, 1H), 7.0 (s, 1H), 7.65 (s, 1H).

Step D 4-(1H-imidazol-1-yl)-piperidine

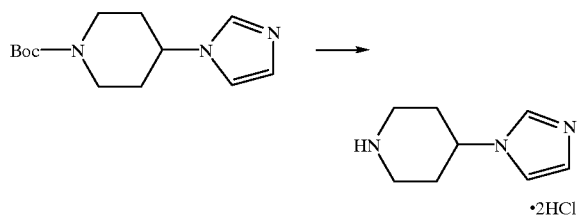

The title compound(0.21 g, 0.836 mmoles) from Step C was stirred in 4N HCl in dioxane (5 mL) for 2 h and then evaporated to dryness to give the title compound which was used to couple with the tricylic acid.

Preparative Example 54

3-(R) and (S)-(1H-imidazol-1-yl)-pyrrolidines

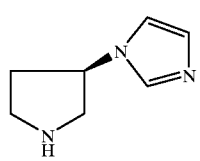

(R)

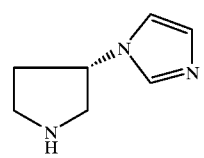

(S)

Step A 1N-benzyl-3-(R) and (S)-methanesulfonyloxy)-pyrrolidines

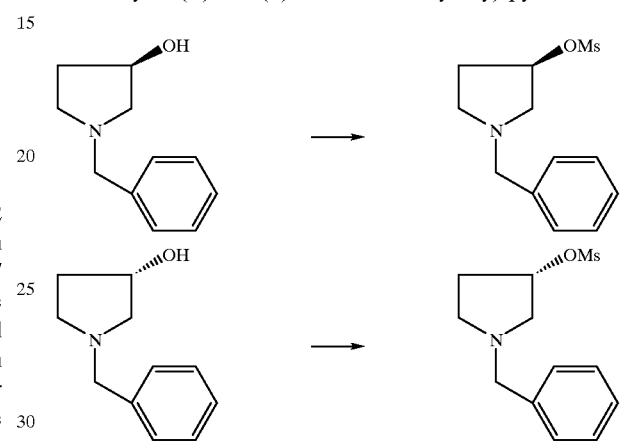

1N-Benzyl-3(R)-hydroxy-pyrrolidines (5 g, 28.21 mmoles) and triethylamine (7.86 mL, 56.35 mmoles) were dissolved in CH₂Cl₂ (50 mL) and the mixture was stirred under nitrogen at 0° C. Methanesulfonylchloride (2.62 mL, 33.87 mmoles) was added and the solution was stirred at room temperature for 2 h. The solution was diluted with CH₂Cl₂ and washed with saturated aqueous sodium bicarbonate, water and dried (MgSO₄), filtered and evaporated to dryness to give the title compound (7.2 g, 96.4%). FABMS (M+1)=256; δ$_H$ (CDCl₃) 2.2 (m, 1H), 2.3 (m, 1H), 2.52 (m, 1H), 2.7–2.85 (m, 3H), 2.95 (s, 3H), 3.65 (q, 2H), 5.16 (m, 1H), 7.3 (s, 5H).

In a similar way (S) isomer was prepared from 1N-Benzyl-3(S)-hydroxy-pyrrolidines (5 g, 28.21 mmoles) to give the title compound (7.15 g, 98%)

Step B 1N-benzyl-3-(S) and (R)-(1H-imidazol-1-yl)-pyrrolidines

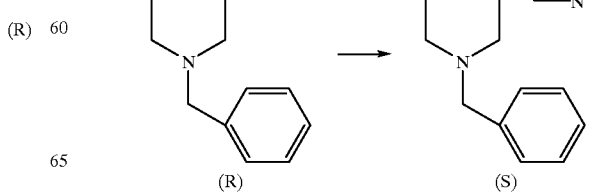

(R)         (S)

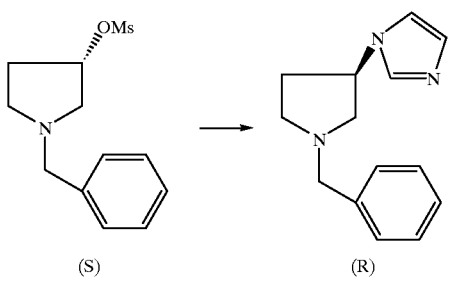

(S)  (R)

A solution of the title compound from Step A (2.0 g, 7.84 mmoles) was added to a stirred solution imidazole (1.1 g, 16.17 mmoles) in DMF (25 mL) under nitrogen atmosphere. The mixture was stirred at 60° C. for 16 h. DMF was evaporated in vacuo. The resulting crude product was extracted with $CH_2Cl_2$ and the extract was successively washed with water and brine, and the $CH_2Cl_2$ was evaporated to leave the title residue which was chromatographed on silica gel using 3% (10% conc $NH_2OH$ in methanol)-$CH_2Cl_2$ as eluant to give the title compound (0.95 g, 50.56%). FABMS (M+1)=228.

In a similar fashion the other isomer was prepared.

Step C 3-(R) and (S)-(1H-imidazol-1-yl)-pyrrolidines

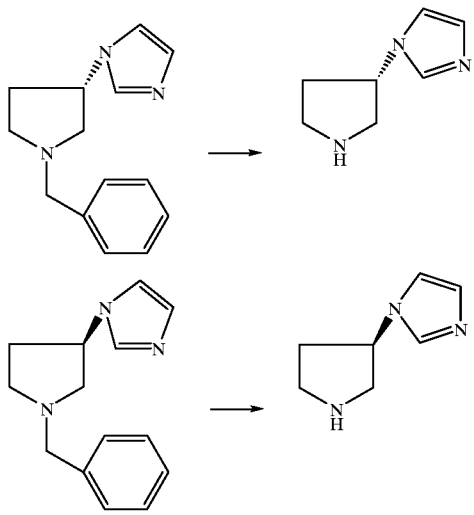

A mixture of the title compound (0.95 g) from Step B and 10% Pd on carbon (0.5 g) in EtOH (20 mL) was stirred at 50 psi under an atmosphere of hydrogen for 24 h. The catalyst was filtered to give the title compound (0.522 g, 99.9%) which was used to couple with the tricylic acid.

In a similar manner (R) isomer was prepared from (1.0 g) and 10% Pd on carbon on carbon (0.6 g) in 99% yield.

Preparative Example 55

(−) 2-methyl-3-(1H-imidazol-4-yl)-pyrrolidine

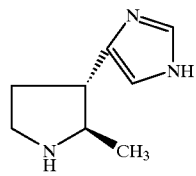

This compound was prepared according to the procedure in J. Med. Chem. 1995, 1593–1599.

Preparative Example 56

3-(1H-imidazol-1-yl)-azetidine

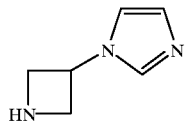

Step A 1N-diphenylmethyl-(1H-imidazol-1-yl)-azetidine

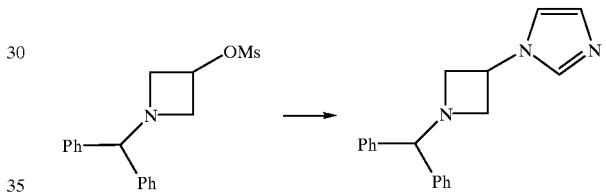

1N-Diphenylmethyl-3-methanesulfonyloxy-azetidine (J. Che. Res. 1996, 430) (10.0 g, 29.26 mmoles) was added to a stirred solution imidazole (5.96 g, 87.78 mmoles) in DMF (100 mL) under nitrogen atmosphere. The mixture was stirred at 60° C. for 16 h. DMF was evaporated in vacuo. The resulting crude product was extracted with $CH_2Cl_2$ and the extract was successively washed with water and brine, and the $CH_2Cl_2$ was evaporated to leave the title residue which was chromatographed on silica gel using 4% (10% conc $NH_4OH$ in methanol)-$CH_2Cl_2$ as eluant to give the title compound (2.87 g, 33.9%). FABMS (M+1)=290; $\delta_H$ (CDCl$_3$) 3.3 (dd, 2H), 3.65 (dt, 2H), 4.45 (s, 1H), 4.8 (m, 1H), 7.1–7.5 (m, 12H), 7.8 (s, 1H).

Step B 3-(1H-imidazol-1-yl)-azetidine

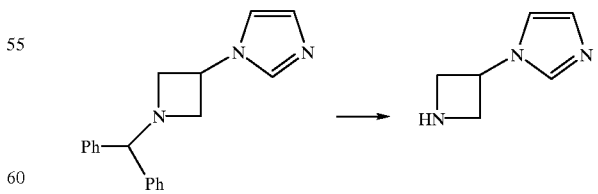

A mixture of the title compound (2.8 g) from Step A and 10% Pd on carbon (1.1 g) in MeOH (25 mL) was stirred at 50 psi under an atmosphere of hydrogen for 24 h. The catalyst was filtered to give the title compound (1.05 g, 99.9%) which was used to couple with the tricylic acid.

EXAMPLE 54

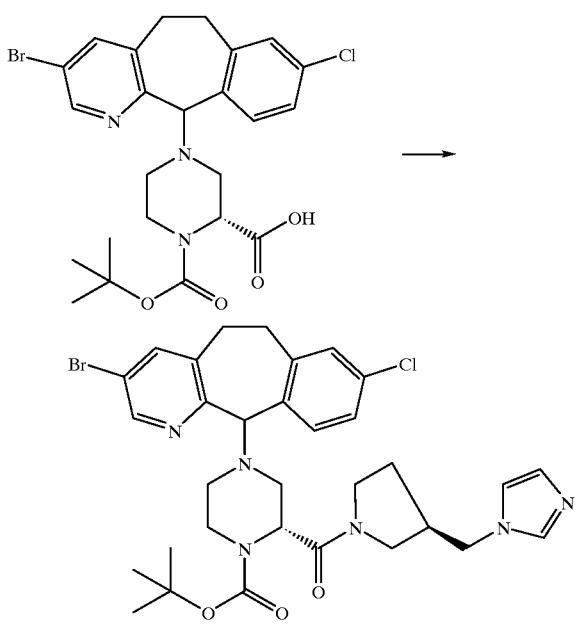

4-(3-bromo-8-chloro-6, 11-dihydro-5H-benzo[5,6]cyclohepta[1,2-b]pyridin-11-yl)-1-[(1,1-dimethylethoxy)carbonyl]-2(R)-piperazinecarboxylic acid (2 g, 3.8 mmoles.) was added to a solution of the title compound from Preparative Example 50 (1.1 g, 4.7 mmol), DEC (1.8 g, 9.4 mmoles.), HOBT (1.28, 9.48 mmoles.) and NMM (2.6 mL, 23.7 mmoles.) in DMF (100 mL). The resulting solution was stirred at room temperature 24 hours. The reaction mixture was diluted with $H_2O$ until precipitation ceased and the slurry filtered. The precipitate was diluted with $CH_2Cl_2$, washed with brine, dried over $Na_2SO_4$ and concentrated. The crude product was purified by flash chromatography using a 5% (10%$NH_4OH$ in MeOH) solution in $CH_2Cl_2$ as eluent to give the title compound (1.48 g, 55% yield) .FABMS (M+1)=669.

EXAMPLE 55 AND EXAMPLE 56

The title compound from Example 1 was separated into individual 11-(R)- and 11-(S)-isomers by Preparative HPLC with a CHIRALPAK AD column using a 15% iPrOH in hexane solution with 0.2% DEA as eluant.

EXAMPLE 55

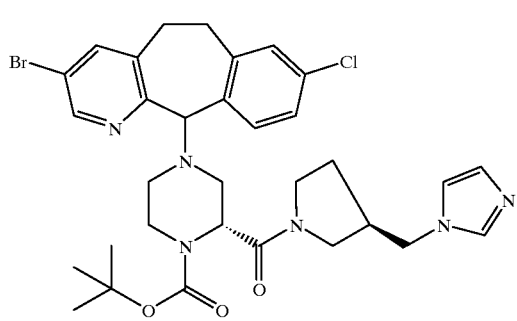

Isomer A: retention time (analytical)=8.885 minutes; $[\alpha]_D$=−13.1 (3.06 mg in 2.0 mL MeOH); FABMS (M+1)= 669.

EXAMPLE 56

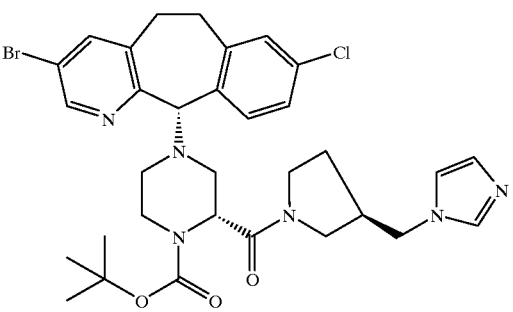

Isomer B: retention time (analytical)=8.885 minutes; $[\alpha]_D$=+12.1 (2.32 mg in 2.0 mL MeOH); FABMS (M+1)= 669.

EXAMPLE 57–69

By essentially the same procedure set forth in Example 1 only substituting the appropriate amines, one can obtain compounds of the formula shown below wherein $R^8$ is defined in Table 9 below.

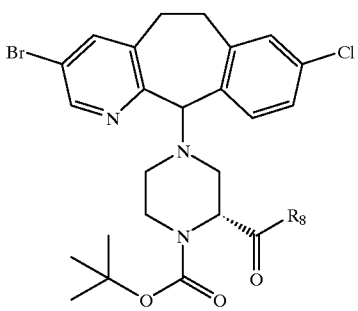

TABLE 9

| Ex. | $R^8$ | CMPD |
|---|---|---|
| 57 | ![structure] | FABMS (M + 1) = 669 |
|  | 11-(R,S) |  |
| 58 | ![structure] | FABMS (M + 1) = 655 |
|  | 11 (R,S) |  |
| 59 | ![structure] | FABMS (M + 1) = 655 |
|  | 11-(R,S) |  |

TABLE 9-continued

| Ex. | R[8] | CMPD |
|---|---|---|
| 60 | (pyrrolidine with CH3 and imidazole) 11-(R,S) | FABMS (M + 1) = 669 |
| 61 | (azetidine-imidazole) 11-(R,S) | FABMS (M + 1) = 641 |
| 62 | (piperidine-CH2-imidazole) 11-(R,S) | FABMS (M + 1) = 683 |
| 63 | (morpholine-CH2-imidazole) 11-(R,S) | FABMS (M + 1) = 685 |
| 64 | (morpholine-CH2-imidazole) 11-(R,S) | FABMS (M + 1) = 685 |
| 65 | (pyrrolidine-CH2-imidazole) 11-(R,S) | FABMS (M + 1) = 669 |
| 66 | (pyrrolidine-CH2-imidazole) 11-S | FABMS (M + 1) = 669 |
| 67 | (pyrrolidine-imidazole) 11-R | FABMS (M + 1) = 669 |
| 68 | (pyrrolidine-CH2-methylimidazole) 11-(R,S) | FABMS (M + 1) = 683 |
| 69 | (azetidine-CH2-imidazole) 11-(R,S) | FABMS (M + 1) = 655 |

EXAMPLE 70

Step A

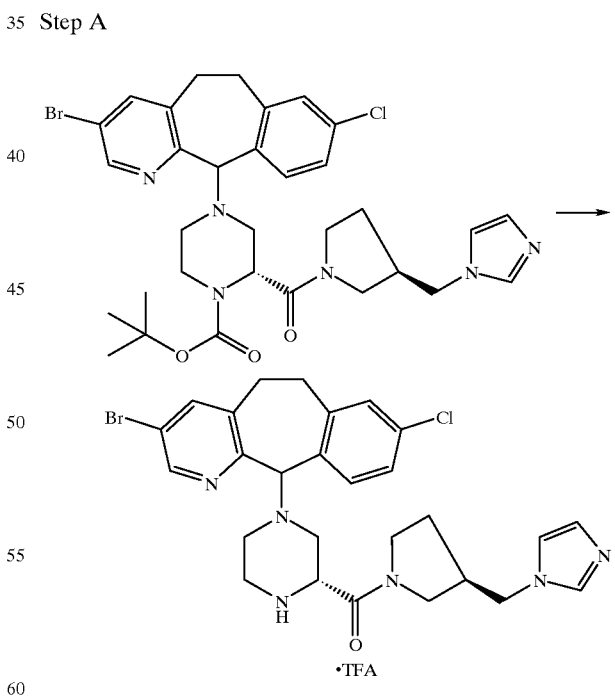

The title compound from Example 54 (0.1 g. 0.15 mmoles) was stirred at room temperature in CH$_2$Cl$_2$ (20 mL) and TFA(1 mL) for 2h. The reaction mixture was evaporated to dryness to give the title compound which was used as such in Step B below.

Step B

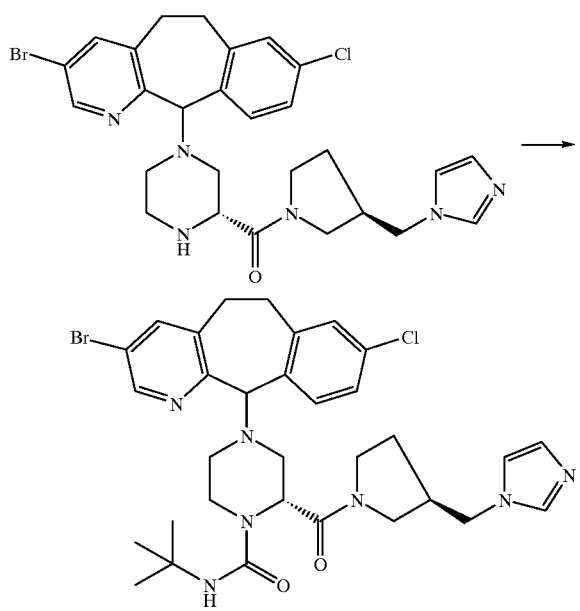

The title compound from Step A (0.186 g, 0.182 mmoles) dissilved in CH$_2$Cl$_2$ (20 mL) and triethyl amine (0.063 g, 0.621 mmoles) and t-butylisocyanate (0.0185 g, 0.187 mmoles ) was added. The resulting solution was stirred at room temperature for 2 h, diluted with water and extracted with CH$_2$Cl$_2$. CH$_2$Cl$_2$ extract was dried (MgSO$_4$) and filtered and concentrated in CH$_2$Cl$_2$ as eluant to give the title compound (0.084 g ) FABMS (M+1)=668.

EXAMPLES 71–73

By essentially the same procedure set forth in Example 1 only substituting with different isocyanates, one can obtain compounds of the formula shown below wherein R$^9$ is as defined in Table 10 below.

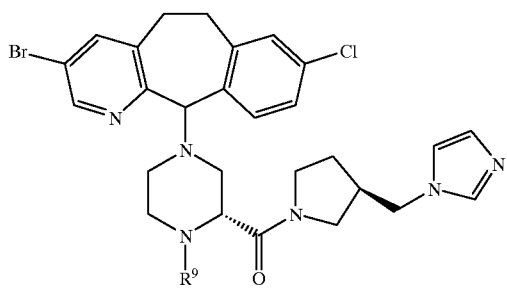

TABLE 10

| R$^9$ | CMPD |
|---|---|
| 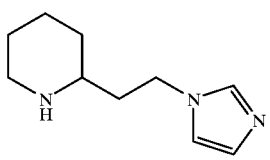 Ex. 71 | FABMS (M + 1) = 668 |

TABLE 10-continued

| R$^9$ | CMPD |
|---|---|
| 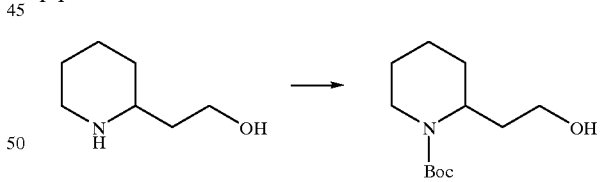 Ex. 72 11-(R,S) | FABMS (M + 1) = 696 |
| Ex. 73 11-(R,S) | FABMS (M + 1) = 710 |

Preparative Example 57

2(R/S)-[2-(1H-imidazol-1-yl)ethyl]piperidine

Step A 1N-tert-butoxycarbonyl-2(R/S)-(2-hydroxyethyl)-piperidine

2(R/S)-(2-Hydroxyethyl)piperidine (5 g, 38.7 mmoles) and sodium hydroxide (1.55 g, 67.4 mmoles) were dissolved in THF-water (1:1) (100 mL) and di-tert-butyldicarbonate (9.29 g, 42.6mmoles) was added and the mixture was stirred at 25° C. for 120 h. The solution was treated with BioRad 50W-X4 (RSO$_3$H) resin (42 mL) and filtered. The resin was washed with water and THF and the combined filtrates were evaporated to dryness. Chromatography on silica gel using 1% (10% conc. NH$_4$OH in methanol)-dichloromethane as the eluant afforded the title compound (8.87 g, 95%): CIMS: m/z 230.2 (MH$^+$); $\delta_H$ (CDCl$_3$) 1.47 ppm (9H, s, CH$_3$); $\delta_C$ (CDCl$_3$) CH$_3$: 28.4, 28.4, 28.4; CH$_2$: 19.2, 25.6, 29.6, 32.3, ~39.6, ~58.3; CH: ~45.9; C: 80.1, carbonyl not visible.

Step B
1N-tert-butoxycarbonyl-2(R/S)-(2-methanesulfonyloxyethyl) piperidine

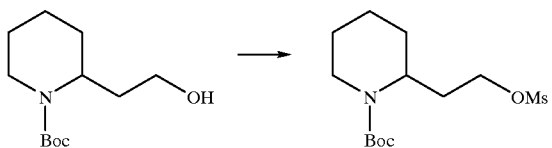

The title compound from Step A above (2 g, 8.72 mmoles) and triethylamine (7.29 mL: 52.4 mmoles) were dissolved in dichloromethane (50 mL) and the mixture was stirred under argon at 0° C. Methanesulfonyl chloride (2.03 mL: 26.2 mmoles) was added and the solution was stirred at 25° C. for 2 h. The solution was diluted with dichloromethane and washed with saturated aqueous sodium bicarbonate, water and dried (MgSO$_4$), filtered and evaporated to dryness. The product was chromatographed on silica gel using 2% (10% conc. NH$_4$OH in methanol)-dichloromethane as the eluant to give the title compound (1.25 g, 61%): ESMS: m/z 308.1 (MH$^+$); $\delta_C$ (CDCl$_3$) 28.5, 28.5, 28.5, 37.4/39.3; CH$_2$: 19.1, 23.8/25.5, 28.9/29.6, 33.1, 45.2; CH: 54.2; C: 79.8, ~155.2.

Step C
1N-tert-butoxycarbonyl-2(R/S)-[2-(1H-imidazol-1-yl)ethyl]piperidine

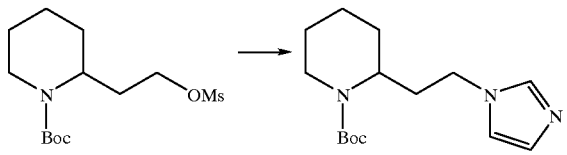

The title compound from Step B above (2.68 g, 8.72 mmoles) (crude product, prior to chromatography) was dissolved in anhydrous DMF (30mL) and sodium imidazole (1.18 g, 13.1 mmoles) was added. The mixture was heated at 70° C. for 2 h and then evaporated to dryness. The product was directly chromatographed on silica gel using 1% (10% conc. NH$_4$OH in methanol)-dicholoromethane as the eluant to give the title compound (1.69 g, 69%): ESMS: m/z 280.1 (MH$^+$); d$_H$ (CDCl$_3$) 1.48 ppm (9H, s, CH$_3$); d$_C$ (CDCl$_3$) CH$_3$: 28.5, 28.5, 28.5; CH$_2$: 19.1, 25.5, 28.9, 31.8, ~39.1, 44.3; CH: 48.1, 118.9, 129.5, 137.1; C: 80.1, carbonyl not visible.

Step D
2(R/S)-[2-(1H-imidazol-1-yl)ethyl]piperidine

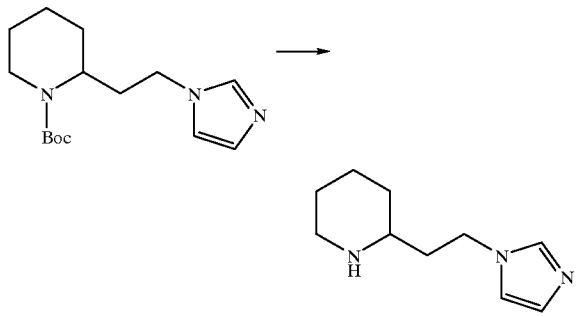

The title compound from Step C above (1.6 g, 5.73 mmoles) was dissolved in methanol (10 mL) and 10% conc. H$_2$SO$_4$ in dioxane (v/v) (40 mL) was added and the solution was stirred at 25° C. for 2 h. The mixture was treated with BioRad AG1-X8 (OH) resin until basic. The resin was filtered off and washed with methanol. The combined filtrates were evaporated to dryness and the product was chromatographed on silica gel using 5% (10% conc. NH$_4$OH in methanol)-dichloromethane as the eluant to give the title compound (1.02 g, 99%): CIMS: m/z 180.35 (MH$^+$); $\delta_H$ (CDCl$_3$) 6.94 (1H, s, Im-H$_5$), 7.18 (1H, s, Im-H$_4$) and 7.50 ppm (1H, s, Im-H$_2$); $\delta_C$ (CDCl$_3$) CH$_2$: 24.6, 26.8, 33.2, 38.6, 43.8, 47.0; CH: 53.9, 118.9, 129.5, 118.8.

Preparative Example 58
2(R/S)-[3-(1H-4-methylimidazol-1-yl)propyl]piperidine

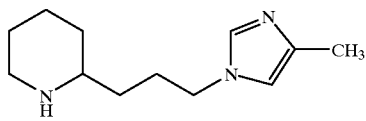

Step A
2(R/S)-(3-hydroxypropyl)piperidine

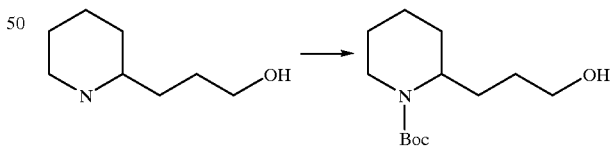

2-(3-Hydroxypropyl)pyridine (5 g, 36.4 mmoles) was dissolved in 1N HCl (36.4 mL, 36.4 mmoles) and water (63.6 mL) and platinum (IV) oxide monohydrate (1 g, 4.08 mmoles) was added under an argon atmosphere. The mixture was hydrogenated at 55 psi in a Parr bomb at 25° C. for 96 h. The catalyst was filtered off through Celite® and washed with water. The combined filtrates were treated with BioRad AG1-X8 (OH) resin until basic. The resin was filtered off and washed with water. The combined filtrates were evaporated to dryness and the product was chromatographed on silica gel using 10% increasing to 20% (10% conc. NH$_4$OH in methanol)dichloromethane as the eluant to give the title compound (5.22 g, 100%): CIMS: m/z 144.40 (MH$^+$); $\delta_C$ (d$_6$-DMSO) CH$_2$: 24.0, 25.3, 28.8, 31.5, 32.8, 45.9, 60.8; CH: 56.1.

Step B
1N-tert-butoxycarbonyl-2(R/S)-(3-hydroxypropyl) piperidine

The title compound from Step A above (3 g, 20.9 mmoles) was reacted with di-tert-butyldicarbonate (5.03 g, 23 mmoles) and sodium hydroxide (0.8378 g, 20.9 mmoles) essentially as described in Preparative Example 57, Step A above, but allowing the reaction to proceed for 166 h. The product was chromatographed on silica gel using 3% (10% conc. NH$_4$OH in methanol)-dichloromethane as the eluant to give the title compound (4.04 g, 79%): ESMS: m/z 244.0 (MH$^+$); $\delta_H$ (CDCl$_3$) 1.45 ppm (9H, s, CH$_3$); $\delta_C$ (CDCl$_3$) CH$_3$: 28.5, 28.5, 28.5; CH$_2$: 19.0, 25.6, 26.2, 29.2, ~38.8, 62.8; CH: ~50.0; C: 79.3, ~155.2.

Step C
1N-tert-butoxycarbonyl-2(R/S)-[3-(4-toluenesulfonyloxy) propyl]piperidine

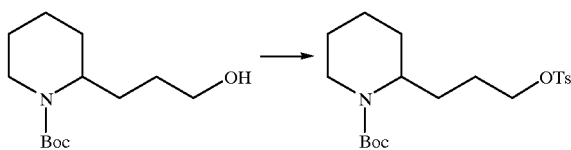

The title compound from Step B above (2 g, 8.22 mmoles) was dissolved in anhydrous pyridine (10 mL) and the solution was cooled with stirring to 0° C. 4-Toluenesulfonyl chloride (1.88 g, 9.86 mmoles) was added and the mixture was stirred at 0° C. for 2 h. The mixture was evaporated to dryness and the residue was taken up in dichloromethane and washed with saturated aqueous sodium bicarbonate, water, dried (MgSO$_4$), filtered and evaporated to dryness. The product was chromatographed on silica gel using 0.25% methanol in dichloromethane as the eluant to give the title compound (2.53 g, 77%): ESMS: m/z 398.1 (MH$^+$). $\delta_H$ (CDCl$_3$) 1.41 (9H, s, CH$_3$), 2.45 (3H, s, Ar—CH$_3$), 4.06 (2H, m, CH$_2$O), 7.36 (2H, d, Ar—H$_3$ and Ar—H$_5$) and 7.79 ppm (2H, m, Ar—H$_2$ and Ar—H$_6$); $\delta_C$(CDCl$_3$)CH$_3$: 19.1, 28.5, 28.5, 28.5; CH$_2$: 21.7, 22.8, 25.7, 25.8, 28.8, 38.7, 70.6; CH: ~49.6, 127.9, 127.9, 129.9, 129.9;C: 71.1, 133.2, 144.6, 155.1.

Step D
1N-tert-butoxycarbonyl-2(R/S)-[3-(1H-4/5-methylimidazol-1-yl)propyl]piperidine

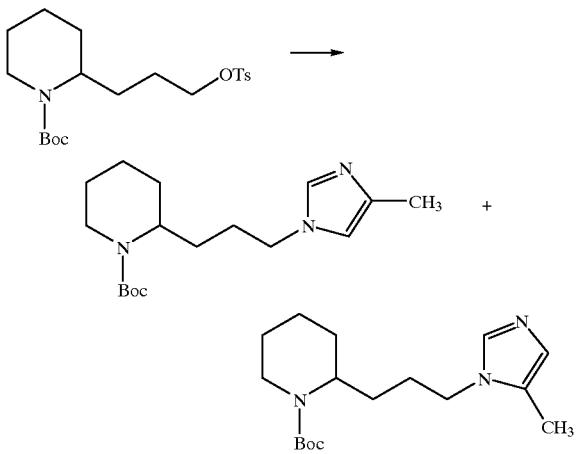

4-Methylimidazol (0.5453 g, 6.64 mmoles) was dissolved in anhydrous DMF(15mL) and 95% sodium hydride (0.1678 g, 6.64 mmoles) was added. The mixture was stirred at 25° C. for 0.5 h. under argon. The title compound from Preparative Example 58, Step C, (2.4 g, 6.04 mmoles) in anhydrous DMF (10 mL) was added and the mixture was stirred at 25° C. for 1 h. The product was worked up as described in Preparative Example 2, Step A and chromatographed on silica gel using 3% methanol in dichloromethane as the eluant to give a mixture of the title compounds (1.459 g, 79%) (4-Me:5-Me::63:37): CIMS: m/z 308.25 (MH$^+$) 4-Me: $\delta_H$ (CDCl$_3$) 1.43 (9H, s, CH$_3$), 2.18 (3H, s, Im-4-Me), 3.87 (2H, m, CH$_2$-Im), 6.58 (1H, s, Im-H$_5$) and 7.33 ppm (1H, s, Im-H$_2$); $\delta_C$ (CDCl$_3$); CH$_3$: 13.8, 28.5, 28.5, 28.5; CH$_2$: 19.0, 25.6, 26.4, 27.7, 28.7, 38.9, 46.5; CH: ~49.4, 115.2, 136.2; C: 79.4, 138.7, 155.1 and 5-Me: $\delta_H$ (CDCl$_3$) 1.43 (9H, s, CH$_3$), 2.16 (3H, s, Im-5-Me), 3.87 (2H, m, CH$_2$-Im), 6.74 (1H, s, Im-H$_4$) and 7.37 ppm (1H, s, Im-H$_2$); $\delta_C$ (CDCl$_3$) CH$_3$: 9.3, 28.5, 28.5, 28.5; CH$_2$: 19.0, 25.6, 26.5, 27.3, 28.7, 39.0, 44.4; CH: ~49.4, 126.9, 136.8; C: 79.4, ~138.7, 155.1.

Step E
1N-tert-butoxycarbonyl-2(R/S)-[3-(1H-4-methylimidazol-1-yl) propyl]piperidine

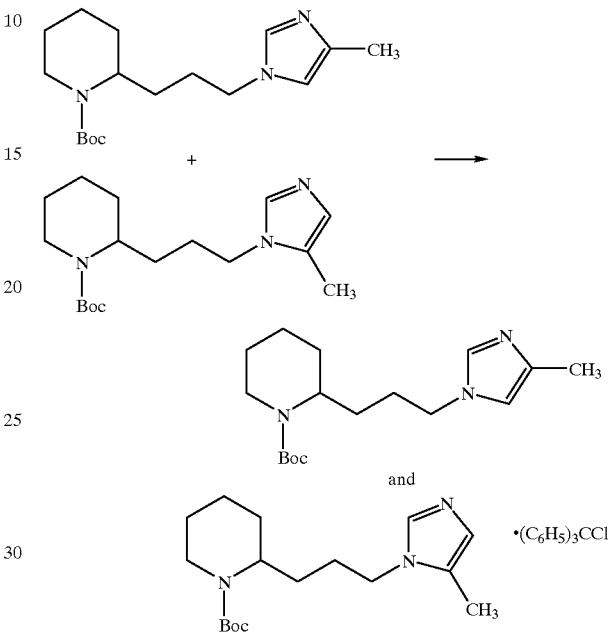

The mixture of compounds from Step D above (1.054 g) was dissolved in anhydrous CH$_2$Cl$_2$ (10 mL) at 0° C. under argon. Trityl chloride (0.3891 g. 1.1 equivalents per equivalent of the 5-methyl isomer) was added and the mixture was stirred at 0° C. for 2 h. The reaction mixture was introduced directly onto a silica gel column and the column was eluted with 50% ethyl acetate in acetone to give the pure 4-methyl isomer (0.7242 g, 69%): 4-Me: CIMS: m/z 308.30 (MH$^+$); $\delta_H$ (CDCl$_3$) 1.43 (9H, s, CH$_3$), 2.18 (3H, s, Im-4-Me), 3.84 (2H, m, CH$_2$-Im), 6.58 (1H, s, Im-H$_5$) and 7.30 ppm (1H, s, Im-H$_2$); $\delta_C$ (CDCl$_3$) CH$_3$: 13.8, 28.5, 28.5, 28.5; CH$_2$: 19.0, 25.5, 26.4, 27.7, 28.7, 38.8, 46.5; CH: ~49.4, 115.2, 136.2; C: 79.3, 138.4, 155.1.

Step F
2-(R/S)-[3-(1H-4-methylimidazol-1-yl)propyl]piperidine

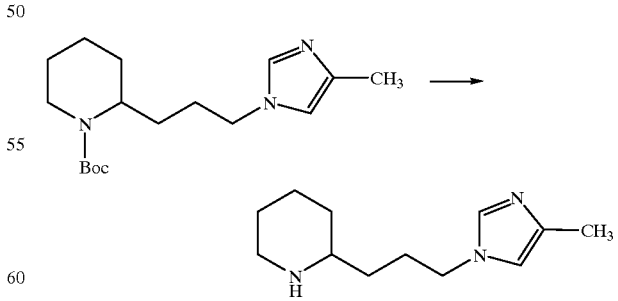

The title compound from Step E above (0.4456 g, 1.5 mmoles) was deprotected as described in Preparative Example 57, Step D and the product was chromatographed on silica gel using 20% (10% conc. NH$_4$OH in methanol)-dichloromethane as the eluant to give the title compound (0.2627 g, 87%): CIMS: m/z 208.25 (MH⁺); $\delta_H$ (CDCl₃) 2.14 (3H, s, Im-4-Me), 3.79 (2H, m, CH₂-Im), 6.52 (1H, s, Im-H₅) and 7.24 ppm (1H, s, Im-H₂); $\delta_C$ (CDCl₃) CH₃: 13.7; CH₂: 24.7, 26.6, 27.5, 32.9, 34.3, 47.0, 47.1; CH: 56.3, 115.2, 136.1; C: 138.4.

Preparative Example 59

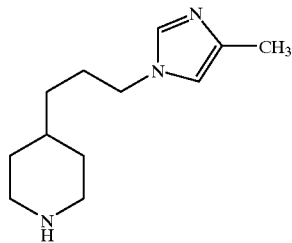

Step A
4(R/S)-(3-hydroxypropyl)piperidine

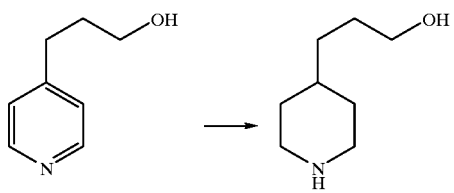

4-(3-Hydroxypropyl)pyridine (5 g, 36.4 mmoles) was dissolved in 1N HCl (36.4 mL, 36.4 mmoles) and water (63.6 mL) and platinum (IV) oxide monohydrate (1 g, 4.08 mmoles) was added under an argon atmosphere. The mixture was hydrogenated at 55 psi in a Parr bomb at 25° C. for 66 h. The catalyst was filtered off through Celite® and washed with water. The combined filtrates were treated with BioRad AG1-X8 (OH) resin until basic. The resin was filtered off and washed with water. The combined filtrates were evaporated to dryness and the product was chromatographed on silica gel using 7% (10% conc. NH₄OH in methanol)-dichloromethane as the eluant to give the title compound (4.91 g, 94%): CIMS: m/z 144.40 (MH⁺); $\delta_C$ (d₆-DMSO) CH₂: 29.4, 31.6, 31.6, 32.8, 45.1, 45.1, 60.8; CH: 34.8.

Step B
N-tert-butoxycarbonyl-4(R/S)-(3-hydroxypropyl)piperidine

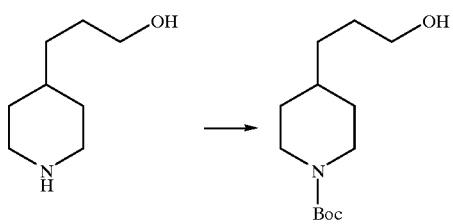

The title compound from Step A above (3 g, 20.9 mmoles) was reacted with di-tert-butyldicarbonate (5.03 g, 23 mmoles) and sodium hydroxide (0.8378 g, 20.9 mmoles) essentially as described in Preparative Example 57, Step A above, but allowing the reaction to proceed for 166 h. The product was chromatographed on silica gel using 3% (10% conc. NH₄OH in methanol)-dichloromethane as the eluant to give the title compound (3.33 g, 65%): ESMS: m/z 244.2 (MH⁺); $\delta_H$ (CDCl₃) 1.47 ppm (9H, s, CH₃); $\delta_C$ (CDCl₃) CH₃: 28.5, 28.5, 28.5; CH₂: 29.9, 29.9, 32.2, 32.6, 44.1, 44.1; CH: 35.9; C: 79.3, ~154.8.

Step C 1N-tert-butoxycarbonyl-4(R/S)-[3-(4-toluenesulfonyloxy) propyl]piperidine

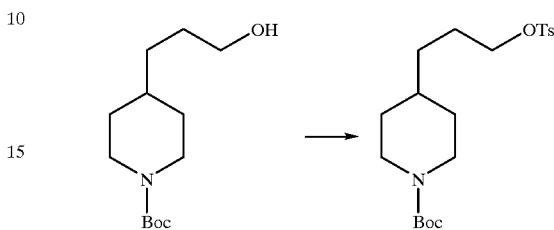

The title compound from Step B above (2 g, 8.22 mmoles) was dissolved in anhydrous pyridine (10 mL) and the solution was cooled with stirring to 0° C. 4-Toluenesulfonyl chloride (1.88 g, 9.86 mmoles) was added and the mixture was stirred at 0° C. for 2 h. The mixture was evaporated to dryness and the residue was taken up in dichloromethane and washed with saturated aqueous sodium bicarbonate, water, dried (MgSO₄), filtered and evaporated to dryness. The product was chromatographed on silica gel using 0.5% methanol in dichloromethane as the eluant to give the title compound (2.86 g, 88%): ESMS: m/z 398.1 (MH⁺).

$\delta_H$ (CDCl₃) 1.44 (9H, s, CH₃), 2.46 (3H, s, Ar—CH₃), 4.01 (2H, m, CH₂O), 7.35 (2H, d, Ar—H₃ and H₅) and 7.79 ppm (2H, d, Ar—H₂ and H₆); $\delta_C$ (CDCl₃) CH₃: 21.7, 28.6, 28.6, 28.6; CH₂: 26.1, 32.0, 32.0, 32.1, 43.9, 43.9, 70.7; CH: 35.5, 127.9, 127.9, 129.9, 129.9; C: 79.3, 133.1, 144.8, 154.9.

Step D 1N-tert-butoxycarbonyl-4-[3-(1H-4/5-methylimidazol-1-yl) propyl]piperidine

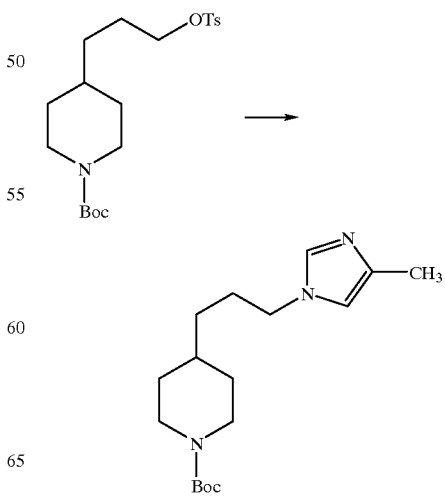

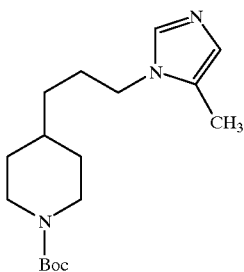

4-Methylimidazole (0.5453 g, 6.64 mmoles) was dissolved in anhydrous DMF (15 mL) and 95% sodium hydride (0.1678 g, 6.64 mmoles) was added to the stirred solution at 25° C. under argon. The solution was stirred at 25° C. for 0.5 h. The title compound from Preparative Example 59, Step C, (2.4 g, 6.04 mmoles) in anhydrous DMF (10 mL) was added and the mixture was stirred at 25° C. for 1 h. The product was worked up as described in Preparative Example 2, Step A and chromatographed on silica gel using 3% methanol in dichloromethane as the eluant to give the title mixture of compounds (1.584 g, 85%) (4-Me::5-Me::58:42): CIMS: m/z 308.25 (MH$^+$); 4-Me: $\delta_H$ (CDCl$_3$) 1.44 (9H, s, CH$_3$), 2.21 (3H, s, Im-4-Me), 3.82 (2H, m, CH$_2$-Im), 6.59 (1H, s, Im-H$_5$) and 7.33 ppm (1H, s, Im-H$_2$); $\delta_C$ (CDCl$_3$) CH$_3$: 13.8, 28.5, 28.5, 28.5; CH$_2$: 28.3, 32.1, 33.4, 33.4, 44.0, 47.1, 47.1; CH: 35.8, 115.2, 136.2; C: 79.3, 138.5, 154.9 and 5-Me: $\delta_H$ (CDCl$_3$) 1.44 (9H, s, CH$_3$), 2.19 (3H, s, Im-5-Me), 3.82 (2H, m, CH$_2$-Im), 6.77 (1H, s, Im-H$_4$) and 7.39 ppm (1H, s, Im-H$_2$); $\delta_C$ ((CDCl$_3$) CH$_3$: 9.3, 28.5, 28.5, 28.5; CH$_2$: 28.1, 32.1, 33.4, 33.4, 44.0, 44.0, 44.9; CH: 35.8, 127.0, 136.2; C: 79.3, 133.7, 154.9.

Step E
1N-tert-butoxycarbonyl-4-[3-(1H-4-methylimidazol- 1-yl)propyl]piperidine

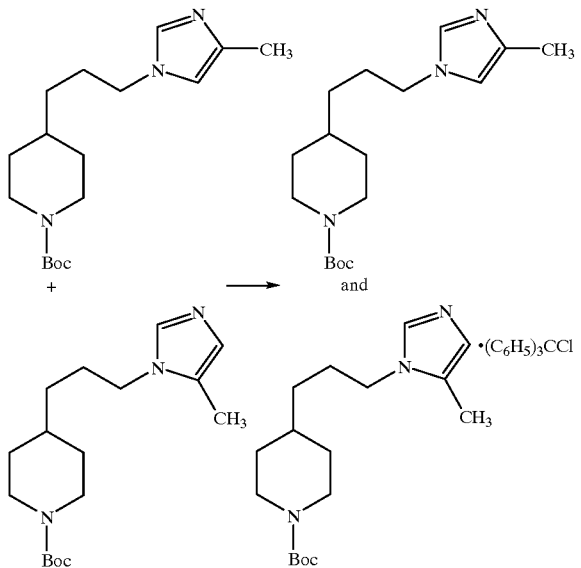

The mixture of compounds from Step D above (1.51 g) was dissolved in anhydrous CH$_2$Cl$_2$ (10mL) at 0° C. under argon. Trityl chloride (1.15 g, 2 equivalents per equivalent of the 5-methyl isomer) was added and the mixture was stirred at 0° C. for 2 h. The reaction mixture was introduced directly onto a silica gel column and the column was eluted with 50% ethyl acetate in acetone to give the pure 4-methyl isomer (0.635 g, 65%): 4-Me: CIMS: m/z 308.30 (MH$^+$); $\delta_H$ (CDCl$_3$) 1.44 (9H, s, CH$_3$), 2.22 (3H, s, Im-4-Me), 3.83 (2H, m, CH$_2$-Im), 6.60 (1H, s, Im-H$_5$) and 7.33 ppm (1H, s, Im-H$_2$); $\delta_C$ (CDCl$_3$) CH$_3$: 13.8, 28.5, 28.5, 28.5; CH$_2$: 28.2, 32.0, 33.4, 33.4, 43.9, 47.1, 47.1; CH: 35.7, 115.2, 136.2; C: 79.3, 138.5, 154.8.

Step F
4-[3-(1H-4-methylimidazol-1-yl)propyl]piperidine

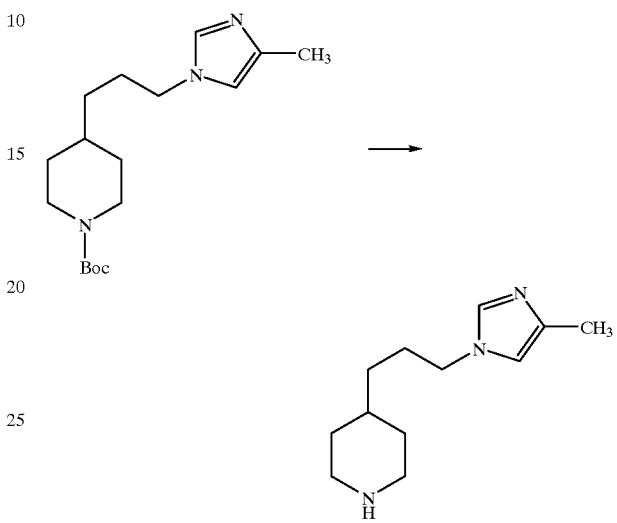

The title compound was deprotected as described in Preparative Example 57, Step D to give after chromatography on silica gel using 20% (10% conc. NH$_4$OH in methanol)-dichloromethane as the eluant, the title compound (0.3581 g, 89%): CIMS: m/z 208.25 (MH$^+$); $\delta_H$ (CDCl$_3$) 2.12 (3H, s, Im-4-Me), 3.74 (2H, m, CH$_2$-Im), 6.51 (1H, s, Im-H$_5$) and 7.25 ppm (1H, s, Im-H$_2$); $\delta_C$ (CDCl$_3$) CH$_3$: 13.6; CH$_2$: 28.1, 33.3, 33.3, 33.9, 46.5, 46.5, 47.1; CH: 35.8, 115.1, 136.0; C: 138.2.

Preparative Example 60
3(R/S)-[(1H-imidazol-1-yl)methyl]-1,2,3,4-tetrahydroquinoline

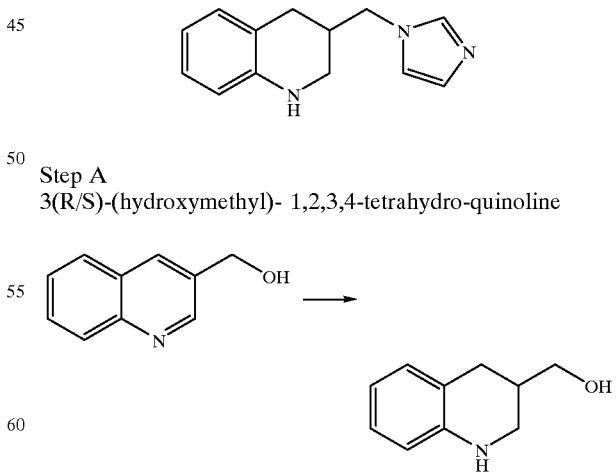

Step A
3(R/S)-(hydroxymethyl)- 1,2,3,4-tetrahydro-quinoline

3-Hydroxymethylquinoline (0.45 g, 2.83 mmoles) (prepared as described in: B. R. Brown, D. Ll. Hammick and B. H. Thewlis, J. Chem. Soc., 1951,1145–1149.) was dissolved in methanol (100 mL) and placed in a Parr bomb.

Platinum (IV) oxide monohydrate (0.225 g, 0.918 mmoles) was added and the mixture was hydrogenated at 50 psi at 25° C. for 6 h. The catalyst was removed by decantation and washed with methanol. The methanol was evaporated to dryness and the product was chromatographed on silica gel using 3% (10% conc. $NH_4OH$ in methanol)-dichloromethane as the eluant to give the title compound (0.3843 g, 83%): CIMS: m/z 164.35 ($MH^+$); $\delta_H$ ($CDCl_3$) 6.50 (1H, d, Ar—$H_8$), 6.64 (1H, t, Ar—$H_6$), 6.98 (1H, d, Ar—$H_5$) and 6.99 ppm(1H, m, Ar—$H_7$); $\delta_C$ ($CDCl_3$) $CH_2$: 29.5, 44.0, 65.2; CH: 34.9, 114.2, 117.4, 126.9, 129.8; C: 120.2, 144.5.

Step B
1N-tert-butoxycarbonyl-3(R/S)-(hydroxymethyl)-1,2,3,4-tetrahydroquinoline

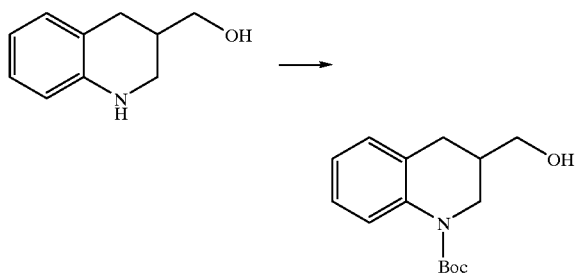

The title compound from Step A above (2.578 g, 15.79 mmoles) was dissolved in THF (51.5 mL) and sodium hydroxide (0.634 g, 15.79 mmoles) in water (51.5 mL) was added. Di-tert-butyldicarbonate (6.888 g, 31.58 mmoles) was added and the mixture was stirred at 25° C. for 187 h. Additional di-tert-butyl dicarbonate (0.6888 g, 3.16 mmoles) was added and the reaction was allowed to proceed for a total of 301 h. The product was worked up and purified as described in Preparative Example 1, Step A to give the title compound (3.794 g, 91%): FABMS: m/z 264.1 ($MH^+$); $\delta_H$ ($CDCl_3$) 1.50 (9H, s, $CH_3$), 7.03 (1H, m, Ar—H), 7.19-7.10 (2H, m, Ar—H) and 7.58 ppm (1H, d, Ar—H); $\delta_C$ ($CDCl_3$) $CH_3$: 28.3, 28.3, 28.3; $CH_2$: 29.5, 45.1, 63.6; CH: 36.1, 124.0, 124.6, 125.6, 129.2; C: 81.5, 128.2, ~138.8, ~154.7.

Step C
1N-tert-butoxycarbonyl-3(R/S)-[(4-tosyloxy)methyl]-1,2,3,4-tetrahydroquinoline

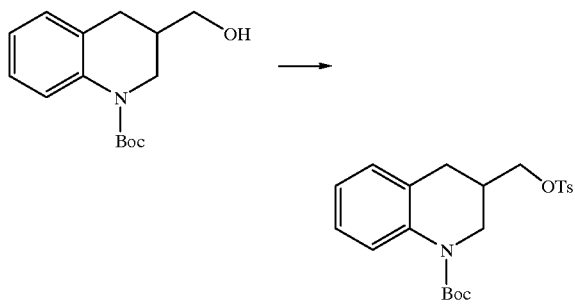

The title racemic compound from Step B above (0.322 g, 1.22 mmoles) was dissolved in anhydrous pyridine (2 mL) and the solution was cooled to 0° C. 4-Toluenesulfonyl chloride (0.28 g, 1.464 mmoles) was added and the reaction was stirred at 0° C. for 5 h. The mixture was then heated at 40° C. for 13 h and worked up as described in Preparative Example 2, Step C to give the title compound (0.481 g) which was used directly in Step E below.

The individual pure enantiomers from Step C above may be similarly treated to give the 3(R) and 3(S) enantiomers of the title compound.

Step D
1N-tert-butoxycarbonyl-3(R/S)-[(1H-imidazol-1-yl)methyl]-1,2,3,4-tetrahydroquinoline

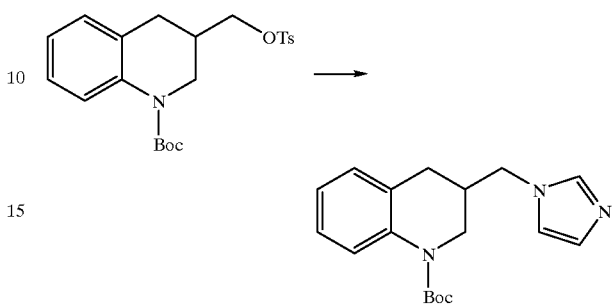

The title racemic product from Step D above was dissolved in anhydrous DMF (5 mL) and sodium imidazole (0.1652 g, 1.83 mmoles) was added. The mixture was heated at 65° C. under argon for 4 h. The solution was evaporated to dryness and the residue was taken up in dichloromethane, washed with water, dried ($MgSO_4$), filtered and evaporated to dryness. Chromatography on silica gel using 2.5% (10% conc. $NH_4OH$ in methanol)-dichloromethane afforded the title compound (0.3284 g, 86%): ESMS: m/z 314.1 ($MH^+$); $\delta_H$ ($CDCl_3$) 1.51 (9H, s, $CH_3$), 6.97 (1H, s, Im-$H_5$), 7.01 (1H, t, Ar—$H_6$), 7.06 (1H, t, Ar—$H_7$), 7.12 (1H, s, Im-$H_4$), 7.17 (1H, t, Ar—$H_5$), 7.51 (1H, s, Im-$H_2$) and 7.68 ppm (1H, d, Ar—$H_8$); $\delta_C$ ($CDCl_3$) $CH_3$: 28.4, 28.4, 28.4; $CH_2$: 31.0, 46.7, 49.5; CH: 35.9, 119.1, 123.8/123.9, 126.4, 126.9, 129.0, 129.8, 137.5; C: 81.5, 137.5, 138.2, 153.7.

The individual pure enantiomers from Step D above may be similarly treated to give the 3(R) and 3(S) enantiomers of the title compound.

Step E
3(R/S)-[(1H-imidazol-1-yl)methyl]-1,2,3,4-tetrahydroquinoline

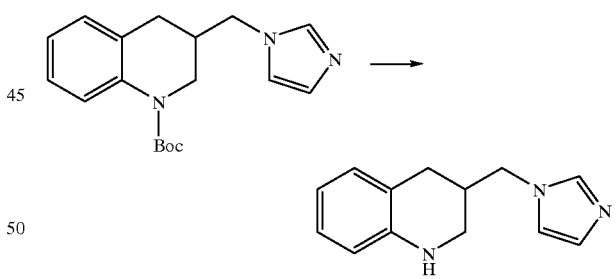

The title racemic compound from Step E above (0.3208 g, 1.024 mmoles) was dissolved in anhydrous methanol (5.42 mL) and 10% conc. $H_2SO_4$/dioxane (v/v) (13.95 mL) was added and the mixture was stirred at 25° C. for 1 h. The product was worked up as described in Preparative Example 1, Step D above. Chromatography on silica gel using 2.5% (10% conc. $NH_4OH$ in methanol)dichloromethane as the eluant gave the title compound (0. 19 g, 90%): CIMS: m/z 214.2 ($MH^+$); $\delta_H$ ($CDCl_3$) 3.97 (2H, m, Im-$CH_2$), 6.51 (1H, d, Ar—$H_8$), 6.65 (1H, t, Ar—$H_6$), 6.95 (1H, s, Im-$H_5$), 6.96 (1H, t, Ar—$H_7$), 7.01 (1H, t, Ar—$H_5$), 7.09 (1H, s, Im-$H_4$) and 7.50 ppm (1H, s, Im-$H_2$); $\delta_C$ ($CDCl_3$) $CH_2$: 30.2, 43.5, 49.0; CH: 33.7, 114.2, 117.7, 119.3, 127.3, 129.5, 130.0, 137.7; C: 118.4, 143.9.

Step F
3(R)-[(1H-imidazol-1-yl)methyl]-1,2,3,4-tetrahydroquinoline and
3(S)-[(1H-imidazol-1-yl)methyl]-1,2,3,4-tetrahydroquinoline

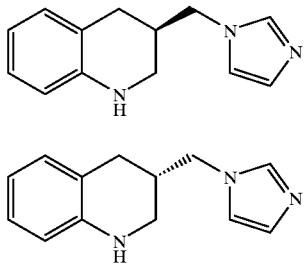

3R

3S

The racemic title compound (0.6545 g) from Step E above was separated by preparative HPLC on a Chiralpak® AD column (50×5 cm) using hexane-iso-propanol-dimethylamine::80:20:0.2 as the eluant to give a less polar (−)-enantiomer (0.3244 g): CIMS: m/z 214.15 (MH$^+$); $\delta_H$ (CDCl$_3$) 3.97 (2H, m, Im-CH$_2$), 6.52 (1H, d, Ar—H$_8$), 6.68 (1H, t, Ar—H$_6$) 6.96 (1H, s, Im-H$_5$), 6.96 (1H, t, Ar—H$_7$), 7.02 (1H, t, Ar—H$_5$), 7.10 (1H, s, Im-H$_4$) and 7.49 ppm (1H, s, Im-H$_2$); $\delta_C$ (CDCl$_3$) CH$_2$: 30.2, 43.5, 49.0; CH: 33.7, 114.2, 117.7, 119.3, 127.3, 129.6, 130.0, 137.7; C: 118.5, 143.9; $[\alpha]_D^{20°\ C.}$ −57.30° (c=10.43 mg/2 mL, methanol) and a more polar (+)-enantiomer (0.3286 g): CIMS: m/z 214.15 (MH$^+$); $\delta_H$ (CDCl$_3$) 3.97 (2H, m, Im-CH$_2$), 6.52 (1H, d, Ar—H$_8$), 6.67 (1H, t, Ar—H$_6$), 6.96 (1H, s, Im-H$_5$), 6.96 (1H, t, Ar—H$_7$), 7.01 (1H, t, Ar—H$_5$), 7.11 (1H, s, Im-H$_4$) and 7.50 ppm (1H, s, Im-H$_2$); $\delta_C$ (CDCl$_3$) CH$_2$: 30.2, 43.5, 49.0; CH: 33.7, 114.2, 117.7, 119.3, 127.3, 129.6, 130.1, 137.7; C: 118.5, 143.9; $[\alpha]_D^{20°\ C.}$ +56.80° (c=10.70 mg/2 mL, methanol), corresponding to the title compounds.

Preparative Example 61
3-[(1H-4-methylimidazol-1-yl)methyl]-1,2,3,4-tetrahydroquinoline

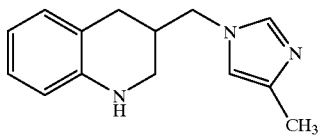

Step A
1N-tert-butoxycarbonyl-3-[(1H-4-methylimidazol-1-yl)methyl]-1,2,3,4-tetrahydroquinoline

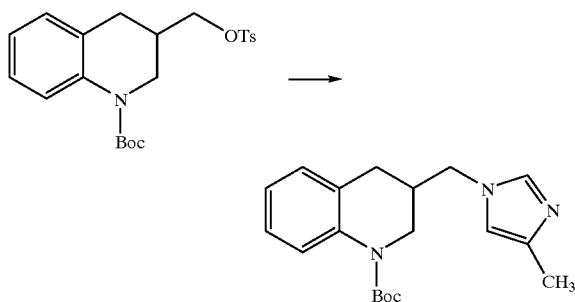

4-Methylimidazole (0.9504 g, 11.6 mmoles) was dissolved in anhydrous DMF (52 mL) and 95% sodium hydride (0.2924 g, 11.6 mmoles) was added in portions to the stirred solution at 25° C. under argon. The mixture was stirred for 1 h. The title racemic compound from Preparative Example 60. Step C (4.394 g, 10.5 mmoles) in anhydrous DMF (25 mL) was added and the mixture was stirred at 25° C. for 1 h and then at 55–60° C. for 7 h. The mixture was evaporated to dryness and the residue was chromatographed on silica gel using 0.5%-2%-4%-6%-10% (10% conc. NH$_4$OH in methanol)-dichloromethane as the eluant to give the racemic title compound (1.93 g, 56%) (4-Me:5-Me::1.46:1.0): CIMS: m/z 328.25 (MH$^+$); $\delta_H$ (CDCl$_3$) 1.51 (9H, s, CH$_3$), 2.20/2.24 (3H, s, 5-Me/4-Me), 3.81/3.88 (2H, m, 5-Me-Im-CH$_2$/4-Me-Im-CH$_2$), 6.65/6.83 (1H, s, 4-Me-Im-H$_5$/5-Me-Im-H$_4$), 6.99–7.07 (2H, m, Ar—H$_7$ and Ar—H$_8$), 7.17/7.20 (1H, d, Ar—H$_6$), 7.36/7.43 (1H, s, 4-Me-Im-H$_2$/5-Me-Im-H$_2$) and 7.67/7.71 ppm (1H, d, Ar—H$_9$); $\delta_C$ (CDCl$_3$) 4-Me: CH$_3$: 13.8, 28.4, 28.4, 28.4; CH$_2$: 31.0, 46.8, 49.4; CH: 35.8, 115.6, 123.8, 123.9, 126.3, 129.1, 136.7; C: 81.4, 127.0, 138.2, 153.7; and 5-Me: CH$_3$: 9.4, 28.4, 28.4, 28.4; CH$_2$: 31.0, 46.9, 47.1; CH: 35.3, 123.9, 123.9, 126.4, 126.9, 129.1, 137.3; C: 81.5, 127.3, 138.9, 153.7.

Step B
3-[(1H-4-methylimidazol-1-yl)methyl]-1,2,3,4-tetrahydroquinoline

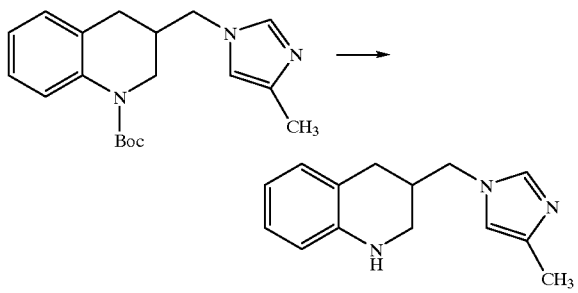

The title compound from Step A above was deprotected essentially as described in Preparative Example 57, Step D above and chromatographed on silica gel to give the title compound.

Preparative Example 62
6-[(1H-imidazol-1-yl)methyl]-1,2,3,4-tetrahydroquinoline

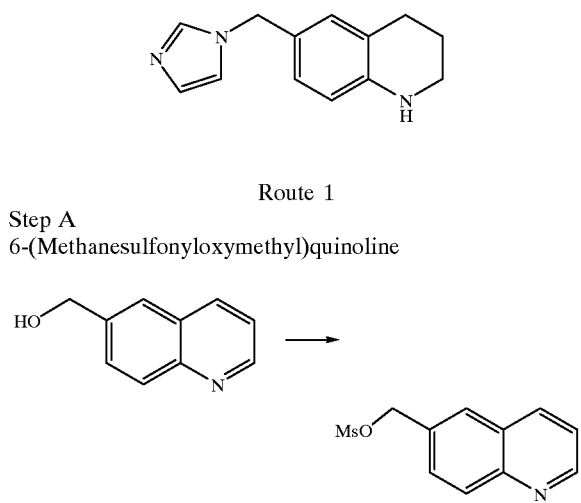

Route 1
Step A
6-(Methanesulfonyloxymethyl)quinoline

6-Hydroxymethylquinoline (0.4325 g, 2.72 mmoles) (prepared by the method of: C. E. Kaslow and W. R. Clark, J. Org. Chem., 1953, 18, 55–58.) and triethylamine (1.5147 mL, 10.87 mmoles) were dissolved in anhydrous dichloromethane (16 mL) and the mixture was cooled to 0° C. Methanesulfonyl chloride (0.421 mL, 5.43 mmoles) was added and the mixture was stirred under argon at 0° C. for 1 h. Additional triethylamine (0.758 mL, 5.435 mmoles) and methanesulfonyl chloride (0.211 mL, 2.72 mmoles) were added and the reaction was allowed to proceed for a further 1 h at 0° C. The mixture was evaporated to dryness to give the title compound which was used without further purification in the next step.

Step B

6-[(1H-imidazol-1-yl)methyl]quinoline

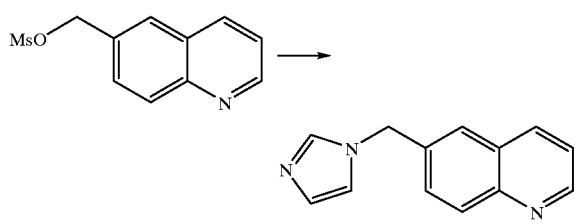

The title product from Step A above was dissolved in anhydrous DMF (10 mL) and sodium imidazole (0.367 g, 4.08 mmoles) was added. The mixture was heated at 70° C. under argon for 2 h and then evaporated to dryness. The product was chromatographed on silica gel to give the title compound (0. 1559 g, 27%): FABMS: m/z 210.0 (MH$^+$); $\delta_H$ (CDCl$_3$) 5.34 (1H, s, CH$_2$), 6.97 (1H, s, Im-H$_5$), 7.15 (1H, s, Im-H$_4$), 7.44 (1H, dd, Ar—H$_3$), 7.52 (2H, m, Ar—H$_5$ and Ar—H$_7$), 7.64 (1H, s, Im-H$_2$), 8.12 (2H, d, Ar—H$_4$ and Ar—H$_8$) and 8.95 ppm (1H, d, Ar—H$_2$); $\delta_C$ (CDCl$_3$) CH$_2$: 50.6; CH: 119.4, 121.8, 125.9, 128.4, 130.1, 130.5, 136.0, 137.6, 151.0; C: 128.2, 134.6, 147.9.

Step C

6-[(1H-imidazol-1-yl)methyl-1,2,3,4-tetrahydroquinoline

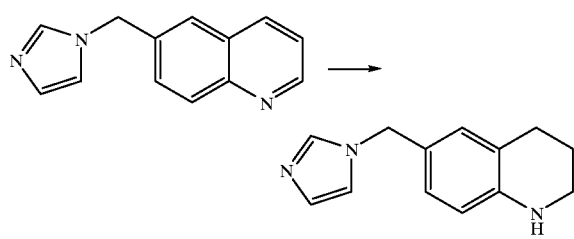

The title compound from Step B above (0.045 g, 0.215 mmoles) and methanol (11 mL) were placed in a Parr bomb and platinum (IV) oxide monohydrate (0.05 g, 0.204 mmoles) was added. The mixture was hydrogenated at 50 psi at 25° C. for 2 h. The catalyst was removed by decantation and washed with methanol. The methanol was evaporated to dryness and the product was chromatographed on silica gel using 3% (10% conc. NH$_4$OH in methanol)-dichloromethane as the eluant to give the title compound (0.0325 g, 71%): CIMS: m/z 214.15 (MH$^+$); $\delta_H$ (CDCl$_3$) 1.92 (2H, t, 3-CH$_2$), 2.61 (2H, m, 4-CH$_2$), 3.30 (2H, m, 2-CH$_2$), 4.93 (2H, s, CH$_2$), 6.42 (1H, d, Ar—H$_8$), 6.77 (1H, s, Ar—H$_5$), 6.79 (1H, d, Ar—H$_7$), 6.90 (1H, bs, Im-H$_5$), 7.07 (1H, bs, Im-H$_4$) and 7.52 ppm (1H, bs, Im-H$_2$); $\delta_C$ (CDCl$_3$) CH$_2$: 21.9, 27.0, 41.9, 50.8; CH: 114.2, 119.2(b), 126.4, 128.7, 129.1, 137.2(b): C: 121.6, 123.8, 144.8.

ROUTE 2

Step A

6-Hydroxymethyl-1,2,3,4-tetrahydroquinoline

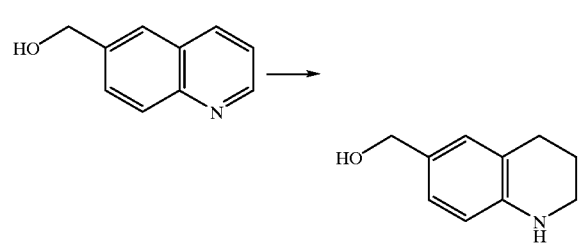

6-Hydroxymethylquinoline (1 g, 6.28 mmoles) (prepared by the method of: C. E. Kaslow and W. R. Clark, J. Org. Chem., 1953, 18, 55–58.) and methanol (200 mL) were placed in a Parr bomb and platinum (IV) oxide monohydrate (0.5 g, 2.04 mmoles) was added. The mixture was hydrogenated at 50 psi at 25° C. for 2 h. The catalyst was filtered off and washed with methanol. The combined filtrates were evaporated to dryness and the product was chromatographed on silica gel using 1.5% (10% conc. NH$_4$OH in methanol) dichloromethane as the eluant to give the title compound (0.7044 g, 68%): CIMS: m/z 164.35 (MH$^+$); $\delta_H$ (CDCl$_3$) 1.93 (2H, m, 3-CH$_2$) and 2.76 (2H, t, 4-CH$_2$), 3.30 (2H, m, 2-CH$_2$), 4.50 (2H, s, CH$_2$OH), 6.45 (1H, d, Ar—H$_8$), 6.96 ppm (2H, m, Ar—H$_5$ and Ar—H$_7$); $\delta_C$ (CDCl$_3$) CH$_2$: 22.1, 27.0, 42.0, 65.6; CH: 114.2, 126.4, 129.2; C: 121.5, 129.4, 144.5.

Step B 1N-tert-butoxycarbonyl-6-hydroxymethyl-1,2,3,4-tetrahydroquinoline

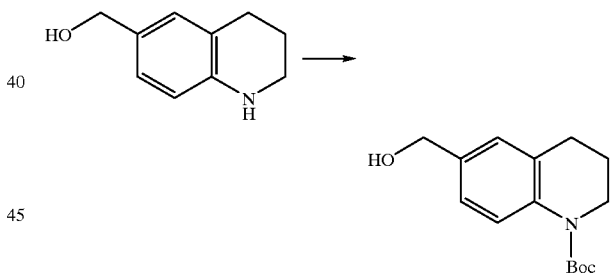

The title compound from Step A above (0.684 g, 4.19 mmoles) was dissolved in THF (25 mL) and sodium hydroxide 0.21 g, 5.25 mmoles) in water (10 mL) was added. Di-tert-butyldicarbonate (1.26 g, 5.76 mmoles was added and the mixture was stirred at 25° C. for 92 h. Additional di-tert-butyldicarbonate (0.628 g, 2.88 mmoles) was added and the reaction was continued for a total of 116 h. The reaction was worked up as described in Preparative Example 1 Step A above and the product was chromatographed on silica gel using 0.5% (10% conc. NH$_4$OH in methanol)-dichloromethane as the eluant to give the title compound (0.7978 g, 72%): ESMS: m/z 264.1 (MH$^+$); $\delta_H$ (CDCl$_3$) 1.52 (9H, s, CH$_3$), 1.91 (2H, m, 3-CH$_2$), 2.76 (2H, t, 4-CH$_2$), 3.70 (2H, m, 2-CH$_2$), 4.60 (2H, s, CH$_2$OH), 7.09 (1H, s, Ar—H$_5$), 7.12 (1H, d, Ar—H$_7$) and 7.64 ppm (1H, d, Ar—H$_8$); $\delta_C$ (CDCl$_3$) CH$_3$: 28.4, 28.4, 28.4; CH$_2$: 23.5, 27.6, 44.7, 65.1; CH: 124.3, 124.7, 127.4; C: 80.9, 130.1, 135.6, ~138.4, ~154.2.

Step C
1N-tert-butoxycarbonyl-6-(4-toxyloxymethyl)-1,2,3,4-tetrahydroquinoline

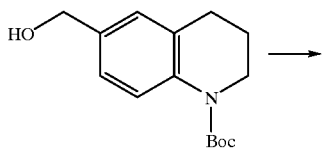

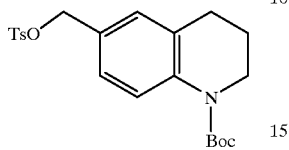

The title compound from Step B above may be reacted with 4-toluenesulfonyl chloride and pyridine under essentially the same conditions as described in Preparative Example 58, Step C and chromatographed on silica gel to give the title compound.

Step D
1N-tert-butoxycarbonyl-6-[(1H-imidazol-1-yl)methyl]-1,2,3,4-tetrahydroquinoline

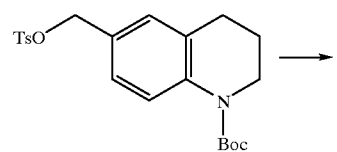

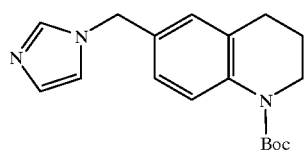

The title compound from Step C above may be reacted with sodium imidazole in anhydrous DMF under essentially the same conditions as described in Preparative Example 62, Route 1, Step B and chromatographed on silica gel to give the title compound.

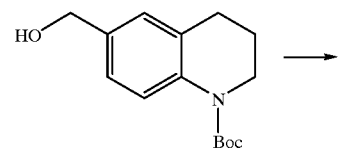

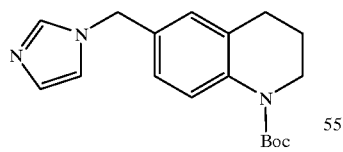

The title compound from Route 2, Step B above (0.5166 g, 1.96 mmoles) was dissolved in anhydrous THF (5.5 mL) and N,N'-carbonyldiimidazole (0.668 g, 4.12 mmoles) was added and the mixture was heated under reflux at 75° C. for 4.5 h. The solution was evaporated to dryness and chromatographed on silica gel using 2% (10% conc. NH₄OH in methanol)-dichloromethane as the eluant to give the title compound (0.0612 g, 10%): CIMS: m/z 314.25 (MH⁺); $\delta_H$ (CDCl₃) 1.51 (9H, s, CH₃), 1.92 (2H, m, 3-CH₂), 2.72 (2H, d, 4-CH₂), 3.69 (2H, d, 2-CH₂), 5.04 (2H, s, CH₂-Im), 6.85 (1H, s, Im-H₅), 6.91 (1H, s, Ar—H₆), 6.97 (1H, d, Ar—H₈), 7.08 (1H, s, Im-H₄), 7.59 (1H, s, Im-H₂) and 7.67 ppm (1H, d, Ar—H₉): $\delta_C$ (CDCl₃) CH₃: 28.4, 28.4, 28.4; CH₂: 23.4, 27.6, 44.8, 50.5; CH: 119.4, 124.5, 125.0, 127.6, 129.4, 137.3; C: 81.1, 130.5, 130.5, 138.7, 153.9.

Step E
6-[(1H-imidazol-1-yl)methyl]-1.2.3.4-tetrahydroquinoline

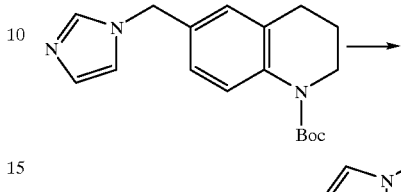

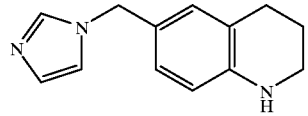

The title compound from Step D above may be deprotected essentially as described in Preparative Example 57, Step D and chromatographed on silica gel to give the title compound.

Preparative Example 63
4(R/S)-[(1H-4/5methylimidazol-1-yl)methyl]-1,2,3,4-tetrahydroisoquinoline

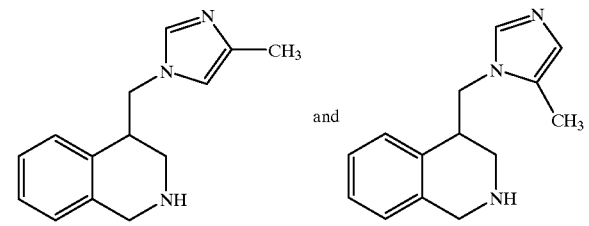

Route 1
Step A
4-Hydroxymethylisoquinoline

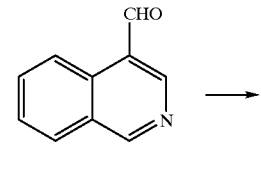

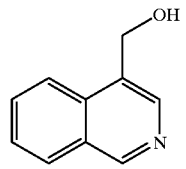

4-Isoquinolinecarboxaldehyde (6.15 g, 39.13 mmoles) (prepared by the method of: J. B. Wommack. T. G. Barbee, Jr., D. J. Thoennes, M. A. McDonald and D. E. Pearson, J. Heterocyclic Chem., 1969, 6, 243–245.) was dissolved in anhydrous dichloromethane (369 mL) and the solution was cooled to 0° C. Borane-dimethyl sulfide complex (1 M in THF) (5.23 mL, 5.09 mmoles) (as described in: E. Mincione, J. Org. Chem., 1978, 43, 1829–1830) was added and the mixture was stirred at 0° C. for a 1.5 h. Additional borane-dimethylsulfide complex (1 M in THF) (10.455 mL, 1.35 mmoles) was added and the reaction was stirred for an additional 2 h at 0° C. Methanol (93.3 mL) was added and the solution was evaporated to dryness and chromatographed on silica gel using 2–3% (10% conc. NH$_4$OH in methanol)-dichloromethane as the eluant to give unreacted 4-Isoquinolinecarboxaldehyde (~23%), 4(1.2-dihydroisoquinoline)carboxaldehyde (identical to that described in Preparative Example 63. Route 3, Step A (~27%) and the title compound (1.94 g, 31%).

Alternatively the title compound may be prepared by catalytic hydrogenation of 4-isoquinolinecarboxaldehyde using 10% Pd—AL$_2$O$_3$ as the catalyst (as described in: J. Vassant, G, Smets, J. P. Declercq, G. Germain and M. Van Meerssche, J. Org. Chem., 1980, 45, 1557–1565).

Step B
4-[(4-Toluenesulfonyloxy)methyl]isoquinoline

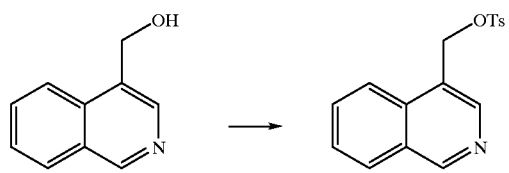

To a stirred solution of the title compound from Step A above (1.94 g, 12.2 mmoles) in anhydrous pyridine (14 mL) at 0° C. was added 4-toluenesulfonyl chloride (2.784 g, 14.6 mmoles) and the mixture was stirred at 0° C. for 2.5 h. The solution was evaporated to dryness and the product was azeotroped with toluene and then taken up in dichloromethane and washed with saturated aqueous sodium bicarbonate, filtered and evaporated to give the title compound which was used without purification in the next step.

Step C
4-[(1H-4/5-methylimidazol-1-yl)methyl]isoquinoline

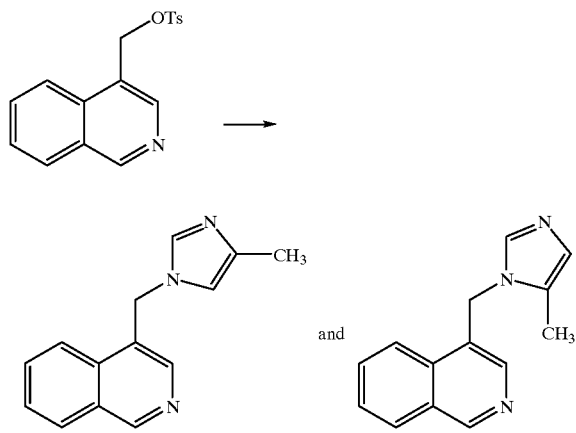

4-Methylimidazole (1.099g, 13.38 mmoles) was dissolved in anhydrous DMF (33.5 mL) and 95% sodium hydride (0.338 g, 13.42 mmoles) was added in portions to the stirred solution at 25° C. The title compound from Step B above was dissolved in anhydrous DMF (14 mL) and added dropwise to the stirred solution at 25° C. over 20 min. The mixture was stirred at 25° C. for 17 h and evaporated to dryness. The residue was taken up in dichloromethane and washed with water, dried(MgSO$_4$), filtered and evaporated to dryness. The product was chromatograped on silica gel using 2.5% methanol in dichloromethane as the eluant to give a mixture of the title compounds (0.5085 g, 19%) (4-Me:5-Me::1.2:1): δ$_H$ (CDCl$_3$) 2.18/2.22 (3H, s, 4-Me/5-Me), 5.46 (2H, s, CH$_2$-Im), 6.63/6.89 (1H, s, 4-Me: Im-H$_5$/5-Me: Im-H$_4$), 7.43/7.55 (1H, s, 5-Me: (1H, s, 5-Me: Ar—H$_3$/4-Me: Ar—H$_3$), 8.05 (0.5H, d, 5-Me: Ar—H$_3$) and 9.26/9.28 ppm (1H, s, 5-Me: Ar—H$_1$/4-Me: Ar—H$_1$), δ$_C$ (CDCl$_3$)4-Me: CH$_3$: 13.6; CH$_2$: 46.5; CH: 115.7, 121.8, 127.8, 128.7, 131.6, 136.3, 143.3, 154.1; C: 124.7, 128.5, 133.8, 138.7; and 5-Me: CH$_3$: 9.5; CH$_2$: 44.4; CH: 121.6, 127.4, 127.8, 128.7, 131.5, 137.2, 142.0, 153.7; C: 124.8, 128.2, 133.4, 138.7.

Step D
4-[(1H-4-methylimidazol-1-yl)methyl]isoquinoline
and
4-[(1H-5-methylimidazol-1-yl)methyl]isoquinoline

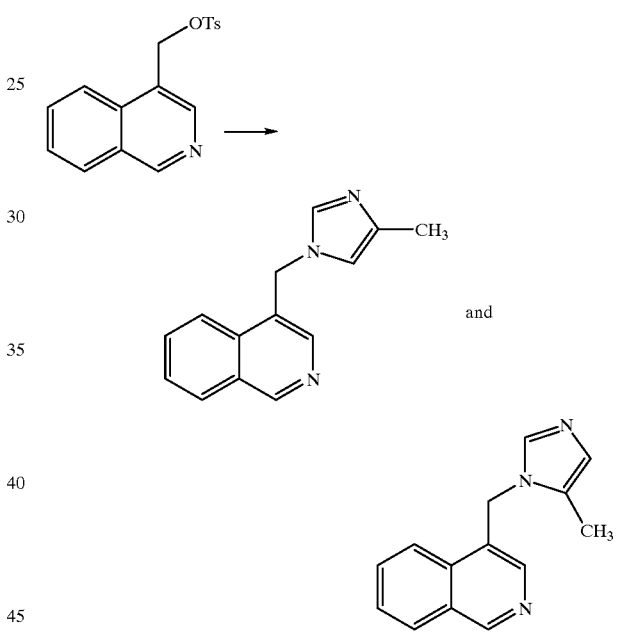

The title mixture of regio-isomers from Step C above (0.45 g) was subjected to chiral HPLC on a Chiralpak® HPLC column using hexane:isopropanol:diethylamine::85:15:09.2 to give first the 4-methyl isomer (0.0406 g): FABMS: m/z 224.0 (MH$^+$); δ$_H$ (CDCl$_3$) 2.18 (3H, s, 4-CH$_3$), 5.46 (2H, s, CH$_2$-Im), 6.62 (1H, s, Im-H$_5$), 7.54 (1H, s, Im-H$_2$), 7.67 (1H, t, Ar—H$_8$) 7.76 (1H, t, Ar—H$_7$), 7.84 (1H, d, Ar—H$_6$), 8.04 (1H, d, Ar—H$_9$), 8.39 (1H, s, Ar—H$_3$) and 9.27 ppm (1H, s, Ar—H$_1$); δ$_C$ (CDCl$_3$) CH$_3$: 13.6; CH$_2$: 46.5: CH: 115.7, 121.8, 127.8, 128.7, 131.6, 136.3, 143.3, 154.1; C: 124.7, 128.7, 133.8, 138.8; and then the 5-methyl isomer (0.0361 g): FABMS: m/z 224.1 (MH$^+$); δ$_H$ (CDCl$_3$) 2.20 (3H, s, 5-CH$_3$), 5.45 (2H, s, CH$_2$-Im), 6.86 (1H, s, Im-H$_4$), 7.41 (1H, s, Im-H$_2$), 7.68 (1H, t, Ar—H$_8$), 7.98 (1H, t, Ar—H$_7$), 7.84 (1H, d, Ar—H$_6$), 8.02 (1H, s, Ar—H$_3$), 8.05 (1H, d, Ar—H$_9$) and 9.22 ppm (1H, s, Ar—H$_1$); δ$_C$ (CDCl$_3$) CH$_3$: 9.4; CH$_2$: 44.3; CH: 121.5, 126.9, 127.9, 128.8, 131.7, 137.0, 141.7, 153.6; C: 124.9, 128.2, 133.4, 138.7 and an overlap fraction (0.28 g).

Step E
4[(1H-4/5-methylimidazol-1-yl)methyl]-1,2,3,4-tetrahydroisoquinoline

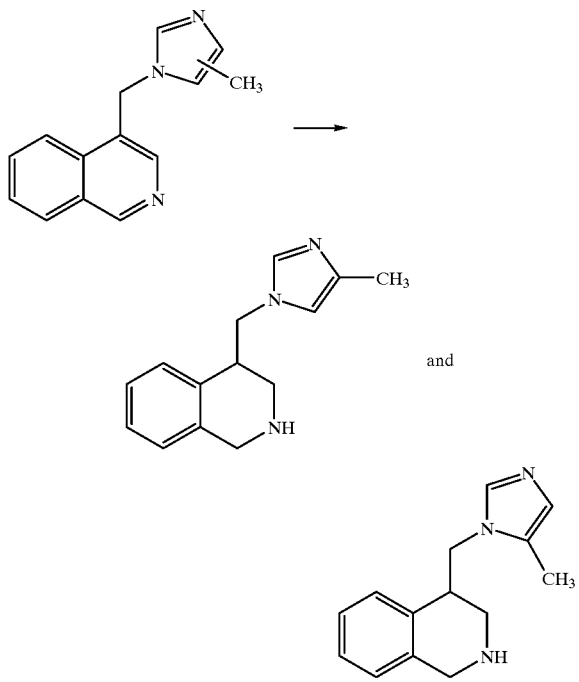

The title compound from Step C above (0.346 g, 1.55 mmoles) was dissolved in anhydrous methanol (80 mL) and platinum (IV) oxide.monohydrate (0.11 g) was added. The mixture was hydrogenated at 25° C. at 50 psi in a Parr bomb for 2 h. The catalyst was filtered off and washed with methanol and the methanol filtrates were evaporated to dryness. The residue was chromatographed on silica gel using 3% (10% conc. $NH_4OH$ in methanol)-dichloromethane as the eluant to give the title 4-methyl compound (0.0299 g, 9%): ESMS: m/z 228.0; $\delta_H$ ($CDCl_3$) 2.24 (3H, s, Im-4-$CH_3$), 2.81 (1H, bs, NH), 2.93 (2H, m, 3-$CH_2$), 3.03 (1H, m, 4-CH), 4.04 (2H, s, 1-$CH_2$), 4.08, 4.27 (2H, dd, $CH_2$-Im), 6.68 (1H, Im-$H_2$), 7.01–7.09 (2H, m, Ar—H), 7.18 (2H, m, Ar—H) and 7.36 ppm (1H, s. Im-$H_5$); $\delta_C$ ($CDCl_3$) $CH_3$: 13.8; $CH_2$: 45.0, 48.4, 51.1; CH: 39.6, 115.6, 126.5, 126.8, 126.9, 129.1, 136.9; C: 134.5, 135.7, 138.6, and the title 5-methyl compound (0.0641 g, 18%): $CH_3$: 9.3; $CH_2$: 44.9, 48.8, 50.5; CH: 39.4, 126.5, 126.9, 126.9, 129.0, 136.7; C: 127.0, 134.4, 135.7, 138.5.

Route 2
Step A
4-Hydroxymethylisoquinoline

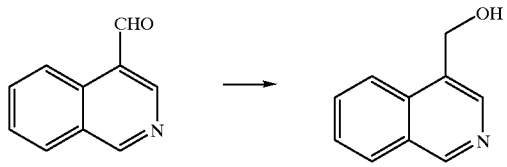

4-Isoquinolinecarboxaldehyde (1 mmole) (prepared by the method of: J. B. Wommack, T. G. Barbee, Jr., D. J. Thoennes, M. A. McDonald and D. E. Pearson, J. Heterocyclic Chem., 1969, 6, 243–245.) is dissolved in anhydrous THF (50 mL) and treated with borane-methyl sulfide (0.3 mmoles) (as described in: E. Mincione, J. Org. Chem., 1978, 43, 1829–1830) at 0° C. for 0.5–1 h and worked up in the usual way to give the title compound.

Alternatively the title compound may be prepared by catalytic hydrogenation of 4-isoquinolinecarboxaldehyde using 10% Pd—$Al_2O_3$ as the catalyst (as described in: J. Vassant, G, Smets, J. P. Declercq, G. Germain and M. Van Meerssche, J. Org. Chem., 1980, 45, 1557–1565).

Step B
4-[(4-toluenesulfonyloxy)methyl]isoquinoline

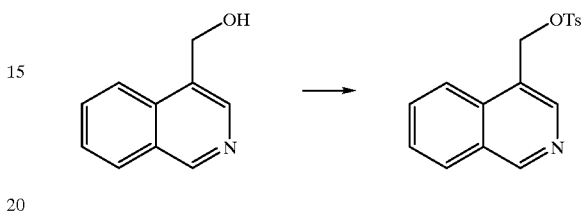

The title compound from Step A above is dissolved in anhydrous pyridine and cooled to 0° C. with stirring, 4-Toluenesulfonyl chloride is added and the reaction is carried out as described in Preparative Example 60, Step D to give the title compound which may be used without further purification.

Step C
4-hydroxymethyl-1.2-dihydroisoquinoline

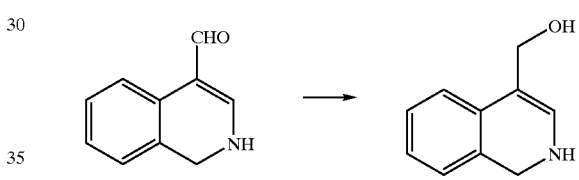

The title compound from Step A above may be selectively reduced with freshly prepared zinc borohydride (as described in: D. C. Sakar, A. R. Das and B. C. Ranu, J. Org. Chem., 1990, 55, 5799–5801.) to give title allylic alcohol.

Step D
N-tert-butoxycarbonyl-4-hydroxymethyl-1,2-dihydroisoquinoline

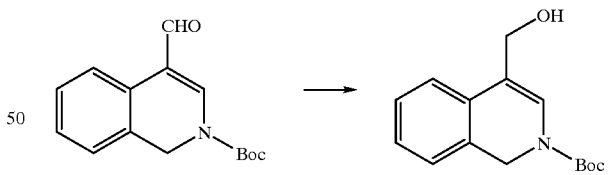

The title compound from Step B above is reacted with zinc borohydride as described in Step C above to give the title compound.

Alternatively:

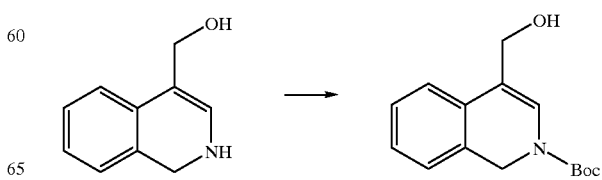

The title compound from Step C above is reacted with di-tert-buylydicarbonate and sodium hydroxide as described in Preparative Example 57, Step A to give the title compound.

Step E

4(R/S)-[(1H-4/5-methylimidazol-1-yl)methyl]-1,2-dihydroisoquinoline

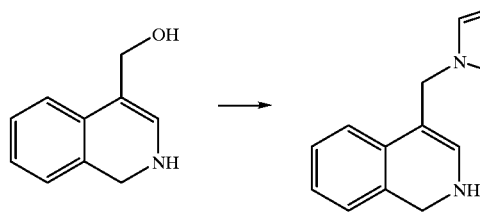

The title compound from Step C above may be reacted with N,N'-carbonyldiimidazole using the procedure described in Preparative Example 22, part two of Step D, to give the title compounds.

Step F

4(R/S)-[(1H-4/5-methylimidazol-1-yl)methyl]-1,2,3,4-tetrahydroisoquinoline

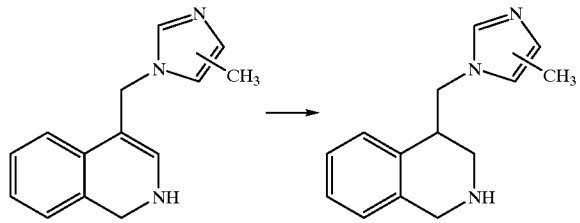

The title compounds of Step E above is reduced with platinum (IV) oxide as described in Route 1, Step D above to give the title compounds.

Step G

4[4-(toluenesulfonyloxy)methyl]-1,2-dihydroisoquinoline

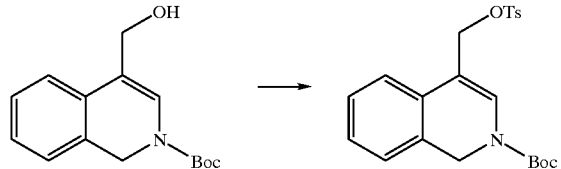

The title compound from Step D above is reacted with 4-toluenesulfonyl chloride in pyridine as described in Preparative Example 4, Step D to give the title compound.

Step H 2N-tert-butoxycarbonyl-4(R/S)-[(1H-4/5-methylimidazol-1-yl)methyl]-1,2-dihydroisoquinoline

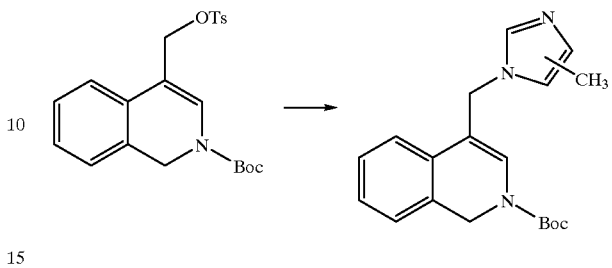

The title compounds from Step G above was reacted with sodium 4-methylimidazole as described in Route 1, Step C above to give the title compounds.

The regio-isomers may be separated by chiral HPLC on a Chiralpak® column, or by treatment with trityl chloride as described above.

Step I 2N-tert-butoxycarbonyl-4(R/S)-[(1H-4/5-methylimidazol-1-yl)methyl]-1,2,3,4-tetrahydroisoquinoline

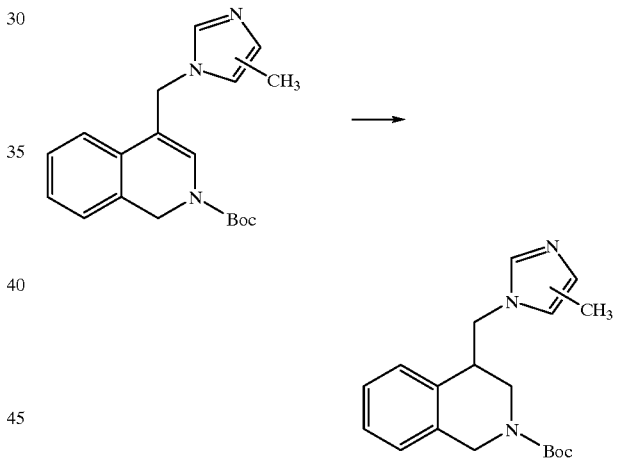

The title compounds from Step H above were reduced with platinum (IV) oxide as described in Route 1 Step D above to give the title compounds.

Step J

4(R/S)-[(1H-4/5-methylimidazol-1-yl)methyl]-1,2,3,4-tetrahydroisoquinoline

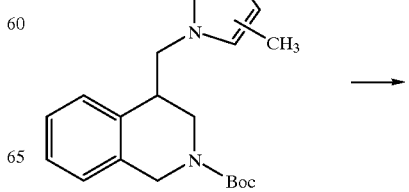

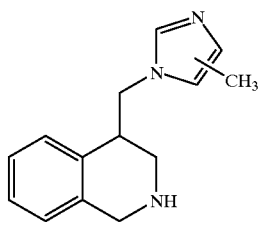

The title compounds from Step H above were deprotected as described in Preparative Example 57, Step D, to give the title compounds.

EXAMPLE 74
1,1-dimethylethyl-4-(3-bromo-8-chloro-6,11-dihydro-5H-benzo[5,6]cyclohepta[1,2-b]pyridin-11-yl)-2(R)-[[2-[2-(1H-imidazol-1-yl)ethyl]-1-piperidinyl]carbonyl]-1-piperazinecarboxylate Route 1

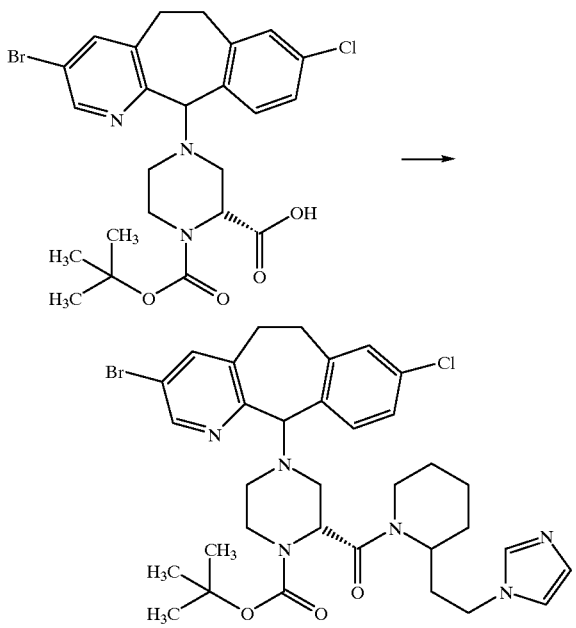

1,1-Dimethylethyl-4-(3-bromo-8-chloro-6,11-dihydro-5H-benzo [5,6]cyclohepta[1,2-b]pyridin-11-yl)-2(R)-carboxy-1-piperazinecarboxylate (0.250 g, 0.466 mmoles) (prepared as described in Preparative Example 6), 2-[2-(1H-imidazol-1-yl) ethyl]piperidine (0.1085 g, 0.6054 mmoles) (prepared as described in Preparative Example 1), 1-(3-dimethylamino-propyl)-3-ethylcarbodiimide hydrochloride (0.116 g, 0.6054 mmoles), 1-hydroxybenzotriazole (0.0818 g, 0.6054 mmoles) and 4-methylmorpholine (0.0665 mL, 0.6054 mmoles) were dissolved in anhydrous DMF (10 mL) and the mixture was stirred under argon at 25° C. for 18 h. The solution was evaporated to dryness and the residue was washed with water, dried (MgSO$_4$), filtered and evaporated to dryness. The residue was chromatographed silica gel using 1% (10% conc. NH$_4$OH in methanol)-dichloromethane as the eluant to give the title compound (0.0617 g, 19%): ESMS: m/z 697.2 (MH$^+$); δ$_H$ (CDCl$_3$) 6.97 (1H, broad s, Im-H$_5$), 7.04 (1H, broad s, Im-H$_4$), 7.09–7.20 (broad m, Ar—H), 7.56 (2H, broad s, Ar—H and Im-H$_2$) and 8.38 ppm (1H, broad s, Ar—H$_2$); δ$_C$ (CDCl$_3$) CH$_3$: 28.4, 28.4, 28.4; CH$_2$: 18.9/19.1, 25.2/25.3/25.8, 30.4, 30.5, 31.4/31.6, 36.6, 40.2, 42.9, 43.4/43.7, 50.3, 52.7/53.0; CH: 45.8/46.4, 50.1/51.7/52.2, 78.3/78.4/~79.3, ~119.0, 126.3, ~129.8, 130.7/130.8, 132.5/132.6, ~137.1, 141.4/141.5, 146.9; C: 80.4, 120.0, 134.3, 134.8, 137.5, 141.0, 155.9, 156.8, 157.2.

Route 2

Step A 4-(3-bromo-8-chloro-6,11-dihydro-5H-benzo[5,6]cyclohepta[1,2-b]pyridin-11-yl)-2(R)-[[2-[2-(1H-imidazol-1-yl)ethyl]-1-piperidinyl]carbonyl]1-piperazine

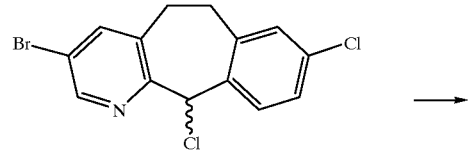

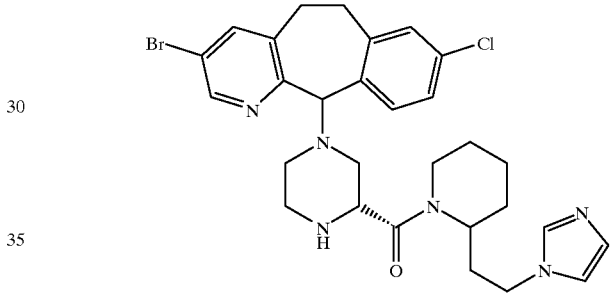

3-Bromo-8,11-dichloro-6,11-dihydro-5H-benzo[5,6]cyclohepta[1,2-b]pyridine (prepared as described in Preparative Example 40 (U.S. Pat. No. 5,719,148) was reacted with the title compound from Preparative Example 1, Step B, and triethylamine, in a mixture of anhydrous THF and dichloromethane at 25° C. to give the title compound.

Step B 1,1-dimethylethyl 4-(3-bromo-8-chloro-6,11-dihydro-5H-benzo[5,6]cyclohepta[1,2-b]pyridin-11-yl)-2(R)-[[2-[2-[(1H-imidazol-1-yl)ethyl]-1-piperidinyl]carbonyl]-1-piperazinecarboxylate

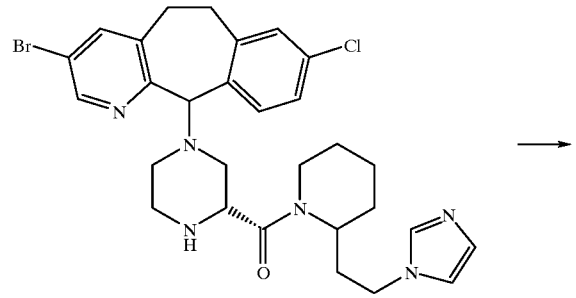

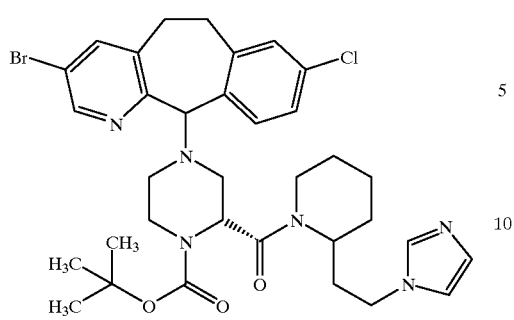

The title compound from Example 74, Step A was reacted with di-tert-butyldicarbonate and sodium hydroxide in THF-water (1:1) at 25° C. as described in Preparative Example 57, Step A, and the product was chromatographed on silica gel, to give the title compound.

EXAMPLES 75–86

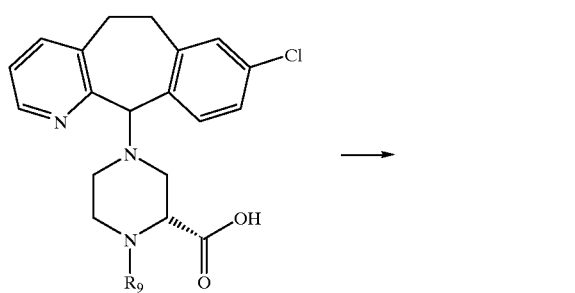

11(R), 2(R)

↓

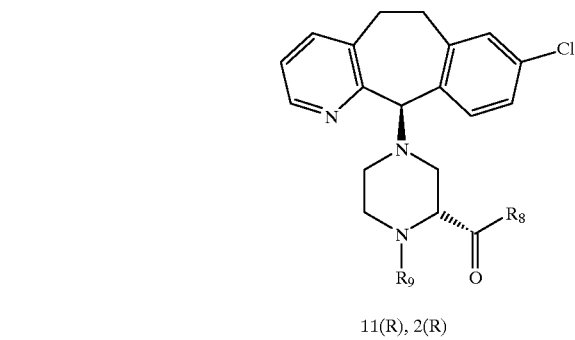

11(R), 2(R)

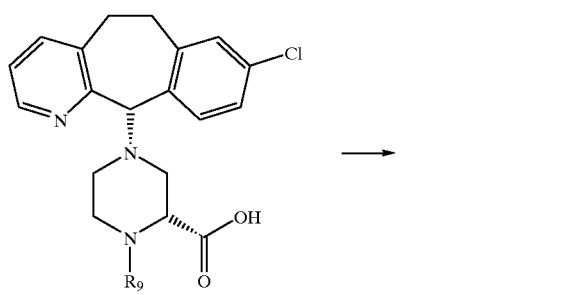

11(S), 2(R)

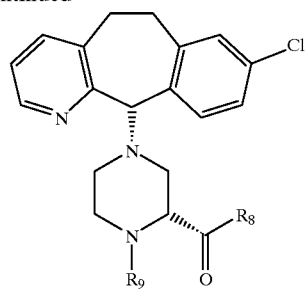

11(S), 2(R)

Where $R^9 =$ 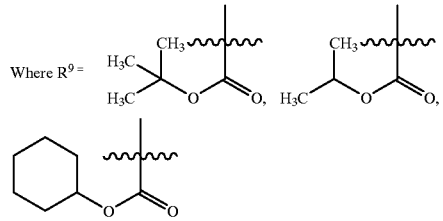

Using essentially the same procedure as described in Example 74 above the 11(R),2(R) and 11(S),2(R) acids from Preparative Example 30, may be reacted with the product from Preparative Example 58, Step E to give the targets of Examples 75–80; or with the product from Preparative Example 59, Step E to give the targets of Examples 81–86, respectively (Table 11).

TABLE 11

| | Product | |
|---|---|---|
| Ex | $R^9$ | $R^8$ |
| 75 | ![tBuO-C(=O)-] 11(R), 2(R) | ![piperidine-CH2CH2CH2-imidazole-CH3] 2(R/S) |
| 76 | ![tBuO-C(=O)-] 11(S), 2(R) | ![piperidine-CH2CH2CH2-imidazole-CH3] 2(R/S) |
| 77 | ![iPrO-C(=O)-] 11(R), 2(R) | ![piperidine-CH2CH2CH2-imidazole-CH3] 2(R/S) |

TABLE 11-continued

| Ex | R⁹ | R⁸ |
|---|---|---|
| 78 | (isopropyl ester) 11(S), 2(R) | (2-(3-(4-methylimidazol-1-yl)propyl)piperidin-1-yl) 2(R/S) |
| 79 | (cyclohexyl ester) 11(R), s(R) | (2-(3-(4-methylimidazol-1-yl)propyl)piperidin-1-yl) 2(R/S) |
| 80 | (cyclohexyl ester) 11(S), 2(R) | (2-(3-(4-methylimidazol-1-yl)propyl)piperidin-1-yl) 2(R/S) |
| 81 | (tert-butyl ester) 11(R), 2(R) | (4-(3-(4-methylimidazol-1-yl)propyl)piperidin-1-yl) 4(R/S) |
| 82 | (tert-butyl ester) 11(S), 2(R) | (4-(3-(4-methylimidazol-1-yl)propyl)piperidin-1-yl) 4(R/S) |
| 83 | (isopropyl ester) 11(R), 2(R) | (4-(3-(4-methylimidazol-1-yl)propyl)piperidin-1-yl) 4(R/S) |
| 84 | (isopropyl ester) 11(S), 2(R) | (4-(3-(4-methylimidazol-1-yl)propyl)piperidin-1-yl) 4(R/S) |
| 85 | (cyclohexyl ester) 11(R), 2(R) | (4-(3-(4-methylimidazol-1-yl)propyl)piperidin-1-yl) 4(R/S) |
| 86 | (cyclohexyl ester) 11(S), 2(R) | (4-(3-(4-methylimidazol-1-yl)propyl)piperidin-1-yl) 4(R/S) |

EXAMPLE 87–110

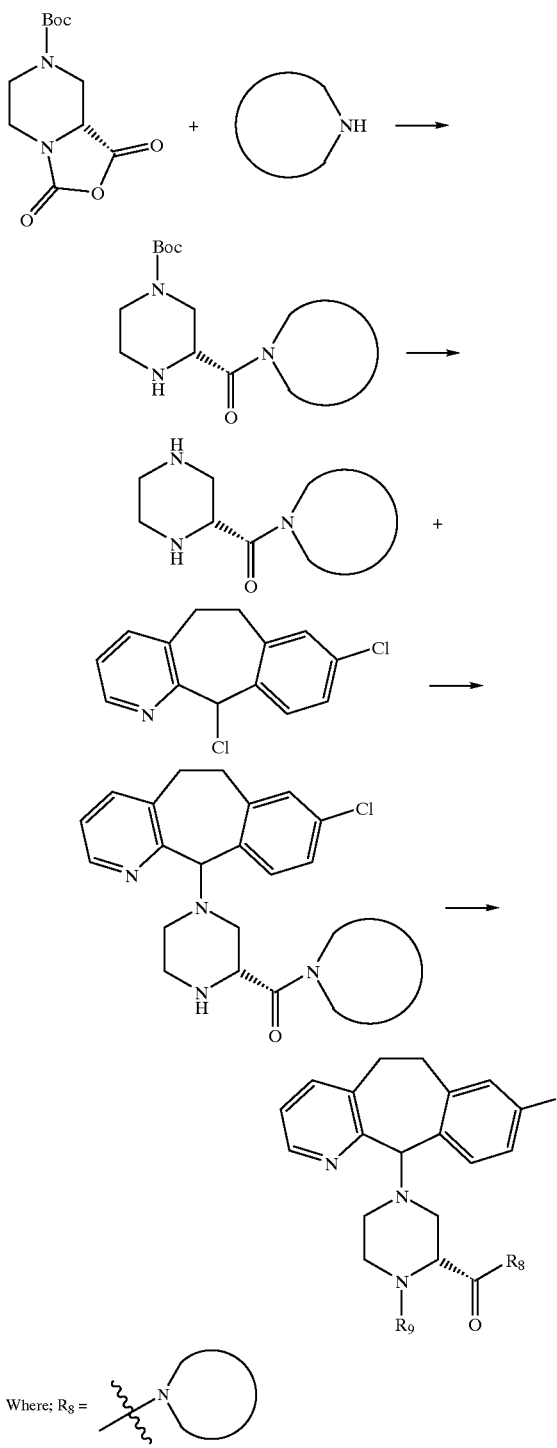

By reacting the anhydride from Preparative Example 3 as shown in the scheme above. with the product of Preparative Example 60, Steps E, or F, one may obtain the intermediate of Examples 87–98: or faith the product of Preparative Example 61, Step B, one may obtain the intermediate of Examples 99–102; or with the product of Preparative Example 62, Step C, one may obtain the intermediate of Examples 103–106; or with the intermediate of Preparative Example 63, Step D of Route 1, or Steps F or J of Route 2 one may obtain the intermediate of Examples 107–110. By reacting the intermediates so obtained with 8,11-dichloro-6,11-dihydro-5H-benzo[5.6]cyclohepta[1,2-b]pyridine (prepared as described in U.S. Pat. No. 5,807,853, Sep. 15, 1998) one may obtain, after reaction with either di-tert-butyldicarbonate and sodium hydroxide, or with isopropyl chloroformate and triethylamine, or with cyclohexyl chloroformate and triethylamine as described herein, the title compounds of Examples 87–110 (Table 12).

TABLE 12

| Ex | $R^9$ | $R^8$ |
|---|---|---|
| 87 | (isopropyl carbonate group) 11(R), 2(R) | (tetrahydroquinoline-imidazole group) 3(R/S) |
| 88 | (isopropyl carbonate group) 11(S), 2(R) | (tetrahydroquinoline-imidazole group) 3(R/S) |
| 89 | (cyclohexyl carbonate group) 11(R), 2(R) | (tetrahydroquinoline-imidazole group) 3(R/S) |
| 90 | (cyclohexyl carbonate group) 11(S), 2(R) | (tetrahydroquinoline-imidazole group) 3(R/S) |
| 91 | (isopropyl carbonate group) 11(R), 2(R) | (tetrahydroquinoline-imidazole group) 3(R) |

TABLE 12-continued

| Ex | Product R⁹ | Product R⁸ |
|---|---|---|
| 92 | 11(S), 2(R) | 3(R) |
| 93 | 11(R), 2(R) | 3(R) |
| 94 | 11(S), 2(R) | 3(R) |
| 95 | 11(R), 2(R) | 3(S) |
| 96 | 11(S), 2(R) | 3(S) |
| 97 | 11(R), 2(R) | 3(S) |
| 98 | 11(S), 2(R) | 3(S) |
| 99 | 11(R), 2(R) | 3(R/S) |
| 100 | 11(S), 2(R) | 3(R/S) |
| 101 | 11(R), 2(R) | 3(R/S) |
| 102 | 11(S), 2(R) | 3(R/S) |
| 103 | 11(R), 2(R) | |

TABLE 12-continued

| Ex | R⁹ | R⁸ |
|---|---|---|
| 104 | (isopropyl ester) 11(S), 2(R) | (imidazolylmethyl-tetrahydroquinoline) |
| 105 | (cyclohexyl ester) 11(R), 2(R) | (imidazolylmethyl-tetrahydroquinoline) |
| 106 | (cyclohexyl ester) 11(S), 2(R) | (imidazolylmethyl-tetrahydroquinoline) |
| 107 | (isopropyl ester) 11(R), 2(R) | (4-methylimidazolylmethyl-tetrahydroisoquinoline) 4(R/S) |
| 108 | (isopropyl ester) 11(S), 2(R) | (4-methylimidazolylmethyl-tetrahydroisoquinoline) 4(R/S) |
| 109 | (piperidinyl-propyl-methylimidazole) 11(R), 2(R) | (4-methylimidazolylmethyl-tetrahydroisoquinoline) 4(R/S) |
| 110 | (cyclohexyl ester) 11(S), 2(R) | (4-methylimidazolylmethyl-tetrahydroisoquinoline) 4(R/S) |

Preparative Example 64

Step A

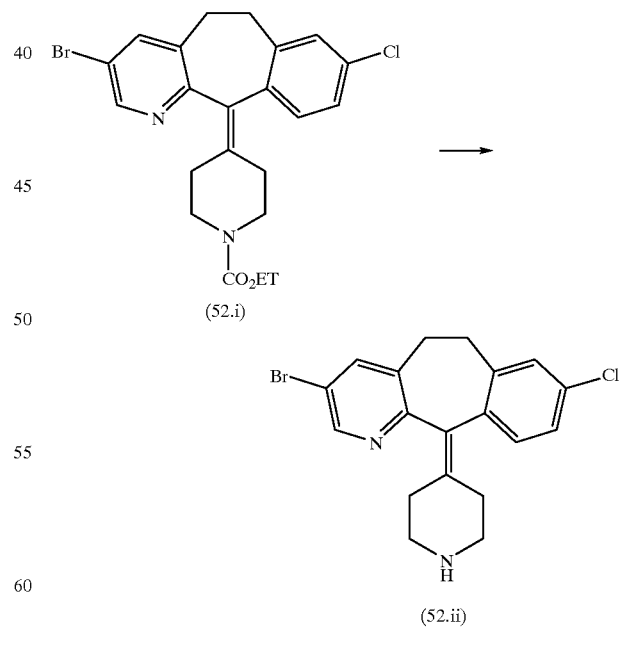

A solution of 52.i (J. Med. Chem. 4890–4902 (1988))(205 g) in collc. HCl (1 L) and water (100 mL) is refluxed for 18 h, then poured into ice (3 Kg). Aq. 50% NaOH is added to pH 12 followed by extraction with EtOAc (3×4 L). the extracts are washed with brine, dried and evaporated to afford 52.ii (166 g).

Step B

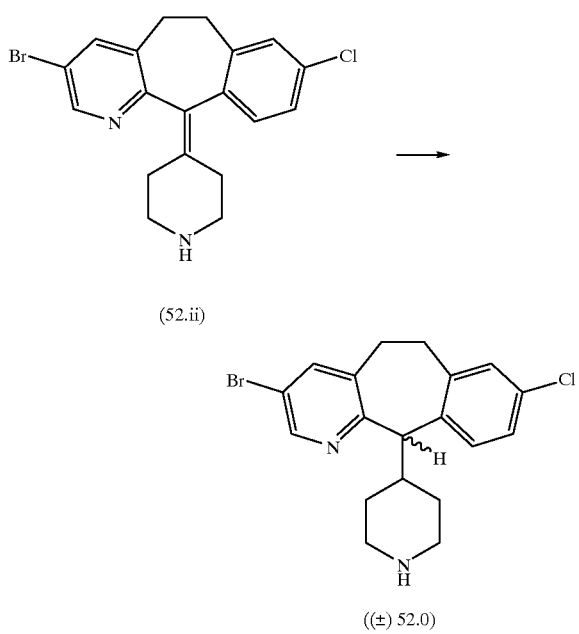

(52.ii)

((±) 52.0)

A 1M solution of DIBAL in toluene (908 mL) is added dropwise during 2 h to a solution of 52.ii (166 g) in toluene (4 L) at rt. followed by stirring for 18 h. The mixture is cooled to 0–5° C. and stirred for 1 h and extracted with 1N HCl (2 L). The aqueous extract is basified to pH 10 with 50% NaOH and extracted with EtOAc (3×2 L). The extracts are evaporated and chromatographed on silica-gel (1 Kg). Elution with 10% MeOH/CH$_2$Cl$_2$ affords the title compound (±) 52.0 (104 g): HRMS (FAB) calcd for C$_{19}$H$_{21}$N$_2$$^{79}$BrCl 393.0556, found 393.0554.

Step C

The racemate (±) 52.0 (96 g) is resolved by HPLC on a 8×30 cm CHIRALPAK AD column at 25° C. with the UV detector set at 290 nm. Elution with 0.05% diethylamine-methanol affords: Peak 1 (−) 52.0 (40 g): $[\alpha]_D^{20}$−28.4° (c 0.3, MeOH): Further elution with the same solvent affords: Peak 2 (+) 52.0 (42 g): $[\alpha]_D^{20}$+27.5° (c 0.3, MeOH).

Preparative Example 65

Step A

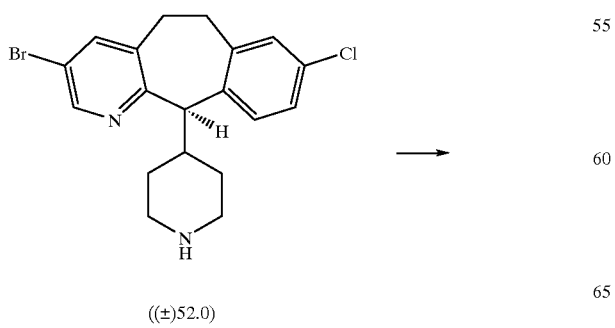

((±)52.0)

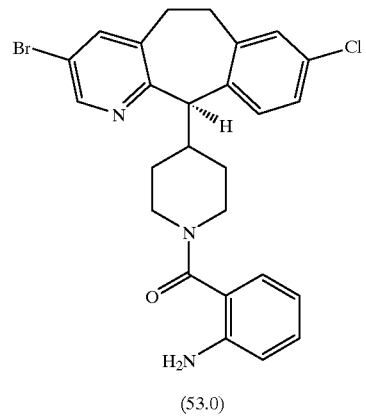

(53.0)

A solution of (+)-52.0 (2.3 g) in dimethylformamide (30 ml) is reacted with isatoic anhydride (1.25 g) in the presence of DMAP (0.1 g) at r.t. for 3 hrs and is then evaporated under reduced pressure and residual dimethylformamide is azeotroped with toluene. The residue is dissolved in ethylacetate (50 ml) and the solution is extracted with 10% sodium carbonate (3×100 ml). The organic layer is filtered through silica-gel (100 ml) followed by elution with ethylacetate. The filtrate is evaporated under reduced pressure to afford the title compound 53.0 as an amorphous solid (3.68 g). MS(FAB): m/z 510 (MH)$^+$.

Step B (53.0) →

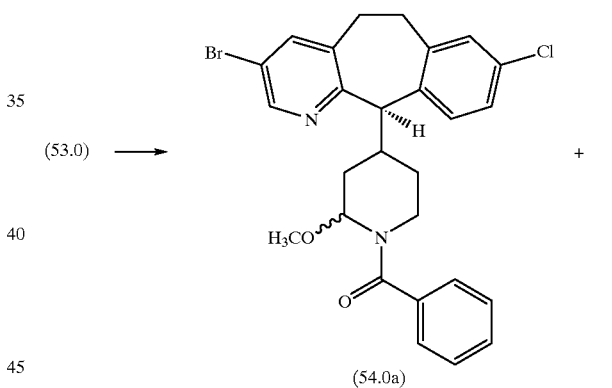

(54.0a)

+

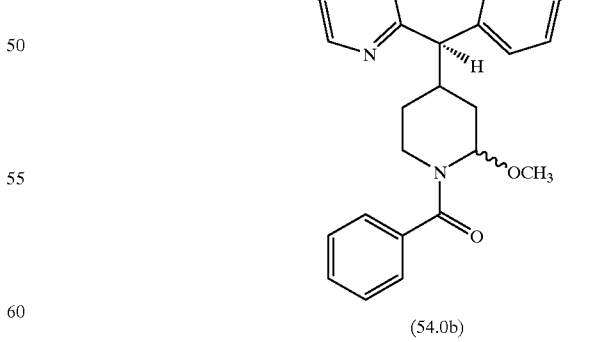

(54.0b)

A solution of 53.0 (3.1 g) and sodium nitrite (0.8 g) in methanol (500 ml) is stirred at r.t. under nitrogen with cuprous chloride (0.15 g) while adding dropwise over 10 minutes a 4M hydrochloric acid/dioxane solution (3.9 ml). The reaction mixture is stirred for 24 hrs followed by the addition of 10% sodium carbonate to pH 8. concentrated under reduced pressure, diluted with water (200 ml) and extracted with dichloromethane (4×100 ml). The combined extract is evaporated under reduced pressure and the crude reaction product is flash chromatographed on silica-gel (400 ml). Elution with 25% ethylacetate-hexane affords after evaporation the title compound 54.0a and 540.b as an off-white amorphous solid (2.97 g). $^1$H NMR (CDCl$_3$, 300 MHz) d 3.30 (s, 3H); MS (FAB) m/e 525 (MH)$^+$.

Steps C–E

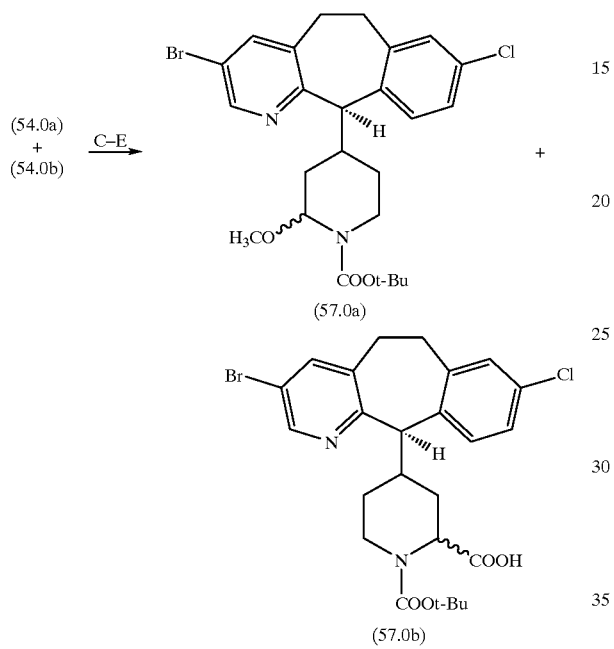

A solution of 54.0a and 54.0b (17 g) in methanol (150 ml) and 2N hydrochloric acid (170 ml) and conc. HCl (60 ml) is heated under reflux for 17 hrs, followed by evaporation under reduced pressure. The resulting amorphous solid is dissolved in methanol (160 ml) and sodium cyanide (15 g) is added with stirring until the reaction is basic (pH 8). The reaction is stirred for 2 h, diluted with dichloromethane (300 ml) and filtered. The filtrate is evaporated and the residue is dissolved in conc HCl (150 ml) and the mixture is heated in an oil bath (120° C.) for 4 h and is then evaporated under reduced pressure. The residue is dissolved in THF (100 ml) and 10% NaOH (30 ml) is added to pH>8 followed by the dropwise addition of a solution of (BOC)$_2$O (9 g) in THF (50 ml) with vigorous stirring for 24 h. The solution is concentrated to a low volume, stirred with hexane (2×120 ml) and ice-water followed by acidification of the aqueous layer with citric acid and extraction with EtOAc. The crude product obtained by evaporating the extract is purified by flash chromatography to afford the mixture of 57.0a and 57.0b as light tan solid that appears as a single tlc spot (16 g). $^1$H NMR (CDCl$_3$, 300 MHz) d 1.40 (s, 9H): MS (FAB) m/z 535 (MH)$^+$.

The single tlc spot is a mixture of four isomers.

Following the above procedure (Steps A–E), except using Compound (−)-52.0 (17 g), a mixture of 58.0a and 58.0b is obtained as a light solid that appears as a single tlc spot (17 g). MS(ES) m/z 535 (MH$^+$).

EXAMPLE 118

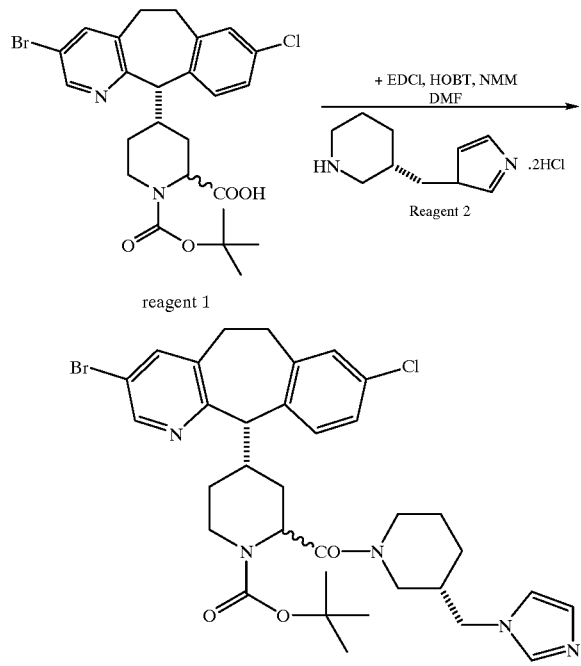

The imidazole (reagent 2), (220 mg,0.92 mmol) was added to a solution of the Boc-acid (reagent 1), (0.45 g,0.842 mmol), EDCI (200 mg, 1.043 mmol), HOBT (130 mg, 0.962 mmol), and N-methyl morpholine (0.2 ml, 1.81 mmol) in DMF (anhydrous, 3 ml) at room temperature (20° C.). The resultant solution was stirred overnight at 20° C. The solvent was evaporated, water (70 ml) and EtOAC (120 ml) were added. The organic layer was separated, and washed with 10% Na$_2$CO$_3$ solution (50 ml), then dried over MgSO$_4$, filtered and evaporated solvent yielding an oil, which chromatographed on silica gel eluting with 5% MeOH:MeCl$_2$ yielding the product as a white solid (425 mg,74%). Mixture of 4 isomers A,B,C,D.

Mass Spec (ES,MH,682) High Resolution Mass Spec Estimated(MH) 684.2139(Br=81) Observed 684.2120

EXAMPLE 119

Step A

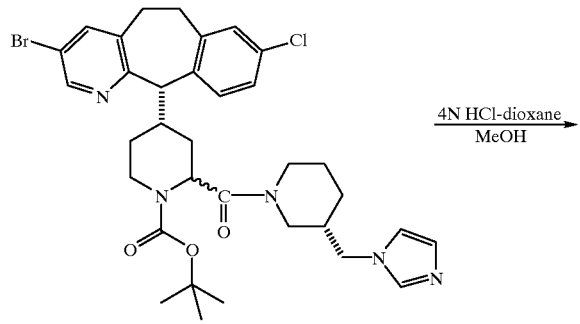

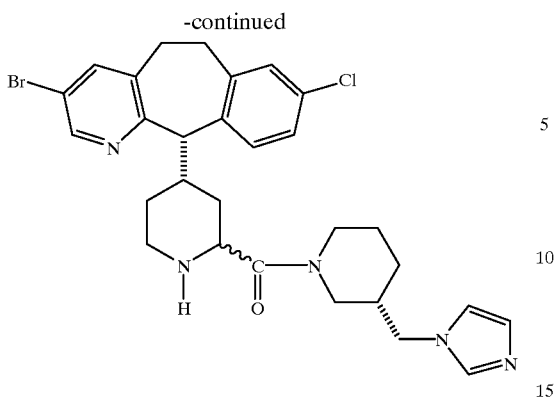

A solution of the tricycle Isomers (A,B,C,D) from Example 118 (150 mg,0.205 mmol) in 4N Hcl-dioxane (3 ml) and MeOH(3 ml) was stirred at 20° C. for 3 hours. The solvent was evaporated,water (25 ml) and 10% NaOH (4 ml) were added,then extracted with MeCl₂ (2×100 ml). The organic layer was separated, dried over MgSO₄, and solvent evaporated yielding a solid which was purified by chromatography on silica gel eluting with 3% MeOH-MeCl₂ containing 2% NH₄OH yielding the product as a white solid (70 mg, 54% yield). Mixture of 2 Isomers(C,D) (PRODUCT 1) Mass Spec ES (MH) 582.

Further elution yielded a white solid (25 mg, 20% yield). Mixture of 2 isomers.(A,B) (PRODUCT 2) Mass Spec ES (MH⁺) 582.

Step B

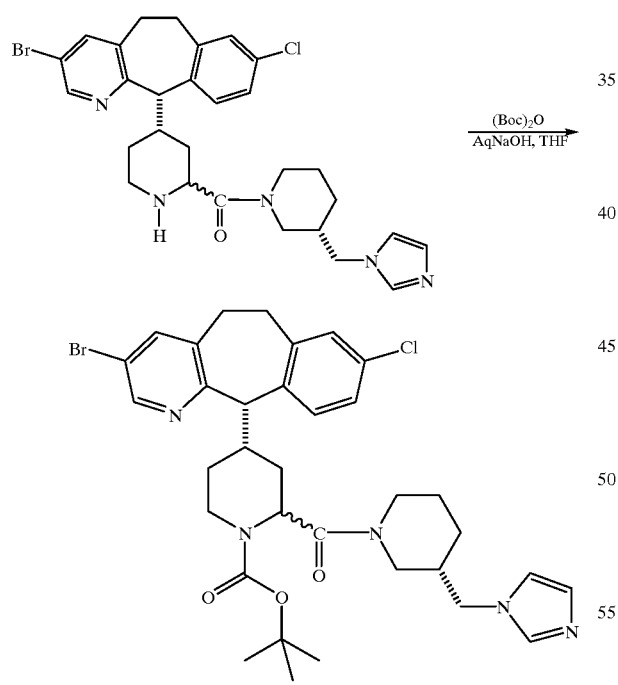

A solution of Boc dicarbonate (100 mg, 0.45 mmol) in THF(2 ml) was added to a solution of the tricycle (170 mg, 0.29 mmol )-(Isomers (C.D) Product 1 Step A in THF:H₂O (V/V 1:1) (10 ml), and 10% NaOH (2 ml) at 20° C. Then stirred at this temperature for 60 minutes. Water (5 ml), and MeCl₂ (10 ml) were added. The organic layer was separated, dried over MgSO₄, filtered and solvent evaporated yielding an oil, which chromatographed on silica gel, eluting with 3% v/v MeOH:MeCl₂ yielding the product as a white solid (170 mg) as a mixture of 2 isomers. Isomers C,D. Mass Spec (ES,MH) 682.

Following the above procedure but, substituting Product 2 from Step A (isomers A/B) for Product 1, the title Product 2 was obtained as a mixture of 2 isomers (A/B). Mass Spec (ES,MH) 682.

EXAMPLE 120

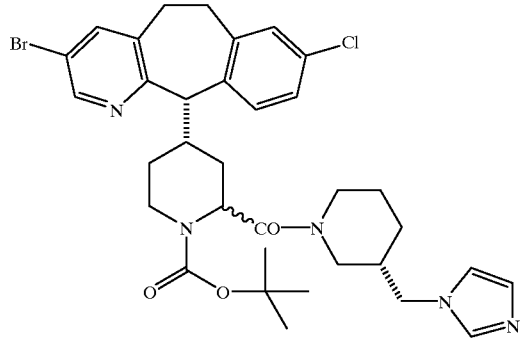

Compounds with (R) stereochemistry at C₁₁ were obtained using the procedures of Examples 118 and 119, but substituting reagent 1, Example 118 with the corresponding (R) tricyclic isomer.

EXAMPLES 121–126

By substituting reagent 2, Example 118, with the corresponding 2-methyl imidazole analog, the following structures were obtained

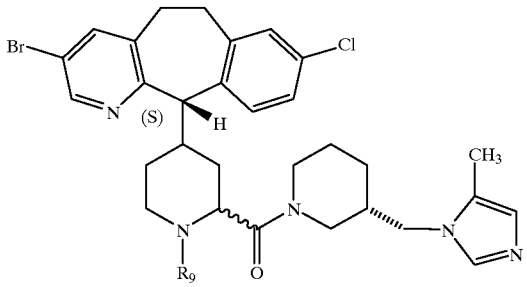

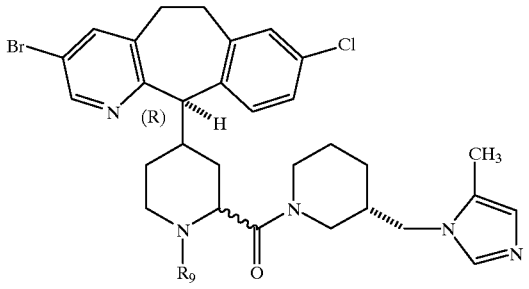

wherein $R^9$ is defined in Table 14 below.

TABLE 14

| Ex. | $R^9$ | Isomer | C-11 Isomer |
|---|---|---|---|
| 121 | H3C-C(CH3)(CH3)-O-C(=O)- ; MS ES (MH) = 696 | A, B, C, D | S |
| 122 | H3C-C(CH3)(CH3)-O-C(=O)- ; MS ES (MH) = 696 | A, B, C, D | R |
| 123 | H3C-C(CH3)(CH3)-O-C(=O)- ; MS ES (MH) = 696 | C, D | S |
| 124 | H3C-C(CH3)(CH3)-O-C(=O)- ; MS ES (MH) = 696 | A, B | S |
| 125 | H3C-C(CH3)(CH3)-O-C(=O)- ; MS ES (MH) = 696 | C, D | R |
| 126 | H3C-C(CH3)(CH3)-O-C(=O)- ; MS ES (MH) = 696 | A, B | |

EXAMPLES 127–132

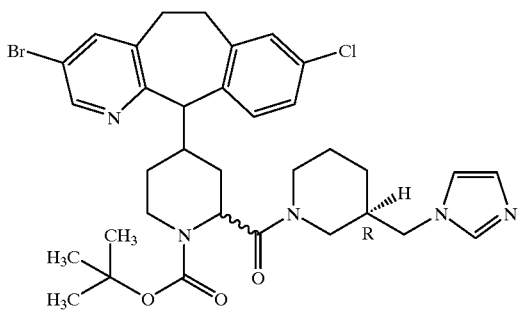

Following the procedures of Examples 118 and 119 the isomers identified in Table 15 below are obtained.

TABLE 15

| Ex. | C-11 Isomer | Isomer | mass spectra observed (estimate) |
|---|---|---|---|
| 127 | R | A, B, C, D | 684.2123 (684.2139) |
| 128 | R | A, B | 684.2163 (684.2139) |
| 129 | R | C, D | 684.2163 (684.2139) |
| 130 | S | A, B, C, D | 684.2149 684.2139 |
| 131 | S | A, B, | 684.2139 (684.2139) |

Preparative Example 66

Step A

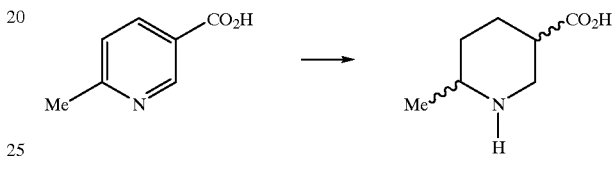

A solution of 6-methylnicotinic acid (9.97 g, 72.7 mmol), water (100 mL) and ammonium hydroxide was hydrogenated (40 psi) in a Parr low-pressure hydrogenation apparatus with 5% Rh—$Al_2O_3$ (3.22) catalyst over 72 hours. The mixture was filtered and the filtrate was concentrated in vacuo to give the title compound as a white solid (10.58 g, 100%, $MH^+$=144).

Step B

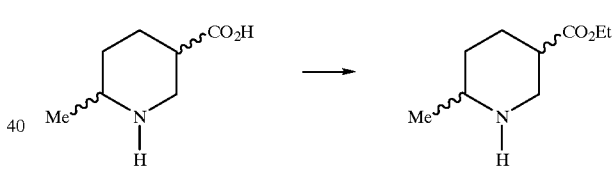

A mixture of the title compound from Step A (10.40 g, 72.72 mmol), ethyl alcohol (190 proof, 50 ml) and HCl (4 ml) was stirred at reflux for 4 hours. The reaction mixture was cooled to room temperature and poured into water. Basification of the mixture to pH=10 with 10% aqueous NaOH, extraction of the aqueous layer with EtOAc and drying of the organic phase over anhydrous $Na_2SO_4$ gave the title compound after filtration and concentration in vacuo (1.85 g, 15%, $MH^+$=172).

Step C

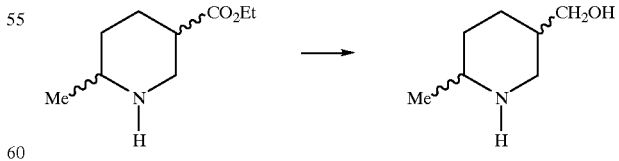

Following the procedure set forth in Preparative Example 7 Step B but using the title compound from Preparative Example 66 Step B instead of the title compound from Preparative Example 7 Step A, the product was isolated as a mixture of diastereomers and used directly in Step D ($MH^+$=130).

Step D

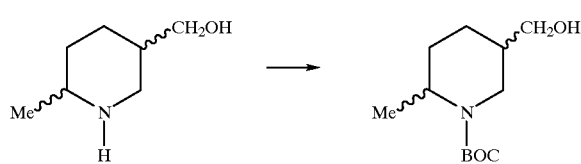

Following the procedure set forth in Preparative Example 7 Step C but using the title compound from Preparative Example 66 Step C instead of the title compound from Preparative Example 7 Step B, the product was isolated as a mixture of diastereomers (1.7 g, 70%, MH$^+$=230).

Step E

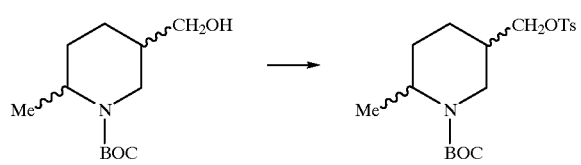

Following the procedure set forth in Preparative Example 7 Step D but using the title compound from Preparative Example 66 Step D instead of the title compound from Preparative Example 7 Step C, the product was isolated as a mixture of diastereomers and used directly in Step F (MH$^+$=384).

Step F

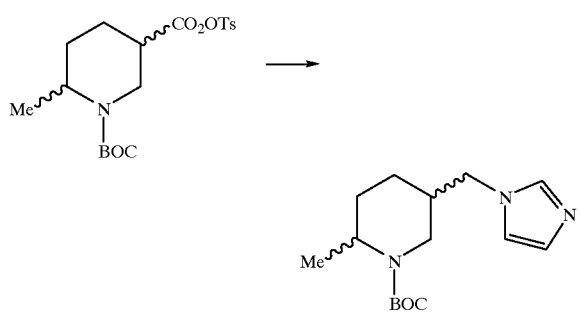

Following the procedure set forth in Preparative Example 7 Step E but using the title compound from Preparative Example 66 Step E instead of the title compound from Preparative Example 7 Step D, the product was isolated as a 5:1 mixture of diastereomers (328 mg 16%, MH$^+$=280).

Step G

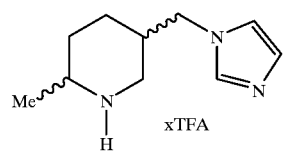

Following the procedure set forth in Preparative Example 7, Step F, except using the title compound from Preparative Example 66, Step F instead of the title compound from Preparative Example 7, Step E, the amine hydrochloride was obtained (290 mg, 100%): MH$^+$=180.

Preparative Example 67

Step A

If the procedures set forth in Preparative Example 66 Steps A–E were followed, except using 5-hydroxynicotinic acid instead of 6-methylnicotinic acid in Step A, the alcohol

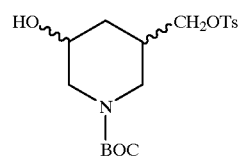

would be obtained.

Step B

If the product from Step A were treated with PCC according to standard procedures set forth in the literature, then the ketone

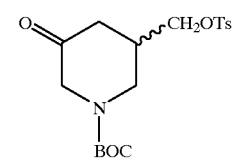

would be obtained.

Step C

If the procedures set forth in Preparative Example 7 Steps E–F were followed, except using the title compound from Preparative Example 67 Step B instead of the title compound from Preparative Example 7 Step D in Step E, the amine hydrochloride

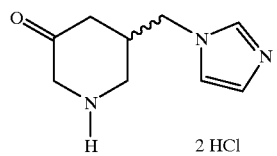

would be obtained.

Step D

If the product from Preparative Example 67 Step C were treated with excess NaBH$_4$ according to standard procedures set forth in the literature, then the alcohol

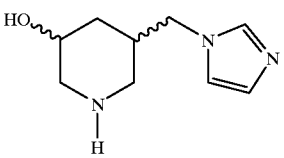

would be obtained.

Preparative Example 68

Step A

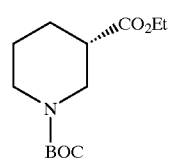

Following the procedure set forth in Preparative Example 7 Step C, except using the title compound from Preparative Example 7. Step A instead of the title compound from Preparative Example 7, Step B the ester was obtained (62 g, 96%): MH⁺=258.
Step B

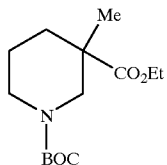

The product from Preparative Example 68, Step A was treated with LDA in anhydrous THF and the resulting anion was alkylated with methyl iodide to afford the title product (3.53 g, 82%): MH⁺=272.
Step C

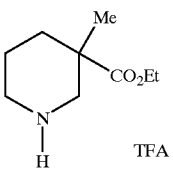

The title compound from Preparative Example 68, Step B was treated with TFA in $CH_2Cl_2$ to afford the amine as a TFA salt (1.63 g, 84%): MH⁺=172.
Step D

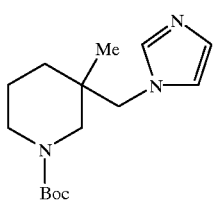

Following the procedures set forth in Preparative Example 7, Steps B–E. except using the title compound from Preparative Example 68, Step C instead of the title compound from Preparative Example 7, Step A in Step B, the imidazole product was obtained (0.445 g, 100%): MH⁺=280.
Step E

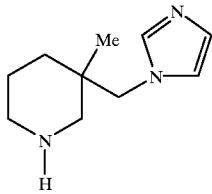

Following the procedure set forth in Preparative Example 68 Step C, except using the title compound from Preparative Example 68 Step D, the amine was obtained as its TFA salt. The mixture was basified with 1N NaOH and extracted with $CH_2Cl_2$ to afford the product (14.6 g, 96%): MH⁺=194.

Preparative Example 69

Following the procedures set forth in Preparative Example 68 Steps A–D, except using benzyl bromide in Preparative Example 68 Step B instead of methyl iodide, the amine hydrochloride

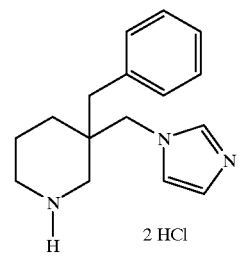

would be obtained.

EXAMPLE 133

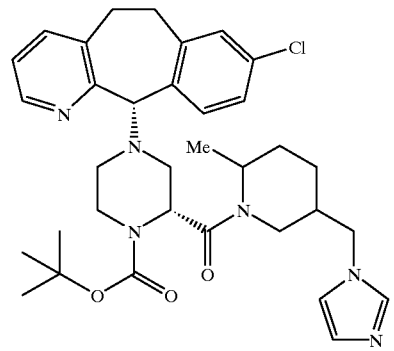

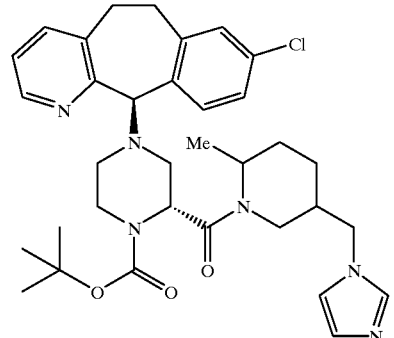

If the procedure set forth for preparing the compounds in Table 4 were followed using the title compound from Preparative Example 66 Step G, the 11(S) or 11(R) isomers of the carboxylic acid from Preparative Example 30, DEC, HOBt and NMM, the title products would be obtained.

EXAMPLE 134

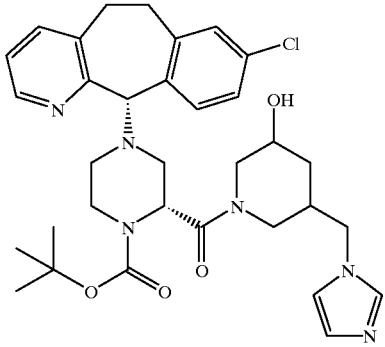

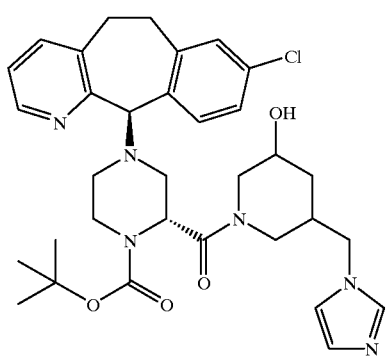

If the procedure set forth for preparing the compounds in Table 4 were followed using the title compound from Preparative Example 67 Step D, the 11(S) or 11(R) isomers of the carboxylic acid from Preparative Example 30, DEC, HOBt and NMM, the title products would be obtained.

EXAMPLE 135

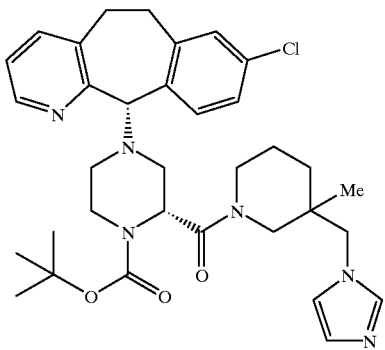

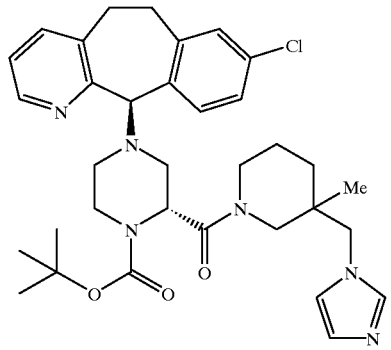

If the procedure set forth for preparing the compounds in Table 4 were followed using the title compound from Preparative Example 68 Step D, the 11(S) or 11(R) isomers of the carboxylic acid from Preparative Example 30, DEC, HOBt and NMM, the title products would be obtained.

EXAMPLE 136

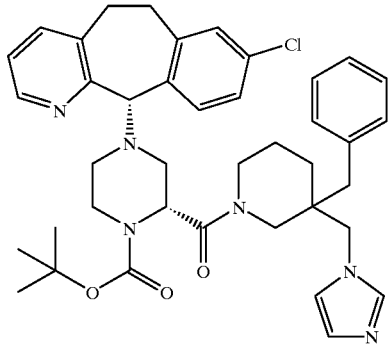

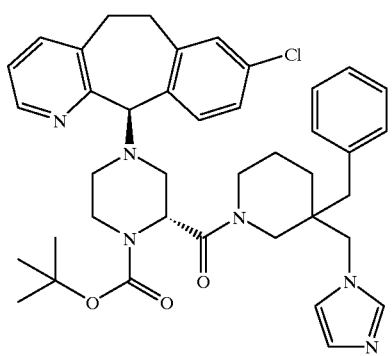

If the procedure set forth for preparing the compounds in Table 4 were followed using the title compound from Preparative Example 69, the 11(S) or 11(R) isomers of the carboxylic acid from Preparative Example 30. DEC, HOBT and NMM, the title products would be obtained.

EXAMPLE 137

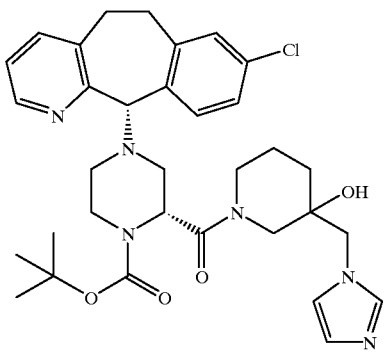

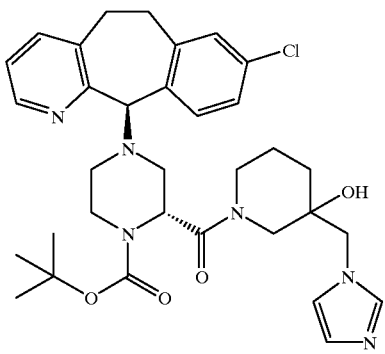

If the procedure set forth for preparing the compounds in Table 4 were followed using the title compound from Preparative Example 70 Step B, the 11(S) or 11(R) isomers of the carboxylic acid from Preparative Example 30. DEC, HOBt and NMM, the title products would be obtained.

Preparative Example 71

2(R)-[[2-[2-(1H-imidazol-1-yl)Ethyl]-1-piperdinyl]carbonyl]piperazine

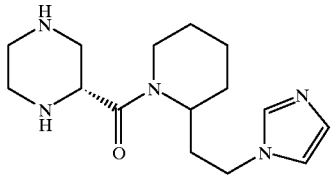

Step A
Bis-(1,1-dimethylethyl)2(R)-[[2-[2-(1H-imidazol-1-yl)ethyl]-1-piperidinyl]carbonyl]-1,4-piperazinedicarboxylate

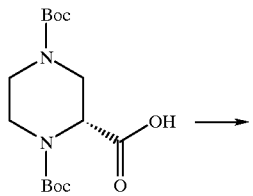

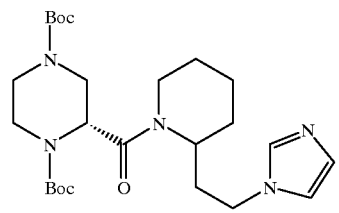

1,4-Di-N-tert-butoxycarbonylpiperazine-2(R)-carboxylate (prepared as described in Preparative Example 2) (0.6946 g, 2.1 mmoles), 2(R/S)-[2-(1H-imidazol-1-yl)ethyl]piperidine (0.49 g, 2.73 mmoles) (prepared as described in Preparative Example 57, Step D) (INO972). 1-(3-dimethylaminopropyl)-3-ethylcarbodiimide hydrochloride (0.524 g, 2.73 mmoles), 1-hydroxybenzotriazole (0.3693 g, 2.73 mmoles) and 4-methylmorpholine (0.2765 g, 0.3005 mL, 2.73 mmoles) were dissolved in anhydrous DMF (3 mL) and the mixture was stirred under argon at 25° C. for 122 h. The mixture was evaporated to dryness and chromatographed on silica gel using 2–3%(10% conc. ammonium hydroxide in methanol)dichloromethane as the eluant to give the title compound (0.3127 g, 30%): CIMS: m/z 492.4 (MH$^+$): $\delta_{11}$ (CDCl$_3$) 1.47 (18H, s, CH$_3$), 7.01 (1H, s, Im-H,), 7.05 (1H, s, Im-H$_4$) and 7.63 ppm (1H, s, Im-H$_2$); $\delta_C$ (CDCl$_3$) CH$_3$: 28.2, 28.2, 28.2, 28.4, 28.4, 28.4: CH$_2$: 19.1, 25.9, 26.2, 31.9, 40.8/41.3, 41.7, 43.0, 44.0: CH: 46.0, ~52.1, 128.4, 137.2: C:~80.4, 80.6, ~154.3, ~154.3 and 169.8.

Step B 2(R)-[[2-[2-(1H-imidazol-1-yl)ethyl)]-1-piperidinyl]carbonyl]piperazine

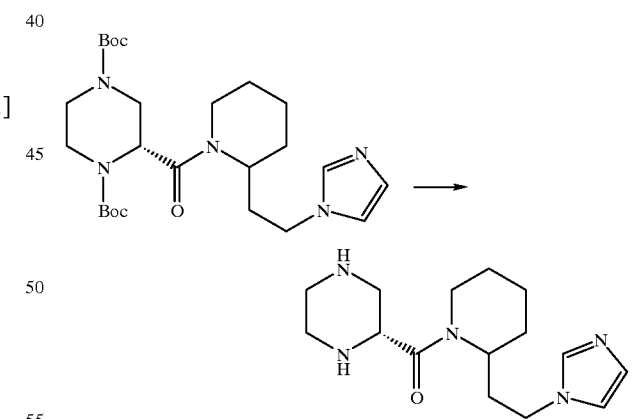

The title compound from Step A above was deprotected as described in Preparative Example 57, Step D and chromatographed on silica gel to give the title compound.

EXAMPLE 138

1,1-dimethylethyl 4-(3-bromo-8-chloro-6,11-dihydro-5H-benzo[5,6]cyclohepta[1,2-b]pyridin-11(S)-yl)-2(R)-[[2-[2-(1H-imidazol-1-yl)ethyl]-1-piperidinyl]carbonyl]-1-piperazinecarboxylate

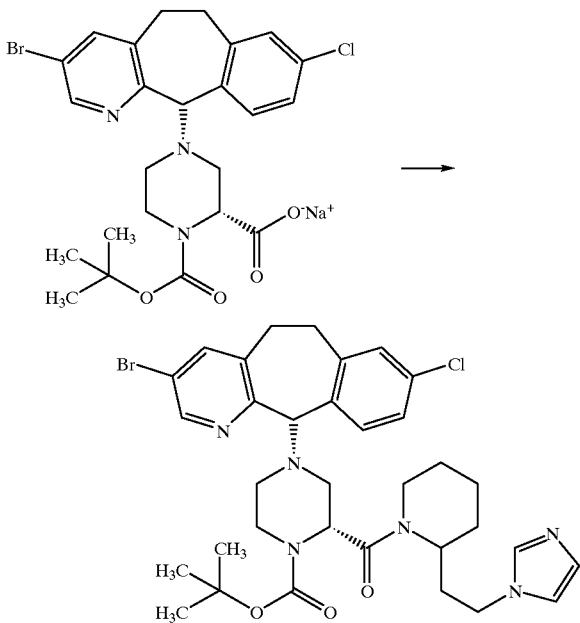

Sodium 1.1-dimethylethyl 4-(3-bromo-8-chloro-6,11-dihydro-5H-benzo[5,6]cyclohepta[1,2-b]pyridin-11(S)-yl)-2(R)-carboxy-1-piperazinecarboxylate (prepared as described in Preparative Example 6 (sodium salt)) (0.1 g, 0.79 mmoles), 2-[2-(1H-imidazol-1-yl)ethylpiperdidine (prepared as described in Preparative Example 57, Step D) (0.0417 g, 0.233 mmoles), 1-(3-dimethylaminopropyl)-3-ethylcarbodiimide hydrochloride (0.0446 g, 0.233 mmoles), 1-hydroxybenzotriazole (0.0314 g, 0.233mmoles) and 4-methylmorpholine (0.0512 mL, 0.466 mmoles) were dissolved in anhydrous DMF (4 mL) and the mixture was stirred under argon at 25° C. for 42 h. The solution was evaporated to dryness and the residue was taken up in dichloromethane and washed with 1N NaOH, dried (MgSO$_4$), filtered and evaporated to dryness. The residue was chromatographed on silica gel using 2.5%-4.5%-7.5% (10% conc. NH$_4$OH in methanol)-dichloromethane as the eluant to give the title compound (0.0172 g, 14%): HRFABMS: m/z 697.2285 (MH$^+$) (Calcd. m/z 697.2269); $\delta_H$ (CDCl$_3$) 1.38/1.41 (9H, s, CH$_3$), 4.31 (1H, s, H$_{11}$), 4.68 (1H, bs, H$_2$), 7.03–7.20 (5H, bm, Ar—H and Im-H$_4$ and Im-H$_5$), 7.57 (1H, Im-H$_2$), 7.83/8.19 (s, Ar—H) and 8.38 ppm (1H, s, Ar—H$_2$): $\delta_C$ (CDCl$_3$) CH$_3$: 28.4, 28.4, 28.4; CH$_2$: 19.1, 24.8/24.9, 28.3, 30.3, 30.5, 31.4, 40.3, 42.9/43.2, 44.1/44.6, 45.6, 50.2/50.5; CH: 44.1/44.6, 52.4, 78.4, 119.2, 126.2, 127.9, 130.8/130.9, 132.6, 136.7, 141.6, 146.9/147.2: C: 80.4, 119.8/120.2, 134.4, 135.9, 137.0, 141.5, 155.0, 156.7/157.1, 170.3/170.9.

EXAMPLE 139

1,1-dimethylethyl 4-(8-chloro-6,11-dihydro-5H-benzo[5,6]cyclohepta[1,2-b]pyridin-11(S)-yl)-2(R)-[[2-[2-(1H-imidazol-1-yl)ethyl]-piperidinyl]carbonyl]-1-piperazinecarboxylate

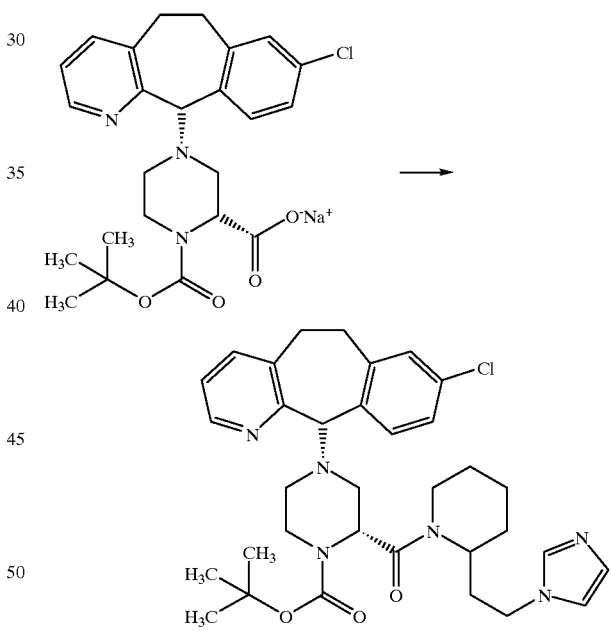

Sodium 1,1-dimethylethyl 4-(8-chloro-6,11-dihydro-5H-benzo[5,6]cyclohepta[1,2-b]pyridin-11(S)-yl)-2(R)-carboxy-1-piperazinecarboxylate (prepared as described in Preparative Example 6 (sodium salt)) (0.5239 g, 1.09 mmoles), 2-[2-(1H-imidazol-1-yl)ethyl]piperidine (prepared as described in Preparative Example 57, Step D) (0.2544 g, 1.42 mmoles), 1-(3-dimethylaminopropyl)-3-ethylcarbodiimide hydrochloride (0.272 g, 1.42 mmoles), 1-hydroxybenzotriazole (0.1918 g, 1.42 mmoles) and 4-methylmorpholine (0.156mL, 1.42 mmoles) were dissolved in anhydrous DMF (23.5 mL) and the mixture was stirred under argon at 25° C. for 286 h. The solution was evaporated to dryness and the residue was taken up in dichloromethane and washed with 1N NaOH, dried (MgSO$_4$), filtered and evaporated to dryness. The residue was chromatographed on silica gel using 2.5% (10% conc. NH$_4$OH in methanol)-dichloromethane as the eluant to give the title compound (0.2298 g, 32%): HRFABMS: m/z 619.3169 (MH$^+$) (Calcd. m/z 691.3163).

EXAMPLE 140

4-(8-chloro-6,11-dihydro-5H-benzo[5,6]cyclohepta[1,2-b]pyridin-11(S)-yl]-2(R)-[[2-[2-(1H-imidazol-1-yl)ethyl]-1-piperidinyl]carbonyl]-1-piperazine

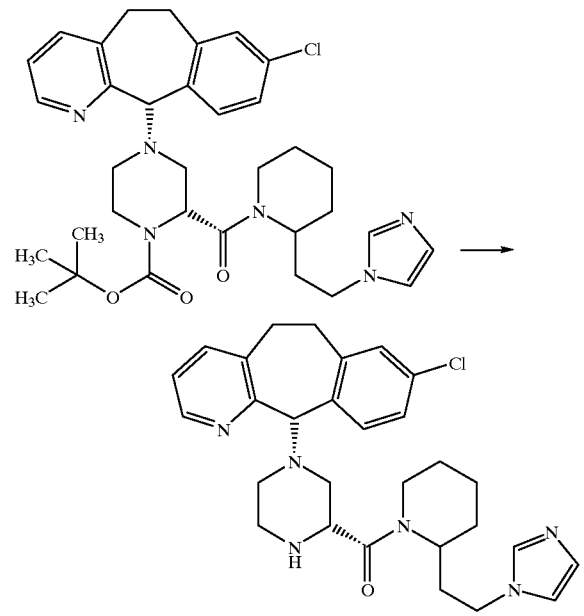

The title compound from Example 2 (0.225 g, 0.363 mmoles) was dissolved in methanol (2 mL). A 10% (v/v) solution of conc. H$_2$SO$_4$ in dioxane (v/v) (4.92 mL) was added and the mixture was stirred at 25° C. for 30 h. The mixture was diluted with methanol (300 mL) and then treated with BioRad AG1-X8 (OH) resin until it was basic. The resin was filtered off and washed with methanol. The combined filtrates were evaporated to dryness and the residue was chromatographed on silica gel using 4% (10% conc. NH$_4$OH in methanol)-dichloromethane as the eluant to give the title compound (0.1692 g, 90%): HRFABMS: m/z 519.2655 (MH$^+$) (Calcd. m/z 519.26390), $\delta_{11}$ (CDCl$_3$) 4.43 (1H, s, H$_{11}$), 6.89, 6.93,7.00, 7.10, 7.13, 7.19, 7.21, 7.43, 7.45, 7.50, 7.58, 8.03, 8.30 and 8.33 ppm (8H, Ar—H and Im-H): $\delta_C$(CDCl$_3$) CH$_2$: 19.0/19.1, 25.0/25.7/26.1, 28.3/29.0, 30.7/30.8, 30.9/31.0, 31.5/31.9, 40.0/40.7, 43.5, 44.1/44.2/44.4, 49.3, 51.5/52.3: CH: 45.7/46.1, 54.4/55.8, 79.5/79.7, 118.3/118.9, 123.1, 126.1/126.2, 129.1/129.5/129.7, 130.4/130.5, 132.7/132.8, 137.0/137.5, 138.9, 146.3; C: 134.0, 134.9, 135.5, 141.3, 157.1 and 169.8/170.5.

EXAMPLE 141 cyclohexyl 4-(8-chloro-6,11-dihydro-5H-benzo[5,6]cyclohepta[1,2-b]pyridin-11(S)-yl)-2(R)-[[2-[2(R/S)-(1H-imidazol-1-yl)ethyl-1-piperidinyl]carbonyl]-1-piperazinecarboxylate

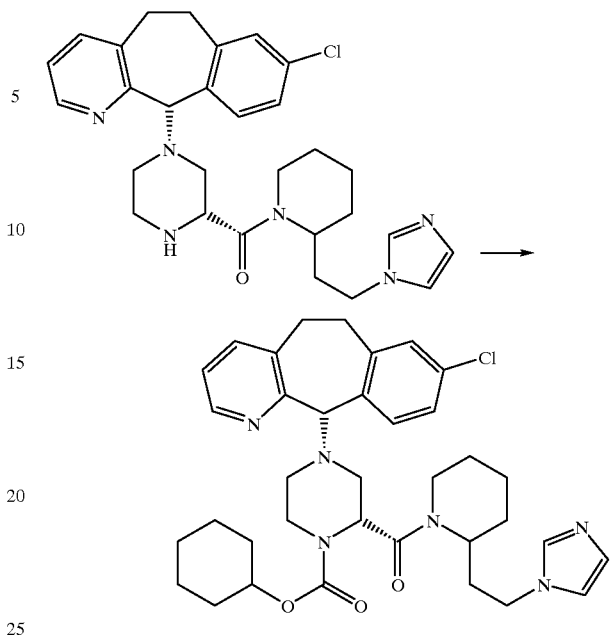

The title compound from Example 3 (0.165 g, 0.318 mmoles) and triethylamine (0.1329 mL, 0.954 mmoles) were dissolved in anhydrous dichloromethane (5 mL). Cyclohexylchloroformate (0.0517 g, 0.318 mmoles) dissolved in anhydrous dichloromethane (3.18 mL) was added and the mixture was stirred at 25° C. for 18 h. Additional cyclohexylchloroformate (0.0129 g, 0.0795mmoles) was added and the stirring was continued for a total of 43 h. Methanol (10 mL) was added and the mixture was evaporated to dryness. The residue was chromatographed on silica gel using 2% (10% conc. NH$_4$OH in methanol)-dichloromethane as the eluant to give the title compound (0.153 g, 75%): HRFABMS: m/z 645.3323 (MH$^+$) (Calcd. MH$^+$ for C$_{36}$H$_{46}$N$_6$O$_3$Cl: m/z 645.3320).

EXAMPLE 142 cyclohexyl 4-(8-chloro-6,11-dihydro-5H-benzo[5,6]cyclohepta[1,2-b]pyridin-11(S)-yl)-2(R)-[[2-[2(S)-(1H-imidazol-1-yl)ethyl-1-piperidinyl]carbonyl]-1-piperazinecarboxylate Isomer 1

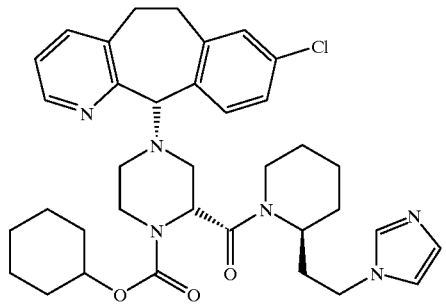

and (−)-cyclohexyl 4-(8-chloro-6,11-dihydro-5H-benzo[5,6]cyclohepta[1,2-b]pyridin-11(S)-yl)-2-(R)-[[2-[2(R)-(1H-imidazol-1-yl)ethyl-1-piperdinyl]carbonyl]-1-piperazinecarboxylate Isomer 2

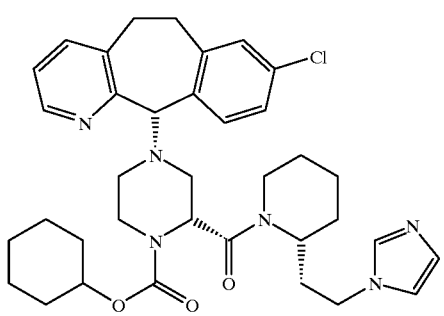

The diastereoisomeric mixture of compounds from Example 4 (0.154 g) was separated using chiral HPLC on a Chiralpak AD® analytical column using hexane:isopropanol:diethylamine::85:15:0.2 as the eluant to give firstly isomer 1 (0.0376 g): HRFABMS: m/z 645.3305 (MH$^+$) (Calcd. MH$^+$ for $C_{36}H_{46}N_6O_3Cl$: m/z 645.3320): $\delta_{b\ 67\ 11}$ (CDCl$_3$) 4.30 (1H, s, H$_{11}$), 6.69, 7.00, 7.08, 7.11, 7.16, 7.18, 7.42, 7.70, 8.32 ppm (9H, s and m, Ar—H and Im-H): $\delta_c$(CDCl$_3$) CH$_2$: 18.9, 23.6, 23.6, 24.8/25.1, 25.5, 28.0/28.2, 30.7/30.8, 30.9, 31.4, 31.8, 31.8, 42.7, 43.9/44.2, 50.9, 52.7; CH: 49.9/50.5, 52.3, 73.6, 79.3/79.9, 119.1/119.3, 123.3, 126.0, 128.7, 132.8, 137.1, 139.0/139.3, 146.3/146.9; C: 134.0, 135.1, 136.4, 141.8/142.0, 156.1, 157.0 and 170.1 [α]$_D^{20°\ C}$·0° (c=6.89 mg/2 mL, MeOH) and then isomer 2 (0.0867 g): HRFABMS: m/z 645,3305 (MH$^+$) (Calcd. MH$^+$ for $C_{36}H_{46}N_6O_3Cl$: m/z 645.3320); $\delta_H$(CDCl$_3$) 4.34 (1H, s, H$_{11}$), 6.93, 6.99, 7.06, 7.12, 7.17, 7.21, 7.43, 7.70 and 8.33 ppm (9H, s and m, Ar—H and Im-H); $\delta_C$(CDCl$_3$) CH$_2$: 19.1, 23.5, 23.5, 24.7/24.8, 25.5, 28.9, 30.6/30.8, 31.5, 31.7, 31.7, 36.7, 40.4, 42.8, 44.1, 50.5, 52.5; CH: 45.9, 52.3, 73.7, 79.2/79.4, 119.4, 123.4, 126.0, 128.1, 130.7, 132.7, 137.1, 139.4, 146.3/146.9: C: 134.1, 135.1, 136.6, 142.0, 156.1, 157.0 and 170.2; [α]$_D^{20°\ C}$·-44.1° (c=10.05 mg/2 mL, MeOH). An overlap cut consisting of a mixture of isomer 1 and isomer 2 was also obtained (0.0196 g).

Preparative Example 72

2(R/S)-[2-(1H-4-methylimidazol-1-yl)ethyl]piperidine

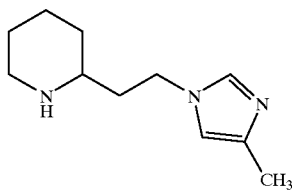

Step A 1N-tert-butoxycarbonyl-2(R/S)-[2-(1H-4/5-methylimidazol-1-yl)ethyl]piperidine

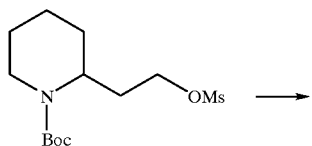

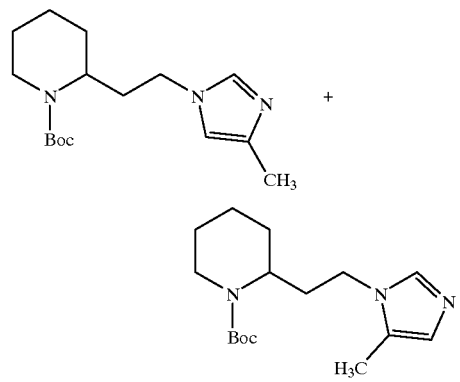

4-Methylimidazole (6.46 g, 78.64 mmoles) was dissolved in anhydrous DMF (300 mL) and 95% sodium hydride (1.987 g, 86.5 mmoles) was added in portions over 0.25 h to the stirred solution at 25° C. under argon. The mixture was stirred for 1.5 h. A solution of 1-tert-butoxycarbonyl-2(R/S)-(2-methanesulfonyloxyethyl)piperidine (21.97 g, 71.49 mmoles) (prepared as described in Preparative Example 57, Step B) in anhydrous DMF (70 mL) was added and the mixture was heated under reflux at 65° C. for 2.25 h. The mixture was evaporated to dimness and the residue was taken up in dichloromethane and washed with water, dried (MgSO$_4$), filtered and evaporated to dryness. The product was chromatographed on silica gel using 1% (10% conc. NH$_4$OH in methanol)-dichloromethane to give a mixture of the title compounds (12.06 g, 58%) (4-Me:5-Me::63:37): CIMS: m/z 294.25 (MH$^+$); 4-Me: $\delta_H$ (CDCl$_3$) 1.43 (9H, s, CH$_3$), 2.20 (3H, s, Im-4-CH$_3$), 6.63 (1H, s, Im-H$_5$) and 7.35 ppm (1H, s, Im-H$_2$); $\delta_C$(CDCl$_3$) CH$_3$: 13.6, 28.4, 28.4, 28.4; CH$_2$: 19.0, 25.4, 28.7, 31.6, 38.8, 44.1; CH: 48.0 115.2, 136.1; C: 79, 138.3, 155.0 and 5-Me: $\delta_H$(CDCl$_3$) 1.43 (9H, s, CH$_3$), 2.19 (3H, s, Im-5-Me), 6.75 (1H, s, Im-H$_4$) and 7.4 ppm (1H, s, Im-H$_2$: (CDCl$_3$) CH$_3$: 9.2, 28.4, 28.4, 28.4; CH$_2$; 19.0, 25.4, 28.7, 31.4, 38.8. 42.0: CH: 48.0, 126.9, 136.5: C: 79.7, 138.3, 155.0.

Step B 1N-tert-butoxycarbonyl-2(R/S)-[2-(1H-4-methylimidazol-1-yl)ethyl]piperidine

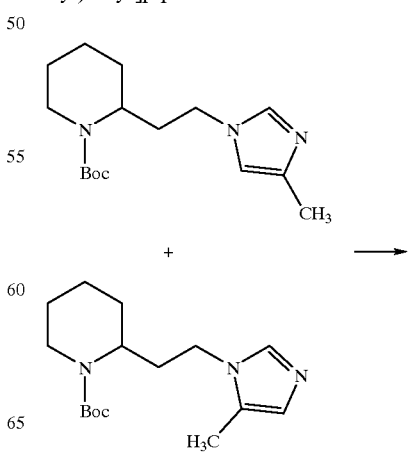

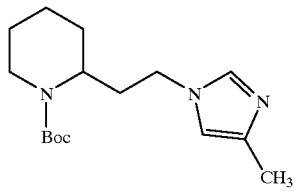

and

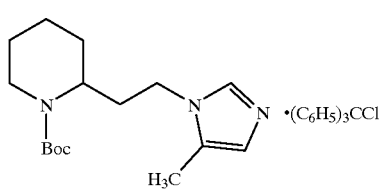

The mixture of compounds from Step A above (1.77 g) was dissolved in anhydrous CH$_2$Cl$_2$ (18.6 mL) at 0° C. under argon. Trityl chloride (1.2445 g, 2 equivalents per equivalent of the 5-methyl isomer) was added and the mixture was stirred at 0° C. for 2 h. The reaction mixture was introduced directly onto a silica gel column and the column was eluted with 50% ethyl acetate in acetone to give the pure 4-methyl isomer (0.6267 g, 56%): 4-Me: $\delta_H$ (CDCl$_3$) 1.44 (9H, s, CH$_3$), 2.20 (3H, s, Im-4-CH$_3$), 6.64 (1H, s, Im-H$_5$) and 7.36 ppm (1H, s, Im-H$_2$): $\delta_C$(CDCl$_3$) CH: 13.7, 28.5, 28.5, 28.54 CH$_2$: 19.1 25.5, 28.9, 31.7, 39.0, 44.2: CH: 48.1, 115.1, 136.2; C: 79.8, 138.4, 155.1.

Step C

2(R/S)-[2-(1H-4-methylimidazol-1-yl)ethyl]piperidine

The pure 4-methyl isomer (0.7518 g, 2., 56 mmoles) was deprotected as described in Preparative Example 57, Step D, to give after purification, the title compound (0.4366 g, 88%): FABMS: m/z 194.2 (MH$^+$); $\delta_H$(CDCl$_3$) 1.76 (2H, m, CH$_2$), 2.19 (3H, s, Im-4-CH$_3$), 3.94 (2H, m, CH$_2$-Im), 6.60 (1H, s, Im-H$_5$) and 7.33 ppm (1H, s, Im-H$_2$); $\delta_C$(CDCl$_3$) CH$_3$: 13.7: CH$_2$: 24.5, 26.6, 32.9, 38.4, 43.6, 46.8: CH: 53.9, 115.2, 136.2: C: 138.4.

EXAMPLE 143 cyclohexyl 4-(8-chloro-6,11-dihydro-5H-benzo[5,6]cyclohepta[1,2-b]pyridin-11(S)-yl)-2(R)-[[2-[2(R/S)-(4-methyl-1H-imidazol-1-yl)ethyl-1-piperidinyl]carbonyl]-1-piperazinecarboxylate

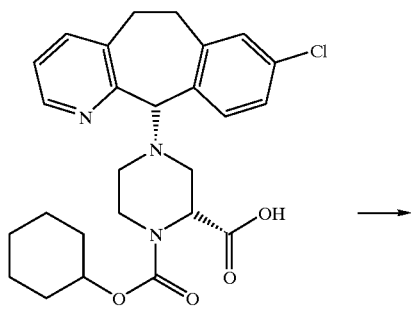

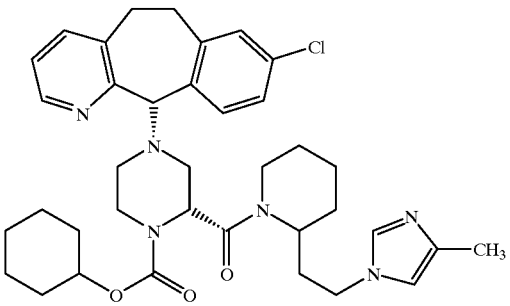

Cyclohexyl 4-(8-chloro-6,11-dihydro-5H-benzo[5,6]cycloheptal 1,2-bipyridin-11(S)-yl)-2(R)-carboxy-1-piperazinecarboxylate (0.275 g, 0.568 mmoles) (prepared as described in Preparative Example 32), 2-[2(R/S)-(4-methyl-1H-imidazol-1-yl)ethyl]piperidine (0.1428 g, 0.7386 mmoles) (prepared as described in Preparative Example 2, Step C), 1-(3-dimethylaminopropyl)-3-ethylcarbodiimide hydrochloride (0.1416 g, 0.7386 mmoles), 1-hydroxybenzotriazole (0.0998 g, 0.7386 mmoles) and 4-methylmorpholine (0.0812 mL, 0.7386 mmoles) were dissolved in anhydrous DMF (12.2 mL) and the mixture was stirred at 25° C. for 212 h under argon. The solution was evaporated to dryness and taken up in dichloromethane and washed with 1N NaOH. The aqueous layer was extracted 3×with dichloromethane (200 mL) and the combined organic layers were dried (MgSO$_4$), filtered and evaporated. The product was chromatographed on silica gel using 2% (10% conc. NH$_4$OH in methanol)-dichloromethane as the eluant to give the title compound (0.149 g, 40%): FABMS: m/z 659.62 (MH$^+$).

EXAMPLE 144

(−)-cyclohexyl 4-(8-chloro-6,11-dihydro-5H-benzo[5,6]cycohepta[1,2-b]pyridin-11(S)-yl)-2(R)-[[2-[2(S)-(4-methyl-1H-imidazol-1-yl)ethyl-1-piperidinyl]carbonyl]-1-piperazinecarboxylate Isomer 1

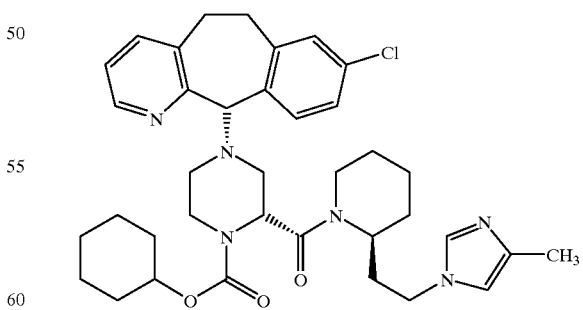

and (−)-cyclohexyl 4-(8-chloro-6,11-dihydro-5H-benzo[5,6]cyclohepta[1,2-b]pyridin-11(S)-yl)-2(R)-[[2-[2-(R)-(4-methyl-1H-imidazol-1-yl)ethyl-1-piperidinyl]carbonyl]-1-piperazinecarboxylate Isomer 2

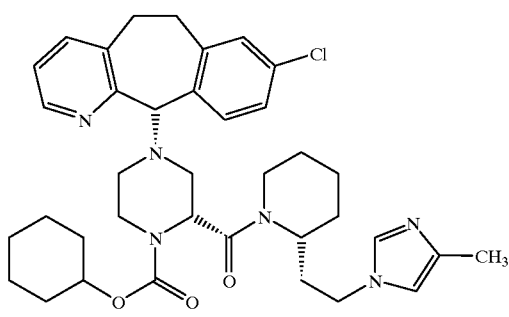

The diastereoisomeric mixture of compounds from Example 6 (0.145 g) was separated using chiral HPLC on a Chiralpak AD® analytical column using hexane:isopropanol: diethylamine::70:30:0.2 as the eluant to give firstly isomer 1 (0.0475 g): FABMS: m/z 659.4 (MH$^+$); $\delta_h$ (CDCl$_3$) 1.66 (2H, m, CH$_2$), 2.23 (3H, s, Im-4-CH$_3$), 3.71 (2H, m, CH$_2$-Im), 4.32 (1H, s, H$_{11}$), 6.58, 6.72, 6.75, 7.10, 7.14, 7.20, 7.41, 7.60 and 8.34 ppm (9H, s and m, Ar—H and Im-H); $\delta_C$(CDCl$_3$) CH$_3$: 13.4/13.7; CH$_2$: 18.9, 23.5, 23.5, 24.2/25.1, 25.5, 28.1, 30.7, 30.8, 31.4, 31.8, 31.8, 36.7, 42.4/42.6, 43.8/44.1, 50.5/50.8, 52.8; CH: 49.8, 52.3, 73.6, 79.3/80.0, 115.5/115.8, 123.3, 126.0, 130.6/130.8. 132.8, 136.0, 139.2/139.3, 146.3: C: 134.0, 135.0/135.1, 136.2/136.5, 137.8, 141.8/142.0, 156.1, 157.0, 170.1; $[\alpha]_D^{20°}$ $_{C.}$-4.3° (c=8.07 mg/2 mL, MeOH), and then isomer 2 (0.852 g): HRFABMS: m/z 659.3492 (MH$^+$) (Calcd. MH$^+$ for C$_{37}$H$_{48}$N$_6$O$_3$Cl: m/z 659.3476): $\delta_H$ (CDCl$_3$) 1.64 (2H, m, CH$_2$), 2.22 (3H, s, Im-4-CH$_3$), 3.72 (2H, m, CH$_2$-Im), 4.35 (1H, s, H$_{11}$), 6.61, 6.67, 7.12, 7.17, 7.22, 7.43, 7.57 and 8.35 ppm (9H, s and m, Ar—H and Im-H): $\delta_C$ (CDCl$_3$) CH$_3$: 13.3/13.5: CH$_2$: 19.1, 23.5. 23.5, 24.7, 25.5, 28.7/28.9, 30.6, 30.8, 31.5, 31.7, 31.7, 40.3, 42.1/42.8, 44.1/44.2, 50.5/50.7, 52.6/52.7: CH: 46.0/46.2, 52.5, 73.7, 79.3/79.4, 115.6/115.8, 123.4, 126.0, 130.7, 132.7, 136.0/136.2, 139.4, 146.3: C: 134.1, 135.1, 136.2/136.6, 137.2, 142.0, 156.1, 157.1, 170.3: $[\alpha]_D^{20° \; C.}$ -44.7° (c=9.0 mg/2 mL, MeOH).

Preparative Example 73

2(R/S)-[3-(1H-imidazol-1-yl)propyl]piperidine

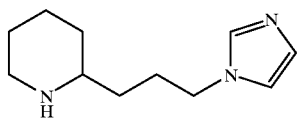

Step A 1N-tert-BUTOXYCARBONYL-2(R/S)-[3-(1H-IMIDAZOL-I- YL)PROPYL]PIPERIDINE

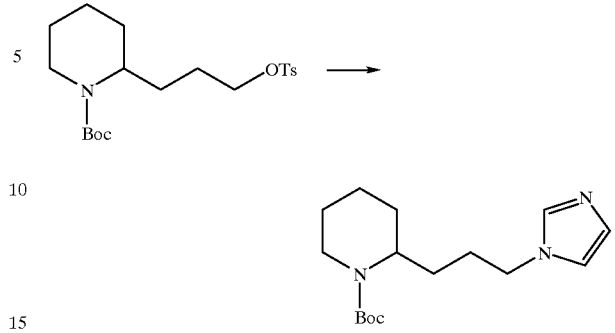

The title compound from Preparative Example 58, Step C, (1.29 g, 4.3mmoles) was dissolved in anhydrous DMF (15 mL). Sodium imidazole (0.3215 g, 4.7 mmoles) was added and the mixture was stirred at 25° C. under argon for 3 h. The solution was evaporated to dryness and the residue was chromatographed on silica gel using 2% (10% conc. NH$_4$OH in methanol)-dichloromethane as the eluant to give the title compound (0.6813 g, 72%): CIMS: m/z 294.25 (MH$^+$); S, (CDCl$_3$) 1.43 (9H, s, CH$_3$), 3.97 (2H, m, CH$_2$-Im), 6.90 (1H, s, Im-H$_5$), 7.04 (1H, s, Im-H$_4$) and 7.45 ppm (1H, s, Im-H$_2$): $\delta_C$(CDCl$_3$) CH$_2$: 28.4, 28.4, 28.4: CH$_2$: 18.9, 25.4, 26.3, 27.7, 28.6, 38.8, 46.5: CH: 49.0, 118.6, 129.4, 137.1: C: 79.3, 155.0.

Step B
2(R/S)-[3-(1H-IMIDAZOL-I-YL)PROPYL]PIPERIDINE

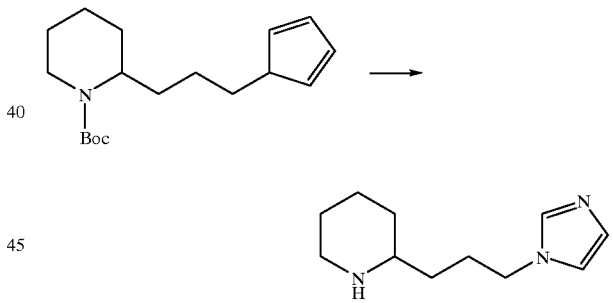

The title compound from Step A above (0.6075 g, 2.1 mmoles) was deprotected as described in Preparative Example 57, Step D, and chromatographed on silica gel using 10% (10% conc. NH$_4$OH in methanol)-dichloromethane as the eluant to give the title compound (0.3805 g, 95%): CIMS: m/z 194.20 (MH$^+$): $\delta_H$ (CDCl$_3$) 3.89 (2H, m, CH$_2$-Im), 6.84 (1H, s, Im-H), 6.99 (1H, s, Im-H$_4$) and 7.41 ppm (1H, s, Im-H$_2$): $\delta_C$(CDCl$_3$) CH$_2$: 24.9, 26.7, 27.2, 33.1, 34.4, 47.2, 47.2; CH: 56.4, 118.8, 129.6, 137.1.

EXAMPLE 145

1,1-Dimethylethyl 4-(3-bromo-8-chloro-6,11-dihydro-5H-benzo[5,6]cyclohepta[1,2-b]pyridin-11-yl)-2(R)-[[2-[3-(1H-imidazol-1-yl)propyl]-1-piperdinyl]carbonyl]-1-piperazinecarboxylate

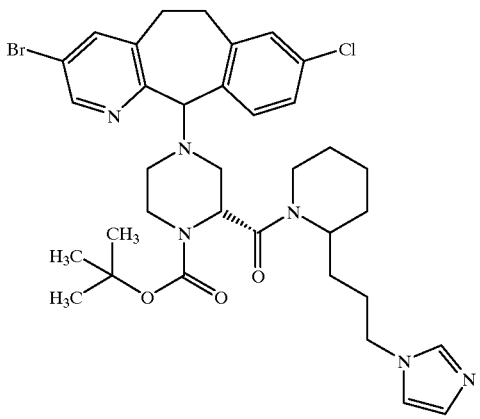

Isomers 1, 2, 3 and 4.

1,1-dimethylethyl 4-(3-bromo-8-chloro-6,11-dihydro-5H-benzo[5,6]cyclohepta[1,2-b]pyridin-11-yl)-2(R)-carboxy-1-piperazinecarboxylate (0.7225 g, 1.3 mmoles) (prepared as described in Preparative Example 6), the title compound from Preparative Example 8, Step B (0.3382 g, 1.7 mmoles), 1-(3-dimethylaminopropyl)-3-ethylcarbodiimide hydrochloride (0.3354 g, 1.7 mmoles), 1-hydroxybenzotriazole (0.2364 g, 1.7 mmoles) and 4-methylmorpholine (0.192 mL, 1.7 mmoles) were dissolved in anhydrous DMF (3 mL) and the mixture was stirred under argon at 25° C. for 319 h. The solution was evaporated to dryness and the residue was taken up in dichloromethane and washed with saturated aqueous sodium bicarbonate, water, dried ($MgSO_4$), filtered and evaporated to dryness. The residue was chromatographed on silica gel using 3% (10% conc. $NH_4OH$ in methanol)-dichloromethane as the eluant to give the partially purified title compounds. The appropriate fractions were rechromatographed using 1.5% (10% conc. $NH_4OH$-methanol)-dichloromethane as the eluant to give title compound as a mixture of 4 diastereoisomers (0.3718 g, 39%): FABMS: m/z 711.4 (MH$^+$); $\delta_H$ (CDCl$_3$) 1.39 (9H, s, CH$_3$), 6.91, 7.08, 7.13, 7.17, 7.56, 7.67 (Ar—H), 6.97 (1H, s, Im-H$_5$), 7.04 (1H, s, Im-H$_4$), 7.58 (1H, s, Im-H$_2$) and 8.38 ppm (1H, m, Ar—H$_2$): $\delta_C$(CDCl$_3$) CH$_3$: 28.3/28.4, 28.3/28.4, 28.3/28.4: CH$_2$: 18.9, 24.9/25.0/25.5, 26.8, 30.2, 30.5, 36.2, 40.1, 42.7/43.0, 46.5/46.7, 50.1/50.3/50.7, 52.7/52.9; CH: 46.9, 51.6/52.0, 78.5, 119.0, 126.2/126.3, 128.6, 130.8/130.9, 132.6, 137.0, 141.5, 146.9/147.2: C: 80.2, ~120.1, 134.3, 134.9, 137.6, 140.8, ~155.1/156.1, ~156.8, 170.3.

A portion of the diastereomeric mixture (0.28 g) was subjected to chiral HPLC on a Chiralpak® AD column using hexane: iso-propanol: diethylamine::85:15:0.2 as the eluant to give only a partial separation. Isomer 1 (0.0604 g) was obtained pure while isomers 3 and 4 (0.0376 g) were obtained as a 97% pure mixture. The remaining overlap cuts could not be separated.

Isomer 1: HRFABMS: m/z 711.2429 (MH$^+$) (Calcd. MH$^+$ for C$_{35}$H$_{45}$N$_6$O$_3$BrCl: m/z 711.2425): $\delta_H$ (CDCl$_3$) 1.41 (9H, s, CH$_3$), 4.29 (1H, s, H$_{11}$), 6.92. 7.14, 7.18. 7.20 (Ar—H), 6.98 (1H, s, Im-H$_5$), 7.08 (1H, s, Im-H$_4$), 7.58 (1H, s, Ar—H$_4$) and 8.38 ppm (1H, s, Ar—H$_2$): $\delta_C$(CDCl$_3$) CH$_3$: 28.3, 28.3, 28.3: CH$_2$: 18.9, 24.7, 25.4, 26.7, 28.8, 30.3, 30.5, 40.2, 43.1, 46.6, 50.6/50.7, 52.6; CH: 46.9/47.1, 52.1, 78.5/78.6, 119.1, 126.2, 128.3, 130.9, 132.6, 136.9, 141.5, 146.9/147.2: C: 79.7/80.2, 120.2, 133.6, 134.2, 136.9, 136.9, 155.1, 156.7, 170.2: [α]$_D^{20°}$ C. -22.2° (c=6.74 mg/2 mL, MeOH).

Isomers 3 and 4: FABMS: m/z 711.3 (MH$^+$); $\delta_H$ (CDCl$_3$) 1.39, 1.42 (9H, s, CH$_3$), 4.27, 4.29 (1H, s, H$_{11}$), 6.85, 6.91, 7.05, 7.12–7.18, 7.43 (Ar—H), 6.98 (1H, s, Im-H$_5$), 7.08 (1H, s, Im-H$_4$), 7.56 (1H, s, Im-H$_2$), 7.60, 7.71 (1H, s, Ar—H$_4$) and 8.38 ppm (1H, s, Ar—H$_2$); $\delta_C$(CDCl$_3$) CH$_3$: 28.3/28.4, 28.3/28.4, 28.3/28.4; CH$_2$: 18.8, 25.2, 25.3, 26.8, 28.6, 30.2, 30.4/30.5, 36.4, 42.8, 46.6, 50.5, 52.7/53.3; CH: 46.9/47.2, 51.6/52.2, 78.5/78.6, 119.2, 126.2, 128.6, 130.7/130.8, 132.6, 137.0, 141.5, 146.9; C: 80.1, 80.1, 120.0, 134.4, 134.8, 137.5/137.6, 141.0, 156.1, 156.6, 156.6, 170.0/170.2, 170.0/170.2.

Preparative Example 74

4-[3-(1H-imidazol-1-yl)propyl]piperidine

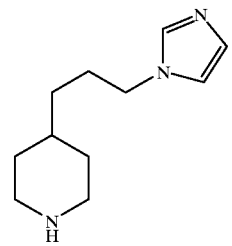

Step A 1N-tert-butoxycarbonyl-4-[3-(1H-imidazol-1-yl)propyl]piperidine

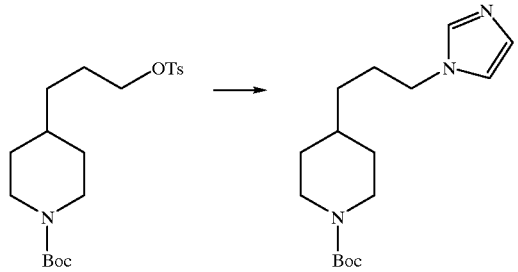

The title compound from Preparative Example 59, Step C (1.39 g, 3.5 mmoles) was dissolved in anhydrous DMF (10 mL) and sodium imidazole (0.3464 g, 3.85 mmoles) was added and the mixture was stirred at 25° C. for 3 h under argon. The solution was evaporated to dryness and the residue was chromatographed on silica gel using 2% (10% conc. $NH_4OH$ in methanol)-dichloromethane as the eluant to give the title compound (0.7637 g, 74%): FABMS: m/z 294.20 (MH$^+$); $\delta_H$ (CDCl$_3$) 1.39 (9H, s, CH$_3$), 3.88 (2H, m, CH$_2$-Im), 6.85 (1H, s, Im-H$_5$), 7.00 (1H, s, Im-H$_4$) and 7.40 ppm (1H, s, Im-H$_2$); $\delta_C$ (CDCl$_3$) CH$_3$: 28.5, 28.5, 28.5; CH$_2$: 28.3, 32.0, 33.3, 33.3, 44.0, 44.0, 47.2, 118.7, 129.5, 137.1; CH: 35.7; C: 79.3, 154.8.

Step B

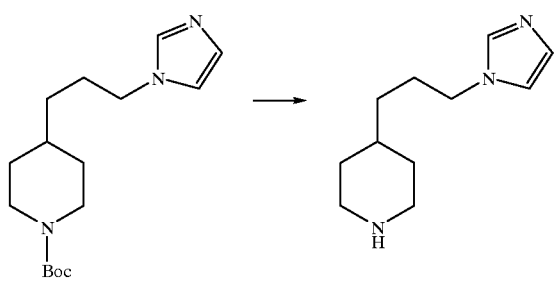

The title compound from Preparative Example 4, Step A above was deprotected as described in Preparative Example 57, Step D, to give after chromatography on silica gel using 20% (10% conc. NH$_4$OH in methanol)-dichloromethane as the eluant, the title compound (0.4346 g, 95%): CIMS: m/z 194.20 (MH$^+$); $\delta_H$(CDCl$_3$) 3.89 (2H, m, CH$_2$-Im), 6.88 (1H, s, Im-H$_5$), 7.02 (1H, s, Im-H$_4$) and 7.42 ppm (1H, s, Im-H$_2$); $\delta_C$ (CDCl$_3$) CH$_2$: 28.3, 33.5, 33.5, 34.1, 46.7, 46.7, 47.4; CH: 36.0, 118.8, 129.6, 137.2.

Preparative Example 75
2(R)-[[4-[3-(1H-imidazol-1-yl)propyl]-1-piperidinal] carbonyl]piperazine

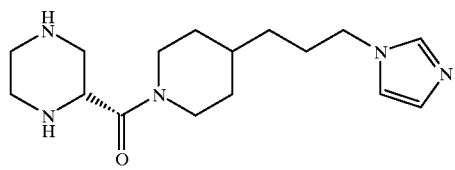

Step A
1,4-bis-1,1-dimethylethyl 2(R)-[[4-[3-(1H-imidazol-1-yl) propyl]-1-piperidinyl]carbonyl]piperazine-1,4-bis-carboxylate

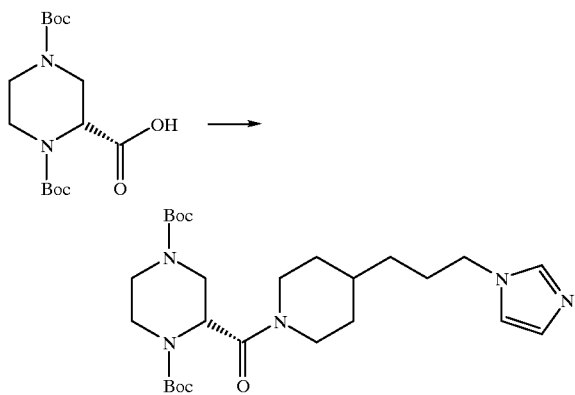

1,4-Di-N-tert-bultoxycarbonylpiperazine-2(R)-carboxylate (0.521 g, 1.6 mmoles) (prepared as described in Preparative Example 2), 1-(3-dimethylaminopropyl)-3-ethylcarbodiimide hydrochloride (0.393 g, 2.1 mmoles), 1-hydroxybenzotriazole (0.0.277 g, 2.1 mmoles) and 4-methylmorpholine (0.225 mL, 2.1 mmoles) were dissolved in anhydrous DMF (3 mL) and the mixture was stirred under argon at 25° C. for 150 h. The solution was evaporated to dryness and the residue was taken up in dichloromethane and washed with saturated aqueous sodium bicarbonate, water, dried (MgSO$_4$), filtered and evaporated to dryness. The residue was chromatographed on silica gel using 3% (10% conc. NH$_4$OH in methanol)-dichloromethane as the eluant to give the title compound (0.693 g, 87%): CIMS: m/z 506.35 (MH$^+$); $\delta_H$(CDCl$_3$) 1.42 (18H, s, CH$_3$), 3.91 (2H, m, CH$_2$-Im.), 6.88 (1H, s, Im-H$_5$), 7.03 (1H, s, Im-H$_4$) and 7.43 ppm (1H, s, Im-H$_2$); $\delta_C$ (CDCl$_3$) CH$_3$: 28.4, 28.4, 28.4, 28.4, 28.4, 28.4; CH$_2$: 28.4, 31.8, 33.1, 33.1, 41.2/41.6, 43.8, 43.8, 45.6, 47.1, ~51.0; CH: 35.8, 52,9, 118.7, 129.6, 137.1; C: 80.1, 80.4, 168.1, 168.1 168.1.

Step B

2(R)-[[4-[3-(1H-imidazol-1-yl)propyl]-1-piperidinyl] carbonyl]piperazine

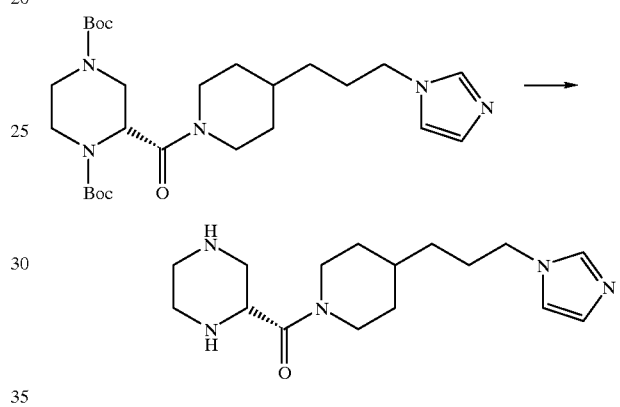

The title compound from Preparative Example 5, Step A above (0.6344 g, 1.26 mmoles) was deprotected as described in Preparative Example 57, Step D, and the product was chromatographed on silica gel using 10% (10% conc. NH$_4$OH in methanol)-dichloromethane as the eluant to give the title compound (0.3076 g, 80%): CIMS: m/z 306.30 (MH$^+$); $\delta_H$ (CDCl$_3$) 3.87 (2H, m, CH$_2$Im), 6.82 (1H, s, Im-H$_5$), 6.99 (1H, s, Im-H$_4$) and 7.38 ppm (1H, s, Im-H$_2$); $\delta_C$(CDCl$_3$) CH$_2$: 28.1, 31.7, 32.6/32.9, 33.0/33.1, 42.0/42.2, 45.2/45.5, 46.9/47.0, 46.9/47.0, 46.9; CH: 35.7/35.8, 55.6, 118.7, 129.4, 137.0; C: 169.7.

EXAMPLE 146

4-(3-bromo-8-chloro-6,11-dihydro-5H-benzo[5,6] cyclohepta[1,2-b]pyridin-11-yl)-2(R)-[[4-[3-(1H-imidazol-1-yl)propyl]-1-piperidinyl]carbonyl]piperazinecarboxylate

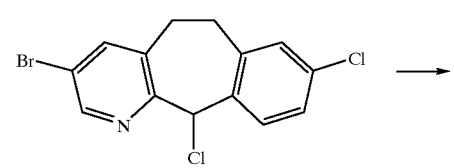

-continued

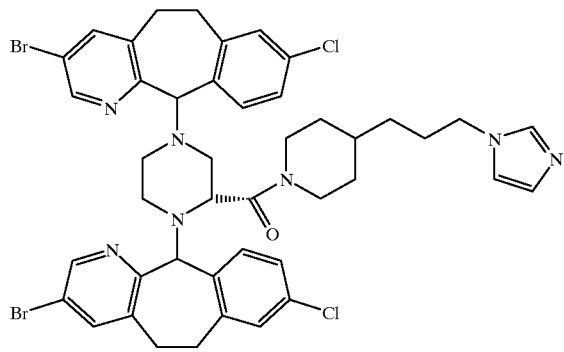

and

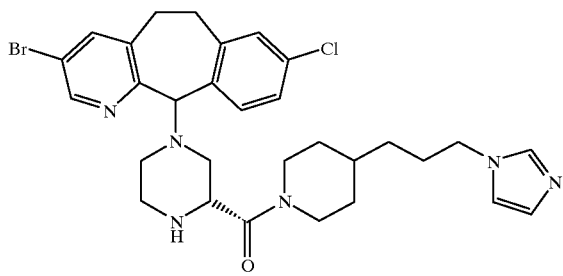

3-Bromo-8,11-dichloro-6.11-dihydro[5,6]cyclohepta[1,2-b]pyridine (0.2043 g, 0.596 mmoles) (prepared as described in Preparative Example 40 (U.S. Pat. No. 5,719,148)), the titled compound from Preparative Example 5, Step B (0.2729 g, 0.894 mmoles) and triethylamine (0.249 mL, 1.79 mmoles) were dissolved in anhydrous THF (8 mL) and anhydrous dichloromethane (20 mL) and the mixture was stirred at 25° C. for 72 h under argon. The solution was evaporated to dryness and the residue was chromatographed on silica gel using 3% then 5% and the 10% (10% conc. $NH_4OH$ in methanol)-dichloromethane as the eluant to give first the dimer (Sch 377314) (0.0681 g, 12%): SIMS: m/z 916.2 ($MH^+$); $\delta_H$ ($CDCl_3$) 3.99 (4H, m, $CH_2$-Im), 6.95, 7.08, 7.10, 7.12, 7.26, 7.54, 7.69, 8.28, 8.31 and 8.34 ppm (13H, s and m, Ar—H and Im-H); $\delta_C$($CDCl_3$) $CH_2$: 28.3/28.5, 30.3/30.4, 30.5, 31.3/31.5, 33.1, 33.1, 41.0/41.1, 41.0/41.1, 45.0, 47.5, 51.2/51.3/52.0, 53.9/54.1/54.2; CH: 35.7, 78.8/79.0, 119.7/119.9, 125.9/126.0/126.2, 128.6/128.7, 130.7, 133.8/134.1, 136.9/137.6, 141.5, 146.7/146.9; C: 119.0, 130.0, 132.5/133.2, 134.6, 141.1/141.3, 156.2, 156.8, 170.0 and the then monomer (Sch 377318) (0.2291 g, 63%): CIMS: m/z 611.20 ($MH^+$); $\Delta_H$ ($CDCl_3$) 3.93 (2H, m, $CH_2$-Im), 6.90, 6.92, 7.07, 7.12, 7.14, 7.47, 7.49, 7.57, 7.59, 8.33, 8.35 and 8.38 ppm (8H, s and m, Ar—H and Im-H); $\delta_C$($CDCl_3$) $CH_2$: 28.3, 30.6, 30.6, 31.6/31.7/31.9, 33.1/33.3, 33.1/33.3, 41.6/42.2, 44.4/44.9, 44.4/44 9, 45.3/45.7, 47.2, 52.2/52.7, 55.0; CH: 35.6, 55.4, 78.8, 118.8, 126.2/126.3, 129.6, 130.3/130.6, 133.0/133.2, 137.1, 141.3,146.9/147.1: C: 120.1, 134.1, 135.0, 137.2, 141.1, 154.4/155.9, 169.0/170.0.

EXAMPLE 147

1,1-dimethylethyl 4-(3-bromo-8-chloro-6,11-dihydro-5H-benzo[5,6]cyclohepta[1,2-b]pyridin-11-yl)-2(R)-[[4-[3-(1H-imidazol-1-yl)propyl]-1-piperidinyl]carbonyl] piperazinecarboxylate

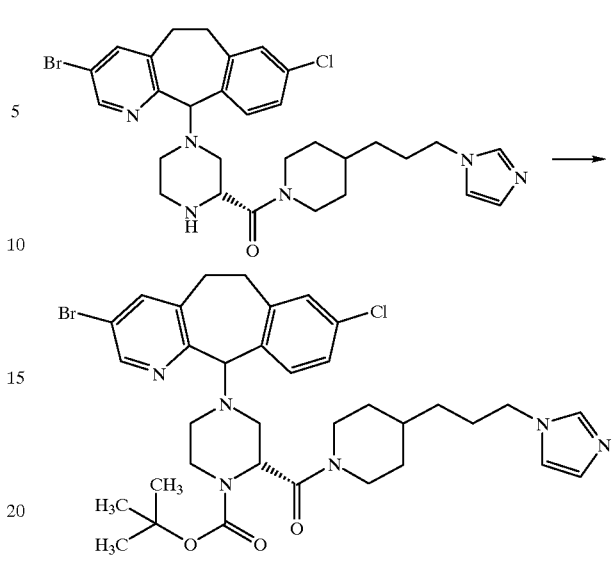

The title compound from Example 9 (0.1768 g, 0.29 mmoles) was reacted with di-tert-butyldicarbonate (0.0694 g, 0.319 mmoles) and sodium hydroxide (0.0116 g, 0.29 mmoles) in THF-water (1:1) (5 mL) and purified as described in Preparative Example 57, to give the title compound (0. 1294 g, 63%): FABMS: m/z 711.1 ($MH^+$); $\delta_H$ ($CDCl_3$) 1.38/1.40 (9H, s, $CH_3$), 3.98 (2H, m, $CH_2$-Im),6.93, 7.03, 7.09, 7.18, 7.54, 7.58, 7.63, 8.32 and 8.38 ppm (8H, s and m, Ar—H and Im-H); $\delta_C$ ($CDCl_3$) $CH_3$: 28.4, 28.4, 28.4; $CH_2$: 28.3, 30.2, 30.7, 31.3/31.8, 33.2, 33.2, 42.2/42.6, 44.4/45.4, 44.6, 44.6, 47.4, ~50.4, ~50.9: CH: 35.8, 78.6/78.8, 118.9, 126.3, 130.2, 130.8, 132.7, 137.0, 140.7/141.5, 147.2; C: 80.0, 119.9, 133.4, 134.0, 137.5, 141.4, 156.2, 156.2, 168.8.

Preparative Example 71A

Step A

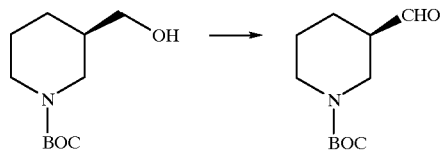

To the title compound from Preparative Example 8, Step B (1.63 g, 7.57 mmol) in DMSO (5.0 mL) was added $iPr_2NEt$ (6.59 mL, 5.0 eq.) followed by $pyr.SO_3$ (7.23 g, 3.0 eq.) in DMSO (10 mL). The resulting solution was stirred 1 hour, diluted with EtOAc and washed with 1N HCl, $H_2O$ and sat. $NaHCO_3$. The organics were dried over $Na_2SO_4$, filtered, and concentrated under reduced pressure. The residue was used without purification (1.26 g, 76% yield): LCMS: $MH^+$=214.

Step B

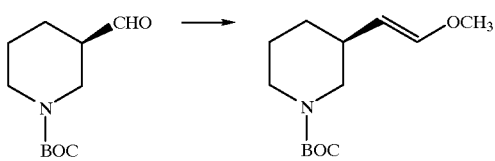

NaHMDS (14.7 mL, 1M in THF, 1.5 eq.) was added to a solution of $CH_3OCH_2P^+Ph_3Cl$ (5.06 g, 1.5 eq.) in THF (25 mL) at 0° C. The resulting solution was stirred 15 minutes before adding via canulae to a solution of the title compound from Preparative Example 71A. Step A (2.1 g, 9.80 mmol) in THF (25 mL) at −78° C. The reaction mixture was stirred 1 hour at −78° C., warmed to 0° C. and stirred 1 hour. The resulting solution was diluted with $Et_2O$, washed with $H_2O$, and dried over $Na_2SO_4$. The organics were dried over $Na_2SO_4$, filtered and concentrated. The crude product was purified by flash chromatography using a 65:35 hexanes EtOAc solution as eluent (1.51 g, 64% yield).

Step C

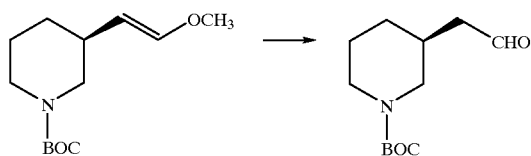

The title compound from Preparative Example 7 1A, Step B (0.70 g, 2.90 mmol) was stirred in 40% HCl (6.6 mL) at room temperature overnight at which time additional 40% HCl (3.0 mL) was added and the reaction mixture stirred an additional 4 hours. The resulting solution was neutralized with $Na_2CO_3$ (aq.) and extracted with $Et_2O$. The combined organics were dried over $Na_2SO_4$, filtered, and concentrated in vacuo. The residue was purified by flash chromatography using a 65:35 hexanes:EtOAc solution as eluent (0.30 g, 46% yield+SM): LCMS: $MH^{30}$ 228.

Step D

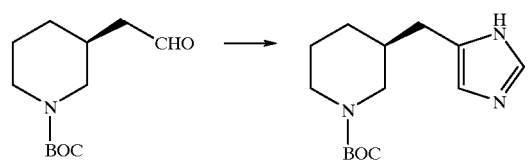

The title compound from Preparative Example 71A, Step C (0.90 g, 1.02 eq.) was stirred with TosMIC (0.77 g, 3.88 mmol) and NaCN (0.0194 g, 0.1 eq.) in EtOH (7.0 mL) for 30 minutes. The reaction mixture was transferred to a sealed tube, diluted with 7M $NH_3$ in MeOH (13.0 mL) and heated to 90° C. for 22 hours. The resulting solution was cooled, concentrated under reduced pressure, diluted with 1N NaOH and extracted with $CH_2Cl_2$. The combined organics were dried over $Na_2SO_4$, filtered, and concentrated. The crude product was purified by flash chromatography using a 5% (10% $NH_4OH$ in MeOH) solution in $CH_2Cl_2$ as eluent (0.53 g, 51% yield): LCMS: $MH^+$=266.

Step E

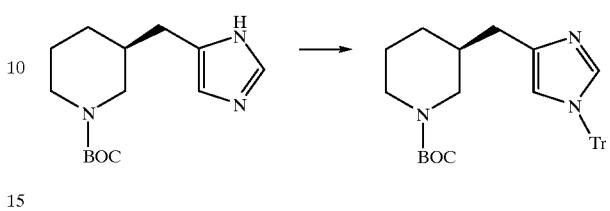

The title compound from Preparative Example 71A, Step D (0.34 g, 1.28 mmol) in $CH_2Cl_2$ was treated with TrCl (0.38 g, 1.05 eq.) and TEA (0.27 mL, 1.5 eq.). The resulting solution was stirred 2 hours at room temperature. diluted with saturated $NaHCO_3$, and extracted with $CH_2Cl_2$. The combined organics were dried over $Na_2SO_4$, filtered, and concentrated in vacuo. The crude product was purified by flash chromatography using a 3% (10% $NH_4OH$ in MeOH) solution in $CH_2Cl_2$ as eluent (0.43 g, 66%): LCMS: $MH^+$= 508.

Step F

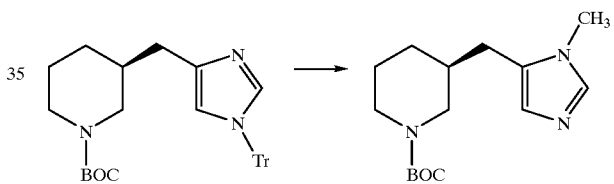

The title compound from Preparative Example 71A, Step E (0.43 g, 0.846 mmol) in $Et_2O$ was treated with MeI (0.79 mL, 15 eq.) and stirred overnight and filtered. The resulting solid washed with $Et_2O$, dissolved in MeOH and heated at reflux overnight. The reaction mixture was concentrated in vacuo and purified by flash chromatography using a 5% (10% $NH_4OH$ in MeOH) solution in $CH_2Cl_2$ as eluent (0. 14 g, 79% yield): LCMS: $MH^+$=280.

Preparative Example 72A

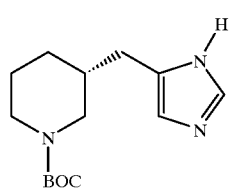

By essentially the same procedure set forth in Preparative Example 71A, the title compound was prepared.

Preparative Example 73A

Step A

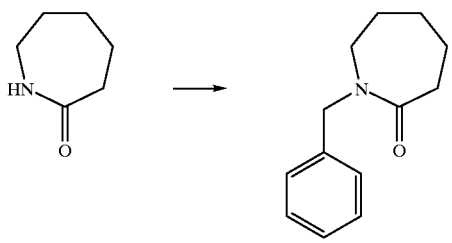

A solution of ε-caprolactam (6.86 g, 60 mmol, 1.0 eq.) in anhydrous THF (50 mL) was added dropwise over a period of 50 minutes to a stirred suspension of sodium hydride (1.59 g, 1.05 eq.) in anhydrous THF (20 mL) at 0° C. under a nitrogen atmosphere. The snow-white mixture was stirred at room temperature for 2 h, whereupon a solution of benzyl bromide (7.65 mL, 1.05 eq.) in anhydrous THF (20 mL) was added dropwise over a period of 30 minutes. The mixture was stirred at room temperature for 2 h and filtered through CELITE 521 to remove sodium bromide. The volatiles were evaporated under house vacuum at 30° C. to give the title compound as a dark-yellow oil which was used without further purification(10.60 g, 87% yield). FABMS: $MH^+$= 204.

Step B

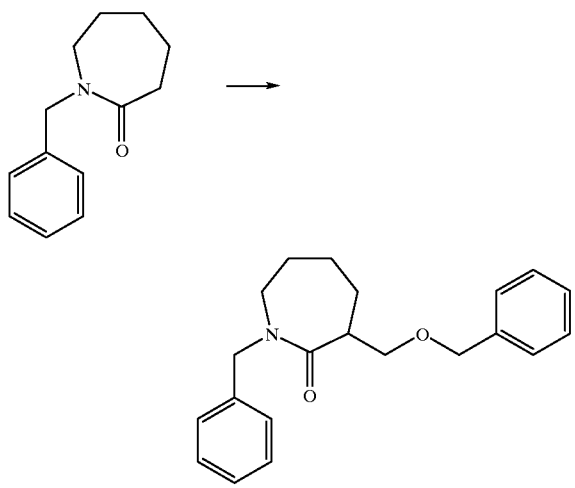

A 2.45 M solution of n-butyllithium in hexanes (18.1 mL, 44.3 mmol, 1.44 eq.) was added dropwise over a period of 30 minutes to a stirred solution of diisopropylamine (5.2 mL, 36.9 mmol, 1.2 eq.) in anhydrous THF (100 mL) at 0° C. under a nitrogen atmosphere. The yellow solution was stirred at 0° C. for another 30 minutes and was then cooled to −78° C. A solution of the title compound from Preparative Example 73A, Step A (6.25 g, 1.0 eq.) in anhydrous THF (50 mL) was subsequently added dropwise over a period of 25 minutes and the solution was stirred at −78° C. for another 3 h. Neat benzyl chloromethyl ether (7.0 mL, 1.3 eq.) was added dropwise over a period of 10 minutes. The dirty-brown solution was slowly (3 h) warmed to room temperature and stirred for another 12 h. The volatiles were removed under house vacuum at 30° C. The residual deep-yellow oil was partitioned between distilled water (100 mL) and diethyl ether (100 mL). The layers were separated and the aqueous phase was extracted with diethyl ether (5×50 mL). The organic layer of earlier and the ethereal extracts were combined and washed with brine (50 mL), dried over $Na_2SO_4$, filtered, and concentrated under house vacuum at 30° C. The oily residue was flash-chromatographed (hexanes:acetone=8:2 v/v) over silica gel to give the title compound as a lime-green oil (6.77 g, 68% yield). [M+H$^+$]: 324; HRMS (FAB+): Calculated for $C_{21}H_{26}NO_2$ ([M+H]$^+$): 324.1961; Observed: 324.1964.

Step C

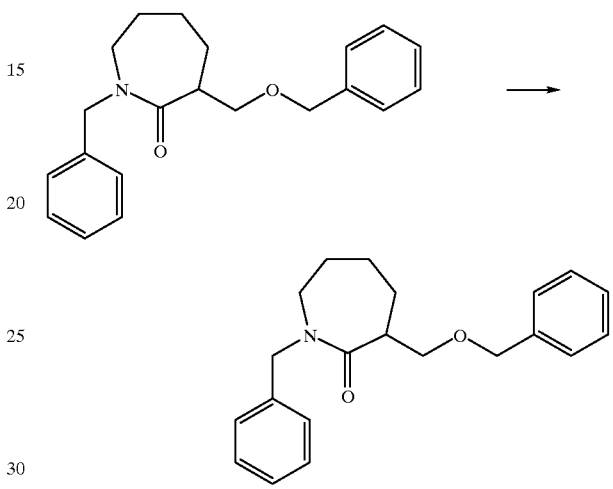

A 1 M solution of lithium aluminum hydride in diethyl ether (23 mL, 1.1 eq.) was added dropwise over a period of 25 minutes to a stirred solution of the title compound from Preparative Example 73A, Step B (6.77 g, 20.9 mmol) in anhydrous THF (100 mL) at −20° C. under a nitrogen atmosphere. The yellow solution was slowly (3 h) warmed to room temperature and stirred for another 12 h. The solution was cooled to 0° C. and carefully treated with a saturated, aqueous, $NA_2SO_4$ solution (10 mL) to give a snow-white slurry. The mixture was filtered and the precipitate was carefully washed with diethyl ether (3×50 mL) and absolute alcohol (3×50 mL). The filtrate was concentrated under house vacuum at 30° C., redissolved in acetone (100 mL) and dried over $Na_2SO_4$, filtered, and again concentrated under house vacuum at 30° C. The oily residue was flash-chromatographed (hexanes:acetone=9:1 v/v) over silica gel to give the title compound as a lime-green oil (5.08 g, 78% yield): [M+H]$^+$: 310; HRMS (FAB+): Calculated for $C_{21}H_{28}NO$ ([M+H]$^+$): 310.2173; Observed: 310.2171.

Step D

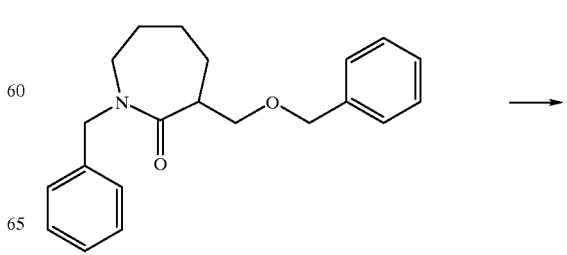

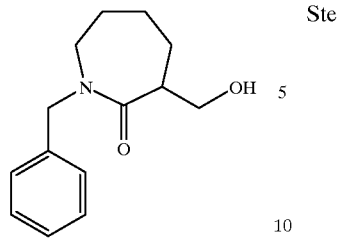

A mixture of the title compound from Preparative Example 73A, Step C (5.08 g, 16.4 mmol) 20 wt. % Pd(OH)$_2$ ("Pearlman's catalyst." 2.54 g, 50 wt. % reagent), and absolute alcohol (100 mL) was hydrogenated at 4.5 atmosphere pressure and room temperature for 8 h. The mixture was filtered through CELITE 521 and the filtrate was concentrated under house vacuum at 30° C. The residual oil was flash-chromatographed (CH$_2$Cl$_2$: 10% NH$_4$OH—MeOH=9:1 v/v) over silica gel to give the title compound as a yellow oil (2.86 g, 79% yield): [M+H]$^+$: 220; HRMS (FAB+): Calculated for C$_{14}$H$_{22}$NO ([M+H]$^+$): 220.1698; Observed: 220.1701.

Step E

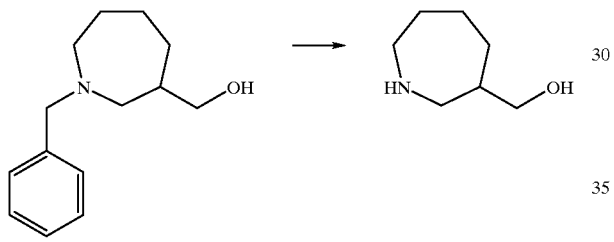

Potassium metal (2.60 g, 5.0 eq.) was added portionwise to a stirred solution of the title compound fro Preparative Example 73A, Step D (2.86 g, 13.0 mmol) and t-butanol (1.5 mL, 1.2 eq.) in a mixture of liquefied ammonia (125 mL) and anhydrous THF (125 mL) at −60° C. under a nitrogen atmosphere. The dark-blue mixture was slowly (12 h) warmed to room temperature and the volatiles were removed under house vacuum at 30° C. The residue was taken up in distilled water (50 mL) and extracted with diethyl ether (5×50 mL). The ethereal extracts were discarded and the aqueous layer was concentrated under house vacuum at 50° C. to give the title compound (1.70 g, 100% crude yield): [M+H]$^+$: 130; HRMS (FAB+): Calculated for C$_7$H$_{16}$NO ([M+H]$^+$): 130.1232; Observed: 130.1231.

Step F

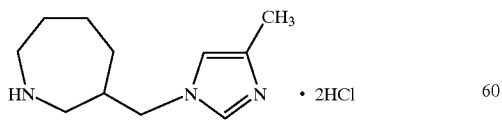

By essentially the same procedure set forth in Preparative Example 7, Step C through Step F only substituting the title compound from Preparative Example 73A, Step F, the title compound was prepared.

Preparative Example 74A

Step A

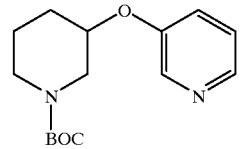

Di-isopropyl azodicarboxylate (0.54 mL, 1.5 eq.) was added to N-t-butoxycarbonylpiperidin-3-ol (0.37, 1.83 mmol), 3-hydroxypyridine (0.26 g, 1.5 eq.), and PPh3 (0.72 g, 1.5 eq.) in THF (5.0 mL). The resulting solution was stirred at room temperature overnight, concentrated in vacuo, and purified by flash chromatography using a 30% hexanes in EtOAc solution as eluent (0. 14 g, 27% yield): LCMS: MH$^+$=279.

Step B

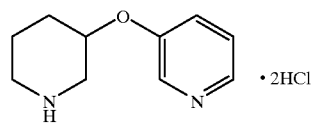

By essentially the same procedure set forth in Preparative Example 8, the title compound was prepared.

Preparative Examples 74B and 74C

The title compound from Preparative Example 74A was separated into individual C-3 isomers by Preparative HPLC using a CHIRALPAK AD column using a 20% iPrOH in hexanes with 0.2% DEA as eluent.

Preparative Example 74A

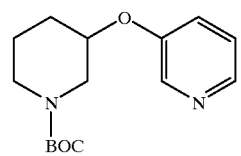

First eluting isomer: LCMS: MH$^+$=279.

Preparative Example 74B

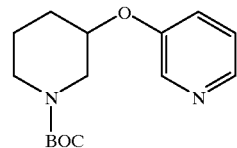

Second eluting isomer: LCMS: MH$^+$=279.

Preparative Example 74C

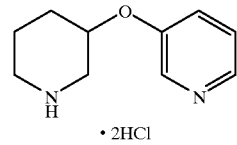

By essentially the same procedure set forth in Preparative Example 8 only substituting the title compound from Preparative Example 74A, the title compound was prepared.

By essentially the same procedure as set forth in Preparative Example 74A, the title compounds in Column 4 of Table 16 were prepared using the 3-hydroxypyridine derivative in Column 2 of Table 16.

hours before adding 3-bromomethylpyridine hydrobromide (1.39 g, 8.09 mmol). The reaction mixture was warmed slowly to room temperature and stirred overnight. The resulting solution was diluted with saturated $NH_4Cl$ (20 mL), extracted with $CH_2Cl_2$ (3×75 mL), dried over $Na_2SO_4$, filtered and concentrated to give a yellow oil (0.63 g, 28% yield): LCMS:$MH^+$=281.

TABLE 16

| Prep. Ex. | Column 2 | Column 3 | Column 4 |
|---|---|---|---|
| 75A | | | |
| 76 | | | |

Preparative Example 77

Step A

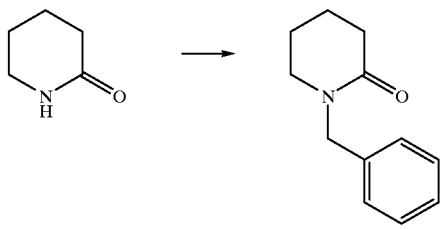

By essentially the same procedure set forth in Preparative Example 73A, Step A, the title compound was prepared: LCMS: $MH^+$=190.

Step B

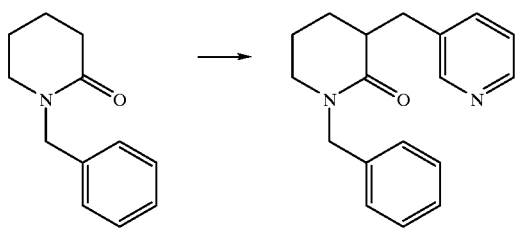

To a solution of the title compound from Preparative Example 77, Step A (3.68 g, 2.4 eq.) in THF (50 mL) was added LiHMDS (19.4 mL, 2.4 eq., 1M solution in THF) at −78° C. The resulting solution was stirred at −78° C, for 2.5

Step C

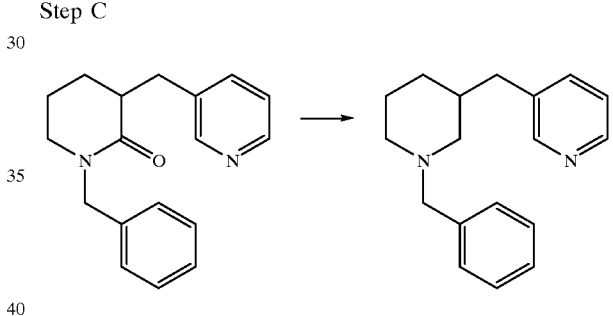

To a solution of the title compound from Preparative Example 77, Step B (0.65 g, 2.31 mmol) in THF (3.0 mL) was added LAH (2.54 mL, 1M in $Et_2O$) and the resulting solution stirred at room temperature overnight. The reaction mixture was quenched by the addition of saturated $Na_2SO_4$, filtered through Celite and concentrated under reduced pressure. The product was purified by flash chromatography using a 20% hexanes in EtOAc solution as eluent a give a yellow oil (0.42 g, 68% yield): LCMS: $MH^+$=267.

Step D

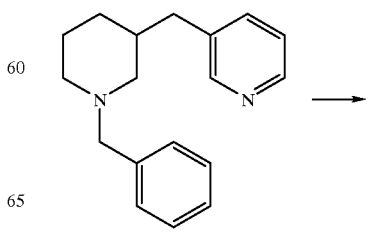

-continued

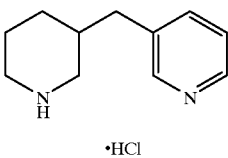
·HCl

The title compound from Preparative Example 77, Step C (0.40 g, 1.50 mmol) in dichloroethane (3 mL) was treated with 1-chloroethylchloroformate (0.37 mL, 2.3 eq.). The resulting solution was stirred 3 hours, concentrated under reduced pressure, diluted with MeOH, and heated at reflux for 3 hours. The reaction mixture was cooled, concentrated under educed pressure, and purified by flash chromatography using a 10% (10%$NH_4OH$ in MeOH) in $CH_2Cl_2$ solution as eluent (0.20 g, 63% yield): LCMS: $MH^+$=177.

Preparative Example 78
Step A

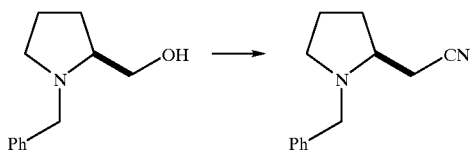

To a solution of (S)-1-benzyl-2-pyrrolidinemethanol (15.5 g, 81.03 mmoles) and TEA (16.38 g, 161.93 mmoles) in $CH_2Cl_2$ (200 mL). MsCl (11.13 g, 97.16 mmoles) was added at 10° C. and stirred at room temperature overnight. Washed with $H_2O$ and evaporated to dryness to give mesylate (15.6 g) which without further purification, was mixed with NaCN (5.64 g, 115 mmoles) and heated at 80° C. in DMF (100 mL) overnight. The reaction mixture was evaporated to dryness and extracted with EtOAc, washed with $H_2O$, and dried ($MgSO_4$). The solvent evaporated to give (S)-1-benzyl-2-cyanomethyl-pyrrolidine (11.5 g): (MS, $MH^+$=201.

Step B

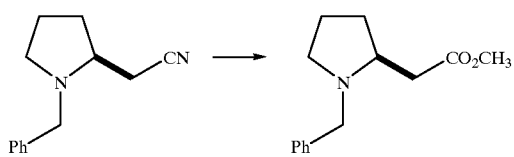

The title compound from Preparative Example 78, Step A (13.0 g) was refluxed in concentrated HCl (100 mL) overnight and evaporated to dryness. The semisolid residue was stirred in MeOH (100 mL), $MgSO_4$ (5 g) and concentrated $H_2SO_4$ (2 mL) at 80° C. overnight. The reaction mixture was evaporated to dryness to give (S)-1-benzyl-methy-2-pyrrolidineacetate (11.5 g): MS, $MH^+$=234.

Step C

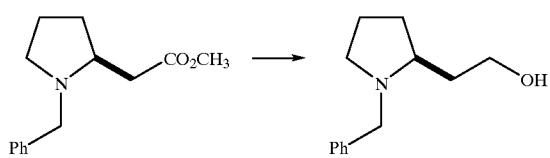

The title compound from Preparative Example 78, Step B (13 g, 55.76 mmoles) was dissolved in THF (100 mL) and cooled to 10° C. (ice water bath). 1M LAH in ether (111.52 mL, 111.46 mmoles) was added slowly and the resulting mixture was refluxed for 2 h. The reaction mixture was cooled to room temperature and decomposed with the addition of ice. The residue was extracted with EtOAc and washed with brine and $H_2O$. The organics were dried and evaporated to a residue which was flash chromatographed on a silica gel column in $CH_2Cl_2$/5% $CH_3OH$ to give (S)-benzyl-hydroxyethyl-pyrrolidine (7.8 g): MS, $MH^+$=206.

Step D

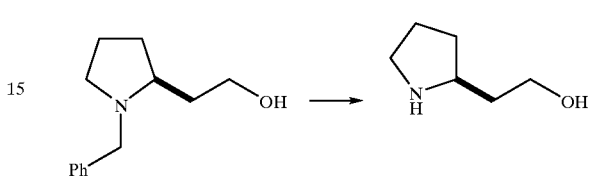

The title compound from Preparative Example 78, Step C (7.7 g) was dissolved in EtOH (80 mL) and hydrogenated over $Pd(OH)_2$ (2.5 g) at room temperature at 50 psi overnight. The catalyst was filtered and solvent was removed to give (S)-2-hydroxyethyl-pyrrolidine (4.4 g): MS, $MH^+$=116.

Step E

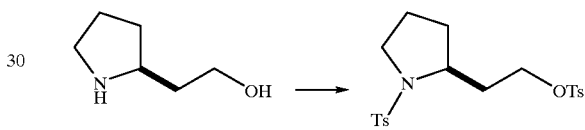

The title compound from Preparative Example 78, Step D (2.4 g, 20.85 mmoles) was dissolved in $CH_2Cl_2$ (250 mL) and cooled to 10° C . TsCl (11.92 g, 62.52 mmloes) followed by TEA (10.54 g, 104.2 mmoles) were added and stirred at room temperature overnight. The reaction mixture was diluted with $CH_2Cl_2$ and washed with brine and $H_2O$. The organics were dried and solvent evaporated to give (S)-tosyl-2-O-tosylethyl-pyrrolidine (3.96 g): MS, $MH^+$=332.

Step F

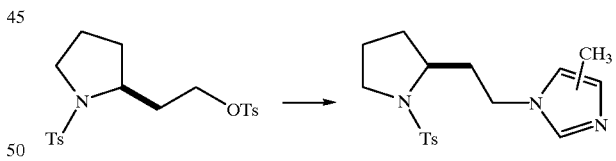

The title compound from Preparative Example 78, Step E (3.96 g, 9.2 mmoles) was dissolved in DMF (15 mL) and cooled to 10° C. NaH (0.74 g, 60%, 18.43 mmoles) was added slowly and stirred at room temperature until a clear solution was obtained. 4-Methyl-imidazole (1.51 g, 18.43 mmoles) was then added and heated at 80° C. overnight. The resulting solution was evaporated to dryness and the residue was extracted with $CH_2Cl_2$ and washed with brine and $H_2O$. The comboned organics were dried and solvent evaporated to give a crude product which was flash chromatographed on a silica get column in $CH_2Cl_2$/5% ($CH_3OH$-10%$NH_4OH$) to give a mixture (S)-tosyl-2-(4-methyl-1H-imidazol)-ethyl-1-pyrrolidine (2.98 g, MS,): $MH^+$=334) and (S)-tosyl-2-(5-methyl-1H-imidazol)-ethyl-1-pyrrolidine (2.98 g): MS, $MH^+$=334.

Step G

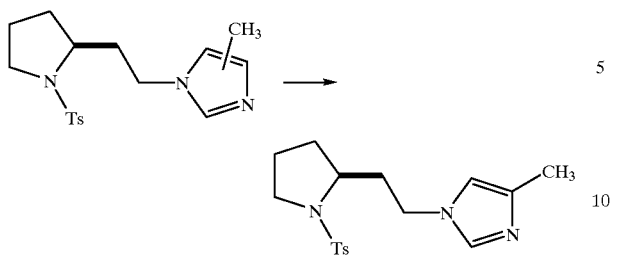

The title compound from 78, Step F (2.9 g) and trityl chloride (1.5 g) were stirred in $CH_2Cl_2$ (35 mL) at 10° C. overnight. The reaction mixture was flash chromatographed on a silica gel column in acetone /ethyl acetate (1:1) to give (S)-tosyl-2-(4-methyl-1H-imidazol)-ethyl-1-pyrrolidine (0.827 g): (MS, $MH^+$=334).

Step H

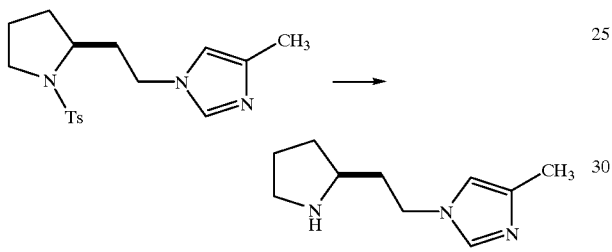

The title compound from Preparative Example 78, Step G (0.82 g) was dissolved in dry THF (2 mL) and liquid ammonia (150 mL). Sodium pieces were added until the blue colour remained and the resulting solution was stirred for ½ hr. EtOH was added dropwise until the blue coloured disappeared. The resulting solution was evaporated to dryness to give sticky white solid which as chromatographed on a flash silica gel column in $CH_2Cl_2$/20% ($CH_3OH$-10% $NH_4OH$) to give the title compound (S)-2-(4-methyl-1H-imidazol)-ethyl-1-pyrrolidine, (0.375 g): MS, $MH^+$=180.

Preparative Example 79

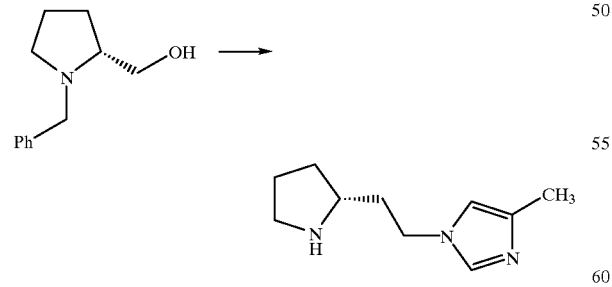

By essentially the same procedure as that set forth in Preparative Example 78, (R)-2-(4-methyl-1H-imidazol)-ethyl-1-pyrrolidine was prepared from (R)-1-benzyl-2-pyrrolidinemethanol.

Preparative Example 80

Step A

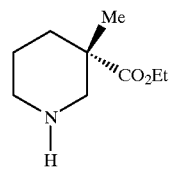

The title compound from Preparative Example 68, Step C was treated with D-(−)-Tartaric acid and recrystallized from acetone-water to afford a piperidine salt enriched in the 3-(S) isomer which was neutralized with hydroxide to afford the title compound (11.1 g, 18%): $MH^+$=172.

Step B

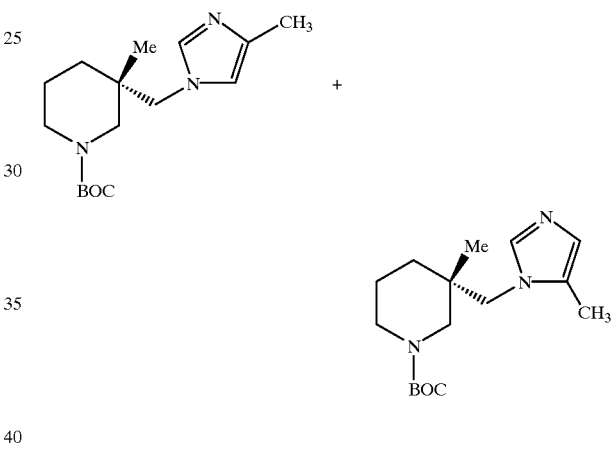

Following the procedures set forth in Preparative Example 7, Steps B–E, except using the title compound from Preparative Example 80, Step A instead of the title compound from Preparative Example 7, Step A in Step B, and using 4-methylimidazole and NaH instead of sodium imidazole in Step E, the regioisomeric imidazole products were obtained (1.1 g, 84%): $MH^+$=294.

Step C

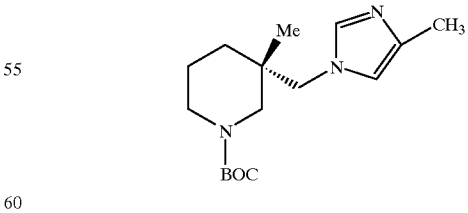

Following the procedure set forth in Preparative Example 17, except using the title compound from Preparative Example 80, Step B instead of the title compound from Preparative Example 13, the 4-methylimidazole product was obtained (0.501 g, 68%): $MH^+$=294.

Step D

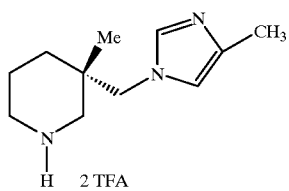

Following the procedure set forth in Preparative Example 68 Step C, except using the title compound from Preparative Example 80 Step C, the amine was obtained as its TFA salt (0.72 g, 100%): MH$^+$=194.

Preparative Example 81

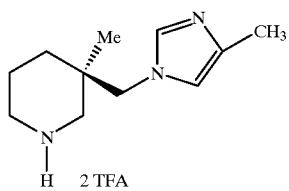

Following essentially the same procedures set forth in Preparative Example 80, Steps A–D, except using L-(+)-Tartaric acid instead of D-(−)-Tartaric acid in Step A, the amine enriched in the 3-(R) isomer was obtained as its TFA salt (0.157 g, 100%): MH$^+$=194.

Preparative Example 82
Step A

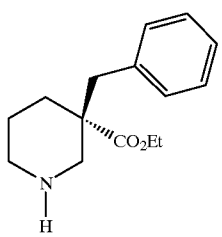

Following essentially the same procedure set forth in Preparative Example 80, Steps A, except using the benzylpiperidine prepared as described in *J. Med. Chem.* 41, 2439 (1998) instead of the title compound from Preparative Example 68, Step C, the amine enriched in the 3-(S) enantiomer was obtained (6.81 g, 25%): MH$^+$=248.

Step B

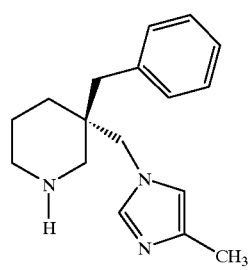

Following the procedures set forth in Preparative Example 80, Steps B–D, except using the title compound from Preparative Example 82, Step A instead of the title compound from Preparative Example 80, Step A in Step B, the 4-methylimidazole product was obtained as its TFA salt which was neutralized with NaOH (aq.) to give the amine product (0.163 g, 86%): MH$^+$=270.

Preparative Example 83

Step A

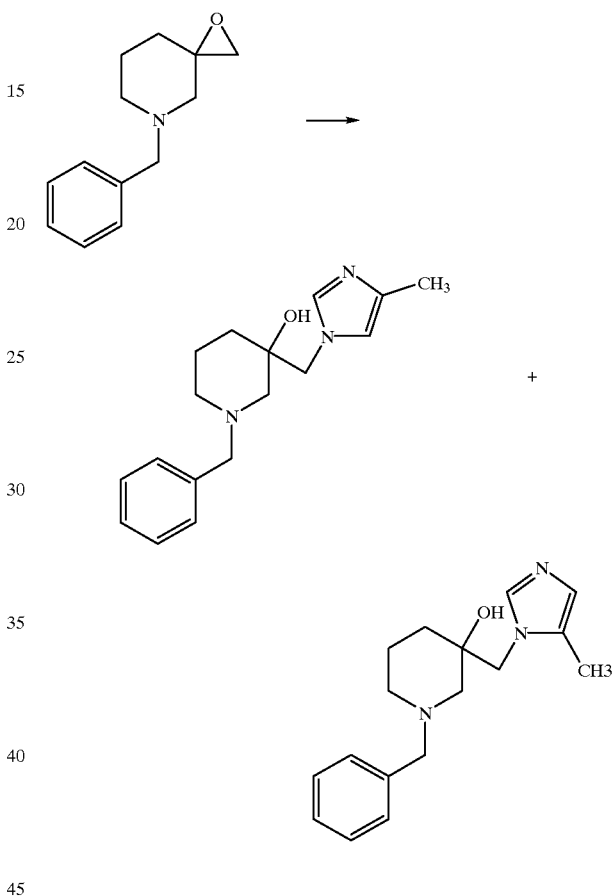

The epoxide (*J. Med. Chem.* 30(1), 1987, pps. 222–225) was treated with 4-methylimidazole and NaH in anhydrous DMF to obtain the resulting mixture of regioisomeric imidazole products (7.77 g, 100%): MH$^+$=302.

Step B

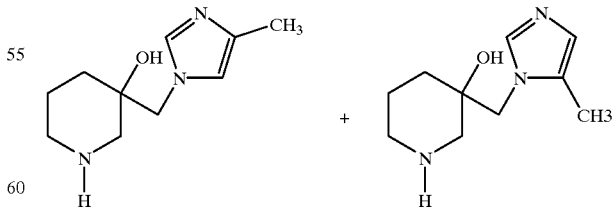

The product from Preparative Example 83, Step A was treated with H$_2$, Pd(OH)$_2$/C and EtOH in a Parr hydrogenator to afford the amine as a mixture of imidazole regioisomers which were used directly in Step C.

Step C

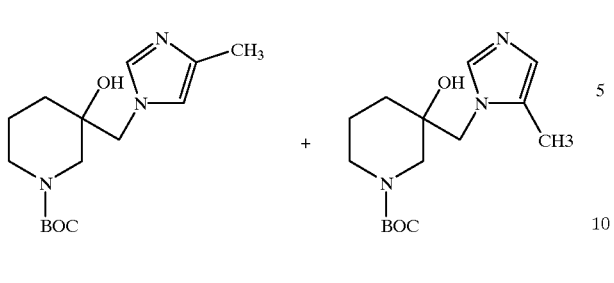

Following the procedure set forth in Preparative Example 7, Step C except using the title compound from Preparative Example 83, Step B instead of the title compound from Preparative Example 7, Step B the BOC derivatives of the regioisomeric methylimidazole products were obtained (5.4 g, 87%): $MH^+ = 296$.

Step D

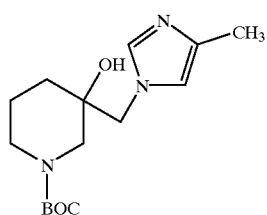

Following the procedure set forth in Preparative Example 17, except using the title compound from Preparative Example 83, Step C instead of the title compound from Preparative Example 13, the 4-methylimidazole products were obtained as an enantiomeric mixture (1.03 g, 43%): $MH^+ = 296$.

Step E

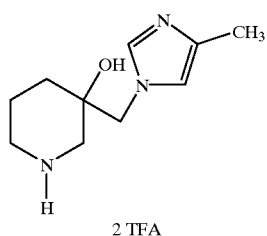

Following the procedure set forth in Preparative Example 68, Step C except using the title compound from Preparative Example 83, Step D the amine was obtained as its TFA salt (6.3 g, 100%): $MH^+ = 197$.

Preparative Example 84

Step A

N-Butoxycarbonyl-[(1triazolyl-imidazol-5-yl) hydroxymethyl]-4-thiomorpholinyl]carbonyl]-1-piperazinecarboxylate s,s-dioxide

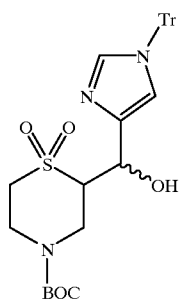

N-Butoxycarbonyl-thiomorpholine (3.19 gm, 13.5 mmol) was dissolved in 70 ml of THF and cooled to =78° C. under a nitrogen atmosphere. 1.2 equivalents of LDA was added to the reaction mixture and stirred for 20 minutes. 1-N-trityl-imidazole-4-carboxaldehyde (4.62 gm, 13.6 mmol) was dissolved in in 70 ml of THF and added to the reaction mixture. After 4 hours the reaction mixture was poured into sat. $NH_4Cl$ solution and extracted with EtOAc three times. The extracts were combined, dried over $MgSO_4$ and the solvent evaporated under reduced pressure. The crude mixture was chromatographed on a silica gel column using 1% $MeOH/CH_2Cl_2$ to obtain 3.21 gm of title product.

Step B
N-Butoxycarbonyl-[(1triazolyl-imidazol-5-yl)methylen]-4-thiomorpholinyl]carbonyl]-1-piperazinecarboxylate s,s-dioxide

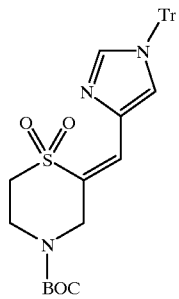

N-Butoxycarbonyl-[(1triazolyl-imidazol-5-yl) hydroxymethyl]-4-thiomorpholinyl]carbonyl]-1-piperazinecarboxylate s,s-dioxide (2.4 gm) was dissolved in $CH_2Cl_2$ (48 mL). TEA (1.32 ml) and MsCl (0.4 ml) was added and the reaction mixture stirred under dry nitrogen. After 24 hours the reaction mixture was added to brine and the product extracted with $CH_2Cl_2$ to obtain 1.56 gm of title product.

Step C
N-Butoxycarbonyl-[(1H-imidazol-5-yl)methyl]-4-thiomorpholinyl]carbonyl]-1-piperazinecarboxylate s,s-dioxide

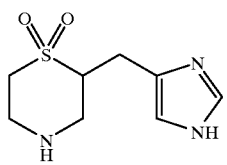

N-Butoxycarbonyl-[(1triazolyl-imidazol-5-yl) methylene]-4-thiomorpholinyl]carbonyl]-1-piperazinecarboxylate s, s-dioxide (0.68 gm) was dissolved in EtOH. 10% Pd/C (0. g) was added and the mixture hydrogenated under balloon $H_2$ conditions for 24 hours. The catalyst was filtered and the filtrate evaporated to obtain 0.3 g of a mixture which was then treated with 1N HCl/$Et_2O$ to obtain the HCl salt.

Preparative Example 85
Step A

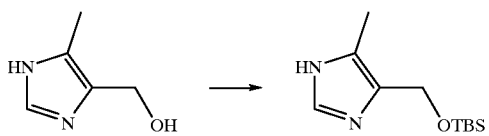

4-Hydroxymethyl-5-methylimidazole hydrochloride (4 g, 30 mmol) was dissolved in DMF. TBDMSCl (6.1 g, 45 mmol) and imidazole (5.1 g, 75 mmol) were added and the reaction mixture stirred at ambient temperature for 24 hours. The reaction mixture was poured into water and extracted with EtOAc to obtain 7 gms of title product.
Step B

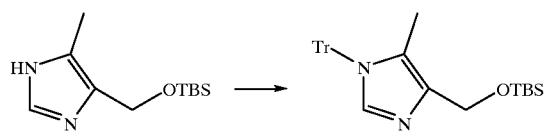

4-tert.butyldimethylsilyloxymethyl-5-methyl-imidazole (9 gm, 40 mmol) was dissolved in 100 ml of $CH_2Cl_2$. TEA (6 ml) and TrCl (11 gm, 40 mmol) were added and the reaction mixture stirred for six hours. The reaction mixture was added to brine, extracted with EtOAc, and purified on a silica gel column to obtain 7.97 gm of title product as a white solid.
Step C

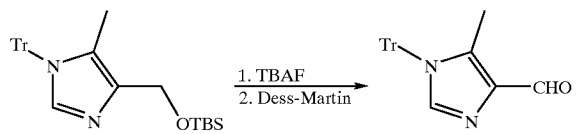

1-trityl-4-tert.butyldimethylsilyloxymethyl-5-methyl-imidazole (7.92 gm, 17 mmol) was dissolved in dry THF and 17 ml of 1M TBAF in THF was added. The reaction mixture was stirred at room temperature before 3 hours. 100 ml of $H_2O$ was added and the precipitate was filtered and dried under vacuum to obtain 5.33 gm of title product.
Step D
N-Butoxycarbonyl-[(1H-4-methyl-imidazol-5-yl) methylene]-4-thiomorpholinyl]carbonyl]-1-piperazinecarboxylate s,s-dioxide

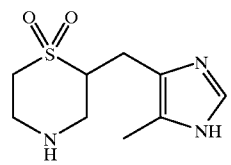

By essentially the same procedure set forth in Preparative Example 84, Step 1 through Step C, the title product was prepared.

Preparative Example 85A

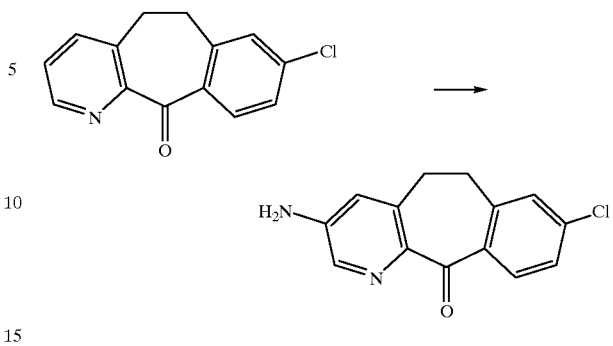

By essentially the same procedure set forth in Njoroge et. al. (J. Med. Chem. (1997),40, 4290) for the preparation of 3-aminoloratadine only substituting the 3-H ketone (J. Het. Chem (1971) 8, 73) for loratadine, the title compound was prepared.

Preparative Example 86

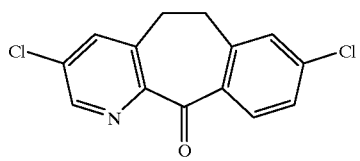

The title compound from Preparative Example 85A(1.0 g, 3.87 mmol) was added portionwise to t-butyl nitrite (0.69 mL, 1.5 eq.) and $CuCl_2$ (0.62 g, 1.2 eq.) in $CH_3CN$ (20 mL) at 0° C. The resulting solution was warmed slowly to room temperature and stirred 72 hours. The reaction mixture was quenched with 1N HCl (10 mL), neutralized with 15% $NH_4OH$ and extracted with EtOAc (3×50 mL). The combined organics were dried over $Na_2SO_4$, filtered, and concentrated under reduced pressure. The crude product was purified by flash chromatography using a 50:50 EtOAc:hexanes mixture as eluent to give a pale yellow solid (0.72 g, 67% yield). FABMS: $MH^+=278$.

Preparative Example 87

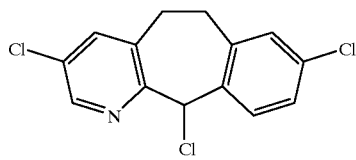

The title compound from Preparative Example 85A (0.72 g. 2.59 mmol) was dissolved in THF (10 mL) and treated with $NaBH_4$ (0. 13 g, 1.3 eq.). The resulting solution was stirred at room temperature 1 hour. The reacton mixture was quenched by the addition of 1N NaOH and the resulting solution extracted with EtOAc (3×50 mL). The combined organics were dried over $Na_2SO_4$, filtered, and concentrated under reduced pressure to give a tan solid which was used without further purification (0.71 g, 97% crude yield). The crude product was dissolved in toluene (15 mL), cooled to 0° C., and treated with $SOCl_2$ (0.32 mL, 1.75 eq.). The resulting solution was stirred at 0° C. for 1 hour and room temperature for 2 additional hours. The reaction mixture was diluted with CH₂Cl₂ (30 mL) and washed with 1N NaOH (20 mL) and the organic layer dried over Na₂SO₄, filtered, concentrated, and used without further purification (0.76 g, 100 crude yield).

Preparative Example 88

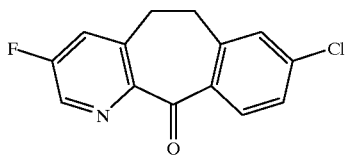

The title compound from Preparative Example 85A (1.62 g, 6.26 mmol) was added portionwise to NO⁺BF4 (0.81 g, 1.1 eq.) in toluene (10 mL) at 0° C. The resulting slurry was stirred at 0° C. for 2.5 hours before warming to room temperature. The reaction mixture was heated at reflux for 2 hours, cooled, neutralized with 1N NaOH and extracted with EtOAc (3×50 mL). The combined organics were washed with 1N HCl (2×25 ml), saturated NaHCO₃ (1×25 mL), and water (1×15 mL), dried over Na₂SO₄, filtered, and concentrated under reduced pressure. The crude product was purified by flash chromatography using a 70:30 hexanes:EtOAc mix as eluent to yield a yellow solid (0.68 g, 42% yield). LCMS: MH⁺=262.

Preparative Example 89

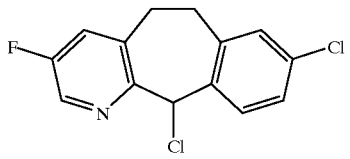

By essentially the same procedure set forth in Preparative Example 87, the title compound was prepared and used without further purification (0.66 g, 100% crude yield).

Preparative Example 90

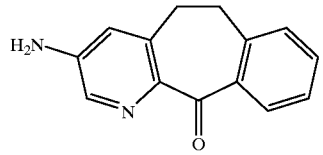

⁺NH₄HCO₂ (2.44 g, 10 eq.) was added to a solution of the title compound from Preparative Example 73A (2.00 g, 7.74 mmol) and 5% Pd/C (0.50 g) in EtOH (100 mL) and the resulting solution was heated to reflux for 2 hours. The reaction mixture was cooled, filtered through a plug of Celite and concentrated under reduced pressure. The residue was diluted with H₂O (100 mL) and extracted with CH₂Cl₂ (3×75 mL). The combined organics were dried over Na₂SO₄, filtered, and concentrated in vacuo to give a yellow solid (1.22 g, 70% yield) which was used without further purification: FABMS: MH⁺=225.

Preparative Example 91

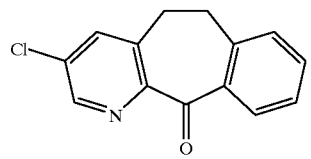

By essentially the same procedure set forth in Preparative Example 86, the title compound was prepared (0.81 g, 61% yield):FABMS: MH⁺=244.

Preparative Example 92

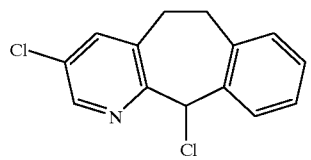

By essentially the same procedure set forth in Preparative Example 87, the title compound was prepared and used without further purification.

Preparative Example 92A

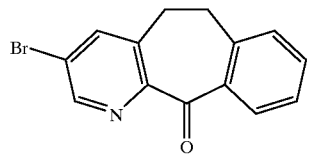

By essentially the same procedure set forth in Preparative Example 86, only substituting CuBr₂ for CuCl₂ the title compound was prepared (1.33 g, 60% yield):FABMS: MH⁺=244.

Preparative Example 93

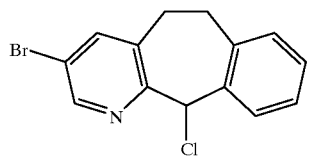

By essentially the same procedure set forth in Preparative Example 87, the title compound was prepared and used without further purification.

Preparative Example 94

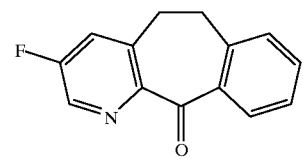

By essentially the same procedure set forth in Preparative Example 88 only substituting the title compound from Preparative Example 90, the title compound was prepared. FABMS: MH⁺=228.

Preparative Example 95

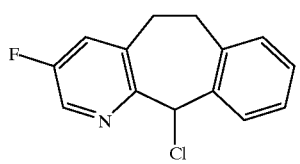

By essentially the same procedure set forth in Preparative Example 87, the title compound was prepared.

Preparative Example 96

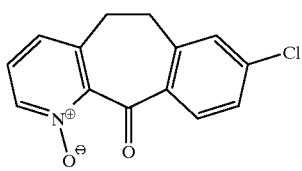

A solution of 3-peroxybenzoic acid (25 g, 2.5 eq.) in anhydrous dichloromethane (250 mL) was added dropwise over a period of one hour to a stirred solution of 8-chloro-4-aza-10,11-dihydro-5H-dibenzo[a,d]cyclohepten-5-one (10 g, 41.04 mmol) in anhydrous $CH_2Cl_2$ (100 mL) at 0° C. under a nitrogen atmosphere. The solution was slowly (3 h) warmed to room temperature and stirred for another 12 h. The solution was extracted with 1 M NaOH (5×100 mL), washed with brine (2×100 mL), dried over $NA_2SO_4$, filtered, and concentrated under house vacuum at 30° C. to give a canary-yellow solid which was used without purification (10 g, 94% yield): [M+H]⁺: 260: HRMS (FAB+): Calculated for $C_{14}H_{11}ClNO_2$ ([M+H]⁺): 260.0475 Observed: 260.0478.

Preparative Example 97

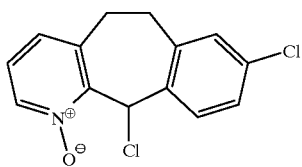

By essentially the same procedure set forth in Preparative Example 87, the title compound was prepared (9.55 g, 99% yield).

Preparative Example 98

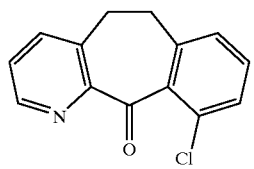

The title compound was prepared according to the methods described in U.S. Pat. No. 3,419,565.

Preparative Example 99

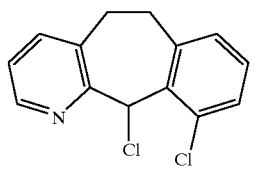

By essentially the same procedure set forth in Preparative Example 87, the title compound was prepared (2.4 g, 87% yield).

Preparative Example 100

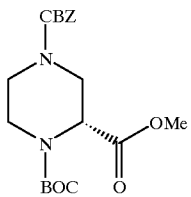

MeI (1.75 mL, 3.0 eq.) added to a solution of $Cs_2CO_3$ (9.12 g, 3.0 eq.) and the title compound from Preparative Example 4 (3.40 g, 9.33 mmol) in DMF (10 mL). The resulting solution was stirred at room temperature 4 hours. The reaction mixture was concentrated under reduced pressure, diluted with $H_2$ (50 mL) and extracted with $CH_2Cl_2$ (3×50 mL). The combined organics were dried over $NA_2SO_4$, filtered, and concentrated in vacuo. The crude product was purified using a 50:50 EtOAc:hexanes mix as eluent (1.4 g, 40% yield). FABMS: MH⁺=379.

Preparative Example 101

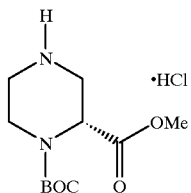

A solution of the title compound from Preparative Example 100 (1.40 g, 3.70 mmol) and 5% Pd/C (0.50 g) in MeOH (20 mL) and 1N HCl (5 mL) was stirred under 1 atm of $H_2$ overnight. The reaction mixture was filtered through a plug of Celite and concentrated in vacuo to give a white solid (1.02 g, 98% yield) which was used without purification. FABMS: MH⁺=245.

Preparative Example 102

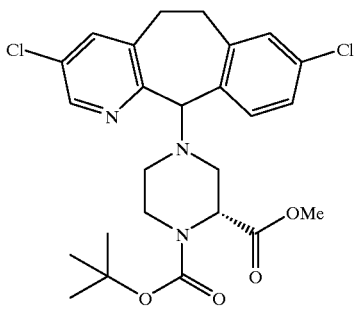

A solution of the title compound from Preparative Example 101 (1.01 g, 3.78 mmol) and TEA (2.63 mL, 5 eq.) in DMF (10 mL) were stirred at room temperature for 30 minutes before adding the title compound from Preparative Example 87 (1.68 g, 1.5 eq.). The resulting solution was stirred at room temperature overnight and concentrated under reduced pressure. The residue wasdiluted with saturated NaHCO$_3$ (25 mL) and extrated with CH$_2$Cl$_2$ (3×50 mL). The combined orgaincs were dried over Na$_2$SO$_4$, filtered, and concentrated and the crude product purified by flash chromatography using a 3% EtOAc in CH$_2$Cl$_2$ solution as eluent to give an off-white solid (1.1 g, 39% yield): LCMS: MH$^+$=506.

The individual C-11 (R)- and (S)-isomers were separated by Preparative HPLC using a CHIRALPAK AD column using a 15% iPrOH in hexanes with 0.2% DEA solution as eluent.

11-(R)-isomer (first eluting isomer): FABMS: MH$^+$=506; [α]$_D$=+70° (5.0 mg in 2.0 mL MeOH).

11-(S)-isomer (second eluting isomer): FABMS: MH$^+$=506; [α]$_D$=° (28 mg in 2.0 mL MeOH).

Preparative Example 103

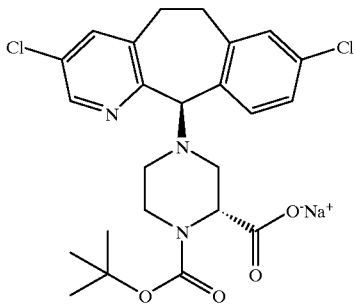

A solution of the title compound (C-11 (R)-isomer) from Preparative Example 102 (0.465 g, 0.918 mmol) and 1N NaOH (2.76 mL, 3.0 eq.) in MeOH (15 mL) was heated at reflux 2 hours. The reaction mixture was cooled, concentrated, diluted with EtOAc (25 mL) and washed with brine (10 mL). The organics were dried over Na$_2$SO$_4$, filtered, and concentrated under reduced pressure to give a white solid (0.45 g, 96% yield): FABMS: MH$^+$=492; [α]$_D$=+57.4° (5.0 mg in 2.0 mL MeOH).

Preparative Example 104

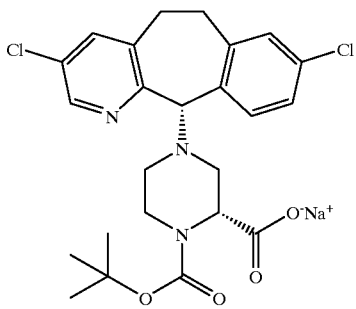

By essentially the same procedure set forth in Preparative Example 103, the title compound (C-11 (S)-isomer) was prepared (0.45 g, 96% yield): FABMS: MH$^+$=492; [α]$_D$=+13.7° (5.0 mg in 2.0 mL MeOH).

Preparative Example 105

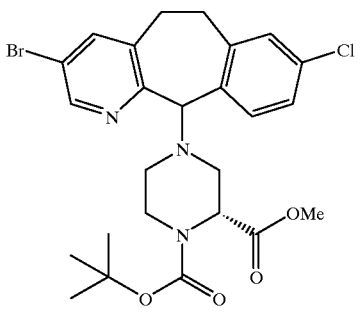

By essentially the same procedure set forth in Prepartive Example 102, the title compound (C-11 (R)- and (S)-isomers) was prepared only the C-11 (R)- and (S)-isomers were separated by flash chromatography using a 3% EtOAc in CH$_2$Cl$_2$ solution as eluent.

Preparative Example 106

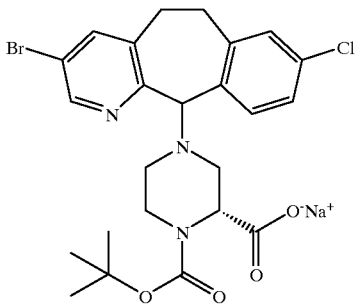

By essentially the same procedure set forth in Preparative Example 103, the title compounds (individual C-11 (R)- and (S)-isomers) were prepared.

Preparative Example 107

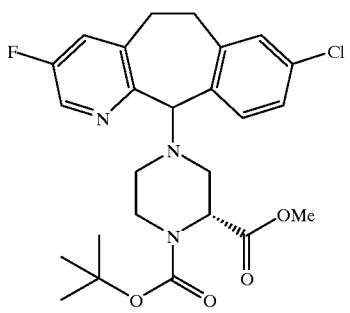

By essentially the same procedure set forth in Preparative Example 102 only substituting the title compound from Preparative Example 89, the title smpound was prepared (C-11 (R)- and (S)-isomers) (0.71 g, 57% yield): FABMS: MH$^+$=490.

Preparative Example 108

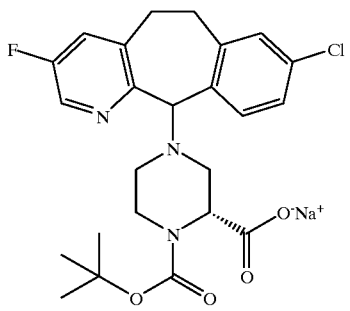

By essentially the same procedure set forth in Preparative Example 103, only using the title compounds (C-11 (R)- and (S)-isomers) from Preparative Example 107, the title compound were prepared. The individual C-11 (R)- and (S)-isomers were separated by flash chromatography using a 12% (10% NH$_4$OH in MeOH) solution in CH$_2$Cl$_2$ as eluent:

C-11 (S)-isomer (first eluting isomer): FABMS: MH$^+$=476.

C-11 (R)-isomer (second eluting isomer): FABMS: MH$^+$=476.

Preparative Example 109

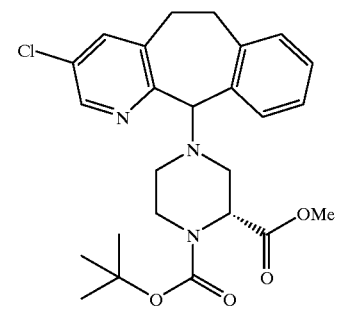

By essentially the same procedure set forth in Preparative Example 102, only substituting the 3-Cl, 8-H title compound from Preparative Example 92 for the 3-Cl, 8-Cl title compound from Preparative Example 101, the title compound (individual C-11 (R)- and C-11 (S)-isomers) was prepared. LCMS: MH$^+$–479.

Preparative Example 110

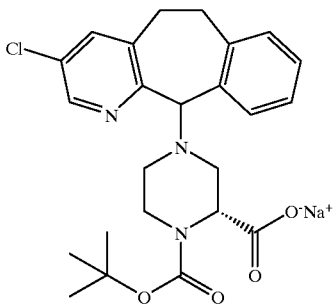

By essentially the same procedure set forth in Preparative Example 103, the title compound (individual C-11 (R)- and C-11 (S)-isomers) was prepared. LCMS MH$^+$=458.

Preparative Example 111

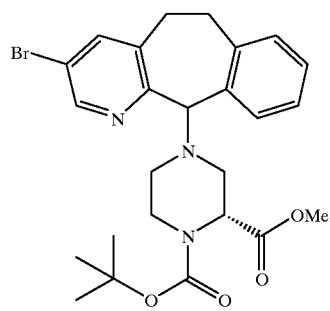

By essentially the same procedure set forth in Preparative Example 102, only substituting the 3-Br, 8-H title compound from Preparative Example 93 for the 3-Cl, 8-Cl title compound from Preparative Example 101, the title compound (individual C-11 (R)- and C-11 (S)-isomers) was prepared.

Preparative Example 112

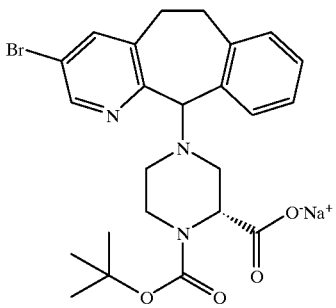

By essentially the same procedure set forth in Preparative Example 103, the title compound (individual C-11 (R)- and C-11 (S)-isomers) was prepared.

Preparative Example 113

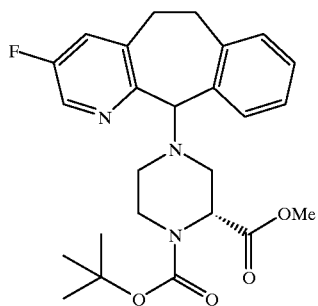

By essentially the same procedure set forth in Preparative Example 102, only substituting the 3-F, 8-H title compound from Preparative Example 95 for the 3-Cl, 8-Cl title compound from Preparative Example 101, the title compound (individual C-11 (R)- and C-11 (S)-isomers) can be prepared.

Preparative Example 114

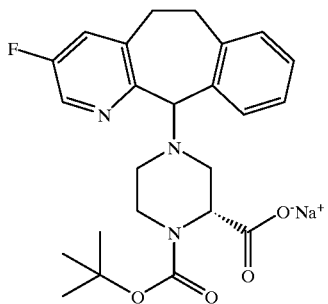

By essentially the same procedure set forth in Preparative Example 103, the title compound (individual C-11 (R)- and C-11 (S)-isomers) can be prepared.

EXAMPLES 138A–168

By essentially the same procedure set forth in Example 1 only substituting the title compounds from Preparative Example 106 (individual (R)- and (S)-isomers) and substituting the appropriate amine, the compunds of the formula shown below with $R^8$ listed in column 3 of Table 17 were obtained.

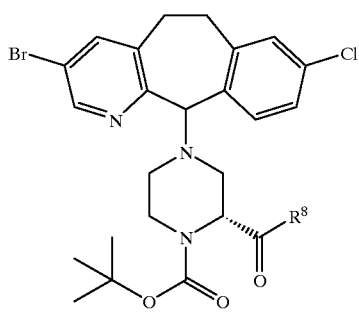

TABLE 17

| Ex. | C-11 isomer | $R^8$ = | MP(° C.) | CMPD |
|---|---|---|---|---|
| 138A | S | (piperidine-CH2-imidazole-CH3) | 131–135 | FABMS: $MH^+$ = 697 |
| 139A | R | (piperidine-CH2-imidazole-CH3) | 120–126 | FABMS: $MH^+$ = 697 |
| 140A | S | (piperidine-CH2-imidazole-CH3) | 114–121 | FABMS: $MH^+$ = 697 |

TABLE 17-continued

| Ex. | C-11 isomer | R⁸ = | MP(° C.) | CMPD |
|---|---|---|---|---|
| 141A | R | (piperidine-CH₂-4-methylimidazole) | 122–126 | FABMS: MH⁺ = 697 |
| 142A | R | (piperidine-CH₂-4-ethylimidazole) | 125–127 | MS: MH⁺ = 712 |
| 143A | S | (piperidine-CH₂-4-ethylimidazole) | 109–112 | MS: MH⁺ = 712 |
| 144A | R | (piperidine-CH₂-4-ethylimidazole) | 68–71 | MS: MH⁺ = 712 |
| 145A | S | (piperidine-CH₂-4-ethylimidazole) | 97–100 | MS: MH⁺ = 712 |
| 146A | S | (thiomorpholine dioxide-CH₂-4-methylimidazole) | — | FABMS: MH⁺ = 749 |

TABLE 17-continued

| Ex. | C-11 isomer | R⁸ = | MP(° C.) | CMPD |
|---|---|---|---|---|
| 147A | R | | — | FABMS: MH⁺ = 749 |
| 148 | S | | — | FABMS: MH⁺ = 749 |
| 149 | R | | — | FABMS: MH⁺ = 749 |
| 150 | R | | — | FABMS: MH⁺ = 749 |
| 151 | S | | — | FABMS: MH⁺ = 749 |
| 152 | S | | — | FABMS: MH⁺ = 749 |

TABLE 17-continued

| Ex. | C-11 isomer | R⁸ = | MP(° C.) | CMPD |
|---|---|---|---|---|
| 153 | S | | — | FABMS: MH⁺ = 749 |
| 154 | S | | — | FABMS: MH⁺ = 749 |
| 155 | S | | — | FABMS: MH⁺ = 735 |
| 156 | S | (Isomer 1) | — | — |
| 157 | S | (Isomer 2) | — | — |
| 158 | R | | — | FABMS: MH⁺ = 727 |

TABLE 17-continued

| Ex. | C-11 isomer | R⁸ = | MP(° C.) | CMPD |
|---|---|---|---|---|
| 159 | S | | — | FABMS: MH⁺ = 727 |
| 160 | R, S | | — | FABMS: MH⁺ = 729 |
| 161 | 1 | | — | FABMS: MH⁺ = 729 |
| 162 | 2 | | — | FABMS: MH⁺ = 729 |
| 163 | S | | — | FABMS: MH⁺ = 699 |
| 164 | S | | — | FABMS: MH⁺ = 699 |
| 165 | S | | — | FABMS: MH⁺ = 685 |

TABLE 17-continued

| Ex. | C-11 isomer | R[8] = | MP(° C.) | CMPD |
|---|---|---|---|---|
| 166 | R | (4-methylimidazolyl-methyl-pyrrolidinyl group) | — | FABMS: MH[+] = 685 |
| 167 | S | (4-methylimidazolyl-methyl-pyrrolidinyl group) | — | FABMS: MH[+] = 685 |
| 168 | R | (4-methylimidazolyl-methyl-pyrrolidinyl group) | — | FABMS: MH[+] = 685 |

Preparative Example 115

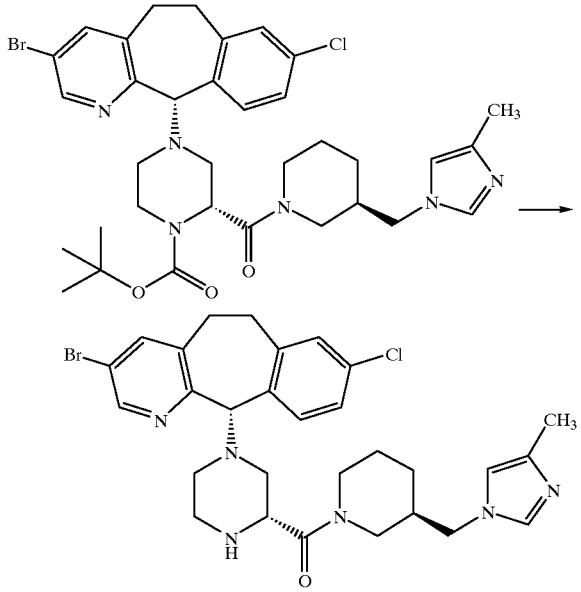

By essentially the same procedure set forth in Preparative Example 24 only using the title compound from Example 73A, the title compound was prepared: FABMS: MH[+]=599.

By essentially the same procedure set forth in Preparative Example 115 only substituting the title compounds from the example listed in column 2, the title compounds of formula shown below with R[8] as listed in column 4 of Table 18 can be obtained.

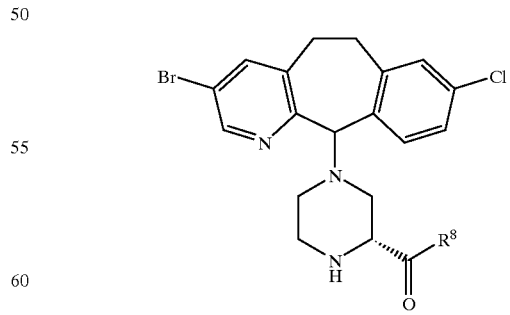

TABLE 18

| Prep Ex. | Ex. | C-11 isomer | R⁸ = |
|---|---|---|---|
| 116 | 139A | R | 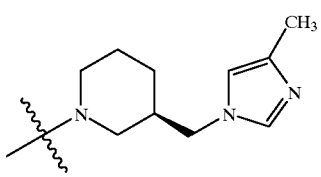 |
| 117 | 140A | S | 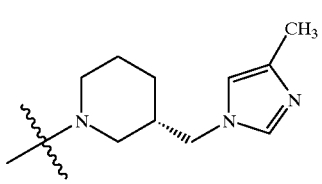 |
| 118 | 141A | R | 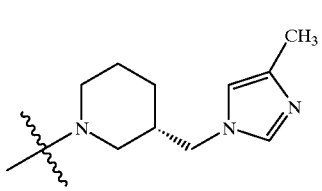 |

EXAMPLES 169–182

By essentially the same procedure set forth in Example 14, only substituting the title compounds from the Preparative Example listed in column 2 of Table 19, the compounds of the formula shown below with $R^9$ as listed in Column 4 of Table 19, were obtained (where data is provided) or can be obtained (where no data is provided) by using the appropriate electrophile.

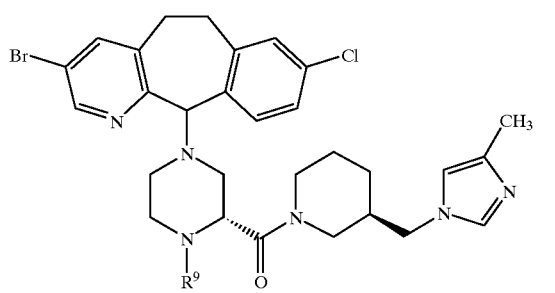

TABLE 19

| Ex. | Prep. Ex. | C-11 isomer | R⁹ = | MP (° C.) | CMPD |
|---|---|---|---|---|---|
| 169 | 116 | R | 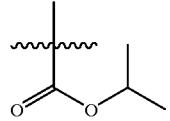 | 123–127 | LCMS: MH⁺ = 683 |
| 170 | 115 | S | 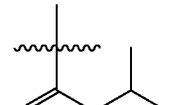 | 117–123 | FABMS: MH⁺ = 683 |
| 171 | 116 | R | 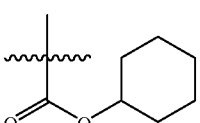 | 78–83 | LCMS: MH⁺ = 723 |
| 172 | 115 | S |  | 129–135 | FABMS: MH⁺ = 723 |
| 173 | 116 | R | 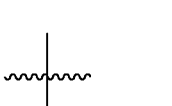 | 129–132 | LCMS: MH⁺ = 711 |
| 174 | 115 | S |  | 121–125 | LCMS: MH⁺ = 711 |
| 175 | 116 | R | 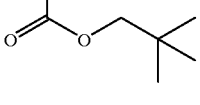 | 108–113 | LCMS: MH⁺ = 694 |
| 176 | 115 | S | 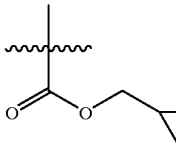 | 101–111 | LCMS: MH⁺ = 694 |
| 177 | 116 | R |  | 148–151 | LCMS: MH⁺ = 696 |
| 178 | 115 | S |  | 149–154 | FABMS: MH⁺ = 696 |

TABLE 19-continued

| Ex. | Prep. Ex. | C-11 isomer | R⁹ = | MP (° C.) | CMPD |
|---|---|---|---|---|---|
| 179 | 116 | R | (pivaloyl: C(=O)C(CH₃)₃) | 129–133 | LCMS: MH⁺ = 681 |
| 180 | 115 | S | (pivaloyl: C(=O)C(CH₃)₃) | 119–123 | FABMS: MH⁺ = 681 |
| 181 | 116 | R | C(=O)NH-cyclohexyl | — | — |
| 182 | 115 | S | C(=O)NH-cyclohexyl | — | — |

EXAMPLES 183–196

By essentially the same procedure set forth in Example 14, only substituting the title compounds from the Preparative Example listed in column 2 of Table 20, the compounds of the formula shown below, with R⁹ as listed in Column 4 of Table 20 were obtained (where data is provided) or can be obtained (where data is not provided) by using the appropriate electrophile.

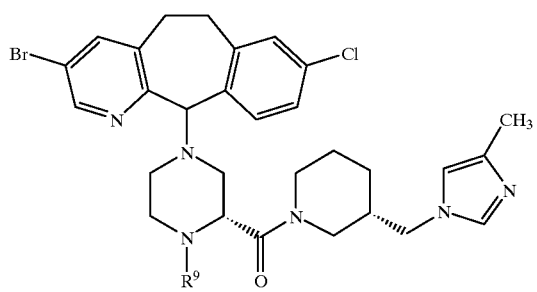

TABLE 20

| Ex. | Prep. Ex. | C-11 isomer | R⁹ = | MP (° C.) | CMPD |
|---|---|---|---|---|---|
| 183 | 118 | R | C(=O)O-isopropyl | 115–118 | FABMS: MH⁺ = 683 |
| 184 | 117 | S | C(=O)O-isopropyl | 109–130 | LCMS: MH⁺ = 683 |
| 185 | 118 | R | C(=O)O-cyclohexyl | 82–85 | FABMS: MH⁺ = 723 |
| 186 | 117 | S | C(=O)O-cyclohexyl | 101–116 | LCMS: MH⁺ = 723 |
| 187 | 118 | R | C(=O)OCH₂C(CH₃)₃ | 122–126 | LCMS: MH⁺ = 711 |
| 188 | 117 | S | C(=O)OCH₂C(CH₃)₃ | 128–131 | FABMS: MH⁺ = 711 |
| 189 | 118 | R | C(=O)OCH₂-cyclopropyl | 111–116 | LCMS: MH⁺ = 695 |
| 190 | 117 | S | C(=O)OCH₂-cyclopropyl | 90–94 | LCMS: MH⁺ = 695 |
| 191 | 118 | R | C(=O)NH-tert-butyl | 149–152 | FABMS: MH⁺ = 696 |

TABLE 20-continued

| Ex. | Prep. Ex. | C-11 isomer | R⁹ = | MP (° C.) | CMPD |
|---|---|---|---|---|---|
| 192 | 117 | S | (structure) | 110–135 | LCMS: MH⁺ = 696 |
| 193 | 118 | R | (structure) | 129–133 | LCMS: MH⁺ = 681 |
| 194 | 117 | S | (structure) | 132–143 | LCMS: MH⁺ = 681 |
| 195 | 118 | R | (structure) | — | — |
| 196 | 117 | S | (structure) | — | — |

EXAMPLE 197

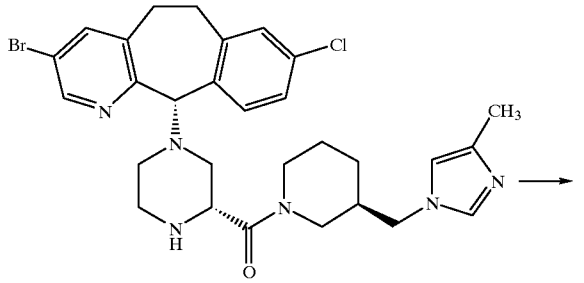

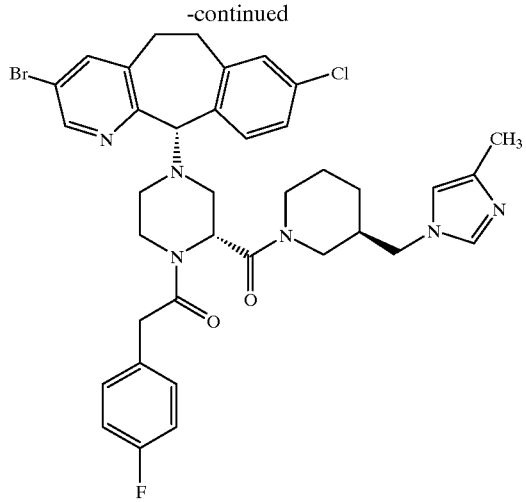

A solution of the title compound from Preparative Example 115 (0.10 g, 0.17 mmol) in $CH_2Cl_2$ (5.0 mL) was treated with p-fluorophenylacetic acid (0.034 g, 1.3 eq.), NMM (0.11 mL, 6.0 eq.), HOBt (0.029 g, 1.3 eq.), and DEC (0.042 g, 1.3 eq.) and the resulting solution was stirred at room temperature overnight. The reaction mixture was concentrated in vacuo and the crude product purified by flash chromatography using a 5% (10%$NH_4OH$ in MeOH) solution in $CH_2Cl_2$ as eluent (0.066 g, 53% yield): mp=105–110° C.; LCMS: MH⁺=733.

EXAMPLES 198–200

By essentially the same procedure set forth in Example 197, only using the title compounds from the Preparative Example listed in column 2 of Table 21, the title compounds of the formula shown below, with R⁸ as listed in column 4 of Table 21, were obtained.

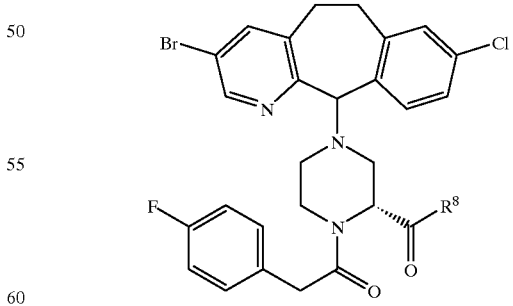

TABLE 21

| Ex. | Prep. Ex. | C-11 isomer | R⁸ = | MP (° C.) | CMPD |
|---|---|---|---|---|---|
| 198 | 116 | R | | 134–136 | LCMS: MH⁺ = 733 |
| 199 | 117 | S | | 88–92 | LCMS: MH⁺ = 733 |
| 200 | 118 | R | | 129–131 | LCMS: MH⁺ = 733 |

EXAMPLES 201–204

By essentially the same procedure set forth in Example 197, only substituting cyclopropylmetllylacetic acid in place of p-fluoro-phenylacetic acid, and using the title compounds from the Preparative Example listed in column 2 of Table 22, the title compounds of the formula shown below, with R⁸ as listed in column 4 of Table 22, were obtained (Examples 201 and 203) or can be obtained (Examples 202 and 204).

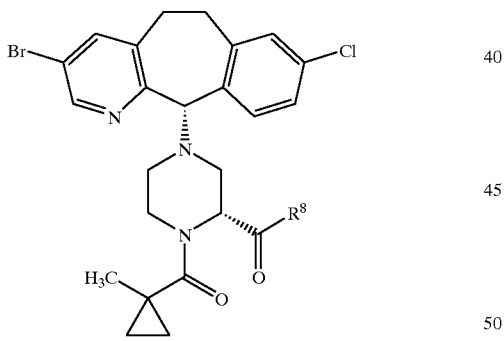

TABLE 22

| Ex. | Prep. Ex. | C-11 isomer | R⁸ = | MP (° C.) | CMPD |
|---|---|---|---|---|---|
| 201 | 115 | S | | 135–137 | LCMS: MH⁺ = 679 |

TABLE 22-continued

| Ex. | Prep. Ex. | C-11 isomer | R⁸ = | MP (° C.) | CMPD |
|---|---|---|---|---|---|
| 202 | 27 | R | 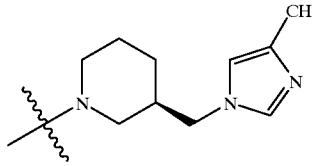 | — | — |
| 203 | 28 | S | 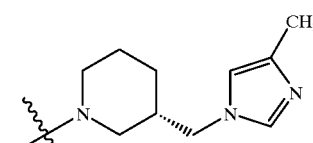 | 135–139 | LCMS: MH⁺ = 679 |
| 204 | 29 | R | 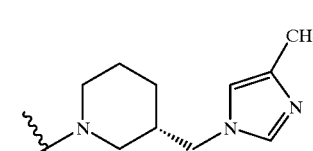 | — | — |

Preparative Examples 119–134

By essentially the same procedure set forth in Preparative Example 115, only substituting the title compounds from the example listed in column 2 of Table 23, the title compounds of the formula shown below, with R⁸ as listed in column 4 of Table 23 were obtained.

TABLE 23

| Prep Ex. | Ex. | C-11 isomer | R⁸ = |
|---|---|---|---|
| 119 | 145A | S | 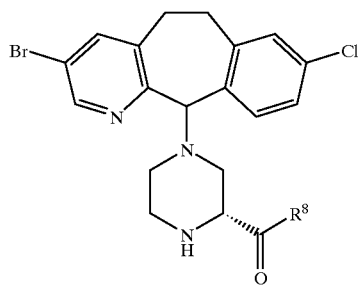 |
| 120 | 144A | R | 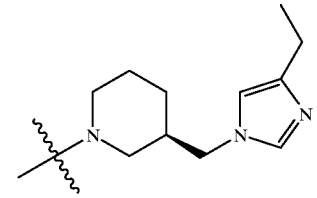 |
| 121 | 143A | S | 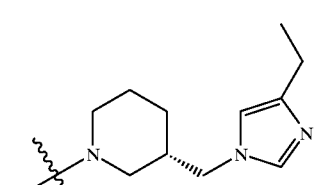 |
| 122 | 142A | R | 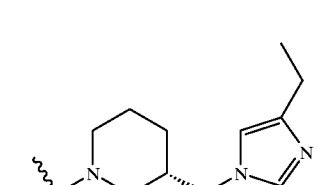 |

TABLE 23-continued

| Prep Ex. | Ex. | C-11 isomer | R⁸ = |
|---|---|---|---|
| 123 | 150 | R | (thiomorpholine-1,1-dioxide-CH₂-4-methylimidazole) |
| 124 | 149 | S | (thiomorpholine-1,1-dioxide-CH₂-4-methylimidazole) |
| 125 | 146A | S | (thiomorpholine-1,1-dioxide-CH₂-4-methylimidazole) |
| 126 | 156 | S | (thiomorpholine-1,1-dioxide-CH₂-4-methylimidazole, Isomer 1) |
| 127 | 157 | S | (thiomorpholine-1,1-dioxide-CH₂-4-methylimidazole, Isomer 2) |
| 128 | 159 | S | (piperidine-CH₂-2,4,5-trimethylimidazole) |
| 129 | 163 | S | (pyrrolidine-CH₂CH₂-4-methylimidazole) |
| 130 | 164 | S | (pyrrolidine-CH₂CH₂-4-methylimidazole) |
| 131 | 165 | S | (pyrrolidine-CH₂-4-methylimidazole) |
| 132 | 166 | R | (pyrrolidine-CH₂-4-methylimidazole) |
| 133 | 167 | S | (pyrrolidine-CH₂-4-methylimidazole) |

TABLE 23-continued
| Prep Ex. | Ex. | C-11 isomer | R⁸ = |
|---|---|---|---|
| 134 | 168 | R | 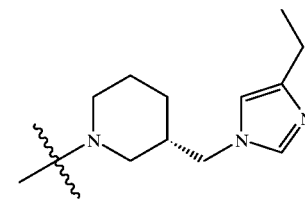 |
EXAMPLES 205–214
By essentially the same procedure set forth in Example 14, only substituting the title compounds from the Preparative Example listed in column 2 of Table 24, the compounds of the formula shown below, with R⁸ as listed in column 4 of Table 24, were obtained.
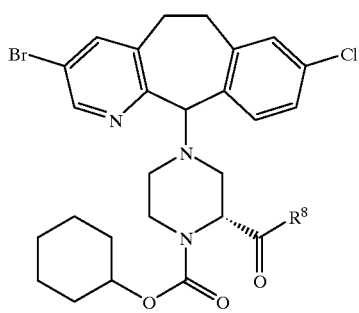
TABLE 24
| Ex. | Prep. Ex. | C-11 isomer | R⁸ = | MP (° C.) | CMPD |
|---|---|---|---|---|---|
| 205 | 122 | R | 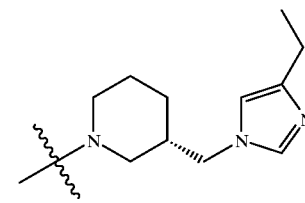 | 68–70 | MS: MH⁺ = 736 |
| 206 | 121 | S | 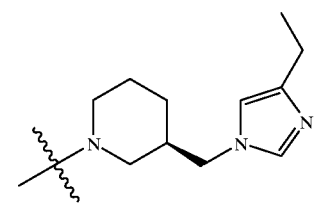 | — | — |
| 207 | 120 | R | 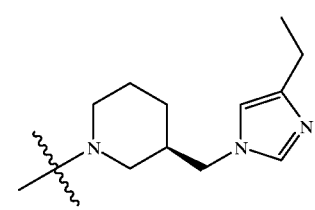 | 80–83 | MS: MH⁺ = 736 |
| 208 | 119 | S |  | 99–101 | MS: MH⁺ = 736 |

TABLE 24-continued
| Ex. | Prep. Ex. | C-11 isomer | R⁸ = | MP (° C.) | CMPD |
|---|---|---|---|---|---|
| 209 | 123 | R | 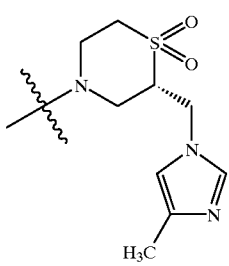 | — | FABMS: MH⁺ = 775 |
| 210 | 124 | S | 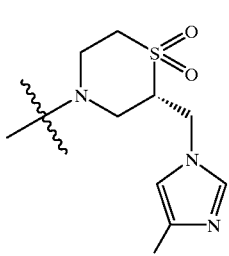 | — | FABMS: MH⁺ = 775 |
| 211 | 126 | S | 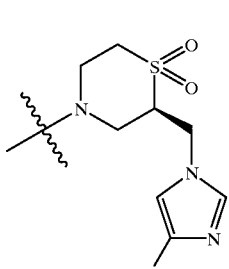 | — | FABMS: MH⁺ = 775 |
| 212 | 126 | S | 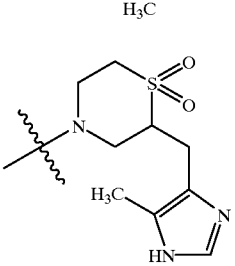(Isomer 1) | — | FABMS: MH⁺ = 775 |
| 213 | 127 | S | 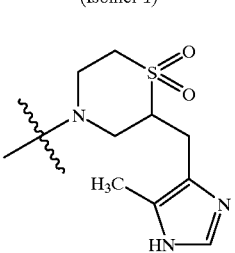(Isomer 2) | — | FABMS: MH⁺ = 775 |
| 214 | 128 | S | 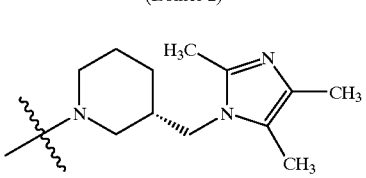 | — | FABMS: MH⁺ = 753 |

EXAMPLE 215

By essentially the same procedure set forth in Example 14, only substituting the title compound from Preparative Example 129, and using the appropriate electrophile, the compound of formula

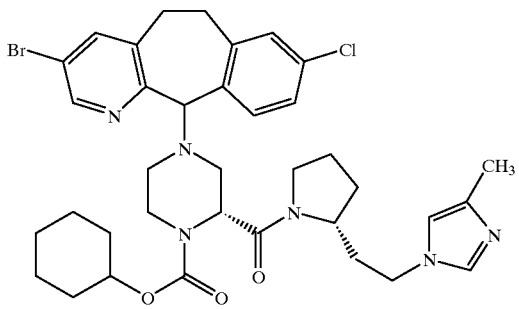

was obtained (C-11 S isomer). FABMS: MH$^+$=725.

EXAMPLE 216

By essentially the same procedure set forth in Example 14, only substituting the title compound from the Preparative Example 130, and using the appropriate electrophile, the compound of formula

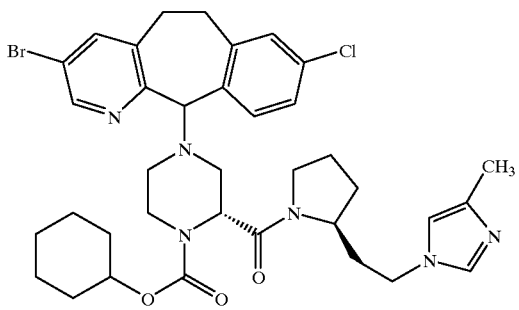

can be obtained (C-11 S isomer). FABMS: MH$^+$=725.

EXAMPLES 217–221

By essentially the same procedure set forth in Example 14, only substituting the title compounds from the Preparative Example listed in column 2 OF Table 25, the compounds of the formula shown below, with R$^9$ as listed in column 4 of Table 25, were obtained by using the appropriate electrophile.

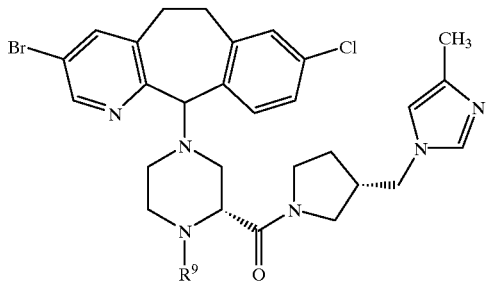

TABLE 25

| Ex. | Prep. Ex. | C-11 isomer | R$^9$ = | MP (° C.) | CMPD |
|---|---|---|---|---|---|
| 217 | 131 | S | cyclohexyl ester | — | FABMS: MH$^+$ = 711 |
| 218 | 132 | R | cyclohexyl ester | — | FABMS: MH$^+$ = 711 |
| 219 | 131 | S | isopropyl ester | — | FABMS: MH$^+$ = 671 |
| 220 | 131 | S | neopentyl ester | — | FABMS: MH$^+$ = 699 |
| 221 | 131 | S | t-butyl amide | — | FABMS: MH$^+$ = 684 |

EXAMPLES 222–226

By essentially the same procedure set forth in Example 14, only substituting the title compounds from the Preparative Example listed in column 2 of Table 26, the compounds of the formula shown below, with R$^9$ as listed in column 4 of Table 26, were obtained by using the appropriate electrophile.

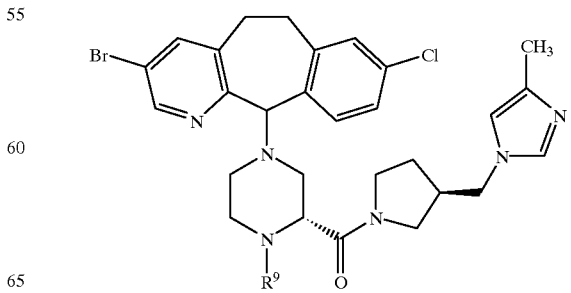

TABLE 26

| Ex. | Prep. Ex. | C-11 isomer | R⁹ = | MP (° C.) | CMPD |
|---|---|---|---|---|---|
| 222 | 133 | S | 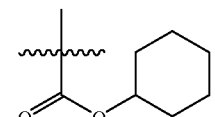 | — | FABMS: MH⁺ = 711 |
| 223 | 134 | R | 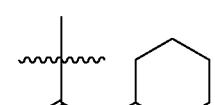 | — | FABMS: MH⁺ = 711 |
| 224 | 133 | S |  | — | FABMS: MH⁺ = 671 |
| 225 | 133 | S |  | — | FABMS: MH⁺ = 699 |

TABLE 26-continued

| Ex. | Prep. Ex. | C-11 isomer | R⁹ = | MP (° C.) | CMPD |
|---|---|---|---|---|---|
| 226 | 133 | S | 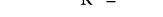 | — | FABMS: MH⁺ = 684 |

EXAMPLES 227–230

By essentially the same procedure set forth in Example 1, only substituting the title compounds from Preparative Example 87 and Preparative Example 101, and substituting the appropriate amine, the compounds of the formula shown below with R⁸ listed in column 3 of Table 27 were obtained.

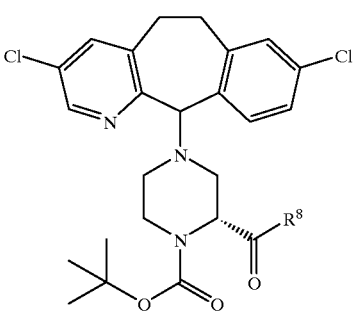

TABLE 27

| Ex. | C-11 isomer | R⁸ = | MP (° C.) | CMPD |
|---|---|---|---|---|
| 227 | S | 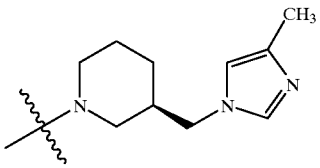 | 100–116 | LCMS: MH⁺ = 653 |
| 228 | R | 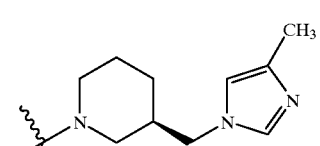 | 115–128 | LCMS: MH⁺ = 653 |
| 229 | S | 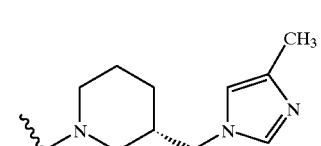 | 102–113 | LCMS: MH⁺ = 653 |

TABLE 27-continued

| Ex. | C-11 isomer | R⁸ = | MP (° C.) | CMPD |
|---|---|---|---|---|
| 230 | R | 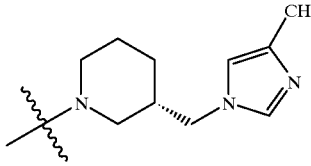 | 121–127 | LCMS: MH⁺ = 653 |

Preparative Examples 135

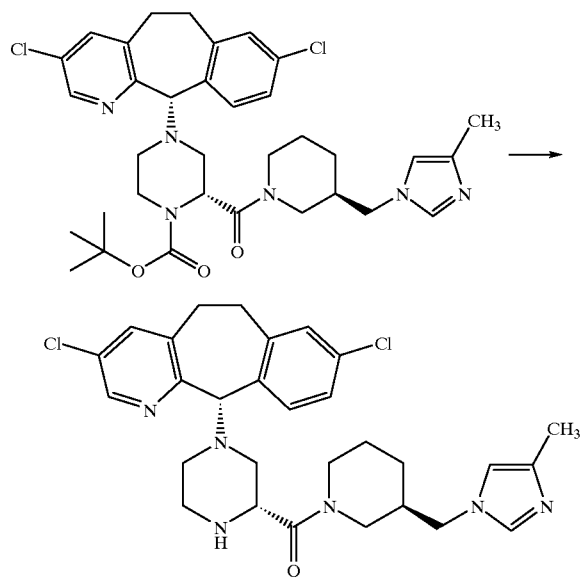

By essentially the same procedure set forth in Preparative Example 24, only using the title compound from Example 227, the title compound was prepared: LCMS: MH⁺=553.

By essentially the same procedure, only substituting the title compounds from the example listed in column 2 of Table 28, the title compounds of the formula shown below, with R⁸ as listed in column 3 of 28, were obtained.

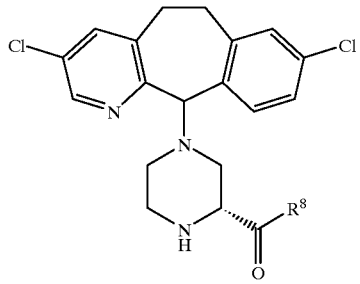

TABLE 28

| Prep Ex. | Ex. | C-11 isomer | R⁸ = |
|---|---|---|---|
| 136 | 228 | R | 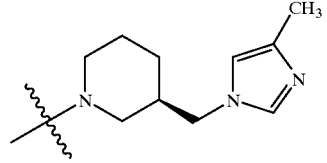 |
| 137 | 229 | S | 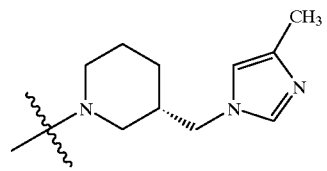 |
| 138 | 230 | R | 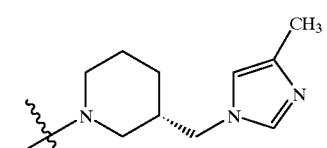 |

EXAMPLES 231–242

By essentially the same procedure set forth in Example 14, only substituting the title compounds from the Preparative Example listed in column 2 of Table 29, the compounds of the formula shown below, with R⁹ as listed in column 4 of Table 29 were obtained (where data is provided) or can be obtained (were no data is provided) by using the appropriate electrophile.

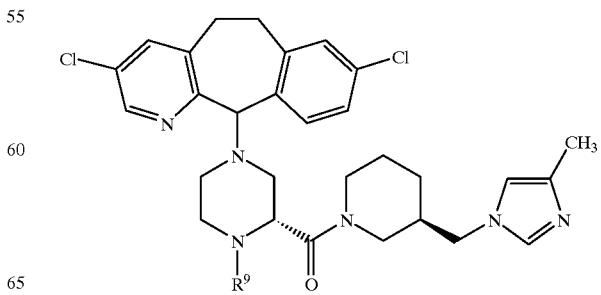

TABLE 29

| Ex. | Prep. Ex. | C-11 isomer | R⁹ = | MP (° C.) | CMPD |
|---|---|---|---|---|---|
| 231 | 136 | R | isopropyl ester | 106–115 | LCMS: MH⁺ = 639 |
| 232 | 135 | S | isopropyl ester | 92–101 | LCMS: MH⁺ = 639 |
| 233 | 136 | R | neopentyl ester | 107–117 | LCMS: MH⁺ = 667 |
| 234 | 135 | S | neopentyl ester | 106–117 | LCMS: MH⁺ = 667 |
| 235 | 136 | R | cyclopropylmethyl ester | — | — |
| 236 | 135 | S | cyclopropylmethyl ester | — | — |
| 237 | 136 | R | t-butyl amide | — | — |
| 238 | 135 | S | t-butyl amide | 107–113 | LCMS: MH⁺ = 652 |
| 239 | 136 | R | t-butyl ketone | 107–114 | LCMS: MH⁺ = 637 |

TABLE 29-continued

| Ex. | Prep. Ex. | C-11 isomer | R⁹ = | MP (° C.) | CMPD |
|---|---|---|---|---|---|
| 240 | 135 | S | t-butyl ketone | 100–112 | LCMS: MH⁺ = 637 |
| 241 | 136 | R | cyclohexyl amide | — | — |
| 242 | 135 | S | cyclohexyl amide | — | — |

EXAMPLES 243–254

By essentially the same procedure set forth in Example 14, only substituting the title compounds from the Preparative Example listed in column 2 of Table 30, the compounds of the formula shown below, with R⁹ as listed in column 4 of Table 30, were obtained (where data is provided) or can be obtained (where no data is provided) by using the appropriate electrophile.

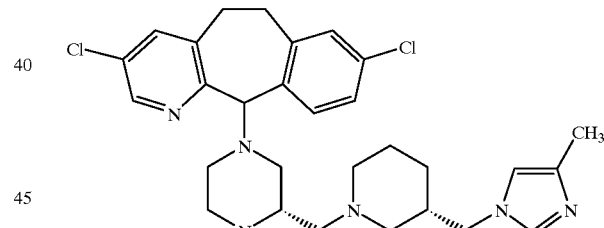

TABLE 30

| Ex. | Prep. Ex. | C-11 isomer | R⁹ = | MP (° C.) | CMPD |
|---|---|---|---|---|---|
| 243 | 138 | R | isopropyl ester | 103–114 | LCMS: MH⁺ = 639 |
| 244 | 137 | S | isopropyl ester | 96–106 | LCMS: MH⁺ = 639 |

TABLE 30-continued

| Ex. | Prep. Ex. | C-11 isomer | R⁹ = | MP (° C.) | CMPD |
|---|---|---|---|---|---|
| 245 | 138 | R | 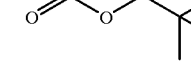 | 104–108 | LCMS: MH⁺ = 667 |
| 246 | 137 | S |  | 100–107 | LCMS: NH⁺ = 667 |
| 247 | 138 | R |  | — | — |
| 248 | 137 | S |  | — | — |
| 249 | 138 | R |  | — | — |
| 250 | 137 | S | 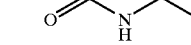 | — | — |
| 251 | 138 | R | 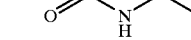 | 104–119 | LCMS: MH⁺ = 637 |
| 252 | 137 | S | 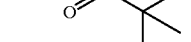 | 100–106 | LCMS: MH⁺ = 637 |
| 253 | 138 | R | 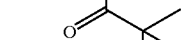 | — | — |
| 254 | 137 | S |  | — | — |

Preparative Example 139

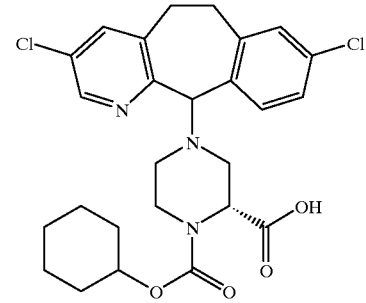

By essentially the same procedure set forth in Preparative Example 32 only substituting the 3-Cl, 8-Cl tricyclic chloride prepared in Preparative Example 87 for the 3-H, 8-Cl tricyclic chloride in Step B, the title compound was prepared. FABMS: MH⁺=518.

Preparative Examples 140 and 141

By essentially the same procedure set forth in Example 1, only substituting the appropriate amine, the compounds of the formula shown below, with R⁸ as listed in column 3 of Table 31, were obtained.

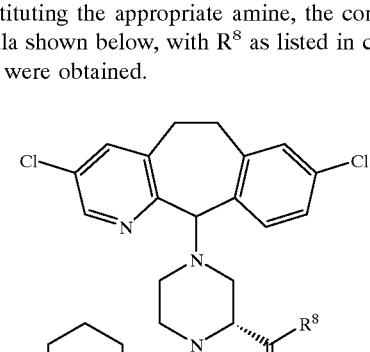

TABLE 31

| Prep. Ex. | C-11 isomer | R⁸ = | MP (° C.) | CMPD |
|---|---|---|---|---|
| 140 | R, S | (structure with piperidine-CH₂-4-methylimidazole) | — | FABMS: MH⁺ = 679 |
| 141 | R, S | (structure with piperidine-CH₂-4-methylimidazole, stereo) | — | LCMS: MH⁺ = 679 |

EXAMPLE 254A

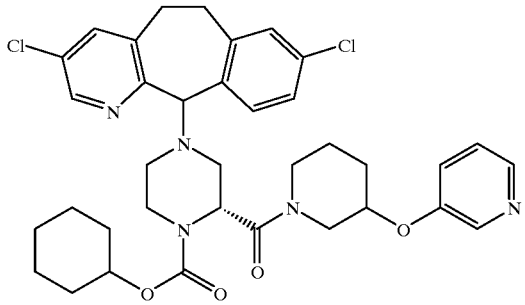

By essentially the same procedure set forth in Example 1 only substituting the title compound from Preparative Example 139 and the amine from Preparative Example 74B, the title compound was prepared. mp=105–113; LCMS: MH⁺=678.

EXAMPLE 255–258

The title compounds from Preparative Examples 140 and 141 were separated into individual C-11 (S)- and (R)-diastereomers by Preparative HPLC with a CHIRALPAK AD column using a 20% iPrOH in hexanes solution with 0.2% DEA as eluent to give the compounds of the formula shown below with R⁸ as listed in Column 3 of Table 32.

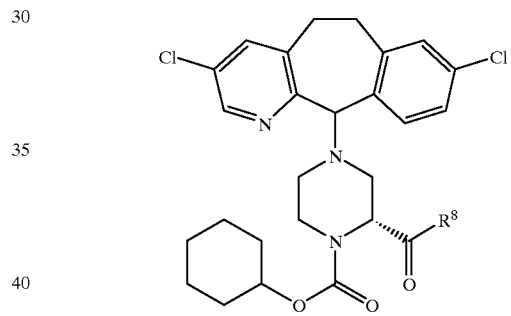

TABLE 32

| Ex. | C-11 isomer | R⁸ = | MP (° C.) | CMPD |
|---|---|---|---|---|
| 255 | S | (piperidine-CH₂-4-methylimidazole) | 116–126 | FABMS: MH⁺ = 679 [α]$_D$ = +21.1 (3.62 mg in 2.0 mL MeOH) |
| 256 | R | (piperidine-CH₂-4-methylimidazole) | 122–128 | FABMS: MH⁺ = 679 [α]$_D$ = −20.7 (5.0 mg in 2.0 mL MeOH) |

TABLE 32-continued

| Ex. | C-11 isomer | R⁸ = | MP (° C.) | CMPD |
|---|---|---|---|---|
| 257 | S | (piperidine-CH₂-4-methylimidazole) | 115–128 | LCMS: MH⁺ = 679<br>$[\alpha]_D = +20.1$<br>(5.0 mg in 2.0 mL MeOH) |
| 258 | R | (piperidine-CH₂-4-methylimidazole) | 115–128 | LCMS: MH⁺ = 679<br>$[\alpha]_D = -13.3$<br>(5.0 mg in 2.0 mL MeOH) |

EXAMPLES 259–262

By essentially the same procedure set forth in Example 1, only substituting the title compounds from Preparative Example 89 and Preparative Example 101 and substituting the appropriate amine, the compounds of the formula shown below, with R⁸ listed in column 3 of Table 33 were obtained.

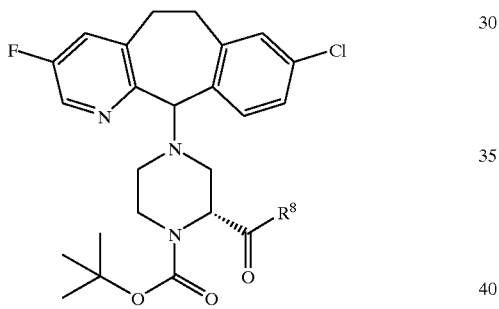

TABLE 33

| Ex. | C-11 isomer | R⁸ = | MP (° C.) | CMPD |
|---|---|---|---|---|
| 259 | S | (piperidine-CH₂-4-methylimidazole) | 126–135 | LCMS: MH⁺ = 637 |
| 260 | R | (piperidine-CH₂-4-methylimidazole) | 110–116 | FABMS: MH⁺ = 637 |

TABLE 33-continued

| Ex. | C-11 isomer | R⁸ = | MP (° C.) | CMPD |
|---|---|---|---|---|
| 261 | S | ![structure] | 115–118 | LCMS: MH⁺ = 637 |
| 262 | R | ![structure] | 122–126 | FABMS: MH⁺ = 637 |

Preparative Example 142

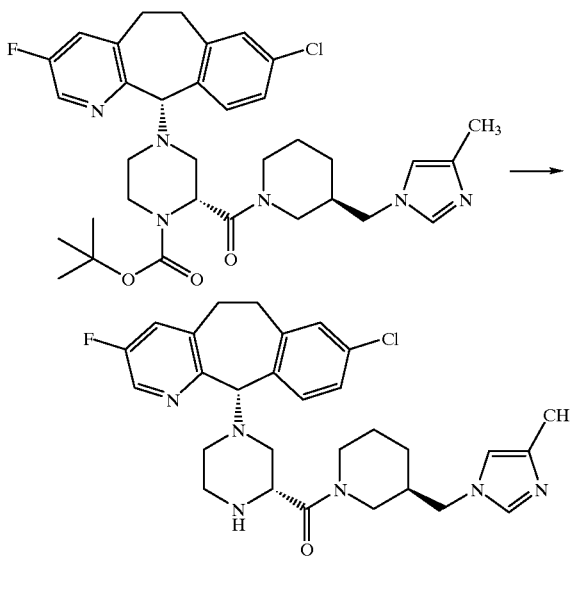

By essentially the same procedure set forth in Preparative Example 24, only using the title compound from Example 259, the title compound can be prepared.

By essentially the same procedure, only substituting the title compounds from the example listed in column 2 of Table 34, the title compounds of the formula shown below, with R⁸ as listed in column 3 of Table 34, can be prepared.

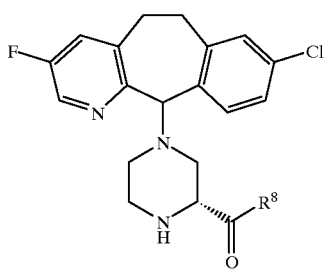

TABLE 34

| Prep Ex. | Ex. | C-11 isomer | R⁸ = |
|---|---|---|---|
| 143 | 260 | R | ![structure with CH₃] |
| 144 | 261 | S | ![structure with CH₃] |
| 145 | 262 | R | ![structure with CH₃] |

EXAMPLES 263–274

By essentially the same procedure set forth in Example 14, only substituting the title compounds from the Preparative Example listed in column 2 of Table 35, the compounds of the formula shown below, with R⁹ as listed in column 4 of Table 35, were obtained (where data is provided) or can be obtained (where no data is provided) by using the appropriate electrophile.

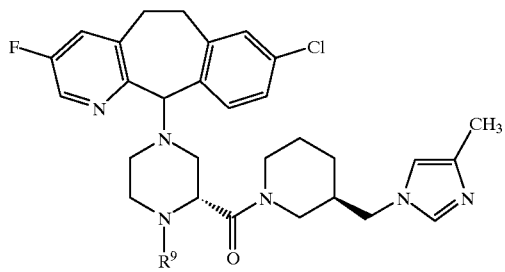

TABLE 35

| Ex. | Prep. Ex. | C-11 iso-mer | R⁹ = | MP (° C.) | CMPD |
|---|---|---|---|---|---|
| 263 | 143 | R | (isopropyl ester) | 92–95 | LCMS: MH⁺ = 623 |
| 264 | 142 | S | (isopropyl ester) | 103–106 | LCMS: MH⁺ = 623 |
| 265 | 143 | R | (neopentyl ester) | 74–81 | LCMS: MH⁺ = 651 |
| 266 | 142 | S | (neopentyl ester) | 90–95 | LCMS: MH⁺ = 651 |
| 267 | 143 | R | (cyclopropylmethyl ester) | 100–104 | LCMS: MH⁺ = 635 |
| 268 | 142 | S | (cyclopropylmethyl ester) | 83–87 | LCMS: MH⁺ = 635 |
| 269 | 143 | R | (t-butyl amide) | — | — |

TABLE 35-continued

| Ex. | Prep. Ex. | C-11 iso-mer | R⁹ = | MP (° C.) | CMPD |
|---|---|---|---|---|---|
| 270 | 142 | S | (t-butyl amide) | — | — |
| 271 | 143 | R | (t-butyl ketone) | 105–107 | LCMS: MH⁺ = 621 |
| 272 | 142 | S | (t-butyl ketone) | 75–77 | LCMS: MH⁺ = 621 |
| 273 | 143 | R | (cyclohexyl amide) | — | — |
| 274 | 142 | S | (cyclohexyl amide) | — | — |

EXAMPLES 275–286

By essentially the same procedure set forth in Example 14, only substituting the title compounds from the Preparative Example listed in column 2 of Table 36, the compounds of the formula shown below, with R⁹ as listed in column 4 of Table 36, can be obtained by using the appropriate electrophile.

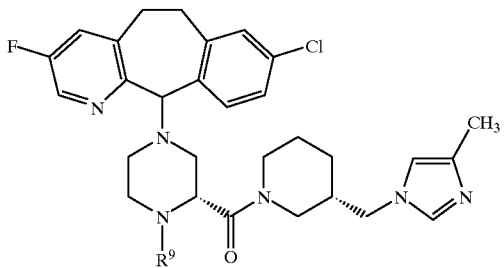

TABLE 36

| Ex. | Prep. Ex. | C-11 isomer | R⁹ = |
|---|---|---|---|
| 275 | 145 | R | 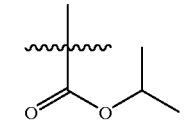 |
| 276 | 144 | S | 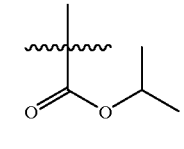 |
| 277 | 145 | R | 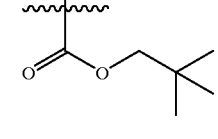 |
| 278 | 144 | S | 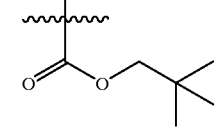 |
| 279 | 145 | R | 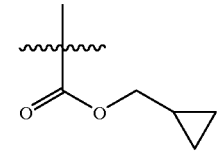 |
| 280 | 144 | S | 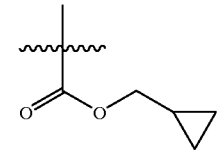 |
| 281 | 145 | R | 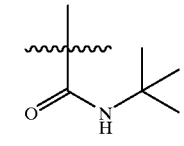 |
| 282 | 144 | S | 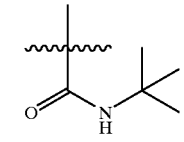 |
| 283 | 145 | R | 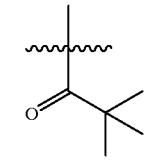 |

TABLE 36-continued

| Ex. | Prep. Ex. | C-11 isomer | R⁹ = |
|---|---|---|---|
| 284 | 144 | S | 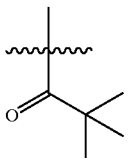 |
| 285 | 145 | R | 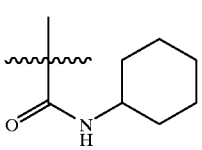 |
| 286 | 144 | R | 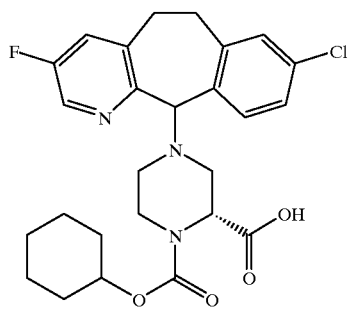 |

Preparative Example 146 and 147

By essentially the same procedure set forth in Preparative Example 36, only substituting the 3-F, 8-Cl tricyclic chloride prepared in Preparative Example 89 for the 3-H, 8-Cl tricyclic chloride in Step B, the title compounds (C-11(S)- and (R)-isomers) were prepared and separated into individual diasteromers by flash chromatography using a 12% (10% NH₄OH in MeOH) solution in CH₂Cl₂:

Preparative Example 146

11-(S)-isomer (first eluting isomer): FABMS: MH⁺=502; $[\alpha]_D$=+7.7° (5.0 mg in 2 mL MeOH).

Preparative Example 147

11-(R)-isomer (second eluting isomer): FABMS: MH⁺= 502; $[\alpha]_D$=+74.6° (5.0 mg in 2 mL MeOH.

EXAMPLES 287–290

By essentially the same procedure set forth in Example 1, only substituting the title compounds from Preparative Example 132 (individual (S)- and (R)-isomers) and substituting the appropriate amine, the compunds of the formula shown below, with R⁸ as listed in Column 3 of Table 37 were obtained.

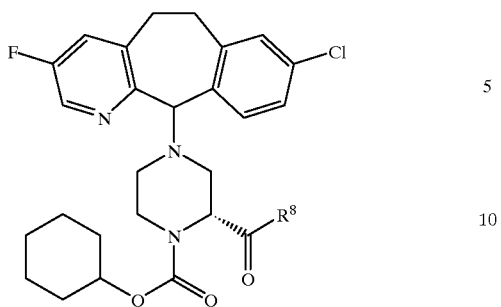

TABLE 37

| Ex. | C-11 isomer | R⁸ = | MP (° C.) | CMPD |
|---|---|---|---|---|
| 287 | S | (N-piperidinyl-CH₂-(4-methylimidazol-1-yl)) | 116–123 | FABMS: MH⁺ = 663 [α]$_D$ = 34.4 (5.0 mg in 2.0 mL MeOH) |
| 288 | R | (N-piperidinyl-CH₂-(4-methylimidazol-1-yl)) | 128–134 | FABMS: MH⁺ = 663 [α]$_D$ = +38.6 (5.0 mg in 2.0 mL MeOH) |
| 289 | S | (N-piperidinyl-CH₂-(4-methylimidazol-1-yl)) | 120–126 | FABMS: MH⁺ = 663 [α]$_D$ = −29.4 (5.0 mg in 2.0 mL MeOH) |
| 290 | R | (N-piperidinyl-CH₂-(4-methylimidazol-1-yl)) | 121–125 | FABMS: MH⁺ = 663 [α]$_D$ = +34.2 (5.0 mg in 2.0 mL MeOH) |

EXAMPLES 291–294

By essentially the same procedure set forth in Example 1, only substituting the title compounds from Preparative Example 110 and substituting the appropriate amine, the compounds of the formula shown below with R⁸ listed in column 3 of Table 38 were prepared.

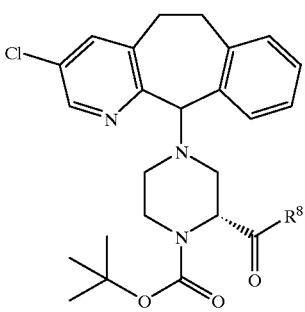

TABLE 38

| Ex. | C-11 isomer | R⁸ = | MP (°C.) | CMPD |
|---|---|---|---|---|
| 291 | S | [piperidine-CH₂-4-methylimidazole] | 99–107 | LCMS: MH⁺ = 619 |
| 292 | R | [piperidine-CH₂-4-methylimidazole] | 95–105 | LCMS: MH⁺ = 619 |
| 293 | S | [piperidine-CH₂-4-methylimidazole, stereo] | 110–123 | LCMS: MH⁺ = 619 |
| 294 | R | [piperidine-CH₂-4-methylimidazole, stereo] | 102–118 | LCMS: MH⁺ = 619 |
| 294 A | S | [piperidine-O-pyridyl] | 93–107 | LCMS: MH⁺ = 618 |
| 294 B | R | [piperidine-O-pyridyl] | 102–113 | LCMS: MH⁺ = 618 |

Preparative Example 148–151

By essentially the same procedure set forth in Preparative Example 107, only substituting the title compounds from the example listed in column 2 of Table 39, the title compounds of formula shown below, with R⁸ as listed in column 4 of Table 39, were prepared.

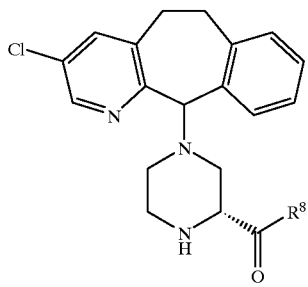

TABLE 39

| Prep Ex. | Ex. | C-11 isomer | R⁸ = | CMPD |
|---|---|---|---|---|
| 148 | 291 | S | 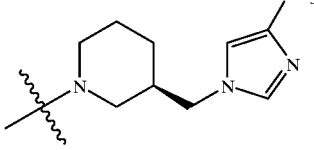 | LCMS: MH⁺ = 519 |
| 149 | 292 | R | 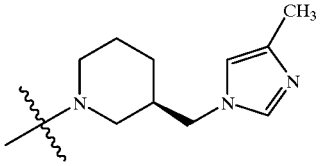 | LCMS: MH⁺ = 519 |
| 150 | 293 | S | 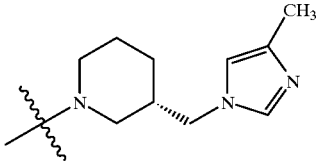 | LCMS: MH⁺ = 519 |
| 151 | 294 | R | 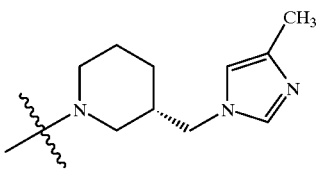 | LCMS: MH⁺ = 519 |

EXAMPLES 295–306

By essentially the same procedure set forth in Example 14, only substituting the title compounds from the Preparative Example listed in column 2 of Table 40, the compounds of the formula shown below, with R⁹ as listed in column 4 of Table 40, were obtained (where data is provided) or can be obtained (where no data is provided) by using the appropriate electrophile.

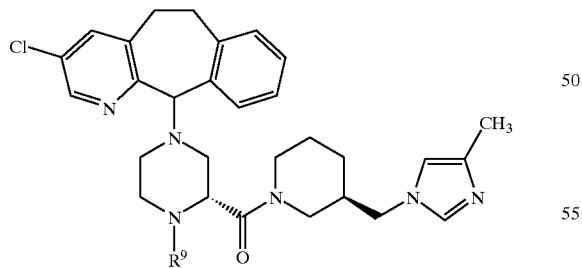

TABLE 40

| Ex. | Prep. Ex. | C-11 isomer | R⁹ = | MP (° C.) | CMPD |
|---|---|---|---|---|---|
| 295 | 149 | R | isopropyl ester | — | — |
| 296 | 148 | S | isopropyl ester | — | — |
| 297 | 149 | R | neopentyl ester | 94–119 | LCMS: MH$^+$ = 633 |
| 298 | 148 | S | neopentyl ester | 110–125 | LCMS: MH$^+$ = 633 |
| 299 | 149 | R | cyclopropylmethyl ester | 95–104 | LCMS: MH$^+$ = 617 |
| 300 | 148 | S | cyclopropylmethyl ester | 95–101 | LCMS: MH$^+$ = 617 |
| 301 | 149 | R | t-butyl amide | 107–119 | LCMS: MH$^+$ = 618 |
| 302 | 148 | S | t-butyl amide | 110–121 | LCMS: MH$^+$ = 618 |
| 303 | 149 | R | t-butyl ketone | 96–119 | LCMS: MH$^+$ = 603 |

TABLE 40-continued

| Ex. | Prep. Ex. | C-11 isomer | R⁹ = | MP (° C.) | CMPD |
|---|---|---|---|---|---|
| 304 | 148 | S | | — | — |
| 305 | 149 | R | | — | — |
| 306 | 148 | S | | — | — |

EXAMPLES 307–318

By essentially the same procedure set forth in Example 14, only substituting the title compounds from the Preparative Example listed in column 2 of Table 41, the compounds of the formula shown below, with R⁹ as listed in column 4 of Table 41, can be obtained by using the appropriate electrophile.

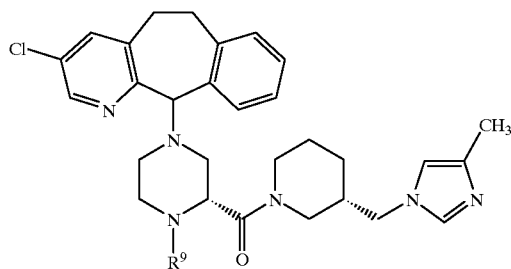

TABLE 41

| Ex. | Prep. Ex. | C-11 isomer | R⁹ = |
|---|---|---|---|
| 307 | 151 | R | |
| 308 | 150 | S | |
| 309 | 151 | R | |
| 310 | 150 | S | |
| 311 | 151 | R | |
| 312 | 150 | S | |
| 313 | 151 | R | |

TABLE 41-continued

| Ex. | Prep. Ex. | C-11 isomer | R⁹ = |
|---|---|---|---|
| 314 | 150 | S | -C(=O)-NH-C(CH₃)₃ |
| 315 | 151 | R | -C(=O)-C(CH₃)₃ |
| 316 | 150 | S | -C(=O)-C(CH₃)₃ |
| 317 | 151 | R | -C(=O)-NH-cyclohexyl |
| 318 | 150 | S | -C(=O)-NH-cyclohexyl |

Preparative Example 152

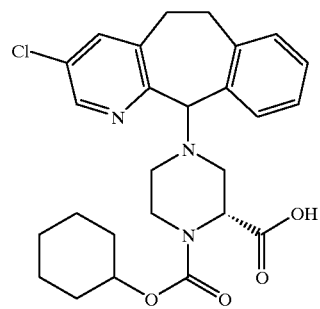

By essentially the same procedure set forth in Preparative Example 36, only substituting the 3-Cl, 8-H tricyclic chloride prepared in Preparative Example 92 for the 3-H, 8-Cl tricyclic chloride in Step B, the title compounds (C-11(S)- and (R)-isomers) was prepared. FABMS: MH⁺=484.

Preparative Examples 153 and 154

By essentially the same procedure set forth in Example 1, only substituting the title compounds from Preparative Example 152 and substituting the appropriate amine, the compounds of the formula shown below, with $R^8$ as listed in column 3 of Table 42, were obtained.

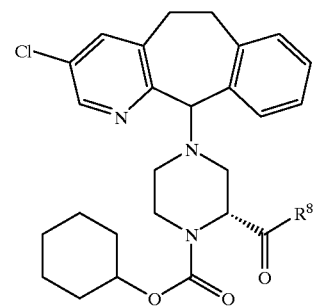

TABLE 42

| Prep. Ex. | C-11 isomer | R⁸ = | CMPD |
|---|---|---|---|
| 153 | R, S | (3-piperidinyl-methyl-4-methylimidazole) | FABMS: MH⁺ = 645 |
| 154 | R, S | (3-piperidinyl-methyl-4-methylimidazole) | FABMS: MH⁺ = 645 |

EXAMPLES 319–322

The title compounds from Preparative Examples 153 and 154 were separated into individual C-11 (S)- and (R)-diastereomers by Preparative HPLC with a CHIRALPAK AD column using a 25% iPrOH in hexanes solution with 0.2% DEA as eluent to give the compounds of the formula shown below with $R^8$ as listed in column 3 of Table 43.

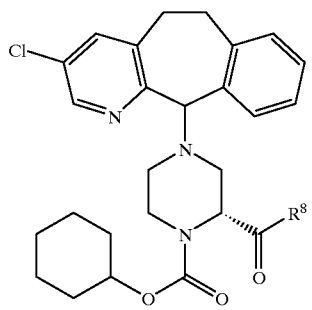

EXAMPLES 323–326

By essentially the same procedure set forth in Example 1, only substituting the title compounds from Preparative Example 112 substituting the appropriate amine, the compounds of the formula shown below, with $R^8$ listed in column 3 of Table 44, can be obtained.

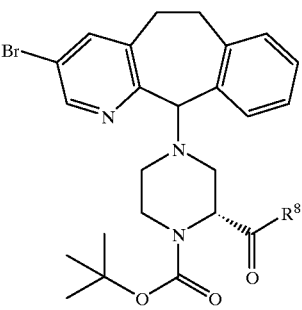

TABLE 43

| Ex. | C-11 isomer | $R^8$ = | MP (° C.) | CMPD |
|---|---|---|---|---|
| 319 | S | | 114–118 | FABMS: $MH^+$ = 645 |
| 320 | R | | 115–120 | FABMS: $MH^+$ = 645 |
| 321 | S | | 112–121 | FABMS: $MH^+$ = 645 |
| 322 | R | | 117–125 | FABMS: $MH^+$ = 645 |

TABLE 44
| Ex. | C-11 isomer | R⁸ = | MP (° C.) | CMPD |
|---|---|---|---|---|
| 323 | S | 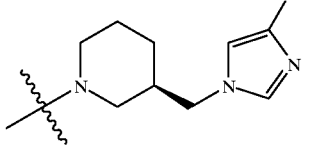 | 109–124 | LCMS: MH⁺ = 663 |
| 324 | R | 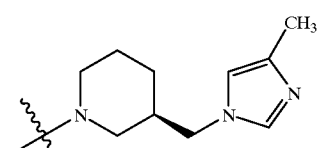 | 102–119 | LCMS: MH⁺ = 663 |
| 325 | S | 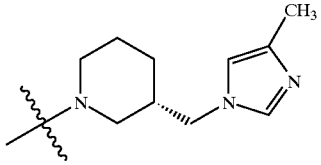 | — | — |
| 326 | R | 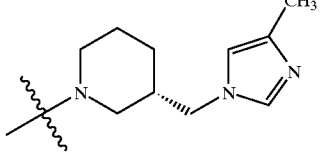 | — | — |
Preparative Example 155–158
By essentially the same procedure set forth in Preparative Example 115, only substituting the title compounds from the example listed in column 2 of Table 45, the title compounds of the formula shown below, with R⁸ as listed in column 4 of Table 45, can be prepared.
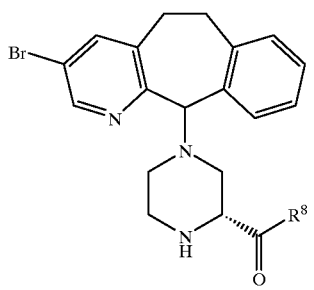
TABLE 45
| Prep Ex. | Ex. | C-11 isomer | R⁸ = |
|---|---|---|---|
| 155 | 323 | S | 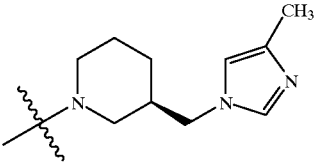 |
| 156 | 324 | R | 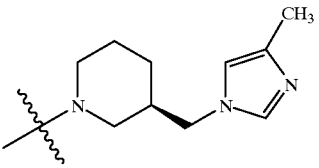 |
| 157 | 325 | S | 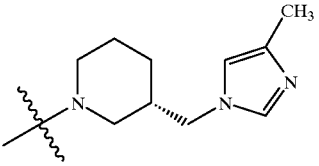 |

TABLE 45-continued

| Prep Ex. | Ex. | C-11 isomer | R⁸ = |
|---|---|---|---|
| 158 | 326 | R | (structure: piperidine-CH₂-imidazole-CH₃) |

EXAMPLES 327–338

By essentially the same procedure set forth in Example 14, only substituting the title compounds from the Preparative Example listed in column 2 of Table 46, the compounds of the formula shown below, with R⁹ as listed in column 4 of Table 46, were obtained (where data is provided) or can be obtained (where no data is provided) by using the appropriate electrophile.

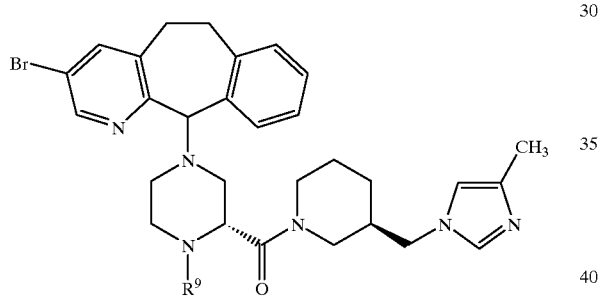

TABLE 46

| Ex. | Prep. Ex. | C-11 isomer | R⁹ = | MP (° C.) | CMPD |
|---|---|---|---|---|---|
| 327 | 156 | R | -C(O)O-iPr | — | — |
| 328 | 155 | S | -C(O)O-iPr | — | — |
| 329 | 156 | R | -C(O)O-CH₂C(CH₃)₃ | 112–118 | LCMS: MH⁺ = 677 |
| 330 | 155 | S | -C(O)O-CH₂C(CH₃)₃ | 98–122 | LCMS: MH⁺ = 677 |
| 331 | 156 | R | -C(O)O-CH₂-cyclopropyl | 93–103 | LCMS: MH⁺ = 661 |
| 332 | 155 | S | -C(O)O-CH₂-cyclopropyl | 89–108 | LCMS: MH⁺ = 661 |
| 333 | 156 | R | -C(O)NH-tBu | 84–108 | LCMS: MH⁺ = 662 |
| 334 | 155 | S | -C(O)NH-tBu | 91–118 | LCMS: MH⁺ = 662 |
| 335 | 156 | R | -C(O)-C(CH₃)₃ | 103–113 | LCMS: MH⁺ = 647 |
| 336 | 155 | S | -C(O)-C(CH₃)₃ | 115–124 | LCMS: MH⁺ = 647 |
| 337 | 156 | R | -C(O)NH-cyclohexyl | — | — |
| 338 | 155 | S | -C(O)NH-cyclohexyl | — | — |

EXAMPLES 339–350

By essentially the same procedure set forth in Example 14, only substituting the title compounds from the Preparative Example listed in column 2 of Table 47, the compounds of the formula shown below with $R^9$ as listed in column 4 of Table 47, can be obtained by using the appropriate electrophile.

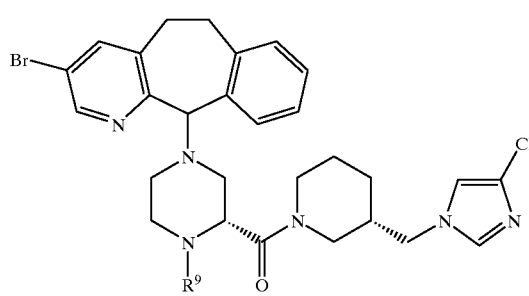

TABLE 47

| Ex. | Prep. Ex. | C-11 isomer | $R^9$ = |
|---|---|---|---|
| 339 | 158 | R | isopropyl ester |
| 340 | 157 | S | isopropyl ester |
| 341 | 158 | R | neopentyl ester |
| 342 | 157 | S | neopentyl ester |
| 343 | 158 | R | cyclopropylmethyl ester |
| 344 | 157 | S | cyclopropylmethyl ester |
| 345 | 158 | R | t-butyl amide |
| 346 | 157 | S | t-butyl amide |
| 347 | 158 | R | t-butyl ketone |
| 348 | 157 | S | t-butyl ketone |
| 349 | 158 | R | cyclohexyl amide |
| 350 | 157 | S | cyclohexyl amide |

Preparative Example 159

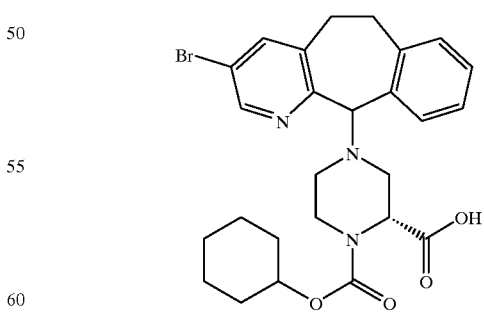

By essentially the same procedure set forth in Preparative Example 36, only substituting the 3-Br, 8-H tricyclic chloride prepared in Preparative Example 93 for the 3-H, 8-Cl tricyclic chloride in Step B, the title compounds (C-11(S)- and (R)-isomers) were prepared. FABMS: $MH^+$=528.

Preparative Examples 160 and 161

By essentially the same procedure set forth in Preparative Example 126, only substituting the title compounds from Preparative Example 144 and substituting the appropriate amine, the compounds of the formula shown below, with $R^8$ as listed in column 3 of Table 48, were obtained.

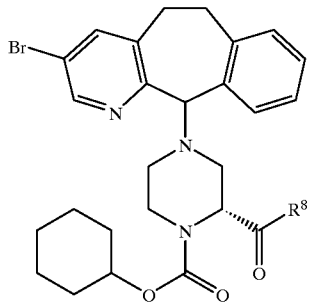

TABLE 48

| Prep. Ex. | C-11 isomer | $R^8$ = | CMPD |
|---|---|---|---|
| 160 | R, S | 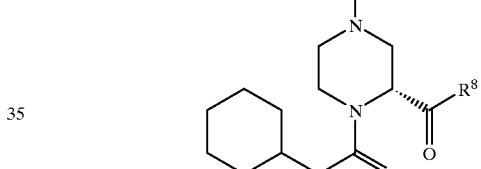 | FABMS: $MH^+ = 689$ |

TABLE 48-continued

| Prep. Ex. | C-11 isomer | $R^8$ = | CMPD |
|---|---|---|---|
| 161 | R, S | 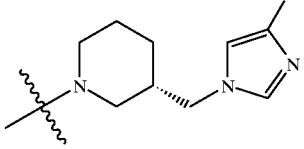 | FABMS: $MH^+ = 689$ |

EXAMPLES 351–354

The title compounds from Preparative Examples 160 and 161 were separated into individual C-11 (S)- and (R)-diastereomers by Preparative HPLC with a CHIRALPAK AD column using a iPrOH in hexanes solution with 0.2% DEA as eluent to give the compounds of the formula shown below with $R^8$ as listed in column 3 of Table 49.

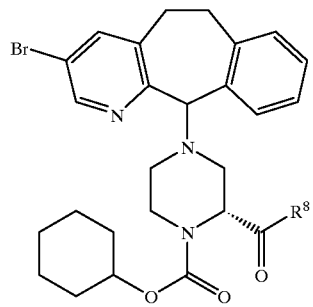

TABLE 49

| Ex. | C-11 isomer | $R^8$ = | MP (° C.) | CMPD |
|---|---|---|---|---|
| 351 | S | 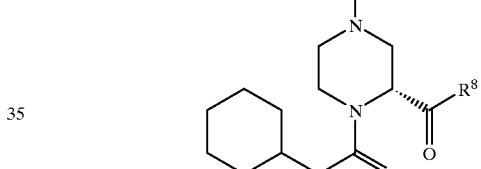 | 120–124 | FABMS: $MH^+ = 689$ |
| 352 | R | 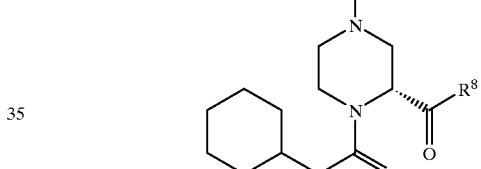 | 122–125 | FABMS: $MH^+ = 689$ |
| 353 | S | 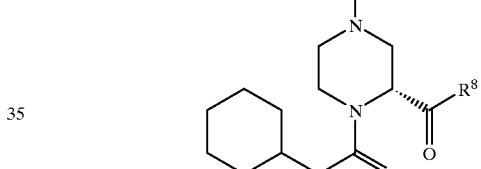 | 121–127 | FABMS: $MH^+ = 689$ |

TABLE 49-continued

| Ex. | C-11 isomer | R⁸ = | MP (° C.) | CMPD |
|---|---|---|---|---|
| 354 | R | (structure) | 124–128 | FABMS: MH⁺ = 689 |

EXAMPLES 355–358

By essentially the same procedure set forth in Example 1 only substituting the title compounds from Preparative Example 114 and substituting the appropriate amine, the compounds of the formula shown below, with $R^8$ listed in column 3 of Table 50, can be obtained.

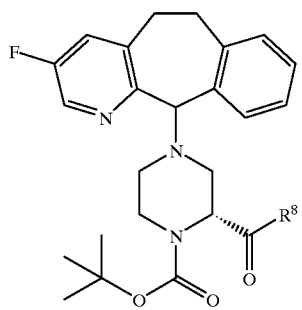

TABLE 50

| Ex. | C-11 isomer | R⁸ = |
|---|---|---|
| 355 | S | (structure) |
| 356 | R | (structure) |
| 357 | S | (structure) |

TABLE 50-continued

| Ex. | C-11 isomer | R⁸ = |
|---|---|---|
| 358 | R | (structure) |

Preparative Example 162–165

By essentially the same procedure set forth in Preparative Example 115, only substituting the title compounds from the example listed in column 2 of Table 51, the title compounds of the formula shown below, with $R^8$ as listed in column 4 of Table 51, can be prepared.

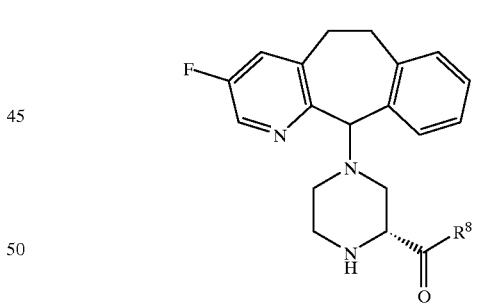

TABLE 51

| Prep Ex. | Ex. | C-11 isomer | R⁸ = |
|---|---|---|---|
| 162 | 355 | S | (structure) |

TABLE 51-continued

| Prep Ex. | Ex. | C-11 isomer | R⁸ = |
|---|---|---|---|
| 163 | 356 | R | 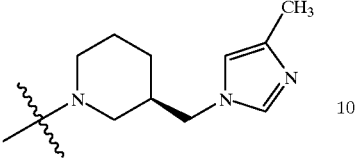 |
| 164 | 357 | S | 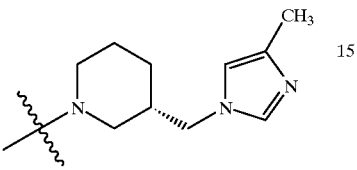 |
| 165 | 358 | R | 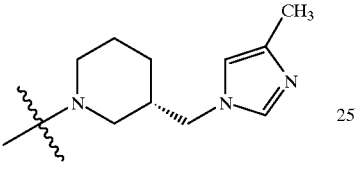 |

EXAMPLES 359–370

By essentially the same procedure set forth in Example 14, only substituting the title compounds from the Preparative Example listed in column 2 of Table 52, the compounds of the formula shown below, with R⁹ as listed in column 4 of Table 52, can be obtained by using the appropriate electrophile.

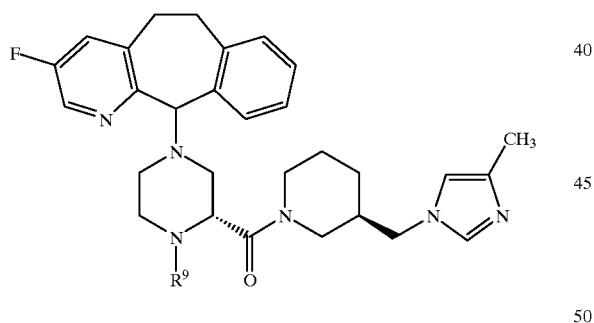

TABLE 52

| Prep. | C-11 | R⁹ = |
|---|---|---|
| 359 | 163 | R | 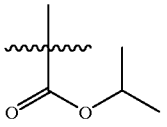 |
| 360 | 162 | S | 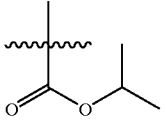 |

TABLE 52-continued

| Prep. | C-11 | R⁹ = |
|---|---|---|
| 361 | 163 | R | 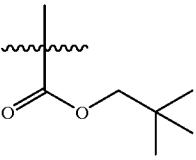 |
| 362 | 162 | S | 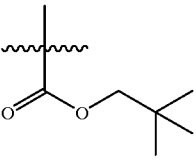 |
| 363 | 163 | R | 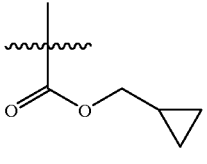 |
| 364 | 162 | S | 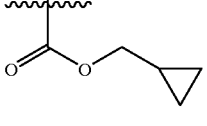 |
| 365 | 163 | R | 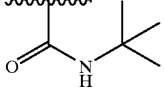 |
| 366 | 162 | S | 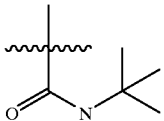 |
| 367 | 163 | R | 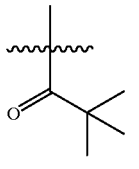 |
| 368 | 162 | S | 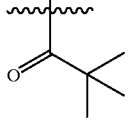 |
| 369 | 163 | R | 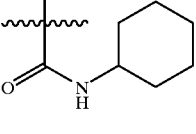 |

TABLE 52-continued

| | Prep. | C-11 | R⁹ = |
|---|---|---|---|
| 370 | 162 | S | 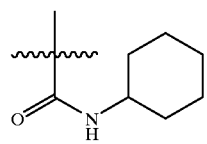 |

EXAMPLES 371–382

By essentially the same procedure set forth in Example 14, only substituting the title compounds from the Preparative Example listed in column 2 of Table 53, the compounds of the formula shown below, with R⁹ as listed in Column 4 of Table 53, can be obtained by using the appropriate electrophile.

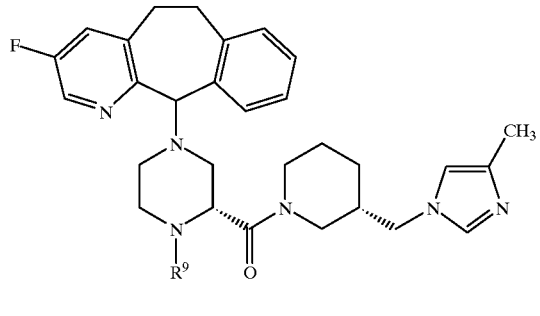

TABLE 53

| Ex. | Prep. Ex. | C-11 isomer | R⁹ = |
|---|---|---|---|
| 371 | 165 | R | 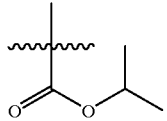 |
| 372 | 164 | S | 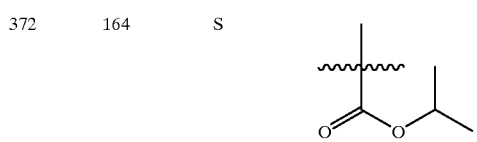 |
| 373 | 165 | R | 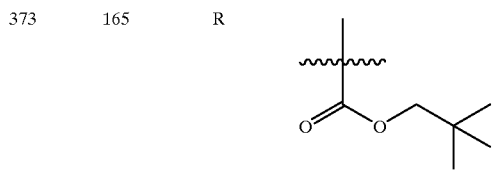 |
| 374 | 164 | S | 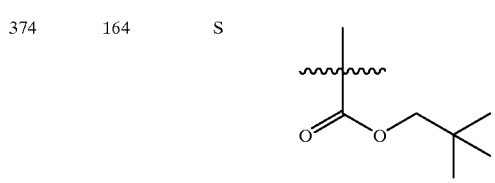 |

TABLE 53-continued

| Ex. | Prep. Ex. | C-11 isomer | R⁹ = |
|---|---|---|---|
| 375 | 165 | R | 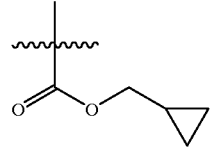 |
| 376 | 164 | S | 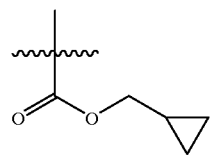 |
| 377 | 165 | R | 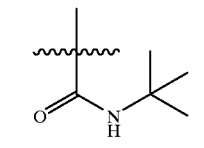 |
| 378 | 164 | S | 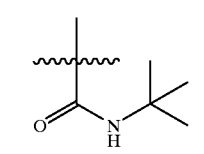 |
| 379 | 165 | R | 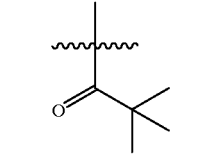 |
| 380 | 164 | S | 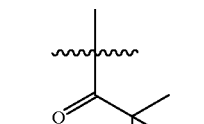 |
| 381 | 165 | R | 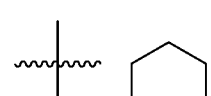 |
| 382 | 164 | S | 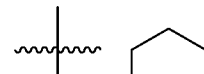 |

Preparative Example 166

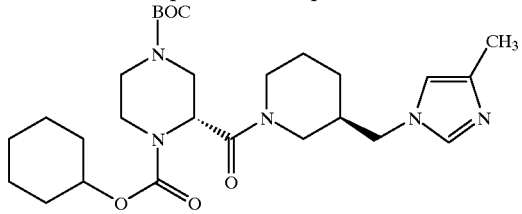

By essentially the same procedure set forth in Example 1 only substituting the title compound from Preparative Example 32 Step A and the title amine from Preparative Example 21, the title compound was prepared. FABMS: MH$^+$=518.

Preparative Example 166A

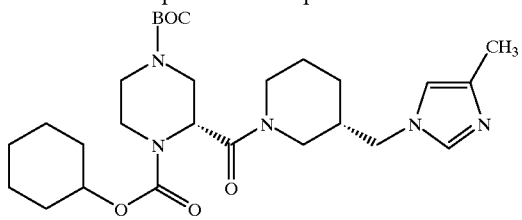

By essentially the same procedure set forth in Example 1 only substituting the title compound from Preparative Example 32 Step A and the title amine from Preparative Example 20, the title compound ca be prepared.

Preparative Examples 167 and 168

By essentially the same procedure set forth in Preparative Example 32, only substituting the title compounds from Preparative Example 166 and 166A and the 3-F, 8-H tricyclic chloride from Preparative Example 95, the compound of the formula shown below with R$^8$ as listed in Column 3 of Table 54 was prepared (Prep. Example 167) or can be prepared (Prep. Example 168).

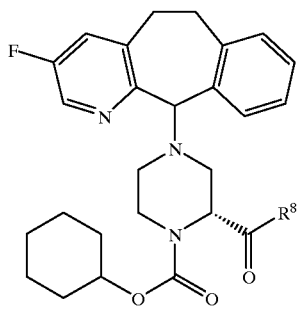

TABLE 54

| Prep. Ex. | C-11 isomer | R$^8$ = | CMPD |
|---|---|---|---|
| 167 | R, S | 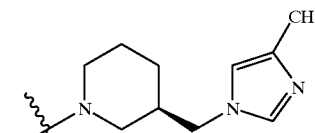 | FABMS: MH$^+$ = 629 |
| 168 | R, S | 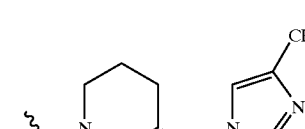 | — |

EXAMPLES 383–386

The title compounds from Preparative Examples 167 and 168 were (Preparative Examples 167) and can be (Preparative Example 168) separated into individual C-11 (S)- and (R)-diastereomers by Preparative HPLC with a CHIRALPAK AD column using an iPrOH in hexanes solution with 0.2% DEA as eluent to give the compounds of the formula shown below with R$^8$ as listed in Column 3 of Table 55.

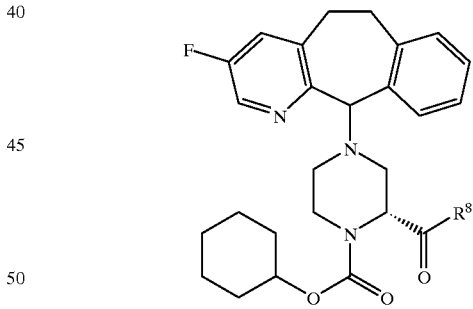

TABLE 55

| Ex. | C-11 isomer | R$^8$ = | MP (° C.) | CMPD |
|---|---|---|---|---|
| 383 | S | 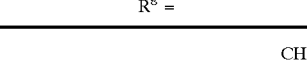 | 121–126 | FABMS: MH$^+$ = 629 |

TABLE 55-continued
| Ex. | C-11 isomer | R[8] = | MP (° C.) | CMPD |
|---|---|---|---|---|
| 384 | R | 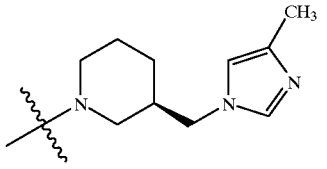 | 104–111 | FABMS: MH[+] = 629 |
| 385 | S | 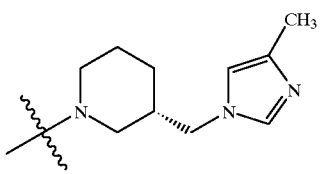 | — | — |
| 386 | R | 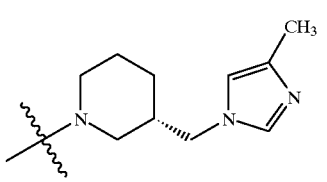 | — | — |
Preparative Example 168A
Preparation of the tricyclic N-oxide Moiety
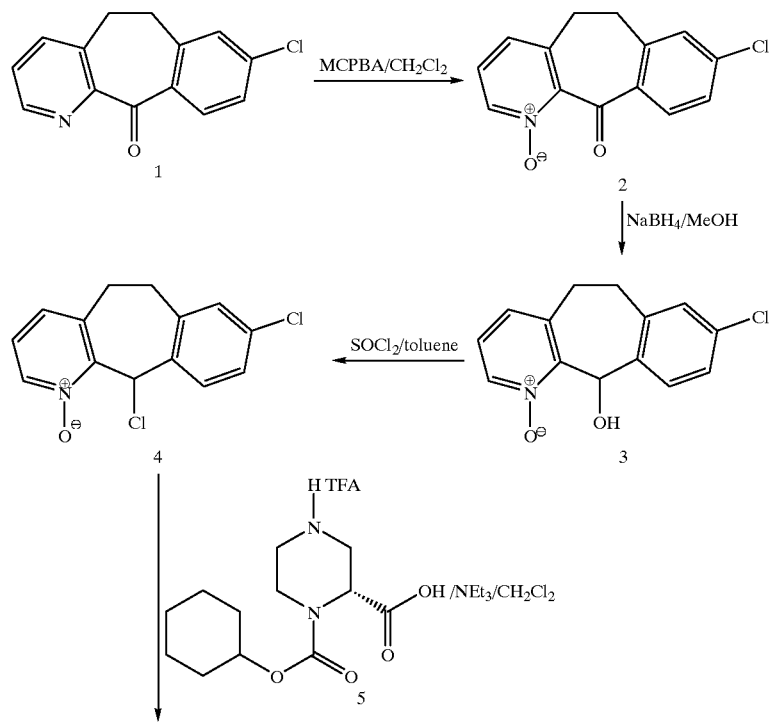

-continued

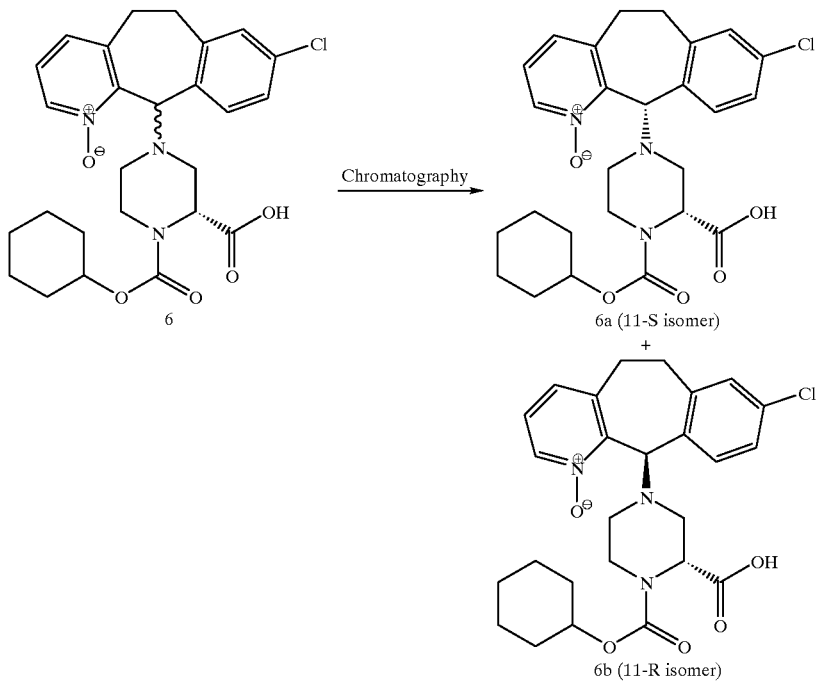

6 → 6a (11-S isomer) + 6b (11-R isomer)

[1→2] A solution of 3-peroxybenzoic acid (25 g, 102.59 mmol, 2.5 eq.) in anhydrous dichloromethane (250 mL) was added dropwise over a period of one hour to a stirred solution of 8-chloro-4-aza-10,11-dihydro-5H-dibenzo[a,d]cyclohepten-5-one 1 (10 g, 41.04 mmol, 1.0 eq.) in anhydrous dichloromethane (100 mL) at 0° C. under a nitrogen atmosphere. The solution was slowly (3 h) warmed to room temperature and stirred for another 12 h. The solution was extracted with 1 M aqueous sodium hydroxide solution (5×100 mL), washed with brine (2×100 mL), dried over $Na_2SO_4$, filtered, and concentrated under house vacuum at 30° C. to give 2 as a canary-yellow solid. The title compound 2 was used directly without further attempts at purification.

Yield: 10 g=38.51 mmol=94%
$[M+H]^+$: 260
HRMS (FAB+):
Calculated for $C_{14}H_{11}ClNO_2$ ($[M+H]^+$): 260.0475
Observed: 260.0478

[2→3] Sodium borohydride (2.21 g, 57.76 mmol, 1.5 eq.) was added portionwise over a period of 15 minutes to a solution of 2 (10 g, 38.51 mmol, 1.0 eq.) in anhydrous methanol (500 mL) at 0° C. under a nitrogen atmosphere. The resulting suspension was stirred at 0° C. for one hour and at room temperature for another hour. The volatiles were removed under house vacuum at 30° C. and the residue was taken up in 1 M aqueous NaOH solution (250 mL). The aqueous solution was extracted with dichloromethane (5×100 mL). The combined organic extracts were washed with brine (100 mL), dried over $Na_2SO_4$, filtered, and concentrated under house vacuum at 30° C. to give 3 as a lime-green solid. Compound 3 was used directly without any attempts at purification.

Yield: 9 g=34.39 mmol=89%
$[M+H]^+$: 262
HRMS (FAB+):
Calculated for $C_{14}H_{13}ClNO_2$ ($[M+H]^+$): 262.0635
Observed: 262.0636

[3→4] Thionyl chloride (5 mL, 68.78 mmol, 2.0 eq.) was added dropwise over a period of 10 minutes to a stirred suspension of 3 (9 g, 34.39 mmol, 1.0 eq.) and anhydrous toluene (150 mL) at 0° C. under a nitrogen atmosphere. The cream-colored suspension was slowly (3 h) warmed to room temperature and stirred for another 12 h. The volatiles were removed under house vacuum at 30° C. The residue was taken up in dichloromethane (250 mL) and washed with ice-cold, saturated aqueous $NaHCO_3$ solution (5×100 mL) until the aqueous washings were moderately basic at pH 9. The organic layer was washed with brine (100 mL), dried over $Na_2SO_4$, filtered, and concentrated under house vacuum at 30° C. to give 4 as a cream-colored solid in essentially quantitative yield. Due to its high reactivity, compound 4 was used directly without any attempts at purification or characterization (other than $^1$H NMR).

Yield: 9.55 g=34.09 mmol=99%

[4→6] Triethylamine (18 mL, 126.65 mmol, 5.0 eq.) was added dropwise to a stirred solution of 5 (previously described in the art; 9.38 g, 25.33 mmol, 1.0 eq.) in anhydrous dichloromethane (50 mL) at room temperature under a nitrogen atmosphere. The solution was stirred at room temperature for 30 minutes and was cooled to 0° C. A solution of 4 (8.52 g, 30.39 mmol, 1.2 eq.) in anhydrous dichloromethane (50 mL) was added dropwise over a period of 25 minutes. The mixture was slowly (3 h) warmed to room temperature and stirred for another 12 h. The volatiles were removed under house vacuum at 30° C. The residue was taken up in 50% m/v aqueous citric acid solution (100 mL) and extracted with ethyl acetate (5×100 mL). The organic extracts were combined and dried over $Na_2SO_4$, filtered, and concentrated under house vacuum at 30° C. The residual cream-colored solid was flash-chromatographed ($CH_2Cl_2$:MeOH=19:1 v/v) to give the diastereomerically pure isomers 6a and 6b at C-11 of the tricycle.

For 6a
  Yield: 5.75 g≡11.50 mmol≡45%
  Off-white foam; M.p.: 78–83° C.
  [M+H]⁺: 500
  HRMS (FAB+):
  Calculated for $C_{26}H_{31}ClN_3O_5$ ([M+H]⁺): 500.1953
  Observed: 500.1952
For 6b
  Yield: 3.00 g≡6.00 mmol≡24%
  Off-white solid; M.p.: 94–99° C.
  [M+H]⁺: 500
  HRMS (FAB+):
  Calculated for $C_{26}H_{31}ClN_3O_5$ ([M+H]⁺): 500.1953
  Observed: 500.1952

EXAMPLE 387

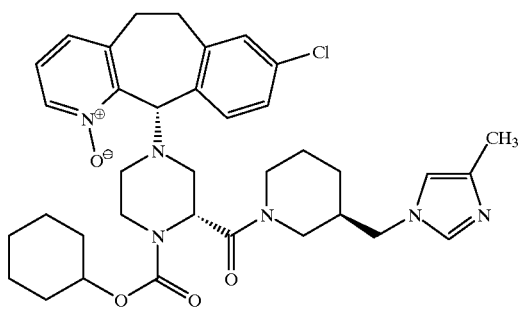

By essentially the same procedure set forth in Example 47A, only substituting the title compound from Preparative Example 168A, the title compound was prepared: mp=85–90° C.; [M+H]⁺: 661.

EXAMPLE 388

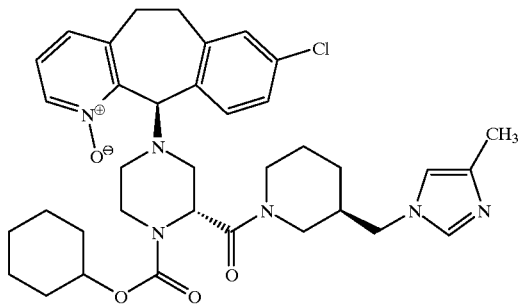

By essentially the same procedure set forth in Example 42 (see Table 6), only substituting the title compound from Preparative Example 168A, the title compound was prepared: mp=108–113° C.; [M+H]⁺: 661.

Preparative Example 169

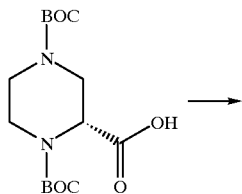

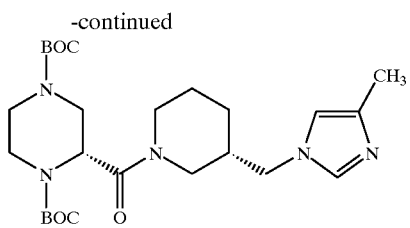

By essentially the same procedure set forth in Example 1, only substituting the title compound from Preparative Example 2 and susbtituting the appropriate amine, the title compound was prepared.

Preparative Example 170

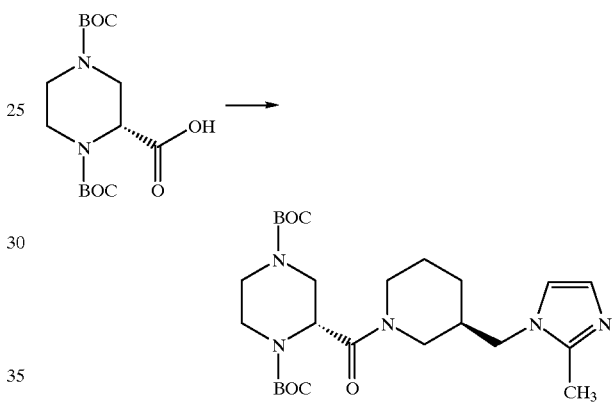

By essentially the same procedure set forth in Preparative Example 147, the title compound was prepared.

Preparative Example 171

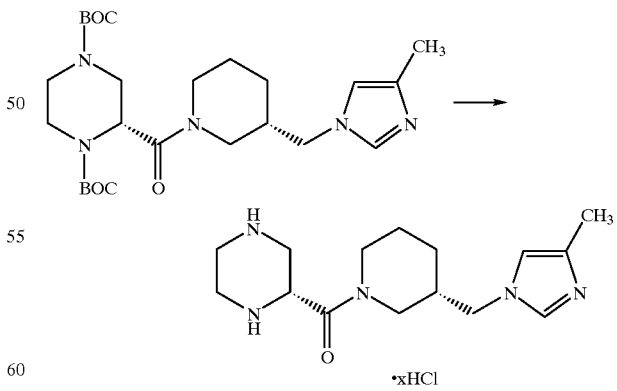

By essentially the same procedure set forth in Preparative Example 8, the title compound was prepared and used without further purification.

Preparative Example 172

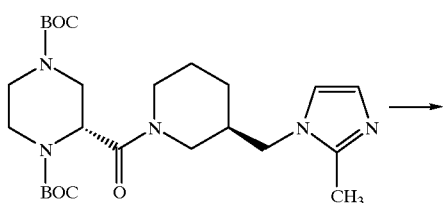

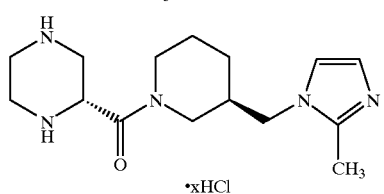

By essentially the same procedure set forth in Preparative Example 8, the title compound was prepared and used without further purification.

Preparative Example 173

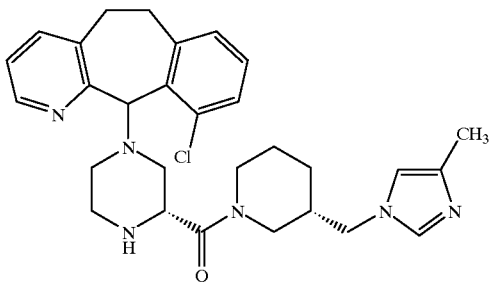

By essentially the same procedure set forth in Preparative Example 6, only substituting the title compounds from Preparative Example 171 and Preparative Example 99, the title compound was obtained: FABMS: MH+=519.

By essentially the same procedure set forth in Example 14, only substituting the title compounds from the Preparative Example listed in column 2 of Table 56, the compounds of the formula shown below, with $R^9$ as listed in column 4 of Table 56, were obtained by using the appropriate acylating agent.

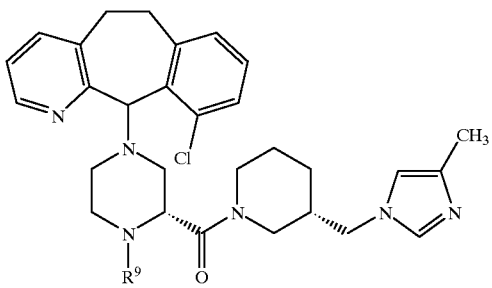

TABLE 56

| Ex. | Prep. Ex. | C-11 isomer | $R^9$ = | CMPD |
|---|---|---|---|---|
| 389 | 173 | R | 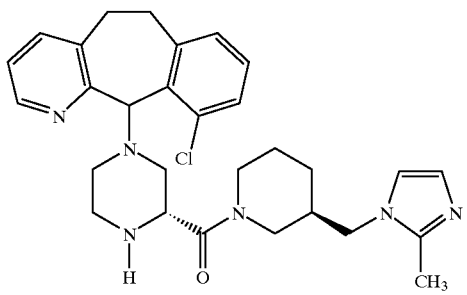 | FABMS: MH+ = 644 |
| 390 | 173 | S | | FABMS: MH+ = 644 |
| 391 | 173 | A | | FABMS: MH+ = 645 |
| 392 | 173 | B | | FABMS: MH+ = 645 |
| 393 | 173 | R | | FABMS: MH+ = 619 |
| 394 | 173 | S | | FABMS: MH+ = 619 |

Preparative Example 174

By essentially the same procedure set forth in Preparative Example 6, only substituting the title compounds from Preparative Example 172 and Preparative Example 99 the title compound was obtained: FABMS: MH+=519.

EXAMPLES 395–397

By essentially the same procedure set forth in Example 14, only substituting the title compounds from the Preparative Example listed in column 2 of Table 57, the compounds of the formula shown below, with $R^9$ as listed in column 4 of Table 57, was obtained by using the appropriate acylating agent.

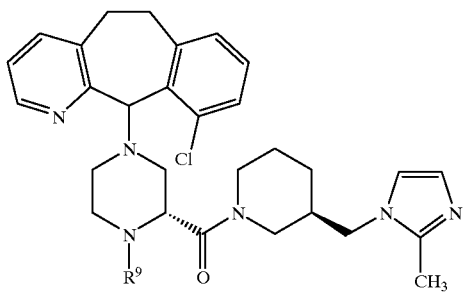

TABLE 57

| Ex. | Prep. Ex. | C-11 isomer | R = | CMPD |
|---|---|---|---|---|
| 395 | 174 | R, S | | FABMS: MH⁺ = 619 |
| 396 | 174 | A | | FABMS: MH⁺ = 619 |
| 397 | 174 | B | | FABMS: MH⁺ = 619 |

EXAMPLE 398

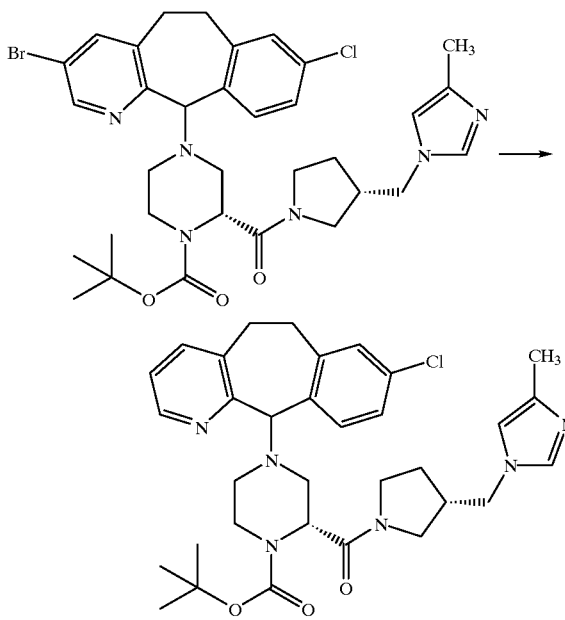

The title compound from Example 165 (0.076 g) was balloon hydrogenated over 10% Pd/C (0.025 g) in EtOH (15 mL) overnight at room temperature. The catalyst and the solvent removed to give the title compound: MS MH⁺=606.

EXAMPLES 399–402

By essentially the same procedures set forth in Preparative Example 24 and Example 14, only using the title compound from Example 398, the title compounds of the formula shown below, with $R^9$ listed in column 3 of Table 58, were obtained.

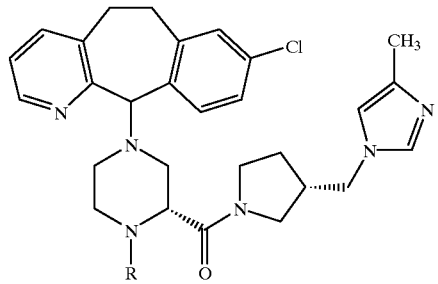

TABLE 58

| Ex. | C-11 isomer | $R^9$ = | CMPD |
|---|---|---|---|
| 399 | S | | FABMS: MH⁺ = 632 |
| 400 | S | | FABMS: MH⁺ = 592 |
| 401 | S | | FABMS: MH⁺ = 620 |
| 402 | S | | FABMS: MH⁺ = 605 |

EXAMPLES 403–406

By essentially the same procedure set forth in Example 399, compounds of the formula shown below, with $R^9$ listed in column 4 of Table 59, were obtained.

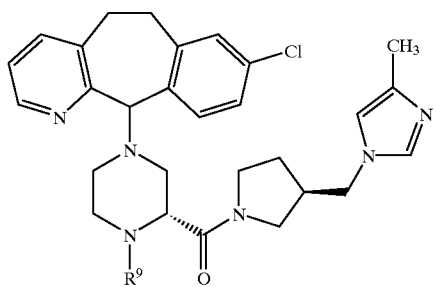

TABLE 59

| Ex. | C-11 isomer | R⁹ = | CMPD |
|---|---|---|---|
| 403 | S | (cyclohexyl ester) | FABMS: MH⁺ = 632 |
| 404 | S | (isopropyl ester) | FABMS: MH⁺ = 592 |
| 405 | S | (neopentyl ester) | FABMS: MH⁺ = 620 |
| 406 | S | (t-butyl amide) | FABMS: MH⁺ = 605 |

EXAMPLES 407–408

By essentially the same procedure set forth in Example 1, only substituting the appropriate amine, the compounds of the formula shown below, with R⁸ as listed in column 3 of Table 60 were obtained.

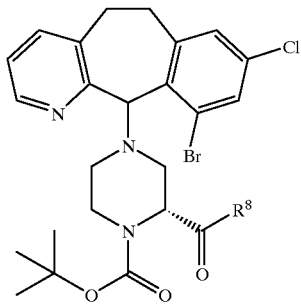

TABLE 60

| Ex. | C-11 isomer | R⁸ = | CMPD |
|---|---|---|---|
| 407 | 1 | (4-methylimidazolyl-methyl piperidine) | FABMS: MH⁺ = 699 |
| 408 | 2 | (4-methylimidazolyl-methyl piperidine) | FABMS: MH⁺ = 699 |

EXAMPLES 409 and 410

The title compound from Example 47(CC) was separated into individual diasteromers using a CHIRALPAK AD column using a 15% iPrOH in hexanes with 0.2% DEA as eluent to give the title compounds of formula shown below wherein R⁸ is as defined in column 3 of Table 60A.

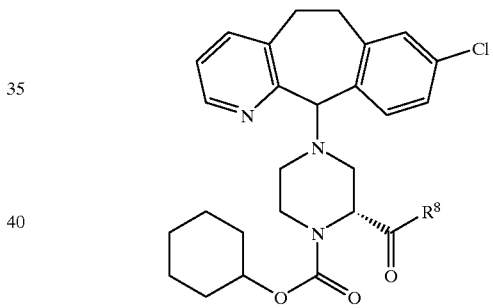

TABLE 60A

| Ex. | C-11 isomer | R⁸ = | CMPD |
|---|---|---|---|
| 409 | S | Isomer 1 | FABMS: MH⁺ = 659 |
| 410 | S | Isomer 2 | FABMS: MH⁺ = 659 |

Preparative Example 175

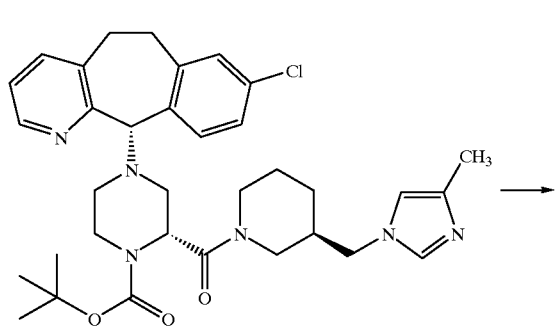

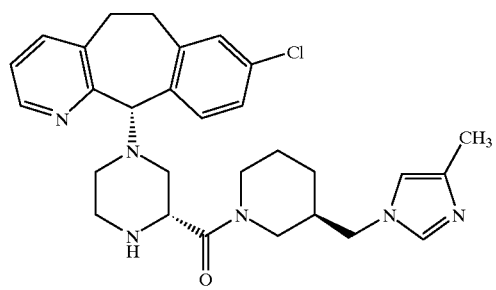

By essentially the same procedure put forth in Preparative Example 115 only substituting the title compound from Example 32, the compound was prepared.

EXAMPLE 411

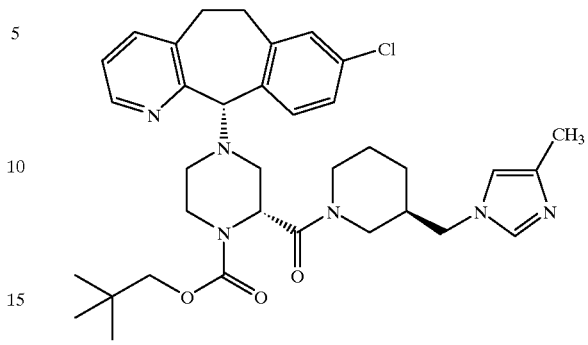

By essentially the same procedure set forth in Example 14, only substituting the title compound from Preparative Example 175 and neopentyl chloroformate, the title compound was prepared: mp=103–115° C.; LCMS: MH$^+$=633.]

EXAMPLES 412 and 413

The title compounds of the formula shown below with R$^9$ as listed in column 3 of the Table 61 were prepared by essentially the same procedure as set forth in Example 1, only substituting the title compound from Preparative Example 175 and the appropriate carboxylic acid.

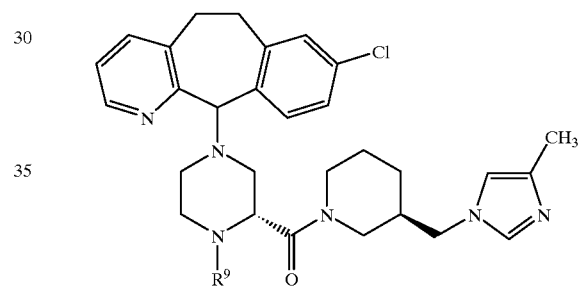

TABLE 61

| Ex. | C-11 isomer | R$^9$ = | MP (° C.) | CMPD |
|---|---|---|---|---|
| 412 | S | (4-pyridyl N-oxide CH$_2$C(O)—) | 175 (dec.) | FABMS: MH$^+$ = 654 |
| 413 | S | (H$_2$N-C(O)-piperidine-CH$_2$C(O)—) | 150–152 | FABMS: MH$^+$ = 687 |

Preparative Example 175A

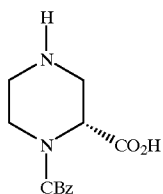

By essentially the same procedure set forth in Preparative Example 31, Step A only substituting CBz-NOS for isopropyl chloroformate, the title compound was prepared.

Preparative Examples 175B and 175C

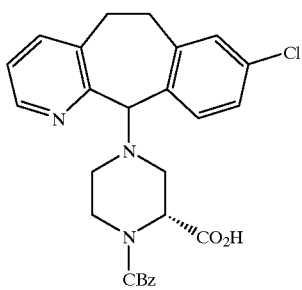

By essentially the same procedure set forth in Preparative Example 31, Step B only substituting the title compound from Preparative Example 175A. the title compounds (individual C-11 (S)- and (R)-isomers) were prepared.

Example 175B: C-11 (S)-isomer, Yield=13%, MH$^+$=492.
Example 175C: C-11 (R)-isomer, Yield=13%, MH$^+$=492.

Preparative Examples 175D and 175E

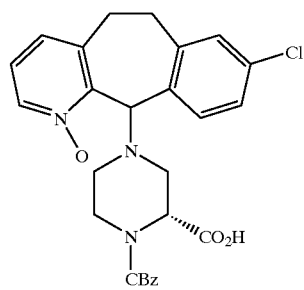

By essentially the sames procedure set forth in Preparative Example 31, Step B only substituting the title compounds from Preparative Example 97 and Preparative Example 175A, the title compounds (individual C-11 (S)- and (R)-isomers) were prepared.
Example 175D: C-11 (S)-isomer, Yield=12%, MH$^+$=508.
Example 175E: C-11 (R)-isomer, Yield=15%, MH$^+$=508.

EXAMPLE 414

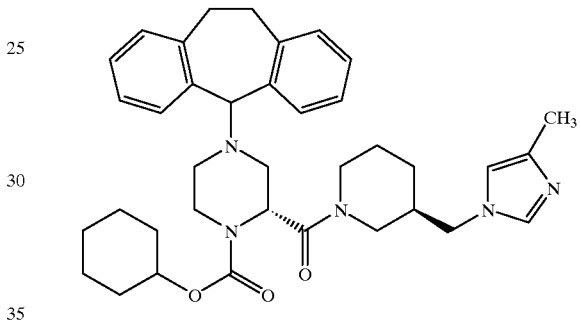

The title compound was prepared by essentially the same procedure as set forth in Example 387, only substituting the dibenzosuberyl chloride for the tricyclic chloride: mp=98–112° C.; FABMS: MH$^+$=610.]

EXAMPLES 415–425

Following essentially the same procedure set forth in Example 1, only substituting the Carboxylic acid (11-(S) or 11-(R) isomer) from the Preparative Example listed in Table 62 and the appropriately substituted piperidine (Amine), the pure isomeric products were prepared and separated by Preparative HPLC (AD column) using IPA-hexanes.

TABLE 62

| Ex. | Prep. Ex. 1. Amine 2. Acid | Product |
|---|---|---|
| 415 | 1. 68 Step E 2. 32 11(S) isomer | (structure shown) 1. Yield (%): 82 |

TABLE 62-continued
| Ex. | Prep. Ex.<br>1. Amine<br>2. Acid | Product |
|---|---|---|
| | | 2. MH⁺: 645<br>3. mp (° C.): 116.2 |
| 416 | 1. 80<br>Step D<br>2. 32<br>11(S)<br>isomer | 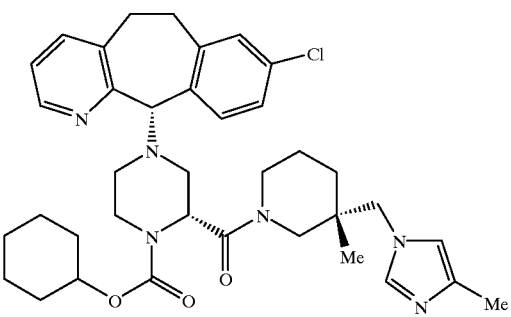<br>1. Yield (%): 50.8<br>2. MH⁺: 659<br>3. mp (° C.): 112.5–116.3 |
| 417 | 1. 81<br>2. 32<br>11(S)<br>isomer | 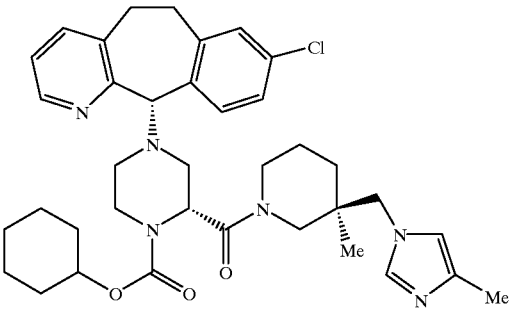<br>1. Yield (%): 51.4<br>2. MH⁺: 659<br>3. mp (° C.): 85.1–115 |
| 418 | 1. 82<br>Step B<br>2. 32<br>11(S)<br>isomer | 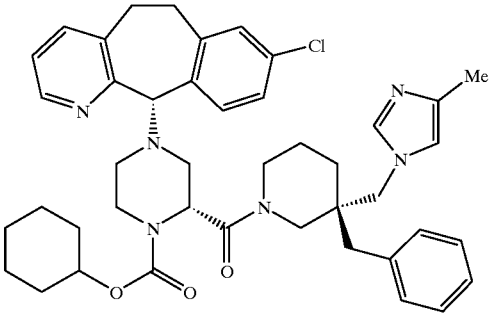<br>1. Yield (%): 63<br>2. MH⁺: 735<br>3. mp (° C.): 135.9 |

TABLE 62-continued
| Ex. | Prep. Ex.<br>1. Amine<br>2. Acid | Product |
|---|---|---|
| 419 | 1. 83<br>Step E<br>2. 32<br>11(S)<br>isomer | Isomer A<br>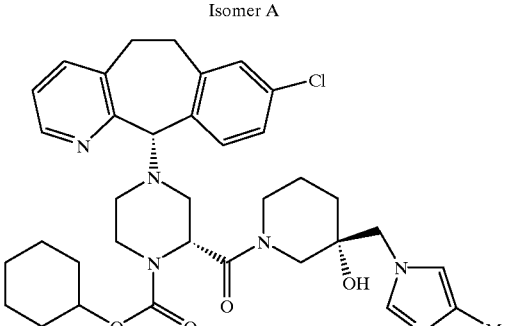<br>1. Yield (%): 35.7<br>2. MH⁺: 661<br>3. mp (° C.): 117.6–124.8<br><br>Isomer B<br>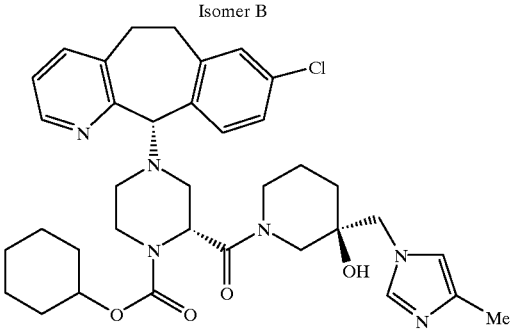<br>1. Yield (%): 35.7<br>2. MH⁺: 661<br>3. mp (° C.): 95.7–107.2 |
| 420 | 1. 83<br>Step E<br>2. 168A<br>11(S)<br>isomer | Isomer A<br>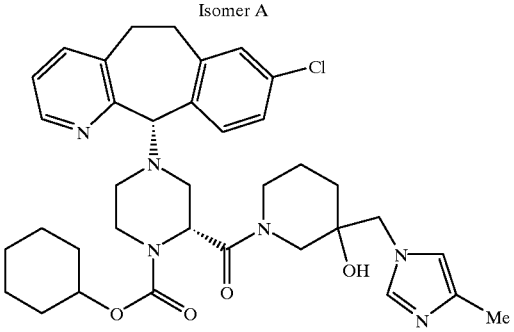<br>1. Yield (%): 36<br>2. MH⁺: 677<br>3. mp (° C.): 172.4 |

TABLE 62-continued
| Ex. | Prep. Ex. 1. Amine 2. Acid | Product |
|---|---|---|
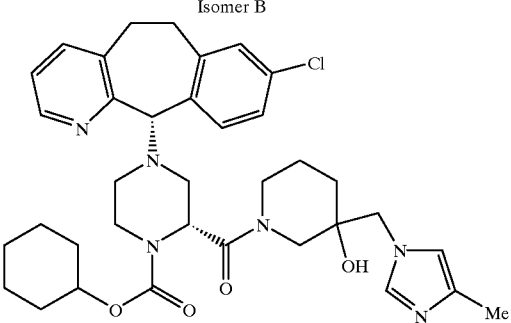
Isomer B
1. Yield (%): 36
2. MH+: 677
3. mp (° C.): 152.9
421  1. 83
     Step E
     2. 168A
     11(R)
     isomer
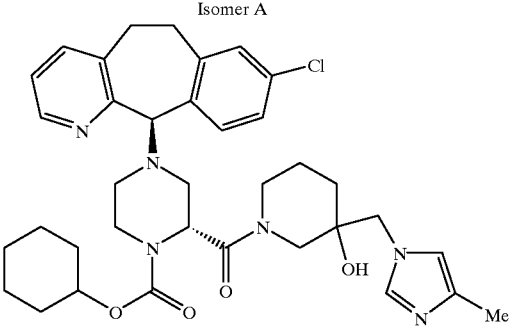
Isomer A
1. Yield (%): 50
2. MH+: 677
3. mp (° C.): 152.6
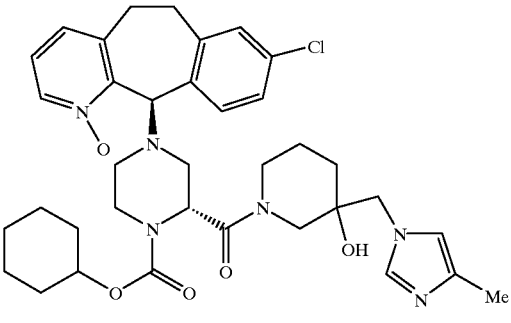
Isomer B
1. Yield (%): 50
2. MH+: 677
3. mp (° C.): 145.4

TABLE 62-continued

| Ex. | Prep. Ex. 1. Amine 2. Acid | Product |
|---|---|---|
| 422 | 1. 83 Step E 2. 175B 11(S) isomer | Isomer A<br>1. Yield (%): 32.7<br>2. MH$^+$: 669<br>3. mp (° C.): 142.2–150.9<br><br>Isomer B<br>1. Yield (%): 32.7<br>2. MH$^+$: 669<br>3. mp (° C.): 133.2–148.1 |
| 423 | 1. 83 Step E 2. 175C 11(R) isomer | Isomer A<br>1. Yield (%): 27<br>2. MH$^+$: 669<br>3. mp (° C.): 177.7 |

TABLE 62-continued
| Ex. | Prep. Ex. 1. Amine 2. Acid | Product |
|---|---|---|
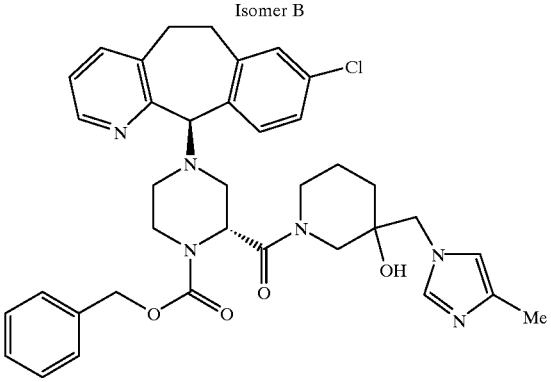
Isomer B
1. Yield (%): 32
2. MH+: 669
3. mp (° C.): 140.1
424  1. 66
     Step G
     2. 32
     11(S)
     isomer
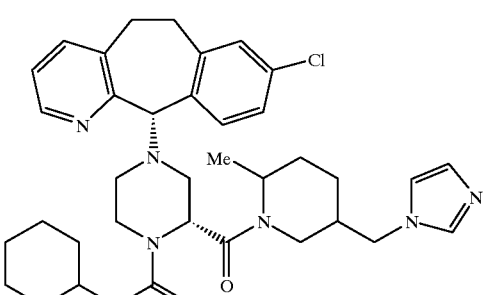
1. Yield (%): 54.5
2. MH+: 645
3. mp (° C.): 127.3
425  1. 83
     Step E
     2. 175 D
     11(S)
     isomer
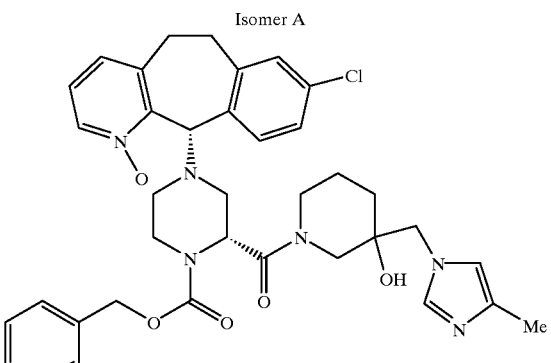
Isomer A
1. Yield (%): 35
2. MH+: 685
3. mp (° C.): 140–142

TABLE 62-continued
| Ex. | Prep. Ex. 1. Amine 2. Acid | Product |
|---|---|---|
| | | Isomer B 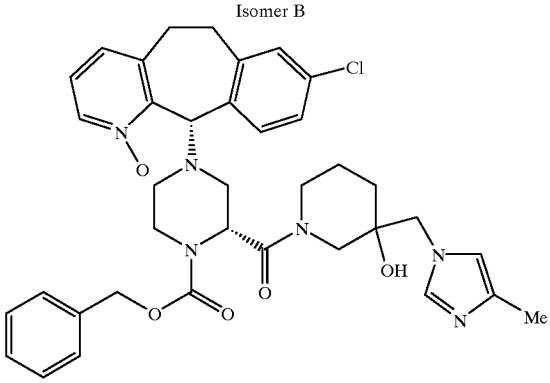 1. Yield (%): 19  2. MH⁺: 685  3. mp (° C.): 133–135 |
Preparative Examples 176–179
Stirring the benzyloxycarbonyl (CBZ) compounds listed in Column 2 of Table 63 and Palladium on carbon catalyst in EtOH under 1 atmosphere of hydrogen gas afforded the Product amines.
TABLE 63
| Prep. Ex. | CBZ compound from Example No. | Product |
|---|---|---|
| 176 | 422 Isomer A | 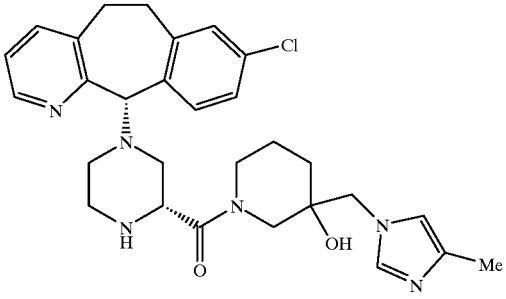 1. Yield (%): 95  2. MH⁺: 535  Isomer A |
| 177 | 422 Isomer B | 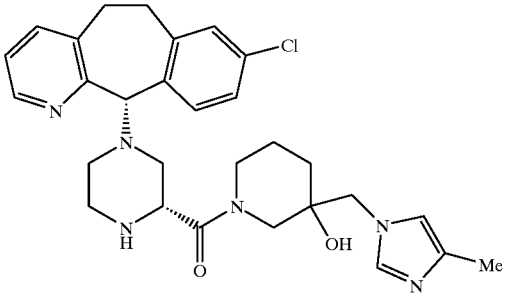 |

TABLE 63-continued

| Prep. Ex. | CBZ compound from Example No. | Product |
|---|---|---|

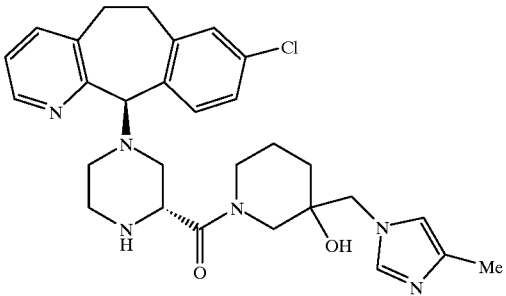

1. Yield (%): 82
2. MH+: 535
Isomer B

178 | 423 Isomer A

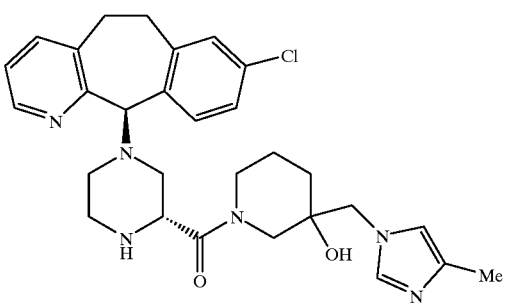

Isomer A

179 | 423 Isomer B

Isomer B

EXAMPLES 426–434

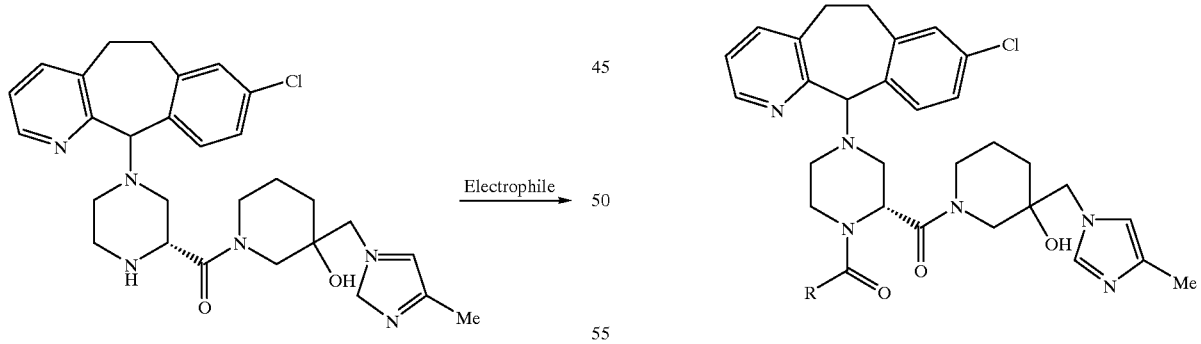

By essentially the same procedure as set forth in Example 14, only substituting the piperazine amines (isomer A or B) listed in column 2 of Table 64 for the title compound from Preparative Example 24, and using as the Electrophile either an isocyanate to give the urea products, or a carboxylic acid, HOBt, DEC and DMF to give the amide products listed in Table 64.

TABLE 64
| Ex. | Prep. Ex. No. of Amine Electrophile | Product |
|---|---|---|
| 426 | 1. 176<br>2. 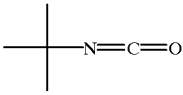 | 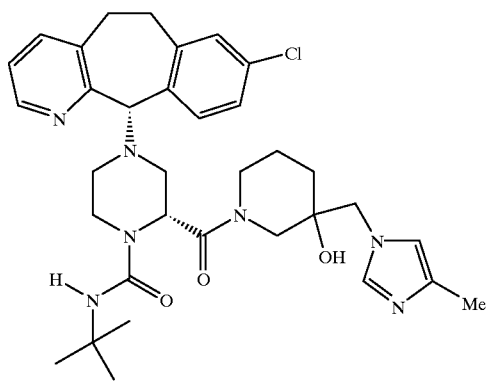<br>1. Yield (%): 100<br>2. MH+: 634<br>3. mp (° C.): 240.2–253.7<br>Isomer A |
| 427 | 1. 177<br>2. 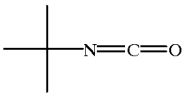 | 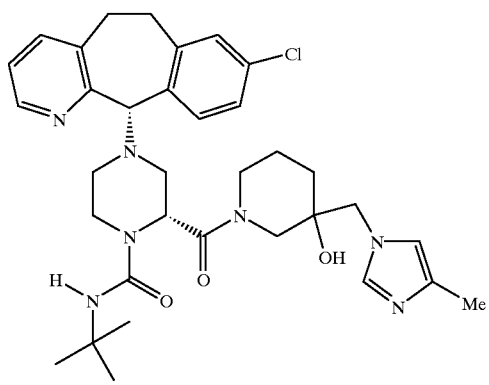<br>1. Yield (%):<br>2. MH+: 634<br>3. mp (° C.): 148.7–164.2<br>Isomer B |
| 428 | 1. 176<br>2. 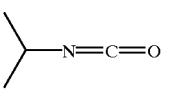 | 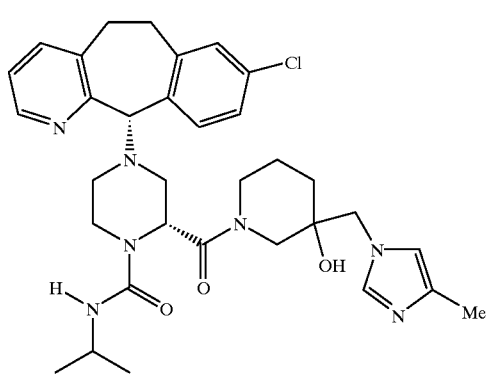<br>1. Yield (%): 75<br>2. MH+: 620<br>3. mp (° C.): 165.5–178.2<br>Isomer A |

TABLE 64-continued
| Ex. | Prep. Ex. No. of Amine Electrophile | Product |
|---|---|---|
| 429 | 1. 176<br>2. 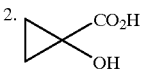 | 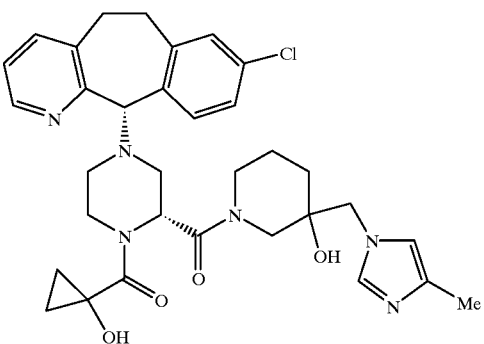<br>1. Yield (%): 21.4<br>2. MH$^+$: 619<br>3. mp (° C.): 148.7–168.3<br>Isomer A |
| 430 | 1. 177<br>2. 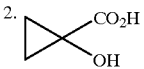 | 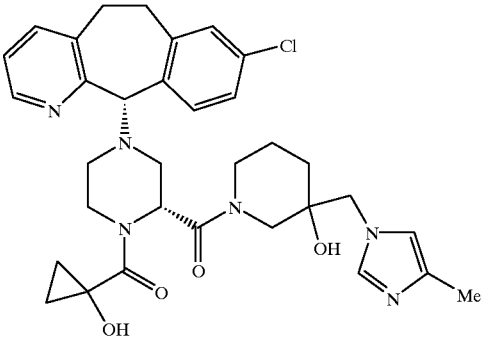<br>1. Yield (%): 10<br>2. MH$^+$: 619<br>3. mp (° C.): 169.2–190.9<br>Isomer B |
| 431 | 1. 176<br>2.  | 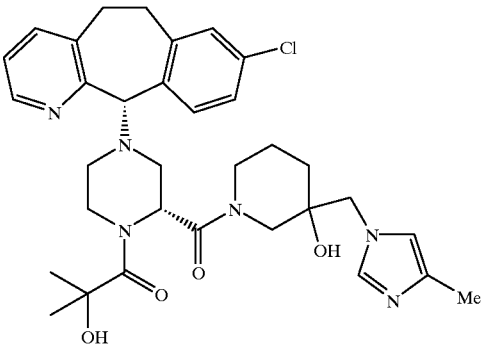<br>1. Yield (%): 29<br>2. MH$^+$: 621<br>3. mp (° C.): 146.5–153.6<br>Isomer A |

TABLE 64-continued

| Ex. | Prep. Ex. No. of Amine Electrophile | Product |
|---|---|---|
| 432 | 1. 177 2. (2-hydroxyisobutyric acid) | 1. Yield (%): 31<br>2. MH+: 621<br>3. mp (° C.): 138.3–161.3<br>Isomer B |
| 433 | 1. 176 2. (2-ethyl-2-hydroxybutyric acid) | 1. Yield (%): 36<br>2. MH+: 649<br>3. mp (° C.): 123.4–133.9<br>Isomer A |
| 434 | 1. 177 2. (2-ethyl-2-hydroxybutyric acid) | 1. Yield (%): 35<br>2. MH+: 649<br>3. mp (° C.): 119.3–135.7<br>Isomer B |

TABLE 64-continued

| Ex. | Prep. Ex. No. of Amine Electrophile | Product |
|---|---|---|
| 435 | 1. 178<br>2. [tert-butyl isocyanate structure] | [Structure]<br>1. Yield (%): 63<br>2. MH⁺: 634<br>3. mp (° C.): 159.2<br>Isomer A |
| 436 | 1. 179<br>2. [tert-butyl isocyanate structure] | [Structure]<br>1. Yield (%): 69<br>2. MH⁺: 634<br>3. mp (° C.): 175<br>Isomer B |
| 437 | 1. 178<br>2. [isopropyl isocyanate structure] | [Structure]<br>1. Yield (%): 77<br>2. MH⁺: 620<br>3. mp (° C.): 167.2<br>Isomer A |

EXAMPLES 438–457

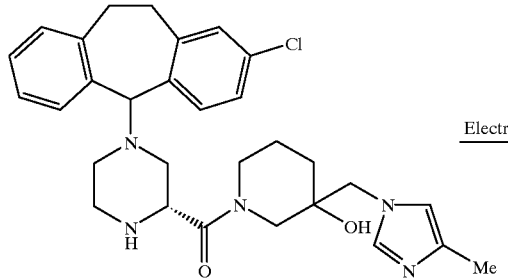

→ Electrophile →

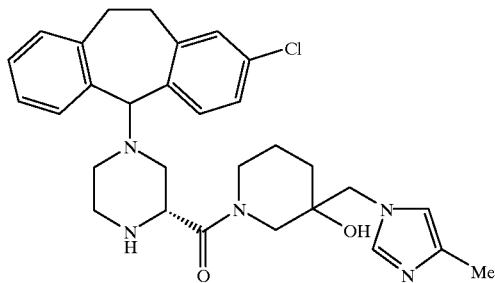

-continued

If the procedure described for Example 426 were followed using the piperazine amines (isomer A or B) listed in column 2 of Table 65 and, as the Electrophile, either an isocyanate, or a carboxylic acid and HOBt, DEC and DMF, then the urea or amide products, respectively, listed in Table 65 would be obtained.

TABLE 65

| Ex. | Prep. Ex. No. of Amine / Electrophile | Product |
|---|---|---|
| 438 | 1. 179<br>2. ⟨isopropyl isocyanate⟩ | ⟨structure⟩ Isomer B |
| 439 | 1. 177<br>2. ⟨isopropyl isocyanate⟩ | ⟨structure⟩ Isomer B |

TABLE 65-continued
| Ex. | Prep. Ex. No. of Amine Electrophile | Product |
|---|---|---|
| 440 | 1. 178<br>2. 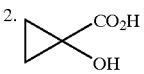 | 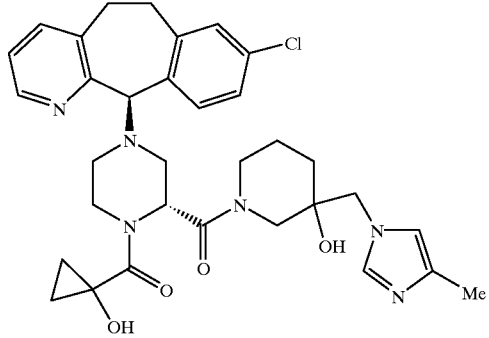<br>Isomer A |
| 441 | 1. 179<br>2. 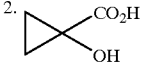 | 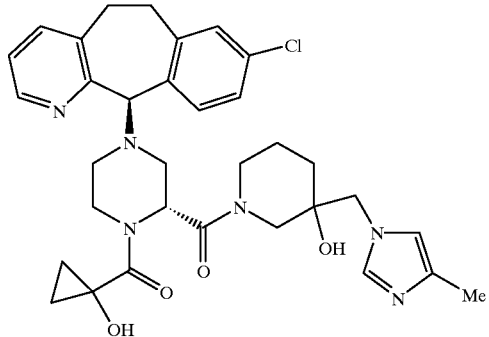<br>Isomer B |
| 442 | 1. 178<br>2.  | 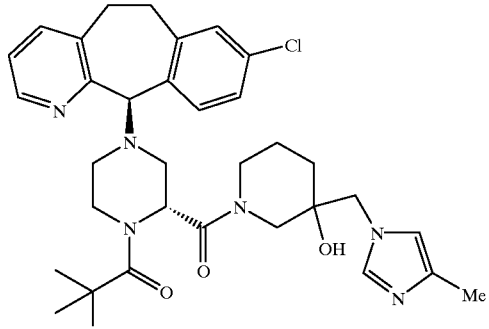<br>Isomer A |
| 443 | 1. 179<br>2. 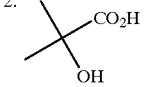 | 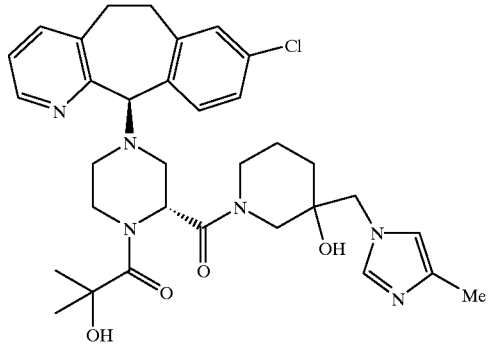<br>Isomer B |

TABLE 65-continued
| Ex. | Prep. Ex. No. of Amine Electrophile | Product |
|---|---|---|
| 444 | 1. 178<br>2. 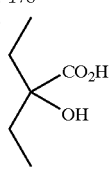 | 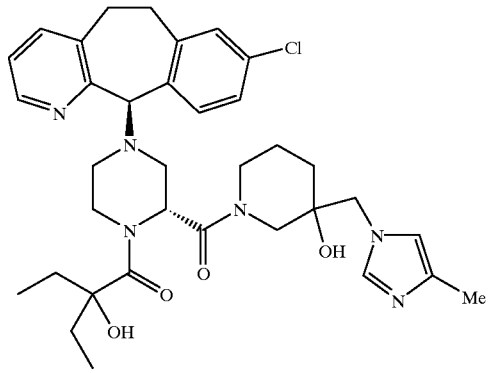<br>Isomer A |
| 445 | 1. 179<br>2. 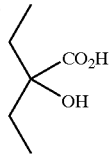 | 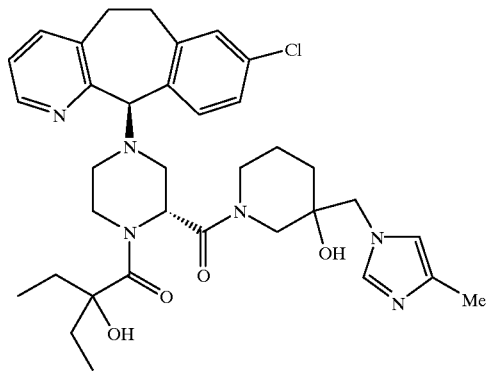<br>Isomer B |
| 446 | 1. 178<br>2. 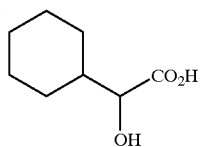 | 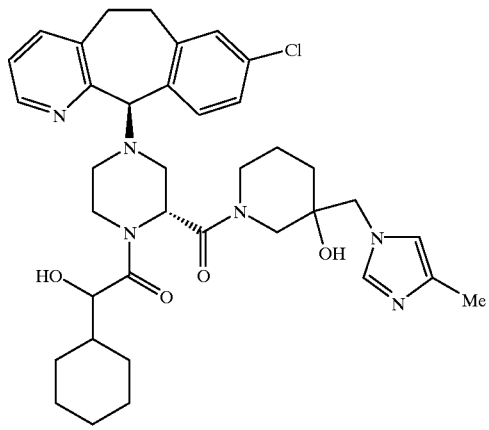<br>Isomer A |

TABLE 65-continued

| Ex. | Prep. Ex. No. of Amine Electrophile | Product |
|---|---|---|
| 447 | 1. 179 2. (cyclohexyl-CH(OH)-CO2H) | (structure) Isomer B |
| 448 | 1. 176 2. (cyclohexyl-CH(OH)-CO2H) | (structure) Isomer A |
| 449 | 1. 177 2. (cyclohexyl-CH(OH)-CO2H) | (structure) Isomer B |

TABLE 65-continued
| Ex. | Prep. Ex. No. of Amine Electrophile | Product |
|---|---|---|
| 450 | 1. 176<br>2. 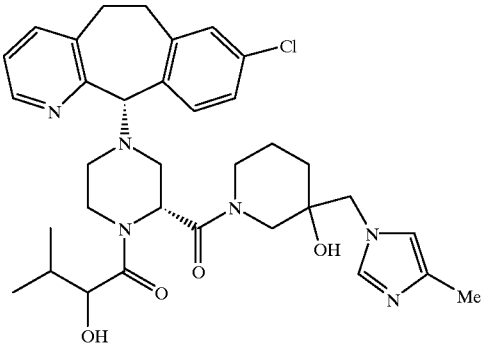 | 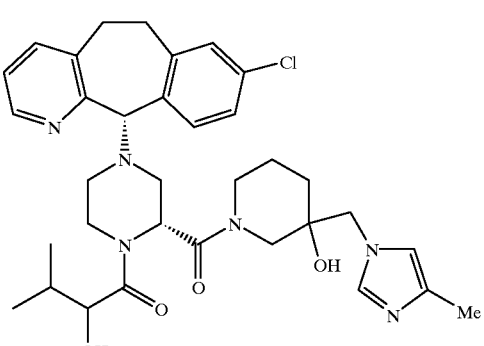<br>Isomer A |
| 451 | 1. 177<br>2. 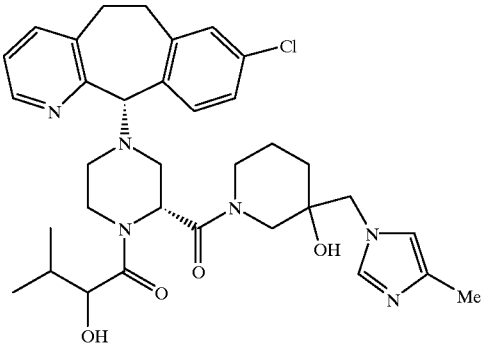 | 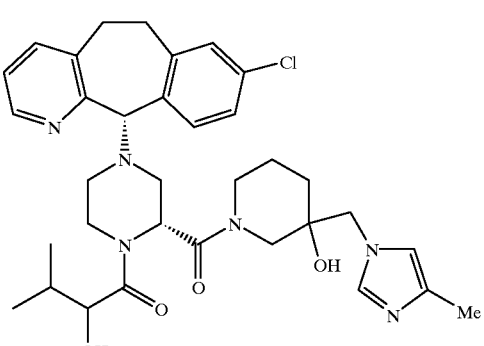<br>Isomer B |
| 452 | 1. 178<br>2. 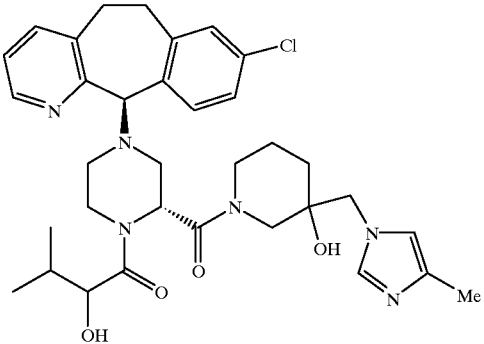 | 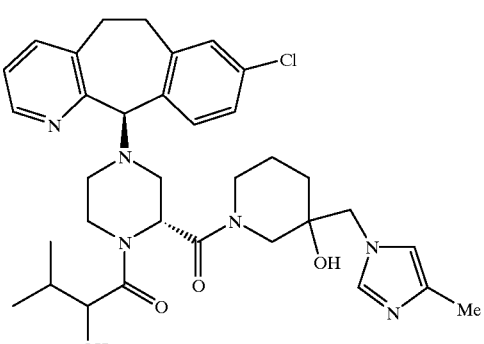<br>Isomer A |
| 453 | 1. 179<br>2. 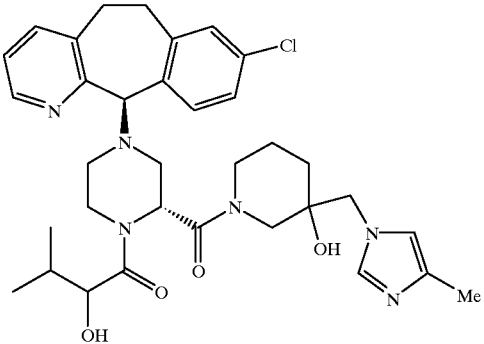 | 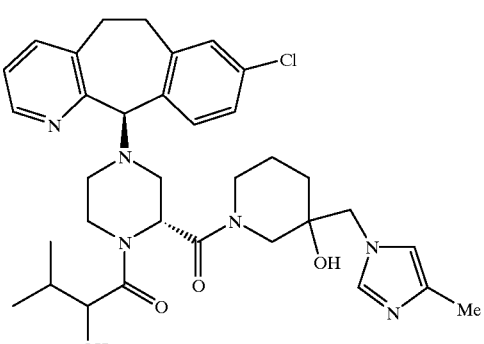<br>Isomer B |

TABLE 65-continued
| Ex. | Prep. Ex. No. of Amine Electrophile | Product |
|---|---|---|
| 454 | 1. 176<br>2. 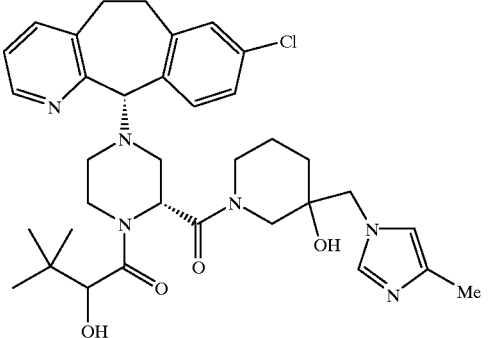 | 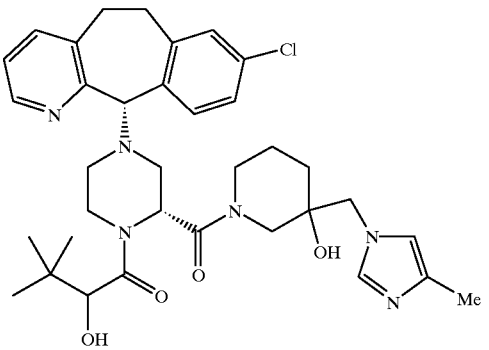<br>Isomer A |
| 455 | 1. 177<br>2. | Isomer B |
| 456 | 1. 178<br>2. 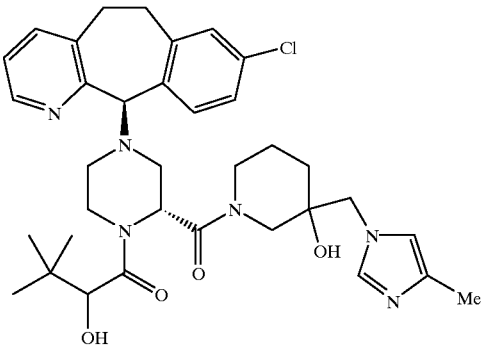 | Isomer A |
| 457 | 1. 179<br>2. | 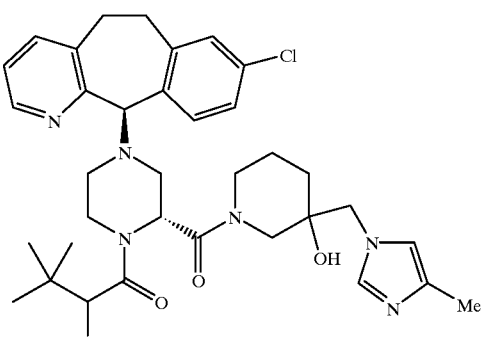<br>Isomer B |

EXAMPLES 458–463

Using a similar procedure as that described for Example 14, only using the piperazine amine from Preparative Example 175 instead of the title compound from Preparative Example 24, and using as the Electrophile either a chloroformate to give a carbamate or an anhydride, or a carboxylic acid, HOBt, DEC and DMF to give the amide products listed in Table 66.

TABLE 66

| Ex. | Electrophile | Product | 1. Yield (%) 2. MH+ 3. mp (° C.) |
|---|---|---|---|
| 458 | cyclopropane with CO₂H and OH | structure | 1. 54.1 2. 603 3. 145.2 |
| 459 | (CH₃)₂C(OH)CO₂H | structure | 1. 67.8 2. 605 3. 86.7 |
| 462 | 3,3-dimethyl dihydrofuran-2,5-dione | structure | 1. 100 2. 647 3. 86.2 |

TABLE 66-continued

| Ex. | Electrophile | Product | 1. Yield (%) 2. MH+ 3. mp (° C.) |
|---|---|---|---|
| 463 | | | 1. 100 2. 661 3. 65.1 |
| 463A | | | 1. 85 2. 647 3. 52.1 |

Preparative Example 180

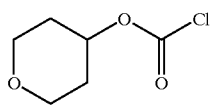

Following essentially the same procedure as that used in Example 466 Step A, except using tetrahydro-4H-pyran-4-ol, the title compound was prepared (3.1 g, 78%, MH+=165).

EXAMPLE 464

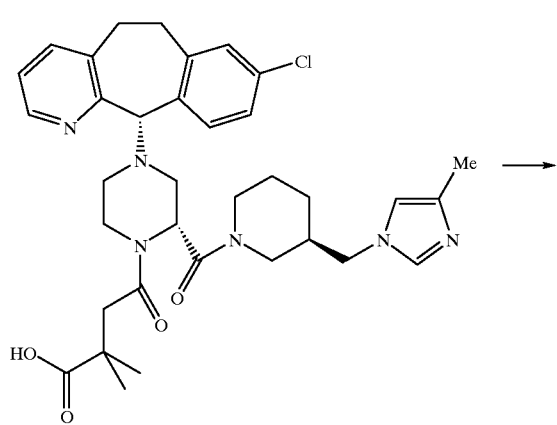

⟶

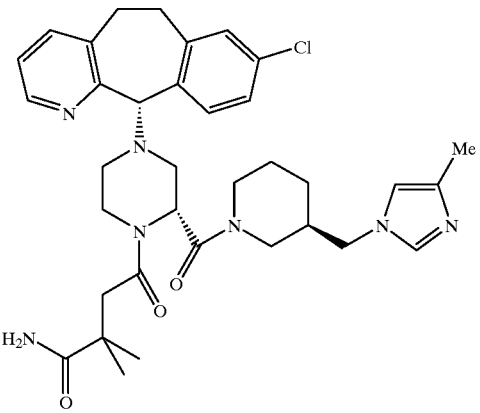

The title compound from Preparative Example 462 (0.205 g), 0.5 M ammonia in dioxane (2 mL), DEC (0.175 g), HOBt (0.123 g) and anhydrous DMF (5 mL) were stirred at room temperature overnight. Purification by preparative plate chromatography (silica, 5% MeOH-CH$_2$Cl$_2$, NH$_4$OH saturated) afforded the title compound (0.136 g, 66%, MH+= 646).

EXAMPLE 465

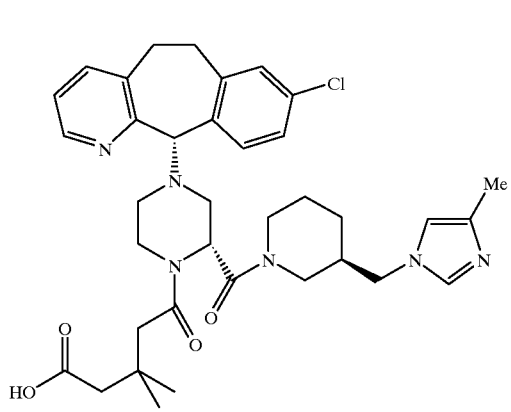

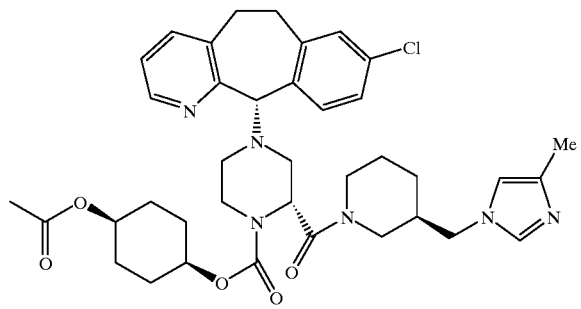

The title compound from Preparative Example 463 (0.228 g), 0.5 M ammonia in dioxane (2 mL), DEC (0.175 g), HOBt (0.123 g) and anhydrous DMF (5 mL) were stirred at room temperature overnight. Purification by preparative plate chromatography (silica, 5% MeOH-CH$_2$Cl$_2$, NH$_4$OH saturated) afforded the title compound (0.139 g, 61%, MH$^+$= 660).

EXAMPLE 466

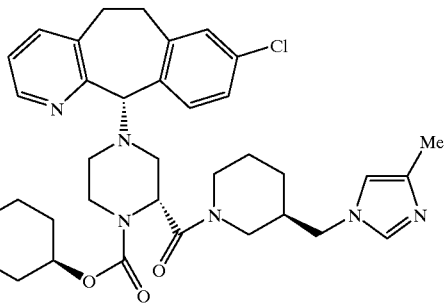

Step A

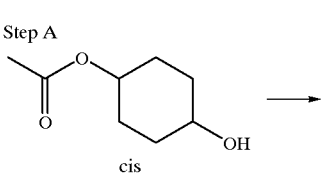

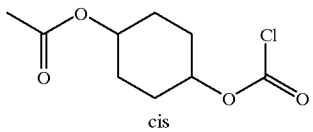

Step A

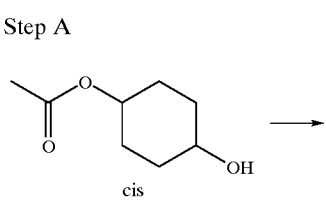

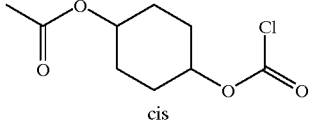

The commercially available cis-acetoxycyclohexanol (0.25 g) was treated with phosgene (2 mL). Concentration in vacuo afforded the chloroformate (0.307 g, 88%).

Step B

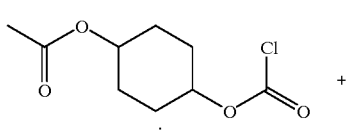

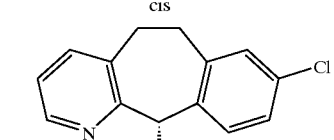

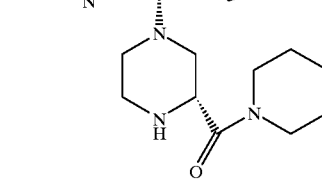

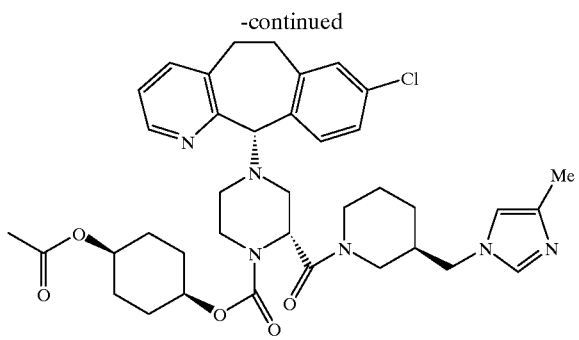

Combining the chloroformate (0.052 g) from Step A with the piperazine amine (0.103 g) from Preparative Example 175 and following a similar procedure as that described in Example 14, the title compound was obtained (0.07 g, 50%, $MH^+=703$).

EXAMPLE 467

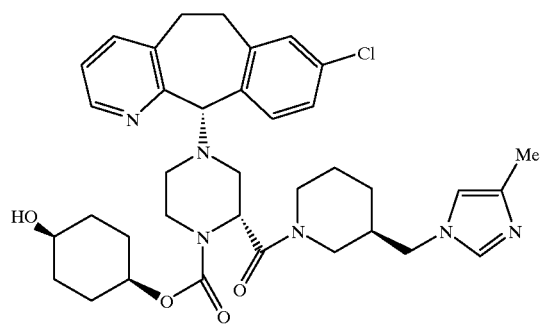

Treatment of the product from Example 466 (0.06 g) with potassium carbonate (0.2 g) in MeOH (2 mL) afforded the title compound (0.056 g, 100%, $MH^+=661$).

EXAMPLE 468

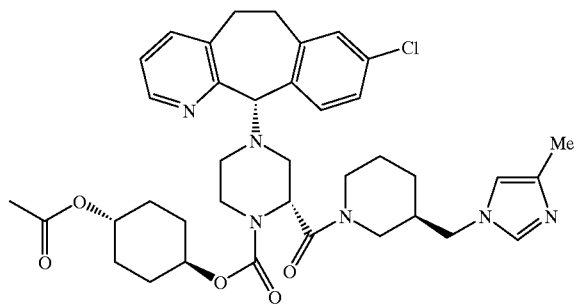

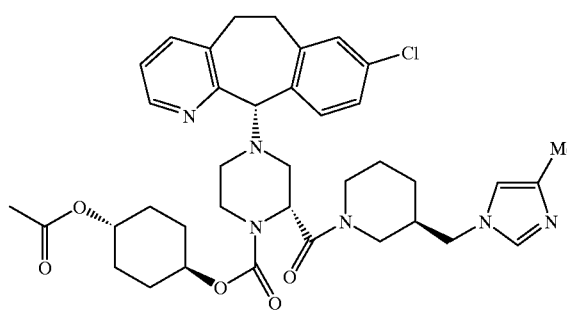

Step A

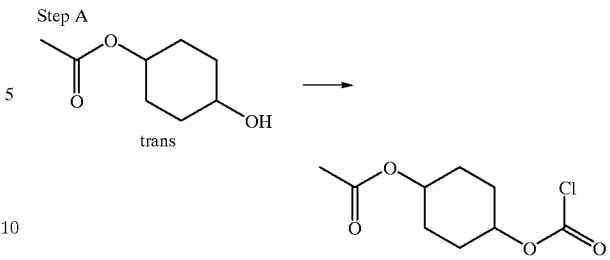

Step A

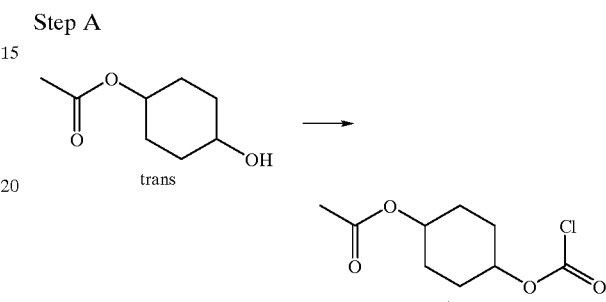

The commercially available trans-acetoxycyclohexanol (0.05 g) was treated with phosgene (0.5 mL). Concentration in vacuo afforded the chloroformate (0.062 g, 89%).

Step B

Step B

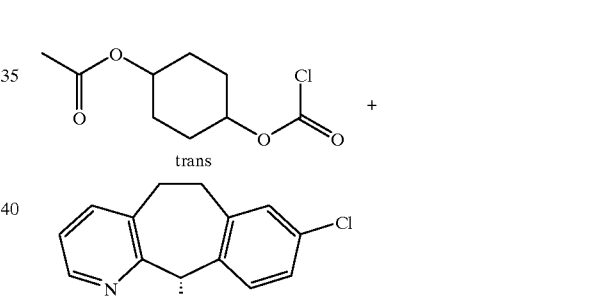

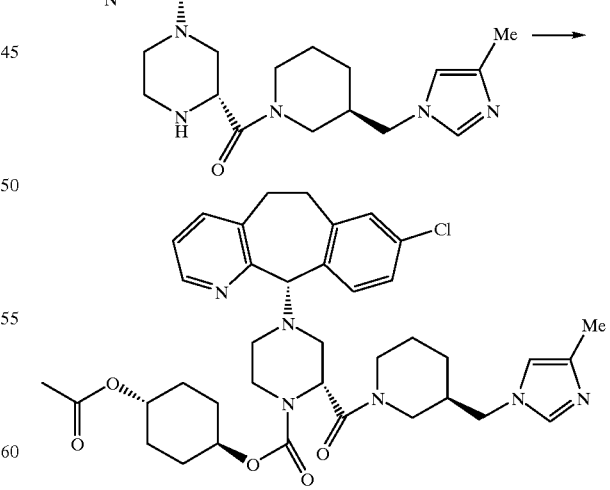

Combining the chloroformate (0.062 g) from Step A with the piperazine amine (0.103 g) from Preparative Example 175 and following a similar procedure as that described in Example 14, the title compound was obtained (0.058 g, 42%, $MH^+=703$).

EXAMPLE 469

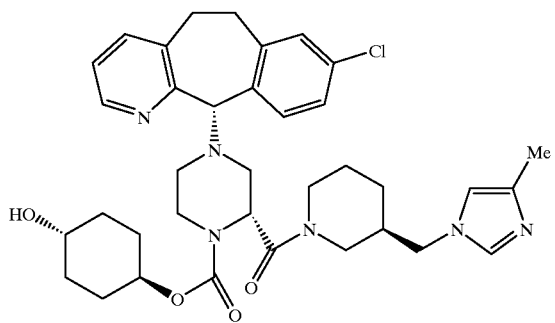

Treatment of the product from Example 466 (0.05 g) with potassium carbonate (0.2 g) in MeOH (2 mL) afforded the title compound (0.047 g, 100%, MH$^+$=661).

EXAMPLE 470

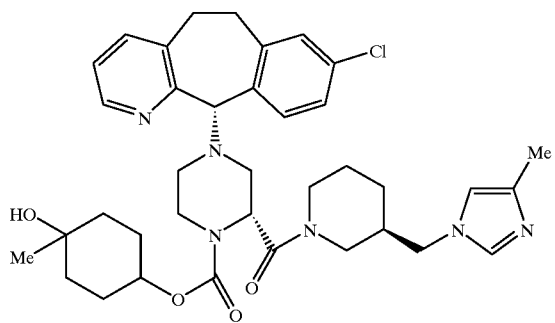

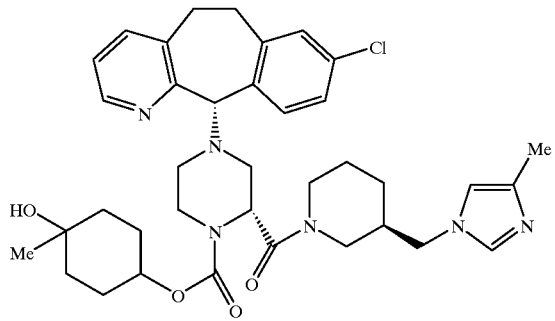

Step A

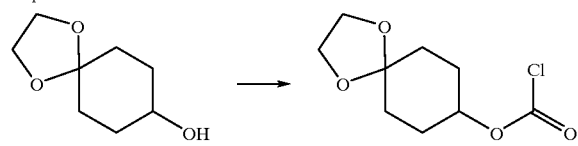

Step A

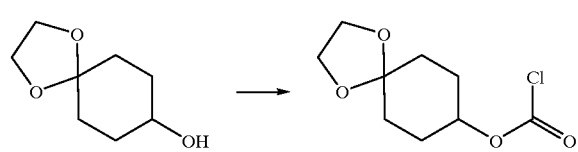

If the commercially available cyclohexanol were treated with phosgene then the chloroformate would be obtained.

Step B

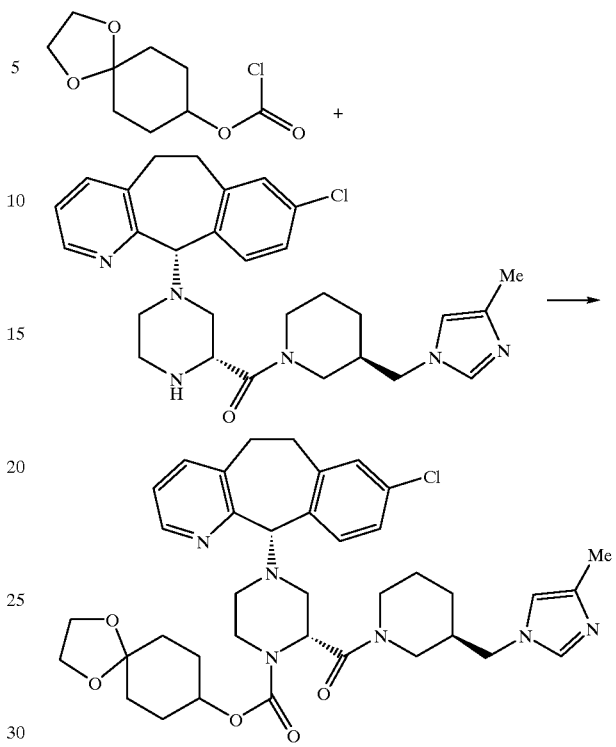

If the chloroformate from Step A were combined with the piperazine amine shown above according to the procedure described for Example 461 then the ketal would be obtained.

Step C

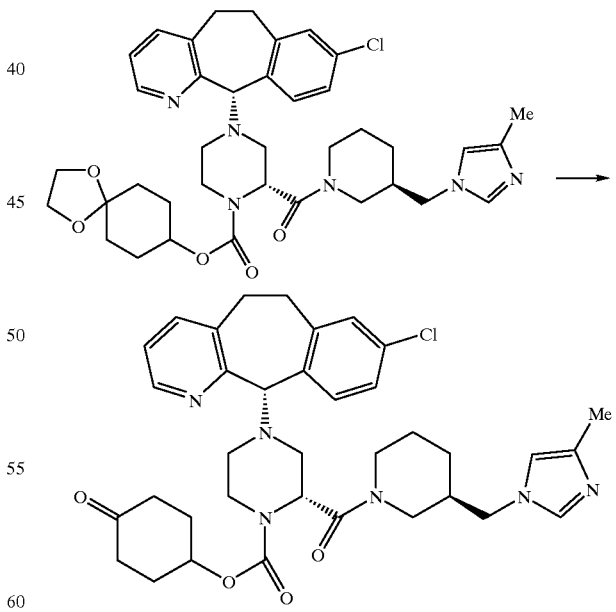

If the product of Step B were treated with aqueous acid the ketone would be obtained.

Step D

If the product of Step C were treated with MeMgBr or MeLi then the title product would be obtained.

EXAMPLE 471

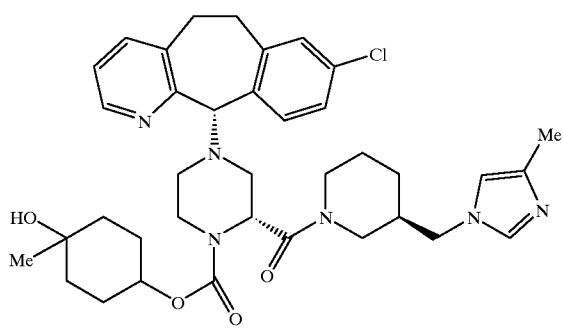

Step A

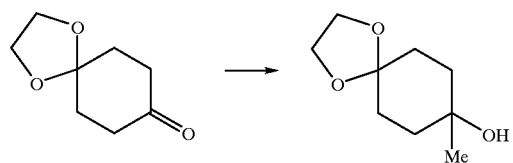

If the commercially available ketone were treated with methyl magnesium bromide, then the desired alcohol would be obtained.

Step B

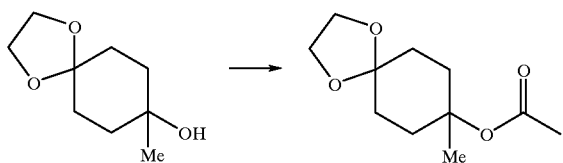

If the product of Step A above were treated with acetic anhydride, then the desired acetate would be obtained.

Step C

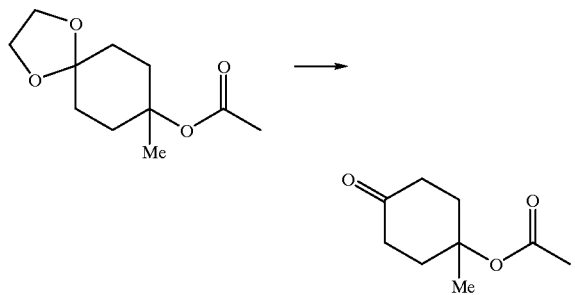

If the product of Step B were treated with formic acid, then the desired ketone would be obtained.

ASSAYS

FPT $IC_{50}$ (inhibition of farnesyl protein transferase, in vitro enzyme assay) was determined following the assay procedures described in WO 95/10516, published Apr. 20, 1995. GGPT $IC_{50}$ (inhibition of geranylgeranyl protein transferase, in vitro enzyme assay), Cell Mat Assay, COS Cell $IC_{50}$ (Cell-Based Assay), and anti-tumor activity (in vivo anti-tumor studies) could be determined by the assay procedures described in WO 95/10516. The disclosure of WO 95/10516 is incorporated herein by reference thereto.

Additional assays can be carried out by following essentially the same procedure as described above, but with substitution of alternative indicator tumor cell lines in place of the T24-BAG cells. The assays can be conducted using either DLD-1-BAG human colon carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10–16 days at 37° C. under 5% $CO_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

Compounds of this invention had an FPT $IC_{50}$ within the range of <0.04 nM to 20 nM, and a Soft Agar $IC_{50}$ within the range of <0.5 nM to >500 nM.

Compounds of Examples 1–4, 4.1, 4.2, 5, 7, 8, 10–19, 24–51, and 74, 138, 142, 144, 145 had an FPT $IC_{50}$ within the range of <0.04 nM to 2.7 nM. Compounds of Examples 1–4, 4.1, 4.2, 5, 7, 10–19, 24–51, and 74, 138, 142, 144, 145 had a Soft Agar $IC_{50}$ within the range of <0.5 nM to 30 nM.

Compounds of Examples 35(A), 35(C), 35(D), 35(E), 35(F), 41(A), 41(B), 41(C), 47(A), 47(B), 47(D), 47(G), 47(H), 47(I), 47(K), 47(L), 47(M), 47(N), 47(O), 47(P), 47(R), 47(S), 47(T), 47(U), 47(CC), 51(A) to 51 (D), 138 A to 147A, 148 to 158, 160, 161, 163, 169 to 180, 183 to 188, 191, 192, 197, 201, 207 to 216, 227 to 234, 238 to 240, 245, 255 to 262, 287 to 294, 297 to 303, 316 to 324, 351 to 354, 383, 384, 387, 388, 391, 392, 394 to 397, 407, 408, 409, 410, 411, 412, 414, 415 to 417, 419, 422 and 424 had an FPT $IC_{50}$ within the range of <0.04 to 2.7 nM, and a Soft Agar $IC_{50}$ within the range of <0.05 to 30 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

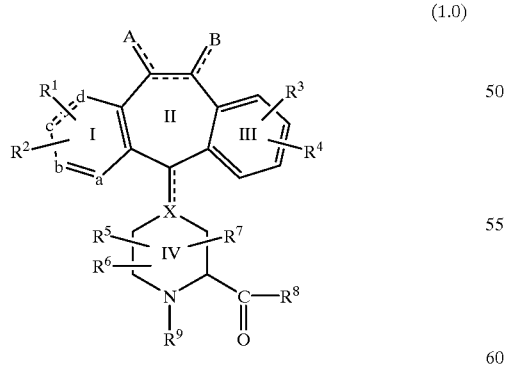

(1.0)

or a pharmaceutically acceptable salt or solvate thereof, wherein one of a, b, c and d represents N or N$^+$O$^-$, and the remaining a, b, c and d groups represent CR$^1$ or CR$^2$; each R$^1$ and each R$^2$ is independently selected from H, halo, —CF$_3$, —OR$^{10}$, —COR$^{10}$, —SR$^{10}$, —S(O)$_t$R$^{11}$ (wherein t is 0, 1 or 2), —N(R$^{10}$)$_2$, —OC(O)R$^{10}$, —CO$_2$R$^{10}$, —OCO$_2$R$^{11}$, —CN, —NR$^{10}$COOR$^{11}$, —SR$^{11}$C(C(O)OR$^{11}$, —SR$^{11}$N(R$^{75}$)$_2$ (provided that R$^{11}$ in —SR$^{11}$N(R$^{75}$)$_2$ is not —CH$_2$—) wherein each R$^{75}$ is independently selected from H, —C(O)OR$^{11}$, benzotriazol-1-yloxy, tetrazol-5-ylthio, substituted tetrazol-5-ylthio, alkynyl, alkenyl or alkyl, said alkyl or alkenyl group optionally being substituted with halo, —OR$^{10}$ or —CO$_2$R$^{10}$;

R$^3$ and R$^4$ are the same or different and each independently represents H, any of the substituents of R$^1$ and R$^2$, or R$^3$ and R$^4$ taken together represent a saturated or unsaturated C$_5$–C$_7$ fused ring to the benzene ring (Ring III);

R$^5$, R$^6$, and R$^7$ each independently represents H, —CF$_3$, —COR$^{10}$, alkyl or aryl, said alkyl or aryl optionally being substituted with —OR$^{10}$, —SR$^{10}$, —S(O)$_t$R$^{11}$, —NR$^{10}$COOR$^{11}$, —N(R$^{10}$)$_2$, —NO$_2$, —COR$^{10}$, —OCOR$^{10}$, —OCO$_2$R$^{11}$, —CO$_2$R$^{10}$, OPO$_3$R$^{10}$, or R$^5$ is combined with R$^6$ to represent =O or =S; provided that for the groups —OR$^{10}$, —SR$^{10}$, and —N(R$^{10}$)$_2$R$^{10}$ is not H;

R$^{10}$ represents H, alkyl, aryl, or aralkyl;

R$^{11}$ represents alkyl or aryl;

X represents N and the optional bond (represented by the dotted line) to carbon atom 11 is absent;

the dotted line between carbon atoms 5 and 6 represents an optional bond, such that when a double bond is present, A and B independently represent —R$^{10}$, halo, —OR$^{11}$, —OCO$_2$R$^{11}$ or —OC(O)R$^{10}$, and when no double bond is present between carbon atoms 5 and 6, A and B each independently represent H$_2$, —(OR$^{11}$)$_2$, H and halo, dihalo, alkyl and H, (alkyl)$_2$, —H and —OC(O)R$^{10}$, H and —OR$^{10}$, =O, aryl and H, =NOR$^{10}$ or —O—(CH$_2$)$_p$—O— wherein p is 2, 3 or 4;

R$^8$ represents a heterocyclic ring selected from:

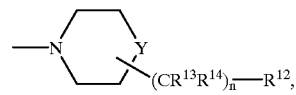

(2.0)

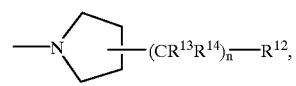

(3.0)

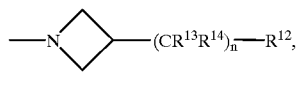

(4.0)

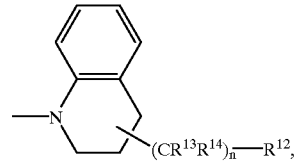

(5.0)

(6.0)

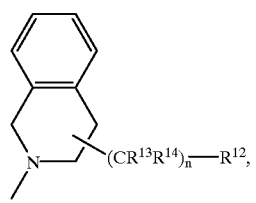

(7.0)

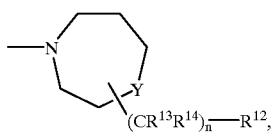

(2.1)

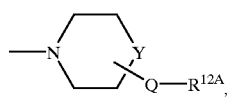

(3.1)

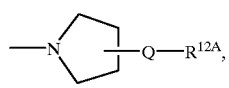

(4.1)

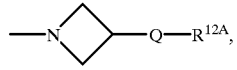

(5.1)

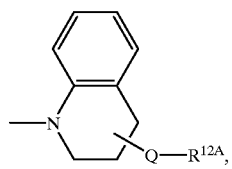

(6.1)

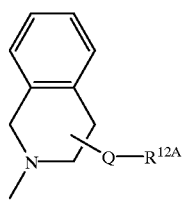

or (7.1)

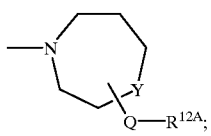

said heterocyclic rings (2.0 to 7.0 and 2.1 to 7.1) being optionally substituted with one or more substituents independently selected from:
(a) alkyl,
(b) substituted alkyl wherein said substituents are selected from: halo, aryl, —OR$^{15}$, —N(R$^{15}$)$_2$, heteroaryl, heterocycloalkyl, or cycloalkyl, wherein each R$^{15}$ group is the same or different, provided that said optional substituent is not bound to a carbon atom that is adjacent to an oxygen or nitrogen atom, and wherein R$^{15}$ is selected from: H, alkyl, aryl, arylalkyl, heteroaryl, heteroarylalkyl, cycloalkyl, or cycloalkylalkyl;
(c) hydroxyl, with the proviso that carbon atoms adjacent to the nitrogen, sulfur or oxygen atoms of the ring are not substituted with hydroxyl;
(d) alkyloxy; or
(e) arylalkyloxy;

Y represents CH$_2$, NR$^{16}$, O, S, SO, or SO$_2$ wherein R$^{16}$ is selected from: H, alkyl, cycloalkyl, cycloalkylalkyl, aryl, arylalkyl, heteroaryl, heteroarylalkyl, acyl, aroyl, carbamoyl, carboxamido, alkylsulfonyl, arylsulfonyl, arylalkylsulfonyl, sulfonamido, alkylsulfonamido, arylsulfonamido or arylalkylsulfonamido;

n is 0 to 6;

Q represents O or N, provided that Q is not adjacent to a heteroatom in the heterocycloalkyl rings of 2.1, 3.1, 4.1, 5.1, 6.1 and 7.1;

R$^{12}$ is selected from:

(8.0)

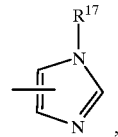

(9.0)

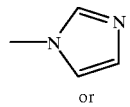

or (9.1)

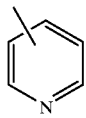

wherein R$^{17}$ is selected from: (1) H, (2) alkyl, (3) aryl, (4) arylalkyl, (5) substituted arylalkyl wherein the substituents are selected from halo or CN, (6) —C(aryl)$_3$, (7) cycloalkyl, (8) substituted alkyl (as defined above in (b)), or (9) cycloalkylalkyl;

R$^{12A}$ is selected from rings 8.0 or 9.1, defined above;

said imidazolyl ring 8.0 optionally being substituted with one or two substituents, said imidazole ring 9.0 optionally being substituted with 1–3 substituents, and said pyridyl ring 9.1 optionally being substituted with 1–4 substituents, wherein said optional substituents for rings 8.0, 9.0 and 9.1 are bound to the carbon atoms of said rings and are independently selected from: —NHC(O)R$^{15}$, —C(R$^{16}$)$_2$OR$^{19}$, —OR$^{15}$, —SR$^{15}$, F, Cl, Br, alkyl, substituted alkyl (as defined above in (b)), aryl, arylalkyl, cycloalkyl, or —N(R$^{15}$)$_2$; R$^{15}$ is as defined above; each R$^{18}$ is independently selected from H or alkyl; $R^{19}$ is selected from H or —C(O)NHR$^{20}$, and $R^{20}$ is as defined below;

$R^{13}$ and $R^{14}$ for each n are independently selected from: H, F, alkyl, aryl, arylalkyl, heteroaryl, heteroarylalkyl, cycloalkyl, cycloalkylalkyl or —CON($R^{15}$)$_2$ (wherein $R^{15}$ is as defined above), —OR$^{15}$ or —N($R^{15}$)$_2$ provided that the —OR$^{15}$ and —N($R^{15}$)$_2$ groups are not bound to a carbon atom that is adjacent to a nitrogen atom, and provided that there can be only one —OH group on each carbon; and the substitutable $R^{13}$ and $R^{14}$ groups are optionally substituted with one or more substituents selected from: F, alkyl, cycloalkyl, arylalkyl, or heteroarylalkyl; or $R^{13}$ and $R^{14}$, for each n, together with the carbon atom to which they are bound, form a $C_3$ to $C_6$ cycloalkyl ring;

$R^9$ is selected from:

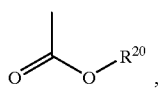
(12.0)

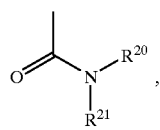
(13.0)

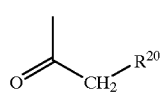
(14.0)

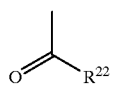
(15.0)

or

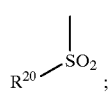
(16.0)

$R^{20}$ is selected from: H, alkyl, aryl, arylalkyl, cycloalkyl, cycloalkylalkyl, heteroaryl, heteroarylalkyl, heterocycloalkyl, or heterocyloalkylalkyl, provided that $R^{20}$ is not H when $R^9$ is group 12.0 or 16.0;

when $R^{20}$ is other than H, then said $R^{20}$ group is optionally substituted with one or more substituents selected from, halo, alkyl, aryl, —OC(O)R$^{15}$, —OR$^{15}$ or —N($R^{15}$)$_2$, wherein each $R^{15}$ group is the same or different, and wherein $R^{15}$ is as defined above, provided that said optional substituent is not bound to a carbon atom that is adjacent to an oxygen or nitrogen atom;

$R^{21}$ is selected from: H, alkyl, aryl, arylalkyl, cycloalkyl, cycloalkylalkyl, heteroaryl, heteroarylalkyl, heterocycloalkyl or heterocycloalkylalkyl;

$R^{21}$ is other than H, then said $R^{21}$ group is optionally substituted with one or more substituents selected from: alkyl, or aryl; and $R^{22}$ is selected from cycloalkyl, heterocycloalkyl, aryl, substituted aryl, alkyl, substituted alkyl or substituted cycloalkyl.

2. The compound of claim 1 having the structure

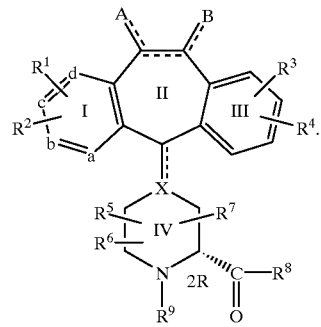
(1.0A)

3. The compound of claim 1 having the structure:

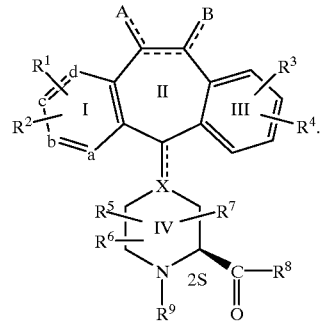
(1.0B)

4. The compound of claim 1 wherein $R^1$ to $R^4$ is independently selected from H, Br, F or Cl; $R^5$ to $R^7$ is H; a is N and the remaining b, c and d substituents are carbon; A and B are $H_2$; and n is 1 to 3.

5. The compound of claim 1 wherein $R^8$ is ring 2.0 and the —(CR$^{13}$R$^{14}$)$_n$—R$^{12}$ substituent is in the 2- or 3-position.

6. The compound of claim 1 wherein $R^8$ is ring 2.0 and the —(CR$^{13}$R$^{14}$)$_n$—R$^{12}$ substituent is in the 2- or 3-position, and Y is $CH_2$.

7. The compound of claim 1 wherein $R^{13}$ and $R^{14}$ are H.

8. The compound of claim 1 wherein Y is selected from S, SO, or $SO_2$.

9. The compound of claim 1 wherein Y is O.

10. The compound of claim 1 wherein Y is NR$^{16}$.

11. The compound of claim 1 wherein $R^9$ is group 12.0.

12. The compound of claim 1 wherein $R^9$ is group 13.0.

13. The compound of claim 1 wherein $R^9$ is group 15.0.

14. The compound of claim 1 wherein $R^1$ to $R^4$ is independently selected from H, Br, F or Cl; $R^5$ to $R^7$ is H, a is N and the remaining b, c and d substituents are carbon; A and B are $H_2$; and n is 1 to 3; $R^8$ is ring 2.0 and the —(CR$^{13}$R$^{14}$)$_n$—R$^{12}$ substituent is in the 2- or 3-position, and Y is $CH_2$.

15. The compound of claim 2 wherein $R^1$ to $R^4$ is independently selected from H, Br, F or Cl; $R^5$ to $R^7$ is H, a is N and the remaining b, c and d substituents are carbon; A and B are H$_2$; and n is 1 to 3; r$^5$ is ring 2.0 and the —(CR$^{13}$R$^{14}$)$_n$—R$^{12}$ substituent is in the 2- or 3-position, and Y is CH$_2$.

16. The compound of claim 15 wherein R$^{13}$ and R$^{14}$ are H.
17. The compound of claim 16 wherein R$^{12}$ is 9.0.
18. The compound of claim 16 wherein R$^9$ is 12.0.
19. The compound of claim 16 wherein R$^9$ is 13.0.
20. The compound of claim 16 wherein R$^9$ is 15.0.
21. The compound of claim 16 wherein R$^{20}$ is selected from t-butyl, i-propyl, neopentyl, cyclohexyl, cyclopropylmethyl,

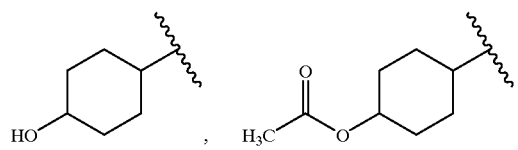

,

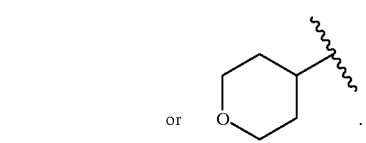

or .

22. The compound of claim 15 wherein R$^9$ is selected from 12.0 or 13.0, and wherein R$^{21}$ for 13.0 is H.

23. A method of inhibiting the abnormal growth of cells selected from: pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, melanoma, breast tumor cells or prostate tumor cells in a patient in need thereof by the inhibition of farnesyl protein transferase comprising administering to the patient an effective amount of a compound of claim 1.

24. A method of inhibiting farnesyl protein transferase in a patient in need thereof comprising administering to the patient an effective amount of the compound of claim 1.

25. A pharmaceutical composition comprising an effective amount of compound of claim 1 in combination with a pharmaceutically acceptable carrier.

26. A compound selected from:
(1) A compound selected from:

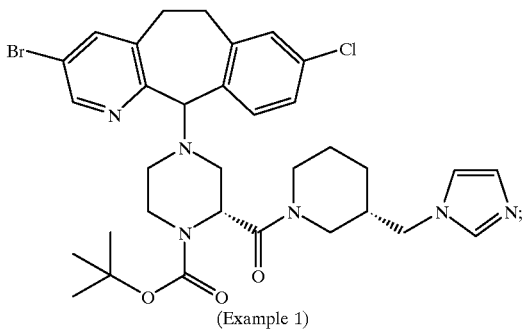

(Example 1)

(2) a compound of the formula:

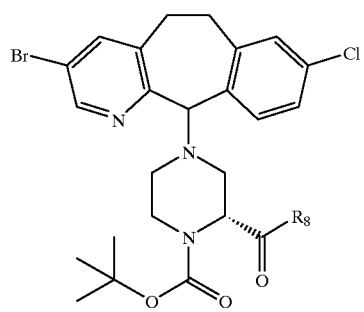

wherein R$^8$ is selected from:

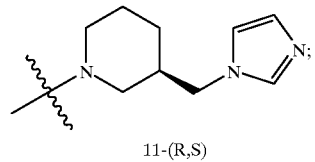

11-(R,S)

(Example 2)

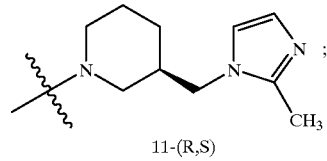

11-(R,S)

(Example 3)

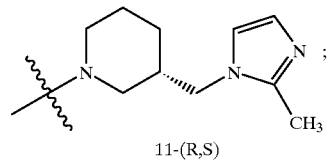

11-(R,S)

(Example 4)

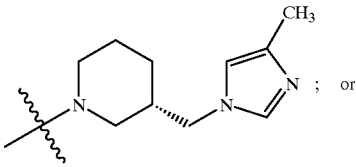

; or (Example 4.1)

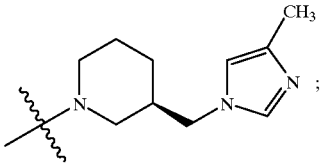

;

(Example 4.2)

(3) a compound of the formula:
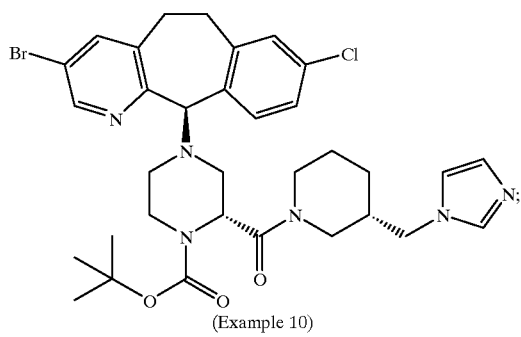
(Example 10)
(4) a compound of the formula:
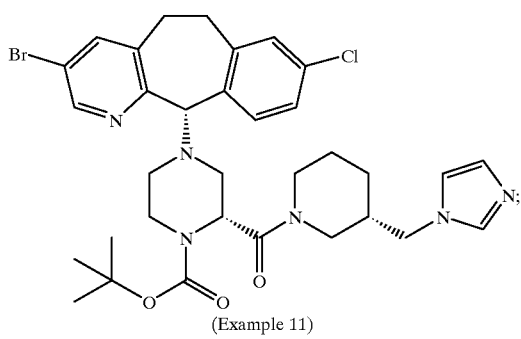
(Example 11)
(5) a compound of the formula:
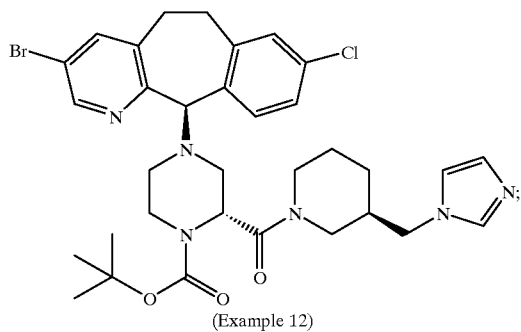
(Example 12)
(6) a compound of the formula:
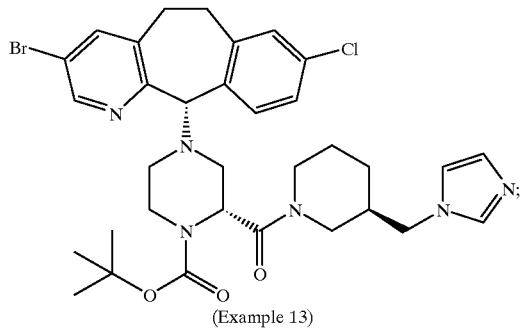
(Example 13)
(7) a compound of the formula:
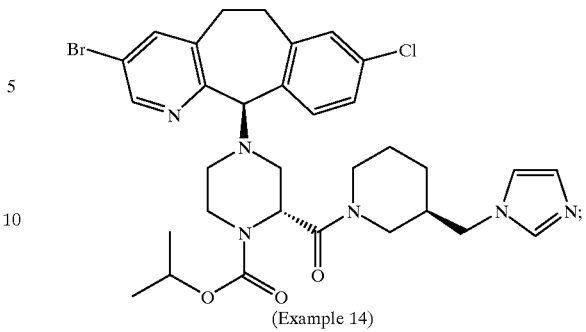
(Example 14)
(8) a compound of the formula:
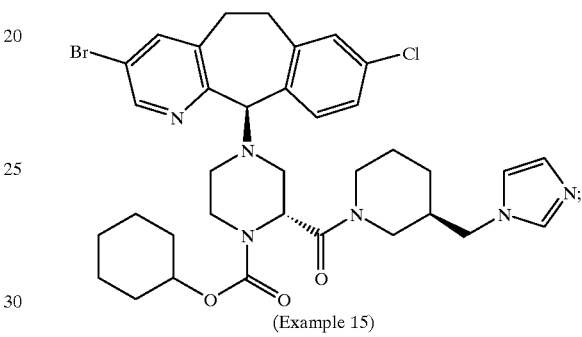
(Example 15)
(9) a compound of the formula:
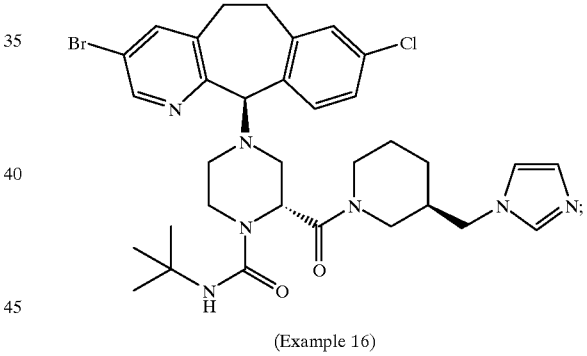
(Example 16)
(10) a compound of the formula:
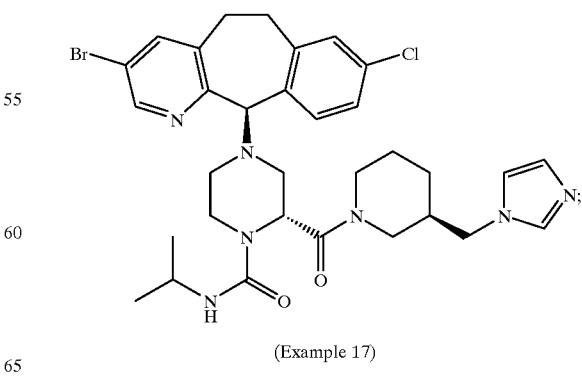
(Example 17)

(11) a compound of the formula:
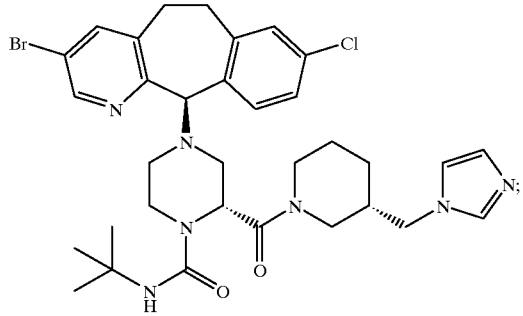
(Example 18)
(12) a compound of the formula:
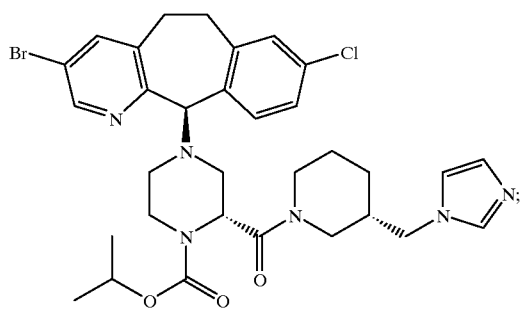
(Example 19)
(13) a compound of the formula:
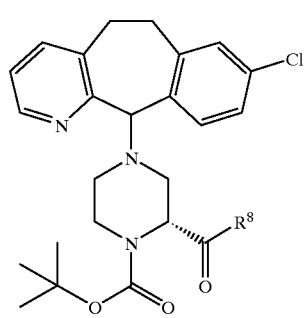
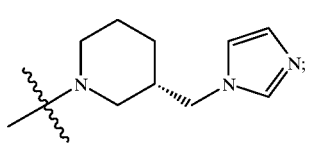
(Example 24)
(C-11 isomer: S)
-continued
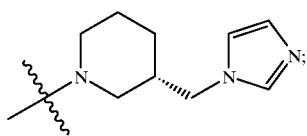
(Example 25)
(C-11 isomer: R)
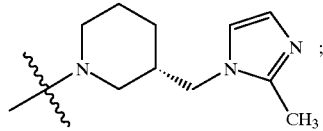
(Example 26)
(C-11 isomer: S)
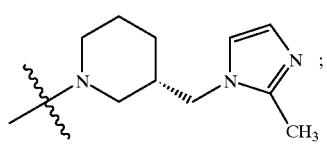
(Example 27)
(C-11 isomer: R)
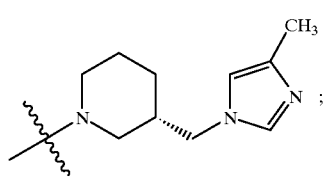
(Example 28)
(C-11 isomer: S)
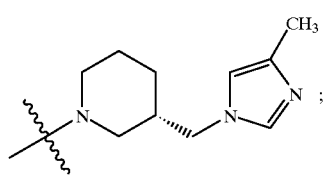
(Example 29)
(C-11 isomer: R)
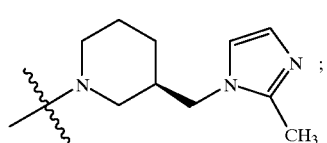
(Example 30)
(C-11 isomer: S)
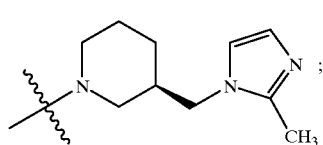
(Example 31)
(C-11 isomer: R)

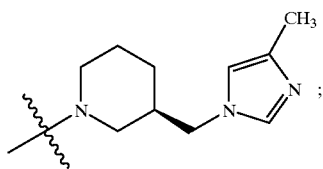
(Example 32)
(C-11 isomer: S)
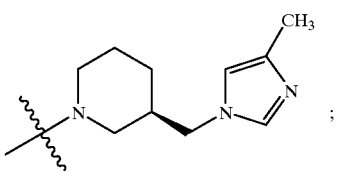
(Example 33)
(C-11 isomer: R)
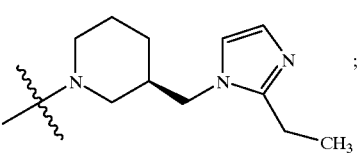
(Example 34)
(C-11 isomer: S)
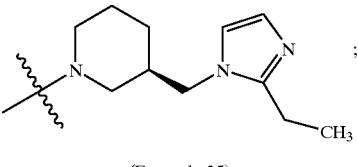
(Example 35)
(C-11 isomer: R)
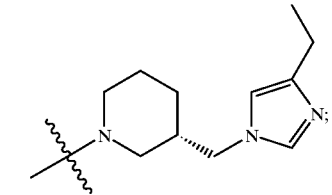
(Example 35A)
(C-11 isomer: S)
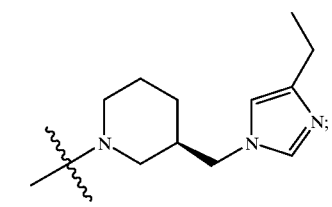
(Example 35C)
(C-11 isomer: S)
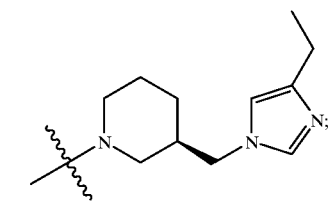
(Example 35D)
(C-11 isomer: R)
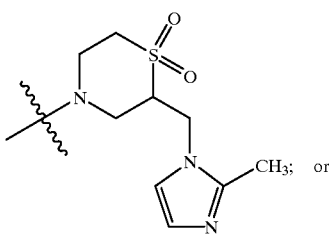
(Example 35E)
(C-11 isomer: R)
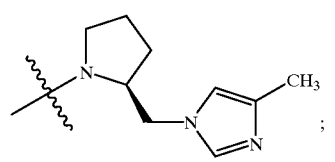
(Example 35F)
(C-11 isomer: S)
(14) a compound of the formula:
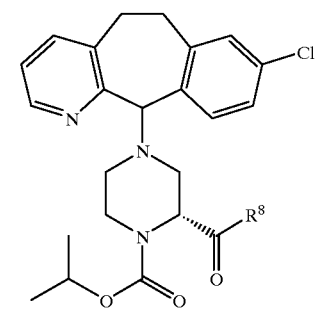
wherein $R^8$ is selected from:
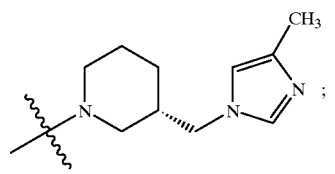
(Example 36)
(C-11 isomer: S)
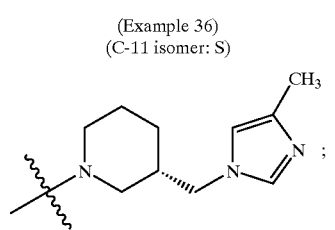
(Example 37)
(C-11 isomer: R)
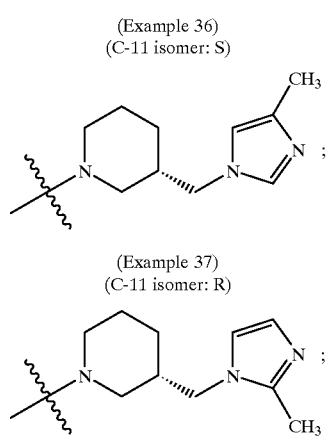
(Example 38)
(C-11 isomer: S)

-continued
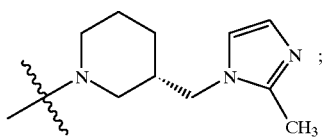
(Example 39)
(C-11 isomer: R)
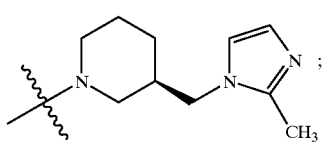
(Example 40)
(C-11 isomer: S)
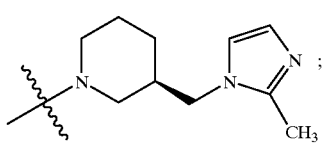
(Example 41)
(C-11 isomer: R)
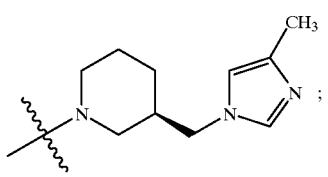
(Example 41A)
(C-11 isomer: S)
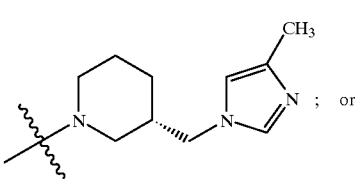     ; or
(Example 41B)
(C-11 isomer: R)
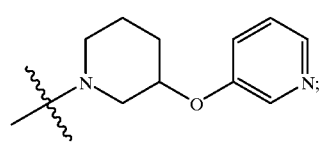
Isomer 1,2
(Example 41C)
(C-11 isomer: S)
(15) a compound of the formula:
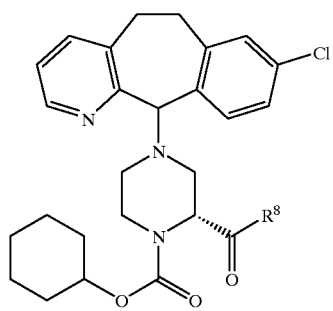
wherein R$^8$ is selected from:
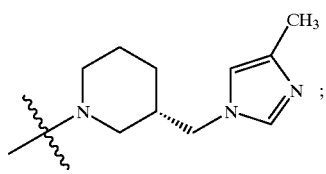
(Example 42)
(C-11 isomer: S)
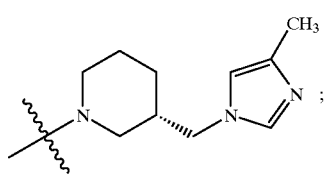
(Example 43)
(C-11 isomer: R)
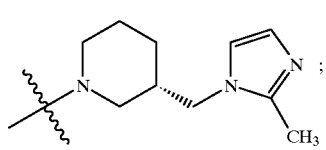
(Example 44)
(C-11 isomer: S)
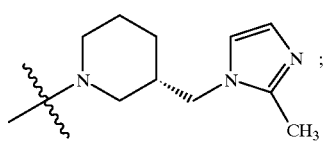
(Example 45)
(C-11 isomer: R)
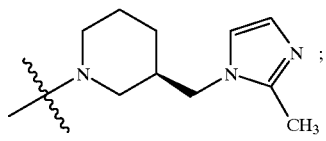
(Example 46)
(C-11 isomer: S)

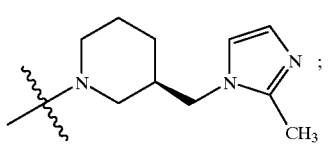
(Example 47)
(C-11 isomer: R)
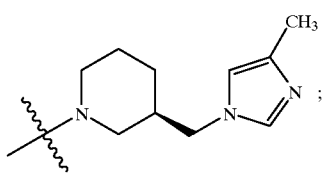
(Example 47A)
(C-11 isomer: S)
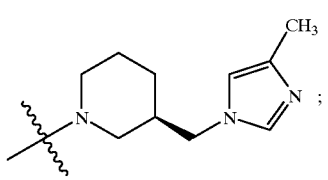
(Example 47B)
(C-11 isomer: R)
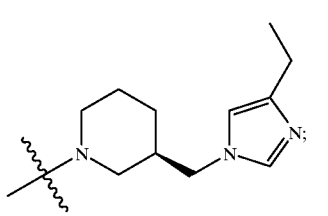
(Example 47D)
(C-11 isomer: S)
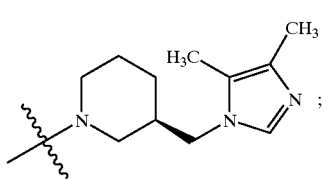
(Example 47G)
(C-11 isomer: S)
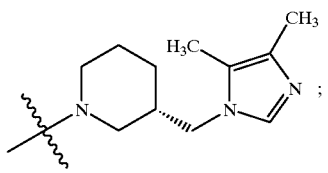
(Example 47H)
(C-11 isomer: S)
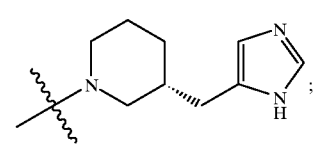
(Example 47I)
(C-11 isomer: S)
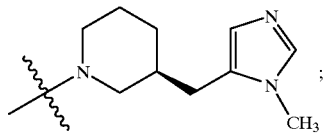
(Example 47K)
(C-11 isomer: S)
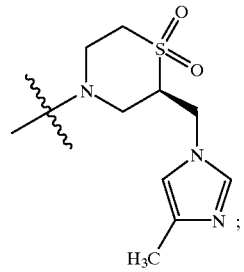
(Example 47L)
(C-11 isomer: S)
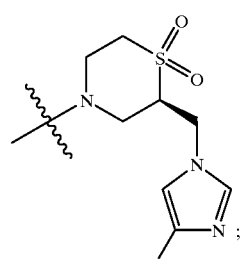
(Example 47M)
(C-11 isomer: R)
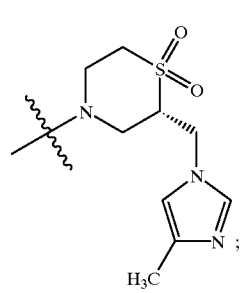
(Example 47N)
(C-11 isomer: S)
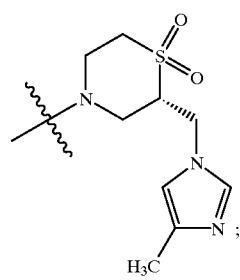
(Example 47O)
(C-11 isomer: R)

-continued
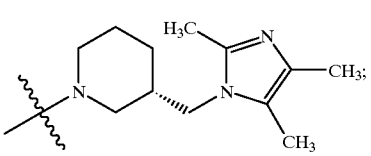
(Example 47P)
(C-11 isomer: S)
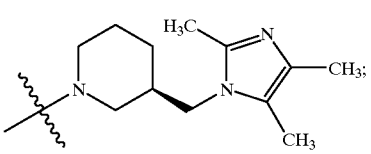
(Example 47R)
(C-11 isomer: S)
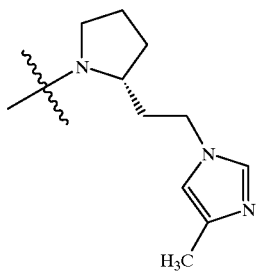
(Example 47S)
(C-11 isomer: S)
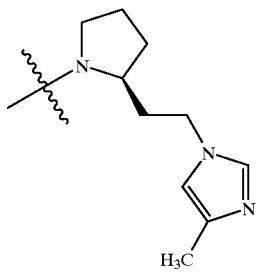
(Example 47T)
(C-11 isomer: S)
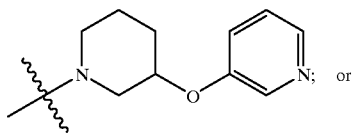
Isomer 1
(Example 47U)
(C-11 isomer: S)
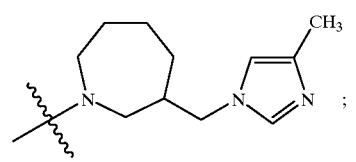
Isomer 1,2
(Example 47CC)
(C-11 isomer: S)
(16) a compound of the formula:
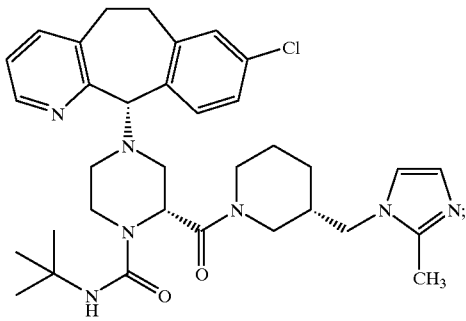
(Example 48)
(17) a compound of the formula:
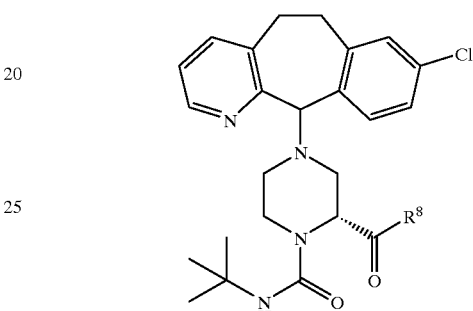
wherein $R^8$ is selected from:
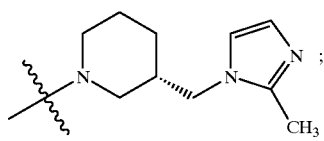
(Example 49)
(C-11 isomer: R)
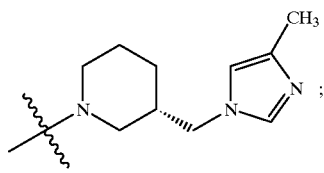
(Example 50)
(C-11 isomer: S)
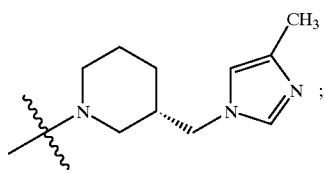
(Example 51)
(C-11 isomer: R)
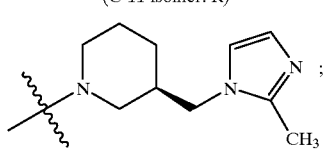
(Example 51A)
(C-11 isomer: S)

-continued
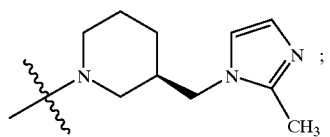
(Example 51B)
(C-11 isomer: R)
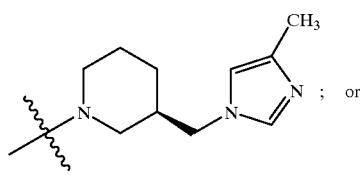
(Example 51C)
(C-11 isomer: S)
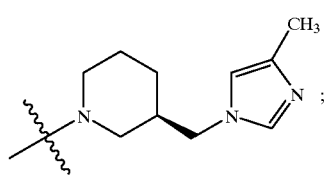
(Example 51D)
(C-11 isomer: R)
(18) a compound of the formula:
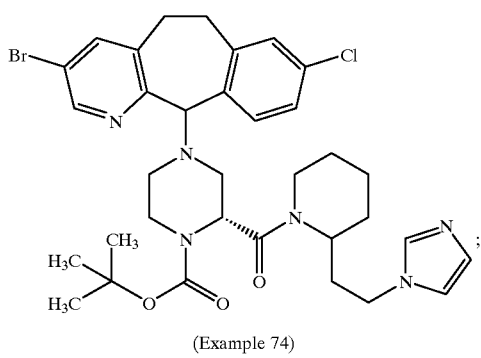
(Example 74)
(19) a compound of the formula:
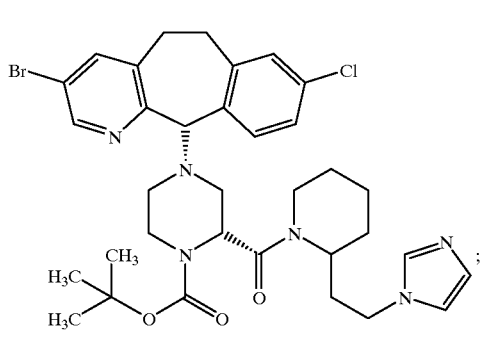
(Example 138)
(20) a compound of the formula:
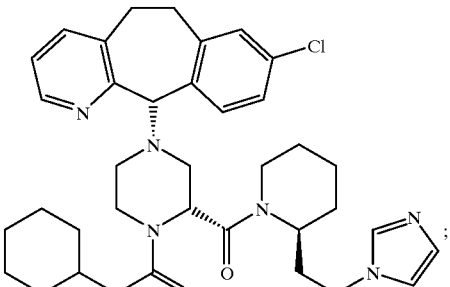
(Example 142 isomer 1)
(21) a compound of the formula:
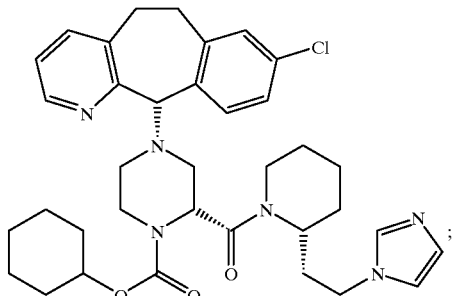
(Example 142 isomer 2)
(22) a compound of the formula:
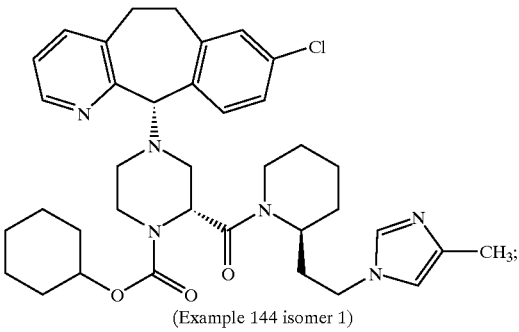
(Example 144 isomer 1)
(23) a compound of the formula:
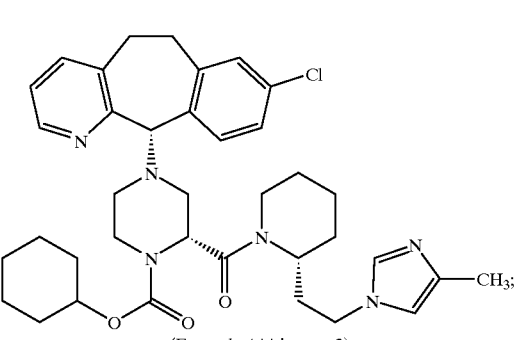
(Example 144 isomer 2)

(24) a compound of the formula:
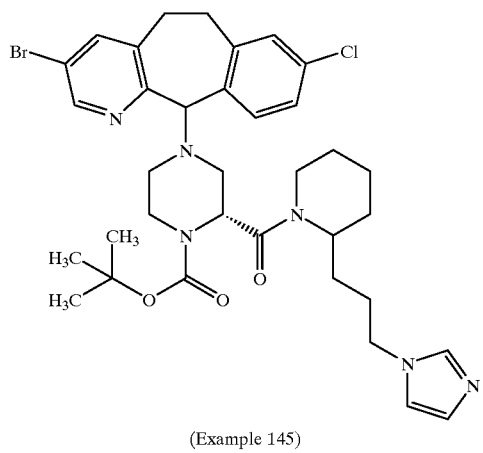
(Example 145)
(25) a compound of the formula:
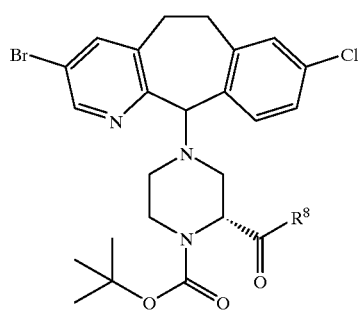
wherein R⁸ is selected from:
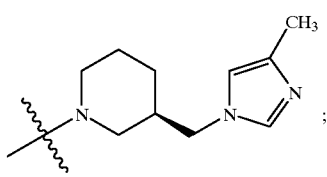
(Example 138A)
(C-11 isomer: S)
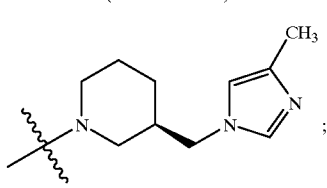
(Example 139A)
(C-11 isomer: R)
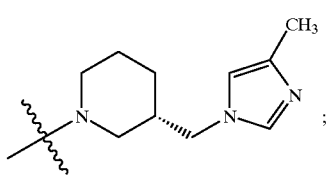
(Example 140A)
(C-11 isomer: S)
-continued
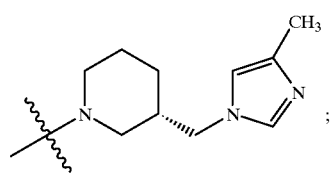
(Example 141A)
(C-11 isomer: R)
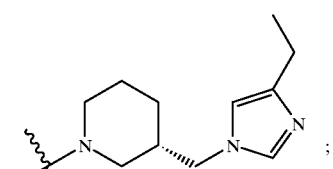
(Example 142A)
(C-11 isomer: R)
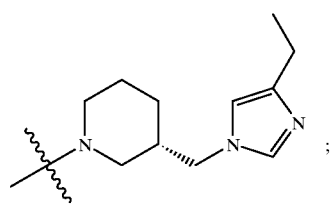
(Example 143A)
(C-11 isomer: S)
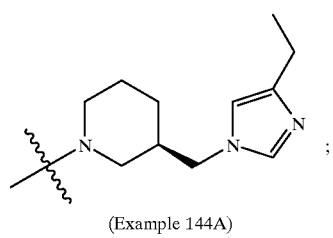
(Example 144A)
(C-11 isomer: R)
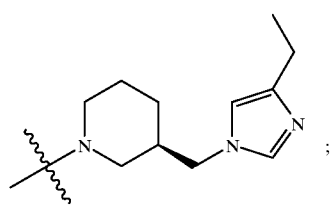
(Example 145A)
(C-11 isomer: S)
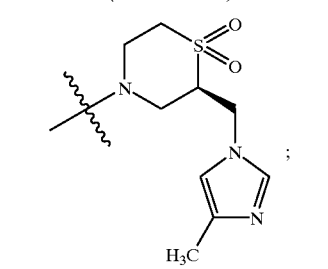
(Example 146A)
(C-11 isomer: S)

-continued
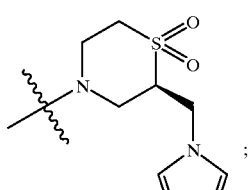
(Example 147A)
(C-11 isomer: R)
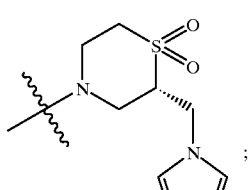
(Example 148)
(C-11 isomer: S)
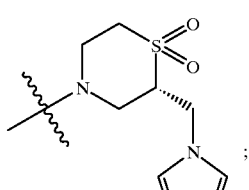
(Example 149)
(C-11 isomer: R)
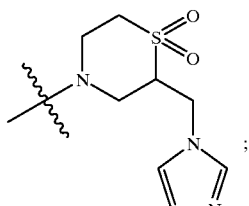
(Example 150)
(C-11 isomer: R)
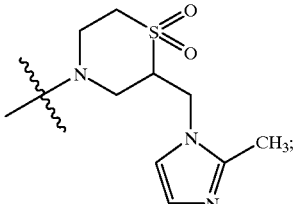
(Example 151)
(C-11 isomer: S)
-continued
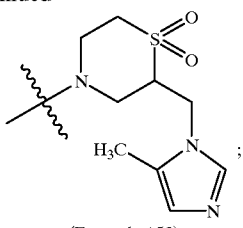
(Example 152)
(C-11 isomer: S)
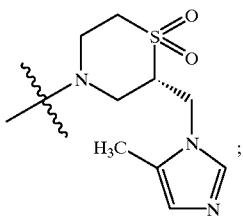
(Example 153)
(C-11 isomer: S)
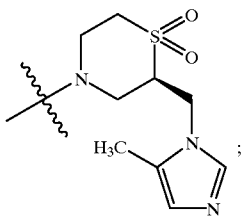
(Example 154)
(C-11 isomer: S)
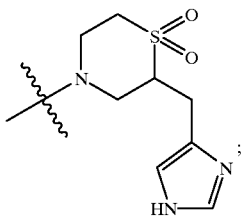
(Example 155)
(C-11 isomer: S)
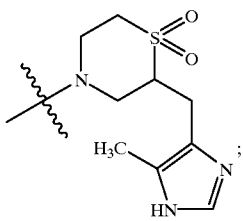
(Isomer 1)
(Example 156)
(C-11 isomer: S)
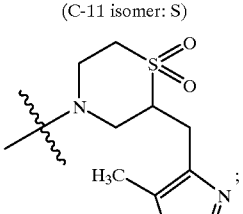
(Isomer 2)
(Example 157)
(C-11 isomer: S)

-continued
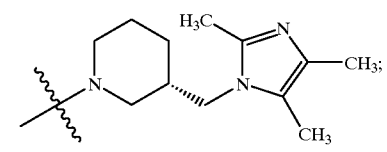
(Example 158)
(C-11 isomer: R)
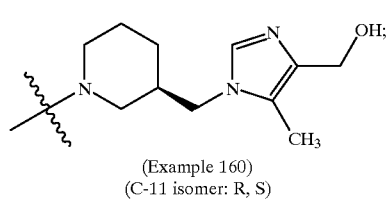
(Example 160)
(C-11 isomer: R, S)
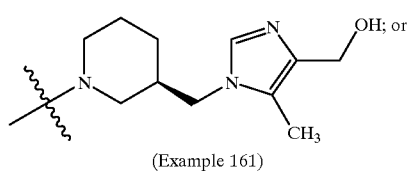
(Example 161)
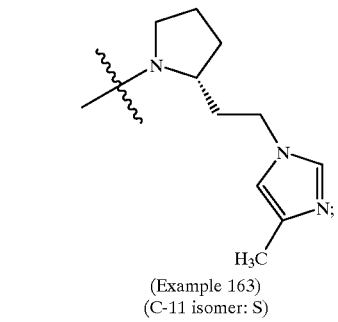
(Example 163)
(C-11 isomer: S)
(26) a compound of the formula:
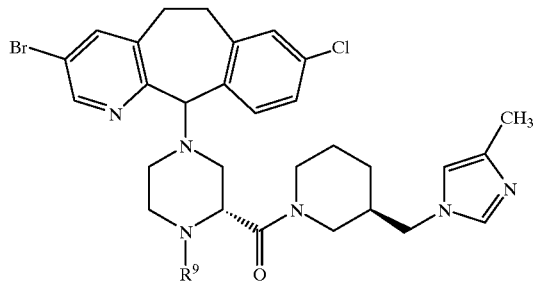
wherein $R^9$ is selected from:
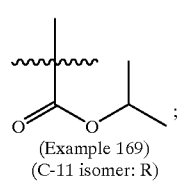
(Example 169)
(C-11 isomer: R)
-continued
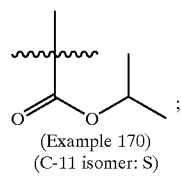
(Example 170)
(C-11 isomer: S)
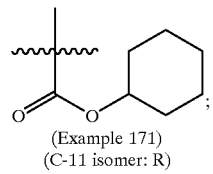
(Example 171)
(C-11 isomer: R)
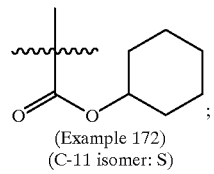
(Example 172)
(C-11 isomer: S)
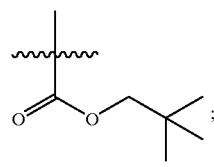
(Example 173)
(C-11 isomer: R)
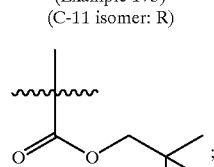
(Example 174)
(C-11 isomer: S)
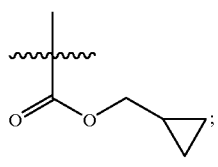
(Example 175)
(C-11 isomer: R)
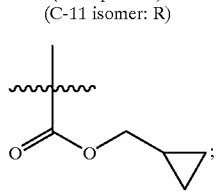
(Example 176)
(C-11 isomer: S)
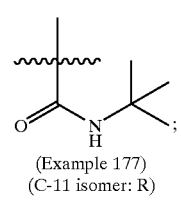
(Example 177)
(C-11 isomer: R)

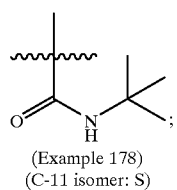
(Example 178)
(C-11 isomer: S)
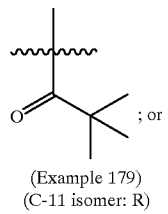
(Example 179)
(C-11 isomer: R)
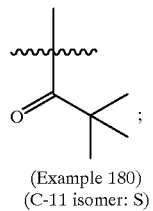
(Example 180)
(C-11 isomer: S)
(27) a compound of the formula:
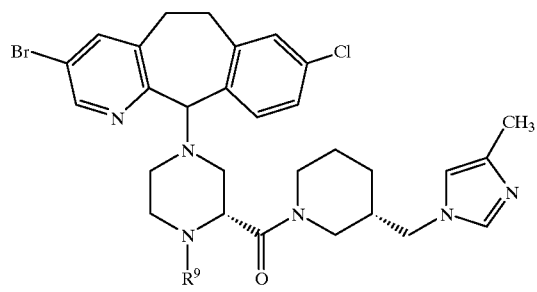
wherein R⁹ is selected from:
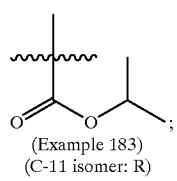
(Example 183)
(C-11 isomer: R)
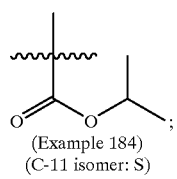
(Example 184)
(C-11 isomer: S)
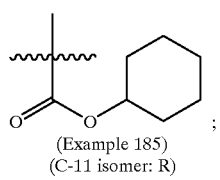
(Example 185)
(C-11 isomer: R)
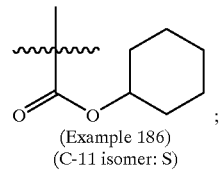
(Example 186)
(C-11 isomer: S)
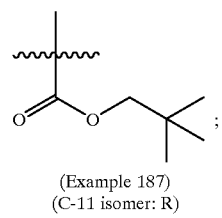
(Example 187)
(C-11 isomer: R)
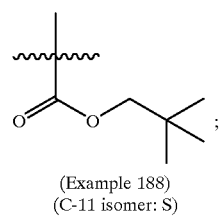
(Example 188)
(C-11 isomer: S)
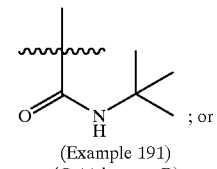
(Example 191)
(C-11 isomer: R)
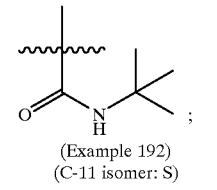
(Example 192)
(C-11 isomer: S)
(28) a compound of the formula:
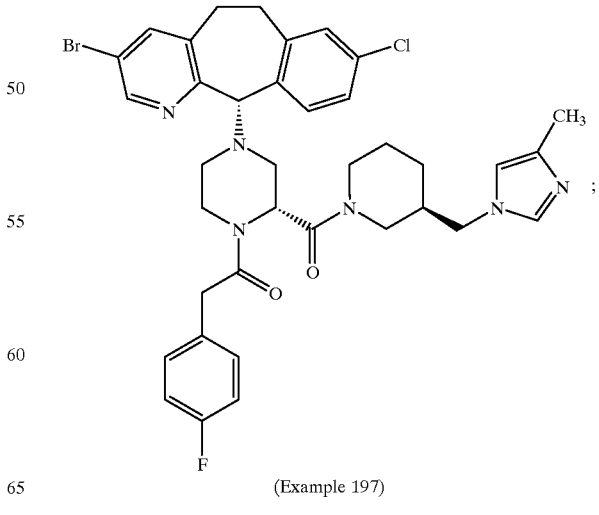
(Example 197)

(29) a compound of the formula:
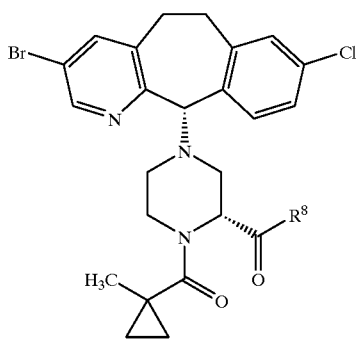
wherein R⁸ is
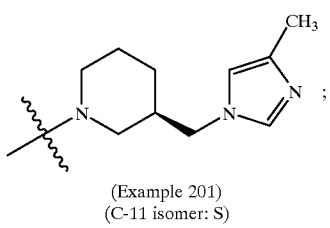
(Example 201)
(C-11 isomer: S)
(30) a compound of the formula:
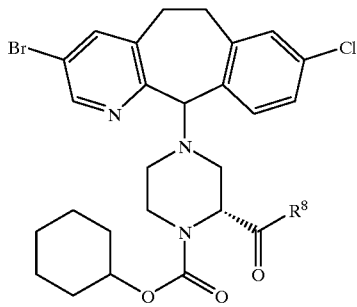
wherein R⁸ is selected from:
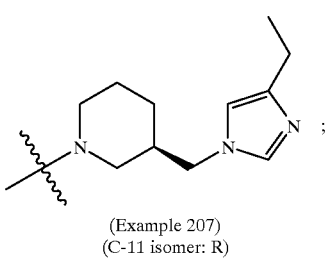
(Example 207)
(C-11 isomer: R)
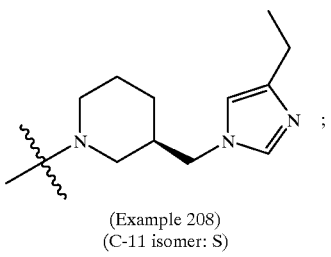
(Example 208)
(C-11 isomer: S)
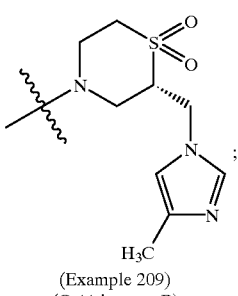
(Example 209)
(C-11 isomer: R)
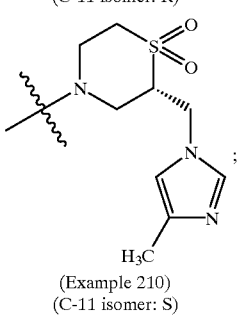
(Example 210)
(C-11 isomer: S)
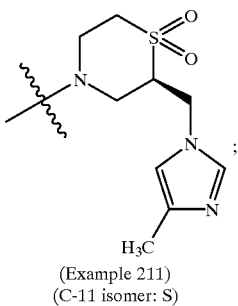
(Example 211)
(C-11 isomer: S)
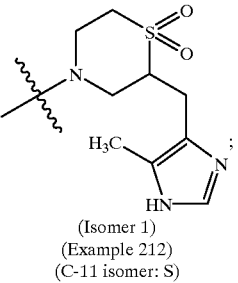
(Isomer 1)
(Example 212)
(C-11 isomer: S)
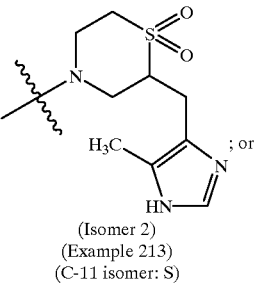
(Isomer 2)
(Example 213)
(C-11 isomer: S)
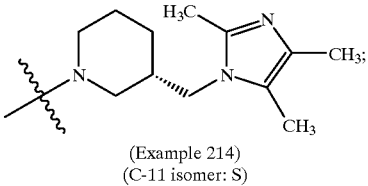
(Example 214)
(C-11 isomer: S)

(31) a compound of the formula:
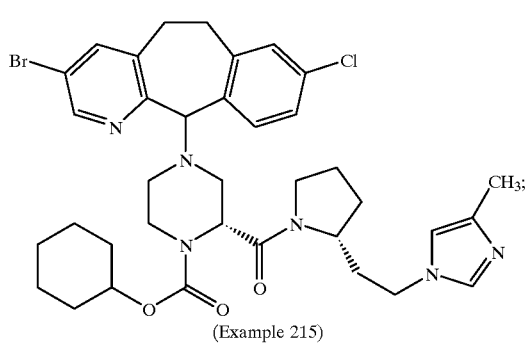
(Example 215)
(32) a compound of the formula:
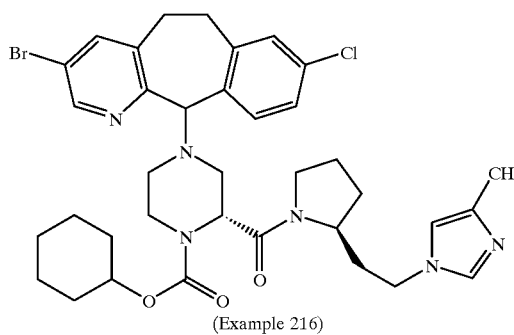
(Example 216)
(33) a compound of the formula:
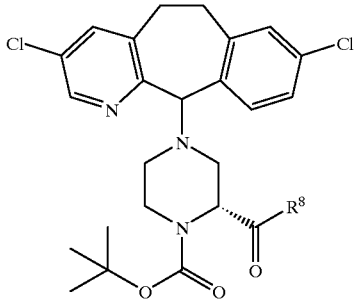
wherein $R^8$ is selected from:
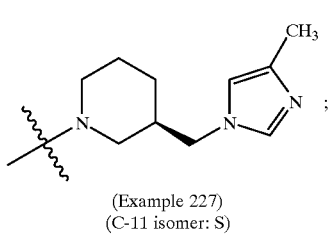
(Example 227)
(C-11 isomer: S)
-continued
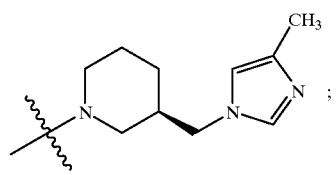
(Example 228)
(C-11 isomer: R)
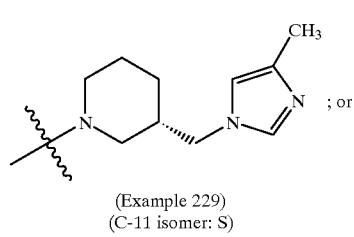
(Example 229)
(C-11 isomer: S)
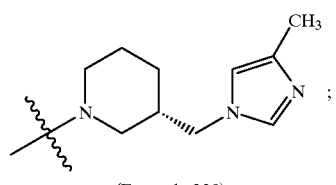
(Example 230)
(C-11 isomer: R)
(34) a compound of the formula:
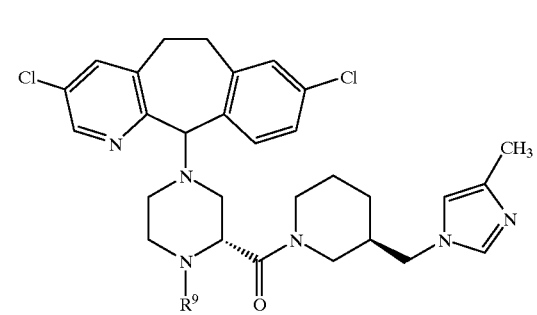
wherein $R^9$ is selected from:
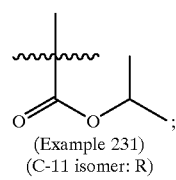
(Example 231)
(C-11 isomer: R)
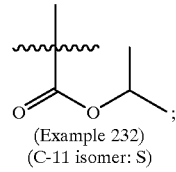
(Example 232)
(C-11 isomer: S)

-continued
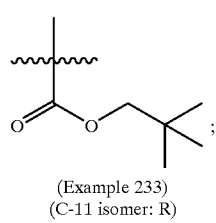
(Example 233)
(C-11 isomer: R)
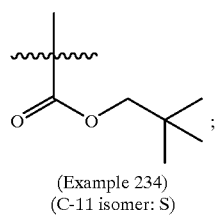
(Example 234)
(C-11 isomer: S)
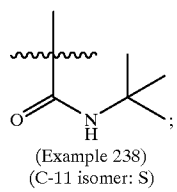
(Example 238)
(C-11 isomer: S)
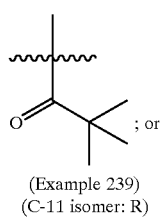
; or
(Example 239)
(C-11 isomer: R)
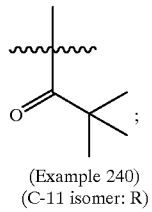
(Example 240)
(C-11 isomer: R)
(35) a compound of the formula:
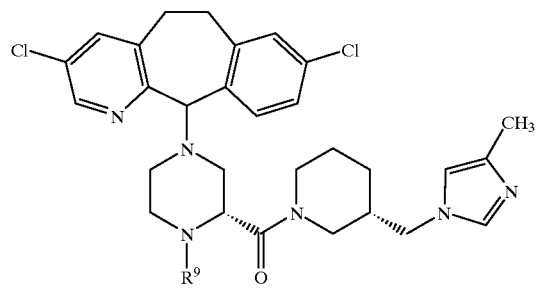
wherein $R^9$ is:
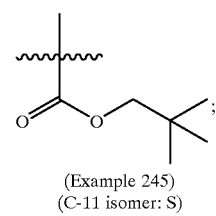
(Example 245)
(C-11 isomer: S)
(36) a compound of the formula:
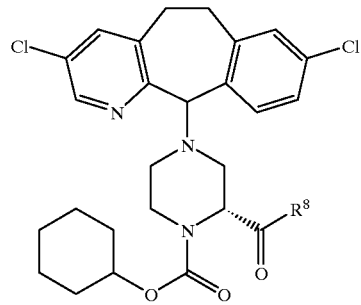
wherein $R^8$ is selected from:
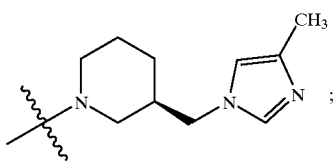
(Example 255)
(C-11 isomer: S)
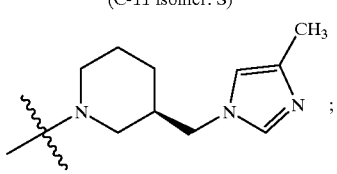
(Example 256)
(C-11 isomer: R)
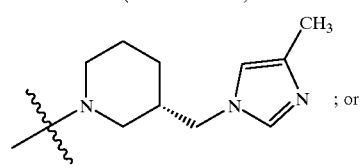
; or
(Example 257)
(C-11 isomer: S)
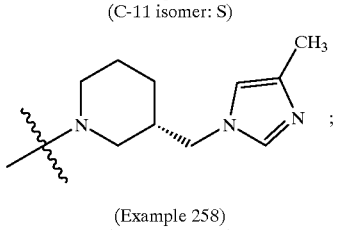
(Example 258)
(C-11 isomer: R)

(37) a compound of the formula:
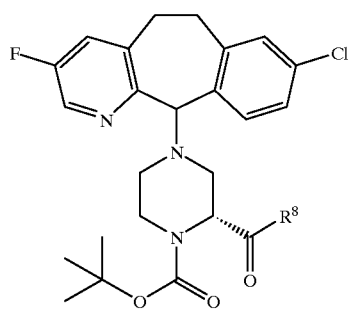
wherein R⁸ is selected from:
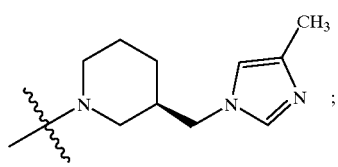
(Example 259)
(C-11 isomer: S)
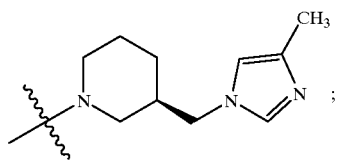
(Example 260)
(C-11 isomer: R)
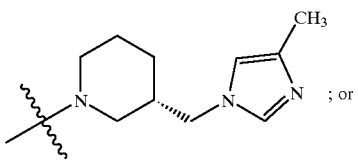  ; or
(Example 261)
(C-11 isomer: S)
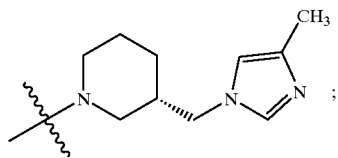
(Example 262)
(C-11 isomer: R)
(38) a compound selected from:
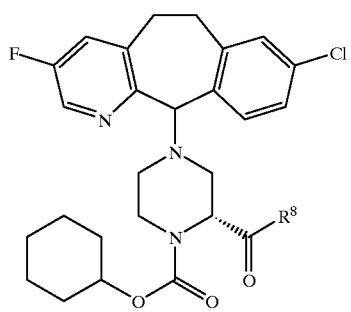
wherein R⁸ is selected from:
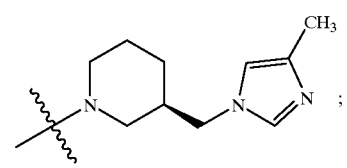
(Example 287)
(C-11 isomer: S)
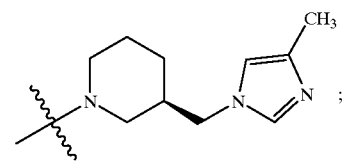
(Example 288)
(C-11 isomer: R)
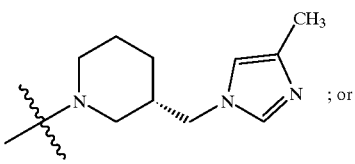  ; or
(Example 289)
(C-11 isomer: S)
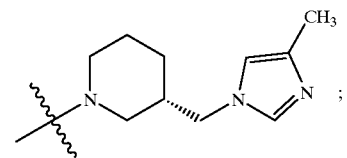
(Example 290)
(C-11 isomer: R)

(39) a compound selected from:
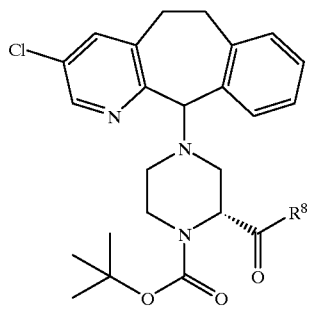
wherein R⁸ is selected from:
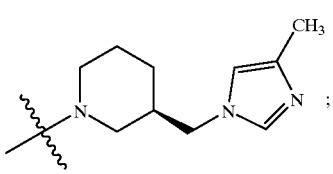
(Example 291)
(C-11 isomer: S)
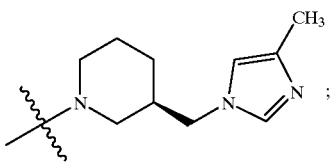
(Example 292)
(C-11 isomer: R)
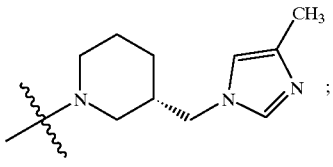
(Example 293)
(C-11 isomer: S)
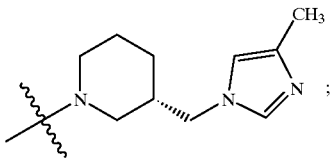
(Example 294)
(C-11 isomer: R)
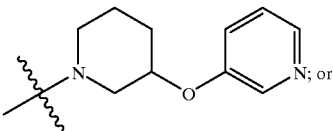
(Example 294A)
(C-11 isomer: S)
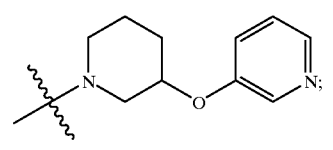
(Example 294B)
(C-11 isomer: R)
(40) a compound of the formula:
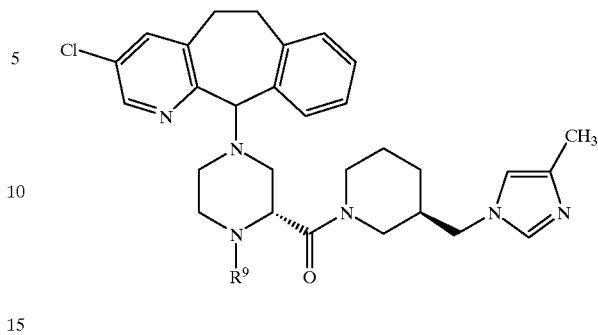
wherein R⁹ is selected from:
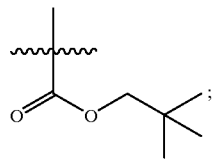
(Example 297)
(C-11 isomer: R)
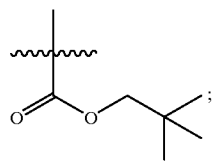
(Example 298)
(C-11 isomer: S)
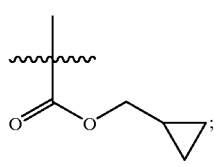
(Example 299)
(C-11 isomer: R)
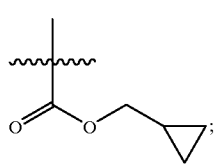
(Example 300)
(C-11 isomer: S)
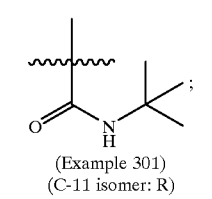
(Example 301)
(C-11 isomer: R)
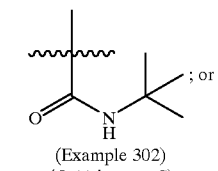
(Example 302)
(C-11 isomer: S)

-continued
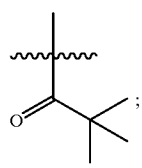
(Example 303)
(C-11 isomer: R)
(41) a compound selected from:
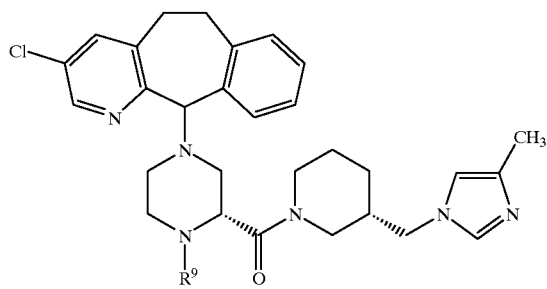
wherein $R^9$ is selected from:
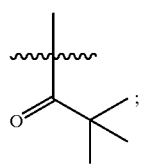
(Example 316)
(C-11 isomer: S)
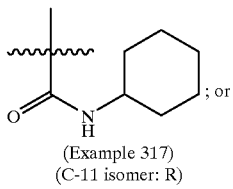
; or
(Example 317)
(C-11 isomer: R)
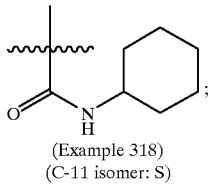
(Example 318)
(C-11 isomer: S)
(42) a compound of the formula:
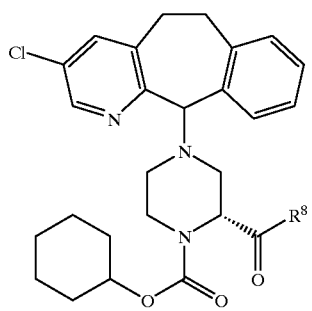
wherein $R^8$ is selected from:
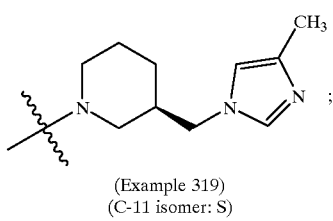
(Example 319)
(C-11 isomer: S)
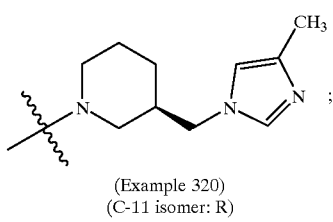
(Example 320)
(C-11 isomer: R)
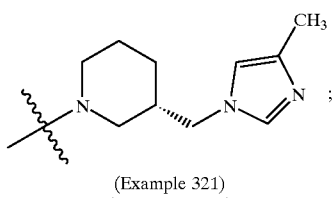
(Example 321)
(C-11 isomer: S)
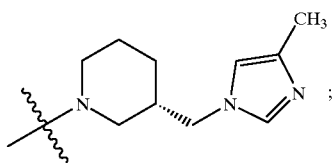
(Example 322)
(C-11 isomer: R)
(43) a compound of the formula:
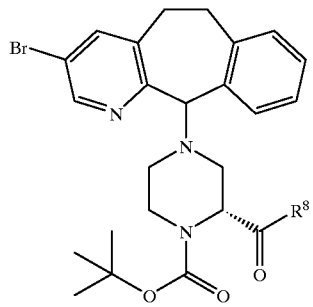
wherein $R^8$ is selected from:
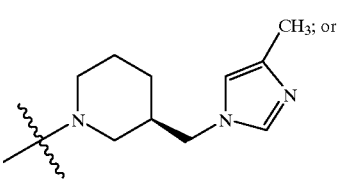
(Example 323)
(C-11 isomer: S)

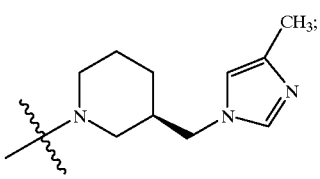
(Example 324)
(C-11 isomer: R)
(44) a compound of the formula:
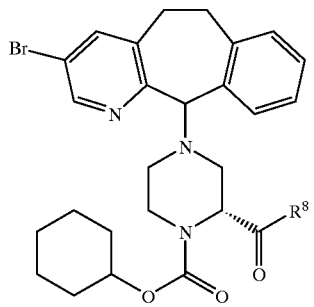
wherein $R^8$ is selected from:
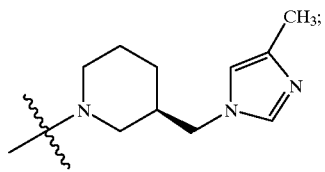
(Example 351)
(C-11 isomer: S)
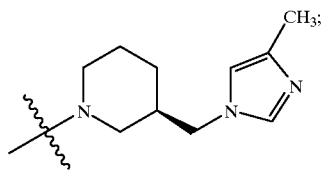
(Example 352)
(C-11 isomer: R)
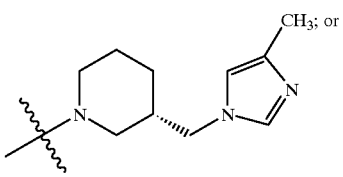
(Example 353)
(C-11 isomer: S)
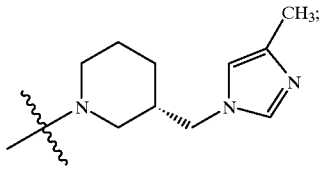
(Example 354)
(C-11 isomer: R)
(45) a compound of the formula;
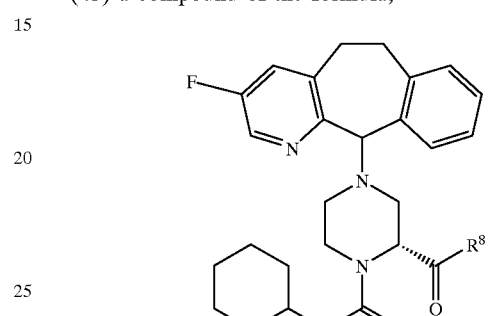
wherein $R^8$ is selected from:
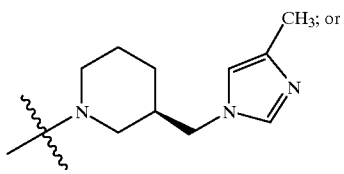
(Example 383)
(C-11 isomer: S)
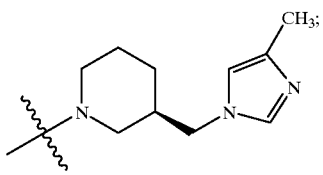
(Example 384)
(C-11 isomer: R)
(46) a compound of the formula:
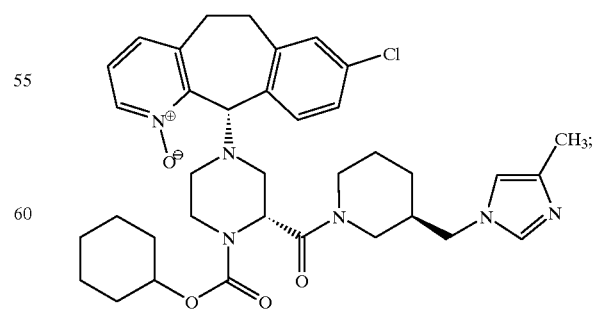
(Example 387)

(47) a compound of the formula:
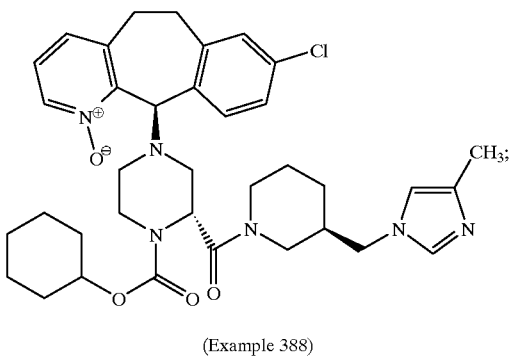
(Example 388)
(48) a compound of the formula:
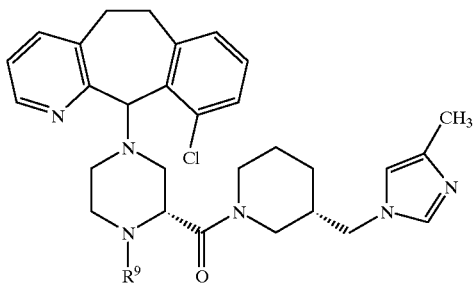
wherein R⁹ is selected from:
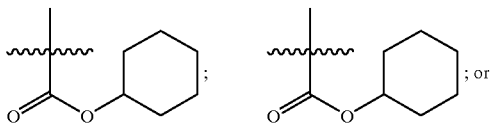
(Example 391) (isomer A)  (Example 392) (isomer B)
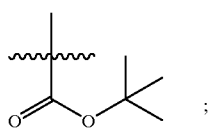
(Example 394)
(C-11 isomer: S)
(49) a compound of the formula:
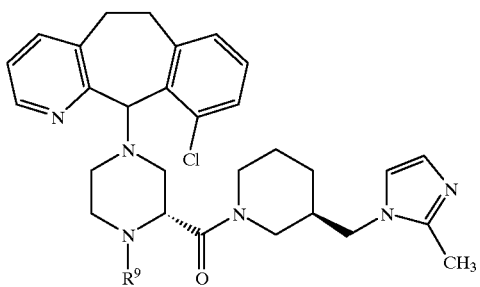
wherein R⁹ is selected from:
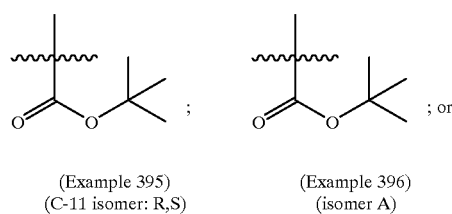
(Example 395)                (Example 396)
(C-11 isomer: R,S)           (isomer A)
(Example 397)
(isomer B)
(50) a compound of the formula:
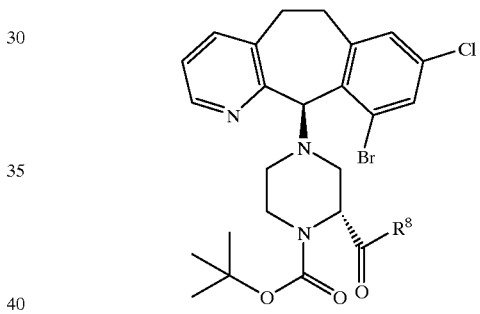
wherein R⁸ is selected from:
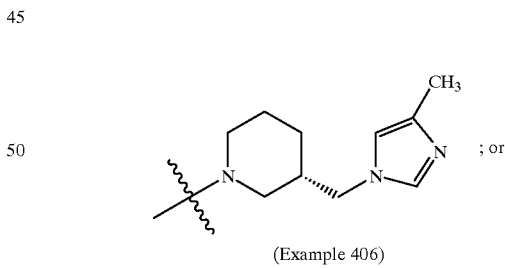
(Example 406)
(isomer 1)
(Example 408)
(isomer 2)

(51) a compound of the formula:
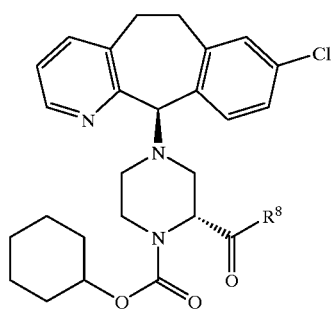
wherein R⁸ is selected from:
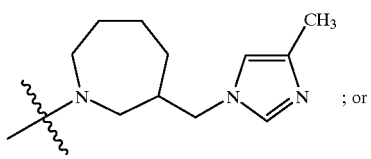
Isomer 1
(Example 409)
(C-11 isomer: S)
; or
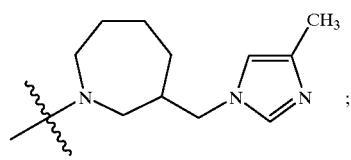
Isomer 2
(Example 410)
(C-11 isomer: S)
;
(52) a compound of the formula:
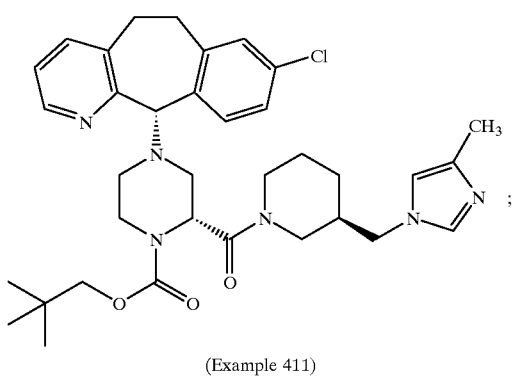
(Example 411)
(53) a compound of the formula:
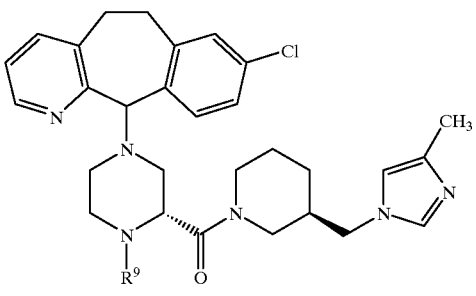
wherein R⁹ is
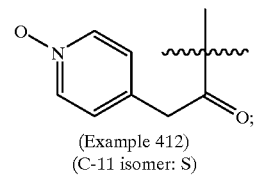
(Example 412)
(C-11 isomer: S)
;
(54) a compound of the formula:
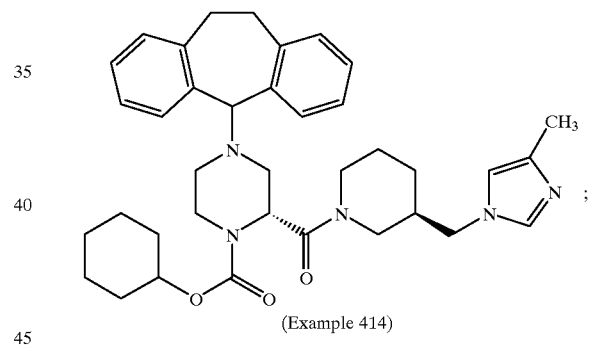
(Example 414)
(55) a compound of the formula:
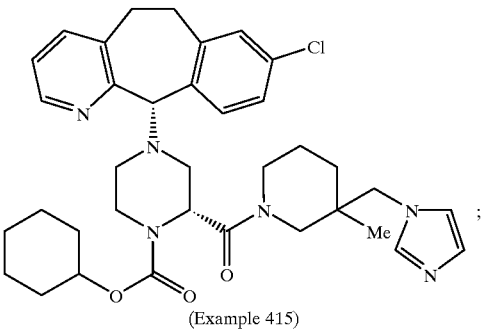
(Example 415)

(56) a compound of the formula:
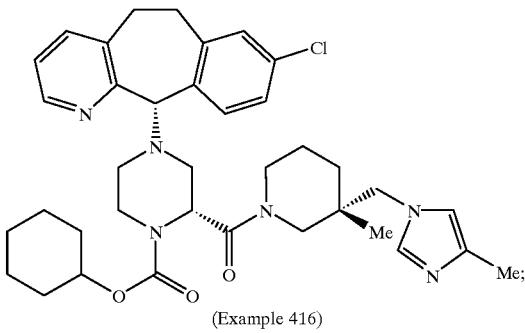
(Example 416)
(57) a compound of the formula:
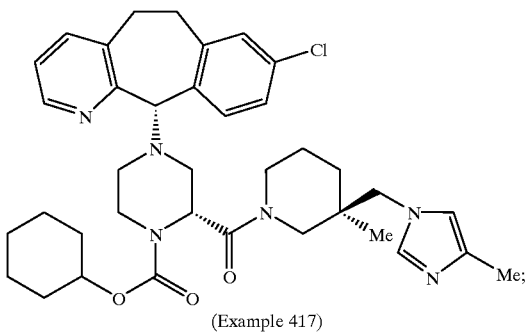
(Example 417)
(58) a compound of the formula:
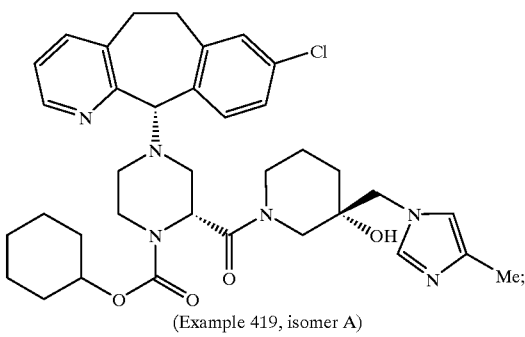
(Example 419, isomer A)
(59) a compound of the formula:
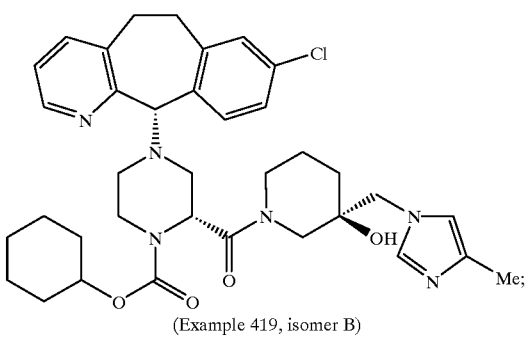
(Example 419, isomer B)
(60) a compound of the formula:
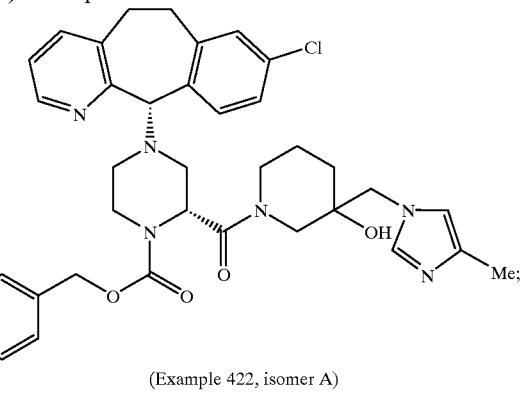
(Example 422, isomer A)
(61) a compound of the formula:
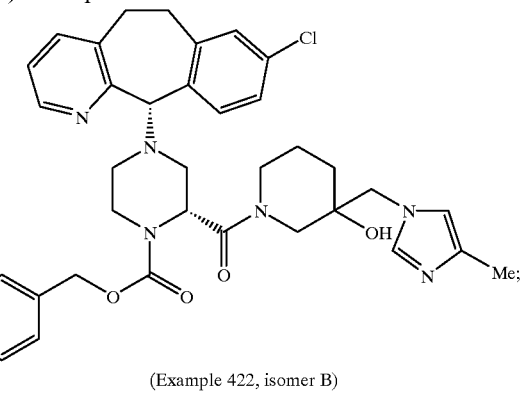
(Example 422, isomer B)
(62) a compound of the formula:
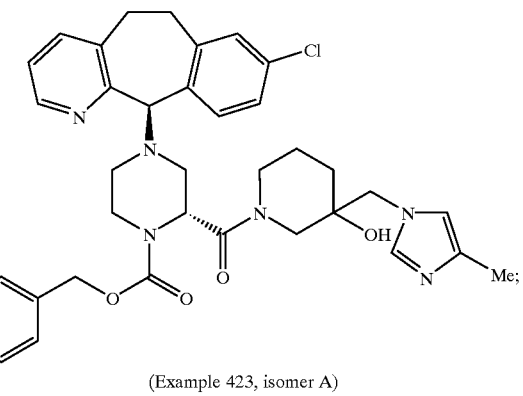
(Example 423, isomer A)
(63) a compound of the formula:
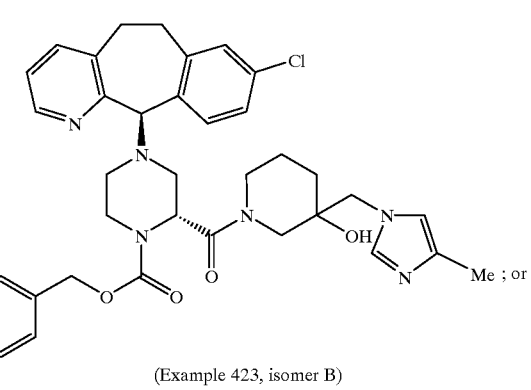
(Example 423, isomer B)

(64) a compound of the formula:
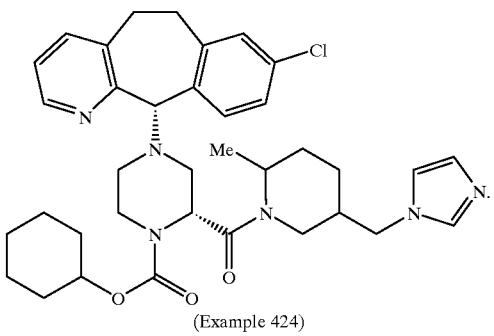
(Example 424)
27. A compound selected from:
(1) a compound of the formula:
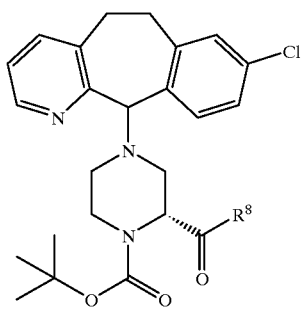
wherein R⁸ is
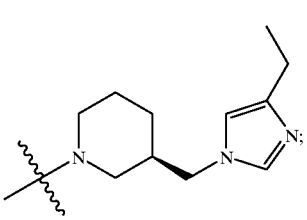
(Example 35C)
(C-11 isomer: S)
(2) a compound of the formula:
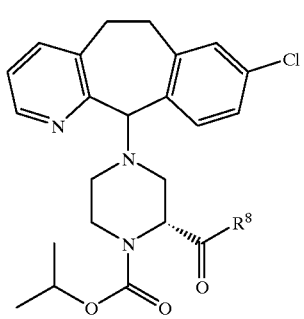
wherein R⁸ is
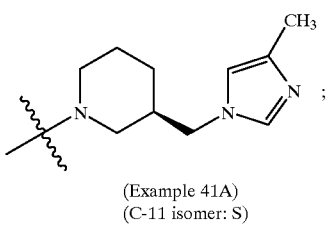
(Example 41A)
(C-11 isomer: S)
(3) a compound of the formula:
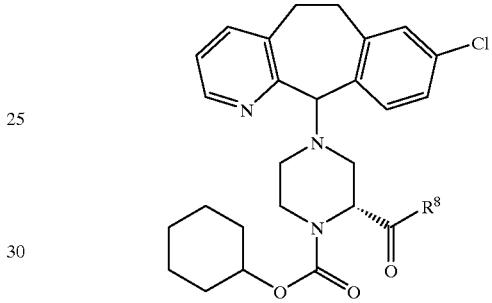
wherein R⁸ is selected from:
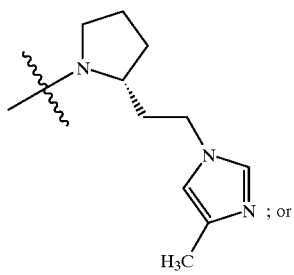
(Example 47S)
(C-11 isomer: S)
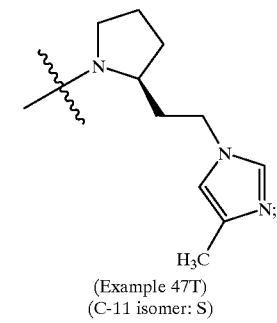
(Example 47T)
(C-11 isomer: S)

(4) a compound of the formula:
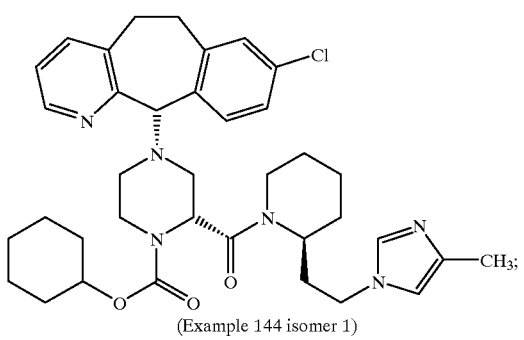
(Example 144 isomer 1)
(5) a compound of the formula:
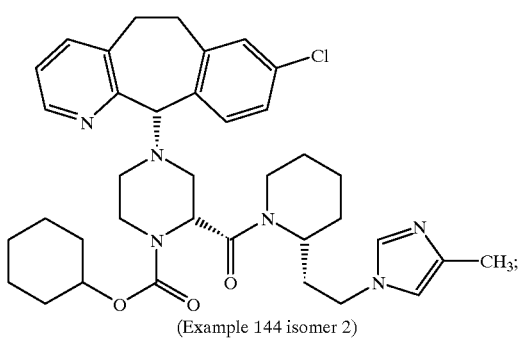
(Example 144 isomer 2)
(6) a compound of the formula:
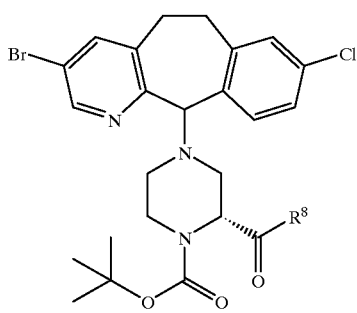
wherein $R^8$ is selected from:
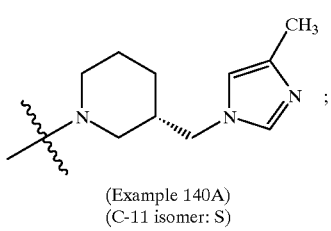
(Example 140A)
(C-11 isomer: S)
-continued
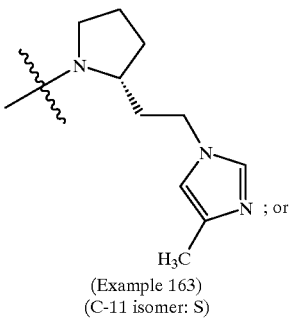
(Example 163)
(C-11 isomer: S)
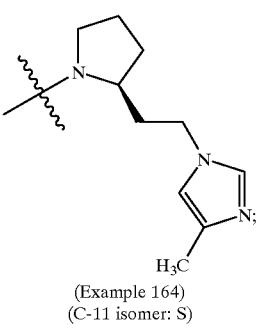
(Example 164)
(C-11 isomer: S)
(7) a compound of the formula:
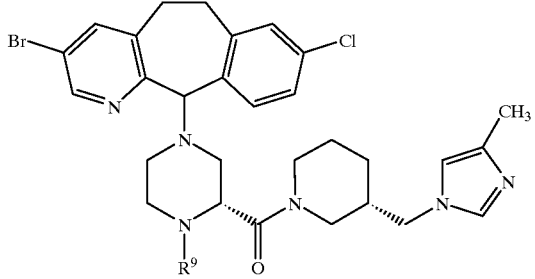
wherein $R^9$ is selected from:
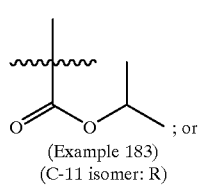
(Example 183)
(C-11 isomer: R)
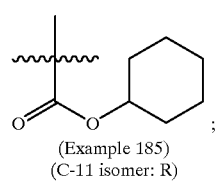
(Example 185)
(C-11 isomer: R)

(8) a compound of the formula:
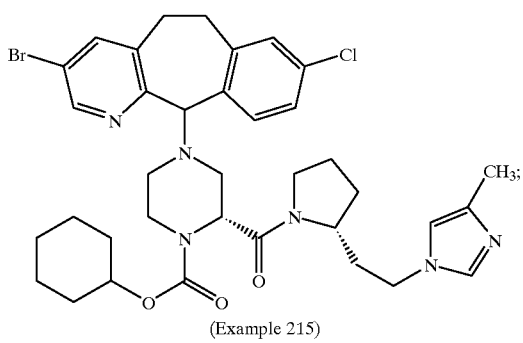
(Example 215)
(9) a compound of the formula:
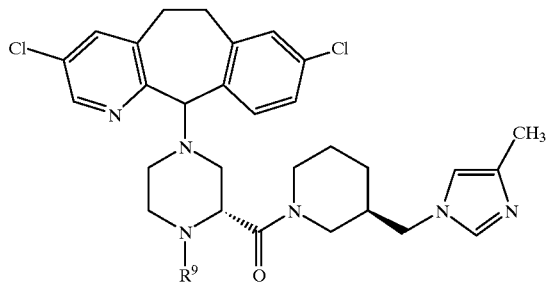
wherein R⁹ is
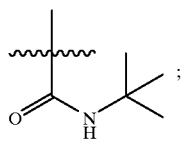
(Example 238)
(C-11 isomer: S)
(10) a compound of the formula:
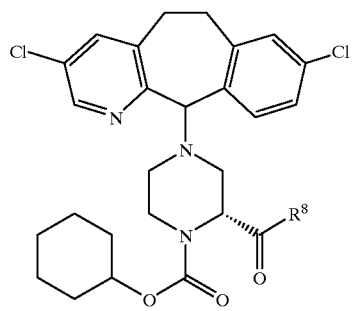
wherein R⁸ is
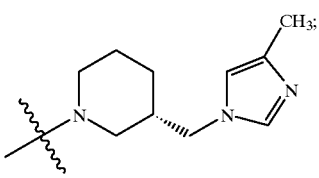
(Example 258)
(C-11 isomer: R)
(11) a compound of the formula:
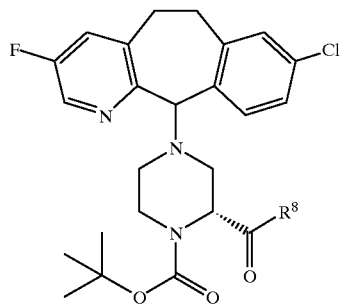
wherein R⁸ is
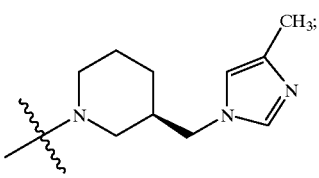
(Example 259)
(C-11 isomer: S)
(12) a compound selected from:
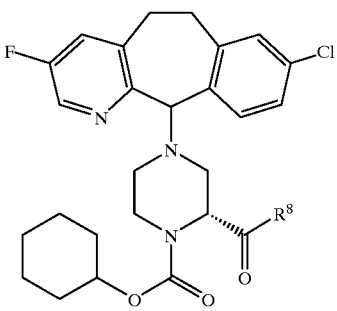

wherein R[8] is
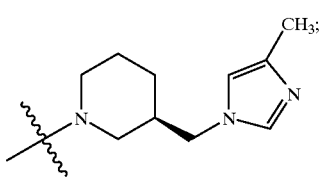
(Example 257)
(C-11 isomer: S)
(13) a compound selected from:
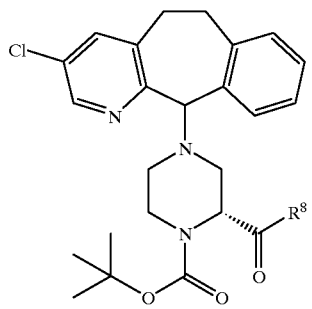
wherein R[8] is
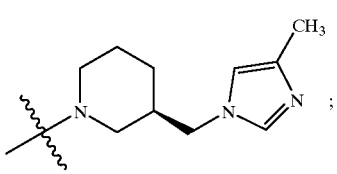
(Example 292)
(C-11 isomer: R)
(14) a compound of the formula:
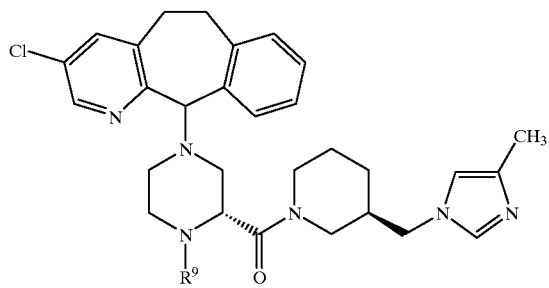
wherein R[9] is selected from:
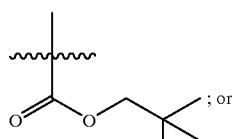
; or
(Example 298)
(C-11 isomer: S)
-continued
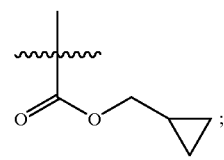
(Example 300)
(C-11 isomer: S)
(15) a compound of the formula:
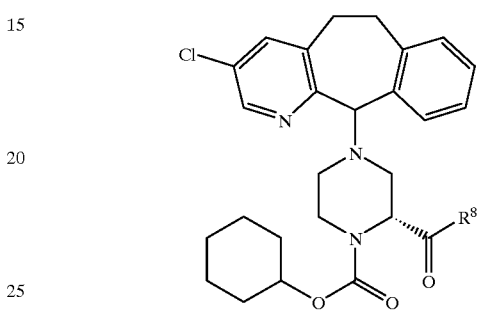
wherein R[8] is
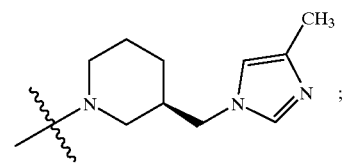
(Example 320)
(C-11 isomer: R)
(16) a compound of the formula:
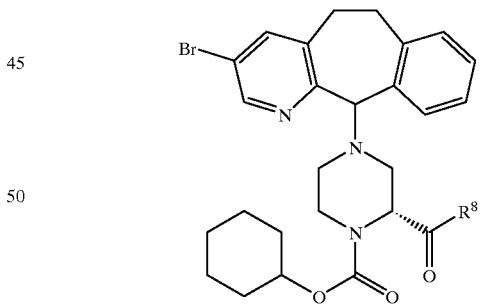
wherein R[8] is selected from:
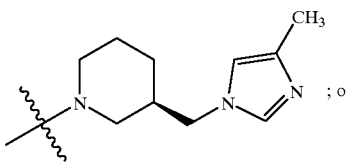
; or
(Example 351)
(C-11 isomer: S)

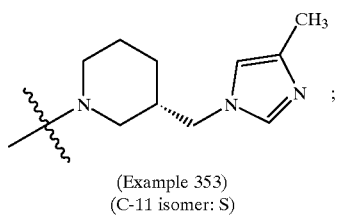
(Example 353)
(C-11 isomer: S)
(17) a compound of the formula:
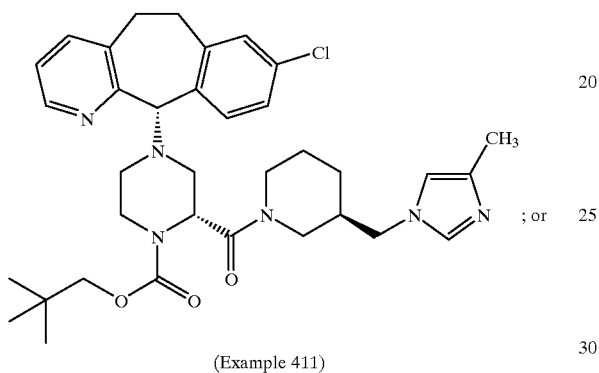
(Example 411)
(18) a compound of the formula:
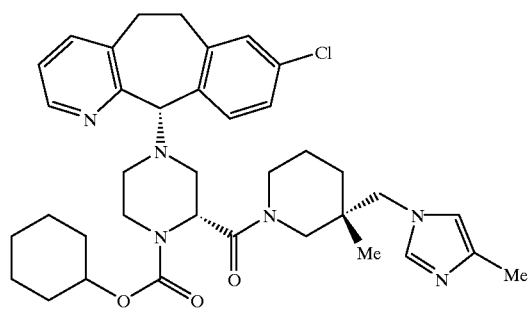
28. A compound selected from:
(1) a compound of the formula:
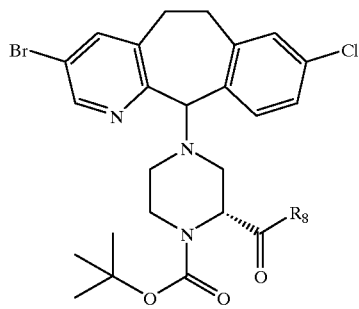
wherein $R^8$ is selected from:
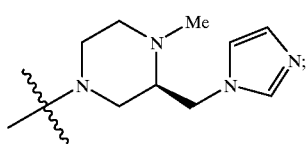
11- (R,S)
(Example 5)
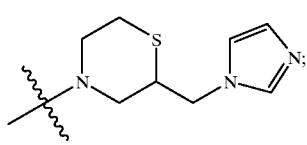
(Example 6)
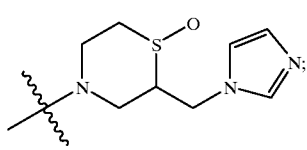
(Example 7)
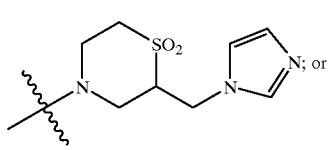
(Example 8)
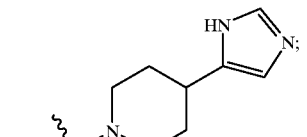
11- (R,S)
(Example 9)
(2) a compound of the formula:
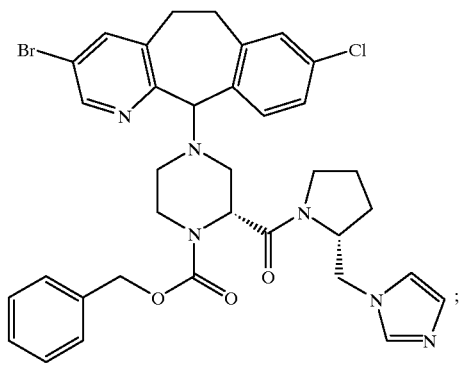
(Example 20)

(3) a compound of the formula:
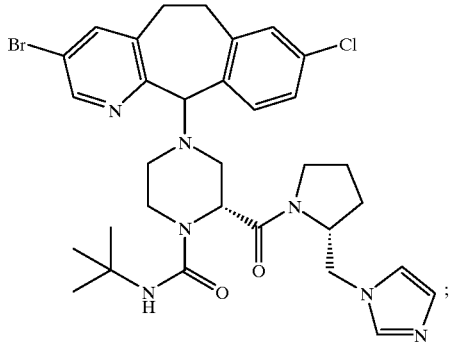
(Example 21)
(4) a compound of the formula:
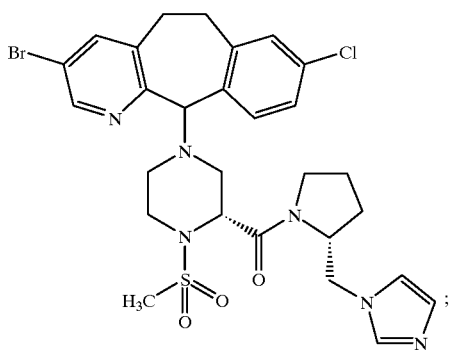
(Example 22)
(5) a compound of the formula:
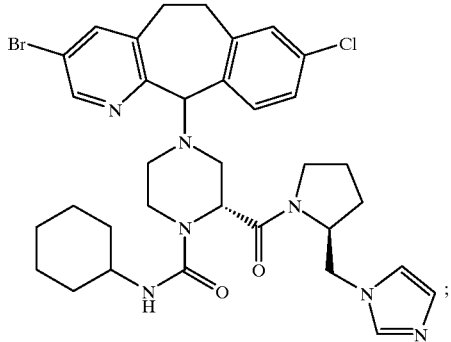
(Example 23)
(6) a compound of the formula:
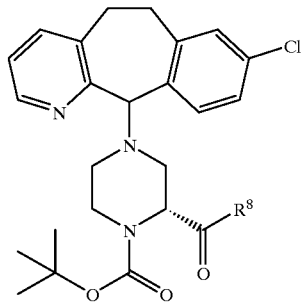
wherein $R^8$ is selected from:
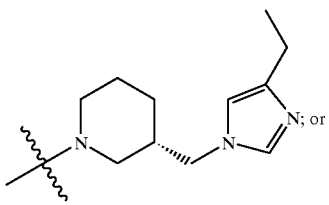
(Example 35B)
(C-11 isomer: R)
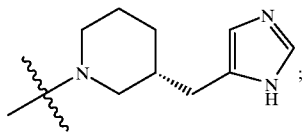
(Example 35G)
(C-11 isomer: S)
(7) a compound of the formula:
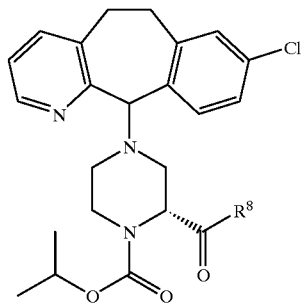
wherein $R^8$ is selected from:
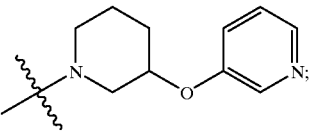
Isomer 1
(Example 41D)
(C-11 isomer: S)

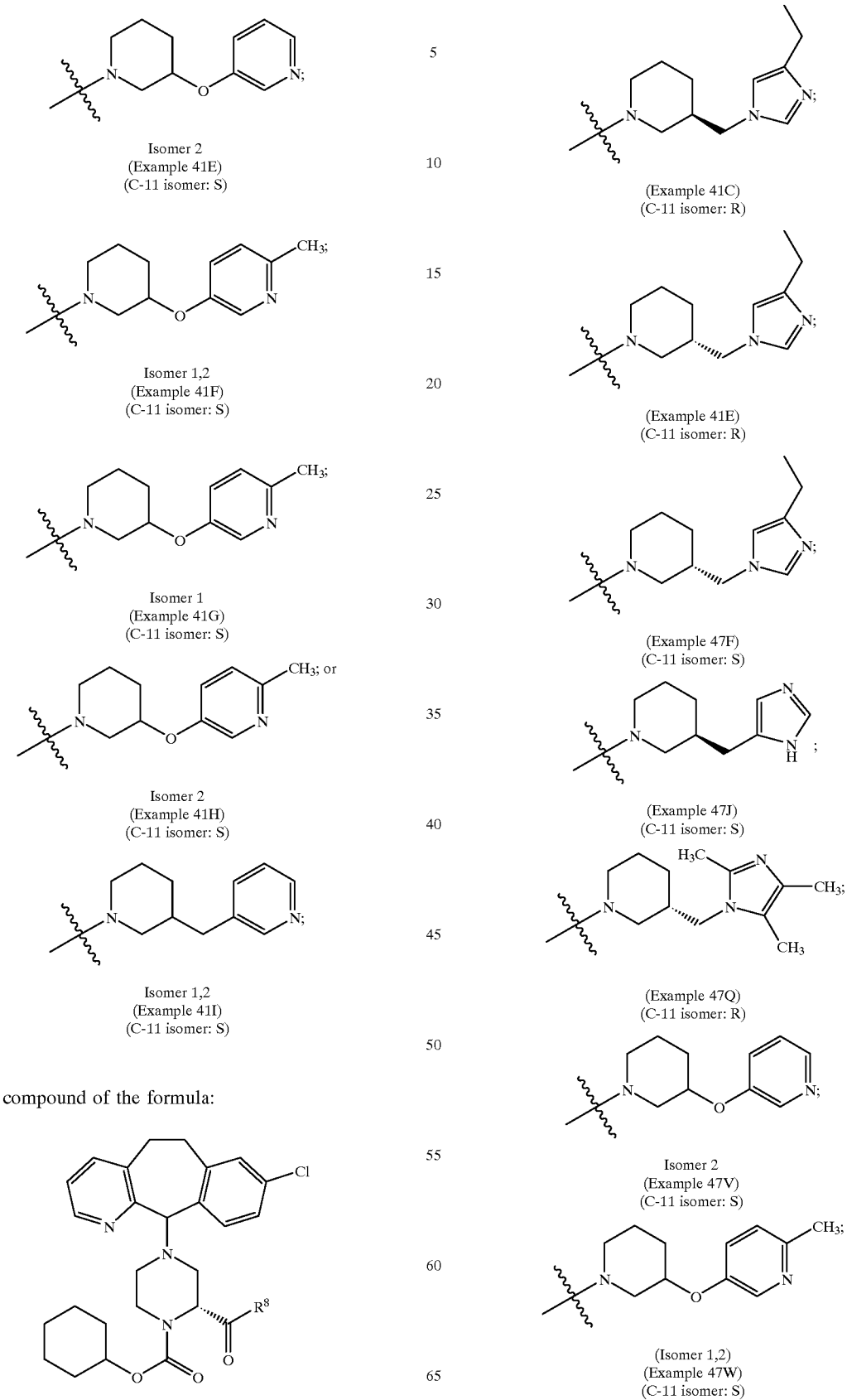

-continued
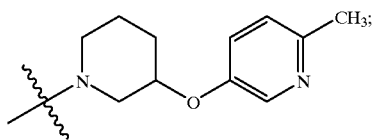
Isomer 1
(Example 47X)
(C-11 isomer: S)
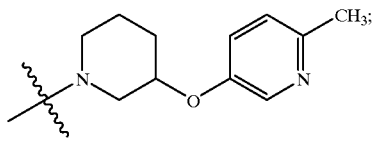
Isomer 2
(Example 47Y)
(C-11 isomer: S)
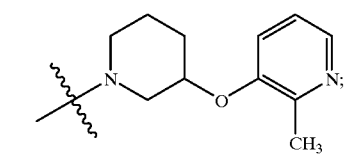
Isomer 1,2
(Example 47Z)
(C-11 isomer: S)
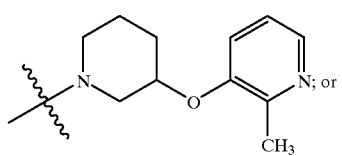
Isomer 1
(Example 47AA)
(C-11 isomer: S)
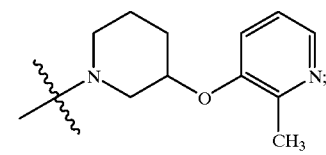
Isomer 2
(Example 47BB)
(C-11 isomer: S)
(9) a compound of the formula:
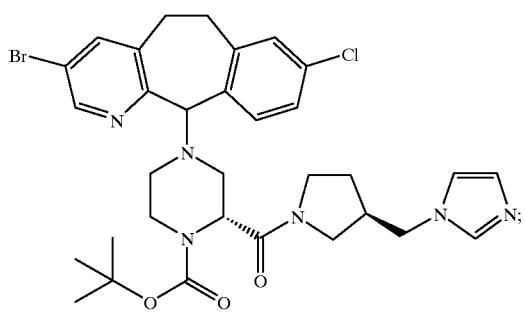
(Example 54)
(10) a compound of the formula:
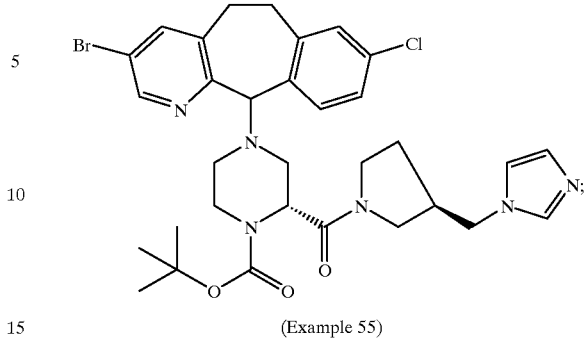
(Example 55)
(11) a compound of the formula:
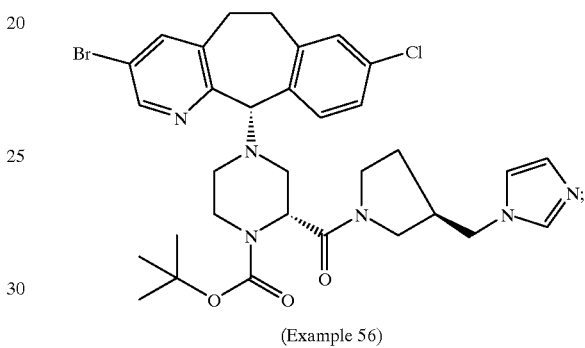
(Example 56)
(12) a compound of the formula:
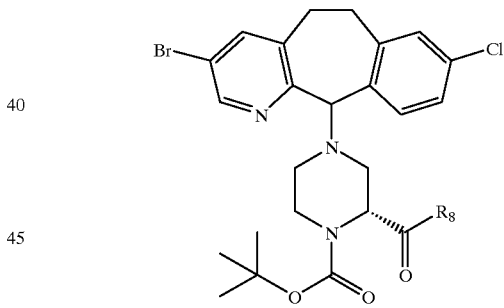
wherein $R^8$ is selected from:
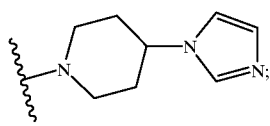
11-(R,S)
(Example 57)
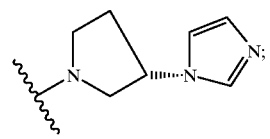
11-(R,S)
(Example 58)

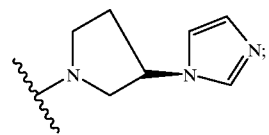
11-(R,S)
(Example 59)
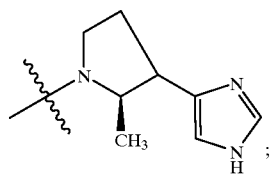
11-(R,S)
(Example 60)
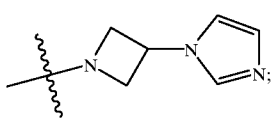
11-(R,S)
(Example 61)
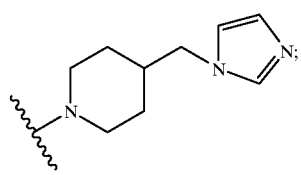
11-(R,S)
(Example 62)
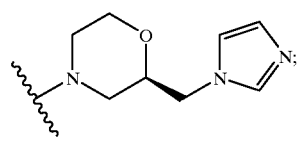
11-(R,S)
(Example 63)
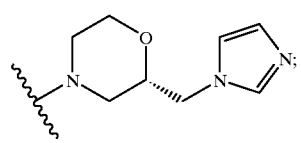
11-(R,S)
(Example 64)
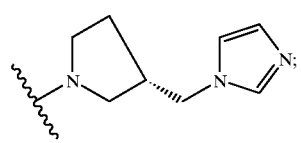
11-(R,S)
(Example 65)
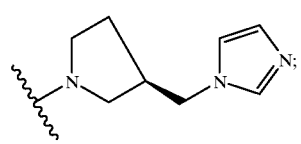
11-S
(Example 66)
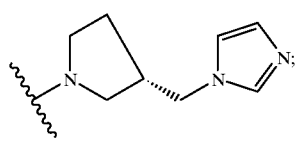
11-R
(Example 67)
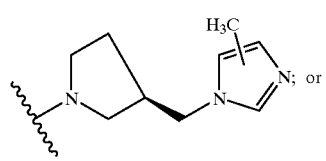
11-(R,S)
(Example 68)
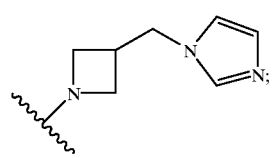
11-(R,S)
(Example 69)
(13) a compound of the formula:
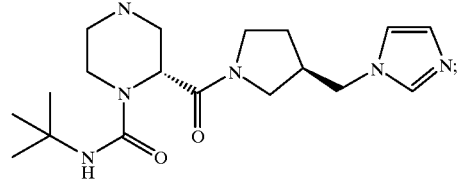
(Example 70)
(14) a compound of the formula:
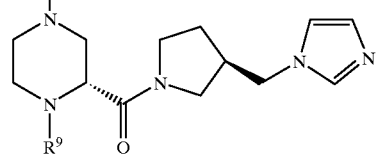

wherein $R^9$ is selected from:
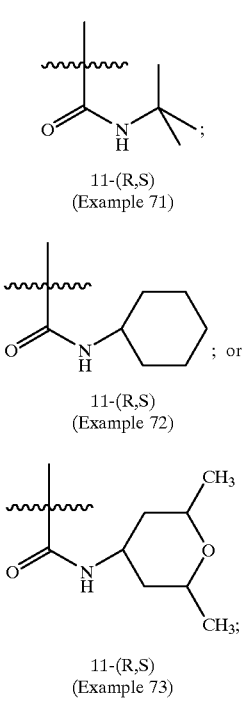
11-(R,S)
(Example 71)
11-(R,S)
(Example 72)
11-(R,S)
(Example 73)
(15) a compound of the formula:
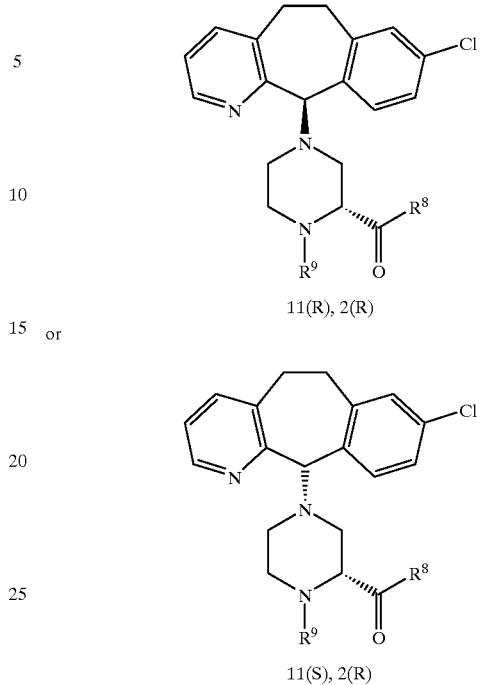
11(R), 2(R)
or
11(S), 2(R)
wherein $R^8$ and $R^9$ are selected from:
| Example | $R^9$ | $R^8$ |
|---|---|---|
| 75 | 11(R), 2(R) | 2(R/S); |
| 76 | 11(S), 2(R) | 2(R/S); |
| 77 | 11(R), 2(R) | 2(R/S); |

-continued

| Example | R⁹ | R⁸ |
|---|---|---|
| 78 | 11(S), 2(R) | 2(R/S); |
| 79 | 11(R), 2(R) | 2(R/S); |
| 80 | 11(S), 2(R) | 2(R/S); |
| 81 | 11(R), 2(R) | 4(R/S); |
| 82 | 11(S), 2(R) | 4(R/S); |

-continued
| Example | R⁹ | R⁸ |
|---|---|---|
| 83 | 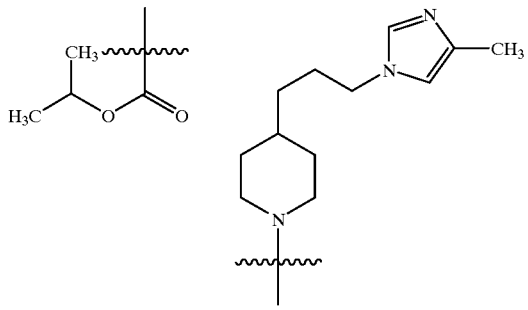<br>11(R), 2(R) | 4(R/S); |
| 84 | 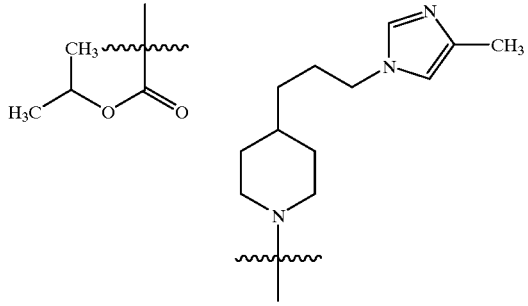<br>11(S), 2(R) | 4(R/S); |
| 85 | 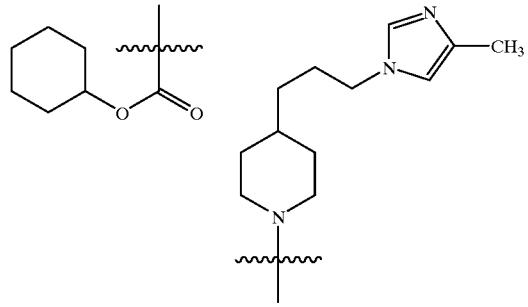<br>11(R), 2(R) | 4(R/S); or |
| 86 | 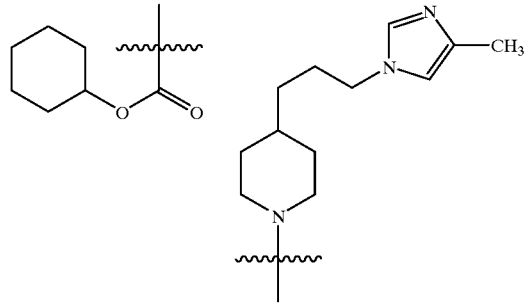<br>11(S), 2(R) | 4(R/S); |

(16) a compound of the formula:

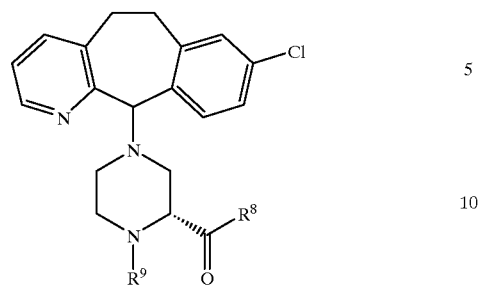

wherein R⁸ and R⁹ are selected from:

| Example | R⁹ | R⁸ |
|---|---|---|
| 87 | (isopropyl ester) 11(R), 2(R) | (tetrahydroquinoline-CH₂-imidazole) 3(R/S); |
| 88 | (isopropyl ester) 11(S), 2(R) | (tetrahydroquinoline-CH₂-imidazole) 3(R/S); |
| 89 | (cyclohexyl ester) 11(R), 2(R) | (tetrahydroquinoline-CH₂-imidazole) 3(R/S); |
| 90 | (cyclohexyl ester) 11(S), 2(R) | (tetrahydroquinoline-CH₂-imidazole) 3(R/S); |
| 91 | (isopropyl ester) 11(R), 2(R) | (tetrahydroquinoline-CH₂-imidazole) 3(R); |

-continued

| Example | R⁹ | R⁸ |
|---|---|---|
| 92 | 11(S), 2(R) | 3(R); |
| 93 | 11(R), 2(R) | 3(R); |
| 94 | 11(S), 2(R) | 3(R); |
| 95 | 11(R), 2(R) | 3(S); |
| 96 | 11(S), 2(R) | 3(S); |
| 97 | 11(S), 2(R) | 3(S); |
| 98 | 11(S), 2(R) | 3(S); |

-continued
| Example | R⁹ | R⁸ |
|---|---|---|
| 99 | 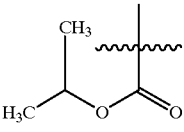<br>11(R), 2(R) | 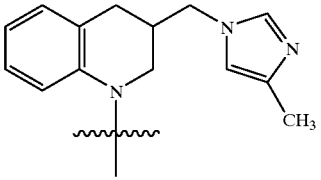<br>3(R/S); |
| 100 | 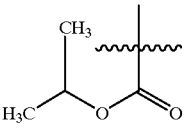<br>11(S), 2(R) | 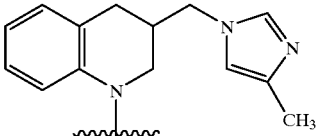<br>3(R/S); |
| 101 | 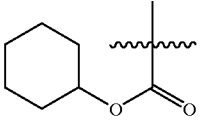<br>11(R), 2(R) | 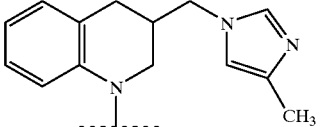<br>3(R/S); |
| 102 | 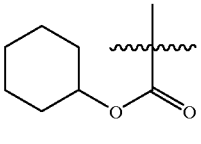<br>11(S), 2(R) | 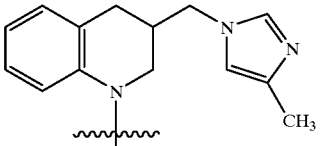<br>3(R/S); |
| 103 | 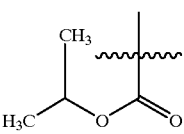<br>11(R), 2(R) | 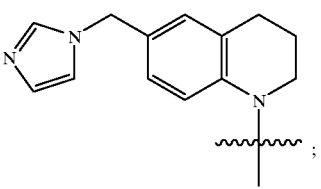 ; |
| 104 | 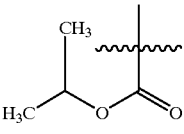<br>11(S), 2(R) | 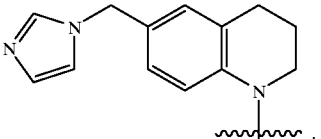 ; |
| 105 | 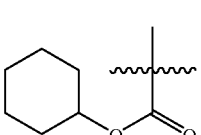 | 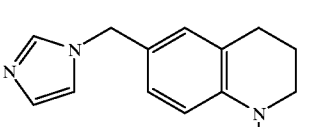 ; |

-continued

| Example | R⁹ | R⁸ |
|---|---|---|
| | | 11(R), 2(R) |
| 106 | (cyclohexyl ester group), 11(S), 2(R) | (imidazol-1-ylmethyl-1,2,3,4-tetrahydroquinoline group); |
| 107 | (isopropyl ester group), 11(R), 2(R) | (4-methylimidazol-1-ylmethyl-tetrahydroisoquinoline group), 4(R/S); |
| 108 | (isopropyl ester group), 11(S), 2(R) | (4-methylimidazol-1-ylmethyl-tetrahydroisoquinoline group), 4(R/S); |
| 109 | (cyclohexyl ester group), 11(R), 2(R) | (4-methylimidazol-1-ylmethyl-tetrahydroisoquinoline group), 4(R/S); or |
| 110 | (cyclohexyl ester group), 11(S), 2(R) | (4-methylimidazol-1-ylmethyl-tetrahydroisoquinoline group), 4(R/S); |

(17) a compound of the formula:
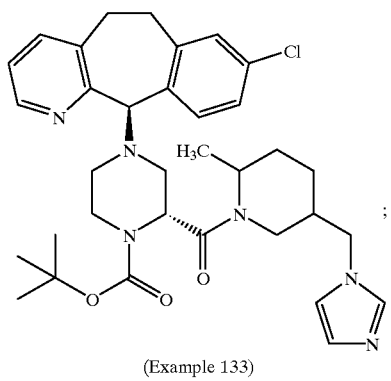
(Example 133)
(18) a compound of the formula:
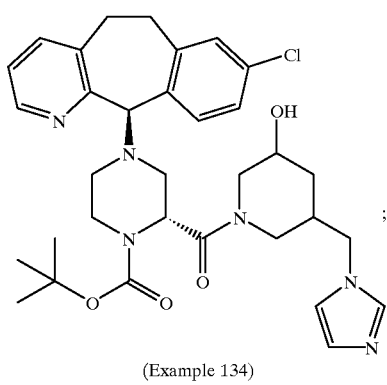
(Example 134)
(19) a compound of the formula:
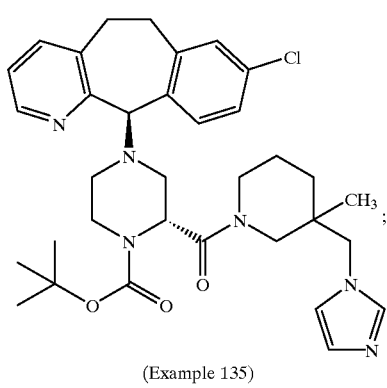
(Example 135)
(20) a compound of the formula:
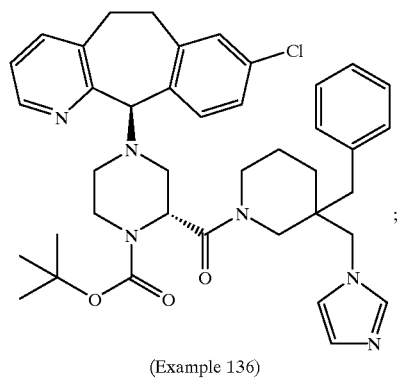
(Example 136)
(21) a compound of the formula:
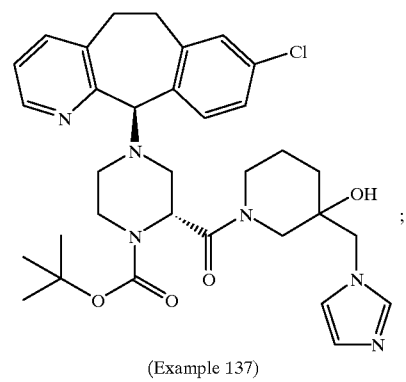
(Example 137)
(22) a compound of the formula:
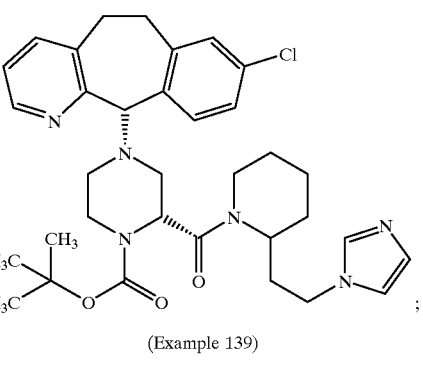
(Example 139)

(23) a compound of the formula:
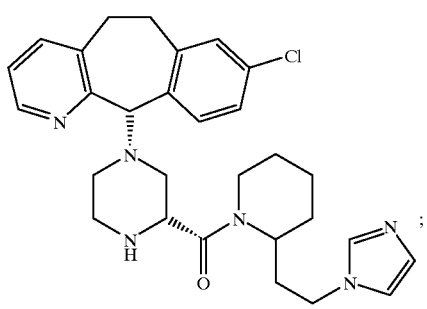
(Example 140)
(24) a compound of the formula:
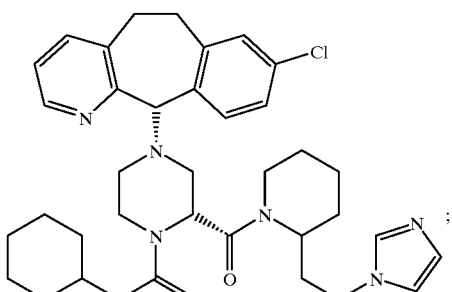
(Example 141)
(25) a compound of the formula:
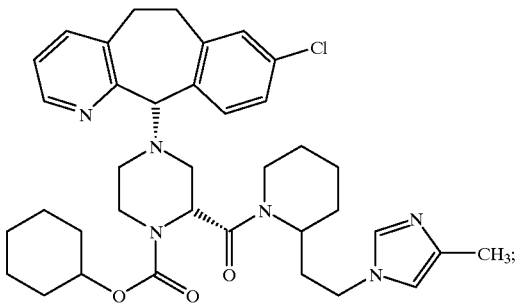
(Example 143)
(26) a compound of the formula:
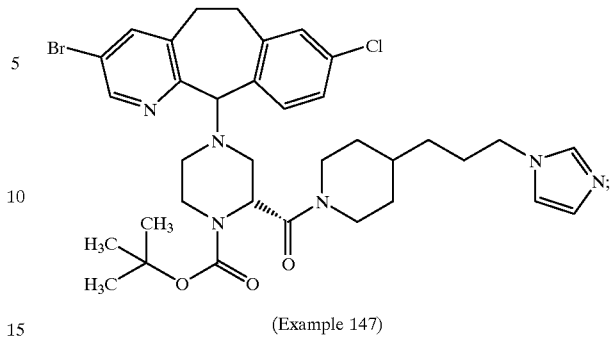
(Example 147)
(27) a compound of the formula:
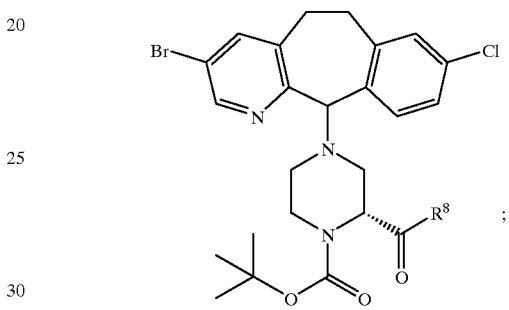
wherein $R^8$ is selected from:
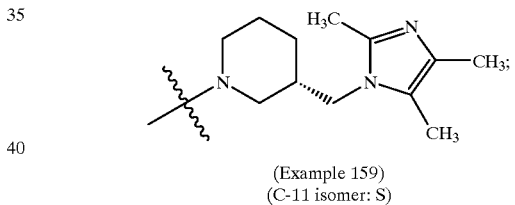
(Example 159)
(C-11 isomer: S)
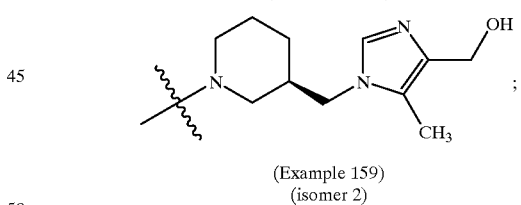
(Example 159)
(isomer 2)
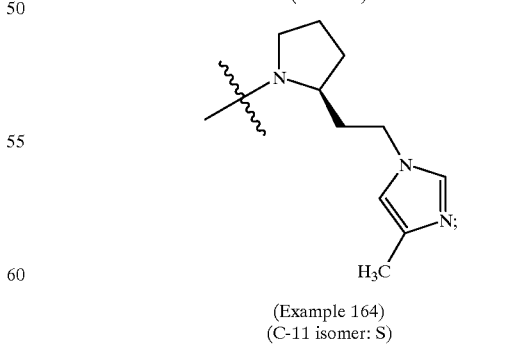
(Example 164)
(C-11 isomer: S)

-continued
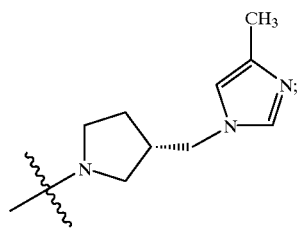
(Example 165)
(C-11 isomer: S)
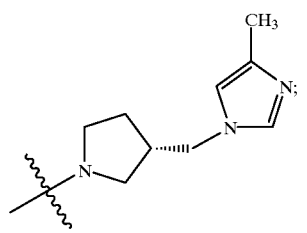
(Example 166)
(C-11 isomer: R)
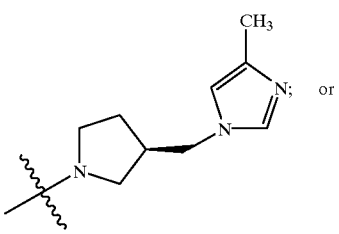
(Example 167)
(C-11 isomer: S)
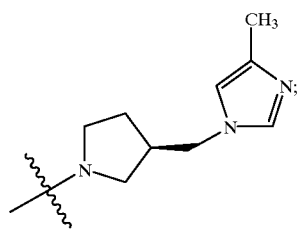
(Example 168)
(C-11 isomer: R)
(28) a compound of the formula:
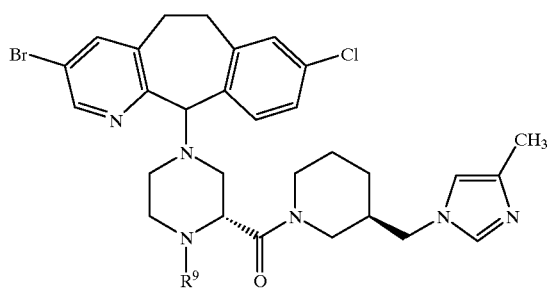
wherein R⁹ is selected from:
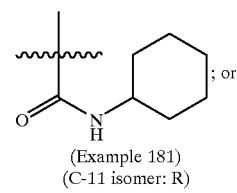
(Example 181)
(C-11 isomer: R)
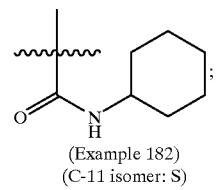
(Example 182)
(C-11 isomer: S)
(29) a compound of the formula:
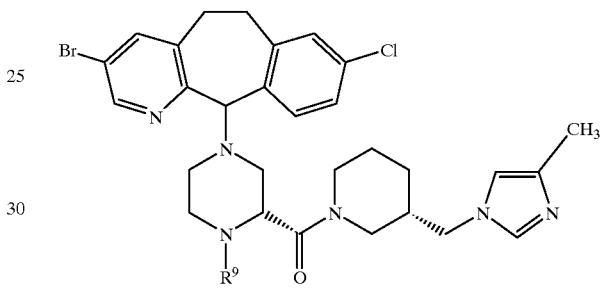
wherein R⁹ is selected from:
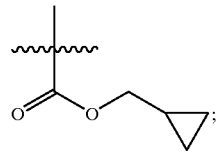
(Example 189)
(C-11 isomer: R)
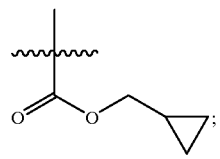
(Example 190)
(C-11 isomer: S)
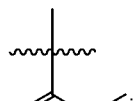
(Example 193)
(C-11 isomer: R)

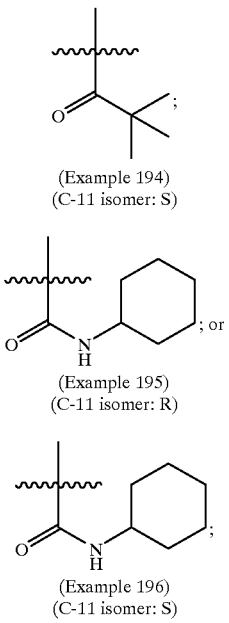
(Example 194)
(C-11 isomer: S)
(Example 195)
(C-11 isomer: R)
(Example 196)
(C-11 isomer: S)
(30) a compound of the formula:
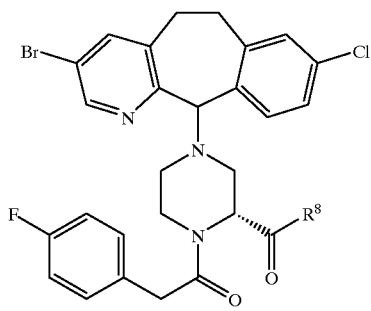
wherein R⁸ is selected from:
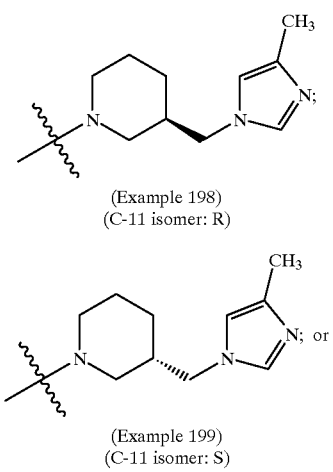
(Example 198)
(C-11 isomer: R)
(Example 199)
(C-11 isomer: S)
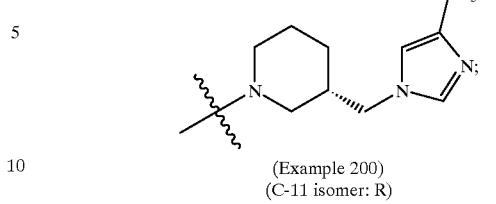
(Example 200)
(C-11 isomer: R)
(31) a compound of the formula:
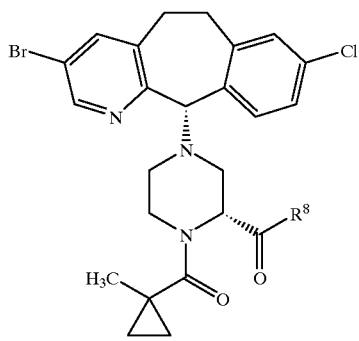
wherein R⁸ is:
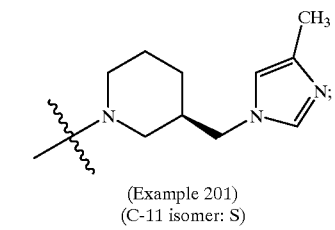
(Example 201)
(C-11 isomer: S)
(32) a compound of the formula:
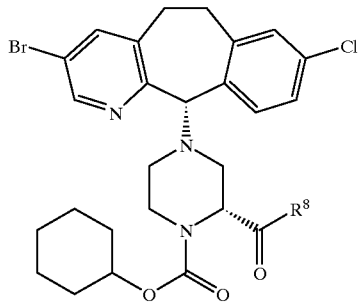

wherein R⁸ is selected from:
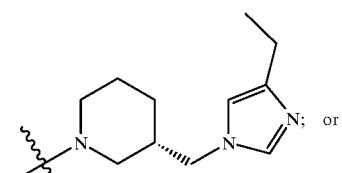
(Example 205)
(C-11 isomer: R)
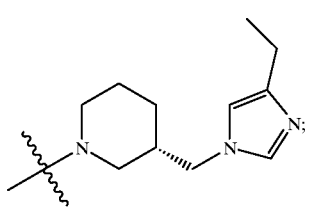
(Example 206)
(C-11 isomer: S)
(33) a compound of the formula:
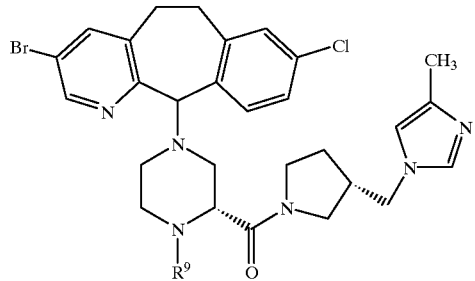
wherein R⁹ is selected from:
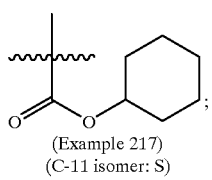
(Example 217)
(C-11 isomer: S)
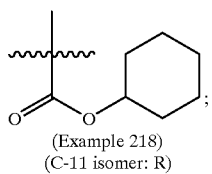
(Example 218)
(C-11 isomer: R)
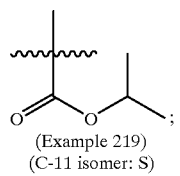
(Example 219)
(C-11 isomer: S)
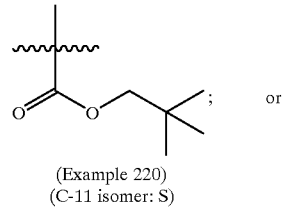
(Example 220)
(C-11 isomer: S)
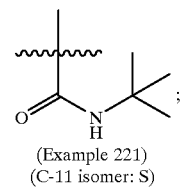
(Example 221)
(C-11 isomer: S)
(34) a compound of the formula:
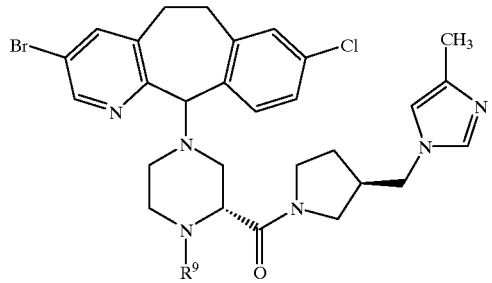
wherein R⁹ is selected from:
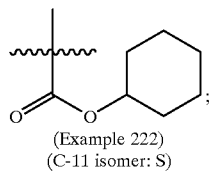
(Example 222)
(C-11 isomer: S)
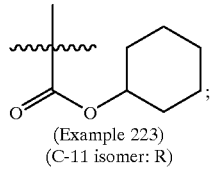
(Example 223)
(C-11 isomer: R)
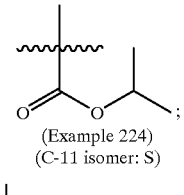
(Example 224)
(C-11 isomer: S)
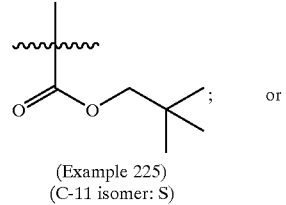
(Example 225)
(C-11 isomer: S)

-continued
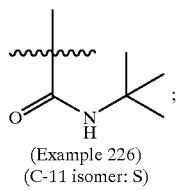
(Example 226)
(C-11 isomer: S)
(35) a compound of the formula:
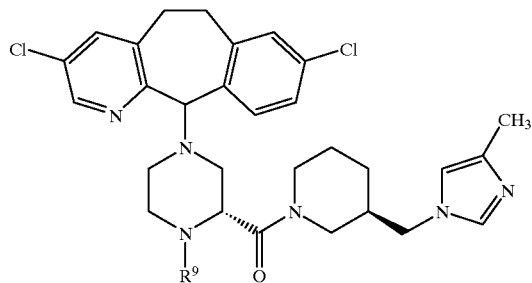
wherein $R^9$ is selected from:
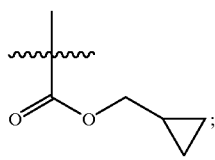
(Example 235)
C-11 isomer: R)
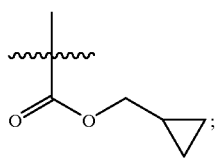
(Example 236)
C-11 isomer: S)
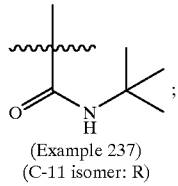
(Example 237)
(C-11 isomer: R)
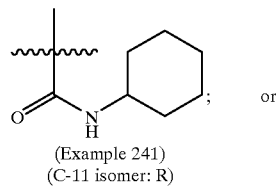 or
(Example 241)
(C-11 isomer: R)
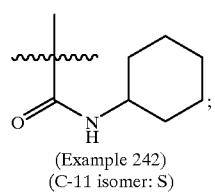
(Example 242)
(C-11 isomer: S)
(36) a compound of the formula:
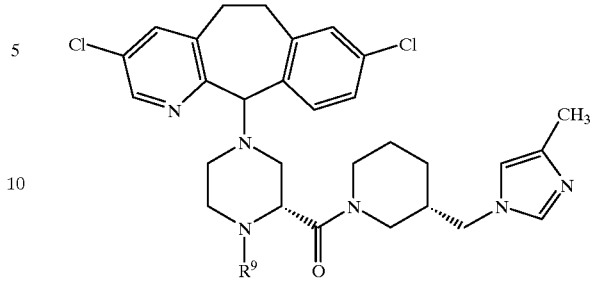
wherein $R^9$ is selected from:
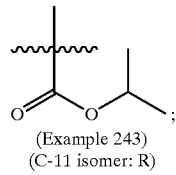
(Example 243)
(C-11 isomer: R)
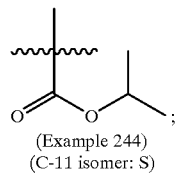
(Example 244)
(C-11 isomer: S)
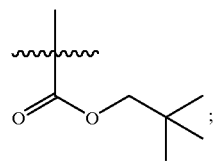
(Example 246)
(C-11 isomer: S)
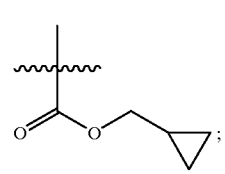
(Example 247)
(C-11 isomer: R)
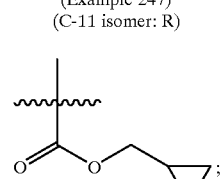
(Example 248)
(C-11 isomer: S)
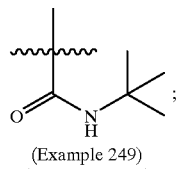
(Example 249)
(C-11 isomer: R)

-continued
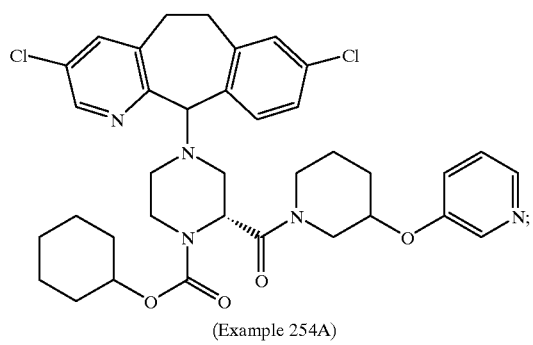
(Example 250)
(C-11 isomer: S)
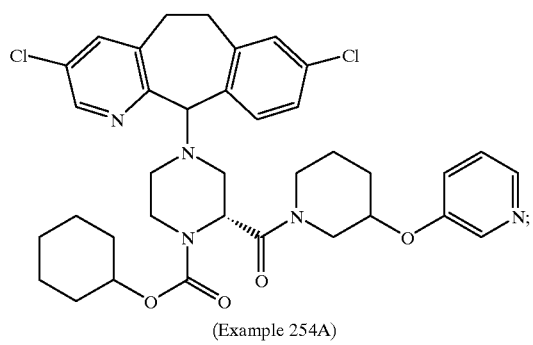
(Example 251)
(C-11 isomer: R)
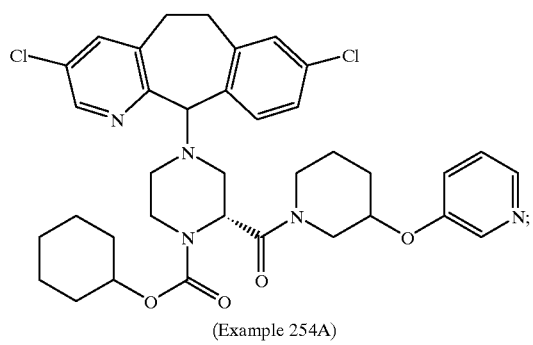
(Example 252)
(C-11 isomer: S)
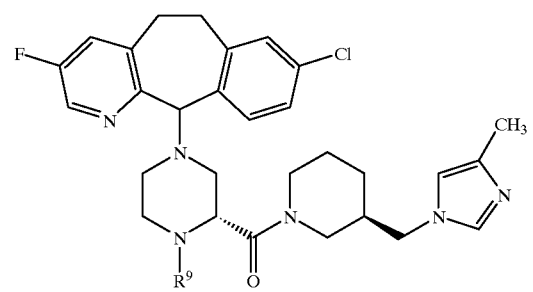
(Example 253)             (Example 254)
(C-11 isomer: R)           (C-11 isomer: S)
(37) a compound of the formula:
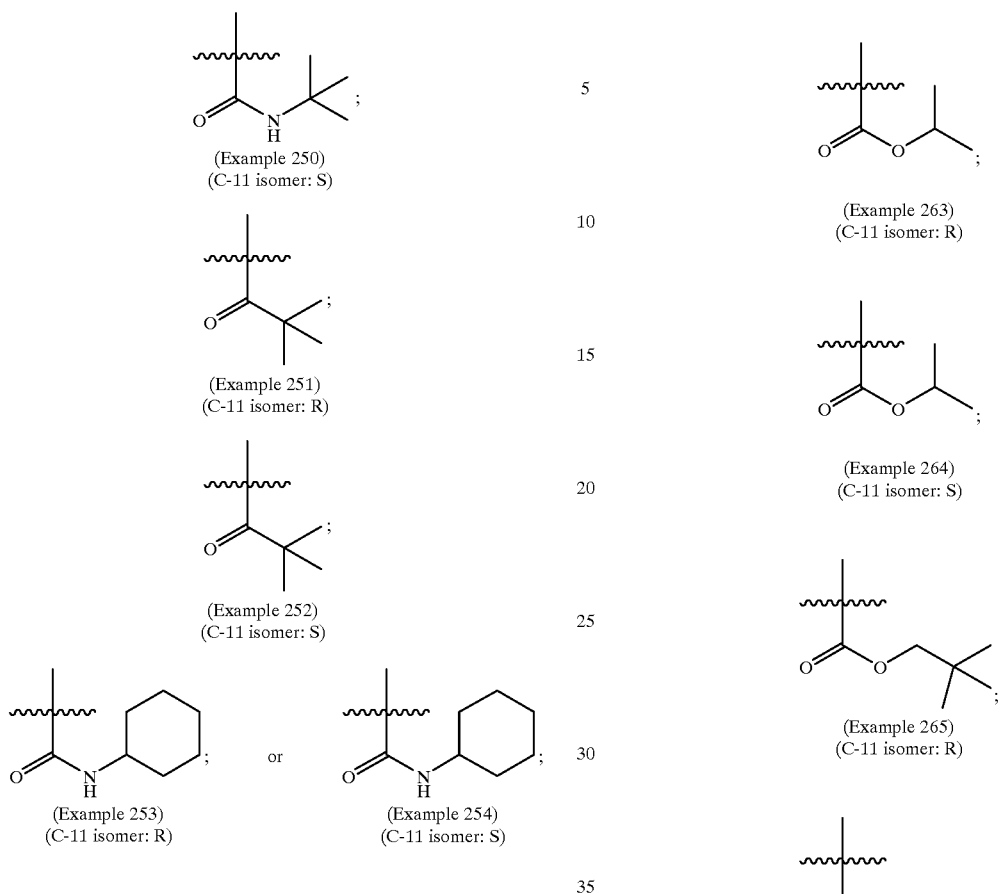
(Example 254A)
(38) a compound of the formula:
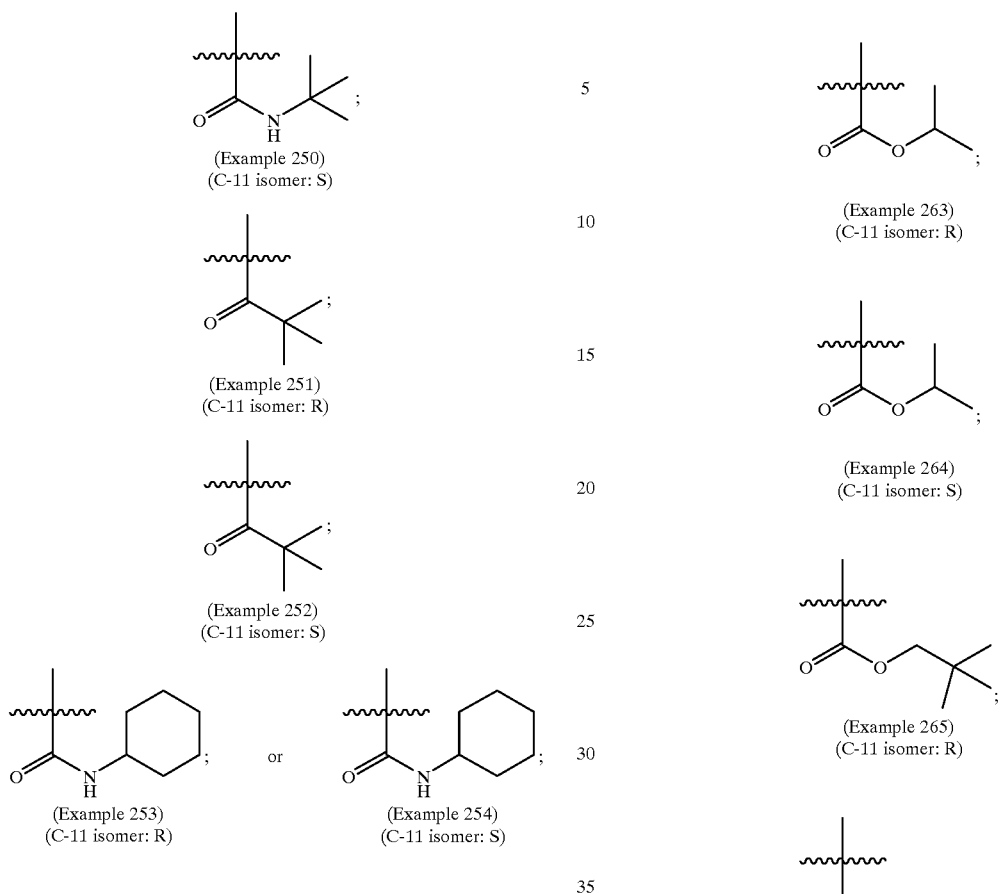
wherein $R^9$ is selected from:
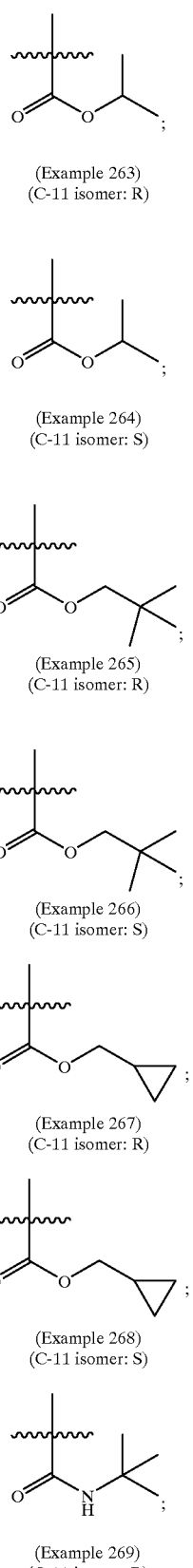
(Example 263)
(C-11 isomer: R)
(Example 264)
(C-11 isomer: S)
(Example 265)
(C-11 isomer: R)
(Example 266)
(C-11 isomer: S)
(Example 267)
(C-11 isomer: R)
(Example 268)
(C-11 isomer: S)
(Example 269)
(C-11 isomer: R)

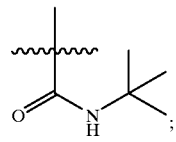
(Example 270)
(C-11 isomer: S)
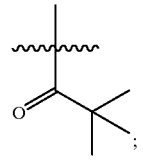
(Example 271)
(C-11 isomer: R)
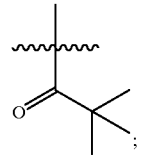
(Example 272)
(C-11 isomer: S)
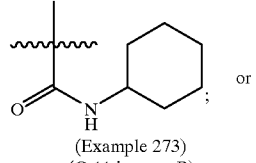
or
(Example 273)
(C-11 isomer: R)
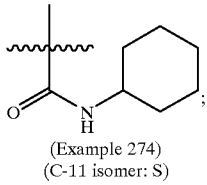
(Example 274)
(C-11 isomer: S)
(39) a compound of the formula:
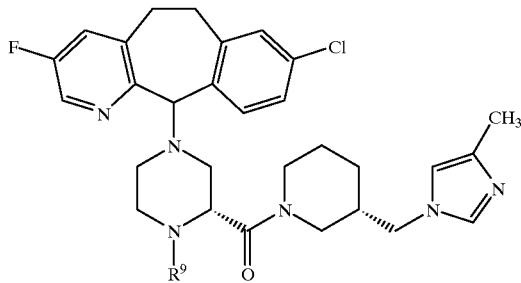
wherein R⁹ is selected from:
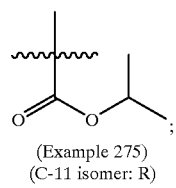
(Example 275)
(C-11 isomer: R)
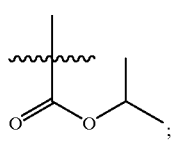
(Example 276)
(C-11 isomer: S)
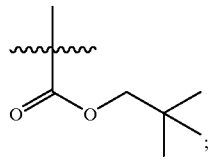
(Example 277)
(C-11 isomer: R)
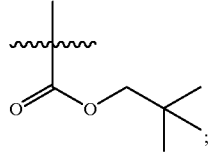
(Example 278)
(C-11 isomer: S)
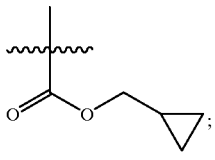
(Example 279)
(C-11 isomer: R)
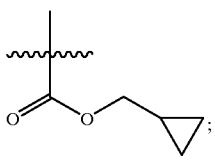
(Example 280)
(C-11 isomer: S)
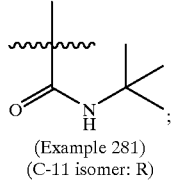
(Example 281)
(C-11 isomer: R)
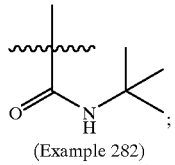
(Example 282)
(C-11 isomer: S)
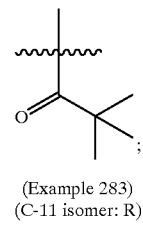
(Example 283)
(C-11 isomer: R)

-continued
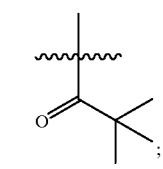
(Example 284)
(C-11 isomer: S)
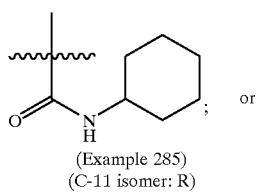; or
(Example 285)
(C-11 isomer: R)
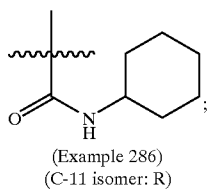;
(Example 286)
(C-11 isomer: R)
(40) a compound of the formula:
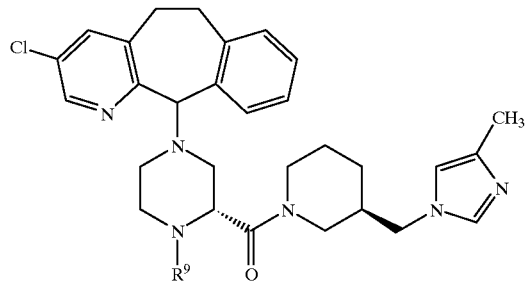
wherein R⁹ is selected from;
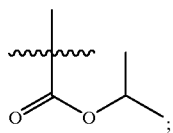;
(Example 295)
(C-11 isomer: R)
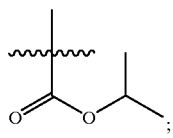;
(Example 296)
(C-11 isomer: S)
-continued
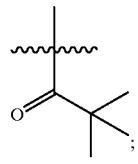;
(Example 304)
(C-11 isomer: S)
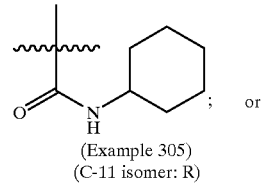; or
(Example 305)
(C-11 isomer: R)
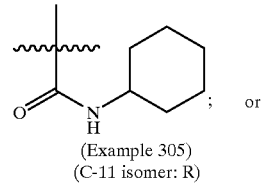;
(Example 306)
(C-11 isomer: S)
(41) a compound of the formula:
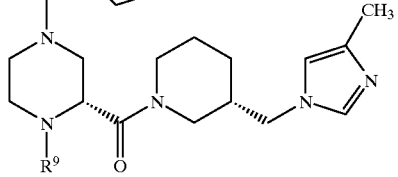
wherein R⁹ is selected from:
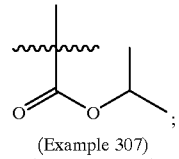;
(Example 307)
(C-11 isomer: R)
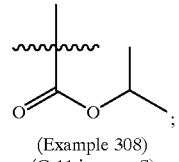;
(Example 308)
(C-11 isomer: S)
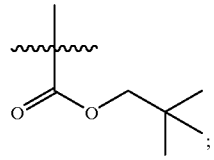;
(Example 309)
(C-11 isomer: R)

-continued
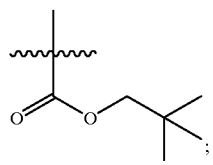
(Example 310)
(C-11 isomer: S)
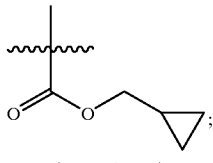
(Example 311)
(C-11 isomer: R)
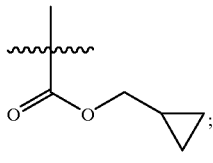
(Example 312)
(C-11 isomer: S)
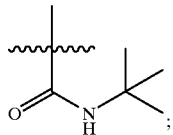
(Example 313)
(C-11 isomer: R)
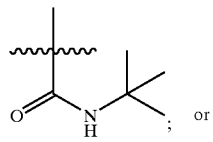  ; or
(Example 314)
(C-11 isomer: S)
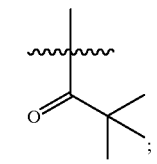
(Example 315)
(C-11 isomer: R)
(42) a compound of the formula:
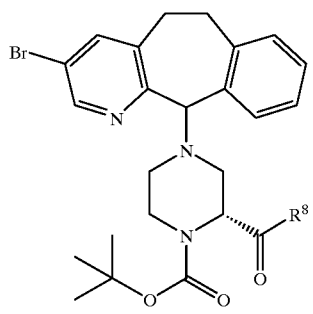
wherein $R^8$ is selected from:
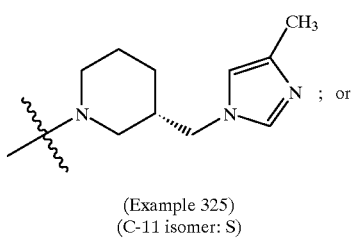 ; or
(Example 325)
(C-11 isomer: S)
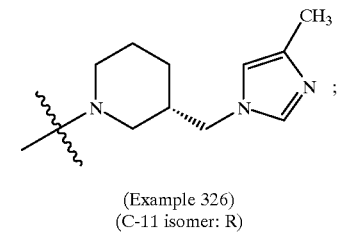 ;
(Example 326)
(C-11 isomer: R)
(43) a compound selected from:
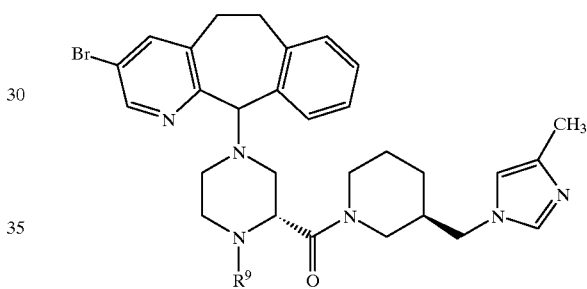
wherein $R^9$ is selected from:
 ;
(Example 327)
(C-11 isomer: R)
 ;
(Example 328)
(C-11 isomer: S)
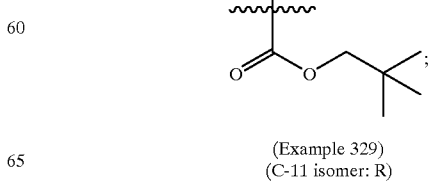 ;
(Example 329)
(C-11 isomer: R)

-continued

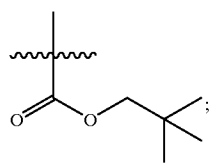

(Example 330)
(C-11 isomer: S)

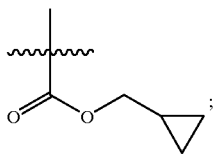

(Example 331)
(C-11 isomer: R)

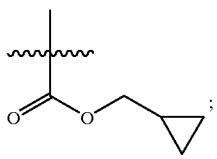

(Example 332)
(C-11 isomer: S)

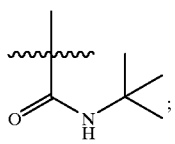

(Example 333)
(C-11 isomer: R)

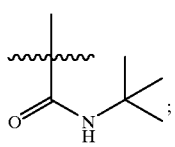

(Example 334)
(C-11 isomer: S)

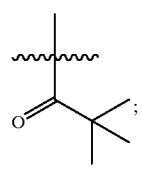

(Example 335)
(C-11 isomer: R)

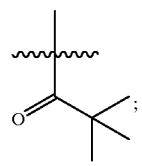

(Example 336)
(C-11 isomer: S)

-continued

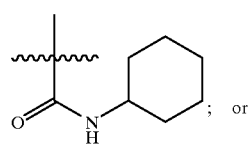

(Example 337)
(C-11 isomer: R)

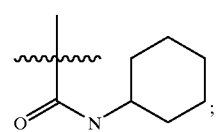

(Example 338)
(C-11 isomer: S)

(44) a compound of the formula:

[Structure with Br, pyridine fused to benzocycloheptane, piperazine with $R^9$, carbonyl, piperidine, methylimidazole with CH$_3$]

wherein $R^9$ is selected from;

[Structure: isopropyl ester]

(Example 339)
(C-11 isomer: R)

[Structure: isopropyl ester]

(Example 340)
(C-11 isomer: S)

[Structure: neopentyl ester]

(Example 341)
(C-11 isomer: R)

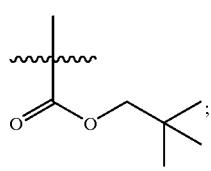
(Example 342)
(C-11 isomer: S)
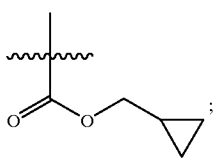
(Example 343)
(C-11 isomer: R)
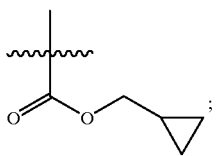
(Example 344)
(C-11 isomer: S)
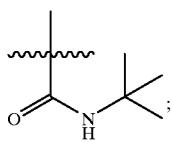
(Example 345)
(C-11 isomer: R)
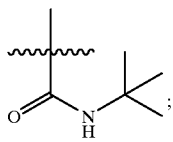
(Example 346)
(C-11 isomer: S)
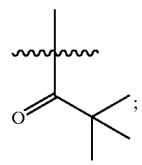
(Example 347)
(C-11 isomer: R)
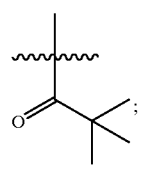
(Example 348)
(C-11 isomer: S)
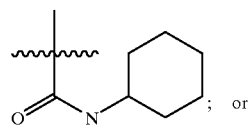
; or
(Example 349)
(C-11 isomer: R)
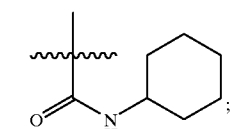
(Example 350)
(C-11 isomer: S)
(45) a compound of the formula:
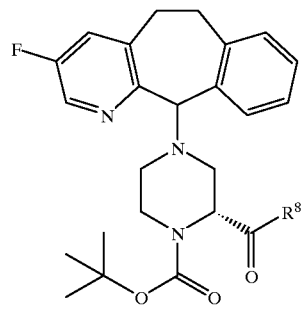
wherein $R^8$ is selected from:
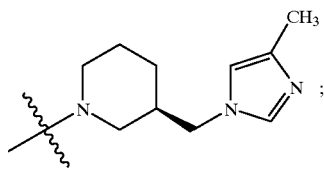
(Example 355)
(C-11 isomer: S)
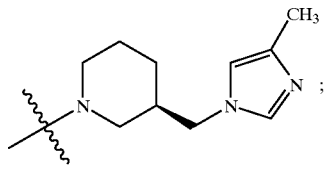
(Example 356)
(C-11 isomer: R)
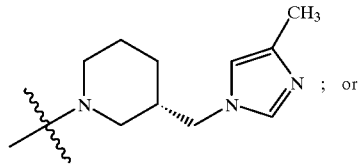
; or
(Example 357)
(C-11 isomer: S)

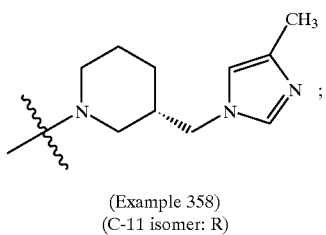

(Example 358)
(C-11 isomer: R)

(46) a compound of the formula:

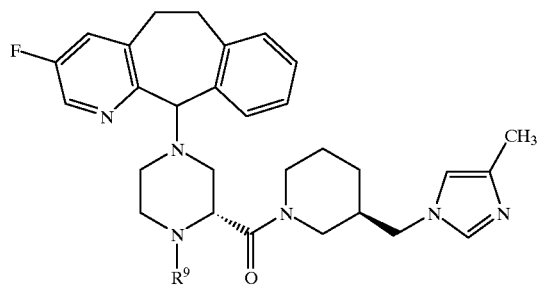

wherein $R^9$ is selected from:

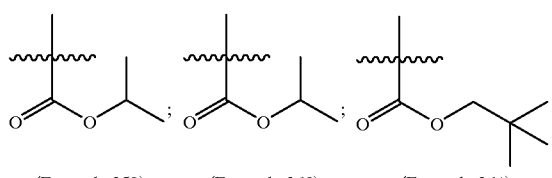

(Example 359)   (Example 360)   (Example 361)
(C-11 isomer: R) (C-11 isomer: S) (C-11 isomer: R)

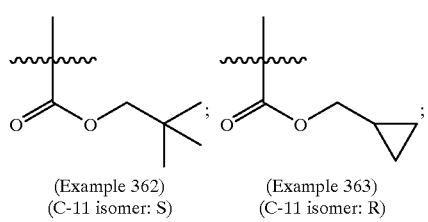

(Example 362)   (Example 363)
(C-11 isomer: S) (C-11 isomer: R)

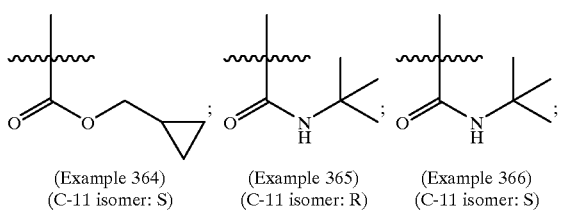

(Example 364)   (Example 365)   (Example 366)
(C-11 isomer: S) (C-11 isomer: R) (C-11 isomer: S)

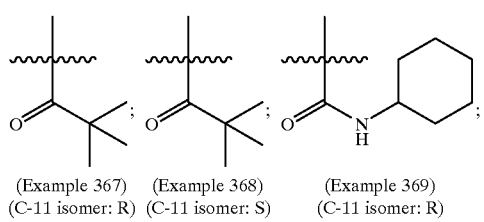

(Example 367)   (Example 368)   (Example 369)
(C-11 isomer: R) (C-11 isomer: S) (C-11 isomer: R)

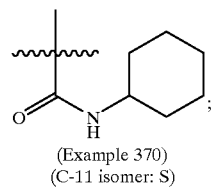

(Example 370)
(C-11 isomer: S)

(47) a compound of the formula:

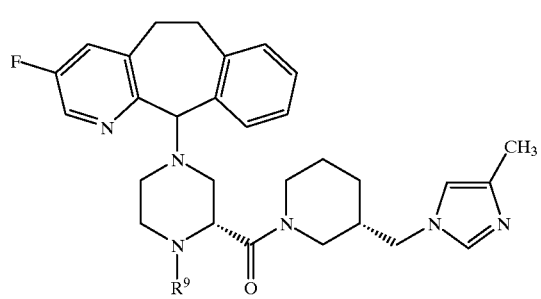

wherein $R^9$ is selected from:

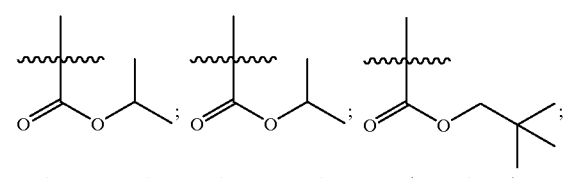

(Example 371)   (Example 372)   (Example 373)
(C-11 isomer: R) (C-11 isomer: S) (C-11 isomer: R)

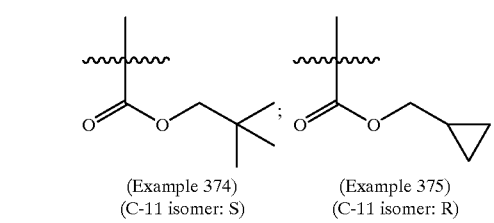

(Example 374)   (Example 375)
(C-11 isomer: S) (C-11 isomer: R)

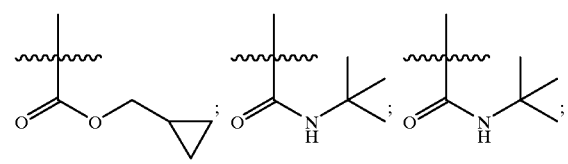

(Example 376)   (Example 377)   (Example 378)
(C-11 isomer: S) (C-11 isomer: R) (C-11 isomer: S)

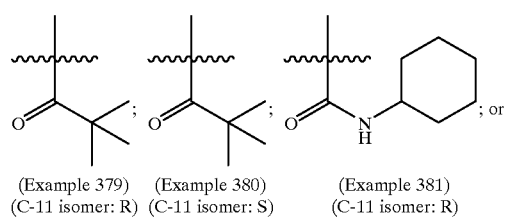

(Example 379)   (Example 380)   (Example 381)
(C-11 isomer: R) (C-11 isomer: S) (C-11 isomer: R)

-continued
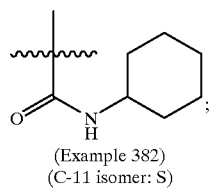
(Example 382)
(C-11 isomer: S)
(48) a compound of the formula:
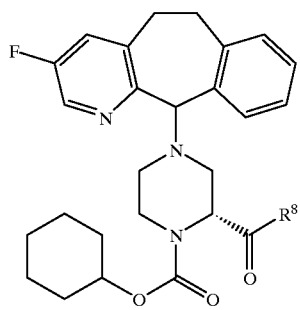
wherein $R^8$ is selected from:
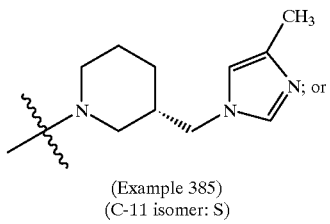
(Example 385)
(C-11 isomer: S)
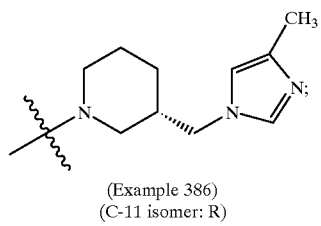
(Example 386)
(C-11 isomer: R)
(49) a compound of the formula:
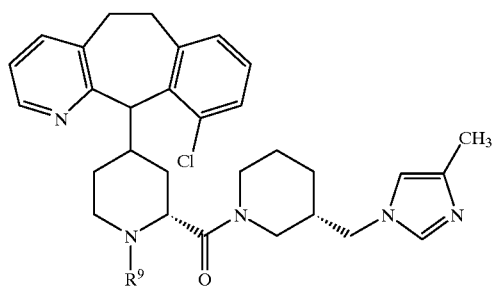
wherein $R^9$ is selected from;
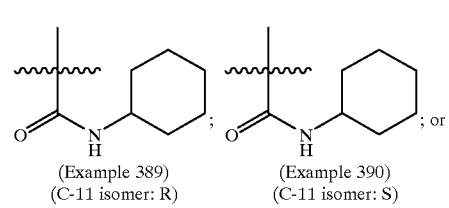
(Example 389)          (Example 390)
(C-11 isomer: R)       (C-11 isomer: S)
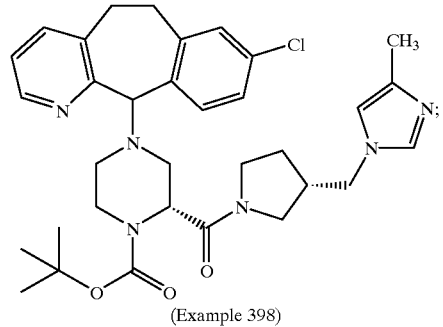
(Example 393)
(C-11 isomer: R)
(50) a compound of the formula:
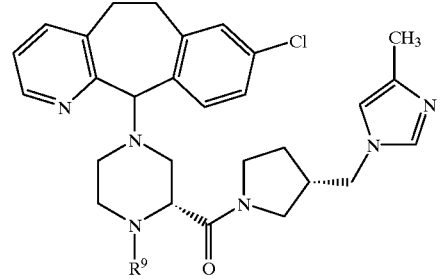
(Example 398)
(51) a compound of the formula:
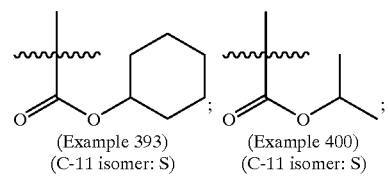
wherein $R^9$ is selected from;
(Example 393)          (Example 400)
(C-11 isomer: S)       (C-11 isomer: S)

-continued
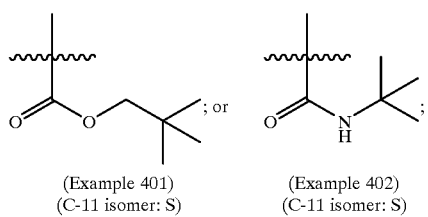
(Example 401) (C-11 isomer: S)    (Example 402) (C-11 isomer: S)
(52) a compound of the formula:
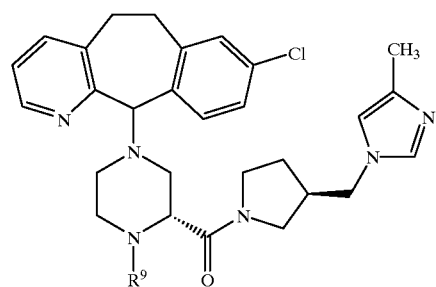
wherein $R^9$ is selected from:
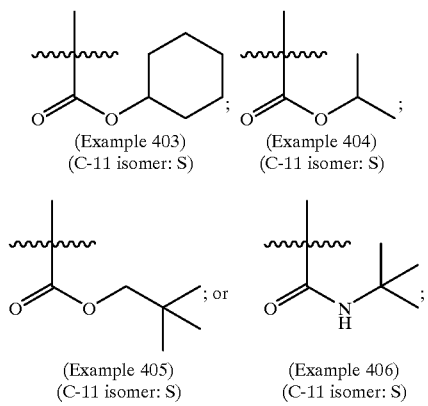
(Example 403) (C-11 isomer: S)    (Example 404) (C-11 isomer: S)
(Example 405) (C-11 isomer: S)    (Example 406) (C-11 isomer: S)
(53) a compound of the formula:
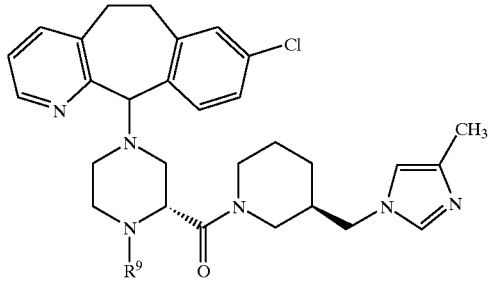
wherein $R^9$ is:
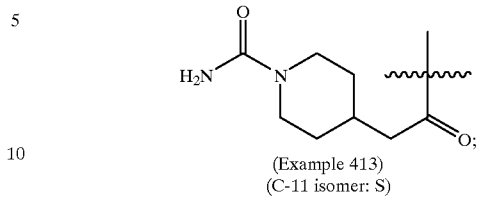
(Example 413) (C-11 isomer: S)
(54) a compound of the formula:
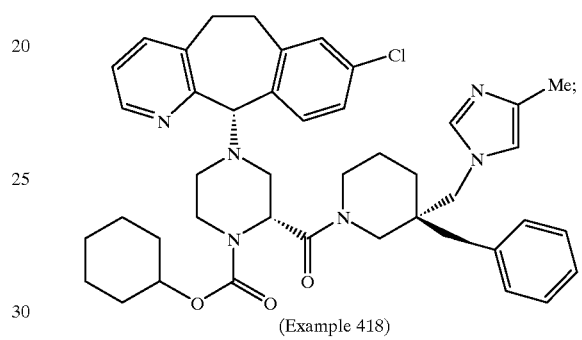
(Example 418)
(55) a compound of the formula:
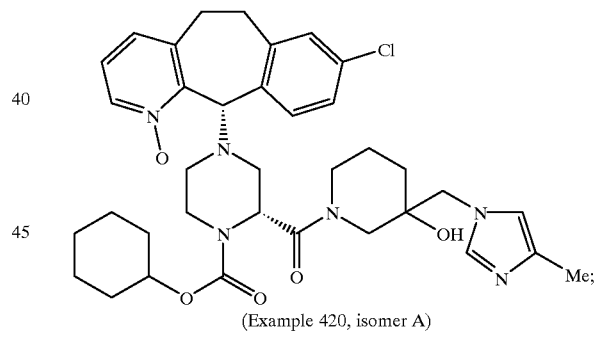
(Example 420, isomer A)
(56) a compound of the formula:
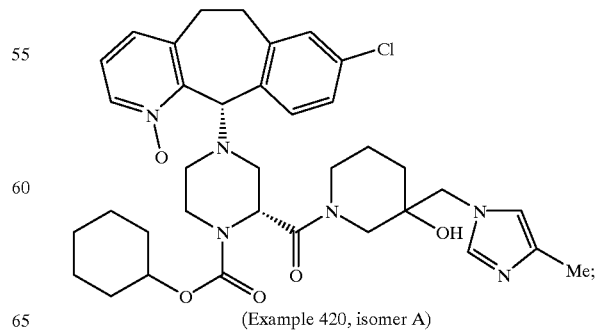
(Example 420, isomer A)

(57) a compound of the formula:
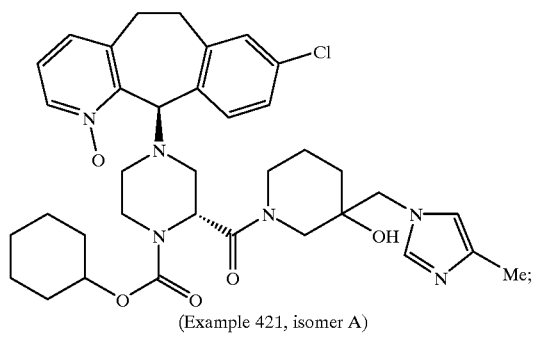
(Example 421, isomer A)
(58) a compound of the formula:
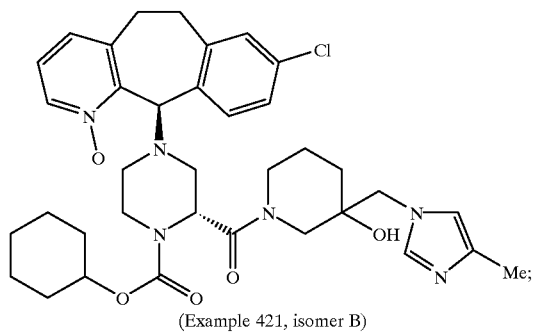
(Example 421, isomer B)
(59) a compound of the formula:
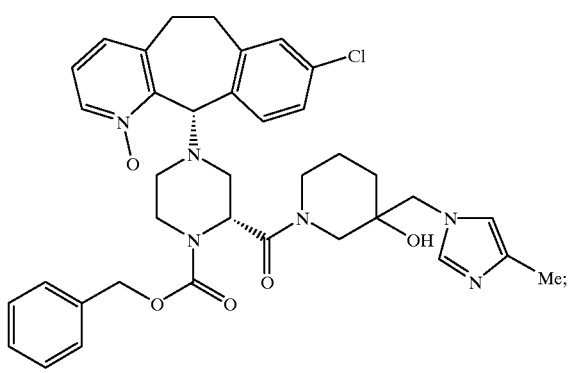
(Example 425, isomer A)
(60) a compound of the formula:
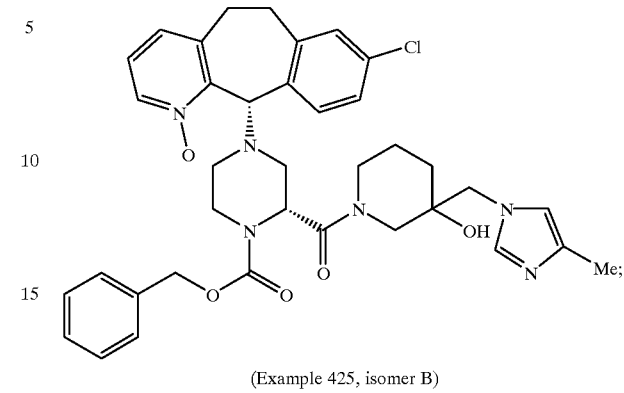
(Example 425, isomer B)
(61) a compound of the formula:
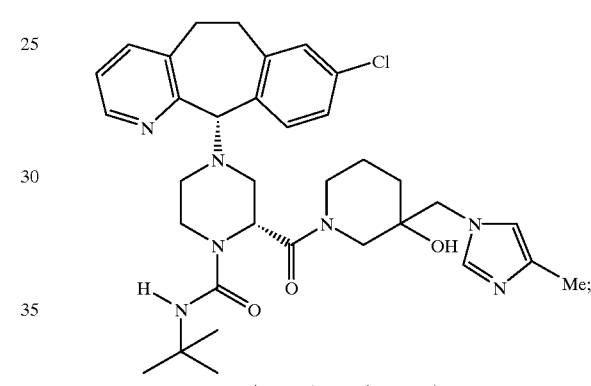
(Example 426, isomer A)
(62) a compound of the formula:
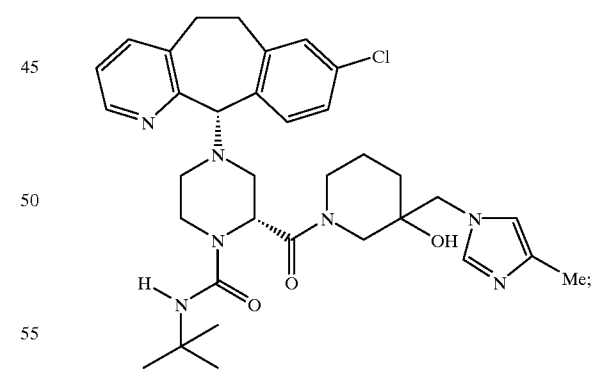
(Example 427, isomer B)

(63) a compound of the formula:
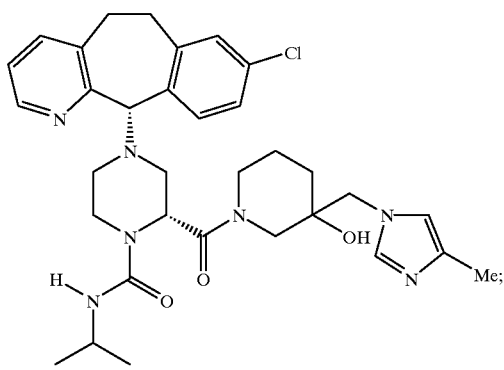
(Example 428, isomer A)
(64) a compound of the formula:
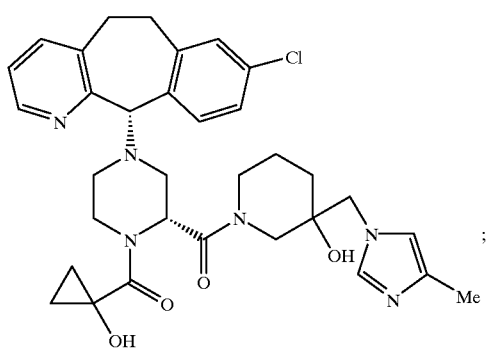
(Example 429, isomer A)
(65) a compound of the formula:
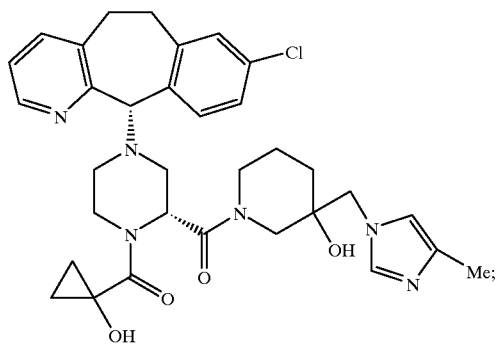
(Example 430, isomer B)
(66) a compound of the formula:
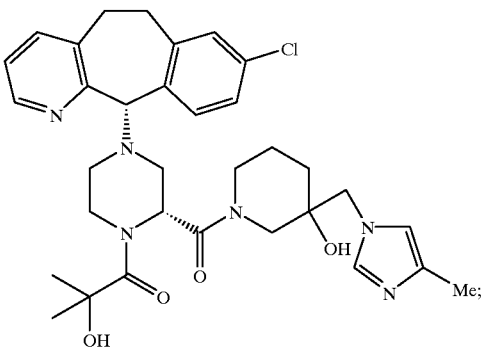
(Example 431, isomer A)
(67) a compound of the formula:
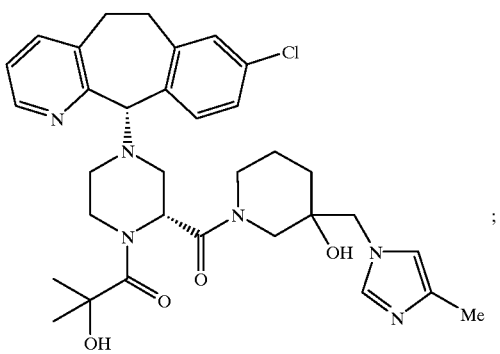
(Example 432, isomer B)
(68) a compound of the formula:
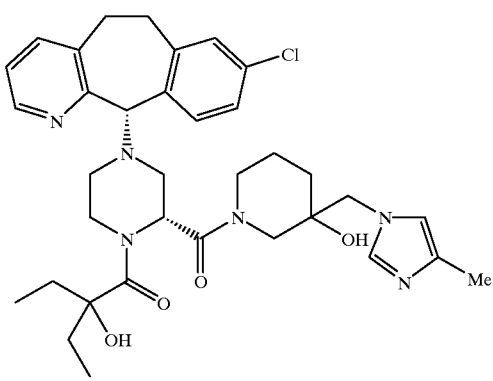
(Example 433, isomer A)

(69) a compound of the formula:
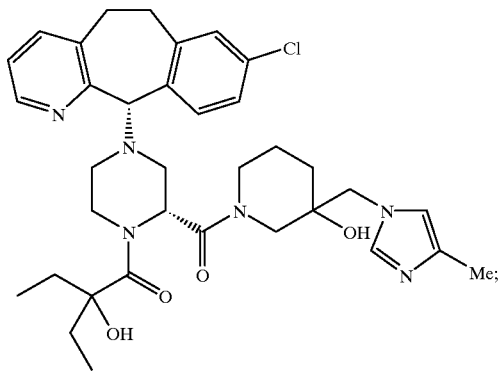
(Example 434, isomer B)
(70) a compound of the formula:
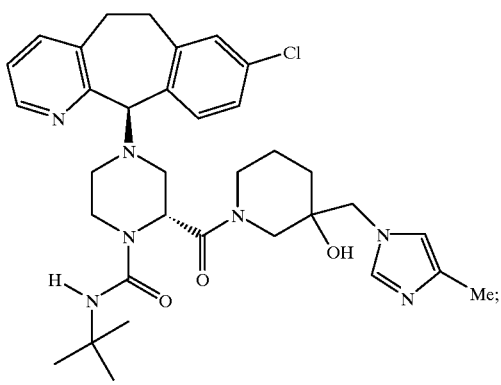
(Example 435, isomer A)
(71) a compound of the formula:
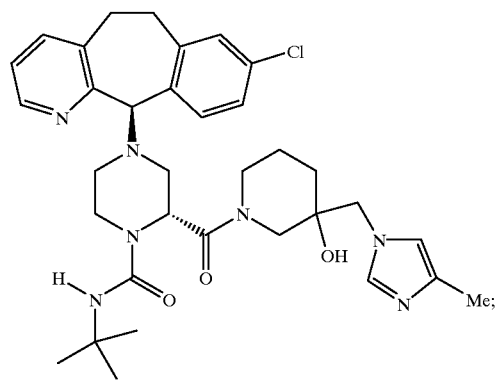
(Example 436, isomer B)
(72) a compound of the formula:
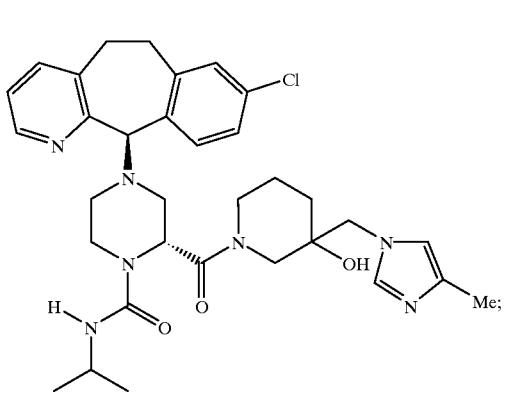
(Example 437, isomer A)
(73) a compound of the formula:
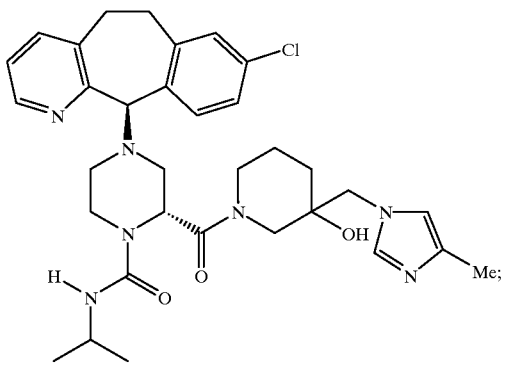
(Example 438, isomer B)
(74) a compound of the formula:
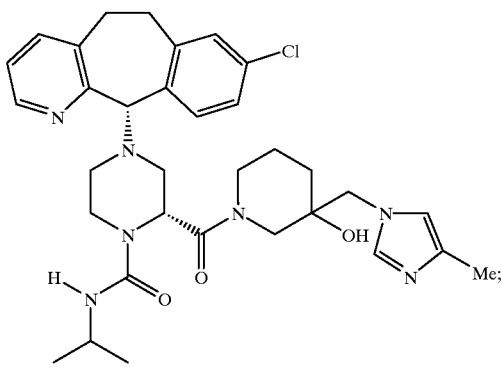
(Example 439, isomer B)

(75) a compound of the formula:
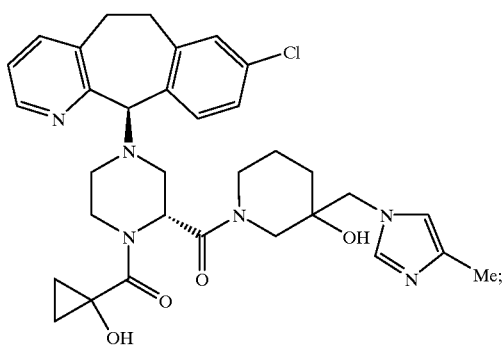
(Example 440, isomer A)
(76) a compound of the formula:
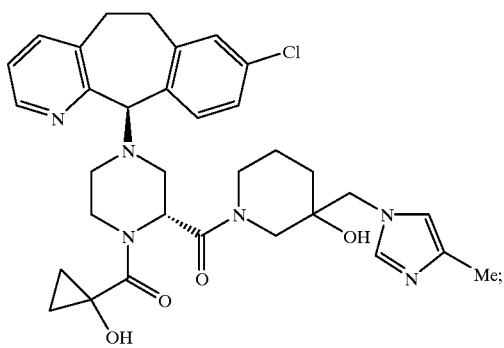
(Example 441, isomer B)
(77) a compound of the formula:
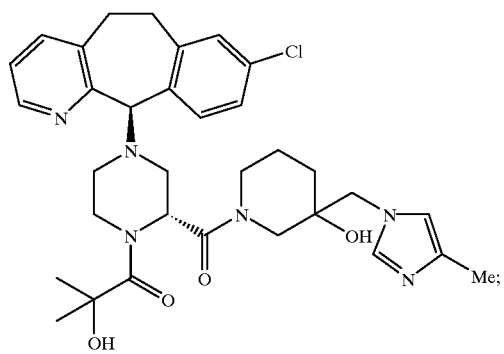
(Example 442, isomer A)
(78) a compound of the formula:
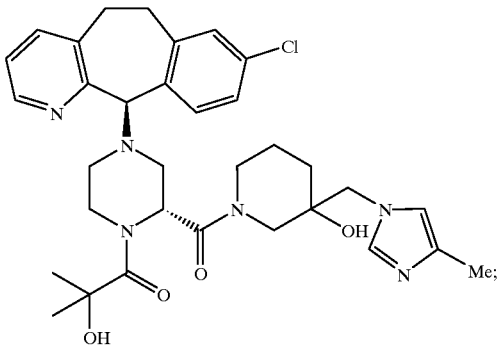
(Example 443, isomer B)
(79) a compound of the formula:
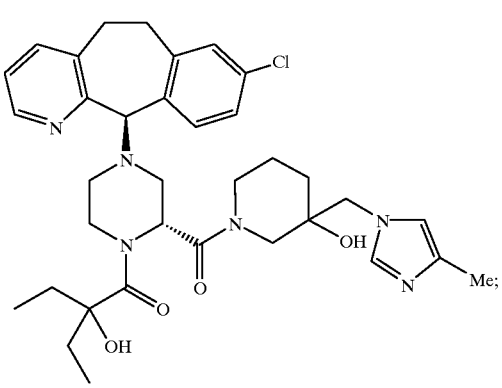
(Example 440, isomer A)
(80) a compound of the formula:
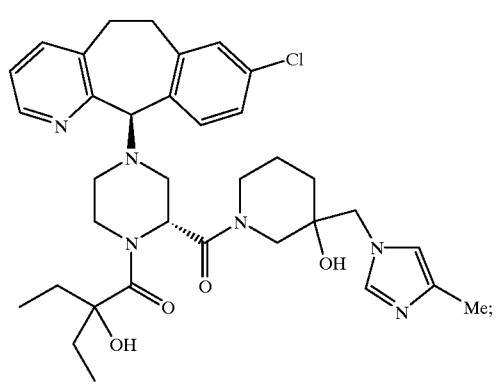
(Example 455, isomer B)

(81) a compound of the formula:
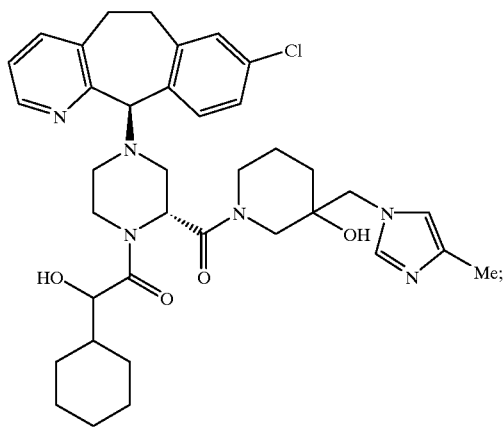
(Example 446, isomer A)
(82) a compound of the formula:
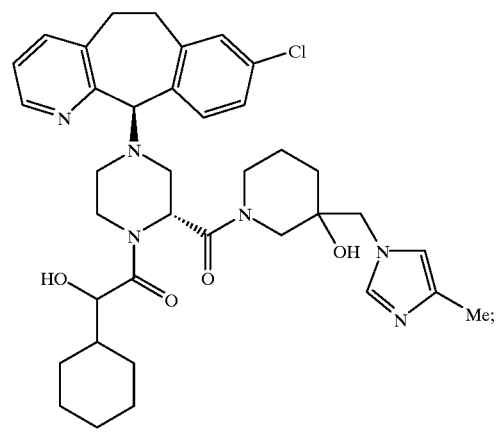
(Example 447, isomer B)
(83) a compound of the formula:
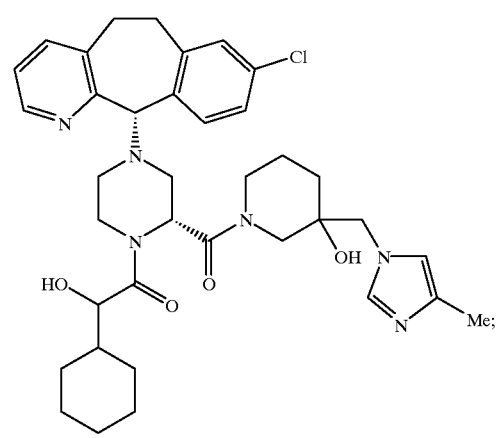
(Example 448, isomer A)
(84) a compound of the formula:
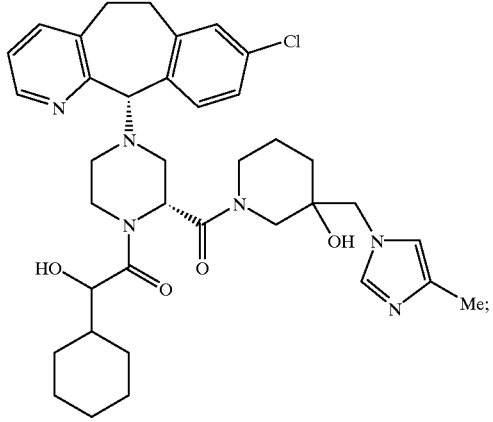
(Example 449, isomer B)
(85) a compound of the formula:
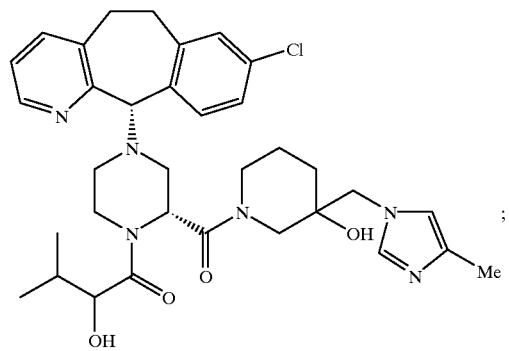
(Example 450, isomer A)
(86) a compound of the formula:
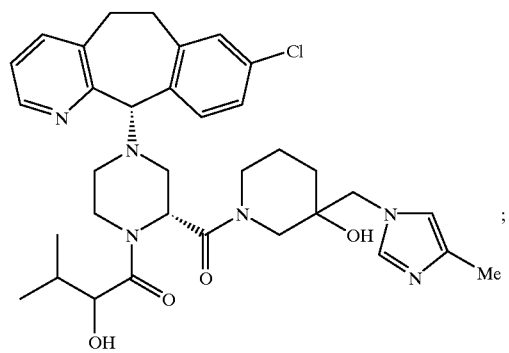
(Example 451, isomer B)

(87) a compound of the formula:
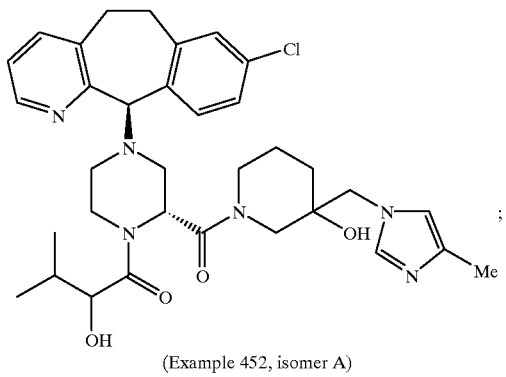
(Example 452, isomer A)
(88) a compound of the formula:
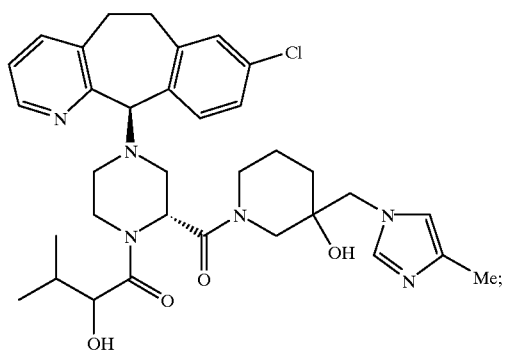
(Example 453, isomer B)
(89) a compound of the formula:
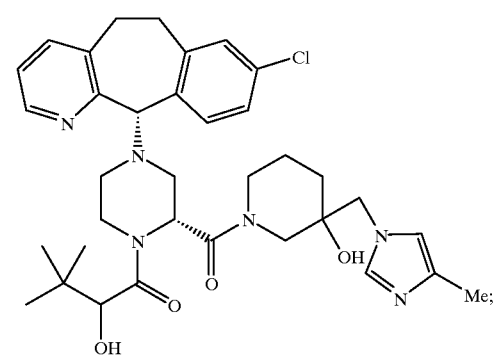
(Example 454, isomer A)
(90) a compound of the formula:
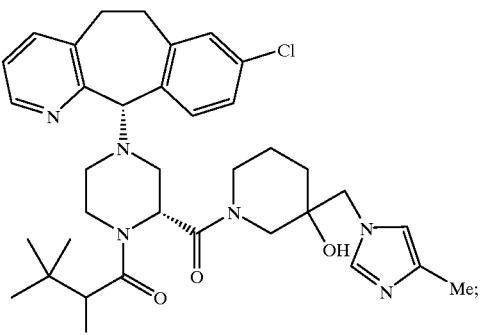
(Example 455, isomer B)
(91) a compound of the formula:
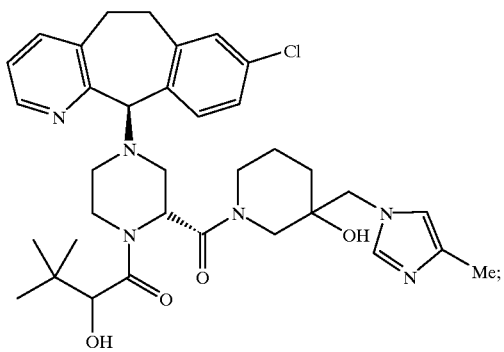
(Example 456, isomer A)
(92) a compound of the formula:
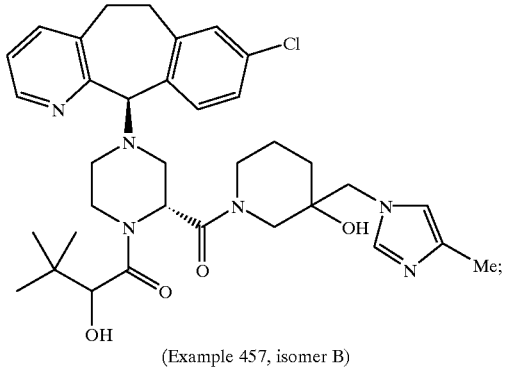
(Example 457, isomer B)

(93) a compound of the formula:
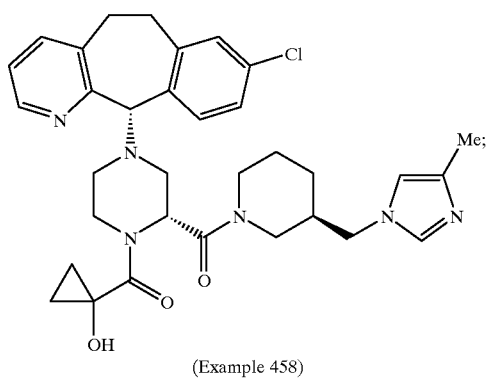
(Example 458)
(94) a compound of the formula:
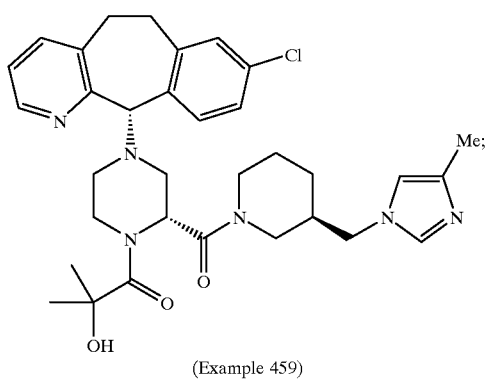
(Example 459)
(95) a compound of the formula:
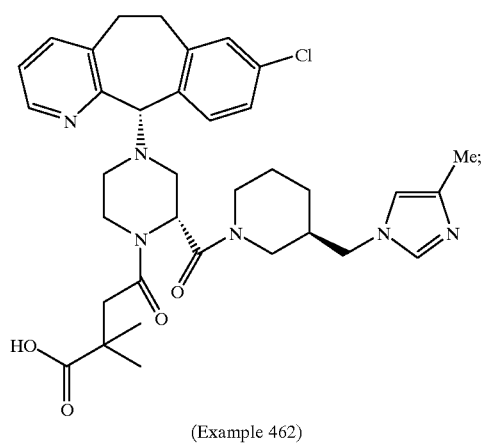
(Example 462)
(96) a compound of the formula:
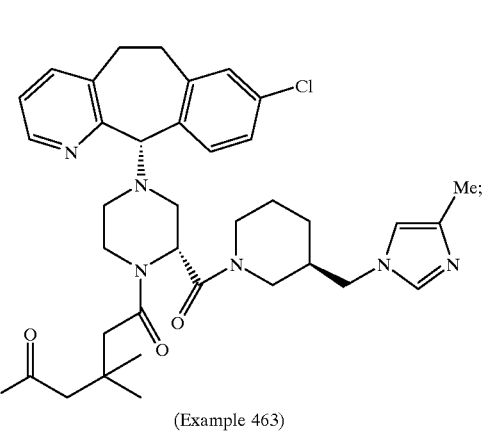
(Example 463)
(97) a compound of the formula:
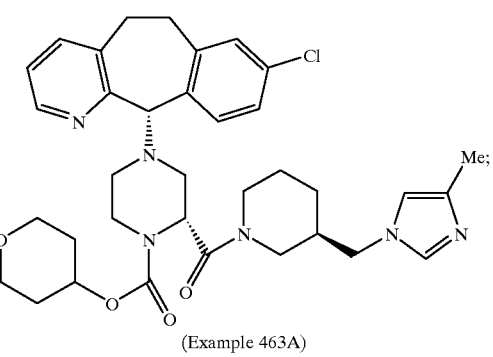
(Example 463A)
(98) a compound of the formula:
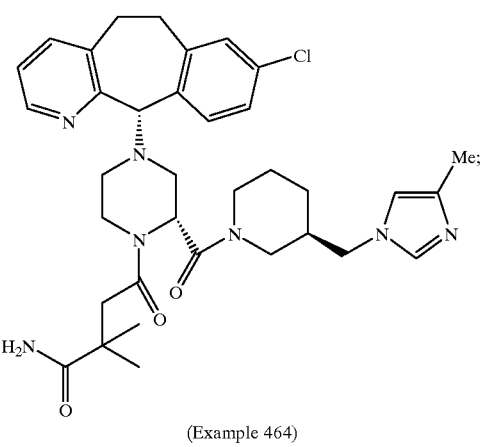
(Example 464)

(99) a compound of the formula:
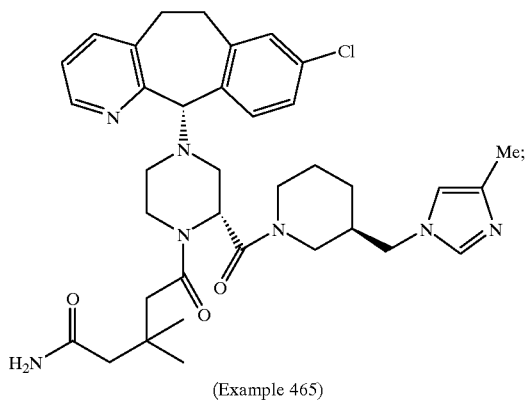
(Example 465)
(100) a compound of the formula:
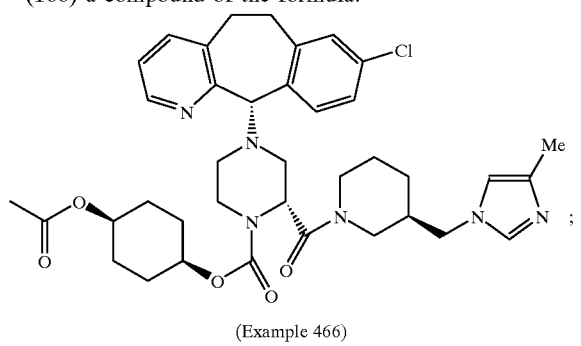
(Example 466)
(101) a compound of the formula:
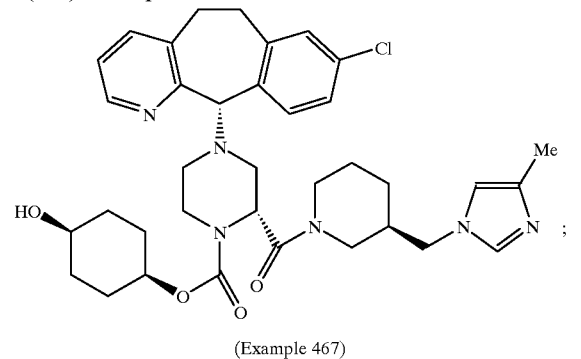
(Example 467)
(102) a compound of the formula:
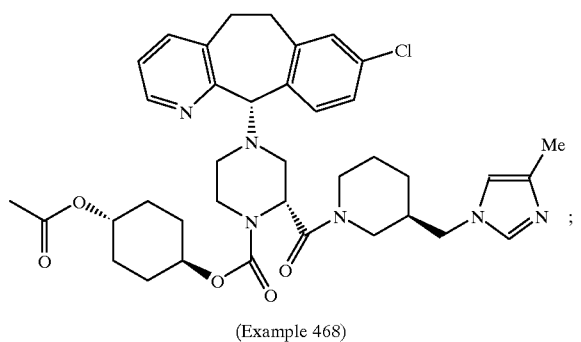
(Example 468)
(103) a compound of the formula:
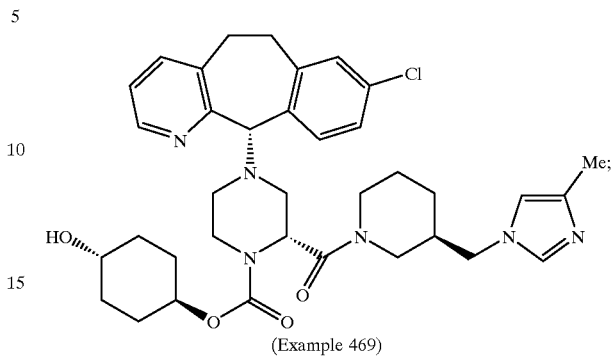
(Example 469)
(104) a compound of the formula:
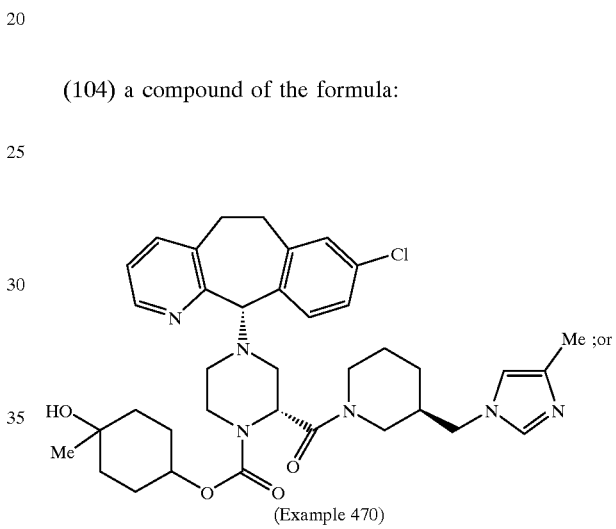
(Example 470)
(105) a compound of the formula:
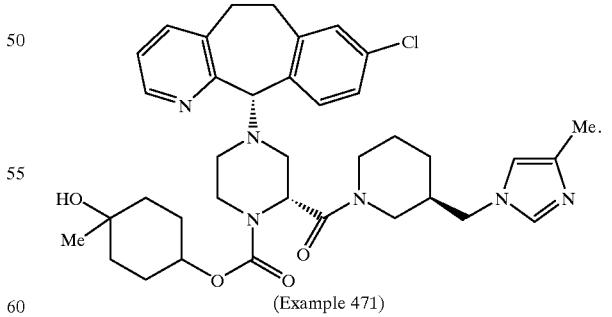
(Example 471)
29. The compound of claim 26 selected from a compound of Examples 47(A) or 140A.
* * * * *